(12) United States Patent
Takyo et al.

(10) Patent No.: US 8,853,238 B2
(45) Date of Patent: Oct. 7, 2014

(54) FUSED HETEROCYCLIC COMPOUND AND USE THEREOF FOR PEST CONTROL

(75) Inventors: Hayato Takyo, Tokyo (JP); Masaki Takahashi, Takarazuka (JP); Takamasa Tanabe, Takarazuka (JP); Yoshihiko Nokura, Takarazuka (JP); Mai Ito, Takarazuka (JP); Atsushi Iwata, Tokyo (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/996,697

(22) PCT Filed: Dec. 22, 2011

(86) PCT No.: PCT/JP2011/080557
§ 371 (c)(1),
(2), (4) Date: Sep. 11, 2013

(87) PCT Pub. No.: WO2012/086848
PCT Pub. Date: Jun. 28, 2012

(65) Prior Publication Data
US 2014/0018373 A1   Jan. 16, 2014

(30) Foreign Application Priority Data

Dec. 24, 2010 (JP) .................. 2010-287412
Jul. 29, 2011 (JP) .................. 2011-166768
Dec. 1, 2011 (JP) .................. 2011-263374

(51) Int. Cl.
*C07D 513/02* (2006.01)
*C07D 515/02* (2006.01)
*A61K 31/44* (2006.01)

(52) U.S. Cl.
USPC ........... 514/301; 514/302; 514/303; 546/114; 546/115; 546/118

(58) Field of Classification Search
CPC .. C07D 513/02; C07D 515/02; C07D 487/13; A61K 31/437; A61K 31/4355; A61K 31/4365; A01N 43/40; A01N 43/44
USPC ........... 546/114, 115, 118; 514/301, 302, 303
See application file for complete search history.

(56) References Cited

U.S. PATENT DOCUMENTS

| 3,985,891 A * | 10/1976 | Kutter et al. ............... 514/303 |
| 4,038,396 A | 7/1977 | Shen et al. |
| 5,212,171 A | 5/1993 | Anderson et al. |
| 2004/0198768 A1 | 10/2004 | Choo et al. |
| 2008/0113994 A1 | 5/2008 | Velten et al. |

FOREIGN PATENT DOCUMENTS

| CN | 1058591 A | 2/1992 |
| CN | 1964977 A | 5/2007 |
| EP | 0262845 A1 | 4/1988 |
| GB | 1175013 A | 12/1969 |
| GB | 1445824 A | 8/1976 |
| JP | H01-501473 A | 5/1989 |
| JP | 2008-308448 A | 12/2008 |
| WO | 8802367 A1 | 4/1988 |

OTHER PUBLICATIONS

Coates et al., Journal of Medicinal Chemistry (1993), 36(10), 1387-92.*
Int'l Search Report and Written Opinion issued Mar. 6, 2012 in Int'l Application No. PCT/JP2011/080557.
Sluka et al, "2-Phenylbenzimidazoles as Potential Anthelminthics," Collection of Czechoslovak Chemical Communications, Institute of Organic Chemistry & Biochemistry, Prague, Czech Republic, vol. 41, pp. 3628-34 (Jan. 1976).
Coates et al, "Cyclic Nucleotide Phosphodiesterase Inhibition by Imidazopyridines: Analogues of Sulmazole and Isomalzole as Inhibitors of the CGMP Specific Phosphodiesterase," Journal of Medicinal Chemistry, vol. 36, No. 10, pp. 1387-92 (May 1993).
Int'l Preliminary Report on Patentability issued Jul. 4, 2013 in Int'l Application No. PCT/JP2011/080557.
Clark et al, "2-(Substituted phenyl)oxazolo[4,5-b]pyridines and 2-(Substituted phenyl)oxazolo[5,4-b] pyridines as Nonacidic Antiinflammatory Agents," Journal of Medicinal Chemistry, vol. 21, No. 11, pp. 1158-62 (1978).
Choi et al, "Solid phase combinatorial synthesis of benzothiazoles and evaluation of topoisomerase II inhibitory activity," Bioorganic & Medicinal Chemistry, vol. 14, pp. 1229-35 (2006).
Office Action issued Jun. 13, 2014 in CN Application No. 201180061142.3.
* cited by examiner

*Primary Examiner* — Niloofar Rahmani
(74) *Attorney, Agent, or Firm* — Panitch Schwarze Belisario & Nadel LLP

(57) ABSTRACT

A fused heterocyclic compound the formula (1): wherein $A^1$ represents —$NR^8$—, and the like; $A^2$ represents a nitrogen atom, and the like; $A^3$ represents a nitrogen atom, and the like; $R^1$ represents a C1-C6 chain hydrocarbon group optionally having one or more atoms or groups selected from Group X, and the like; $R^2$, $R^3$, $R^4$, and $R^5$ are same or different and represent independently a C1-C6 chain hydrocarbon group optionally having one or more halogen atoms, and the like; $R^6$ and $R^7$ are same or different and represent independently a C1-C6 chain hydrocarbon group optionally having one or more atoms or groups selected from Group X, and the like; $R^8$ represents a C1-C6 chain hydrocarbon group optionally having one or more atoms or groups selected from Group W, and the like; n represents 0, 1 or 2. The compound has an excellent activity of controlling pests.

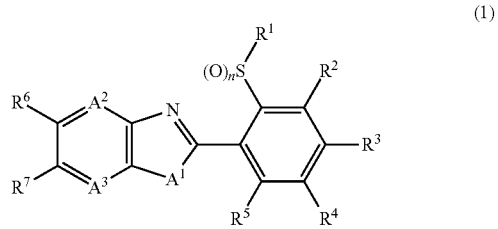

(1)

13 Claims, No Drawings

FUSED HETEROCYCLIC COMPOUND AND USE THEREOF FOR PEST CONTROL

CROSS-REFERENCE TO RELATED APPLICATION

This application is a Section 371 of International Application No. PCT/JP2011/080557, filed Dec. 22, 2011, which was published in the English language on Jun. 28, 2012, under International Publication No. WO 2012/086848 A1, and the disclosure of which is incorporated herein by reference.

TECHNICAL FIELD

The present invention relates to a certain fused heterocyclic compound and use for pest control thereof.

BACKGROUND ART

For controlling pests, various compounds have heretofore been developed and used practically.

Certain fused heterocyclic compounds are known (see, Patent Literature 1).

CITATION LIST

Patent Literature

Patent Literature 1: JP-A-01-501473

SUMMARY OF INVENTION

Technical Problem

An object of the present invention is to provide a compound having an excellent activity of controlling pests and a method of controlling pests using the compound.

Solution to Problem

The present inventors have studied so as to resolve the above problem and found that a fused heterocyclic compound of the following formula (1) has an excellent activity of controlling pests, thus leading to the present invention.

That is, the present invention provides:
[1] A fused heterocyclic compound of the formula (1):

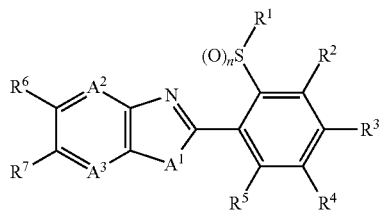

(1)

wherein:
$A^1$ represents —$NR^8$—, an oxygen atom, or a sulfur atom;
$A^2$ represents a nitrogen atom or =$CR^9$—;
$A^3$ represents a nitrogen atom or =$CR^{10}$—;
$R^1$ represents a C1-C6 chain hydrocarbon group optionally having one or more atoms or groups selected from Group X, or a C3-C6 alicyclic hydrocarbon group optionally having one or more atoms or groups selected from Group Y;

$R^2$, $R^3$, $R^4$, and $R^5$ are same or different and independently represent a C1-C6 chain hydrocarbon group optionally having one or more halogen atoms, a phenyl group optionally having one or more atoms or groups selected from Group Z, a 5-membered heterocyclic group optionally having one or more atoms or groups selected from Group Z, a 6-membered heterocyclic group optionally having one or more atoms or groups selected from Group Z, —$OR^{11}$, —$S(O)_m R^{11}$, —$NR^{11}R^{12}$, —$CO_2R^{11}$, —$C(O)R^{11}$, a cyano group, a nitro group, a halogen atom, —$SF_5$, or a hydrogen atom, provided that at least two of $R^2$, $R^3$, $R^4$, and $R^5$ represent a hydrogen atom;

$R^6$ and $R^7$ are same or different and independently represent a C1-C6 chain hydrocarbon group optionally having one or more atoms or groups selected from Group X, a phenyl group optionally having one or more atoms or groups selected from Group Z, a 5-membered heterocyclic group optionally having one or more atoms or groups selected from Group Z, a 6-membered heterocyclic group optionally having one or more atoms or groups selected from Group Z, —$OR^{11}$, $S(O)_m R^{11}$, —$S(O)_2NR^{11}R^{12}$, —$NR^{11}R^{12}$, —$NR^{11}CO_2R^{12}$, —$NR^{11}C(O)R^{12}$, —$CO_2R^{11}$, —$C(O)R^{11}$, a cyano group, a nitro group, a halogen atom, —$SF_5$, or a hydrogen atom;

$R^8$ represents a C1-C6 chain hydrocarbon group optionally having one or more atoms or groups selected from Group W, —$CO_2R^{11}$, —$C(O)R^{11}$, a C3-C6 alicyclic hydrocarbon group optionally having one or more atoms or groups selected from Group Y, or a hydrogen atom;

$R^9$ and $R^{10}$ are same or different and independently represent a C1-C6 chain hydrocarbon group optionally having one or more halogen atoms, —$OR^{11}$, —$S(O)_m R^{11}$, $NR^{11}R^{12}$, —$CO_2R^{11}$, —$C(O)R^{11}$, a cyano group, a nitro group, a halogen atom, or a hydrogen atom;

$R^{11}$ and $R^{12}$ are same or different and independently represent a C1-C6 chain hydrocarbon group optionally having one or more halogen atoms, or a hydrogen atom; and m represents 0, 1, or 2; and n represents 0, 1, or 2;

(except in cases as follows: both $R^6$ and $R^7$ are a hydrogen atom; and in —$S(O)_m R^{11}$, when m is 1 or 2, $R^{11}$ is a hydrogen atom) and when $A^1$ represents —NH— or —N(CH$_3$)—, $A^2$ and $A^3$ represent =CH—, $R^1$ represents a methyl group, $R^2$, $R^3$, $R^4$, and $R^5$ represent a hydrogen atom, and n is 0, 1, or 2, $R^6$ and $R^7$ are same or different and represent independently a C1-C6 chain hydrocarbon group optionally having one or more atoms or groups selected from Group X, a phenyl group optionally having one or more atoms or groups selected from Group Z, a 5-membered heterocyclic group optionally having one or more atoms or groups selected from Group Z, a 6-membered heterocyclic group optionally having one or more atoms or groups selected from Group Z, —$OR^{11}$, —$S(O)_m R^{11}$, —$S(O)_2NR^{11}R^{12}$, —$NR^{11}R^{12}$, —$NR^{11}$—$CO_2R^{12}$, —$NR^{11}C(O)R^{12}$, —$CO_2H$, —$C(O)R^{11}$, a cyano group, a nitro group, a bromine atom, an iodine atom, —$SF_5$ or a hydrogen atom.

the Group X consists of a C1-C6 alkoxy group optionally having one or more halogen atoms, a C2-C6 alkenyloxy group optionally having one or more halogen atoms, a C2-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C2-C6 alkylcarbonyl group optionally having one or more halogen atoms, a C2-C6 alkoxycarbonyl group optionally having one or more halogen atoms, a C3-C6 cycloalkyl group optionally having one or more halogen atoms, a cyano group, a hydroxy group, and a halogen atom;

the Group Y consists of a C1-C6 chain hydrocarbon group optionally having one or more halogen atoms, a C1-C6 alkoxy group optionally having one or more halogen atoms, a C2-C6 alkenyloxy group optionally having one or more halogen atoms, a C2-C6 alkynyloxy group optionally having one or more halogen atoms, a hydroxy group, and a halogen atom;

the Group Z consists of a C1-C6 chain hydrocarbon group optionally having one or more halogen atoms, a C1-C6 alkoxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C2-C6 alkylcarbonyl group optionally having one or more halogen atoms, a C2-C6 alkoxycarbonyl group optionally having one or more halogen atoms, a C1-C6 alkylamino group optionally having one or more halogen atoms, a C2-C8 dialkylamino group optionally having one or more halogen atoms, a halogen atom, a cyano group, and a nitro group; and the Group W consists of a C1-C6 alkoxy group optionally having one or more halogen atoms, a C2-C6 alkenyloxy group optionally having one or more halogen atoms, a C2-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C2-C6 alkylcarbonyl group optionally having one or more halogen atoms, a C2-C6 alkoxycarbonyl group optionally having one or more halogen atoms, a C3-C6 cycloalkyl group optionally having one or more halogen atoms, a halogen atom, a cyano group, and a hydroxy group (hereinafter referred to as the present compound);

[2] The fused heterocyclic compound according to the above [1] wherein $R^6$ and $R^7$ are same or different and are independently a C1-C6 chain hydrocarbon group optionally having one or more halogen atoms, $—OR^{11}$, $—(O)_m R^{11}$, $—NR^{11}R^{12}$, a cyano group, a nitro group, a halogen atom, or a hydrogen atom;

[3] The fused heterocyclic compound according to the above [1] or [2] wherein $R^6$ and $R^7$ are same or different and are independently a C1-C6 chain hydrocarbon group optionally having one or more halogen atoms, $—OR^{11}$, $—S(O)_m R^{11}$, a halogen atom, or a hydrogen atom;

[4] The fused heterocyclic compound according to any one of the above [1]-[3] wherein $A^2$ is $=CH—$;

[5] The fused heterocyclic compound according to any one of the above [1]-[4] wherein $A^3$ is a nitrogen atom or $=CR^{10}—$, and $R^{10}$ is a halogen atom or a hydrogen atom;

[6] The fused heterocyclic compound according to any one of the above [1]-[4] wherein $A^3$ is a nitrogen atom;

[7] The fused heterocyclic compound according to any one of the above [1]-[6] wherein $R^2$, $R^4$, and $R^5$ are same or different and are independently a hydrogen atom or a halogen atom, and $R^3$ is a C1-C6 chain hydrocarbon group optionally having one or more halogen atoms, $—OR^{11}$, a halogen atom, or a hydrogen atom;

[8] The fused heterocyclic compound according to any one of the above [1]-[7] wherein $A^1$ is $—NR^8—$, and $R^8$ is a C1-C6 chain hydrocarbon group having one C1-C6 alkoxy group optionally having one or more halogen atoms, a C1-C6 chain hydrocarbon group optionally having one or more halogen atoms, or a cyclopropyl group;

[9] The fused heterocyclic compound according to any one of the above [1]-[7] wherein $A^1$ is $—NR^8—$, and $R^8$ is a methyl group, an ethyl group, a methoxymethyl group, or an ethoxymethyl group;

[10] The fused heterocyclic compound according to any one of the above [1]-[7] wherein $A^1$ is an oxygen atom;

[11] The fused heterocyclic compound according to any one of the above [1]-[7] wherein $A^1$ is a sulfur atom;

[12] The fused heterocyclic compound according to the above [1] which is represented by the formula (1-1):

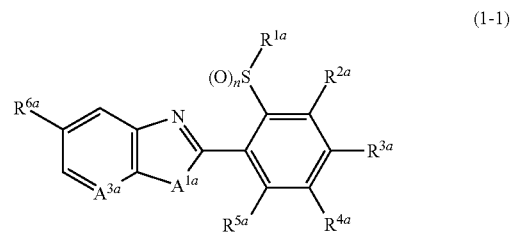

wherein:
$A^{1a}$ represents $—NR^{8a}—$ or a sulfur atom;
$A^{3a}$ represents a nitrogen atom or $=CR^{10a}—$;
$R^{1a}$ represents a C1-C6 chain hydrocarbon group optionally having one or more halogen atoms;
$R^{2a}$, $R^{4a}$, and $R^{5a}$ are same or different and independently represent a C1-C6 chain hydrocarbon group optionally having one or more halogen atoms, a halogen atom, or a hydrogen atom;
$R^{3a}$ represents a C1-C6 chain hydrocarbon group optionally having one or more halogen atoms, $—OR^{11a}$, a halogen atom, or a hydrogen atom;
$R^{6a}$ represents a C1-C6 chain hydrocarbon group optionally having one or more halogen atoms, $—OR^{11a}$, $—S(O)_m R^{11a}$, a bromine atom, or an iodine atom;
$R^{8a}$ represents a C1-C6 chain hydrocarbon group optionally having one or more halogen atoms or a hydrogen atom;
$R^{10a}$ represents a halogen atom or a hydrogen atom;
$R^{11a}$ represents a C1-C6 chain hydrocarbon group optionally having one or more halogen atoms; and
m represents 0, 1, or 2, and n represents 0, 1, or 2; [13] The fused heterocyclic compound according to the above [12] wherein $A^{1a}$ is $—NR^{8a}—$ or a sulfur atom, $R^{8a}$ is a methyl group, $A^{3a}$ is a nitrogen atom, $R^{1a}$ is an ethyl group, $R^{2a}$, $R^{4a}$, and $R^{5a}$ are same or different and are independently a halogen atom or a hydrogen atom, $R^{3a}$ is a trifluoromethyl group, a halogen atom, or a hydrogen atom, and $R^{6a}$ is a C1-C3 alkyl group having one or more fluorine atoms, a C1-C3 alkoxy group having one or more fluorine atoms, a C1-C3 alkylsulfanyl group having one or more fluorine atoms, a C1-C3 alkylsulfinyl group having one or more fluorine atoms, or a C1-C3 alkylsulfonyl group having one or more fluorine atoms;

[14] A pest controlling composition which comprises the fused heterocyclic compound according to any one of the above [1]-[13] and an inert carrier; and

[15] A method of controlling pests which comprises applying an effective amount of the fused heterocyclic compound according to any one of the above [1]-[13] to pests or habitats of pests.

Effect of Invention

The present compound has an excellent activity of controlling pests and is useful as an active ingredient of a pest controlling agent.

DESCRIPTION OF EMBODIMENTS

Various substituents used in the present specification will be illustrated by way of examples.

In the present invention, the "halogen atom" includes a fluorine atom, a chlorine atom, a bromine atom, and an iodine atom.

In the present compound, examples of the "C1-C6 chain hydrocarbon group optionally having one or more atoms or groups selected from Group X" include a C1-C6 alkyl group optionally having one or more atoms or groups selected from Group X such as a methyl group, an ethyl group, a propyl group, an isopropyl group, a butyl group, an isobutyl group, a sec-butyl group, a tert-butyl group, a pentyl group, a neopentyl group, a hexyl group, a methoxymethyl group, an ethoxymethyl group, a propyloxymethyl group, an isopropyloxymethyl group, a butyloxymethyl group, a sec-butyloxymethyl group, a tert-butyloxymethyl group, a 2-methoxyethyl group, a 2-ethoxyethyl group, a 2-propyloxyethyl group, a 2-isopropyloxyethyl group, a 2-butyloxyethyl group, a 2-sec-butyloxyethyl group, a 2-tert-butyloxyethyl group, a trifluoromethyl group, a trichloromethyl group, a 2-fluoroethyl group, a 2,2-difluoroethyl group, a 2,2,2-trifluoroethyl group, a pentafluoroethyl group, a methylsulfanylethyl group, an ethylsulfanylethyl group, a methylsulfinylethyl group, and a methylsulfonylethyl group, a methoxycarbonylethyl group, a cyanomethyl group, a cyclopropylmethyl group, and a cyclobutylmethyl group;

a C2-C6 alkenyl group optionally having one or more atoms or groups selected from Group X such as a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group, a 1-hexenyl group, a 1,1-difluoroallyl group, and a pentafluoroallyl group; and a C2-C6 alkynyl group optionally having one or more atoms or groups selected from Group X such as an ethinyl group, a propargyl group, a 2-butynyl group, a 3-butynyl group, a 1-pentynyl group, a 1-hexynyl group, and a 4,4,4-trifluoro-2-butynyl group.

In the present compound, examples of the "C3-C6 alicyclic hydrocarbon group optionally having one or more atoms or groups selected from Group Y" include a cyclopropyl group, a cyclobutyl group, a cyclopentyl group, a cyclohexyl group, a 1-cyclohexenyl group, a 2-cyclohexenyl group, a 3-cyclohexenyl group, a 1-methylcyclohexyl group, a 2-methylcyclohexyl group, a 3-methylcyclohexyl group, a 4-methylcyclohexyl group, a 2-methoxycyclohexyl group, a 3-methoxycyclohexyl group, a 4-methoxycyclohexyl group, a 1-fluorocyclohexyl group, a 2-fluorocyclohexyl group, a 3-fluorocyclohexyl group, and a 4-fluorocyclohexyl group.

In the present compound, examples of the "C1-C6 chain hydrocarbon group optionally having one or more halogen atoms" include a C1-C6 alkyl group optionally having one or more halogen atoms such as a methyl group, an ethyl group, a propyl group, an isopropyl group, a butyl group, an isobutyl group, a sec-butyl group, a tert-butyl group, a pentyl group, a neopentyl group, a hexyl group, a trifluoromethyl group, a trichloromethyl group, a 2-fluoroethyl group, a 2,2-difluoroethyl group, a 2,2,2-trifluoroethyl group, a pentafluoroethyl group, and a heptafluoroisopropyl group;

a C2-C6 alkenyl group optionally having one or more halogen atoms such as a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group, a 1-hexenyl group, a 1,1-difluoroallyl group, and a pentafluoroallyl group; and a C2-C6 alkynyl group optionally having one or more halogen atoms such as an ethinyl group, a propargyl group, a 2-butynyl group, a 3-butynyl group, a 1-pentynyl group, a 1-hexynyl group, and a 4,4,4-trifluoro-2-butynyl group.

In the present compound, examples of the "phenyl group optionally having one or more atoms or groups selected from Group Z" include a phenyl group, a 2-fluorophenyl group, a 3-fluorophenyl group, a 4-fluorophenyl group, a 2,3-difluorophenyl group, a 2,4-difluorophenyl group, a 2,5-difluorophenyl group, a 2,6-difluorophenyl group, a 3,4-difluorophenyl group, a 3,5-difluorophenyl group, a 2,3,4,5,6-pentafluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group, a 4-iodophenyl group, a 2-trifluoromethylphenyl group, a 3-trifluoromethylphenyl group, a 4-trifluoromethylphenyl group, a 2-trifluoromethoxyphenyl group, a 3-trifluoromethoxyphenyl group, a 4-trifluoromethoxyphenyl group, a 2-trifluoromethylsulfanylphenyl group, a 3-trifluoromethylsulfanylphenyl group, a 4-trifluoromethylsulfanylphenyl group, a 4-methoxycarbonylphenyl group, a 4-nitrophenyl group, a 4-cyanophenyl group, a 4-methylaminophenyl group, a 4-dimethylaminophenyl group, a 4-methylsulfinylphenyl group, a 4-methylsulfonylphenyl group, a 4-acetylphenyl group, and 4-methoxycarbonylphenyl group.

In the present compound, the "heterocyclic group" in the "5-membered heterocyclic group optionally having one or more atoms or groups selected from Group Z" represents a heterocyclic residue. Examples of "5-membered heterocyclic group optionally having one or more atoms or groups selected from Group Z" include a 5-membered saturated heterocyclic group optionally having one or more atoms or groups selected from Group Z such as a pyrrolidin-1-yl group and a tetrahydrofuran-2-yl group; and a 5-membered unsaturated heterocyclic group optionally having one or more atoms or groups selected from Group Z such as a 2-pyrrolyl group, a 2-furyl group, a 3-furyl group, a 5-pyrazolyl group, a 4-pyrazolyl group, a 1-pyrrolyl group, a 1-methyl-2-pyrrolyl group, a 5-bromo-2-furyl group, a 5-nitro-2-furyl group, a 2-methyl-3-furyl group, a 2,5-dimethyl-3-furyl group, a 2,4-dimethyl-3-furyl group, a 5-methyl-2-thienyl group, a 3-methyl-2-thienyl group, a 1-methyl-3-trifluoromethyl-5-pyrazolyl group, a 5-chloro-1,3-dimethyl-4-pyrazolyl group, a pyrazol-1-yl group, a 3-chloro-pyrazol-1-yl group, a 3-bromopyrazol-1-yl group, a 4-chloropyrazol-1-yl group, a 4-bromopyrazol-1-yl group, a imidazol-1-yl group, a pyrrol-1-yl group, a 1,2,4-triazol-1-yl group, a 3-chloro-1,2,4-triazol-1-yl group, a 1,2,3,4-tetrazol-1-yl group, a 1,2,3,5-tetrazol-1-yl group, a 2-thienyl group, a 3-thienyl group, a 3-trifluoromethyl-1,2,4-triazol-1-yl group, and a 4-trifluoromethylpyrazol-1-yl group.

In the present compound, the "heterocyclic group" in the "6-membered heterocyclic group optionally having one or more atoms or groups selected from Group Z" represents a heterocyclic residue. Examples of the "6-membered heterocyclic group optionally having one or more atoms or groups selected from Group Z" include a 6-membered saturated heterocyclic group optionally having one or more atoms or groups selected from Group Z such as a piperidyl group, a morpholinyl group, and a thiomorpholinyl group; and a 6-membered aromatic heterocyclic group optionally having one or more atoms or groups selected from Group Z such as a pyrazinyl group, a 2-pyrimidyl group, a 4-pyrimidyl group, a 5-pyrimidyl group, a 2-pyridyl group, a 3-pyridyl group, a 4-pyridyl group, a 3-fluoro-2-pyridyl group, a 4-fluoro-2-pyridyl group, a 5-fluoro-2-pyridyl group, a 6-fluoro-2-pyridyl group, a 2-pyrimidyl group, and a 5-trifluoromethylpyridin-2-yl group.

In the present compound, the "C1-C6 chain hydrocarbon group optionally having one or more atoms or groups selected from Group W" include a C1-C6 alkyl group optionally having one or more atoms or groups selected from Group W such as a methyl group, an ethyl group, a propyl group, an isopropyl group, a butyl group, an isobutyl group, a sec-butyl group, a tert-butyl group, a pentyl group, a neopentyl group, a hexyl group, a trifluoromethyl group, a trichloromethyl group, a 2-fluoroethyl group, a 2,2-difluoroethyl group, a 2,2,2-trifluoroethyl group, a pentafluoroethyl group, a methoxymethyl group, an ethoxymethyl group, a propyloxymethyl group, an isopropyloxymethyl group, a butyloxymethyl group, a sec-butyloxymethyl group, an isobutyloxymethyl group, a tert-butyloxymethyl group, a methoxyethyl group, an ethoxyethyl group, a propyloxyethyl group, an isopropyloxyethyl group, a butyloxyethyl group, a sec-butyloxyethyl group, an isobutyloxyethyl group, a tert-butyloxyethyl group, a methylsulfanylethyl group, an ethylsulfanylethyl group, a methylsulfinylethyl group, a methylsulfonylethyl group, a methoxycarbonylmethyl group, a methoxycarbonylethyl group, a cyclopropylmethyl group, and a cyclohexylmethyl group;

a C2-C6 alkenyl group optionally having one or more atoms or groups selected from Group W such as a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group, a 1-hexenyl group, a 1,1-difluoroallyl group, and a pentafluoroallyl group; and a C2-C6 alkynyl group optionally having one or more atoms or groups selected from Group W such as an ethinyl group, a propargyl group, a 2-butynyl group, a 3-butynyl group, a 1-pentynyl group, a 1-hexynyl group, and a 4,4,4-trifluoro-2-butynyl group.

In the present compound, examples of the "C1-C6 alkylsulfanyl group optionally having one or more halogen atoms" include a methylsulfanyl group, an ethylsulfanyl group, a propylsulfanyl group, an isopropylsulfanyl group, a butylsulfanyl group, a pentylsulfanyl group, a hexylsulfanyl group, a trifluoromethylsulfanyl group, a 2,2,2-trifluoroethylsulfanyl group, and a pentafluoroethylsulfanyl group.

In the present compound, examples of the "C1-C6 alkylsulfinyl group optionally having one or more halogen atoms" include a methylsulfinyl group, an ethylsulfinyl group, a propylsulfinyl group, an isopropylsulfinyl group, a butylsulfinyl group, a pentylsulfinyl group, a hexylsulfinyl group, a trifluoromethylsulfinyl group, a 2,2,2-trifluoroethylsulfinyl group, and a pentafluoroethylsulfinyl group.

In the present compound, examples of the "C1-C6 alkylsulfonyl group optionally having one or more halogen atoms" include a methylsulfonyl group, an ethylsulfonyl group, a propylsulfonyl group, an isopropylsulfonyl group, a butylsulfonyl group, a pentylsulfonyl group, a hexylsulfonyl group, a trifluoromethylsulfonyl group, a pentafluoroethylsulfonyl group.

In the present compound, examples of the "C1-C6 alkoxy group optionally having one or more halogen atoms" include a methoxy group, a trifluoromethoxy group, an ethoxy group, a 2,2,2-trifluoroethoxy group, a propyloxy group, an isopropyloxy group, a butyloxy group, an isobutyloxy group, a sec-butyloxy group, a tert-butyloxy group, a pentyloxy group, and a hexyloxy group.

In the present compound, examples of the "C2-C6 alkenyloxy group optionally having one or more halogen atoms" include a 2-propenyloxy group, a 2-methyl-2-propenyloxy group, a 2-butenyloxy group, a 3-butenyloxy group, a 2-pentenyloxy group, a 2-hexenyloxy group, a 3,3-difluoroallyloxy group, and a 3,3-dichloroallyloxy group.

In the present compound, examples of the "C2-C6 alkynyloxy group optionally having one or more halogen atoms" include a propargyloxy group, a 2-butynyloxy group, a 3-butynyloxy group, a 2-pentynyloxy group, a 2-hexynyloxy group, and a 4,4,4-trifluoro-2-butynyloxy group.

In the present compound, examples of the "C2-C6 alkylcarbonyl group optionally having one or more halogen atoms" include an acetyl group, a propionyl group, a propylcarbonyl group, a butylcarbonyl group, a pentylcarbonyl group, and a trifluoroacetyl group.

In the present compound, examples of the "C2-C6 alkoxycarbonyl group optionally having one or more halogen atoms" include a methoxycarbonyl group, an ethoxycarbonyl group, a propyloxycarbonyl group, a butyloxycarbonyl group, a pentyloxycarbonyl group, a tert-butyloxycarbonyl group, and a 2,2,2-trifluoroethylcarbonyl group.

In the present compound, examples of the "C1-C6 alkylamino group optionally having one or more halogen atoms" include a methylamino group, an ethylamino group, a 2,2,2-trifluoroethylamino group, a propylamino group, an isopropylamino group, and a butylamino group.

In the present compound, examples of the "C2-C8 dialkylamino group optionally having one or more halogen atoms" include a dimethylamino group, a diethylamino group, a bis(2,2,2-trifluoroethyl)amino group, and a dipropylamino group.

In the present compound, examples of the "C3-C6 cycloalkyl group optionally having one or more halogen atoms" include a cyclopropyl group, a cyclobutyl group, a cyclopentyl group, and a cyclohexyl group.

In the present compound, examples of the "C1-C3 alkyl group having one or more a fluorine atoms" include a fluoromethyl group, a difluoromethyl group, a trifluoromethyl group, a trichloromethyl group, a 2,2,2-trifluoroethyl group, a pentafluoroethyl group, a heptafluoropropyl group, and a heptafluoroisopropyl group.

In the present compound, examples of the "C1-C3 alkoxy group having one or more a fluorine atoms" include a trifluoromethoxy group, a 2,2,2-trifluoroethoxy group, and a pentafluoroethoxy group.

In the present compound, examples of the "C1-C3 alkylsulfanyl group having one or more a fluorine atoms" include a trifluoromethylsulfanyl group, a 2,2,2-trifluoroethylsulfanyl group, a pentafluoroethylsulfanyl group, a heptafluoropropylsulfanyl group, and a heptafluoroisopropylsulfanyl group.

In the present compound, examples of the "C1-C3 alkylsulfinyl group having one or more a fluorine atoms" include a trifluoromethylsulfinyl group, a 2,2,2-trifluoroethylsulfinyl group, a pentafluoroethylsulfinyl group, a heptafluoropropylsulfinyl group, and a heptafluoroisopropylsulfinyl group.

In the present compound, examples of the "C1-C3 alkylsulfonyl group having one or more a fluorine atoms" include a trifluoromethylsulfonyl group, a 2,2,2-trifluoroethylsulfonyl group, a pentafluoroethylsulfonyl group, a heptafluoropropylsulfonyl group, and a heptafluoroisopropylsulfonyl group.

In the present compound, examples of the "C1-C3 alkyl group" include a methyl group, an ethyl group, a propyl group, and an isopropyl group.

In the present compound, examples of the "C1-C3 alkyl group optionally having one or more halogen atoms" include a methyl group, an ethyl group, a propyl group, an isopropyl group, a trifluoromethyl group, a pentafluoroethyl group, a 2,2,2-trifluoroethyl group, a 2,2,2-trichloroethyl group, a heptafluoropropyl group, and a heptafluoroisopropyl group.

Examples of the present compound include the following pyrimidine compounds.

A compound of the formula (1) wherein $A^1$ is $-NR^8-$, an oxygen atom, or a sulfur atom, and $R^8$ is a C1-C6 chain hydrocarbon group having one C1-C6 alkoxy group optionally having one or more halogen atoms, a C1-C6 chain hydrocarbon group optionally having one or more halogen atoms, a C1-C6 chain hydrocarbon group having one C2-C6 alkoxycarbonyl group, $-CO_2R^{11}$, or a cyclopropyl group;

A compound of the formula (1) wherein $A^1$ is $-NR^8-$, an oxygen atom, or a sulfur atom, and $R^8$ is a C1-C6 chain hydrocarbon group having one C1-C6 alkoxy group optionally having one or more halogen atoms, a C1-C6 chain hydrocarbon group optionally having one or more halogen atoms, or a cyclopropyl group;

A compound of the formula (1) wherein $A^1$ is $-NR^8-$, an oxygen atom, or a sulfur atom, and $R^8$ is a C1-C6 chain hydrocarbon group optionally having one or more halogen atoms, or a cyclopropyl group;

A compound of the formula (1) wherein $A^1$ is $-NR^8-$, an oxygen atom, or a sulfur atom, and $R^8$ is a methyl group, an ethyl group, a propyl group, an isopropyl group, a methoxymethyl group, an ethoxymethyl group, or a cyclopropyl group;

A compound of the formula (1) wherein $A^1$ is $-NR^8-$, an oxygen atom, or a sulfur atom, and $R^8$ is a methyl group;

A compound of the formula (1) wherein $A^1$ is $-NR^8-$ or an oxygen atom, and $R^8$ is a C1-C6 chain hydrocarbon group optionally having one or more halogen atoms, or a cyclopropyl group;

A compound of the formula (1) wherein $A^1$ is $-NR^8-$, and $R^8$ is a C1-C6 chain hydrocarbon group having one C1-C6 alkoxy group optionally having one or more halogen atoms, a C1-C6 chain hydrocarbon group optionally having one or more halogen atoms, a C1-C6 chain hydrocarbon group having one C2-C6 alkoxycarbonyl group, $-CO_2R^{11}$, or a cyclopropyl group;

A compound of the formula (1) wherein $A^1$ is $-NR^8-$, and $R^8$ is a C1-C6 chain hydrocarbon group having one C1-C6 alkoxy group optionally having one or more halogen atoms, a C1-C6 chain hydrocarbon group optionally having one or more halogen atoms, or a cyclopropyl group;

A compound of the formula (1) wherein $A^1$ is $-NR^8-$, and $R^8$ is a methyl group, an ethyl group, a propyl group, an isopropyl group, a methoxymethyl group, an ethoxymethyl group, or a cyclopropyl group;

A compound of the formula (1) wherein $A^1$ is $-NR^8-$, and $R^8$ is a methyl group, an ethyl group, a methoxymethyl group, or an ethoxymethyl group;

A compound of the formula (1) wherein $A^1$ is $-NR^8-$, and $R^8$ is a methyl group;

A compound of the formula (1) wherein $A^1$ is an oxygen atom;

A compound of the formula (1) wherein $A^1$ is a sulfur atom;

A compound of the formula (1) wherein $A^2$ is a nitrogen atom;

A compound of the formula (1) wherein $A^2$ is a nitrogen atom or $=CR^9-$, and $R^9$ is a C1-C3 chain hydrocarbon group, a halogen atom, or a hydrogen atom;

A compound of the formula (1) wherein $A^2$ is a nitrogen atom or $=CR^9-$, and $R^9$ is a halogen atom or a hydrogen atom;

A compound of the formula (1) wherein $A^2$ is a nitrogen atom or $=CR^9-$, and $R^9$ is a hydrogen atom;

A compound of the formula (1) wherein $A^2$ is $=CR^9-$, and $R^9$ is a C1-C6 chain hydrocarbon group optionally having one or more halogen atoms, $-OR^{11}$, $-S(O)_mR^{11}$, $-NR^{11}R^{12}$, $-CO_2R^{11}$, $-C(O)R^{11}$, a cyano group, a nitro group, a halogen atom, or a hydrogen atom;

A compound of the formula (1) wherein $A^2$ is $=CR^9-$, and $R^9$ is a C1-C3 chain hydrocarbon group, a halogen atom, or a hydrogen atom;

A compound of the formula (1) wherein $A^2$ is $=CR^9-$, and $R^9$ is a halogen atom or a hydrogen atom;

A compound of the formula (1) wherein $A^2$ is $=CR^9-$, and $R^9$ is a hydrogen atom;

A compound of the formula (1) wherein $A^3$ is a nitrogen atom;

A compound of the formula (1) wherein $A^3$ is a nitrogen atom or $=CR^{10}-$, and $R^{10}$ is a C1-C3 chain hydrocarbon group, a halogen atom, or a hydrogen atom;

A compound of the formula (1) wherein $A^3$ is a nitrogen atom or $=CR^{10}-$, and $R^{10}$ is a halogen atom or a hydrogen atom;

A compound of the formula (1) wherein $A^3$ is a nitrogen atom or $=CR^{10}-$, and $R^1$ is a hydrogen atom;

A compound of the formula (1) wherein $A^3$ is $=CR^{10}-$, and $R^{10}$ is a C1-C6 chain hydrocarbon group optionally having one or more halogen atoms, $-OR^{11}$, $-S(O)_mR^{11}$, $-NR^{11}R^{12}$, $-CO_2R^{11}$, $-C(O)R^{10}$, a cyano group, a nitro group, a halogen atom, or a hydrogen atom;

A compound of the formula (1) wherein $A^3$ is $=CR^{10}-$, and $R^{10}$ is a C1-C3 chain hydrocarbon group, a halogen atom, or a hydrogen atom;

A compound of the formula (1) wherein $A^3$ is $=CR^{10}-$, and $R^{10}$ is a halogen atom or a hydrogen atom;

A compound of the formula (1) wherein $A^3$ is $=CR^{10}-$, and $R^{10}$ is a halogen atom;

A compound of the formula (1) wherein $A^3$ is $=CR^{10}-$, and $R^{10}$ is a hydrogen atom;

A compound of the formula (1) wherein $A^1$ is $-NR^8-$, an oxygen atom, or a sulfur atom, $R^8$ is a C1-C6 chain hydrocarbon group having one C1-C6 alkoxy group optionally having one or more halogen atoms, a C1-C6 chain hydrocarbon group optionally having one or more halogen atoms, a C1-C6 chain hydrocarbon group having one C2-C6 alkoxycarbonyl group, $-CO_2R^{11}$, or a cyclopropyl group, $A^2$ is a nitrogen atom or $=CR^9-$, $R^9$ is a halogen atom or a hydrogen atom, $A^3$ is a nitrogen atom or $=CR^{10}-$, and $R^{10}$ is a halogen atom or a hydrogen atom;

A compound of the formula (1) wherein $A^1$ is $-NR^8-$, an oxygen atom, or a sulfur atom, $R^8$ is a methyl group, an ethyl group, a propyl group, an isopropyl group, a methoxymethyl group, an ethoxymethyl group, or a cyclopropyl group, $A^2$ is a nitrogen atom or $=CR^9-$, $R^9$ is a halogen atom or a hydrogen atom, $A^3$ is a nitrogen atom or $=CR^{10}-$, and $R^{10}$ is a halogen atom or a hydrogen atom;

A compound of the formula (1) wherein $A^1$ is $-NR^8-$, an oxygen atom, or a sulfur atom, $R^8$ is a methyl group, $A^2$ is a nitrogen atom or $=CR^9-$, $R^9$ is a halogen atom or a hydrogen atom, $A^3$ is a nitrogen atom or $=CR^{10}-$, and $R^{10}$ is a halogen atom or a hydrogen atom;

A compound of the formula (1) wherein $A^1$ is $-NR^8-$, an oxygen atom, or a sulfur atom, $R^8$ is a methyl group, $A^2$ is $=CR^9-$, $R^9$ is a hydrogen atom, and $A^3$ is a nitrogen atom;

A compound of the formula (1) wherein $A^1$ is $-NR^8-$, $R^8$ is a C1-C6 chain hydrocarbon group optionally having one or more halogen atoms, $A^2$ is $=CR^9-$, $R^9$ is a hydrogen atom, and $A^3$ is a nitrogen atom;

A compound of the formula (1) wherein $A^1$ is $-NR^8-$, $R^8$ is a methyl group, $A^2$ is $=CR^9-$, $R^9$ is a hydrogen atom, and $A^3$ is a nitrogen atom;

A compound of the formula (1) wherein $A^1$ is an oxygen atom, $A^2$ is =$CR^9$—, $R^9$ is a hydrogen atom, and $A^3$ is a nitrogen atom;

A compound of the formula (1) wherein $A^1$ is a sulfur atom, $A^2$ is =$CR^9$—, $R^9$ is a hydrogen atom, and $A^3$ is a nitrogen atom;

A compound of the formula (1) wherein $R^1$ is a C1-C6 chain hydrocarbon group optionally having one or more atoms or groups selected from Group X;

A compound of the formula (1) wherein $R^1$ is a C1-C6 chain hydrocarbon group optionally having one or more halogen atoms;

A compound of the formula (1) wherein $R^1$ is a C3-C6 alicyclic hydrocarbon group optionally having one or more atoms or groups selected from Group Y;

A compound of the formula (1) wherein $R^1$ is a methyl group, an ethyl group, a propyl group, an isopropyl group, a butyl group, a sec-butyl group, an isobutyl group, a tert-butyl group, a cyclopropyl group, a trifluoromethyl group, and a 2,2,2-trifluoroethyl group;

A compound of the formula (1) wherein $R^1$ is a methyl group, an ethyl group, a propyl group, an isopropyl group, a butyl group, a sec-butyl group, an isobutyl group, a tert-butyl group, a cyclopropyl group, a trifluoromethyl group, and a 2,2,2-trifluoroethyl group, and $R^2$, $R^3$, $R^4$, and $R^5$ are a hydrogen atom;

A compound of the formula (1) wherein $R^1$ is a methyl group, an ethyl group, or a propyl group;

A compound of the formula (1) wherein $R^1$ is an ethyl group;

A compound of the formula (1) wherein $R^2$, $R^3$, $R^4$, and $R^5$ are same or different and are independently a C1-C6 chain hydrocarbon group optionally having one or more halogen atoms, —$OR^{11}$, —$NR^{11}R^{12}$, a cyano group, a nitro group, a halogen atom, or a hydrogen atom;

A compound of the formula (1) wherein $R^2$, $R^3$, $R^4$, and $R^5$ are same or different and are independently a methyl group, an ethyl group, a trifluoromethyl group, or a hydrogen atom;

A compound of the formula (1) wherein $R^2$, $R^3$, $R^4$, and $R^5$ are same or different and are independently a methoxy group, an ethoxy group, a trifluoromethoxy group, or a hydrogen atom;

A compound of the formula (1) wherein $R^2$, $R^3$, $R^4$, and $R^5$ are same or different and are independently an amino group, a methylamino group, a dimethylamino group, or a hydrogen atom;

A compound of the formula (1) wherein $R^2$, $R^3$, $R^4$, and $R^5$ are same or different and are independently a cyano group or a hydrogen atom;

A compound of the formula (1) wherein $R^2$, $R^3$, $R^4$, and $R^5$ are same or different and are independently a nitro group or a hydrogen atom;

A compound of the formula (1) wherein $R^2$, $R^3$, $R^4$, and $R^5$ are same or different and are independently a halogen atom or a hydrogen atom;

A compound of the formula (1) wherein $R^2$, $R^3$, $R^4$, and $R^5$ are same or different and are independently a fluorine atom, a chlorine atom, a bromine atom, an iodine atom, or a hydrogen atom;

A compound of the formula (1) wherein $R^2$, $R^3$, $R^4$, and $R^5$ are same or different and are independently a fluorine atom, a chlorine atom, a bromine atom, a methyl group, a trifluoromethoxy group, a pentafluoroethyl group, a methoxy group, a cyano group, a nitro group, or a hydrogen atom;

A compound of the formula (1) wherein $R^2$, $R^4$, and $R^5$ are same or different and are independently a halogen atom or a hydrogen atom, and $R^3$ is a C1-C6 chain hydrocarbon group optionally having one or more halogen atoms, a C1-C6 alkoxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C2-C6 alkylcarbonyl group optionally having one or more halogen atoms, a C2-C6 alkoxycarbonyl group optionally having one or more halogen atoms, a C1-C6 alkylamino group optionally having one or more halogen atoms, C2-C8 dialkylamino group optionally having one or more halogen atoms, an aldehyde group, a cyano group, a nitro group, a halogen atom, or a hydrogen atom;

A compound of the formula (1) wherein $R^2$, $R^4$, and $R^5$ are same or different and are independently a halogen atom or a hydrogen atom, and $R^3$ is a C1-C6 chain hydrocarbon group optionally having one or more halogen atoms, or a halogen atom;

A compound of the formula (1) wherein $R^2$, $R^4$, and $R^5$ are same or different and are independently a halogen atom or a hydrogen atom, and $R^3$ is a methyl group, a trifluoromethyl group, a trifluoromethoxy group, a fluorine atom, a chlorine atom, a bromine atom, an iodine atom, or a hydrogen atom;

A compound of the formula (1) wherein $R^2$, $R^4$, and $R^5$ are same or different and are independently a halogen atom or a hydrogen atom, and $R^3$ is a trifluoromethyl group;

A compound of the formula (1) wherein $R^2$, $R^4$, and $R^5$ are a hydrogen atom, and $R^3$ is a C1-C6 chain hydrocarbon group optionally having one or more halogen atoms;

A compound of the formula (1) wherein $R^2$, $R^4$, and $R^5$ are a hydrogen atom, and $R^3$ is a methyl group, a trifluoromethyl group, a trifluoromethoxy group, a chlorine atom, a bromine atom, an iodine atom, or a hydrogen atom;

A compound of the formula (1) wherein $R^2$, $R^4$, and $R^5$ are a hydrogen atom, and $R^3$ is a methyl group, a trifluoromethyl group, a trifluoromethoxy group, a fluorine atom, a chlorine atom, a bromine atom, or an iodine atom;

A compound of the formula (1) wherein $R^2$, $R^4$, and $R^5$ are a hydrogen atom, and $R^3$ is a trifluoromethyl group;

A compound of the formula (1) wherein $R^2$, $R^3$, $R^4$, and $R^5$ are a hydrogen atom;

A compound of the formula (1) wherein $R^1$ is an ethyl group, $R^2$, $R^4$, and $R^5$ are same or different and are independently a halogen atom or a hydrogen atom, and $R^3$ is a methyl group, a trifluoromethyl group, a trifluoromethoxy group, a chlorine atom, a bromine atom, an iodine atom, or a hydrogen atom;

A compound of the formula (1) wherein $R^1$ is an ethyl group, $R^2$, $R^4$, and $R^5$ are same or different and are independently a halogen atom or a hydrogen atom, and $R^3$ is a trifluoromethyl group;

A compound of the formula (1) wherein $R^1$ is an ethyl group, $R^2$, $R^4$, and $R^5$ are a hydrogen atom, and $R^3$ is a methyl group, a trifluoromethyl group, a trifluoromethoxy group, a chlorine atom, a bromine atom, an iodine atom, or a hydrogen atom;

A compound of the formula (1) wherein $R^1$ is an ethyl group, $R^2$, $R^4$, and $R^5$ are a hydrogen atom, and $R^3$ is a trifluoromethyl group;

A compound of the formula (1) wherein $R^6$ and $R^7$ are same or different and are independently a C1-C6 chain hydrocarbon group optionally having one or more halogen atoms, —$OR^{11}$, —$S(O)_mR^{11}$, —$NR^{11}R^{12}$, —$CO_2R^{11}$, —$C(O)R^{11}$, a cyano group, a nitro group, a halogen atom, or a hydrogen atom, and $R^{11}$ and $R^{12}$ are same or different and are independently a C1-C6 chain hydrocarbon group optionally having one or more halogen atoms or a hydrogen atom;

A compound of the formula (1) wherein $R^6$ and $R^7$ are same or different and are independently a C1-C6 chain hydrocarbon group optionally having one or more halogen atoms, —$OR^{11}$, —$S(O)_mR^{11}$, a halogen atom, or a hydrogen atom, and $R^{11}$ is a C1-C6 chain hydrocarbon group optionally having one or more halogen atoms, or a hydrogen atom;

A compound of the formula (1) wherein $R^6$ and $R^7$ are same or different and are independently a C1-C6 chain hydrocarbon group optionally having one or more halogen atoms, a phenyl group optionally having one or more halogen atoms, an aldehyde group, a cyano group, a halogen atom, or a hydrogen atom;

A compound of the formula (1) wherein $R^6$ and $R^7$ are same or different and are independently a C1-C6 chain hydrocarbon group optionally having one or more halogen atoms, an aldehyde group, a cyano group, a halogen atom, or a hydrogen atom;

A compound of the formula (1) wherein $R^6$ and $R^7$ are same or different and are independently a trifluoromethyl group, a difluoromethyl group, a fluoromethyl group, a pentafluoroethyl group, a heptafluoroisopropyl group, a trifluoromethoxy group, a trifluoromethylsulfanyl group, a trifluoromethylsulfinyl group, a trifluoromethylsulfonyl group, a chlorine atom, a bromine atom, an iodine atom, or a hydrogen atom;

A compound of the formula (1) wherein $R^6$ is a C1-C6 chain hydrocarbon group optionally having one or more halogen atoms, —$OR^{11}$, —$S(O)_mR^{11}$, or a halogen atom, and $R^7$ is a hydrogen atom;

A compound of the formula (1) wherein $R^6$ is a C1-C6 chain hydrocarbon group optionally having one or more halogen atoms, and $R^7$ is a hydrogen atom;

A compound of the formula (1) wherein $R^6$ is a C1-C6 chain hydrocarbon group having one or more halogen atoms, and $R^7$ is a hydrogen atom;

A compound of the formula (1) wherein $R^6$ is a C1-C6 chain hydrocarbon group having one or more a fluorine atoms, and $R^7$ is a hydrogen atom;

A compound of the formula (1) wherein $R^6$ is –$OR^{11}$, and $R^7$ is a hydrogen atom;

A compound of the formula (1) wherein $R^6$ is —$S(O)_mR^{11}$, and $R^7$ is a hydrogen atom;

A compound of the formula (1) wherein $R^6$ is a C1-C6 chain hydrocarbon group having one or more halogen atoms, —$OR^{11}$, —$S(O)_mR^{11}$, or a halogen atom, and $R^7$ is a hydrogen atom;

A compound of the formula (1) wherein $R^6$ is a trifluoromethyl group, a difluoromethyl group, a fluoromethyl group, a pentafluoroethyl group, a heptafluoroisopropyl group, a trifluoromethoxy group, a trifluoromethylsulfanyl group, a trifluoromethylsulfinyl group, a trifluoromethylsulfonyl group, a bromine atom, or an iodine atom, and $R^7$ is a hydrogen atom;

A compound of the formula (1) wherein $R^6$ is a hydrogen atom, and $R^7$ is a trifluoromethyl group, a difluoromethyl group, a fluoromethyl group, a pentafluoroethyl group, a heptafluoroisopropyl group, a trifluoromethoxy group, a trifluoromethylsulfanyl group, a trifluoromethylsulfinyl group, a trifluoromethylsulfonyl group, a bromine atom, or an iodine atom;

A compound of the formula (1) wherein $R^6$ is a bromine atom, and $R^7$ is a hydrogen atom;

A compound of the formula (1) wherein $R^6$ is an iodine atom, and $R^7$ is a hydrogen atom;

A compound of the formula (1) wherein $R^6$ is a trifluoromethyl group, and $R^7$ is a hydrogen atom;

A compound of the formula (1) wherein $R^6$ is a pentafluoroethyl group, and $R^7$ is a hydrogen atom;

A compound of the formula (1) wherein $R^6$ is a trifluoromethoxy group, and $R^7$ is a hydrogen atom;

A compound of the formula (1) wherein $R^6$ is a trifluoromethylsulfanyl group, and $R^7$ is a hydrogen atom;

A compound of the formula (1) wherein $R^6$ is a trifluoromethylsulfinyl group, and $R^7$ is a hydrogen atom;

A compound of the formula (1) wherein $R^6$ is a trifluoromethylsulfonyl group, and $R^7$ is a hydrogen atom;

A compound of the formula (1) wherein $R^6$ is a heptafluoroisopropyl group, and $R^7$ is a hydrogen atom;

A compound of the formula (1) wherein n is 0;
A compound of the formula (1) wherein n is 1;
A compound of the formula (1) wherein n is 2;
A compound of the formula (1) wherein m is 0;
A compound of the formula (1) wherein m is 1;
A compound of the formula (1) wherein m is 2;

A compound of the formula (1) wherein $A^1$ is —$NR^8$—, $R^8$ is a methyl group, an ethyl group, a methoxymethyl group, or an ethoxymethyl group, $A^2$ is =$CR^9$—, $R^9$ is a hydrogen atom, $A^3$ is a nitrogen atom or =$CR^{10}$—, and $R^{10}$ is a halogen atom or a hydrogen atom;

A compound of the formula (1) wherein $A^1$ is —$NR^8$—, $R^8$ is a methyl group, an ethyl group, a methoxymethyl group, or an ethoxymethyl group, $A^2$ is =$CR^9$—, $R^9$ is a hydrogen atom, $A^3$ is a nitrogen atom or =$CR^{10}$—, $R^{10}$ is a halogen atom or a hydrogen atom, and $R^1$ is a methyl group, an ethyl group, a propyl group, an isopropyl group, a butyl group, a sec-butyl group, an isobutyl group, a tert-butyl group, a cyclopropyl group, a trifluoromethyl group, or a 2,2,2-trifluoroethyl group;

A compound of the formula (1) wherein $A^1$ is —$NR^8$—, $R^8$ is a methyl group, an ethyl group, a methoxymethyl group, or an ethoxymethyl group, $A^2$ is =$CR^9$—, $R^9$ is a hydrogen atom, $A^3$ is a nitrogen atom or =$CR^{10}$—, $R^{10}$ is a halogen atom or a hydrogen atom, $R^1$ is a methyl group, an ethyl group, a propyl group, an isopropyl group, a butyl group, a sec-butyl group, an isobutyl group, a tert-butyl group, a cyclopropyl group, a trifluoromethyl group, or a 2,2,2-trifluoroethyl group, and $R^2$, $R^3$, $R^4$, and $R^5$ are a hydrogen atom;

A compound of the formula (1) wherein $A^1$ is —$NR^8$—, $R^8$ is a methyl group, an ethyl group, a methoxymethyl group, or an ethoxymethyl group, and $R^1$ is a methyl group, an ethyl group, a propyl group, an isopropyl group, a butyl group, a sec-butyl group, an isobutyl group, a tert-butyl group, a cyclopropyl group, a trifluoromethyl group, or a 2,2,2-trifluoroethyl group;

A compound of the formula (1) wherein $A^1$ is —$NR^8$—, $R^8$ is a methyl group, an ethyl group, a methoxymethyl group or an ethoxymethyl group, $R^1$ is a methyl group, an ethyl group, a propyl group, an isopropyl group, a butyl group, a sec-butyl group, an isobutyl group, a tert-butyl group, a cyclopropyl group, a trifluoromethyl group, or a 2,2,2-trifluoroethyl group, and $R^2$, $R^3$, $R^4$, and $R^5$ are a hydrogen atom;

A compound of the formula (1) wherein $A^1$ is —$NR^8$—, $R^8$ is a methyl group, an ethyl group, a methoxymethyl group, or an ethoxymethyl group, $R^1$ is a methyl group, an ethyl group, a propyl group, an isopropyl group, a butyl group, a sec-butyl group, an isobutyl group, a tert-butyl group, a cyclopropyl group, a trifluoromethyl group, or a 2,2,2-trifluoroethyl group, $R^2$, $R^3$, $R^4$, and $R^5$ are a hydrogen atom, $R^6$ is a trifluoromethyl group, a difluoromethyl group, a fluoromethyl group, a pentafluoroethyl group, a heptafluoroisopropyl group, a trifluoromethoxy group, a trifluoromethylsulfanyl group, a trifluoromethylsulfinyl group, a trifluoromethylsulfonyl group, a bromine atom, or an iodine atom, and $R^7$ is a hydrogen atom;

A compound of the formula (1) wherein $A^1$ is $-NR^8-$, $R^8$ is a methyl group, an ethyl group, a methoxymethyl group, or an ethoxymethyl group, $R^1$ is a methyl group, an ethyl group, a propyl group, an isopropyl group, a butyl group, a sec-butyl group, an isobutyl group, a tert-butyl group, a cyclopropyl group, a trifluoromethyl group, or a 2,2,2-trifluoroethyl group, $R^2$, $R^3$, $R^4$, and $R^5$ are a hydrogen atom, and $R^7$ is a trifluoromethyl group, a difluoromethyl group, a fluoromethyl group, a pentafluoroethyl group, a heptafluoroisopropyl group, a trifluoromethoxy group, a trifluoromethylsulfanyl group, a trifluoromethylsulfinyl group, a trifluoromethylsulfonyl group, a bromine atom, or an iodine atom;

A compound of the formula (1) wherein $A^1$ is $-NR^8-$, $R^8$ is a methyl group, an ethyl group, a methoxymethyl group, or an ethoxymethyl group, $A^2$ is $=CR^9-$, $R^9$ is a hydrogen atom, $A^3$ is a nitrogen atom or $=CR^{10}-$, $R^{10}$ is a halogen atom or a hydrogen atom, $R^1$ is a methyl group, an ethyl group, a propyl group, an isopropyl group, a butyl group, a sec-butyl group, an isobutyl group, a tert-butyl group, a cyclopropyl group, a trifluoromethyl group, or a 2,2,2-trifluoroethyl group, $R^2$, $R^3$, $R^4$, and $R^5$ are a hydrogen atom, $R^6$ is a trifluoromethyl group, a difluoromethyl group, a fluoromethyl group, a pentafluoroethyl group, a heptafluoroisopropyl group, a trifluoromethoxy group, a trifluoromethylsulfanyl group, a trifluoromethylsulfinyl group, a trifluoromethylsulfonyl group, a bromine atom, or an iodine atom, and $R^7$ is a hydrogen atom;

A compound of the formula (1) wherein $A^1$ is a sulfur atom, $A^2$ is $=CR^9-$, $R^9$ is a hydrogen atom, $A^3$ is a nitrogen atom or $=CR^{10}-$, $R^{10}$ is a halogen atom or a hydrogen atom, $R^1$ is a methyl group, an ethyl group, a propyl group, an isopropyl group, a butyl group, a sec-butyl group, an isobutyl group, a tert-butyl group, a cyclopropyl group, a trifluoromethyl group, or a 2,2,2-trifluoroethyl group, $R^2$, $R^3$, $R^4$, and $R^5$ are a hydrogen atom, $R^6$ is a trifluoromethyl group, a difluoromethyl group, a fluoromethyl group, a pentafluoroethyl group, a heptafluoroisopropyl group, a trifluoromethoxy group, a trifluoromethylsulfanyl group, a trifluoromethylsulfinyl group, a trifluoromethylsulfonyl group, a bromine atom, or an iodine atom, and $R^7$ is a hydrogen atom;

A compound of the formula (1) wherein $A^1$ is $-NR^8-$, $R^8$ is a methyl group, an ethyl group, a methoxymethyl group, or an ethoxymethyl group, $A^2$ is $=CR^9-$, $R^9$ is a hydrogen atom, $A^3$ is a nitrogen atom or $=CR^{10}-$, $R^{10}$ is a halogen atom or a hydrogen atom, $R^1$ is a methyl group, an ethyl group, a propyl group, an isopropyl group, a butyl group, a sec-butyl group, an isobutyl group, a tert-butyl group, a cyclopropyl group, a trifluoromethyl group, or a 2,2,2-trifluoroethyl group, $R^2$, $R^3$, $R^4$, and $R^5$ are a hydrogen atom, $R^6$ is a trifluoromethyl group, a difluoromethyl group, a fluoromethyl group, a pentafluoroethyl group, a heptafluoroisopropyl group, a trifluoromethoxy group, a trifluoromethylsulfanyl group, a trifluoromethylsulfinyl group, a trifluoromethylsulfonyl group, a bromine atom, or an iodine atom, $R^7$ is a hydrogen atom, and n is 0;

A compound of the formula (1) wherein $A^1$ is $-NR^8-$, $R^8$ is a methyl group, an ethyl group, a methoxymethyl group, or an ethoxymethyl group, $A^2$ is $=CR^9-$, $R^9$ is a hydrogen atom, $A^3$ is a nitrogen atom or $=CR^{10}-$, $R^{10}$ is a halogen atom or a hydrogen atom, $R^1$ is a methyl group, an ethyl group, a propyl group, an isopropyl group, a butyl group, a sec-butyl group, an isobutyl group, a tert-butyl group, a cyclopropyl group, a trifluoromethyl group, or a 2,2,2-trifluoroethyl group, $R^2$, $R^3$, $R^4$, and $R^5$ are a hydrogen atom, $R^6$ is a trifluoromethyl group, a difluoromethyl group, a fluoromethyl group, a pentafluoroethyl group, a heptafluoroisopropyl group, a trifluoromethoxy group, a trifluoromethylsulfanyl group, a trifluoromethylsulfinyl group, a trifluoromethylsulfonyl group, a bromine atom, or an iodine atom, $R^7$ is a hydrogen atom, and n is 1;

A compound of the formula (1) wherein $A^1$ is $-NR^8-$, $R^8$ is a methyl group, an ethyl group, a methoxymethyl group, or an ethoxymethyl group, $A^2$ is $=CR^9-$, $R^9$ is a hydrogen atom, $A^3$ is a nitrogen atom or $=CR^{10}-$, $R^{10}$ is a halogen atom or a hydrogen atom, $R^1$ is a methyl group, an ethyl group, a propyl group, an isopropyl group, a butyl group, a sec-butyl group, an isobutyl group, a tert-butyl group, a cyclopropyl group, a trifluoromethyl group, or a 2,2,2-trifluoroethyl group, $R^2$, $R^3$, $R^4$, and $R^5$ are a hydrogen atom, $R^6$ is a trifluoromethyl group, a difluoromethyl group, a fluoromethyl group, a pentafluoroethyl group, a heptafluoroisopropyl group, a trifluoromethoxy group, a trifluoromethylsulfanyl group, a trifluoromethylsulfinyl group, a trifluoromethylsulfonyl group, a bromine atom, or an iodine atom, $R^7$ is a hydrogen atom, and n is 2;

A compound of the formula (1) wherein $A^1$ is $-NR^8-$, an oxygen atom, or a sulfur atom, $A^2$ is a nitrogen atom or $=CR^9-$, $A^3$ is a nitrogen atom or $=CR^{10}-$, $R^1$ is a C1-C6 chain hydrocarbon group optionally having one or more atoms or groups selected from Group X, $R^2$, $R^3$, $R^4$, and $R^5$ are same or different and are independently a halogen atom or a hydrogen atom, $R^6$ and $R^7$ are same or different and are independently a C1-C6 chain hydrocarbon group optionally having one or more halogen atoms, a phenyl group optionally having one or more halogen atoms, an aldehyde group, a cyano group, a halogen atom, or a hydrogen atom, $R^8$ is a C1-C6 chain hydrocarbon group having one C1-C6 alkoxy group optionally having one or more halogen atoms, a C1-C6 chain hydrocarbon group optionally having one or more halogen atoms, or a cyclopropyl group, $R^9$ and $R^{10}$ are same or different and are independently a halogen atom or a hydrogen atom, and $R^{11}$ is a C1-C6 chain hydrocarbon group optionally having one or more halogen atoms;

A compound of the formula (1) wherein $A^1$ is $-NR^8-$;

A compound of the formula (1) wherein $A^1$ is $-NR^8-$, an oxygen atom, or a sulfur atom, and $R^8$ is a C1-C6 chain hydrocarbon group having one C1-C6 alkoxy group optionally having one or more halogen atoms, a C1-C6 chain hydrocarbon group optionally having one or more halogen atoms, a C1-C6 chain hydrocarbon group having one C2-C6 alkoxycarbonyl group, $-CO_2R^{11}$, a cyclopropyl group, or a hydrogen atom;

A compound of the formula (1) wherein $A^1$ is $-NR^8-$, an oxygen atom, or a sulfur atom, and $R^8$ is a C1-C6 chain hydrocarbon group optionally having one or more halogen atoms;

A compound of the formula (1) wherein $A^1$ is $-NR^8-$, an oxygen atom, or a sulfur atom, and $R^8$ is a C1-C6 chain hydrocarbon group;

A compound of the formula (1) wherein $A^1$ is $-NR^8-$, an oxygen atom, or a sulfur atom, and $R^8$ is a C1-C6 alkyl group;

A compound of the formula (1) wherein $A^1$ is $-NR^8-$, an oxygen atom, or a sulfur atom, and $R^8$ is a C1-C3 alkyl group;

A compound of the formula (1) wherein $A^1$ is $-NR^8-$, an oxygen atom, or a sulfur atom, and $R^8$ is a hydrogen atom;

A compound of the formula (1) wherein $A^1$ is $-NR^8-$, and $R^8$ is a C1-C6 chain hydrocarbon group having one C1-C6 alkoxy group optionally having one or more halogen atoms, a C1-C6 chain hydrocarbon group optionally having one or more halogen atoms, a cyclopropyl group, or a hydrogen atom;

A compound of the formula (1) wherein $A^1$ is $-NR^8-$, and $R^8$ is a C1-C6 chain hydrocarbon group having one C1-C6 alkoxy group optionally having one or more halogen atoms, or a C1-C6 chain hydrocarbon group optionally having one or more halogen atoms;

A compound of the formula (1) wherein $A^1$ is —$NR^8$—, and $R^8$ is a C1-C6 chain hydrocarbon group optionally having one or more halogen atoms;

A compound of the formula (1) wherein $A^1$ is —$NR^8$—, and $R^8$ is a C1-C6 chain hydrocarbon group;

A compound of the formula (1) wherein $A^1$ is —$NR^8$—, and $R^8$ is a C1-C6 alkyl group;

A compound of the formula (1) wherein $A^1$ is —$NR^8$—, and $R^8$ is a C1-C3 alkyl group;

A compound of the formula (1) wherein $A^1$ is —$NR^8$—, and $R^8$ is a methyl group, an ethyl group, a propyl group, or an isopropyl group;

A compound of the formula (1) wherein $A^1$ is —$NR^8$—, and $R^8$ is a methyl group, an ethyl group, a propyl group, an isopropyl group, a methoxymethyl group, an ethoxymethyl group, a cyclopropyl group, or a hydrogen atom;

A compound of the formula (1) wherein $A^1$ is —$NR^8$—, and $R^8$ is an ethyl group;

A compound of the formula (1) wherein $A^1$ is —$NR^8$—, and $R^8$ is a propyl group;

A compound of the formula (1) wherein $A^1$ is —$NR^8$—, and $R^8$ is an isopropyl group;

A compound of the formula (1) wherein $A^1$ is —$NR^8$—, and $R^8$ is a methyl group or a hydrogen atom;

A compound of the formula (1) wherein $A^1$ is —$NR^8$—, and $R^8$ is a hydrogen atom;

A compound of the formula (1) wherein $A^1$ is —$NR^8$—, and $R^8$ is a methoxymethyl group, an ethoxymethyl group, or a hydrogen atom;

A compound of the formula (1) wherein $A^1$ is —$NR^8$— or a sulfur atom;

A compound of the formula (1) wherein $A^1$ is —$NR^8$— or a sulfur atom, and $R^8$ is a methyl group, an ethyl group, a propyl group, or an isopropyl group;

A compound of the formula (1) wherein $A^1$ is —$NR^8$— or a sulfur atom, and $R^8$ is a methoxymethyl group, an ethoxymethyl group, or a hydrogen atom;

A compound of the formula (1) wherein $A^2$ is =$CR^9$—, and $A^3$ is =$CR^{10}$—;

A compound of the formula (1) wherein $A^2$ is =$CR^9$—, $A^3$ is =$CR^{10}$—, and $R^9$ and $R^{10}$ are a hydrogen atom;

A compound of the formula (1) wherein $A^2$ is a nitrogen atom, and $A^3$ is =$CR^{10}$—;

A compound of the formula (1) wherein $A^2$ is =$CR^9$—, and $A^3$ is a nitrogen atom;

A compound of the formula (1) wherein $A^2$ is =$CR^9$—, $R^9$ is a hydrogen atom, and $A^3$ is a nitrogen atom;

A compound of the formula (1) wherein $A^2$ is a nitrogen atom, and $A^3$ is a nitrogen atom;

A compound of the formula (1) wherein $A^1$ is —$NR^8$—, $A^2$ is =$CR^9$—, and $A^3$ is =$CR^{10}$—;

A compound of the formula (1) wherein $A^1$ is —$NR^8$—, $A^2$ is a nitrogen atom, and $A^3$ is =$CR^{10}$—;

A compound of the formula (1) wherein $A^1$ is —$NR^8$—, $A^2$ is =$CR^9$—, and $A^3$ is a nitrogen atom;

A compound of the formula (1) wherein $A^1$ is —$NR^8$—, $A^2$ is a nitrogen atom, and $A^3$ is a nitrogen atom;

A compound of the formula (1) wherein $A^1$ is an oxygen atom, $A^2$ is =$CR^9$—, and $A^3$ is =$CR^{10}$—;

A compound of the formula (1) wherein $A^1$ is an oxygen atom, $A^2$ is a nitrogen atom, and $A^3$ is =$CR^{10}$—;

A compound of the formula (1) wherein $A^1$ is an oxygen atom, $A^2$ is =$CR^9$—, and $A^3$ is a nitrogen atom; A compound of the formula (1) wherein $A^1$ is an oxygen atom, $A^2$ is a nitrogen atom, and $A^3$ is a nitrogen atom;

A compound of the formula (1) wherein $A^1$ is a sulfur atom, $A^2$ is =$CR^9$—, and $A^3$ is =$CR^{10}$—;

A compound of the formula (1) wherein $A^1$ is a sulfur atom, $A^2$ is a nitrogen atom, and $A^3$ is =$CR^{10}$—;

A compound of the formula (1) wherein $A^1$ is a sulfur atom, $A^2$ is =$CR^9$—, and $A^3$ is a nitrogen atom;

A compound of the formula (1) wherein $A^1$ is a sulfur atom, $A^2$ is a nitrogen atom, and $A^3$ is a nitrogen atom;

A compound of the formula (1) wherein $A^1$ is —$NR^8$— or a sulfur atom, $R^8$ is a methyl group, an ethyl group, a propyl group, an isopropyl group, a methoxymethyl group, an ethoxymethyl group, a cyclopropyl group, or a hydrogen atom, $A^2$ is =$CR^9$—, $R^9$ is a hydrogen atom, and $A^3$ is a nitrogen atom;

A compound of the formula (1) wherein $A^1$ is —$NR^8$— or a sulfur atom, $R^8$ is a methyl group, $A^2$ is =$CR^9$—, $R^9$ is a hydrogen atom, and $A^3$ is a nitrogen atom;

A compound of the formula (1) wherein $A^1$ is —$NR^8$—, $R^8$ is a methyl group, an ethyl group, a propyl group, an isopropyl group, a methoxymethyl group, an ethoxymethyl group, a cyclopropyl group, or a hydrogen atom, $A^2$ is =$CR^9$—, $R^9$ is a hydrogen atom, and $A^3$ is a nitrogen atom;

A compound of the formula (1) wherein $A^1$ is —$NR^8$—, $R^8$ is a methyl group, $A^2$ is =$CR^9$—, $R^9$ is a hydrogen atom, and $A^3$ is a nitrogen atom;

A compound of the formula (1) wherein $A^1$ is —$NR^8$—, $R^8$ is a methyl group, $A^2$ is =$CR^9$—, $A^3$ is =$CR^{10}$—, and $R^9$ and $R^{10}$ are a hydrogen atom;

A compound of the formula (1) wherein $A^1$ is an oxygen atom, $A^2$ is =$CR^9$—, $A^3$ is =$CR^{10}$—, and $R^9$ and $R^{10}$ are a hydrogen atom;

A compound of the formula (1) wherein $A^1$ is a sulfur atom, $A^2$ is =$CR^9$—, $A^3$ is =$CR^{10}$—, and $R^9$ and $R^{10}$ are a hydrogen atom;

A compound of the formula (1) wherein $R^1$ is a C1-C6 chain hydrocarbon group optionally having one or more fluorine atoms;

A compound of the formula (1) wherein $R^1$ is a C1-C6 chain hydrocarbon group;

A compound of the formula (1) wherein $R^1$ is a C1-C6 alkyl group;

A compound of the formula (1) wherein $R^1$ is a C1-C3 alkyl group;

A compound of the formula (1) wherein $R^1$ is a C3-C6 alicyclic hydrocarbon group;

A compound of the formula (1) wherein $R^1$ is a cyclopropyl group, a cyclobutyl group, or a cyclopentyl group;

A compound of the formula (1) wherein $R^1$ is a methyl group;

A compound of the formula (1) wherein $R^1$ is a propyl group;

A compound of the formula (1) wherein $R^1$ is an isopropyl group;

A compound of the formula (1) wherein $R^1$ is a trifluoromethyl group;

A compound of the formula (1) wherein $R^1$ is a 2,2,2-trifluoroethyl group;

A compound of the formula (1) wherein $R^2$, $R^3$, $R^4$, and $R^5$ are same or different and are independently a phenyl group optionally having one or more atoms or groups selected from Group Z, a 5-membered heterocyclic group optionally having one or more atoms or groups selected from Group Z, a 6-membered heterocyclic group optionally having one or more atoms or groups selected from Group Z, or a hydrogen atom;

A compound of the formula (1) wherein $R^2$, $R^3$, $R^4$, and $R^5$ are same or different and are independently a phenyl group optionally having one or more halogen atoms or C1-C3 alkyl groups optionally having one or more halogen atoms, a 5-membered heterocyclic group optionally having one or more halogen atoms or C1-C3 alkyl groups optionally having one or more halogen atoms, a 6-membered heterocyclic group optionally having one or more halogen atoms or C1-C3 alkyl groups optionally having one or more halogen atoms, or a hydrogen atom;

A compound of the formula (1) wherein $R^2$, $R^3$, $R^4$, and $R^5$ are same or different and are independently a 2-pyridyl group, a 2-pyrimidyl group, a 3-chloro-2-pyridyl group, a 3-chloro-5-trifluoromethyl-2-pyridyl group, or a hydrogen atom;

A compound of the formula (1) wherein $R^2$, $R^3$, $R^4$, and $R^5$ are same or different and are independently —$SF_5$ or a hydrogen atom;

A compound of the formula (1) wherein $R^2$, $R^3$, $R^4$, and $R^5$ are same or different and are independently a C1-C6 chain hydrocarbon group optionally having one or more halogen atoms or a hydrogen atom;

A compound of the formula (1) wherein $R^2$, $R^3$, $R^4$, and $R^5$ are same or different and are independently a C1-C3 alkyl group optionally having one or more halogen atoms or a hydrogen atom;

A compound of the formula (1) wherein $R^2$, $R^3$, $R^4$, and $R^5$ are same or different and are independently —$OR^{11}$ or a hydrogen atom;

A compound of the formula (1) wherein $R^2$, $R^3$, $R^4$, and $R^5$ are same or different and are independently —$NR^{11}R^{12}$ or a hydrogen atom;

A compound of the formula (1) wherein $R^2$, $R^4$, and $R^5$ are same or different and are independently a halogen atom or a hydrogen atom, $R^3$ is a phenyl group optionally having one or more atoms or groups selected from Group Z, a 5-membered heterocyclic group optionally having one or more atoms or groups selected from Group Z, or a 6-membered heterocyclic group optionally having one or more atoms or groups selected from Group Z;

A compound of the formula (1) wherein $R^2$, $R^4$, and $R^5$ are same or different and are independently a halogen atom or a hydrogen atom, $R^3$ is a phenyl group optionally having one or more halogen atoms or C1-C3 alkyl groups optionally having one or more halogen atoms, a 5-membered heterocyclic group optionally having one or more halogen atoms or C1-C3 alkyl groups optionally having one or more halogen atoms, or a 6-membered heterocyclic group optionally having one or more halogen atoms or C1-C3 alkyl groups optionally having one or more halogen atoms;

A compound of the formula (1) wherein $R^2$, $R^4$, and $R^5$ are same or different and are independently a halogen atom or a hydrogen atom, and $R^3$ is a methyl group;

A compound of the formula (1) wherein $R^2$, $R^4$, and $R^5$ are same or different and are independently a halogen atom or a hydrogen atom, and $R^3$ is a trifluoromethoxy group;

A compound of the formula (1) wherein $R^2$, $R^4$, and $R^5$ are same or different and are independently a halogen atom or a hydrogen atom, and $R^3$ is a fluorine atom;

A compound of the formula (1) wherein $R^2$, $R^4$, and $R^5$ are same or different and are independently a halogen atom or a hydrogen atom, and $R^3$ is a chlorine atom;

A compound of the formula (1) wherein $R^2$, $R^4$, and $R^5$ are same or different and are independently a halogen atom or a hydrogen atom, and $R^3$ is a bromine atom;

A compound of the formula (1) wherein $R^2$, $R^4$, and $R^5$ are same or different and are independently a halogen atom or a hydrogen atom, and $R^3$ is an iodine atom;

A compound of the formula (1) wherein $R^2$, $R^4$, and $R^5$ are a hydrogen atom, and $R^3$ is a C1-C6 alkyl group;

A compound of the formula (1) wherein $R^2$, $R^4$, and $R^5$ are a hydrogen atom, and $R^3$ is a C1-C6 alkyl group optionally having one or more fluorine atoms;

A compound of the formula (1) wherein $R^2$, $R^4$, and $R^5$ are a hydrogen atom, and $R^3$ is a C1-C3 alkyl group;

A compound of the formula (1) wherein $R^2$, $R^4$, and $R^5$ are a hydrogen atom, and $R^3$ is a C1-C3 alkyl group optionally having one or more fluorine atoms;

A compound of the formula (1) wherein $R^2$, $R^4$, and $R^5$ are a hydrogen atom, and $R^3$ is a 5-membered heterocyclic group optionally having one or more atoms or groups selected from Z group, or a 6-membered heterocyclic group optionally having one or more atoms or groups selected from Group Z;

A compound of the formula (1) wherein $R^2$, $R^4$, and $R^5$ are a hydrogen atom, and $R^3$ is a 6-membered heterocyclic group optionally having one or more atoms or groups selected from Group Z;

A compound of the formula (1) wherein $R^2$, $R^4$, and $R^5$ are a hydrogen atom, and $R^3$ is a methyl group;

A compound of the formula (1) wherein $R^2$, $R^4$, and $R^5$ are a hydrogen atom, and $R^3$ is a trifluoromethoxy group;

A compound of the formula (1) wherein $R^2$, $R^4$, and $R^5$ are a hydrogen atom, and $R^3$ is a fluorine atom;

A compound of the formula (1) wherein $R^2$, $R^4$, and $R^5$ are a hydrogen atom, and $R^3$ is a chlorine atom;

A compound of the formula (1) wherein $R^2$, $R^4$, and $R^5$ are a hydrogen atom, and $R^3$ is a bromine atom;

A compound of the formula (1) wherein $R^2$, $R^4$, and $R^5$ are a hydrogen atom, and $R^3$ is an iodine atom;

A compound of the formula (1) wherein $R^2$, $R^4$, and $R^5$ are a hydrogen atom, and $R^3$ is a phenyl group optionally having one or more halogen atoms or C1-C3 alkyl groups optionally having one or more halogen atoms, a 5-membered heterocyclic group optionally having one or more halogen atoms or C1-C3 alkyl groups optionally having one or more halogen atoms, or a 6-membered heterocyclic group optionally having one or more halogen atoms or C1-C3 alkyl groups optionally having one or more halogen atoms;

A compound of the formula (1) wherein $R^2$, $R^4$, and $R^5$ are a hydrogen atom, and $R^3$ is a 2-pyridyl group, a 2-pyrimidyl group, a 3-chloro-2-pyridyl group, or a 3-chloro-5-trifluoromethyl-2-pyridyl group;

A compound of the formula (1) wherein $R^2$, $R^4$, and $R^5$ are a hydrogen atom, and $R^3$ is a 2-pyridyl group;

A compound of the formula (1) wherein $R^2$, $R^4$, and $R^5$ are a hydrogen atom, and $R^3$ is a 2-pyrimidyl group;

A compound of the formula (1) wherein $R^2$, $R^4$, and $R^5$ are a hydrogen atom, and $R^3$ is —$SF_5$;

A compound of the formula (1) wherein $R^2$, $R^4$, and $R^5$ are a hydrogen atom, and $R^3$ is a 2-pyridyl group, a 2-pyrimidyl group, a 3-chloro-2-pyridyl group, a 3-chloro-5-trifluoromethyl-2-pyridyl group, a methyl group, an ethyl group, a propyl group, an isopropyl group, a trifluoromethyl group, a pentafluoroethyl group, a heptafluoropropyl group, a heptafluoroisopropyl group, a fluorine atom, a chlorine atom, or a bromine atom;

A compound of the formula (1) wherein $R^1$ is an ethyl group, $R^2$, $R^4$, and $R^5$ are a hydrogen atom, and $R^3$ is a methyl group;

A compound of the formula (1) wherein $R^1$ is an ethyl group, $R^2$, $R^4$, and $R^5$ are a hydrogen atom, and $R^3$ is a trifluoromethoxy group;

A compound of the formula (1) wherein $R^1$ is an ethyl group, $R^2$, $R^4$, and $R^5$ are a hydrogen atom, and $R^3$ is a chlorine atom;

A compound of the formula (1) wherein $R^1$ is an ethyl group, $R^2$, $R^4$, and $R^5$ are a hydrogen atom, and $R^3$ is a bromine atom;

A compound of the formula (1) wherein $R^1$ is an ethyl group, $R^2$, $R^4$, and $R^5$ are a hydrogen atom, and $R^3$ is an iodine atom;

A compound of the formula (1) wherein $R^6$ is a C1-C3 alkyl group having one or more fluorine atoms, and $R^7$ is a hydrogen atom;

A compound of the formula (1) wherein $R^6$ is a C1-C3 alkoxy group having one or more fluorine atoms, and $R^7$ is a hydrogen atom;

A compound of the formula (1) wherein $R^6$ is a C1-C3 alkylsulfanyl group having one or more fluorine atoms, a C1-C3 alkylsulfinyl group having one or more fluorine atoms or a C1-C3 alkylsulfonyl group having one or more fluorine atoms, and $R^7$ is a hydrogen atom;

A compound of the formula (1) wherein $R^6$ is a halogen atom, and $R^7$ is a hydrogen atom;

A compound of the formula (1) wherein $R^6$ is a C1-C3 alkyl group having one or more fluorine atoms, a C1-C3 alkoxy group having one or more fluorine atoms, a C1-C3 alkylsulfanyl group having one or more fluorine atoms, a C1-C3 alkylsulfinyl group having one or more fluorine atoms, a C1-C3 alkylsulfonyl group having one or more fluorine atoms, or a halogen atom;

A compound of the formula (1) wherein $R^6$ is $-SF_5$, and $R^7$ is a hydrogen atom;

A compound of the formula (1) wherein $A^1$ is $-NR^8-$ or a sulfur atom, $R^8$ is a C1-C6 alkyl group, $A^2$ is $=CR^9-$, $A^3$ is $=CR^{10}-$, $R^9$ and $R^{10}$ are a hydrogen atom, $R^1$ is a C1-C3 alkyl group optionally having one or more fluorine atoms, $R^2$, $R^4$, and $R^5$ are a hydrogen atom, $R^3$ is a C1-C3 alkyl group optionally having one or more fluorine atoms or a halogen atom, $R^6$ is a C1-C3 alkyl group having one or more fluorine atoms, a C1-C3 alkoxy group having one or more fluorine atoms, a C1-C3 alkylsulfanyl group having one or more fluorine atoms, a C1-C3 alkylsulfinyl group having one or more fluorine atoms, a C1-C3 alkylsulfonyl group having one or more fluorine atoms, or a halogen atom, and $R^7$ is a hydrogen atom;

A compound of the formula (1) wherein $A^1$ is $-NR^8-$ or a sulfur atom, $R^8$ is a C1-C6 alkyl group, $A^2$ is $=CR^9-$, $R^9$ is a hydrogen atom, $A^3$ is a nitrogen atom, $R^1$ is a C1-C3 alkyl group optionally having one or more fluorine atoms, $R^2$, $R^4$, and $R^5$ are a hydrogen atom, $R^3$ is a C1-C3 alkyl group optionally having one or more fluorine atoms or a halogen atom, $R^6$ is a C1-C3 alkyl group having one or more fluorine atoms, a C1-C3 alkoxy group having one or more fluorine atoms, a C1-C3 alkylsulfanyl group having one or more fluorine atoms, a C1-C3 alkylsulfinyl group having one or more fluorine atoms, a C1-C3 alkylsulfonyl group having one or more fluorine atoms, or a halogen atom, and $R^7$ is a hydrogen atom;

A compound of the formula (1) wherein $A^1$ is a sulfur atom, $A^2$ is $=CR^9-$, $R^9$ is a hydrogen atom, $A^3$ is a nitrogen atom or $=CR^{10}-$, $R^{10}$ is a halogen atom or a hydrogen atom, $R^1$ is a methyl group, an ethyl group, a propyl group, an isopropyl group, a butyl group, a sec-butyl group, an isobutyl group, a tert-butyl group, a cyclopropyl group, a trifluoromethyl group, or a 2,2,2-trifluoroethyl group, $R^2$, $R^3$, $R^4$, and $R^5$ are a hydrogen atom, $R^6$ is a trifluoromethyl group, a difluoromethyl group, a fluoromethyl group, a pentafluoroethyl group, a heptafluoroisopropyl group, a trifluoromethoxy group, a trifluoromethylsulfanyl group, a trifluoromethylsulfinyl group, a trifluoromethylsulfonyl group, a bromine atom, or an iodine atom, $R^7$ is a hydrogen atom, and n is 0;

A compound of the formula (1) wherein $A^1$ is a sulfur atom, $A^2$ is $=CR^9-$, $R^9$ is a hydrogen atom, $A^3$ is a nitrogen atom or $=CR^{10}-$, $R^{10}$ is a halogen atom or a hydrogen atom, $R^1$ is a methyl group, an ethyl group, a propyl group, an isopropyl group, a butyl group, a sec-butyl group, an isobutyl group, a tert-butyl group, a cyclopropyl group, a trifluoromethyl group, or a 2,2,2-trifluoroethyl group, $R^2$, $R^3$, $R^4$, and $R^5$ are a hydrogen atom, $R^6$ is a trifluoromethyl group, a difluoromethyl group, a fluoromethyl group, a pentafluoroethyl group, a heptafluoroisopropyl group, a trifluoromethoxy group, a trifluoromethylsulfanyl group, a trifluoromethylsulfinyl group, a trifluoromethylsulfonyl group, a bromine atom, or an iodine atom, $R^7$ is a hydrogen atom, and n is 1;

A compound of the formula (1) wherein $A^1$ is a sulfur atom, $A^2$ is $=CR^9-$, $R^9$ is a hydrogen atom, $A^3$ is a nitrogen atom or $=CR^{10}-$, $R^{10}$ is a halogen atom or a hydrogen atom, $R^1$ is a methyl group, an ethyl group, a propyl group, an isopropyl group, a butyl group, a sec-butyl group, an isobutyl group, a tert-butyl group, a cyclopropyl group, a trifluoromethyl group, a 2,2,2-trifluoroethyl group, $R^2$, $R^3$, $R^4$, and $R^5$ are a hydrogen atom, $R^6$ is a trifluoromethyl group, a difluoromethyl group, a fluoromethyl group, a pentafluoroethyl group, a heptafluoroisopropyl group, a trifluoromethoxy group, a trifluoromethylsulfanyl group, a trifluoromethylsulfinyl group, a trifluoromethylsulfonyl group, a bromine atom, or an iodine atom, $R^7$ is a hydrogen atom, and n is 2;

A compound of the formula (1) wherein $A^1$ is $-NR^8-$, $R^8$ is a methyl group, an ethyl group, a propyl group, or an isopropyl group, $A^2$ is $=CR^9-$, $A^3$ is $=CR^{10}-$, $R^9$ and $R^{10}$ are a hydrogen atom, $R^1$ is a methyl group, an ethyl group, a propyl group, an isopropyl group, a trifluoromethyl group, or a 2,2,2-trifluoroethyl group, $R^2$, $R^4$, and $R^5$ are a hydrogen atom, $R^3$ is a methyl group, an ethyl group, a propyl group, an isopropyl group, a trifluoromethyl group, a pentafluoroethyl group, a heptafluoropropyl group, a heptafluoroisopropyl group, a fluorine atom, a chlorine atom, or a bromine atom, $R^6$ is a trifluoromethyl group, a pentafluoroethyl group, a heptafluoropropyl group, a heptafluoroisopropyl group, a trifluoromethoxy group, a trifluoromethylsulfanyl group, a trifluoromethylsulfinyl group, a trifluoromethylsulfonyl group, a chlorine atom, a bromine atom or an iodine atom, and $R^7$ is a hydrogen atom;

A compound of the formula (1) wherein $A^1$ is a sulfur atom, $A^2$ is $=CR^9-$, $A^3$ is $=CR^{10}-$, $R^9$ and $R^{10}$ are a hydrogen atom, $R^1$ is a methyl group, an ethyl group, a propyl group, an isopropyl group, a trifluoromethyl group, or a 2,2,2-trifluoroethyl group, $R^2$, $R^4$, and $R^5$ are a hydrogen atom, $R^3$ is a methyl group, an ethyl group, a propyl group, an isopropyl group, a trifluoromethyl group, a pentafluoroethyl group, a heptafluoropropyl group, a heptafluoroisopropyl group, a fluorine atom, a chlorine atom or a bromine atom, $R^6$ is a trifluoromethyl group, a pentafluoroethyl group, a heptafluoropropyl group, a heptafluoroisopropyl group, a trifluoromethoxy group, a trifluoromethylsulfanyl group, a trifluoromethylsulfinyl group, a trifluoromethylsulfonyl group, a chlorine atom, a bromine atom, or an iodine atom, and $R^7$ is a hydrogen atom;

A compound of the formula (1) wherein $A^1$ is $-NR^8-$, $R^8$ is a methyl group, an ethyl group, a propyl group, or an isopropyl group, $A^2$ is $=CR^9-$, $R^9$ is a hydrogen atom, $A^3$ is a nitrogen atom, $R^1$ is a methyl group, an ethyl group, a propyl group, an isopropyl group, a trifluoromethyl group, or a 2,2,2-trifluoroethyl group, $R^2$, $R^4$, and $R^5$ are a hydrogen atom, $R^3$ is a methyl group, an ethyl group, a propyl group, an isopropyl group, a trifluoromethyl group, a pentafluoroethyl group, a heptafluoropropyl group, a heptafluoroisopropyl group, a fluorine atom, a chlorine atom, or a bromine atom, $R^6$ is a trifluoromethyl group, a pentafluoroethyl group, a heptafluoropropyl group, a heptafluoroisopropyl group, a trifluoromethoxy group, a trifluoromethylsulfanyl group, a trifluoromethylsulfinyl group, a trifluoromethylsulfonyl group, a chlorine atom, a bromine atom, or an iodine atom, and $R^7$ is a hydrogen atom;

A compound of the formula (1) wherein $A^1$ is a sulfur atom, $A^2$ is $=CR^9-$, $R^9$ is a hydrogen atom, $A^3$ is a nitrogen atom, $R^1$ is a methyl group, an ethyl group, a propyl group, an isopropyl group, a trifluoromethyl group, or a 2,2,2-trifluoroethyl group, $R^2$, $R^4$, and $R^5$ are a hydrogen atom, $R^3$ is a methyl group, an ethyl group, a propyl group, an isopropyl group, a trifluoromethyl group, a pentafluoroethyl group, a heptafluoropropyl group, a heptafluoroisopropyl group, a fluorine atom, a chlorine atom or a bromine atom, $R^6$ is a trifluoromethyl group, a pentafluoroethyl group, a heptafluoropropyl group, a heptafluoroisopropyl group, a trifluoromethoxy group, a trifluoromethylsulfanyl group, a trifluoromethylsulfinyl group, a trifluoromethylsulfonyl group, a chlorine atom, a bromine atom, or an iodine atom, and $R^7$ is a hydrogen atom;

A compound of the formula (1-1)

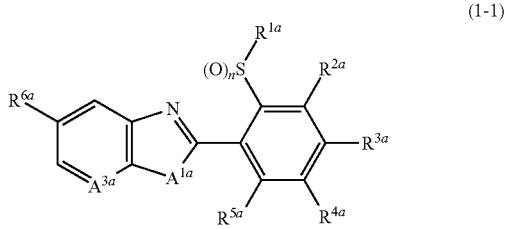

(1-1)

wherein;

$A^{1a}$ represents $-NR^{8a}-$ or a sulfur atom;

$A^{3a}$ represents a nitrogen atom or $=CR^{10a}-$;

$R^{1a}$ represents a C1-C6 chain hydrocarbon group optionally having one or more halogen atoms;

$R^{2a}$, $R^{4a}$, and $R^{5a}$ are same or different and are independently a C1-C6 chain hydrocarbon group optionally having one or more halogen atoms, a halogen atom, or a hydrogen atom;

$R^{6a}$ represents a C1-C6 chain hydrocarbon group optionally having one or more halogen atoms, $-OR^{11a}$, a halogen atom, or a hydrogen atom;

$R^{6a}$ represents a C1-C6 chain hydrocarbon group optionally having one or more halogen atoms, $-OR^{11a}$, $-S(O)_m R^{11a}$, a bromine atom, or an iodine atom;

$R^{8a}$ represents a C1-C6 chain hydrocarbon group optionally having one or more halogen atoms or a hydrogen atom;

$R^{10a}$ represents a halogen atom or a hydrogen atom;

$R^{11a}$ represents a C1-C6 chain hydrocarbon group optionally having one or more halogen atoms, m represents 0, 1, or 2, and n represents 0, 1 or 2;

A compound of the formula (1-1) wherein $A^{1a}$ is $-NR^{8a}-$ or a sulfur atom, $R^{8a}$ is a methyl group, $A^{3a}$ is a nitrogen atom, $R^{1a}$ is an ethyl group, $R^{2a}$, $R^{4a}$, and $R^{5a}$ are a halogen atom or a hydrogen atom, $R^{3a}$ is a trifluoromethyl group, a halogen atom, or a hydrogen atom, and $R^{8a}$ is a C1-C3 chain hydrocarbon group having one or more a fluorine atoms, a C1-C3 alkoxy group having one or more a fluorine atoms, a C1-C3 alkylsulfanyl group having one or more a fluorine atoms, a C1-C3 alkylsulfinyl group having one or more a fluorine atoms, or a C1-C3 alkylsulfonyl group having one or more a fluorine atoms;

A compound of the formula (1-1) wherein $A^{1a}$ is $-NR^{8a}-$ or a sulfur atom, $R^{8a}$ is a methyl group, $A^{3a}$ is a nitrogen atom, $R^{1a}$ is an ethyl group, $R^{2a}$, $R^{4a}$, and $R^{5a}$ are a hydrogen atom, $R^{3a}$ is a chlorine atom, a bromine atom, a trifluoromethyl group, or a hydrogen atom, and $R^{6a}$ is a trifluoromethyl group, a pentafluoroethyl group, a heptafluoroisopropyl group, a trifluoromethoxy group, a trifluoromethylsulfanyl group, a trifluoromethylsulfinyl group, or a trifluoromethylsulfonyl group;

A compound of the formula (1-1) wherein $A^{1a}$ is $-NR^{8a}-$ or a sulfur atom, and $R^{8a}$ is a C1-C6 chain hydrocarbon group optionally having one or more halogen atoms;

A compound of the formula (1-1) wherein $A^{1a}$ is $-NR^{8a}-$, and $R^{8a}$ is a C1-C6 chain hydrocarbon group optionally having one or more halogen atoms;

A compound of the formula (1-1) wherein $A^{1a}$ is $-NR^{8a}-$, and $R^{8a}$ is a methyl group;

A compound of the formula (1-1) wherein $A^{1a}$ is a sulfur atom;

A compound of the formula (1-1) wherein $A^{3a}$ is a nitrogen atom or $=CR^{10a}-$, and $R^{10a}$ is a halogen atom or a hydrogen atom;

A compound of the formula (1-1) wherein $A^{3a}$ is $=CR^{10a}-$, and $R^{10a}$ is a halogen atom or a hydrogen atom;

A compound of the formula (1-1) wherein $A^{3a}$ is a nitrogen atom;

A compound of the formula (1-1) wherein $A^{1a}$ is $-NR^{8a}-$ or a sulfur atom, $R^{8a}$ is a C1-C6 chain hydrocarbon group optionally having one or more halogen atoms, $A^{3a}$ is a nitrogen atom or $=CR^{10a}-$, and $R^{10a}$ is a hydrogen atom;

A compound of the formula (1-1) wherein $A^{1a}$ is $-NR^{8a}-$ or a sulfur atom, $R^{8a}$ is a C1-C6 chain hydrocarbon group optionally having one or more halogen atoms, and $A^{3a}$ is a nitrogen atom;

A compound of the formula (1-1) wherein $A^{1a}$ is $-NR^{8a}-$ or a sulfur atom, $R^{8a}$ is a C1-C6 chain hydrocarbon group optionally having one or more halogen atoms, $A^{3a}$ is $=CR^{10a}-$, and $R^{10a}$ is a hydrogen atom;

A compound of the formula (1-1) wherein $A^{1a}$ is $-NR^{8a}-$ or a sulfur atom, $R^{8a}$ is a methyl group, and $A^{3a}$ is a nitrogen atom;

A compound of the formula (1-1) wherein $A^{1a}$ is $-NR^{8a}-$, $R^{8a}$ is a methyl group, and $A^{3a}$ is a nitrogen atom;

A compound of the formula (1-1) wherein $A^{1a}$ is a sulfur atom, and $A^{3a}$ is a nitrogen atom;

A compound of the formula (1-1) wherein $R^{1a}$ is a C1-C6 chain hydrocarbon group optionally having one or more halogen atoms;

A compound of the formula (1-1) wherein $R^{1a}$ is an ethyl group;

A compound of the formula (1-1) wherein $R^{2a}$, $R^{4a}$, and $R^{5a}$ are same or different and are independently a fluorine atom, a chlorine atom, or a hydrogen atom, and $R^{3a}$ is a fluorine atom, a chlorine atom, a bromine atom, a methyl group, a trifluoromethyl group, or a hydrogen atom;

A compound of the formula (1-1) wherein $R^{2a}$, $R^{4a}$, and $R^{5a}$ are a hydrogen atom, and $R^{3a}$ is a fluorine atom, a chlorine atom, a bromine atom, a methyl group, or a trifluoromethyl group;

A compound of the formula (1-1) wherein $R^{6a}$ is a trifluoromethyl group, a pentafluoroethyl group, a heptafluoroisopropyl group, a trifluoromethoxy group, a trifluoromethylsulfanyl group, a trifluoromethylsulfinyl group, or a trifluoromethylsulfonyl group;

A compound of the formula (1-1) wherein $R^{68}$ is a bromine atom;

A compound of the formula (1-1) wherein $R^{6a}$ is an iodine atom;
A compound of the formula (1-1) wherein $R^{6a}$ is a trifluoromethyl group;
A compound of the formula (1-1) wherein $R^{6a}$ is a pentafluoroethyl group;
A compound of the formula (1-1) wherein $R^{6a}$ is a heptafluoroisopropyl group;
A compound of the formula (1-1) wherein $R^{6a}$ is a trifluoromethoxy group;
A compound of the formula (1-1) wherein $R^{6a}$ is a trifluoromethylsulfanyl group;
A compound of the formula (1-1) wherein $R^{6a}$ is a trifluoromethylsulfinyl group;
A compound of the formula (1-1) wherein $R^{6a}$ is a trifluoromethylsulfonyl group;
A compound of the formula (1-1) wherein $A^{1a}$ is —$NR^{8a}$—, and $R^{8a}$ is a C1-C3 alkyl group;
A compound of the formula (1-1) wherein $A^{1a}$ is —$NR^{8a}$—, and $R^{8a}$ is a methyl group, an ethyl group, a propyl group, or an isopropyl group;
A compound of the formula (1-1) wherein $A^{1a}$ is —$NR^{8a}$—, and $R^{8a}$ is an ethyl group;
A compound of the formula (1-1) wherein is —$NR^{8a}$—, and $R^{8a}$ is a propyl group;
A compound of the formula (1-1) wherein $A^{1a}$ is —$NR^{8a}$—, and $R^{8a}$ is an isopropyl group;
A compound of the formula (1-1) wherein $A^{1a}$ is —$NR^{8a}$—, and $R^{8a}$ is a methyl group or a hydrogen atom;
A compound of the formula (1-1) wherein $A^{1a}$ is —$NR^{8a}$—, and $R^{8a}$ is a hydrogen atom;
A compound of the formula (1-1) wherein $A^{1a}$ is —$NR^{8a}$—, and $R^{8a}$ is a methoxymethyl group, an ethoxymethyl group, or a hydrogen atom;
A compound of the formula (1-1) wherein $A^{3a}$ is =$CR^{10a}$—, and $R^{10a}$ is a hydrogen atom;
A compound of the formula (1-1) wherein $A^{1a}$ is —$NR^{8a}$—, and $A^{3a}$ is =$CR^{10a}$—;
A compound of the formula (1-1) wherein $A^{1a}$ is a sulfur atom, and $A^{3a}$ is =$CR^{10a}$—;
A compound of the formula (1-1) wherein $A^{1a}$ is —$NR^{8a}$—, and $A^{3a}$ is a nitrogen atom;
A compound of the formula (1-1) wherein $A^{1a}$ is —$NR^{8a}$—, $R^{8a}$ is a hydrogen atom group, and $A^{3a}$ is a nitrogen atom;
A compound of the formula (1-1) wherein $R^{1a}$ is a C1-C3 alkyl group;
A compound of the formula (1-1) wherein $R^{1a}$ is a methyl group, an ethyl group, a propyl group, an isopropyl group, a butyl group, a sec-butyl group, an isobutyl group, a tert-butyl group, a cyclopropyl group, a trifluoromethyl group, or a 2,2,2-trifluoroethyl group;
A compound of the formula (1-1) wherein $R^{1a}$ is a methyl group;
A compound of the formula (1-1) wherein $R^{1a}$ is a propyl group;
A compound of the formula (1-1) wherein $R^{2a}$, $R^{3a}$, $R^{4a}$, and $R^{5a}$ are a hydrogen atom;
A compound of the formula (1-1) wherein $R^{6a}$ is a halogen atom;
A compound of the formula (1-1) wherein $A^{1a}$ is —$NR^{8a}$— or a sulfur atom, $R^{8a}$ is a C1-C6 alkyl group, $A^{3a}$ is =$CR^{10a}$—, $R^{10a}$ is a hydrogen atom, $R^{1a}$ is a C1-C3 alkyl group optionally having one or more fluorine atoms, $R^{2a}$, $R^{4a}$, and $R^{5a}$ are a hydrogen atom, $R^{3a}$ is a C1-C3 alkyl group optionally having one or more fluorine atoms or a halogen atom, and $R^{6a}$ is a C1-C3 alkyl group having one or more fluorine atoms, a C1-C3 alkoxy group having one or more fluorine atoms, a C1-C3 alkylsulfanyl group having one or more fluorine atoms, a C1-C3 alkylsulfinyl group having one or more fluorine atoms, a C1-C3 alkylsulfonyl group having one or more fluorine atoms, or a halogen atom;
A compound of the formula (1-1) wherein $A^{1a}$ is —$NR^{8a}$— or a sulfur atom, $R^{8a}$ is a C1-C6 alkyl group, $A^{3a}$ is a nitrogen atom, $R^{1a}$ is a C1-C3 alkyl group optionally having one or more fluorine atoms, $R^{2a}$, $R^{4a}$, and $R^{5a}$ are a hydrogen atom, $R^{1a}$ is a C1-C3 alkyl group optionally having one or more fluorine atoms or a halogen atom, and $R^{6a}$ is a C1-C3 alkyl group having one or more fluorine atoms, a C1-C3 alkoxy group having one or more fluorine atoms, a C1-C3 alkylsulfanyl group having one or more fluorine atoms, a C1-C3 alkylsulfinyl group having one or more fluorine atoms, or a C1-C3 alkylsulfonyl group having one or more fluorine atoms, or a halogen atom;
A compound of the formula (1-0):

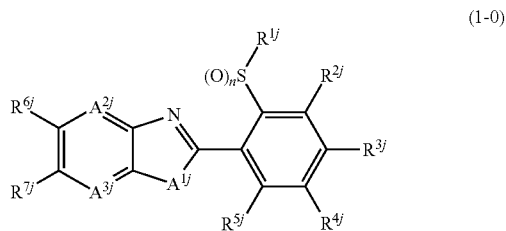

(1-0)

wherein:
$A^{1j}$ represents —$NR^{8j}$—, an oxygen atom, or a sulfur atom;
$A^{2j}$ represents a nitrogen atom or =$CR^{9j}$—;
$A^{3j}$ represents a nitrogen atom or =$CR^{10j}$—;
$R^{1j}$ represents a C1-C6 chain hydrocarbon group optionally having one or more atoms or groups selected from Group $X^j$, or a C3-C6 alicyclic hydrocarbon group optionally having one or more atoms or groups selected from Group $Y^j$;
$R^{2j}$, $R^{3j}$, $R^{4j}$, and $R^{5j}$ are same or different and independently represent a C1-C6 chain hydrocarbon group optionally having one or more halogen atoms, —$OR^{11j}$, —$NR^{11j}R^{12j}$, a cyano group, a nitro group, a halogen atom, or a hydrogen atom: provided that at least two of $R^{2j}$, $R^{3j}$, $R^{4j}$, and $R^{5j}$ represent a hydrogen atom;
$R^{6j}$ and $R^7$ are same or different and independently represent a C1-C6 chain hydrocarbon group optionally having one or more halogen atoms, a phenyl group optionally having one or more halogen atoms, a 5-membered heterocyclic group optionally having one or more halogen atoms, a 6-membered heterocyclic group optionally having one or more halogen atoms, —$OR^{11j}$, —$S(O)_mR^{11j}$, —$NR^{11j}R^{12j}$, —$CO_2R^{11j}$, —$C(O)R^{11j}$, an aldehyde group, a cyano group, a nitro group, a halogen atom, or a hydrogen atom;
$R^{8j}$ represents a C1-C6 chain hydrocarbon group optionally having one or more halogen atoms, a C1-C6 chain hydrocarbon group having one —$OR^{11j}$, or a cyclopropyl group;
$R^{9j}$ and $R^{10j}$ are same or different and independently represent a C1-C3 chain hydrocarbon group, a halogen atom, or a hydrogen atom;
$R^{11j}$ and $R^{12j}$ are same or different and independently represent a C1-C6 chain hydrocarbon group optionally having one or more halogen atoms or a hydrogen atom; and
m represents 0, 1, or 2, and n represents 0, 1, or 2;
(except in cases as follows: both e and $R^7$ are a hydrogen atom; in —$S(O)_mR^{11j}$, when m is 1 or 2, $R^{11j}$ represents a hydrogen atom; and when $A^{1j}$ represents a methylimino group, $A^{2j}$ and $A^{3j}$ represent a methine group, $R^{1j}$ represents a methyl group, $R^{2j}$, $R^{3j}$, $R^{4j}$, and $R^{5j}$ represent a hydrogen atom, and n represents 0 or 1, both $R^{6j}$ and $R^{7j}$ are a chlorine atom and one of e and $R^7$ is a chlorine atom and the other is a hydrogen atom)

the Group $X^j$ consists of $-OR^{11j}$ and a halogen atom; and
the Group $Y^j$ consists of a C1-C6 chain hydrocarbon group, a $-OR^{11j}$, and a halogen atom.

A compound of the formula (Z):

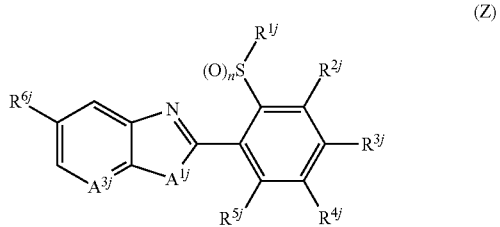

(Z)

wherein, $R^{1j}$, $R^{2j}$, $R^{3j}$, $R^{4j}$, $R^{5j}$, $R^{6j}$, $A^{1j}$, $A^{3j}$, and n are as defined in the formula (1-0);

A compound of the formula (Z) wherein $A^{1j}$ is $-NR^{8j}-$, an oxygen atom, or a sulfur atom, and $R^{8j}$ is a C1-C6 chain hydrocarbon group optionally having one or more halogen atoms;

A compound of the formula (Z) wherein $A^{1j}$ is $-NR^{8j}-$ or a sulfur atom, and $R^{8j}$ is a C1-C6 chain hydrocarbon group optionally having one or more halogen atoms;

A compound of the formula (Z) wherein $A^{1j}$ is $-NR^{8j}-$ or a sulfur atom;

A compound of the formula (Z) wherein $A^{1j}$ is $-NR^{8j}-$;

A compound of the formula (Z) wherein $A^{1j}$ is $-NR^{8j}-$, and $R^{8j}$ is a C1-C6 chain hydrocarbon group having one C1-C6 alkoxy group optionally having one or more halogen atoms, a C1-C6 chain hydrocarbon group optionally having one or more halogen atoms, a cyclopropyl group, or a hydrogen atom;

A compound of the formula (Z) wherein $A^{1j}$ is $-NR^{8j}-$, and $R^{8j}$ is a C1-C6 chain hydrocarbon group having one C1-C6 alkoxy group optionally having one or more halogen atoms or a C1-C6 chain hydrocarbon group optionally having one or more halogen atoms;

A compound of the formula (Z) wherein $A^{1j}$ is $-NR^{8j}-$, and $R^{8j}$ is a C1-C6 chain hydrocarbon group having one C1-C6 alkoxy group optionally having one or more halogen atoms, a C1-C6 chain hydrocarbon group optionally having one or more halogen atoms, or a cyclopropyl group;

A compound of the formula (Z) wherein $A^{1j}$ is $-NR^{8j}-$, and $R^{8j}$ is a C1-C6 chain hydrocarbon group optionally having one or more halogen atoms;

A compound of the formula (Z) wherein $A^{1j}$ is $-NR^{8j}-$, and $R^{8j}$ is a C1-C6 chain hydrocarbon group;

A compound of the formula (Z) wherein $A^{1j}$ is $-NR^{8j}-$, and $R^{8j}$ is a C1-C6 alkyl group;

A compound of the formula (Z) wherein $A^{1j}$ is $-NR^{8j}-$, and $R^{8j}$ is a C1-C3 alkyl group;

A compound of the formula (Z) wherein $A^{1j}$ is $-NR^{8j}-$, and $R^{8j}$ is a methyl group, an ethyl group, a propyl group, or an isopropyl group;

A compound of the formula (Z) wherein $A^{1j}$ is $-NR^{8j}-$, and $R^{8j}$ is a methyl group, an ethyl group, a propyl group, an isopropyl group, a methoxymethyl group, an ethoxymethyl group, a cyclopropyl group, or a hydrogen atom;

A compound of the formula (Z) wherein $A^{1j}$ is $-NR^{8j}-$, and $R^{8j}$ is a methyl group, an ethyl group, a propyl group, an isopropyl group, a methoxymethyl group, an ethoxymethyl group, or a cyclopropyl group;

A compound of the formula (Z) wherein $A^{1j}$ is $-NR^{8j}-$, and $R^{8j}$ is a methyl group, an ethyl group, a methoxymethyl group, or an ethoxymethyl group;

A compound of the formula (Z) wherein $A^{1j}$ is $-NR^{8j}-$, and $R^{8j}$ is a methyl group;

A compound of the formula (Z) wherein $A^{1j}$ is $-NR^{8j}-$, and $R^{8j}$ is an ethyl group;

A compound of the formula (Z) wherein $A^{1j}$ is $-NR^{8j}-$, and $R^{8j}$ is a propyl group;

A compound of the formula (Z) wherein $A^{1j}$ is $-NR^{8j}-$, and $R^{8j}$ is an isopropyl group;

A compound of the formula (Z) wherein $A^{1j}$ is $-NR^{8j}-$, and $R^{8j}$ is a methyl group or a hydrogen atom;

A compound of the formula (Z) wherein $A^{1j}$ is $-NR^{8j}-$, and $R^{8j}$ is a hydrogen atom;

A compound of the formula (Z) wherein $A^{1j}$ is $-NR^{8j}-$, and $R^{8j}$ is a methoxymethyl group, an ethoxymethyl group, or a hydrogen atom;

A compound of the formula (Z) wherein $A^{1j}$ is an oxygen atom;

A compound of the formula (Z) wherein $A^{1j}$ is a sulfur atom;

A compound of the formula (Z) wherein $A^{1j}$ is $-NR^{8j}-$ or a sulfur atom;

A compound of the formula (Z) wherein $A^{1j}$ is $-NR^{8j}-$ or a sulfur atom, and $R^{8j}$ is a methyl group, an ethyl group, a propyl group, or an isopropyl group;

A compound of the formula (Z) wherein $A^{1j}$ is $-NR^{8j}-$ or a sulfur atom, and $R^{8j}$ is a methoxymethyl group, an ethoxymethyl group, or a hydrogen atom;

A compound of the formula (Z) wherein $A^{3j}$ is a nitrogen atom or $=CR^{10j}-$, and $R^{10j}$ is a halogen atom or a hydrogen atom;

A compound of the formula (Z) wherein $A^{3j}$ is $=CR^{10j}-$, and $R^{10j}$ is a halogen atom or a hydrogen atom;

A compound of the formula (Z) wherein $A^{3j}$ is $=CR^{10j}-$, and $R^{10j}$ is a hydrogen atom;

A compound of the formula (Z) wherein $A^{3j}$ is a nitrogen atom;

A compound of the formula (Z) wherein $A^{1j}$ is $-NR^{8j}-$, and $A^{3j}$ is $=CR^{10j}-$;

A compound of the formula (Z) wherein $A^{1j}$ is a sulfur atom, and $A^{3j}$ is $=CR^{10j}-$;

A compound of the formula (Z) wherein $A^{1j}$ is $-NR^{8j}-$, and $A^{3j}$ is a nitrogen atom;

A compound of the formula (Z) wherein $A^{1j}$ is a sulfur atom, and $A^{3j}$ is a nitrogen atom;

A compound of the formula (Z) wherein $A^{1j}$ is $-NR^{8j}-$ or a sulfur atom, $R^{8j}$ is a C1-C6 chain hydrocarbon group optionally having one or more halogen atoms, $A^{3j}$ is a nitrogen atom or $=CR^{10j}-$, and $R^{10j}$ is a hydrogen atom;

A compound of the formula (Z) wherein $A^{1j}$ is $-NR^{8j}-$ or a sulfur atom, $R^{8j}$ is a C1-C6 chain hydrocarbon group optionally having one or more halogen atoms, and $A^{3j}$ is a nitrogen atom;

A compound of the formula (Z) wherein $A^{1j}$ is $-NR^{8j}-$ or a sulfur atom, $R^{8j}$ is a C1-C6 chain hydrocarbon group optionally having one or more halogen atoms, $A^{3j}$ is $=CR^{10j}-$, and $R^{10j}$ is a hydrogen atom;

A compound of the formula (Z) wherein $A^{1j}$ is $-NR^{8j}-$ or a sulfur atom, $R^{8j}$ is a methyl group, and $A^{3j}$ is a nitrogen atom;

A compound of the formula (Z) wherein $A^{1j}$ is —NR$^{8j}$—, R$^{8j}$ is a methyl group, and A$^{3j}$ is a nitrogen atom;

A compound of the formula (Z) wherein R$^{1j}$ is a C1-C6 chain hydrocarbon group optionally having one or more halogen atoms;

A compound of the formula (Z) wherein R$^{1j}$ is a C1-C6 chain hydrocarbon group optionally having one or more fluorine atoms;

A compound of the formula (Z) wherein R$^{1j}$ is a C1-C6 chain hydrocarbon group;

A compound of the formula (Z) wherein R$^{1j}$ is a C1-C6 alkyl group;

A compound of the formula (Z) wherein R$^{1j}$ is a C1-C3 alkyl group;

A compound of the formula (Z) wherein R$^{1j}$ is a methyl group, an ethyl group, a propyl group, an isopropyl group, a butyl group, a sec-butyl group, an isobutyl group, a tert-butyl group, a cyclopropyl group, a trifluoromethyl group, or a 2,2,2-trifluoroethyl group;

A compound of the formula (Z) wherein R$^{1j}$ is a methyl group;

A compound of the formula (Z) wherein R$^{1j}$ is an ethyl group;

A compound of the formula (Z) wherein R$^{1j}$ is a propyl group;

A compound of the formula (Z) wherein R$^{1j}$ is an isopropyl group;

A compound of the formula (Z) wherein R$^{1j}$ is a trifluoromethyl group;

A compound of the formula (Z) wherein R$^{1j}$ is a 2,2,2-trifluoroethyl group;

A compound of the formula (Z) wherein R$^{1j}$ is a C3-C6 alicyclic hydrocarbon group optionally having one or more atoms or groups selected from Group Y$^j$;

A compound of the formula (Z) wherein R$^{1j}$ is a C3-C6 alicyclic hydrocarbon group;

A compound of the formula (Z) wherein R$^{1j}$ is a cyclopropyl group, a cyclobutyl group, or a cyclopentyl group;

A compound of the formula (Z) wherein R$^{2j}$, R$^{4j}$, and R$^{5j}$ are same or different and are independently a fluorine atom, a chlorine atom, or a hydrogen atom, and R$^{3j}$ is a fluorine atom, a chlorine atom, a bromine atom, a trifluoromethyl group, or a hydrogen atom;

A compound of the formula (Z) wherein R$^{2j}$, R$^{4j}$, and R$^{5j}$ are a hydrogen atom, R$^{3j}$ is a C1-C6 chain hydrocarbon group optionally having one or more halogen atoms;

A compound of the formula (Z) wherein R$^{2j}$, R$^{4j}$, and R$^{5j}$ are a hydrogen atom, and R$^{3j}$ is a C1-C6 alkyl group;

A compound of the formula (Z) wherein R$^{2j}$, R$^{4j}$, and R$^{5j}$ are a hydrogen atom, and R$^{3j}$ is a optionally having one or more fluorine atoms C1-C6 alkyl group;

A compound of the formula (Z) wherein R$^{2j}$, R$^{4j}$, and R$^{5j}$ are a hydrogen atom, and R$^{3j}$ is a C1-C3 alkyl group;

A compound of the formula (Z) wherein R$^{2j}$, R$^{4j}$, and R$^{5j}$ are a hydrogen atom, and R$^{3j}$ is a C1-C3 alkyl group optionally having one or more fluorine atoms;

A compound of the formula (Z) wherein R$^{2j}$, R$^{4j}$, and R$^{5j}$ are a hydrogen atom, and R$^{3j}$ is a chlorine atom, a bromine atom, a trifluoromethyl group, or a hydrogen atom;

A compound of the formula (Z) wherein R$^{2j}$, R$^{4j}$, and R$^{5j}$ are a hydrogen atom, and R$^{3j}$ is a fluorine atom;

A compound of the formula (Z) wherein R$^{2j}$, R$^{4j}$, and R$^{5j}$ are a hydrogen atom, and R$^{3j}$ is a chlorine atom;

A compound of the formula (Z) wherein R$^{2j}$, R$^{4j}$, and R$^{5j}$ are a hydrogen atom, and R$^{3j}$ is a bromine atom;

A compound of the formula (Z) wherein R$^{2j}$, R$^{4j}$, and R$^{5j}$ are a hydrogen atom, and R$^{3j}$ is a methyl group;

A compound of the formula (Z) wherein R$^{2j}$, R$^{4j}$, and R$^{5j}$ are a hydrogen atom, and R$^{3j}$ is a trifluoromethyl group;

A compound of the formula (Z) wherein R$^{2j}$, R$^{4j}$, and R$^{5j}$ are a hydrogen atom, and R$^{3j}$ is a trifluoromethoxy group;

A compound of the formula (Z) wherein R$^{2j}$, R$^{3j}$, R$^{4j}$, and R$^{5j}$ are a hydrogen atom;

A compound of the formula (Z) wherein R$^{6j}$ is a halogen atom;

A compound of the formula (Z) wherein R$^{6j}$ is a trifluoromethyl group, a pentafluoroethyl group, a heptafluoroisopropyl group, a trifluoromethoxy group, a trifluoromethylsulfanyl group, a trifluoromethylsulfinyl group, or a trifluoromethylsulfonyl group;

A compound of the formula (Z) wherein R$^{6j}$ is a bromine atom;

A compound of the formula (Z) wherein R$^{6j}$ is an iodine atom;

A compound of the formula (Z) wherein R$^{6j}$ is a trifluoromethyl group;

A compound of the formula (Z) wherein R$^{6j}$ is a pentafluoroethyl group;

A compound of the formula (Z) wherein R$^{6j}$ is a heptafluoroisopropyl group;

A compound of the formula (Z) wherein R$^{6j}$ is a trifluoromethoxy group;

A compound of the formula (Z) wherein R$^{6j}$ is a trifluoromethylsulfanyl group;

A compound of the formula (Z) wherein R$^{6j}$ is a trifluoromethylsulfinyl group;

A compound of the formula (Z) wherein R$^{6j}$ is a trifluoromethylsulfonyl group;

A compound of the formula (Z) wherein R$^{2j}$, R$^{3j}$, R$^{4j}$, and R$^{5j}$ are same or different and are independently a fluorine atom, a chlorine atom, or a hydrogen atom, and R$^{6j}$ is a trifluoromethyl group or a pentafluoroethyl group;

A compound of the formula (Z) wherein R$^{2j}$, R$^{3j}$, R$^{4j}$, and R$^{5j}$ are a hydrogen atom, and R$^{6j}$ is a trifluoromethyl group;

A compound of the formula (Z) wherein R$^{2j}$, R$^{3j}$, R$^{4j}$, and R$^{5j}$ are a hydrogen atom, and R$^{6j}$ is a pentafluoroethyl group or a heptafluoroisopropyl group;

A compound of the formula (Z) wherein R$^{2j}$, R$^{3j}$, R$^{4j}$, and R$^5$ are a hydrogen atom, and R$^{6j}$ is a trifluoromethoxy group;

A compound of the formula (Z) wherein R$^{2j}$, R$^{3j}$, R$^{4j}$, and R$^{5j}$ are a hydrogen atom, and R$^{6j}$ is a trifluoromethylsulfanyl group, a trifluoromethylsulfinyl group, or a trifluoromethylsulfonyl group;

A compound of the formula (Z) wherein A$^{1j}$ is —NR$^{8j}$— or a sulfur atom, R$^{8j}$ is a C1-C6 alkyl group, A$^{3j}$ is =CR$^{10j}$—, R$^{10j}$ is a hydrogen atom, R$^{1j}$ is a C1-C3 alkyl group optionally having one or more fluorine atoms, R$^{2j}$, R$^{4j}$, and R$^{5j}$ are a hydrogen atom, R$^{3j}$ is a C1-C3 alkyl group optionally having one or more fluorine atoms or a halogen atom, and R$^{6j}$ is a C1-C3 alkyl group having one or more fluorine atoms, a C1-C3 alkoxy group having one or more fluorine atoms, a C1-C3 alkylsulfanyl group having one or more fluorine atoms, a C1-C3 alkylsulfinyl group having one or more fluorine atoms, a C1-C3 alkylsulfonyl group having one or more fluorine atoms, or a halogen atom; and A compound of the formula (Z) wherein A$^{1j}$ is —NR$^{8j}$— or a sulfur atom, R$^{8j}$ is a C1-C6 alkyl group, A$^{3j}$ is a nitrogen atom, R$^{1j}$ is a C1-C3 alkyl group optionally having one or more fluorine atoms, R$^{2j}$, R$^{4j}$, and R$^{5j}$ are a hydrogen atom, R$^{3j}$ is a C1-C3 alkyl group optionally having one or more fluorine atoms or a halogen atom, and R$^{6j}$ is a C1-C3 alkyl group having one or more fluorine atoms, a C1-C3 alkoxy group having one or more fluorine atoms, a C1-C3 alkylsulfanyl group having one or more fluorine atoms, a C1-C3 alkylsulfinyl group having one or more fluorine atoms, a C1-C3 alkylsulfonyl group having one or more fluorine atoms, or a halogen atom.

The present compound can be produced, for example, by the following Production methods A-F.

(Production Method A)

The present compound (1) can be produced by reacting Compound (1F) with Compound (5). Alternatively, the present compound (1) can be produced by reacting Compound (F) with Compound (5) to give Compound (B), followed by cyclizing Compound (B):

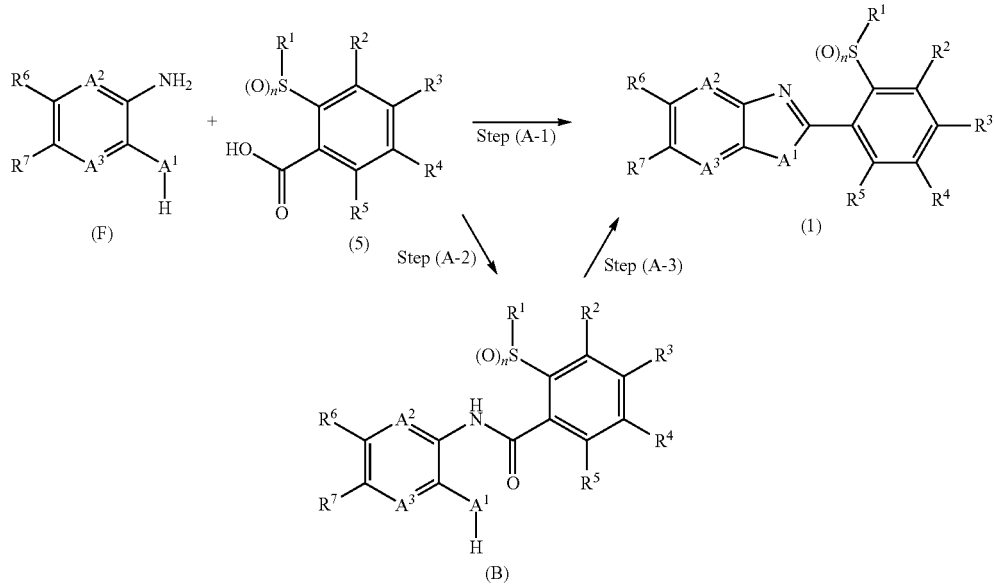

wherein, $R^1$, $R^2$, $R^3$, $R^4$, $R^5$, $R^6$, $R^7$, $A^1$, $A^2$, $A^3$, and n are as defined above.

(Production Method B)

The present compound (1) can be produced by reacting Compound (1F) with Compound (M3). Alternatively, the present compound (1) can be produced by reacting Compound (F) with Compound (5) to give Compound (B), followed by cyclizing Compound (B):

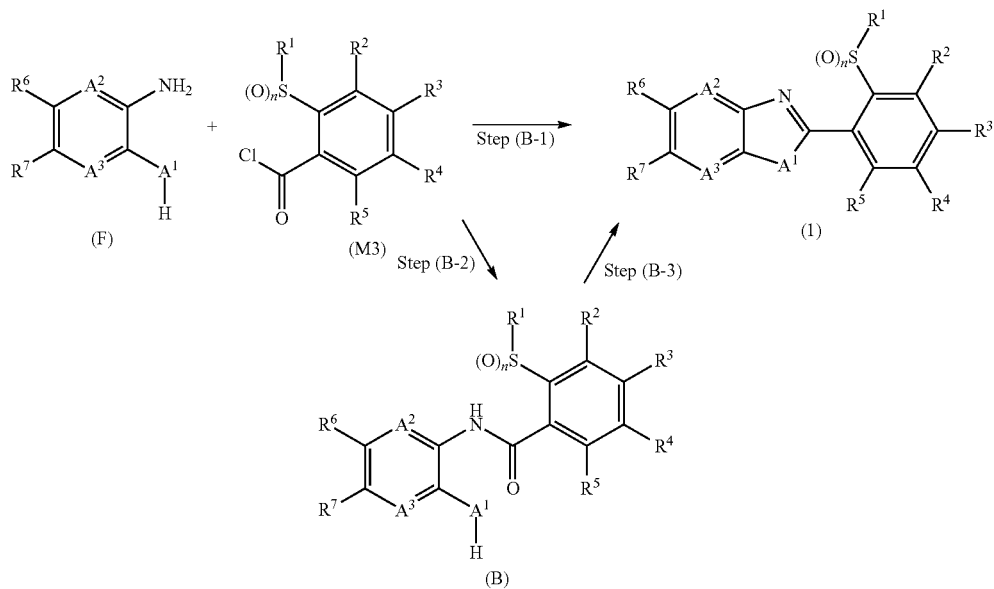

wherein, $R^1$, $R^2$, $R^3$, $R^4$, $R^5$, $R^6$, $R^7$, $A^1$, $A^2$, $A^3$ and n are as defined above.

(Production Method C)

The present compound (1) can be produced by reacting Compound (F) with Compound (3). Alternatively, the present compound (1) can be produced by reacting Compound (1F) with Compound (3) to give Compound (1J), followed by cyclizing Compound (1J):

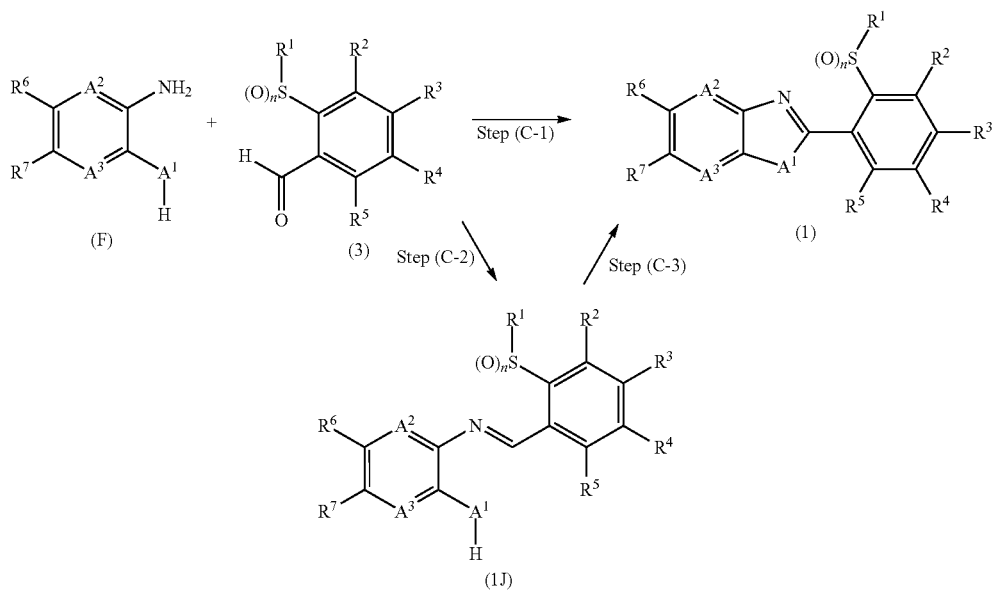

wherein, $R^1$, $R^2$, $R^3$, $R^4$, $R^5$, $R^6$, $R^7$, $A^1$, $A^2$, $A^3$, and n are as defined above.

(Production Method D)

Compound (12) of the formula (1) wherein $A^1$ is a sulfur atom can be produced by reacting Compound (K) with a sulfating agent:

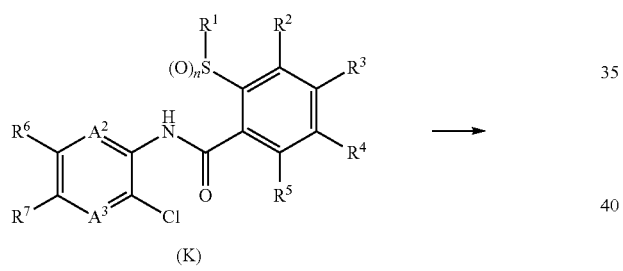

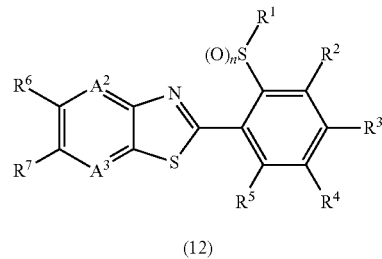

wherein, $R^1$, $R^2$, $R^3$, $R^4$, $R^5$, $R^6$, $R^7$, $A^2$, $A^3$, and n are as defined above.

(Production Method E)

Compound (23) of the formula (1) wherein n is 0 can be produced, for example, by the following method:

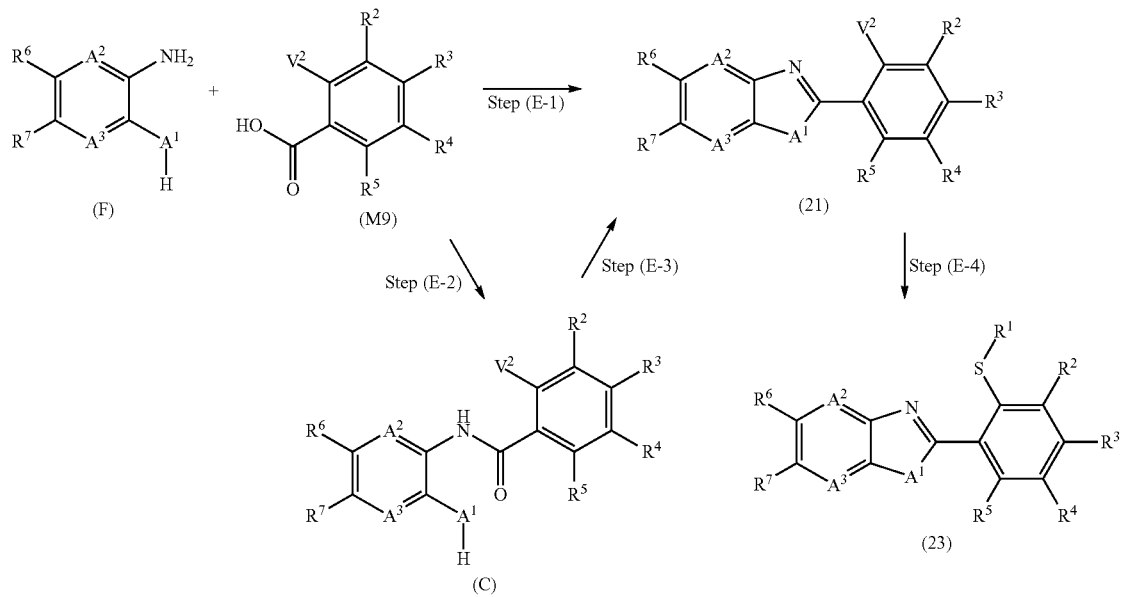

wherein, $R^1$, $R^2$, $R^3$, $R^4$, $R^5$, $R^6$, $R^7$, $A^1$, $A^2$, $A^3$, and n are as defined above, and $V^2$ represents a fluorine atom or a chlorine atom.

(Production Method F)

Compound (23) of the formula (1) wherein n is 0 can be produced, for example, by the following method:

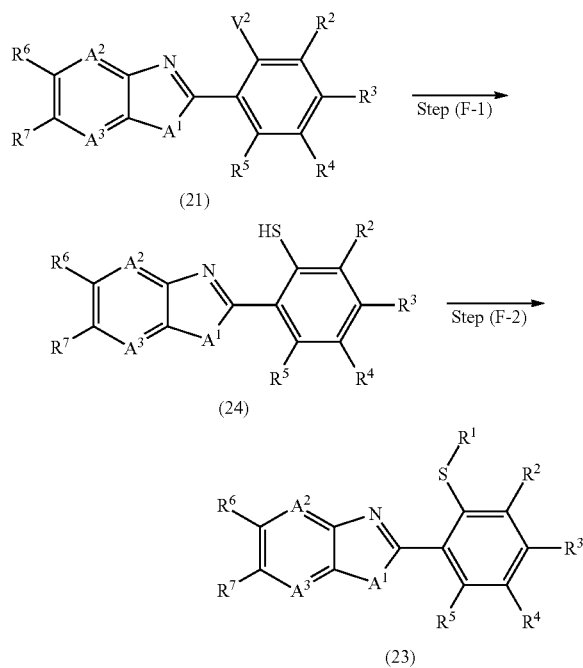

wherein, $R^1$, $R^2$, $R^3$, $R^4$, $R^5$, $R^6$, $R^7$, $A^1$, $A^2$, $A^3$, n, and $V^2$ are as defined above.

The production method of the present compound is illustrated below.

The production methods A-F of the present compound are further illustrated bellow. In addition, the production methods which the present compound is converted to other present compound are illustrated. The present compound can be produced, for example, by the following Production methods 1-26.

(Production Method 1) (Step (C-1))

Compound (4) of the formula (1) wherein $A^1$ is $-NR^8-$ can be produced by reacting Compound (2) with Compound (3):

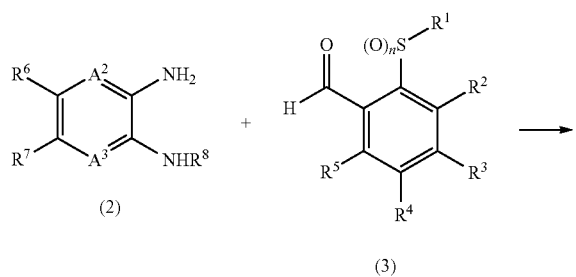

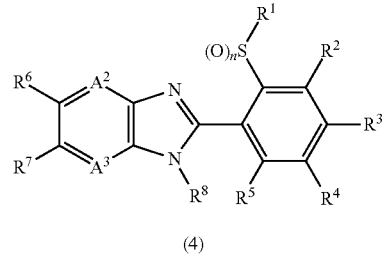

wherein $R^1$, $R^2$, $R^3$, $R^4$, $R^5$, $R^6$, $R^7$, $R^8$, $A^2$, $A^3$, and n are as defined above.

The reaction is usually performed in the presence of a base, acid, sulfite, or disulfite.

The reaction is usually performed in the presence of a solvent.

Examples of the base to be used in the reaction include hydrogen carbonates such as sodium hydrogen carbonate and potassium hydrogen carbonate; carbonates such as sodium carbonate and potassium carbonate; and mixtures thereof.

Examples of the acid to be used in the reaction include sulfonic acids such as p-toluenesulfonic acid; and carboxylic acids such as acetic acid.

Examples of the sulfite to be used in the reaction include sodium sulfite and potassium sulfite.

Examples of the disulfite to be used in the reaction include sodium disulfite and potassium disulfite.

Examples of the solvent to be used in the reaction include ethers such as tetrahydrofuran (hereinafter referred to as THF), ethylene glycol dimethyl ether, tert-butyl methyl ether, and 1,4-dioxane; aliphatic hydrocarbons such as hexane, heptane, and octane; aromatic hydrocarbons such as toluene and xylene; halogenated hydrocarbons such as chlorobenzene; esters such as ethyl acetate and butyl acetate; nitriles such as acetonitrile; acid amides such as N,N-dimethylformamide (hereinafter referred to as DMF) and N-methylpyrrolidone (hereinafter referred to as NMP); sulfoxides such as dimethylsulfoxide (hereinafter referred to as DMSO); nitrogen-containing aromatic compounds such as pyridine and quinoline; and mixtures thereof.

An oxidizing agent can be added to the reaction as necessary.

Examples of the oxidizing agent to be used in the reaction include an oxygen, copper (II) oxide, and 2,3-dichloro-5,6-dicyano-p-benzoquinon.

The amount of Compound (3) to be used in the reaction is usually 1 to 3 moles based on 1 mole of Compound (2). The amount of the base to be used in the reaction is usually 1 to 5 moles based on 1 mole of Compound (2). The amount of the acid to be used in the reaction is usually 1 to 5 moles based on 1 mole of Compound (2). The amount of the sulfite to be used in the reaction is usually 1 to 5 moles based on 1 mole of Compound (2). The amount of the disulfite to be used in the reaction is usually 1 to 5 moles based on 1 mole of Compound (2). The amount of the oxidizing agent to be used in the reaction is usually 1 to 5 moles based on 1 mole of Compound (2).

The reaction temperature of the reaction is usually within a range of 30 to 200° C. The reaction time of the reaction is usually within a range of 0.1 to 24 hours.

After the completion of the reaction, Compound (4) can be isolated by post-treatments, for example, pouring water into the reaction mixture and then extracting the mixture with an organic solvent, followed by drying and concentrating the organic layer. The isolated Compound (4) can be further purified by chromatography, recrystallization, and the like.
(Production Method 2) (Step A-1)

Compound (4) of the formula (1) wherein $A^1$ is —$NR^8$— can be produced by reacting Compound (2) with Compound (5) in the presence of a dehydration-condensing agent:

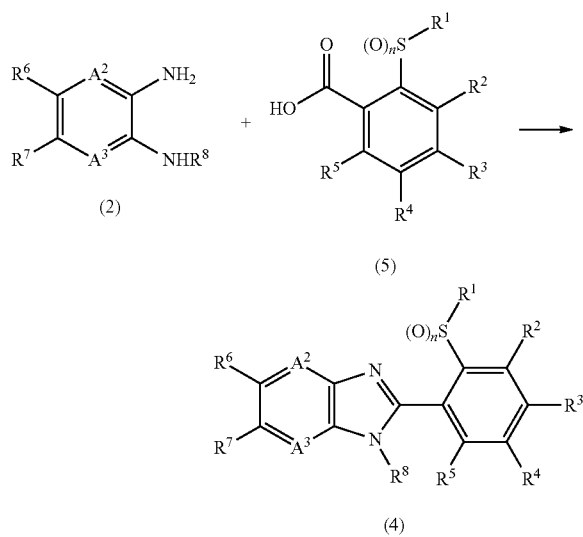

wherein, $R^1$, $R^2$, $R^3$, $R^4$, $R^5$, $R^6$, $R^7$, $R^8$, $A^2$, $A^3$, and n are as defined above.

The reaction is usually performed in the presence of a solvent.

Examples of the solvent to be used in the reaction include ethers such as THF, tert-butyl methyl ether, ethylene glycol dimethyl ether, and 1,4-dioxane; aliphatic hydrocarbons such as hexane, heptane, and octane; aromatic hydrocarbons such as toluene and xylene; halogenated hydrocarbons such as chlorobenzene; esters such as ethyl acetate and butyl acetate; nitriles such as acetonitrile; acid amides such as DMF and NMP; sulfoxides such as DMSO; nitrogen-containing aromatic compounds such as pyridine and quinoline; and mixtures thereof.

Examples of the dehydration-condensing agent to be used in the reaction include carbodiimides such as 1-ethyl-3-(3-dimethylaminopropyl)carbodiimide hydrochloride (hereinafter referred to as WSC), and 1,3-dicyclohexylcarbodiimide; and (benzotriazol-1-yloxy)tris(dimethylamino)phosphonium hexafluorophosphate (hereinafter referred to as BOP reagent).

A catalyst can be added to the reaction as necessary.

Examples of the catalyst to be used in the reaction include 1-hydroxybenzotriazole (hereinafter referred to as HOBt).

The amount of Compound (5) to be used in the reaction is usually 1 to 3 moles based on 1 mole of Compound (2). The amount of the dehydration-condensing agent to be used in the reaction is usually 1 to 5 moles based on 1 mole of Compound (2). The amount of the catalyst to be used in the reaction is usually 0.01 to 0.1 moles based on 1 mole of Compound (2).

The reaction temperature of the reaction is usually within a range of 30 to 200° C. The reaction time of the reaction is usually within a range of 0.1 to 24 hours.

After the completion of the reaction, Compound (4) can be isolated by post-treatments, for example, pouring water into the reaction mixture and then extracting the mixture with an organic solvent, followed by drying and concentrating the organic layer. The isolated Compound (4) can be further purified by chromatography, recrystallization, and the like.

Alternatively, Compound (4) can be produced according to the above method using Compound (M3) instead of Compound (5).

When Compound (M3) is used, the reaction is usually performed without a dehydration-condensing agent.

A base can be added to the reaction as necessary.

Examples of the base to be used in the reaction include carbonates of alkali metal such as sodium carbonate and potassium carbonate; tertiary amines such as triethylamine and diisopropylethylamine; and nitrogen-containing aromatic compounds such as pyridine and 4-dimethylaminopyridine.

The amount of Compound (M3) to be used in the reaction is usually 1 to 3 moles based on 1 mole of Compound (2). The amount of the base to be used in the reaction is usually 1 to 10 moles based on 1 mole of Compound (2).
(Production Method 3) (Step (A-3), Step (B-3))

Compound (4) of the formula (1) wherein $A^1$ is —$NR^8$— can be produced by dehydration-condensing Compound (6):

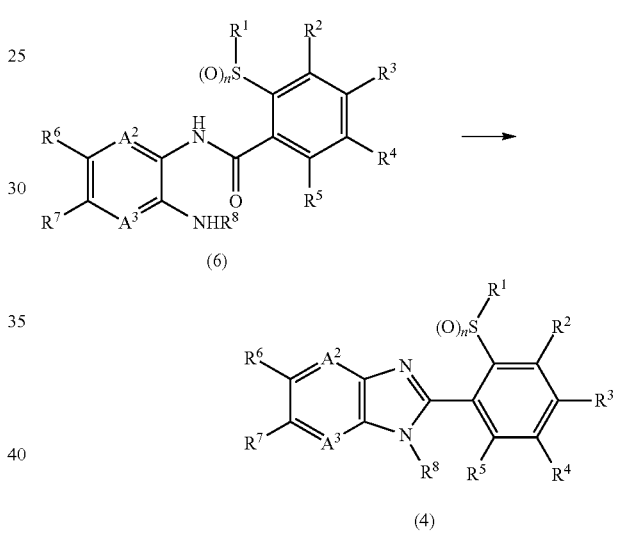

wherein, $R^1$, $R^2$, $R^3$, $R^4$, $R^5$, $R^6$, $R^7$, $R^8$, $A^2$, $A^3$, and n are as defined above.

The reaction is usually performed in the presence of a solvent.

Examples of the solvent to be used in the reaction include ethers such as THF, ethylene glycol dimethyl ether, tert-butyl methyl ether, and 1,4-dioxane; aliphatic hydrocarbons such as hexane, heptane, and octane; aromatic hydrocarbons such as toluene and xylene; halogenated hydrocarbons such as chlorobenzene; esters such as ethyl acetate and butyl acetate; nitriles such as acetonitrile; acid amides such as DMF and NMP; sulfoxides such as DMSO; alcohols such as methanol, ethanol, propanol, butanol, and pentanol; and mixtures thereof.

In the reaction, an acid or a dehydrating agent can be used as necessary. Examples of the acid to be used in the reaction include sulfonic acids such as p-toluenesulfonic acid, and carboxylic acids such as acetic acid. Examples of the dehydrating agent to be used in the reaction include phosphorous oxychloride, acetic anhydride, and trifluoroacetic anhydride.

The amount of the acid or the dehydrating agent to be used in the reaction is usually 1 to 10 moles based on 1 mole of Compound (6).

The reaction temperature of the reaction is usually within a range of 30 to 200° C. The reaction time of the reaction is usually within a range of 0.1 to 24 hours.

After the completion of the reaction, Compound (4) can be isolated by post-treatments, for example, extracting the reaction mixture with an organic solvent, followed by drying and concentrating the organic layer. The isolated Compound (4) can be further purified by chromatography, recrystallization, and the like.

(Production Method 4) (Step (A-3), Step (B-3))

Compound (4) of the formula (1) wherein $A^1$ is —$NR^8$— can be produced by reacting Compound (6) in the presence of a base:

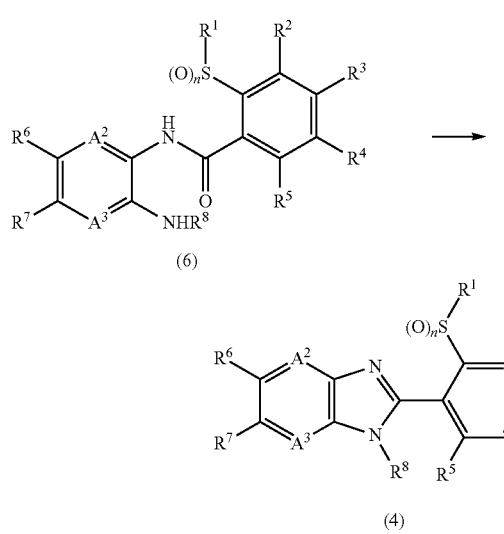

wherein, $R^1$, $R^2$, $R^3$, $R^4$, $R^5$, $R^6$, $R^7$, $R^8$, $A^2$, $A^3$, and n are as defined above.

The reaction is usually performed in the presence of a solvent.

Examples of the solvent to be used in the reaction include ethers such as THF, ethylene glycol dimethyl ether, tert-butyl methyl ether, and 1,4-dioxane; aliphatic hydrocarbons such as hexane, heptane, and octane; aromatic hydrocarbons such as toluene and xylene; halogenated hydrocarbons such as chlorobenzene; esters such as ethyl acetate and butyl acetate; nitriles such as acetonitrile; acid amides such as DMF and NMP; sulfoxides such as DMSO; alcohols such as methanol, ethanol, propanol, butanol, tert-butanol, and pentanol; and mixtures thereof.

Examples of the base to be used in the reaction include tripotassium phosphate.

The amount of the base to be used in the reaction is usually 1 to 10 moles based on 1 mole of Compound (6).

The reaction temperature of the reaction is usually within a range of 30 to 200° C. The reaction time of the reaction is usually within a range of 0.1 to 24 hours.

After the completion of the reaction, Compound (4) can be isolated by post-treatments, for example, extracting the reaction mixture with an organic solvent, followed by drying and concentrating the organic layer. The isolated Compound (4) can be further purified by chromatography, recrystallization, and the like.

(Production Method 5)

Compound (4) of the formula (1) wherein $A^1$ is —$NR^8$— can be produced by reacting Compound (32) with Compound (33) in the presence of a base.

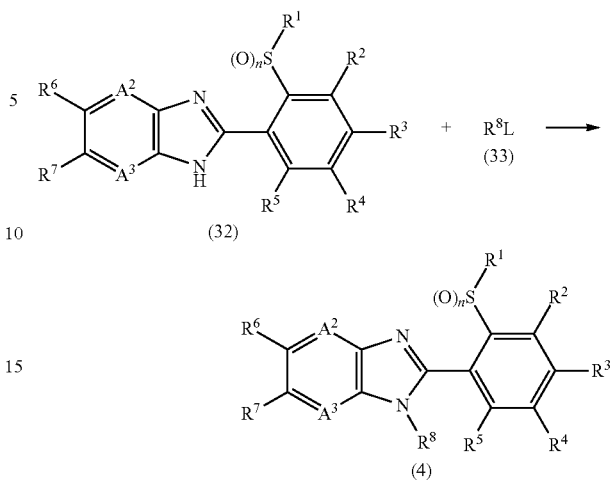

wherein, $R^1$, $R^2$, $R^3$, $R^4$, $R^5$, $R^6$, $R^7$, $R^8$, $A^2$, $A^3$, and n are as defined above, and L represents a leaving group such as a chlorine atom, a bromine atom, an iodine atom, a trifluoromethylsulfonyloxy group and a methylsulfonyloxy group.

The reaction is usually performed in the presence of a solvent.

Examples of the solvent to be used in the reaction include ethers such as THF, ethylene glycol dimethyl ether, tert-butyl methyl ether, and 1,4-dioxane; aromatic hydrocarbons such as toluene and xylene; nitriles such as acetonitrile; acid amides such as DMF and NMP; sulfoxides such as DMSO; and mixtures thereof.

Examples of the base to be used in the reaction include hydrides of alkali metal or alkali earth metal such as sodium hydride, potassium hydride, and calcium hydride; inorganic bases such as sodium carbonate and potassium carbonate; and organic bases such as triethylamine.

The amount of Compound (33) to be used in the reaction is usually 1 to 5 moles based on 1 mole of Compound (32).

The amount of the base to be used in the reaction is usually 1 to 3 moles based on 1 mole of Compound (32).

The reaction temperature of the reaction is usually within a range of 0 to 100° C. The reaction time of the reaction is usually within a range of 0.1 to 24 hours.

After the completion of the reaction, Compound (4) can be isolated by post-treatments, for example, extracting the reaction mixture with an organic solvent, followed by drying and concentrating the organic layer. The isolated Compound (4) can be further purified by chromatography, recrystallization, and the like.

(Production Method 6) (Step (A-1))

Compound (8) of the formula (1) wherein $A^1$ is an oxygen atom can be produced by reacting Compound (7) with Compound (5) in the presence of an acid:

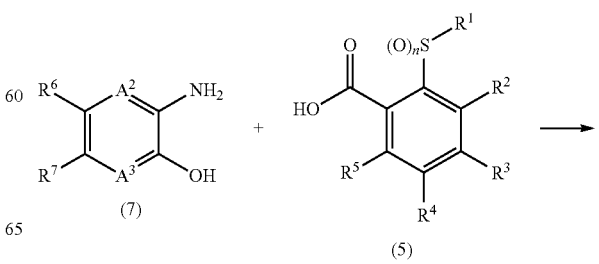

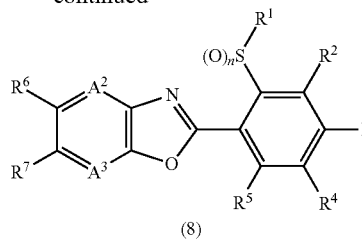

(8)

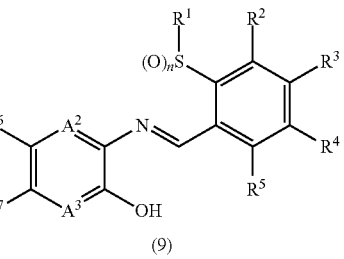

(9)

wherein, $R^1$, $R^2$, $R^3$, $R^4$, $R^5$, $R^6$, $R^7$, $A^2$, $A^3$, and n are as defined above.

The reaction is usually performed in the presence or absence of a solvent.

Examples of the solvent to be used in the reaction include ethers such as THF, ethylene glycol dimethyl ether, tert-butyl methyl ether, and 1,4-dioxane; aliphatic hydrocarbons such as hexane, heptane, and octane; aromatic hydrocarbons such as toluene and xylene; halogenated hydrocarbons such as chlorobenzene and dichlorobenzene; and mixtures thereof.

Examples of the acid to be used in the reaction include polyphosphoric acid and trimethylsilyl polyphosphate.

When polyphosphoric acid is used as an acid, though the reaction is usually performed in the absence of a solvent, the reaction may be performed in the presence of a solvent.

The amount of Compound (5) to be used in the reaction is usually 1 to 3 moles based on 1 mole of Compound (7). The amount of the acid to be used in the reaction is usually 1 to 10 moles based on 1 mole of Compound (7).

The reaction temperature of the reaction is usually within a range of 50 to 200° C. The reaction time of the reaction is usually within a range of 0.5 to 24 hours.

After the completion of the reaction, Compound (8) can be isolated by post-treatments, for example, pouring the reaction mixture into water and then extracting the mixture with an organic solvent, followed by drying and concentrating the organic layer. The isolated Compound (8) can be further purified by chromatography, recrystallization, and the like.

Alternatively, Compound (8) can be produced according to the above method using Compound (M3) instead of Compound (5).

When Compound (M3) is used, the reaction is usually performed without a dehydration-condensing agent.

A base can be added to the reaction as necessary.

Examples of the base to be used in the reaction include carbonates of alkali metal such as sodium carbonate and potassium carbonate; tertiary amines such as triethylamine and diisopropylethylamine; and nitrogen-containing aromatic compounds such as pyridine and 4-dimethylaminopyridine.

The amount of Compound (M3) to be used in the reaction is usually 1 to 3 moles based on 1 mole of Compound (7). The amount of the base to be used in the reaction is usually 1 to 10 moles based on 1 mole of Compound (7).

(Production Method 7) (Step (C-3))

Compound (8) of the formula (1) wherein $A^1$ is an oxygen atom can be produced by oxidizing Compound (9):

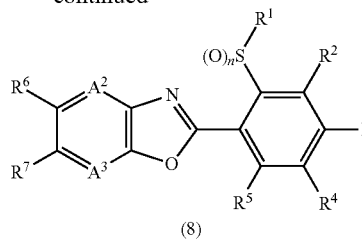

(8)

wherein, $R^1$, $R^2$, $R^3$, $R^4$, $R^5$, $R^6$, $R^7$, $A^2$, $A^3$, and n are as defined above.

The reaction is usually performed in the presence of a solvent.

Examples of the solvent to be used in the reaction include ethers such as THF, ethylene glycol dimethyl ether, tert-butyl methyl ether, and 1,4-dioxane; aliphatic hydrocarbons such as hexane, heptane, and octane; aromatic hydrocarbons such as toluene and xylene; halogenated hydrocarbons such as dichloromethane, chloroform, and chlorobenzene; esters such as ethyl acetate and butyl acetate; alcohols such as methanol and ethanol; nitriles such as acetonitrile; acid amides such as DMF and NMP; sulfoxides such as DMSO; acetic acid; and mixtures thereof.

Examples of the oxidizing agent to be used in the reaction include a metal oxidizing agent such as lead (IV) acetate and lead (IV) oxide, and a hypervalent iodine compound such as iodobenzene diacetate.

The amount of the oxidizing agent to be used in the reaction is usually 1 to 3 moles based on 1 mole of Compound (9).

The reaction temperature of the reaction is usually within a range of 0 to 100° C. The reaction time of the reaction is usually within a range of 0.1 to 24 hours.

After the completion of the reaction, Compound (8) can be isolated by post-treatments, for example, extracting the reaction mixture with an organic solvent, followed by drying and concentrating the organic layer. The isolated Compound (8) can be further purified by chromatography, recrystallization, and the like.

(Production Method 8) (Step (A-3), Step (B-3))

Compound (8) of the formula (1) wherein $A^1$ is an oxygen atom can be produced by reacting Compound (10) in the presence of a dehydration-condensing agent:

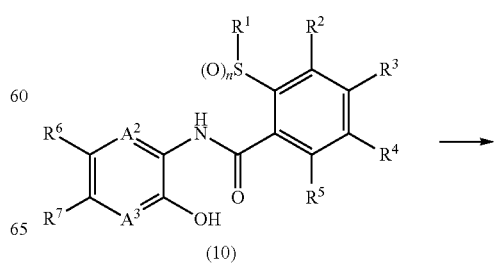

(10)

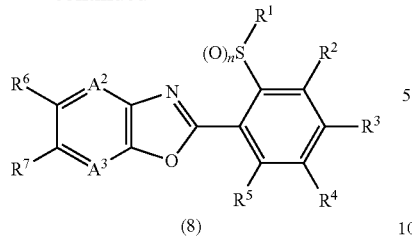

(8)

wherein, $R^1$, $R^2$, $R^3$, $R^4$, $R^5$, $R^6$, $R^7$, $A^2$, $A^3$, and n are as defined above.

The reaction is usually performed in the presence of a solvent.

Examples of the solvent to be used in the reaction include ethers such as THF, ethylene glycol dimethyl ether, tert-butyl methyl ether, and 1,4-dioxane; aromatic hydrocarbons such as toluene and xylene; halogenated hydrocarbons such as dichloromethane, chloroform, carbon tetrachloride, and chlorobenzene; esters such as ethyl acetate and butyl acetate; nitriles such as acetonitrile; and mixtures thereof. Among of them, carbon tetrachloride can be used as a dehydration-condensing agent.

Examples of the dehydration-condensing agent to be used in the reaction include a mixture of triphenylphosphine, a base and carbon tetrachloride or carbon tetrabromide, and a mixture of triphenylphosphine and azodiesters such as diethyl azodicarboxylate ester.

Examples of the base to be used in the reaction include tertiary amines such as triethylamine and diisopropylethylamine.

The amount of the dehydration-condensing agent to be used in the reaction is usually 1 to 3 moles based on 1 mole of Compound (10). The amount of the base to be used in the reaction is usually 1 to 5 moles based on 1 mole of Compound (10).

The reaction temperature of the reaction is usually within a range of −30 to 100° C. The reaction time of the reaction is usually within a range of 0.5 to 24 hours.

After the completion of the reaction, Compound (8) can be isolated by post-treatments, for example, extracting the reaction mixture with an organic solvent, followed by drying and concentrating the organic layer. The isolated Compound (8) can be further purified by chromatography, recrystallization, and the like.

(Production Method 9) (Step (A-3), Step (B-3))

Compound (8) of the formula (1) wherein $A^1$ is an oxygen atom can be produced by reacting Compound (10) in the presence of an acid:

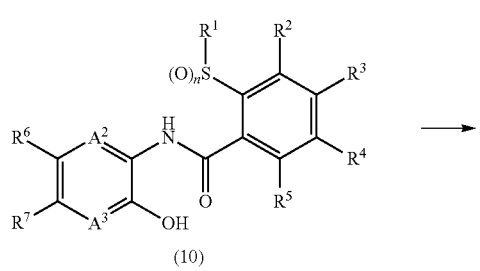

(10)

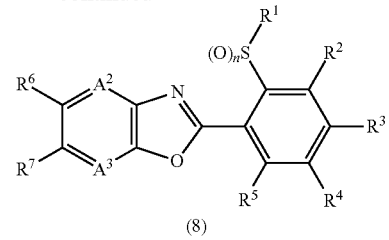

(8)

wherein, $R^1$, $R^2$, $R^3$, $R^4$, $R^5$, $R^6$, $R^7$, $A^2$, $A^3$, and n are as defined above.

The reaction is usually performed in the presence of a solvent.

Examples of the solvent to be used in the reaction include ethers such as THF, ethylene glycol dimethyl ether, tert-butyl methyl ether, and 1,4-dioxane; aromatic hydrocarbons such as toluene and xylene; halogenated hydrocarbons such as dichloromethane, chloroform, and chlorobenzene; and mixtures thereof.

Examples of the acid include sulfonic acids such as p-toluenesulfonic acid and polyphosphoric acid.

The amount of the acid to be used in the reaction is usually 0.1 to 3 moles based on 1 mole of Compound (10).

The reaction temperature of the reaction is usually within a range of 50 to 200° C. The reaction time of the reaction is usually within a range of 1 to 24 hours.

After the completion of the reaction, Compound (8) can be isolated by post-treatments, for example, extracting the reaction mixture with an organic solvent, followed by drying and concentrating the organic layer. The isolated Compound (8) can be further purified by chromatography, recrystallization, and the like.

(Production Method 10) (Step (C-1))

Compound (12) of the formula (1) wherein $A^1$ is a sulfur atom can be produced by reacting Compound (11) with Compound (3):

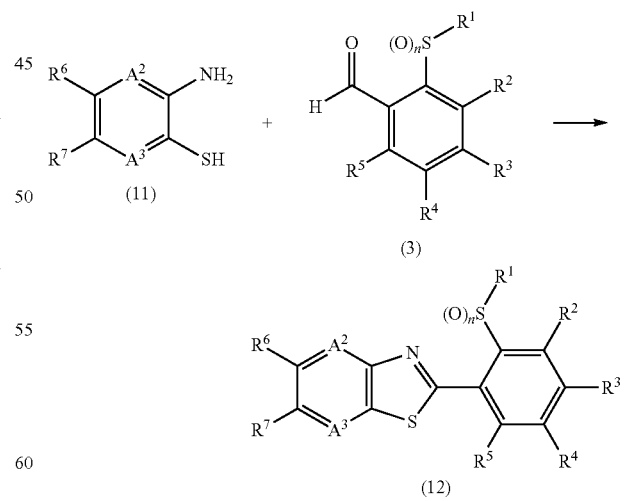

wherein, $R^1$, $R^2$, $R^3$, $R^4$, $R^5$, $R^6$, $R^7$, $A^2$, $A^3$, and n are as defined above.

The reaction is usually performed in the presence of a base, acid, sulfite, or disulfite.

Examples of the base to be used in the reaction include hydrogen carbonates such as sodium hydrogen carbonate and potassium hydrogen carbonate; carbonates such as sodium carbonate and potassium carbonate; and mixtures thereof.

Examples of the acid to be used in the reaction include sulfonic acids such as p-toluenesulfonic acid; and carboxylic acids such as acetic acid.

Examples of the sulfite to be used in the reaction include sodium sulfite and potassium sulfite.

Examples of the disulfite to be used in the reaction include sodium disulfite and potassium disulfite.

The reaction is usually performed in the presence of a solvent.

Examples of the solvent to be used in the reaction include ethers such as THF, ethylene glycol dimethyl ether, tert-butyl methyl ether, and 1,4-dioxane; aliphatic hydrocarbons such as hexane, heptane, and octane; halogenated hydrocarbons such as chlorobenzene; esters such as ethyl acetate and butyl acetate nitriles such as acetonitrile; acid amides such as DMF, and NMP; sulfoxides such as DMSO; aromatic hydrocarbons such as toluene, xylene, nitrobenzene; and mixtures thereof.

An oxidizing agent can be added to the reaction as necessary.

Examples of the oxidizing agent to be used in the reaction include an oxygen, copper (II) oxide, and 2,3-dichloro-5,6-dicyano-p-benzoquinon.

The amount of Compound (3) to be used in the reaction is usually 1 to 3 moles based on 1 mole of Compound (11). The amount of the acid to be used in the reaction is usually 1 to 5 moles based on 1 mole of Compound (11). The amount of the sulfite to be used in the reaction is usually 1 to 5 moles based on 1 mole of Compound (11). The amount of the disulfite to be used in the reaction is usually 1 to 5 moles based on 1 mole of Compound (11). The amount of the oxidizing agent to be used in the reaction is usually 1 to 5 moles based on 1 mole of Compound (11). The reaction temperature of the reaction is usually within a range of 50 to 200° C. The reaction time of the reaction is usually within a range of 0.1 to 24 hours.

After the completion of the reaction, Compound (12) can be isolated by post-treatments, for example, adding the reaction mixture to water and then extracting the mixture with an organic solvent, followed by drying and concentrating the organic layer. The isolated Compound (12) can be further purified by chromatography, recrystallization, and the like.

(Production Method 11) (Step (C-1))

Compound (12) of the formula (1) wherein $A^1$ is a sulfur atom can be produced by reacting hydrochloride of Compound (11) with Compound (3):

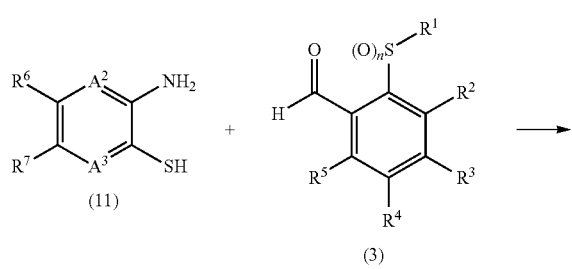

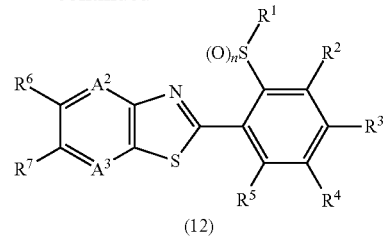

wherein, $R^1$, $R^2$, $R^3$, $R^4$, $R^5$, $R^6$, $R^7$, $A^2$, $A^3$, and n are as defined above.

The reaction is performed in the presence of a base and usually in the presence of a solvent.

Examples of the base to be used in the reaction include tertiary amines such as diisopropylethylamine and triethylamine.

Examples of the solvent to be used in the reaction include sulfoxides such as DMSO; aromatic hydrocarbons such as nitrobenzene; and mixtures thereof.

The amount of Compound (3) to be used in the reaction is usually 0.5 to 3 moles based on 1 mole of Compound (11). The amount of the base to be used in the reaction is usually 1 to 2 moles based on 1 mole of Compound (11).

The reaction temperature of the reaction is usually within a range of 50 to 200° C. The reaction time of the reaction is usually within a range of 0.1 to 24 hours.

After the completion of the reaction, Compound (12) can be isolated by post-treatments, for example, adding the reaction mixture to water and then extracting the mixture with an organic solvent, followed by drying and concentrating the organic layer. The isolated Compound (12) can be further purified by chromatography, recrystallization, and the like.

(Production Method 12)

Compound (14) of the formula (1) wherein $R^6$ is a cyano group or a C1-C6 alkyl group can be produced by reacting Compound (13) with a cyanating agent or di(C1-C6 alkyl) zinc in the presence of a palladium compound:

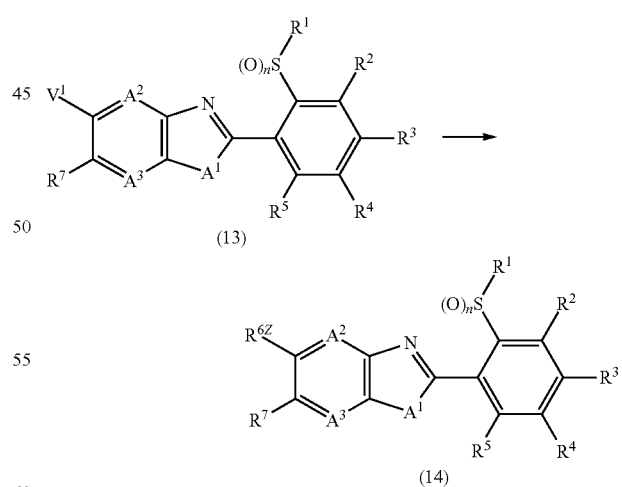

wherein, $R^1$, $R^2$, $R^3$, $R^4$, $R^5$, $R^7$, $A^1$, $A^2$, and $A^3$ are as defined above, $V^1$ represents a leaving group such as a bromine atom and an iodine atom, and $R^{6z}$ represents a cyano group or a C1-C6 alkyl group.

The reaction is usually performed in the presence of a solvent.

Examples of the solvent to be used in the reaction include ethers such as THF, ethylene glycol dimethyl ether, tert-butyl methyl ether, and 1,4-dioxane; aliphatic hydrocarbons such as hexane, heptane, and octane; aromatic hydrocarbons such as toluene and xylene; alcohols such as methanol and ethanol; acid amides such as DMF and NMP; sulfoxides such as DMSO; and mixtures thereof.

Examples of the cyanating agent to be used in the reaction include zinc cyanide. Examples of di(C1-C6 alkyl)zinc to be used in the reaction include dimethyl zinc, diethyl zinc, and diisopropyl zinc.

Examples of the palladium compound to be used in the reaction include tetrakis(triphenylphosphine)palladium.

The amount of the cyanating agent or di(C1-C6 alkyl) zinc to be used in the reaction is usually 1 to 5 moles based on 1 mole of Compound (13). The amount of the palladium compound to be used in the reaction is usually 0.01 to 0.5 moles based on 1 mole of Compound (13).

The reaction temperature of the reaction is usually within a range of 50 to 200° C. The reaction time of the reaction is usually within a range of 0.5 to 24 hours.

After the completion of the reaction, Compound (14) can be isolated by post-treatments, for example, extracting the reaction mixture with an organic solvent, followed by drying and concentrating the organic layer. The isolated Compound (14) can be further purified by chromatography, recrystallization, and the like.

(Production Method 13)

Compound (16) of the formula (1) wherein $R^6$ is $C(O)R^{6y}$ can be produced by reacting Compound (15) with a organometallic agent, then a carbonylating agent:

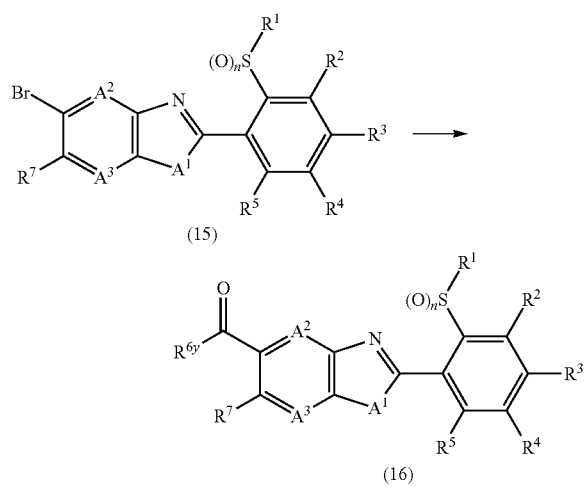

wherein, $R^1$, $R^2$, $R^3$, $R^4$, $R^5$, $R^7$, $A^1$, $A^2$, and $A^3$ are as defined above, $R^{6y}$ is a C1-C6 chain hydrocarbon group optionally having one or more halogen atoms, a hydrogen atom, or —$OR^{11}$, and $R^{11}$ is a C1-C6 chain hydrocarbon group optionally having one or more halogen atoms or a hydrogen atom.

The reaction is usually performed in the presence of a solvent.

Examples of the solvent to be used in the reaction include ethers such as THF, ethylene glycol dimethyl ether, tert-butyl methyl ether, and 1,4-dioxane.

Examples of the organometallic agent to be used in the reaction include alkyllithiums such as n-butyllithium and tert-butyllithium, organic magnesium halides such as isopropylmagnesium chloride.

Examples of the carbonylating agent to be used in the reaction include DMF, 1-formylpiperidine, 4-formylmorpholine, ethyl formate, ethyl acetate, methyl trifluoroacetate, methyl chloroformate, ethyl chloroformate, and carbon dioxide.

The amount of the organometallic agent to be used in the reaction is usually 1 to 3 moles based on 1 mole of Compound (15). The amount of the carbonylating agent to be used in the reaction is usually 1 to 10 moles based on 1 mole of Compound (15).

The reaction temperature of the reaction is usually within a range of −100 to 0° C. The reaction time of the reaction is usually within a range of 0.5 to 24 hours.

After the completion of the reaction, Compound (16) can be isolated by post-treatments, for example, extracting the reaction mixture with an organic solvent, followed by drying and concentrating the organic layer. The isolated Compound (16) can be further purified by chromatography, recrystallization, and the like.

(Production Method 14)

Compound (18) of the formula (1) wherein $R^6$ is a C1-C3 perfluoroalkyl group can be produced by reacting Compound (13) with Compound (17) in the presence of copper iodide:

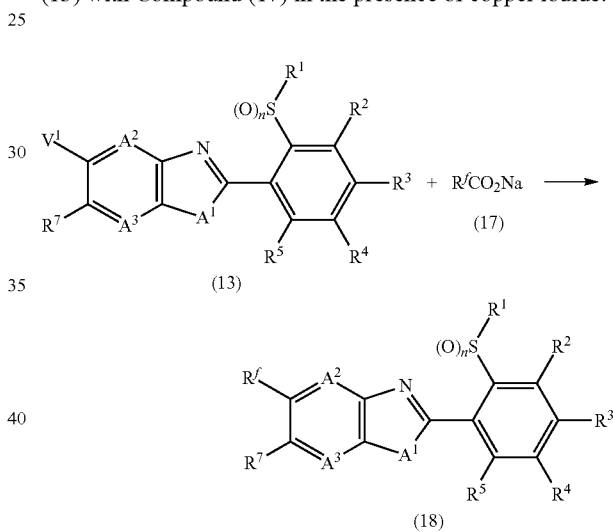

wherein, $R^1$, $R^2$, $R^3$, $R^4$, $R^5$, $R^7$, $A^1$, $A^2$, $A^3$, and $V^1$ are as defined above, and $R^f$ represents a C1-C3 perfluoroalkyl group.

The reaction is usually performed in the presence of a solvent.

Examples of the solvent to be used in the reaction include aromatic hydrocarbons such as toluene and xylene; acid amides such as DMF and NMP; and mixtures thereof.

The amount of Compound (17) to be used in the reaction is usually 1 to 10 moles based on 1 mole of Compound (13). The amount of copper iodide to be used in the reaction is usually 1 to 5 moles based on 1 mole of Compound (13).

The reaction temperature of the reaction is usually within a range of 50 to 200° C. The reaction time of the reaction is usually within a range of 0.5 to 24 hours.

After the completion of the reaction, Compound (18) can be isolated by post-treatments, for example, extracting the reaction mixture with an organic solvent, followed by drying and concentrating the organic layer. The isolated Compound (18) can be further purified by chromatography, recrystallization, and the like.

(Production Method 15)

Compound (20) of the formula (1) wherein $R^6$ is a phenyl group optionally having one or more halogen atoms, a 5-membered heterocyclic group optionally having one or more halogen atoms, or a 6-membered heterocyclic group optionally having one or more halogen atoms can be produced by reacting Compound (13) with boronic acid compound (19) in the presence of a palladium compound:

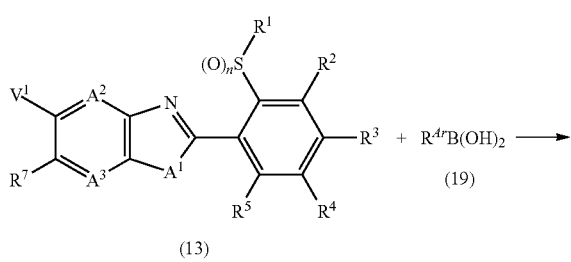

wherein, $R^1$, $R^2$, $R^3$, $R^4$, $R^5$, $R^7$, $A^1$, $A^2$, $A^3$, and $V^1$ are as defined above, and $R^{Ar}$ represents a phenyl group optionally having one or more halogen atoms, a 5-membered heterocyclic group optionally having one or more halogen atoms, or a 6-membered heterocyclic group optionally having one or more halogen atoms.

The reaction is usually performed in the presence of a solvent.

The reaction can be performed in the presence of a base and/or a phase transfer catalyst as necessary.

Examples of the base to be used in the reaction include inorganic salts such as sodium acetate, potassium acetate, potassium carbonate, tripotassium phosphate, and sodium hydrogen carbonate.

Examples of the phase transfer catalyst to be used in the reaction include quaternary ammonium salts such as tetrabutylammonium bromide and benzyltriethylammonium bromide.

The reaction can be performed in the presence of a ligand as necessary.

Examples of the ligand to be used in the reaction include 2-dicyclohexylphosphino-2',6'-dimethoxybiphenyl.

Examples of the solvent to be used in the reaction include ethers such as THF, ethylene glycol dimethyl ether, tert-butyl methyl ether, and 1,4-dioxane; alcohols such as methanol and ethanol; aliphatic hydrocarbons such as hexane, heptane, and octane; aromatic hydrocarbons such as toluene and xylene; acid amides such as DMF and NMP; water; and mixtures thereof.

Examples of the palladium compound to be used in the reaction include palladium acetate, tetrakistriphenylphosphine palladium, {1,1'-bis(diphenylphosphino)ferrocene}dichloropalladium-methylene chloride complex, and bis(triphenylphosphine)palladium dichloride, and tris(dibenzylideneacetone)dipalladium (0).

The amount of boronic acid compound (19) to be used in the reaction is usually 1 to 5 moles based on 1 mole of Compound (13). The amount of the palladium compound to be used in the reaction is usually 0.01 to 0.5 moles based on 1 mole of Compound (13).

The reaction temperature of the reaction is usually within a range of 50 to 200° C. The reaction time of the reaction is usually within a range of 0.5 to 24 hours.

After the completion of the reaction, Compound (20) can be isolated by post-treatments, for example, extracting the reaction mixture with an organic solvent, followed by drying and concentrating the organic layer. The isolated Compound (20) can be further purified by chromatography, recrystallization, and the like.

(Production Method 16) (Step (E-4))

Compound (23) of the formula (1) wherein n is 0 can be produced by reacting Compound (21) with Compound (22) in the presence of a base:

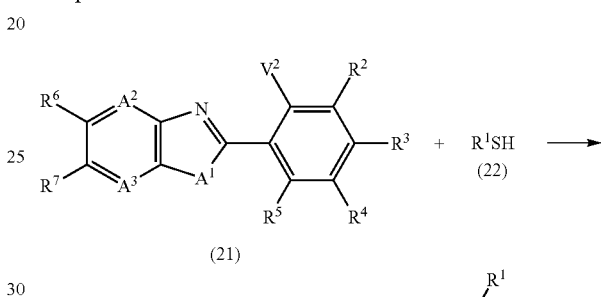

wherein, $R^1$, $R^2$, $R^3$, $R^4$, $R^5$, $R^6$, $R^7$, $A^1$, $A^2$, $A^3$, and $V^2$ are as defined above.

The reaction is usually performed in the presence of a solvent.

Examples of the solvent to be used in the reaction include water; ethers such as THF, ethylene glycol dimethyl ether, tert-butyl methyl ether, and 1,4-dioxane; aromatic hydrocarbons such as toluene and xylene; alcohols such as methanol and ethanol; nitriles such as acetonitrile; acid amides such as DMF and NMP; sulfoxides such as DMSO; and mixtures thereof.

Examples of the base to be used in the reaction include alkali metal hydrides such as sodium hydride.

The amount of Compound (22) to be used in the reaction is usually 1 to 10 moles based on 1 mole of Compound (21). The amount of the base to be used in the reaction is usually 1 to 10 moles based on 1 mole of Compound (21).

The reaction temperature of the reaction is usually within a range of 0 to 150° C. The reaction time of the reaction is usually within a range of 0.5 to 24 hours.

After the completion of the reaction, Compound (23) can be isolated by post-treatments, for example, extracting the reaction mixture with an organic solvent, followed by drying and concentrating the organic layer. The isolated Compound (23) can be further purified by chromatography, recrystallization, and the like.

(Production Method 17) (Step (F-2))

Compound (23) of the formula (1) wherein n is 0 can be produced by reacting Compound (24) with Compound (25) in the presence of a base:

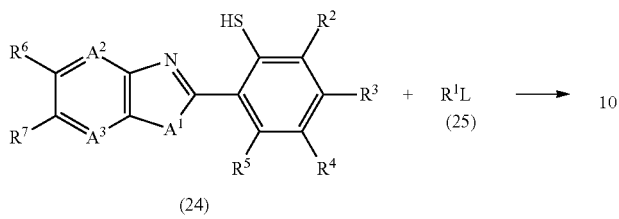

wherein, $R^1$, $R^2$, $R^3$, $R^4$, $R^5$, $R^6$, $R^7$, $A^1$, $A^2$, $A^3$, and L are as defined above.

The reaction is usually performed in the presence of a solvent.

Examples of the solvent to be used in the reaction include ethers such as THF, ethylene glycol dimethyl ether, tert-butyl methyl ether, and 1,4-dioxane; aromatic hydrocarbons such as toluene and xylene; nitriles such as acetonitrile; acid amides such as DMF and NMP; sulfoxides such as DMSO; and mixtures thereof.

Examples of the base to be used in the reaction include hydrides of alkali metal or alkali earth metal such as sodium hydride, potassium hydride, and calcium hydride; inorganic bases such as sodium carbonate and potassium carbonate; and organic bases such as triethylamine.

The amount of the base to be used in the reaction is usually 1 to 3 moles based on 1 mole of Compound (24). The amount of Compound (25) to be used in the reaction is usually 1 to 3 moles based on 1 mole of Compound (24).

The reaction temperature of the reaction is usually within a range of 0 to 100° C. The reaction time of the reaction is usually within a range of 0.1 to 24 hours.

After the completion of the reaction, Compound (23) can be isolated by post-treatments, for example, extracting the reaction mixture with an organic solvent, followed by drying and concentrating the organic layer. The isolated Compound (23) can be further purified by chromatography, recrystallization, and the like.

(Production Method 18)

Compound (26) of the formula (1) wherein n is 1 can be produced by oxidizing Compound (23):

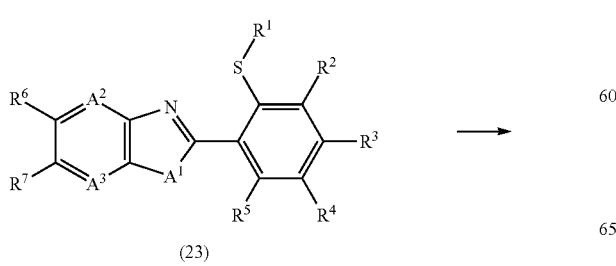

wherein, $R^1$, $R^2$, $R^3$, $R^4$, $R^5$, $R^6$, $R^7$, $A^1$, $A^2$, and $A^3$ are as defined above.

The reaction is usually performed in the presence of a solvent.

Examples of the solvent to be used in the reaction include halogenated hydrocarbons such as dichloromethane and chloroform; alcohols such as methanol and ethanol; acetic acid; water; and mixtures thereof.

Examples of the oxidizing agent to be used in the reaction include sodium periodate or m-chloroperbenzoic acid.

The amount of the oxidizing agent to be used in the reaction is usually 1 to 3 moles based on 1 mole of Compound (23). Preferably, the amount of the oxidizing agent to be used in the reaction is 1 to 1.2 moles based on 1 mole of Compound (23).

The reaction temperature of the reaction is usually within a range of −20 to 80° C. The reaction time of the reaction is usually within a range of 0.1 to 12 hours.

After the completion of the reaction, Compound (26) can be isolated by post-treatments, for example, extracting the reaction mixture with an organic solvent, followed by washing the organic layer with an aqueous solution of a reducing agent (e.g. sodium sulfite, thiosodium sulfate) and an aqueous solution of a base (e.g. sodium hydrogen carbonate) as necessary, followed by drying and concentrating the organic layer. The isolated Compound (26) can be further purified by chromatography, recrystallization, and the like.

(Production Method 19)

Compound (27) of the formula (1) wherein n is 2 can be produced by reacting Compound (23) in the presence of an oxidizing agent:

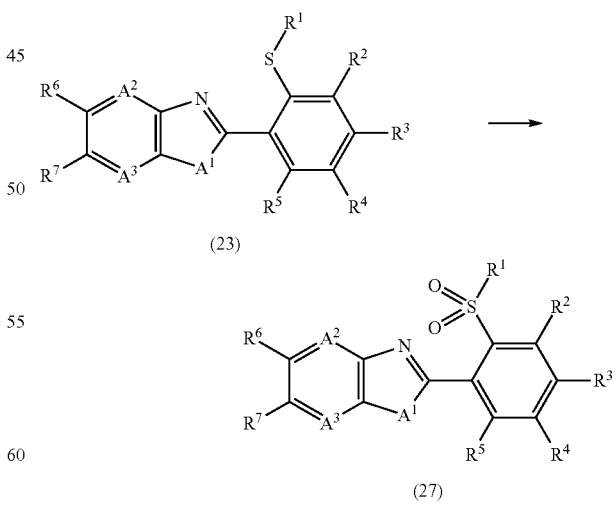

wherein, $R^1$, $R^2$, $R^3$, $R^4$, $R^5$, $R^6$, $R^7$, $A^1$, $A^2$, and $A^3$ are as defined above.

The reaction is usually performed in the presence of a solvent.

Examples of the solvent to be used in the reaction include halogenated hydrocarbons such as dichloromethane and chloroform; alcohols such as methanol and ethanol; acetic acid; water; and mixtures thereof.

Examples of the oxidizing agent to be used in the reaction include m-chloroperbenzoic acid or an aqueous solution of hydrogen peroxide.

The amount of the oxidizing agent to be used in the reaction is usually 2 to 5 moles based on 1 mole of Compound (23). Preferably, the amount of the oxidizing agent to be used in the reaction is 2 to 3 moles based on 1 mole of Compound (23).

The reaction temperature of the reaction is usually within a range of −20 to 120° C. The reaction time of the reaction is usually within a range of 0.1 to 12 hours.

After the completion of the reaction, Compound (27) can be isolated by post-treatments, for example, extracting the reaction mixture with an organic solvent, followed by washing the organic layer with an aqueous solution of a reducing agent (e.g. sodium sulfite, thiosodium sulfate) and an aqueous solution of a base (e.g. sodium hydrogen carbonate) as necessary, followed by drying and concentrating the organic layer. The isolated Compound (27) can be further purified by chromatography, recrystallization, and the like.

(Production Method 20)

Compound (27) of the formula (1) wherein n is 2 can be produced by reacting Compound (26) in the presence of an oxidizing agent:

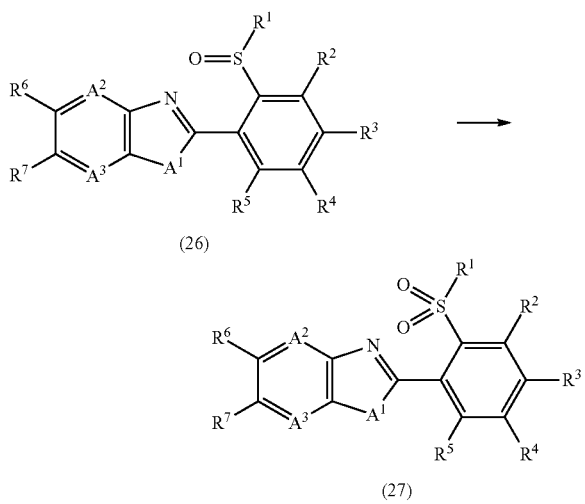

wherein, $R^1$, $R^2$, $R^3$, $R^4$, $R^5$, $R^6$, $R^7$, $A^1$, $A^2$, and $A^3$ are as defined above.

The reaction is usually performed in the presence of a solvent.

Examples of the solvent to be used in the reaction include halogenated hydrocarbons such as dichloromethane and chloroform; alcohols such as methanol and ethanol; acetic acid; water; and mixtures thereof.

Examples of the oxidizing agent to be used in the reaction include m-chloroperbenzoic acid or an aqueous solution of hydrogen peroxide.

The amount of the oxidizing agent to be used in the reaction is usually 1 to 4 moles based on 1 mole of Compound (26). Preferably, the amount of the oxidizing agent to be used in the reaction is 1 to 2 moles based on 1 mole of Compound (26).

The reaction temperature of the reaction is usually within a range of −20 to 120° C. The reaction time of the reaction is usually within a range of 0.1 to 12 hours.

After the completion of the reaction, Compound (27) can be isolated by post-treatments, for example, extracting the reaction mixture with an organic solvent, followed by washing the organic layer with an aqueous solution of a reducing agent (e.g. sodium sulfite, thiosodium sulfate) and an aqueous solution of a base (e.g. sodium hydrogen carbonate) as necessary, followed by drying and concentrating the organic layer. The isolated Compound (27) can be further purified by chromatography, recrystallization, and the like.

(Production Method 21) (Step (A-3), Step (B-3))

Compound (12) of the formula (1) wherein $A^1$ is a sulfur atom can be produced by reacting Compound (35) in the presence of an acid:

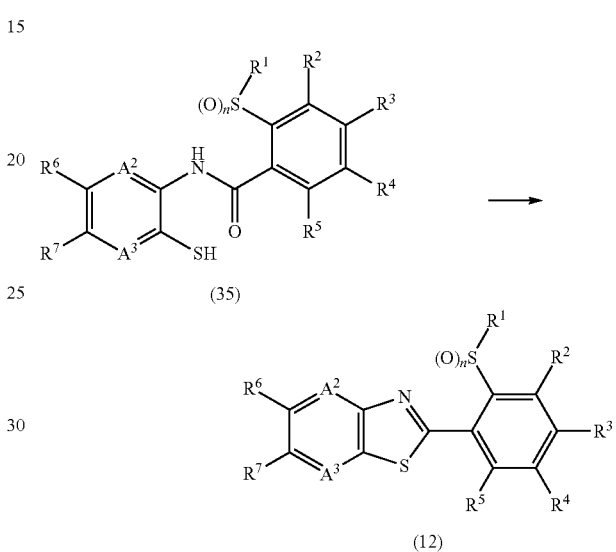

wherein, $R^1$, $R^2$, $R^3$, $R^4$, $R^5$, $R^6$, $R^7$, $A^2$, $A^3$, and n are as defined above.

The reaction is usually performed in the presence of a solvent.

Examples of the solvent to be used in the reaction include ethers such as THF, ethylene glycol dimethyl ether, tert-butyl methyl ether, and 1,4-dioxane; aromatic hydrocarbons such as toluene and xylene; halogenated hydrocarbons such as dichloromethane, chloroform, and chlorobenzene; and mixtures thereof.

Examples of the acid include sulfonic acids such as p-toluenesulfonic acid, and polyphosphoric acid.

The amount of the acid to be used in the reaction is usually 0.1 to 3 moles based on 1 mole of Compound (35).

The reaction temperature of the reaction is usually within a range of 50 to 200° C. The reaction time of the reaction is usually within a range of 1 to 24 hours.

After the completion of the reaction, Compound (12) can be isolated by post-treatments, for example, extracting the reaction mixture with an organic solvent, followed by drying and concentrating the organic layer. The isolated Compound (12) can be further purified by chromatography, recrystallization, and the like.

(Production Method 22)

Compound (34-a) of the formula (1) wherein $R^6$ is SH, Compound (34-b) which is a disulfide form of Compound (34-a), Compound (36) of the formula (1) wherein $R^6$ is $SR^{6x}$, and Compound (37) of the formula (1) wherein $R^6$ is $S(O)$ $mR^{6x}$ can be produced, for example, by the following method:

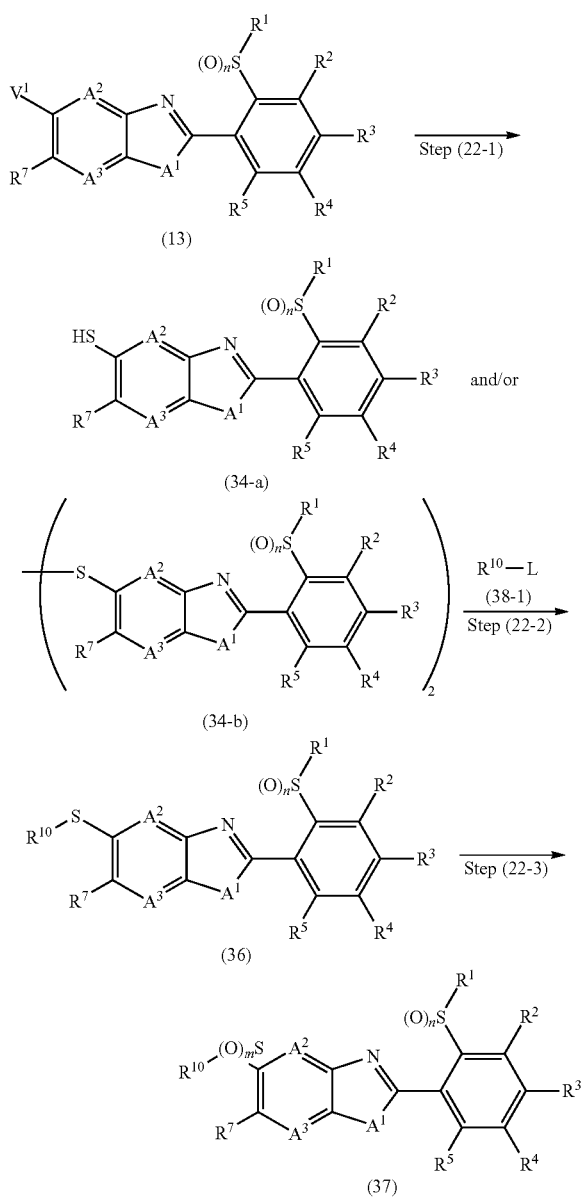

wherein, $R^1$, $R^2$, $R^3$, $R^4$, $R^5$, $R^{10}$, $R^7$, $A^1$, $A^2$, $A^3$, n, m, $V^1$ and L are as defined above.

Step (22-1)

Compound (34-a) and/or Compound (34-b) can be produced by reacting Compound (13) with a thiolating agent in the presence of a catalyst.

The reaction is usually performed in the presence of a solvent.

Examples of the solvent to be used in the reaction include aromatic hydrocarbons such as toluene and xylene; acid amides such as DMF and NMP; sulfoxides such as DMSO; and mixtures thereof.

Examples of the thiolating agent to be used in the reaction include sodium sulfide, sodium sulfide nonahydrate, and thiourea.

Examples of the catalyst to be used in the reaction include copper (I) chloride, copper (I) bromide, and copper (I) iodide.

The reaction can be performed in the presence of a base as necessary.

Examples of the base to be used in the reaction include potassium carbonate, cesium carbonate, tripotassium phosphate, and triethylamine.

The amount of the thiolating agent to be used in the reaction is usually 1 to 10 moles based on 1 mole of Compound (13). The amount of the catalyst to be used in the reaction is usually 0.1 to 5 moles based on 1 mole of Compound (13).

The reaction temperature of the reaction is usually within a range of 50 to 200° C. The reaction time of the reaction is usually within a range of 0.5 to 24 hours.

After the completion of the reaction, Compound (34-a) and/or Compound (34-b) can be isolated by post-treatments, for example, extracting the reaction mixture with an organic solvent, followed by drying and concentrating the organic layer. The isolated Compound (34-a) and/or Compound (34-b) can be further purified by chromatography, recrystallization, and the like.

Step (22-2)

Compound (36) can be produced by reacting Compound (34-a) and/or Compound (34-b) with Compound (38-1) in the presence of a base.

The reaction is usually performed in the presence of a solvent.

Examples of the solvent to be used in the reaction include alcohols such as methanol and ethanol; ethers such as 1,4-dioxane, diethyl ether, THF, and tert-butyl methyl ether; halogenated hydrocarbons such as dichloromethane, chloroform, carbon tetrachloride, 1,2-dichloroethane, and chlorobenzene; hydrocarbons such as toluene, benzene, and xylene; esters such as ethyl acetate and butyl acetate; nitriles such as acetonitrile; aprotic polar solvents such as DMF, NMP, 1,3-dimethyl-2-imidazolidinone, and dimethylsulfoxide; nitrogen-containing aromatic compounds such as pyridine and quinoline; water; and mixtures thereof.

Examples of the base to be used in the reaction include nitrogen-containing heterocyclic compounds such as pyridine, picoline, 2,6-lutidine, DBU, and 1,5-diazabicyclo [4.3.0]-5-nonen; tertiary amines such as triethylamine and N-ethyldiisopropylamine; and inorganic bases such as tripotassium phosphate, potassium carbonate, sodium hydride, sodium hydroxide, and potassium hydroxide.

The amount of Compound (38-1) to be used in the reaction is usually 1 to 10 moles based on 1 mole of Compound (34-a) and/or Compound (34-b). The amount of the base to be used in the reaction is usually 1 to 5 moles based on 1 mole of Compound (34-a) and/or Compound (34-b).

The reaction temperature of the reaction is usually within a range of 0 to 120° C. The reaction time of the reaction is usually within a range of 0.5 to 24 hours.

After the completion of the reaction, Compound (36) can be isolated by post-treatments, for example, extracting the reaction mixture with an organic solvent, followed by drying and concentrating the organic layer. The isolated Compound (36) can be further purified by chromatography, recrystallization, and the like.

Step (22-3)

Compound (37) wherein m is 1 or 2 can be produced by oxidizing Compound (36).

The reaction is usually performed in the presence of a solvent.

Examples of the solvent to be used in the reaction include halogenated hydrocarbons such as dichloromethane and chloroform; alcohols such as methanol and ethanol; acetic acid; water; and mixtures thereof.

Examples of the oxidizing agent to be used in the reaction include m-chloroperbenzoic acid and an aqueous solution of hydrogen peroxide.

The reaction can be performed in the presence of a catalyst as necessary,

Examples of the catalyst to be used in the reaction include sodium tungstate.

The amount of the oxidizing agent to be used in the reaction is usually 1 to 5 moles based on 1 mole of Compound (36).

The reaction temperature of the reaction is usually within a range of −20 to 120° C. The reaction time of the reaction is usually within a range of 0.1 to 12 hours.

After the completion of the reaction, Compound (37) can be isolated by post-treatments, for example, extracting the reaction mixture with an organic solvent, followed by washing the organic layer with an aqueous solution of a reducing agent (e.g. sodium sulfite, thiosodium sulfate) and an aqueous solution of a base (e.g. sodium hydrogen carbonate) as necessary, followed by drying and concentrating the organic layer. The isolated Compound (37) can be further purified by chromatography, recrystallization, and the like.

(Production Method 23)

Compound (39) of the formula (1) wherein $R^6$ is $NH_2$, Compound (40) of the formula (1) wherein $R^5$ is $NHR^{10}$, and Compound (41) of the formula (1) wherein $R^5$ is $NR^{10}R^{11}$ can be produced, for example, by the following method:

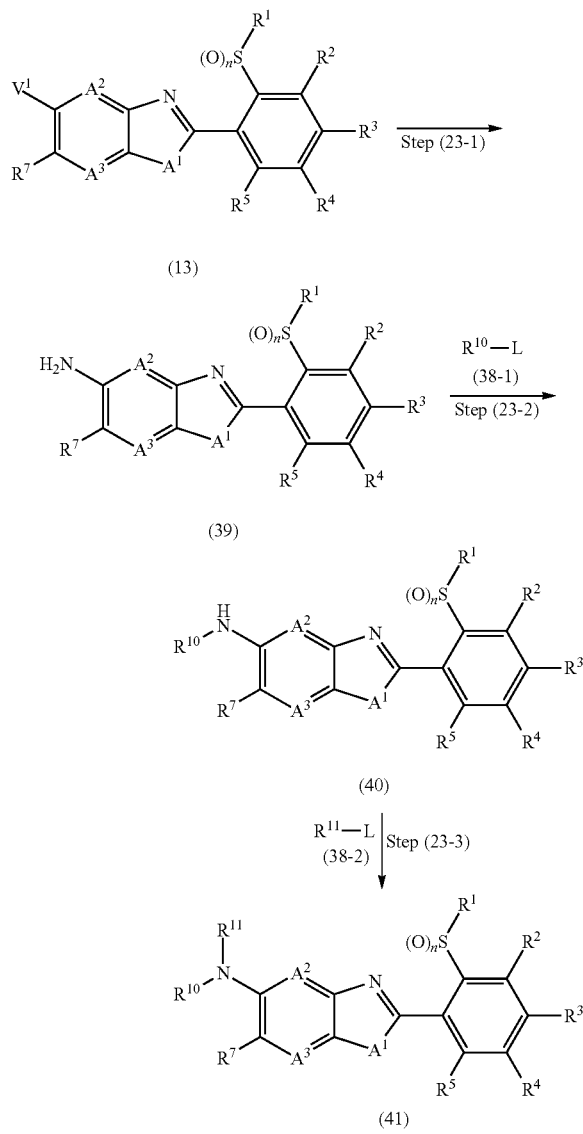

wherein, $R^1$, $R^2$, $R^3$, $R^4$, $R^5$, $R^{10}$, $R^{11}$, $R^7$, $A^1$, $A^2$, $A^3$, n, $V^1$, and L are as defined above.

Step (23-1)

Compound (39) can be produced by aminating Compound (13).

The reaction is usually performed in the presence of a solvent.

Examples of the solvent to be used in the reaction include water; alcohols such as methanol and ethanol; ethers such as 1,4-dioxane, diethyl ether, and THF; esters such as ethyl acetate and butyl acetate; halogenated hydrocarbons such as dichloromethane, chloroform, carbon tetrachloride, and 1,2-dichloroethane; nitriles such as acetonitrile; aprotic polar solvents such as DMF, NMP, and dimethylsulfoxide; nitrogen-containing aromatic compounds such as pyridine and quinoline; and mixtures thereof.

Examples of the aminating agent to be used in the reaction include ammonia, ammonia water, and lithium amide.

Examples of the copper compound to be used in the reaction include copper, copper (I) iodide, copper (I) oxide, copper (II) oxide, copper (II) acetylacetone, copper (II) acetate, and copper (II) sulfate.

A ligand can be added to the reaction as necessary.

Examples of the ligand to be used in the reaction include acetylacetone, salen, and phenanthroline.

A base can be added to the reaction as necessary.

Examples of the base to be used in the reaction include nitrogen-containing heterocyclic compounds such as pyridine, picoline, 2,6-lutidine, DBU, and 1,5-diazabicyclo[4.3.0]-5-nonen; tertiary amines such as triethylamine and N-ethyldiisopropylamine; and inorganic bases such as tripotassium phosphate, potassium carbonate, cesium carbonate, and sodium hydroxide.

The amount of the aminating agent to be used in the reaction is usually 1 to 5 moles based on 1 mole of Compound (13). The amount of the copper compound to be used in the reaction is usually 0.02 to 0.5 moles based on 1 mole of Compound (13). The amount of the ligand to be used in the reaction is 0.02 to 2 moles based on 1 mole of Compound (13) as necessary. The amount of the base to be used in the reaction is 1 to 5 moles based on 1 mole of Compound (13) as necessary.

The reaction temperature of the reaction is usually within a range of 30 to 200° C. The reaction time of the reaction is usually within a range of 0.1 to 24 hours.

After the completion of the reaction, Compound (39) can be isolated by pouring the reaction mixture into water, extracting with an organic solvent, and concentrating the organic layer; pouring the reaction mixture into water, and collecting the generated solids by filtration; or collecting the solids generated in the reaction mixture by filtration. The isolated Compound (39) can be further purified by recrystallization, chromatography, and the like.

Step (23-2)

Compound (40) can be produced by reacting Compound (39) with Compound (38-1) in the presence of a base.

Examples of the solvent to be used in the reaction include ethers such as THF, ethylene glycol dimethyl ether, tert-butyl methyl ether, and 1,4-dioxane; aromatic hydrocarbons such as toluene and xylene; nitriles such as acetonitrile; acid amides such as DMF and NMP; sulfoxides such as DMSO; and mixtures thereof.

Examples of the base to be used in the reaction include hydrides of alkali metal or alkali earth metal such as sodium hydride, potassium hydride, and calcium hydride; inorganic bases such as sodium carbonate and potassium carbonate; and organic bases such as triethylamine.

The amount of Compound (38-1) to be used in the reaction is usually 1 to 5 moles based on 1 mole of Compound (40).

The amount of the base to be used in the reaction is usually 1 to 3 moles based on 1 mole of Compound (40).

The reaction temperature of the reaction is usually within a range of 0 to 100° C. The reaction time of the reaction is usually within a range of 0.1 to 24 hours.

After the completion of the reaction, Compound (40) can be isolated by pouring the reaction mixture into water, extracting with an organic solvent, and concentrating the organic layer; pouring the reaction mixture into water, and collecting the generated solids by filtration; or collecting the solids generated in the reaction mixture by filtration. The isolated Compound (40) can be further purified by recrystallization, chromatography, and the like.

Step (23-3)

Compound (41) can be produced by reacting Compound (40) with Compound (38-2) in the presence of a base.

Examples of the solvent to be used in the reaction include ethers such as THF, ethylene glycol dimethyl ether, tert-butyl methyl ether, and 1,4-dioxane; aromatic hydrocarbons such as toluene and xylene; nitriles such as acetonitrile; acid amides such as DMF and NMP; sulfoxides such as DMSO; and mixtures thereof.

Examples of the base to be used in the reaction include hydrides of alkali metal or alkali earth metal such as sodium hydride, potassium hydride, and calcium hydride; inorganic bases such as sodium carbonate and potassium carbonate; and organic bases such as triethylamine.

The amount of Compound (38-2) to be used in the reaction is usually 1 to 5 moles based on 1 mole of Compound (40). The amount of the base to be used in the reaction is usually 1 to 3 moles based on 1 mole of Compound (40).

The reaction temperature of the reaction is usually within a range of 0 to 100° C. The reaction time of the reaction is usually within a range of 0.1 to 24 hours.

After the completion of the reaction, Compound (41) can be isolated by pouring the reaction mixture into water, extracting with an organic solvent, and concentrating the organic layer; pouring the reaction mixture into water, and collecting the generated solids by filtration; or collecting the solids generated in the reaction mixture by filtration. The isolated Compound (41) can be further purified by recrystallization, chromatography, and the like.

(Production Method 24)

Compound (43) of the formula (1) wherein $R^6$ is $OR^{11}$ can be produced, for example, by the following method:

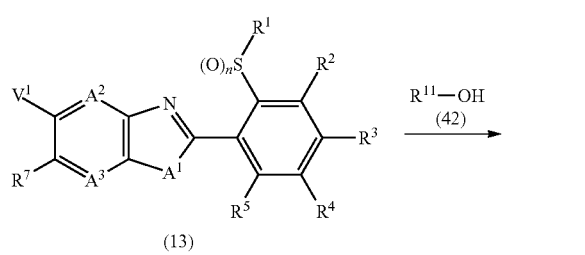
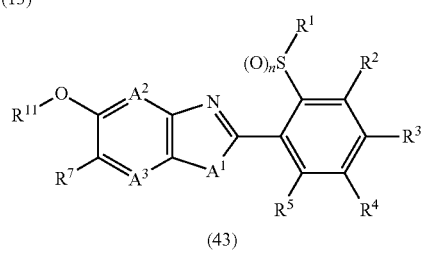

wherein, $R^1$, $R^2$, $R^3$, $R^4$, $R^5$, $R^7$, $R^{11}$, $A^1$, $A^2$, $A^3$, $V^1$, and n are as defined above.

Examples of the solvent to be used in the reaction include ethers such as THF, ethylene glycol dimethyl ether, tert-butyl methyl ether, and 1,4-dioxane; aromatic hydrocarbons such as toluene and xylene; nitriles such as acetonitrile; acid amides such as DMF and NMP; sulfoxides such as DMSO; and mixtures thereof.

Examples of the base to be used in the reaction include hydrides of alkali metal or alkali earth metal such as sodium hydride, potassium hydride, and calcium hydride; inorganic bases such as sodium carbonate, potassium carbonate, and cesium carbonate; and organic bases such as triethylamine.

A copper compound can be added to the reaction as necessary.

Examples of the copper compound to be used in the reaction include copper, copper (I) iodide, copper (I) bromide, and copper (I) chloride.

The amount of Compound (42) to be used in the reaction is usually 1 to 5 moles based on 1 mole of Compound (13). The amount of the base to be used in the reaction is usually 1 to 3 moles based on 1 mole of Compound (13).

The reaction temperature of the reaction is usually within a range of 20 to 250° C. The reaction time of the reaction is usually within a range of 0.1 to 48 hours.

After the completion of the reaction, Compound (43) can be isolated by pouring the reaction mixture into water, extracting with an organic solvent, and concentrating the organic layer; pouring the reaction mixture into water, and collecting the generated solids by filtration; or collecting the solids generated in the reaction mixture by filtration. The isolated Compound (43) can be further purified by recrystallization, chromatography, and the like.

(Production Method 25) (Step (A-1))

Compound (12) of the formula (1) wherein $A^1$ is a sulfur atom can be produced by reacting Compound (11) with Compound (5):

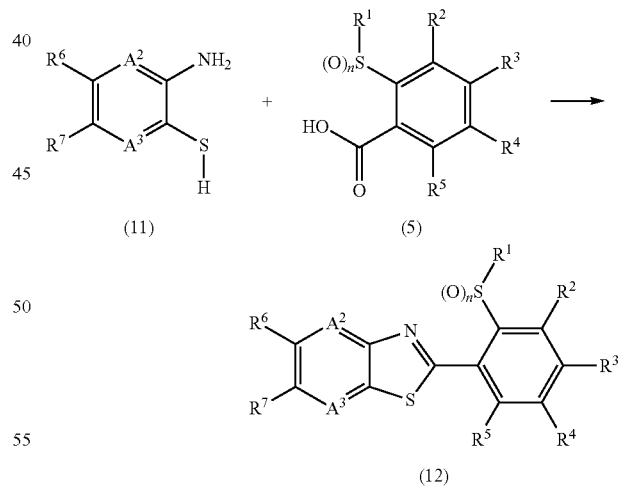

wherein, $R^1$, $R^2$, $R^3$, $R^4$, $R^5$, $R^6$, $R^7$, $A^2$, $A^3$, and n are as defined above.

Compound (12) can be produced according to the method described in Production method 2 using Compound (11) instead of Compound (2).

(Production Method 26) (Production Method D)

Compound (12) of the formula (1) wherein $A^1$ is a sulfur atom can be produced by reacting Compound (1K) with a sulfating agent:

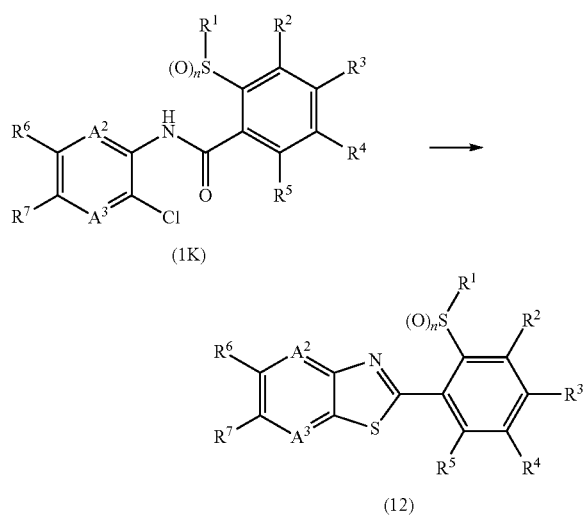

(1K)

(12)

wherein, $R^1$, $R^2$, $R^3$, $R^4$, $R^5$, $R^6$, $R^7$, $A^2$, $A^3$, and n are as defined above.

The reaction is performed in the presence or absence of a solvent.

Examples of the solvent to be used in the reaction include ethers such as 1,4-dioxane, diethyl ether, tetrahydrofuran, tert-butyl methyl ether, and Diglyme; halogenated hydrocarbons such as dichloromethane, chloroform, carbon tetrachloride, 1,2-dichloroethane, and chlorobenzene; hydrocarbons such as toluene, benzene, and xylene; nitrile such as acetonitrile; pyridines such as pyridine, picoline, and lutidine; and mixtures thereof.

Examples of the sulfating agent to be used in the reaction include phosphorus pentasulfide and Lawesson's reagent (2,4-bis-(4-methoxyphenyl)-1,3-dithia-2,4-diphosphetane 2,4-disulfide).

The amount of the sulfating agent to be used in the reaction is usually one or more moles based on 1 mole of Compound (1K).

The reaction temperature of the reaction is usually within a range of 0 to 200° C. The reaction time of the reaction is usually within a range of 1 to 24 hours.

After the completion of the reaction, Compound (12) can be isolated by pouring the reaction mixture into water, extracting with an organic solvent, and concentrating the organic layer; pouring the reaction mixture into water, and collecting the generated solids by filtration; or collecting the solids generated in the reaction mixture by filtration. The isolated Compound (12) can be further purified by recrystallization, chromatography, and the like.

The intermediates of the present invention can be produced, for example, by the following method.
(Production Method of Intermediate 1)

Compound (2) can be produced by the following method:

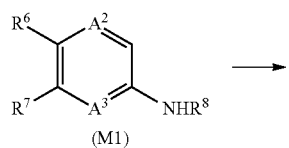

(M1)

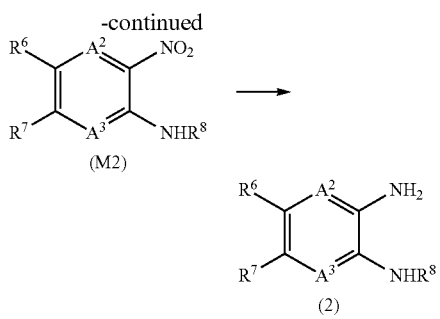

(M2)

(2)

wherein, $R^6$, $R^7$, $R^8$, $A^2$, and $A^3$ are as defined above.
(Step 1)

Compound (M2) can be produced by reacting Compound (M1) in the presence of a nitrating agent.

The reaction is usually performed in the presence of a solvent.

Examples of the solvent to be used in the reaction include halogenated hydrocarbons such as dichloromethane and chloroform, acetic acid, concentrated sulfuric acid, concentrated nitric acid, water and mixtures thereof.

Examples of the nitrating agent to be used in the reaction include concentrated nitric acid.

The amount of the nitrating agent to be used in the reaction is usually 1 to 3 moles based on 1 mole of Compound (M1).

The reaction temperature of the reaction is usually within a range of −10 to 100° C. The reaction time of the reaction is usually within a range of 0.1 to 24 hours.

After the completion of the reaction, Compound (M2) can be isolated by post-treatments, for example, pouring the reaction mixture into water and then extracting the mixture with an organic solvent, followed by drying and concentrating the organic layer. The isolated Compound (M2) can be further purified by chromatography, recrystallization, and the like.
(Step 2)

Compound (2) can be produced by reacting Compound (M2) with hydrogen in the presence of a hydrogenating catalyst.

The reaction is usually performed under 1 to 100 atms of hydrogen in the presence of a catalyst.

Examples of the solvent to be used in the reaction include ethers such as THF, ethylene glycol dimethyl ether, tert-butyl methyl ether, and 1,4-dioxane; esters such as ethyl acetate and butyl acetate; alcohols such as methanol and ethanol; water; and mixtures thereof.

Examples of the hydrogenating catalyst to be used in the reaction include transition metal compounds such as palladium-carbon, palladium hydroxide, Raney® nickel, and platinum oxide.

The amount of hydrogen to be used in the reaction is usually 3 moles based on 1 mole of Compound (M1). The amount of the hydrogenating catalyst to be used in the reaction is usually 0.001 to 0.5 moles based on 1 mole of Compound (M1).

An acid (or base, and the like) can be added to the reaction as necessary.

The reaction temperature of the reaction is usually within a range of −20 to 100° C. The reaction time of the reaction is usually within a range of 0.1 to 24 hours.

After the completion of the reaction, Compound (2) can be isolated by post-treatments, for example, filtrating the reaction mixture and then extracting the mixture with an organic solvent as necessary, followed by drying and concentrating the organic layer. The isolated Compound (2) can be further purified by chromatography, recrystallization, and the like.

(Production Method of Intermediate 2) (Step (A-2))

Compound (6) can be produced by reacting Compound (2) with Compound (5) in the presence of a dehydration-condensing agent:

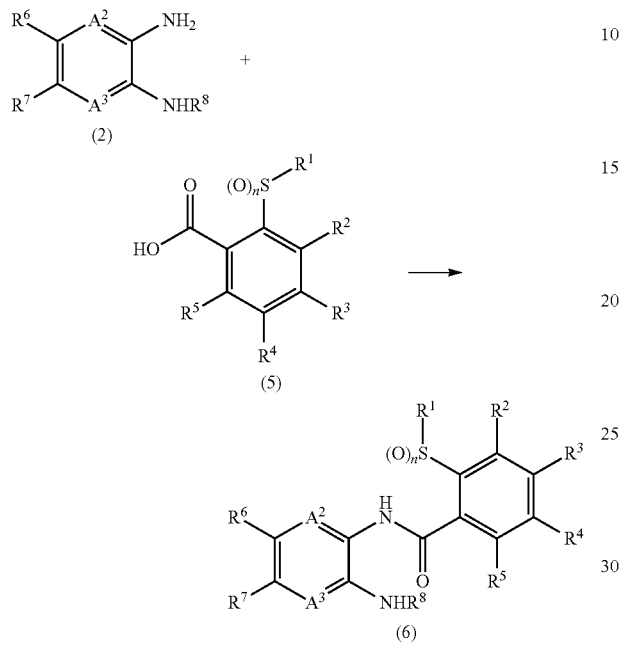

(Production Method of Intermediate 3) (Step (B-2))

Compound (6) can be produced by reacting Compound (2) with Compound (M3) in the presence of a base:

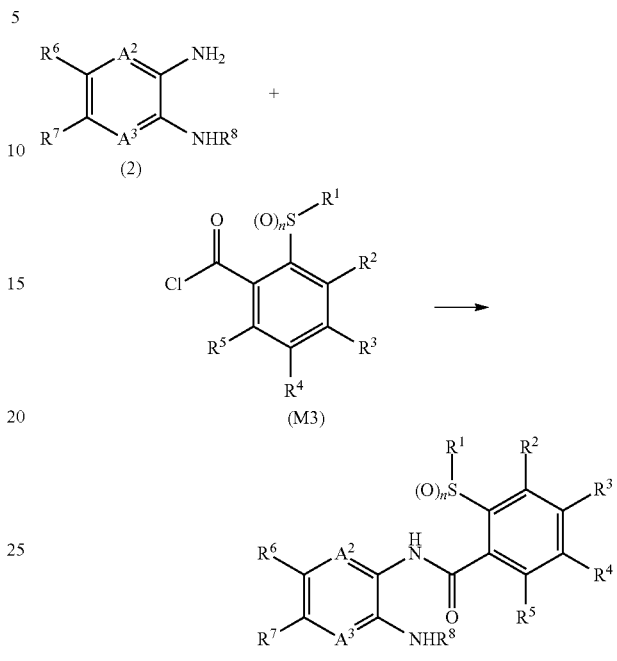

wherein, $R^1$, $R^2$, $R^3$, $R^4$, $R^5$, $R^6$, $R^7$, $R^8$, $A^2$, $A^3$, and n are as defined above.

The reaction is usually performed in the presence of a solvent.

Examples of the solvent to be used in the reaction include ethers such as THF, ethylene glycol dimethyl ether, tert-butyl methyl ether, and 1,4-dioxane; aliphatic hydrocarbons such as hexane, heptane, and octane; aromatic hydrocarbons such as toluene and xylene; halogenated hydrocarbons such as chlorobenzene; esters such as ethyl acetate and butyl acetate; nitriles such as acetonitrile; acid amides such as DMF and NMP; sulfoxides such as DMSO; nitrogen-containing aromatic compounds such as pyridine and quinoline; and mixtures thereof.

Examples of the dehydration-condensing agent to be used in the reaction include carbodiimides such as WSC and 1,3-dicyclohexylcarbodiimide, and BOP reagent.

The amount of Compound (5) to be used in the reaction is usually 1 to 3 moles based on 1 mole of Compound (2). The amount of the dehydration-condensing agent to be used in the reaction is usually 1 to 5 moles based on 1 mole of Compound (2).

The reaction temperature of the reaction is usually within a range of 0 to 140° C. The reaction time of the reaction is usually within a range of 0.1 to 24 hours.

After the completion of the reaction, Compound (6) can be isolated by post-treatments, for example, pouring water into the reaction mixture and then extracting the mixture with an organic solvent, followed by drying and concentrating the organic layer. The isolated Compound (6) can be further purified by chromatography, recrystallization, and the like.

wherein, $R^1$, $R^2$, $R^3$, $R^4$, $R^5$, $R^6$, $R^7$, $R^8$, $A^2$, $A^3$, and n are as defined above.

The reaction is usually performed in the presence of a solvent.

Examples of the solvent to be used in the reaction include ethers such as THF, ethylene glycol dimethyl ether, tert-butyl methyl ether, and 1,4-dioxane; aliphatic hydrocarbons such as hexane, heptane, and octane; aromatic hydrocarbons such as toluene and xylene; halogenated hydrocarbons such as chlorobenzene; esters such as ethyl acetate and butyl acetate; nitriles such as acetonitrile; acid amides such as DMF and NMP; sulfoxides such as DMSO; and mixtures thereof.

Examples of the base include alkali metal carbonates such as sodium carbonate and potassium carbonate; tertiary amines such as triethylamine and diisopropylethylamine; and nitrogen-containing aromatic compounds such as pyridine and 4-dimethylaminopyridine.

The amount of Compound (M3) to be used in the reaction is usually 1 to 3 moles based on 1 mole of Compound (2). The amount of the base to be used in the reaction is usually 1 to 10 moles based on 1 mole of Compound (2).

The reaction temperature of the reaction is usually within a range of −20 to 100° C. The reaction time of the reaction is usually within a range of 0.1 to 24 hours.

After the completion of the reaction, Compound (6) can be isolated by post-treatments, for example, pouring water into the reaction mixture and then extracting the mixture with an organic solvent, followed by drying and concentrating the organic layer. The isolated Compound (6) can be further purified by chromatography, recrystallization, and the like.

(Production Method of Intermediate 4)

Compound (7) can be produced by the following method:

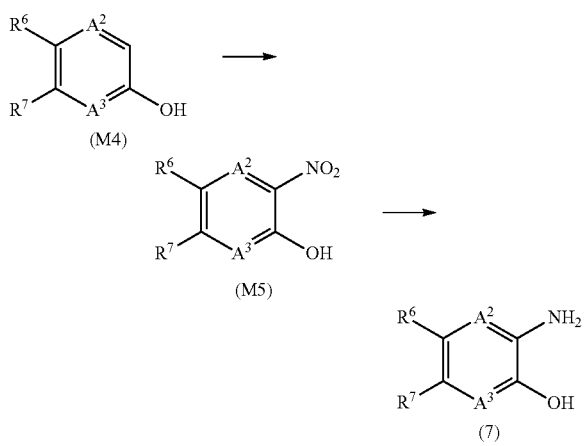

wherein, $R^6$, $R^7$, $A^2$, and $A^3$ are as defined above.

(Step 1)

Compound (M5) can be produced by reacting Compound (M4) in the presence of a nitrating agent.

The reaction is usually performed in the presence of a solvent.

Examples of the solvent to be used in the reaction include halogenated hydrocarbons such as chloroform, acetic acid, concentrated sulfuric acid, concentrated nitric acid, water, and mixtures thereof.

Examples of the nitrating agent to be used in the reaction include concentrated nitric acid.

The amount of the nitrating agent to be used in the reaction is usually 1 to 3 moles based on 1 mole of Compound (M4).

The reaction temperature of the reaction is usually within a range of −10 to 100° C. The reaction time of the reaction is usually within a range of 0.1 to 24 hours.

After the completion of the reaction, Compound (M5) can be isolated by post-treatments, for example, pouring the reaction mixture into water and then extracting the mixture with an organic solvent, followed by drying and concentrating the organic layer. The isolated Compound (M5) can be further purified by chromatography, recrystallization, and the like.

(Step 2)

Compound (7) can be produced by reacting Compound (M5) with hydrogen in the presence of a hydrogenating catalyst.

The reaction is usually performed under 1 to 100 atms of hydrogen in the presence of a catalyst.

Examples of the solvent to be used in the reaction include ethers such as THF, ethylene glycol dimethyl ether, tert-butyl methyl ether, and 1,4-dioxane; esters such as ethyl acetate and butyl acetate; alcohols such as methanol and ethanol; water; and mixtures thereof.

Examples of the hydrogenating catalyst to be used in the reaction include transition metal compounds such as palladium-carbon, palladium hydroxide, Raney® nickel, and platinum oxide.

The amount of hydrogen to be used in the reaction is usually 3 moles based on 1 mole of Compound (M5). The amount of the hydrogenating catalyst to be used in the reaction is usually 0.001 to 0.5 moles based on 1 mole of Compound (M5).

An acid (or base, and the like) can be added to the reaction as necessary.

The reaction temperature of the reaction is usually within a range of −20 to 100° C. The reaction time of the reaction is usually within a range of 0.1 to 24 hours.

After the completion of the reaction, Compound (7) can be isolated by post-treatments, for example, filtrating the reaction mixture and then extracting the mixture with an organic solvent as necessary, followed by drying and concentrating the organic layer. The isolated Compound (7) can be further purified by chromatography, recrystallization, and the like.

(Production Method of Intermediate 5) (Step (C-2))

Compound (9) can be produced by reacting Compound (7) with Compound (3):

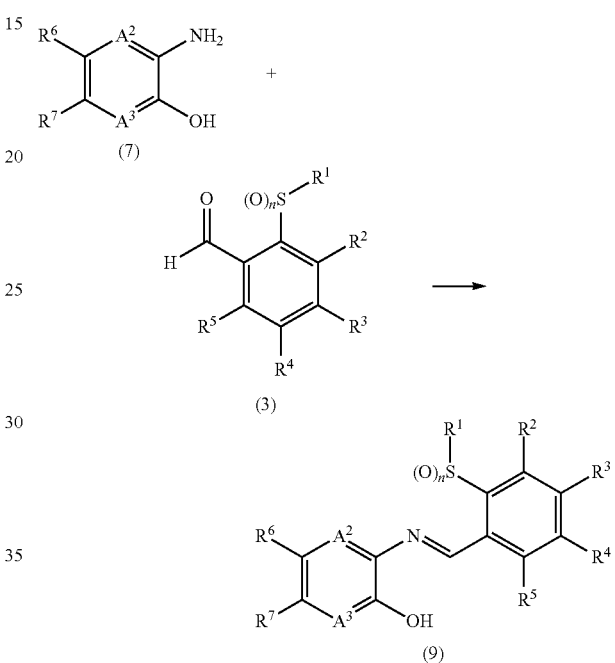

wherein, $R^1$, $R^2$, $R^3$, $R^4$, $R^5$, $R^6$, $R^7$, $A^2$, $A^3$, and n are as defined above.

The reaction is usually performed in the presence of a solvent.

Examples of the solvent to be used in the reaction include alcohols such as methanol and ethanol; ethers such as THF, ethylene glycol dimethyl ether, tert-butyl methyl ether, and 1,4-dioxane; aromatic hydrocarbons such as toluene and xylene; and mixtures thereof.

The amount of Compound (3) to be used in the reaction is usually 1 to 3 moles based on 1 mole of Compound (7).

An acid or base can be added to the reaction as necessary.

The reaction temperature of the reaction is usually within a range of 0 to 150° C. The reaction time of the reaction is usually within a range of 0.1 to 24 hours.

After the completion of the reaction, Compound (9) can be isolated by post-treatments, for example, extracting the reaction mixture with an organic solvent, followed by drying and concentrating the organic layer. The isolated Compound (9) can be further purified by chromatography, recrystallization, and the like.

(Production Method of Intermediate 6) (Step (A-2))

Compound (10) can be produced by reacting Compound (7) with Compound (5) in the presence of a dehydration-condensing agent:

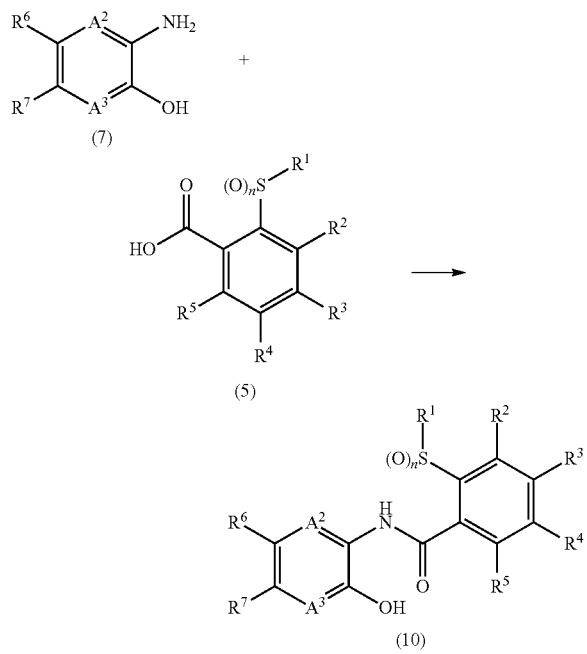

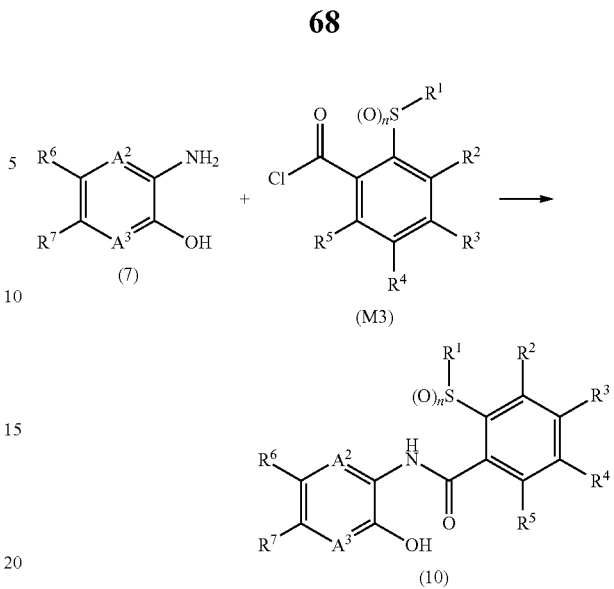

wherein, $R^1$, $R^2$, $R^3$, $R^4$, $R^5$, $R^6$, $R^7$, $A^2$, $A^3$, and n are as defined above.

The reaction is usually performed in the presence of a solvent.

Examples of the solvent to be used in the reaction include ethers such as THF, ethylene glycol dimethyl ether, tert-butyl methyl ether, and 1,4-dioxane; aliphatic hydrocarbons such as hexane, heptane, and octane; aromatic hydrocarbons such as toluene and xylene; halogenated hydrocarbons such as chlorobenzene; esters such as ethyl acetate and butyl acetate; nitriles such as acetonitrile; acid amides such as DMF and NMP; sulfoxides such as DMSO; nitrogen-containing aromatic compounds such as pyridine and quinoline; and mixtures thereof.

Examples of the dehydration-condensing agent to be used in the reaction include carbodiimides such as WSC and 1,3-dicyclohexylcarbodiimide, and BOP reagent.

The amount of Compound (5) to be used in the reaction is usually 1 to 3 moles based on 1 mole of Compound (7). The amount of the dehydration-condensing agent to be used in the reaction is usually 1 to 5 moles based on 1 mole of Compound (7).

The reaction temperature of the reaction is usually within a range of 0 to 140° C. The reaction time of the reaction is usually within a range of 0.1 to 24 hours.

After the completion of the reaction, Compound (10) can be isolated by post-treatments, for example, pouring water into the reaction mixture and then extracting the mixture with an organic solvent, followed by drying and concentrating the organic layer. The isolated Compound (10) can be further purified by chromatography, recrystallization, and the like.

(Production Method of Intermediate 7) (Step (B-2))

Compound (10) cab be produced by reacting Compound (7) with Compound (M3) in the presence of a base:

wherein, $R^1$, $R^2$, $R^3$, $R^4$, $R^5$, $R^6$, $R^7$, $A^2$, $A^3$, and n are as defined above.

The reaction is usually performed in the presence of a solvent.

Examples of the solvent to be used in the reaction include ethers such as THF, ethylene glycol dimethyl ether, tert-butyl methyl ether, and 1,4-dioxane; aliphatic hydrocarbons such as hexane, heptane, and octane; aromatic hydrocarbons such as toluene and xylene; halogenated hydrocarbons such as chlorobenzene; esters such as ethyl acetate and butyl acetate; nitriles such as acetonitrile; acid amides such as DMF and NMP; sulfoxides such as DMSO; and mixtures thereof.

Examples of the base to be used in the reaction include alkali metal carbonates such as sodium carbonate and potassium carbonate; tertiary amines such as triethylamine and diisopropylethylamine; and nitrogen-containing aromatic compounds such as pyridine and 4-dimethylaminopyridine.

The amount of Compound (M3) to be used in the reaction is usually 1 to 3 moles based on 1 mole of Compound (7). The amount of the base to be used in the reaction is usually 1 to 10 moles based on 1 mole of Compound (7).

The reaction temperature of the reaction is usually within a range of –20 to 100° C. The reaction time of the reaction is usually within a range of 0.1 to 24 hours.

After the completion of the reaction, Compound (10) can be isolated by post-treatments, for example, pouring water into the reaction mixture and then extracting the mixture with an organic solvent, followed by drying and concentrating the organic layer. The isolated Compound (10) can be further purified by chromatography, recrystallization, and the like.

(Production Method of Intermediate 8)

Compound (11) can be produced by the following method:

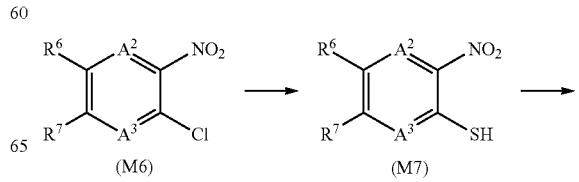

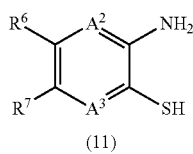

(11)

wherein, $R^6$, $R^7$, $A^2$, and $A^3$ are as defined above.

(Step 1)

Compound (M7) can be produced by reacting Compound (M6) with thiourea in the presence of a base.

The reaction is usually performed in the presence of a solvent.

Examples of the solvent to be used in the reaction include alcohols such as methanol and ethanol; water; and mixtures thereof.

Examples of the base to be used in the reaction include alkali metal hydroxides such as sodium hydroxide and potassium hydroxide.

The amount of thiourea to be used in the reaction is usually 0.5 to 3 moles based on 1 mole of Compound (M6). The amount of the base to be used in the reaction is usually 1 to 10 moles based on 1 mole of Compound (M6).

The reaction temperature of the reaction is usually within a range of 0 to 100° C. The reaction time of the reaction is usually within a range of 0.1 to 24 hours.

After the completion of the reaction, Compound (M7) can be isolated by post-treatments, for example, pouring an acid into the reaction mixture and then extracting the mixture with an organic solvent, followed by drying and concentrating the organic layer. The isolated Compound (M7) can be further purified by chromatography, recrystallization, and the like.

(Step 2)

Compound (11) can be produced by reducing Compound (M7).

The reduction reaction can be performed, for example, in the presence of a reducing agent such as iron powder and zinc powder; acids such as hydrochloric acid and acetic acid; and water.

The reaction can be usually performed in the presence of a solvent.

Examples of the solvent to be used in the reaction include ethers such as THF, ethylene glycol dimethyl ether, tert-butyl methyl ether, and 1,4-dioxane; esters such as ethyl acetate and butyl acetate; alcohols such as methanol and ethanol; acid amides such as DMF and NMP; and mixtures thereof.

The amount of the reducing agent to be used in the reaction is usually 3 to 10 moles based on 1 mole of Compound (M7).

The reaction temperature of the reaction is usually within a range of 0 to 100° C. The reaction time of the reaction is usually within a range of 0.1 to 24 hours.

After the completion of the reaction, Compound (11) can be isolated by post-treatments, for example, adding water to the reaction mixture and then extracting the mixture with an organic solvent, followed by drying and concentrating the organic layer. The isolated Compound (11) can be further purified by chromatography, recrystallization, and the like.

(Production Method of Intermediate 9)

Compound (28) of Compound (21) wherein $A^1$ is —$NR^8$— can be produced by reacting Compound (2) with Compound (M8) in the presence of a base:

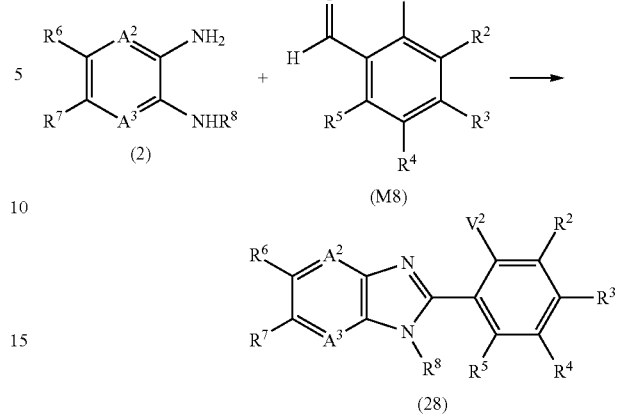

wherein, $R^2$, $R^3$, $R^4$, $R^5$, $R^6$, $R^7$, $R^8$, $A^2$, $A^3$, and $V^2$ are as defined above.

The reaction is usually performed in the presence of a solvent.

Examples of the base to be used in the reaction include hydrogen carbonates such as sodium hydrogen carbonate and potassium hydrogen carbonate; carbonates such as sodium carbonate and potassium carbonate; sulfites such as sodium sulfite and potassium sulfite; and mixtures thereof.

Examples of the solvent to be used in the reaction include ethers such as THF, ethylene glycol dimethyl ether, tert-butyl methyl ether, and 1,4-dioxane; aliphatic hydrocarbons such as hexane, heptane, and octane; aromatic hydrocarbons such as toluene and xylene; halogenated hydrocarbons such as chlorobenzene; esters such as ethyl acetate and butyl acetate; nitriles such as acetonitrile; acid amides such as DMF and NMP; sulfoxides such as DMSO; nitrogen-containing aromatic compounds such as pyridine and quinoline; and mixtures thereof.

The amount of Compound (M8) to be used in the reaction is usually 1 to 3 moles based on 1 mole of Compound (2). The amount of the base to be used in the reaction is usually 1 to 5 moles based on 1 mole of Compound (2).

The reaction temperature of the reaction is usually within a range of 30 to 200° C. The reaction time of the reaction is usually within a range of 0.1 to 24 hours.

After the completion of the reaction, Compound (28) can be isolated by post-treatments, for example, pouring water into the reaction mixture and then extracting the mixture with an organic solvent, followed by drying and concentrating the organic layer. The isolated Compound (28) can be further purified by chromatography, recrystallization, and the like.

(Production Method of Intermediate 10) (Step (E-1))

Compound (28) of Compound (21) wherein $A^1$ is —$NR^8$— can be produced by reacting Compound (2) with Compound (M9) in the presence of a dehydration-condensing agent:

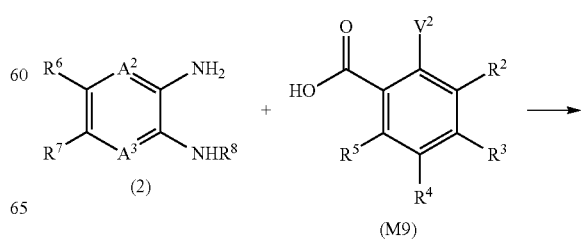

-continued

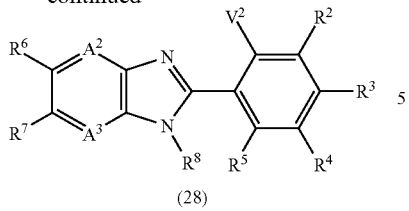

(28)

wherein, $R^2$, $R^3$, $R^4$, $R^5$, $R^6$, $R^7$, $R^8$, $A^2$, $A^3$, and $V^2$ are as defined above.

The reaction is usually performed in the presence of a solvent.

Examples of the solvent to be used in the reaction include ethers such as THF, tert-butyl methyl ether, ethylene glycol dimethyl ether, and 1,4-dioxane; aliphatic hydrocarbons such as hexane, heptane, and octane; aromatic hydrocarbons such as toluene and xylene; halogenated hydrocarbons such as chlorobenzene; esters such as ethyl acetate and butyl acetate; nitriles such as acetonitrile; acid amides such as DMF and NMP; sulfoxides such as DMSO; nitrogen-containing aromatic compounds such as pyridine and quinoline; and mixtures thereof.

Examples of the dehydration-condensing agent to be used in the reaction include carbodiimides such as WSC and 1,3-dicyclohexylcarbodiimide, and BOP reagent.

A catalyst can be added to the reaction as necessary.

Examples of the catalyst to be used in the reaction include 1-hydroxybenzotriazole (hereinafter referred to as HOBt).

The amount of Compound (M9) to be used in the reaction is usually 1 to 3 moles based on 1 mole of Compound (2). The amount of the dehydration-condensing agent to be used in the reaction is usually 1 to 5 moles based on 1 mole of Compound (2). The amount of the catalyst to be used in the reaction is usually 0.01 to 0.1 moles based on 1 mole of Compound (2).

The reaction temperature of the reaction is usually within a range of 30 to 200° C. The reaction time of the reaction is usually within a range of 0.1 to 24 hours.

After the completion of the reaction, Compound (28) can be isolated by post-treatments, for example, pouring water into the reaction mixture and then extracting the mixture with an organic solvent, followed by drying and concentrating the organic layer. The isolated Compound (28) can be further purified by chromatography, recrystallization, and the like.

(Production Method of Intermediate 11) (Step (E-3))

Compound (28) of Compound (21) wherein $A^1$ is —$NR^8$— can be produced by dehydration-condensing Compound (M10):

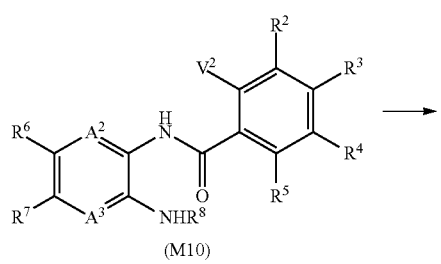

(M10)

-continued

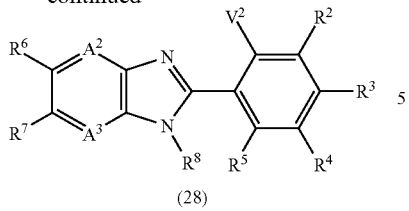

(28)

wherein, $R^2$, $R^3$, $R^4$, $R^5$, $R^6$, $R^7$, $R^8$, $A^2$, $A^3$, and $V^2$ are as defined above.

The reaction is usually performed in the presence of a solvent.

Examples of the solvent to be used in the reaction include ethers such as THF, ethylene glycol dimethyl ether, tert-butyl methyl ether, and 1,4-dioxane; aliphatic hydrocarbons such as hexane, heptane, and octane; aromatic hydrocarbons such as toluene and xylene; halogenated hydrocarbons such as chlorobenzene; esters such as ethyl acetate and butyl acetate; nitriles such as acetonitrile; acid amides such as DMF and NMP; sulfoxides such as DMSO; alcohols such as methanol, ethanol, propanol, butanol, and pentanol; and mixtures thereof.

In the reaction, an acid or a dehydrating agent can be used as necessary. Examples of the acid to be used in the reaction include sulfonic acids such as p-toluenesulfonic acid, and carboxylic acids such as acetic acid. Examples of the dehydrating agent to be used in the reaction include phosphorous oxychloride, acetic anhydride, and trifluoroacetic anhydride.

The amount of the acid or dehydrating agent to be used in the reaction is usually 1 to 10 moles based on 1 mole of Compound (M10).

The reaction temperature of the reaction is usually within a range of 30 to 200° C. The reaction time of the reaction is usually within a range of 0.1 to 24 hours.

After the completion of the reaction, Compound (28) can be isolated by post-treatments, for example, extracting the reaction mixture with an organic solvent, followed by drying and concentrating the organic layer. The isolated Compound (28) can be further purified by chromatography, recrystallization, and the like.

(Production Method of Intermediate 12) (Step (E-3))

Compound (28) of Compound (21) wherein $A^1$ is —$NR^8$— can be produced by reacting Compound (M10) in the presence of a base:

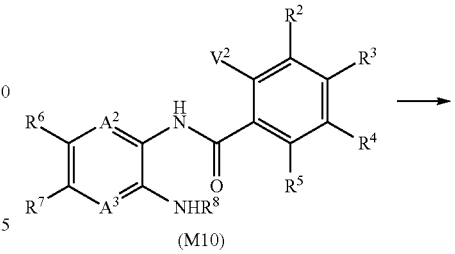

(M10)

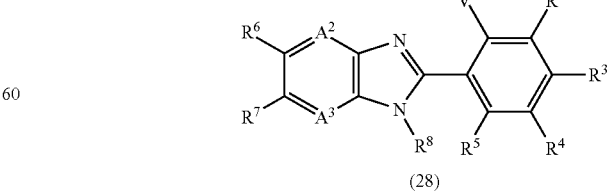

(28)

wherein, $R^2$, $R^3$, $R^4$, $R^5$, $R^6$, $R^7$, $R^8$, $A^2$, $A^3$, and $V^2$ are as defined above.

The reaction is usually performed in the presence of a solvent.

Examples of the solvent to be used in the reaction include ethers such as THF, ethylene glycol dimethyl ether, tert-butyl methyl ether, and 1,4-dioxane; aliphatic hydrocarbons such as hexane, heptane, and octane; aromatic hydrocarbons such as toluene and xylene; halogenated hydrocarbons such as chlorobenzene; esters such as ethyl acetate and butyl acetate; nitriles such as acetonitrile; acid amides such as DMF and NMP; sulfoxides such as DMSO; alcohols such as methanol, ethanol, propanol, butanol, tert-butanol, and pentanol; and mixtures thereof.

Examples of the base to be used in the reaction include tripotassium phosphate.

The amount of the base to be used in the reaction is usually 1 to 10 moles based on 1 mole of Compound (M10).

The reaction temperature of the reaction is usually within a range of 30 to 200° C. The reaction time of the reaction is usually within a range of 0.1 to 24 hours.

After the completion of the reaction, Compound (28) can be isolated by post-treatments, for example, extracting the reaction mixture with an organic solvent, followed by drying and concentrating the organic layer. The isolated Compound (28) can be further purified by chromatography, recrystallization, and the like.

(Production Method of Intermediate 13) (Step (E-2))

Compound (M10) can be produced by reacting Compound (2) with Compound (M9) in the presence of a dehydration-condensing agent:

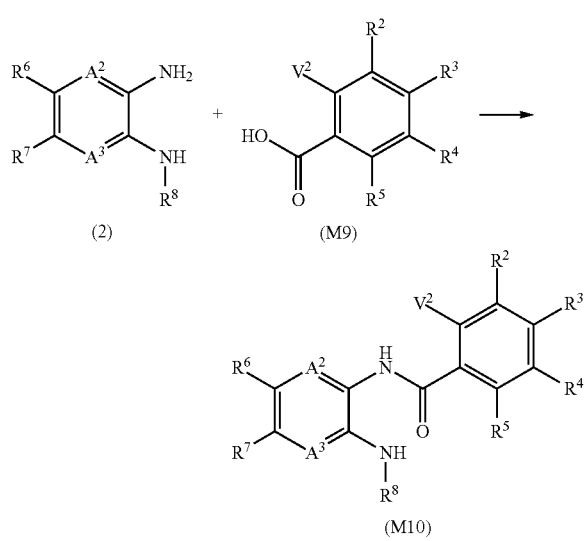

wherein, $R^2$, $R^3$, $R^4$, $R^5$, $R^6$, $R^7$, $R^8$, $A^2$, $A^3$, and $V^2$ are as defined above.

The reaction is usually performed in the presence of a solvent.

Examples of the solvent to be used in the reaction include ethers such as THF, ethylene glycol dimethyl ether, tert-butyl methyl ether, and 1,4-dioxane; aliphatic hydrocarbons such as hexane, heptane, and octane; aromatic hydrocarbons such as toluene and xylene; halogenated hydrocarbons such as chlorobenzene; esters such as ethyl acetate and butyl acetate; nitriles such as acetonitrile; acid amides such as DMF and NMP; sulfoxides such as DMSO; nitrogen-containing aromatic compounds such as pyridine and quinoline; and mixtures thereof.

Examples of the dehydration-condensing agent to be used in the reaction include carbodiimides such as WSC and 1,3-dicyclohexylcarbodiimide, and BOP reagent.

The amount of Compound (M9) to be used in the reaction is usually 1 to 3 moles based on 1 mole of Compound (2). The amount of the dehydration-condensing agent to be used in the reaction is usually 1 to 5 moles based on 1 mole of Compound (2).

The reaction temperature of the reaction is usually within a range of 0 to 140° C. The reaction time of the reaction is usually within a range of 0.1 to 24 hours.

After the completion of the reaction, Compound (M10) can be isolated by post-treatments, for example, pouring water into the reaction mixture and then extracting the mixture with an organic solvent, followed by drying and concentrating the organic layer. The isolated Compound (M10) can be further purified by chromatography, recrystallization, and the like.

(Production Method of Intermediate 14)

Compound (M10) can be produced by reacting Compound (2) with Compound (M12) in the presence of a base:

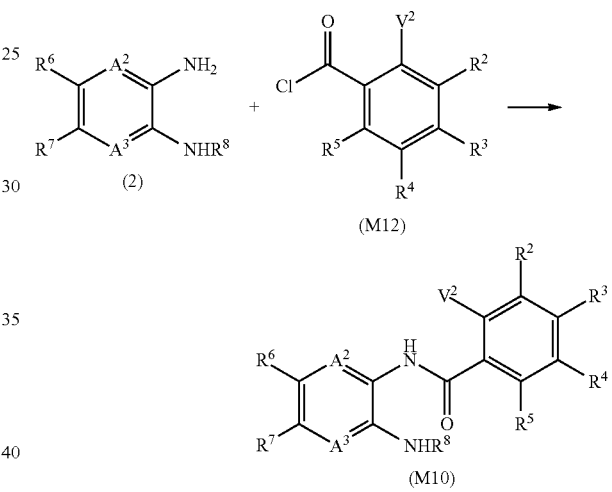

wherein, $R^2$, $R^3$, $R^4$, $R^5$, $R^6$, $R^7$, $R^8$, $A^2$, $A^3$, and $V^2$ are as defined above.

The reaction is usually performed in the presence of a solvent.

Examples of the solvent to be used in the reaction include ethers such as THF, ethylene glycol dimethyl ether, tert-butyl methyl ether, and 1,4-dioxane; aliphatic hydrocarbons such as hexane, heptane, and octane; aromatic hydrocarbons such as toluene and xylene; halogenated hydrocarbons such as chlorobenzene; esters such as ethyl acetate and butyl acetate; nitriles such as acetonitrile; acid amides such as DMF and NMP; sulfoxides such as DMSO; and mixtures thereof.

Examples of the base include alkali metal carbonates such as sodium carbonate and potassium carbonate; tertiary amines such as triethylamine and diisopropylethylamine; and nitrogen-containing aromatic compounds such as pyridine and 4-dimethylaminopyridine.

The amount of Compound (M12) to be used in the reaction is usually 1 to 3 moles based on 1 mole of Compound (2). The amount of the base to be used in the reaction is usually 1 to 10 moles based on 1 mole of Compound (2).

The reaction temperature of the reaction is usually within a range of −20 to 100° C. The reaction time of the reaction is usually within a range of 0.1 to 24 hours.

After the completion of the reaction, Compound (M10) can be isolated by post-treatments, for example, pouring water into the reaction mixture and then extracting the mixture with an organic solvent, followed by drying and concentrating the organic layer. The isolated Compound (M10) can be further purified by chromatography, recrystallization, and the like.
(Production Method of Intermediate 15)

Compound (29) of Compound (3) wherein n is 0 can be produced by the following method:

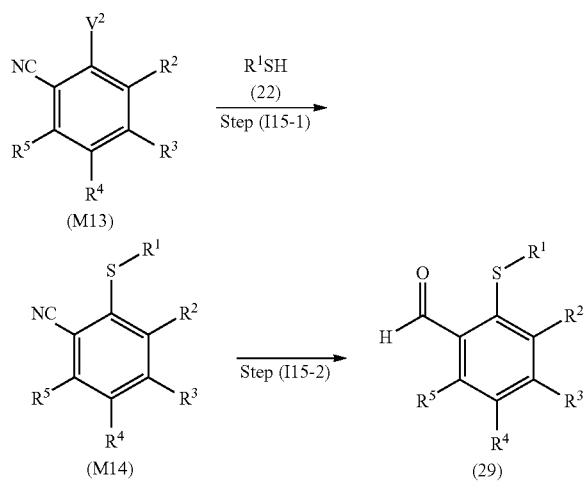

wherein, $R^1$, $R^2$, $R^3$, $R^4$, $R^5$, and $V^2$ are as defined above.
(Step I15-1)

Compound (M14) can be produced by reacting Compound (M13) with Compound (22) in the presence of a base.

The reaction is usually performed in the presence of a solvent.

Examples of the solvent to be used in the reaction include ethers such as THF, ethylene glycol dimethyl ether, tert-butyl methyl ether, and 1,4-dioxane; aromatic hydrocarbons such as toluene and xylene; nitriles such as acetonitrile; acid amides such as DMF and NMP; sulfoxides such as DMSO; and mixtures thereof.

Examples of the base to be used in the reaction include alkali metal hydrides such as sodium hydride.

The amount of Compound (22) to be used in the reaction is usually 1 to 3 moles based on 1 mole of Compound (M13). The amount of the base to be used in the reaction is usually 1 to 10 moles based on 1 mole of Compound (M13).

The reaction temperature of the reaction is usually within a range of 0 to 150° C. The reaction time of the reaction is usually within a range of 0.5 to 24 hours.

After the completion of the reaction, Compound (M14) can be isolated by post-treatments, for example, extracting the reaction mixture with an organic solvent, followed by drying and concentrating the organic layer. The isolated Compound (M14) can be further purified by chromatography, recrystallization, and the like.
(Step I15-2)

Compound (29) can be produced by reducing Compound (M14).

The reaction is usually performed in the presence of a solvent.

Examples of the solvent to be used in the reaction include ethers such as THF, ethylene glycol dimethyl ether, tert-butyl methyl ether, and 1,4-dioxane; aromatic hydrocarbons such as toluene and xylene; halogenated hydrocarbons such as dichloromethane and chloroform; and mixtures thereof.

Examples of the reducing agent to be used in the reaction include diisobutylaluminium hydrate.

The amount of the reducing agent to be used in the reaction is usually 1 to 2 moles based on 1 mole of Compound (M14).

The reaction temperature of the reaction is usually within a range of −20 to 100° C. The reaction time of the reaction is usually within a range of 0.5 to 24 hours.

After the completion of the reaction, Compound (29) can be isolated by post-treatments, for example, extracting the reaction mixture with an organic solvent, followed by drying and concentrating the organic layer. The isolated Compound (29) can be further purified by chromatography, recrystallization, and the like.

(Production Method of Intermediate 16)

Compound (29) of Compound (3) wherein n is 0 can be produced by reacting Compound (M8) with Compound (22) in the presence of a base:

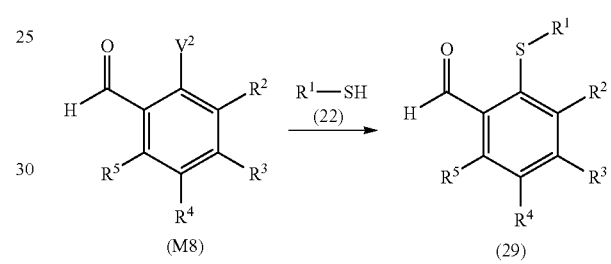

wherein, $R^1$, $R^2$, $R^3$, $R^4$, $R^5$, and $V^2$ are as defined above.

The reaction is usually performed in the presence of a solvent.

Examples of the solvent to be used in the reaction include ethers such as THF, ethylene glycol dimethyl ether, tert-butyl methyl ether, and 1,4-dioxane; aromatic hydrocarbons such as toluene and xylene; nitriles such as acetonitrile; acid amides such as DMF and NMP; sulfoxides such as DMSO; and mixtures thereof.

Examples of the base to be used in the reaction include alkali metal hydrides such as sodium hydride.

The amount of Compound (22) to be used in the reaction is usually 1 to 10 moles based on 1 mole of Compound (M15). The amount of the base to be used in the reaction is usually 1 to 10 moles based on 1 mole of Compound (M8).

The reaction temperature of the reaction is usually within a range of 0 to 150° C. The reaction time of the reaction is usually within a range of 0.5 to 24 hours.

After the completion of the reaction, Compound (29) can be isolated by post-treatments, for example, extracting the reaction mixture with an organic solvent, followed by drying and concentrating the organic layer. The isolated Compound (29) can be further purified by chromatography, recrystallization, and the like.

(Production Method of Intermediate 17)

Compound (30) of Compound (5) wherein n is 0 can be produced by hydrolyzing Compound (M14) in the presence of a base, and Compound (M23) of Compound (5) wherein n is 1 or 2 can be produced by the following method:

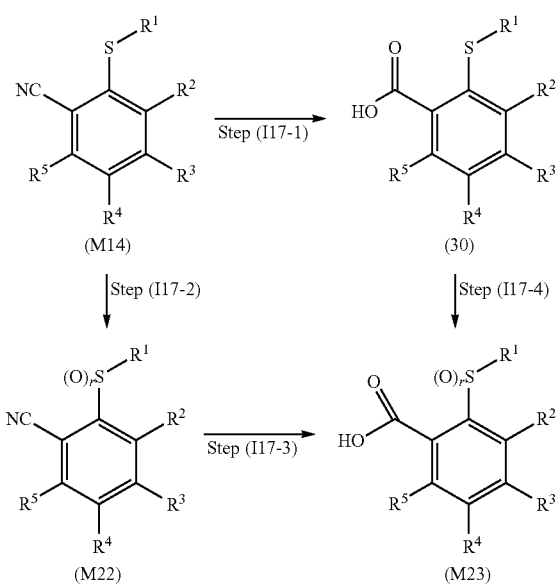

wherein, $R^1$, $R^2$, $R^3$, $R^4$, and $R^5$ are as defined above, and r represents 1 or 2.

(Step I17-1)

The reaction is usually performed in the presence of a solvent.

Examples of the solvent to be used in the reaction include ethers such as THF, ethylene glycol dimethyl ether, tert-butyl methyl ether, and 1,4-dioxane; alcohols such as methanol and ethanol; water; and mixtures thereof.

Examples of the base to be used in the reaction include alkali metal hydroxides such as sodium hydroxide and potassium hydroxide.

The amount of the base to be used in the reaction is usually 1 to 10 moles based on 1 mole of Compound (M14).

The reaction temperature of the reaction is usually within a range of 0 to 120° C. The reaction time of the reaction is usually within a range of 0.1 to 24 hours.

After the completion of the reaction, Compound (30) can be isolated by post-treatments, for example, acidifying the reaction mixture and than extracting with an organic solvent, followed by drying and concentrating the organic layer. The isolated Compound (30) can be further purified by chromatography, recrystallization, and the like.

(Step I17-2)

The reaction is usually performed in the presence of a solvent.

Examples of the solvent to be used in the reaction include halogenated hydrocarbons such as dichloromethane and chloroform; alcohols such as methanol and ethanol; acetic acid; water; and mixtures thereof.

Examples of the oxidizing agent to be used in the reaction include m-chloroperbenzoic acid and an aqueous solution of hydrogen peroxide.

The reaction can be performed in the presence of a catalyst as necessary.

Examples of the catalyst to be used in the reaction include sodium tungstate.

The amount of the oxidizing agent to be used in the reaction is usually 1 to 5 moles based on 1 mole of Compound (M14).

The reaction temperature of the reaction is usually within a range of −20 to 120° C. The reaction time of the reaction is usually within a range of 0.1 to 12 hours.

After the completion of the reaction, Compound (M22) can be isolated by post-treatments, for example, extracting the reaction mixture with an organic solvent, followed by washing the organic layer with an aqueous solution of a reducing agent (e.g. sodium sulfite, thiosodium sulfate) and an aqueous solution of a base (e.g. sodium hydrogen carbonate) as necessary, followed by drying and concentrating the organic layer. The isolated Compound (M22) can be further purified by chromatography, recrystallization, and the like.

(Step I17-3)

The reaction is usually performed in the presence of a solvent.

Examples of the solvent to be used in the reaction include ethers such as THF, ethylene glycol dimethyl ether, tert-butyl methyl ether, and 1,4-dioxane; alcohols such as methanol and ethanol; water; and mixtures thereof.

Examples of the base to be used in the reaction include alkali metal hydroxides such as sodium hydroxide and potassium hydroxide.

The amount of the base to be used in the reaction is usually 1 to 10 moles based on 1 mole of Compound (M22).

The reaction temperature of the reaction is usually within a range of 0 to 120° C. The reaction time of the reaction is usually within a range of 0.1 to 24 hours.

After the completion of the reaction, Compound (M23) can be isolated by post-treatments, for example, acidifying the reaction mixture and than extracting with an organic solvent, followed by drying and concentrating the organic layer. The isolated Compound (M23) can be further purified by chromatography, recrystallization, and the like.

(Step I17-4)

The reaction is usually performed in the presence of a solvent.

Examples of the solvent to be used in the reaction include halogenated hydrocarbons such as dichloromethane and chloroform; alcohols such as methanol and ethanol; acetic acid; water; and mixtures thereof.

Examples of the oxidizing agent to be used in the reaction include m-chloroperbenzoic acid and an aqueous solution of hydrogen peroxide.

The reaction can be performed in the presence of a catalyst as necessary.

Examples of the catalyst to be used in the reaction include sodium tungstate.

The amount of the oxidizing agent to be used in the reaction is usually 1 to 5 moles based on 1 mole of Compound (30).

The reaction temperature of the reaction is usually within a range of −20 to 120° C. The reaction time of the reaction is usually within a range of 0.1 to 12 hours.

After the completion of the reaction, Compound (M23) can be isolated by post-treatments, for example, extracting the reaction mixture with an organic solvent, followed by washing the organic layer with an aqueous solution of a reducing agent (e.g. sodium sulfite, thiosodium sulfate) and an aqueous solution of a base (e.g. sodium hydrogen carbonate) as necessary, followed by drying and concentrating the organic layer. The isolated Compound (M23) can be further purified by chromatography, recrystallization, and the like.

(Production Method of Intermediate 18)

Compound (30) of Compound (5) wherein n is 0 can be produced by hydrolyzing Compound (M14) in the presence of an acid:

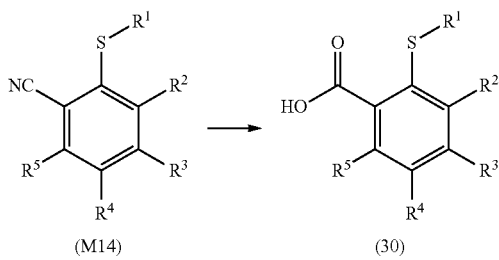

wherein, $R^1$, $R^2$, $R^3$, $R^4$, and $R^5$ are as defined above.

In the reaction, usually, an aqueous solution of the acid is used as a solvent.

Examples of the acid to be used in the reaction include mineral acids such as hydrochloric acid, nitric acid, phosphoric acid, and sulfuric acid, and carboxylic acids such as acetic acid and trifluoroacetic acid.

The reaction temperature of the reaction is usually within a range of 0 to 100° C. The reaction time of the reaction is usually within a range of 0.1 to 24 hours.

After the completion of the reaction, Compound (30) can be isolated by post-treatments, for example, extracting the reaction mixture with an organic solvent, followed by drying and concentrating the organic layer. The isolated Compound (30) can be further purified by chromatography, recrystallization, and the like.

(Production Method of Intermediate 19)

Compound (M3) can be produced by chlorinating Compound (5) in the presence of a chlorinating agent:

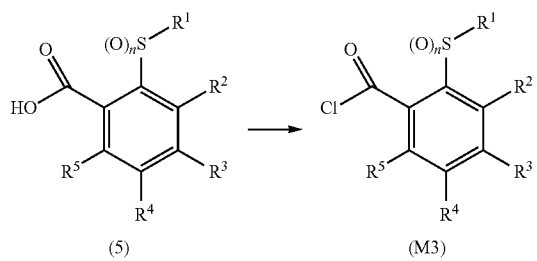

wherein, $R^1$, $R^2$, $R^3$, $R^4$, $R^5$, and n are as defined above.

The reaction is usually performed in the presence of a solvent.

Examples of the solvent to be used in the reaction include ethers such as THF, ethylene glycol dimethyl ether, tert-butyl methyl ether, and 1,4-dioxane; aromatic hydrocarbons such as toluene and xylene; halogenated hydrocarbons such as dichloromethane and chloroform; and mixtures thereof.

Examples of the chlorinating agent to be used in the reaction include thionyl chloride and oxalyl dichloride.

The amount of the chlorinating agent to be used in the reaction is usually 1 to 5 moles based on 1 mole of Compound (5).

The reaction temperature of the reaction is usually within a range of 0 to 100° C. The reaction time of the reaction is usually within a range of 0.1 to 24 hours.

After the completion of the reaction, Compound (M3) can be isolated by evaporating the solvent.

(Production Method of Intermediate 20)

Compound (M21) of Compound (2) wherein $A^3$ is a nitrogen atom can be produced, for example, by the following method:

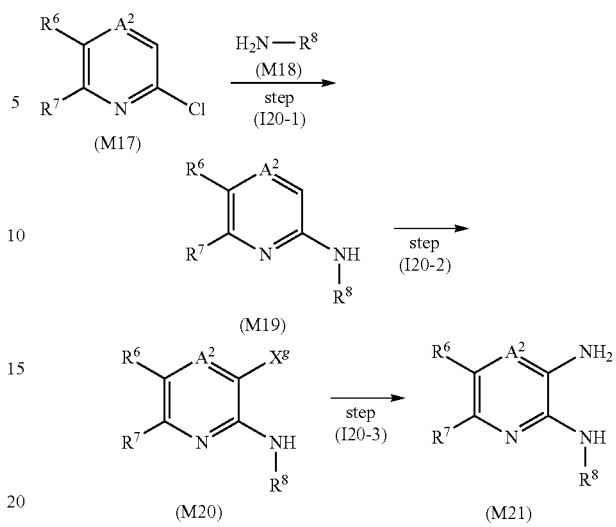

wherein, $R^6$, $R^7$, $R^8$, and $A^2$ are as defined above, and $X^g$ represents a chlorine atom, a bromine atom, or an iodine atom.

(Step I20-1)

Compound (M19) can be produced by reacting Compound (M17) with Compound (M18).

The reaction is performed in the presence or absence of a solvent.

Examples of the solvent to be used in the reaction include water, alcohols such as methanol and ethanol; ethers such as 1,4-dioxane, diethyl ether, and THF; esters such as ethyl acetate and butyl acetate; halogenated hydrocarbons such as dichloromethane, chloroform, carbon tetrachloride, and 1,2-dichloroethane; nitriles such as acetonitrile; aprotic polar solvents such as DMF, NMP, and dimethylsulfoxide; nitrogen-containing aromatic compounds such as pyridine and quinoline; and mixtures thereof.

A base can be added to the reaction as necessary.

Examples of the base to be used in the reaction include nitrogen-containing heterocyclic compounds such as pyridine, picoline, 2,6-lutidine, diazabicycloundecene (hereinafter referred to as DBU), and 1,5-diazabicyclo[4.3.0]-5-nonen; tertiary amines such as triethylamine and N-ethyldiisopropylamine; and inorganic bases such as potassium carbonate, cesium carbonate, and sodium hydroxide.

The amount of Compound (M18) to be used in the reaction is usually 1 to 5 moles based on 1 mole of Compound (M17).

The reaction temperature of the reaction is usually within a range of 0 to 200° C. The reaction time of the reaction is usually within a range of 0.1 to 24 hours.

After the completion of the reaction, Compound (M19) can be isolated by pouring the reaction mixture into water, extracting with an organic solvent, and concentrating the organic layer; pouring the reaction mixture into water, and collecting the generated solids by filtration; or collecting the solids generated in the reaction mixture by filtration. The isolated Compound (M19) can be further purified by recrystallization, chromatography, and the like.

(Step I20-2)

Compound (M20) can be produced by reacting Compound (M19) with a halogenating agent.

The reaction is usually performed in the presence of a solvent.

Examples of the solvent to be used in the reaction include water; acetic acid; ethers such as 1,4-dioxane, diethyl ether, and THF; esters such as ethyl acetate and butyl acetate; halogenated hydrocarbons such as dichloromethane, chloroform, carbon tetrachloride, and 1,2-dichloroethane; nitriles such as acetonitrile; aprotic polar solvents such as DMF and NMP; and mixtures thereof.

Examples of the halogenating agent to be used in the reaction include a chlorinating agent such as N-chlorosuccinimide and chlorine; a brominating agent such as N-bromosuccinimide and bromine; and an iodinating agent such as N-iodosuccinimide and iodine.

The amount of the halogenating agent to be used in the reaction is usually 1 to 3 moles based on 1 mole of Compound (M19).

The reaction temperature of the reaction is usually within a range of −10 to 100° C. The reaction time of the reaction is usually within a range of 0.1 to 24 hours.

After the completion of the reaction, Compound (M20) can be isolated by pouring the reaction mixture into water, extracting with an organic solvent, and concentrating the organic layer; pouring the reaction mixture into water, and collecting the generated solids by filtration; or collecting the solids generated in the reaction mixture by filtration. The isolated Compound (M20) can be further purified by recrystallization, chromatography, and the like.

(Step I20-3)

Compound (M21) can be produced by reacting Compound (M20) with an aminating agent in the presence of a copper compound.

The reaction is usually performed in the presence of a solvent.

Examples of the solvent to be used in the reaction include water; alcohols such as methanol and ethanol; ethers such as 1,4-dioxane, diethyl ether, and THF; esters such as ethyl acetate and butyl acetate; halogenated hydrocarbons such as dichloromethane, chloroform, carbon tetrachloride, and 1,2-dichloroethane; nitriles such as acetonitrile; aprotic polar solvents such as DMF, NMP, and dimethylsulfoxide; nitrogen-containing aromatic compounds such as pyridine and quinoline; and mixtures thereof.

Examples of the aminating agent to be used in the reaction include ammonia, ammonia water, and lithium amide.

Examples of the copper compound to be used in the reaction include copper, copper (I) iodide, copper (I) oxide, copper (II) oxide, copper (II) acetylacetone, copper (II) acetate, and copper (II) sulfate.

A ligand can be added to the reaction as necessary.

Examples of the ligand to be used in the reaction include acetylacetone, salen, and phenanthroline.

A base can be added to the reaction as necessary.

Examples of the base to be used in the reaction include nitrogen-containing heterocyclic compounds such as pyridine, picoline, 2,6-lutidine, DBU, and 1,5-diazabicyclo[4.3.0]-5-nonen; tertiary amines such as triethylamine and N-ethyldiisopropylamine; and inorganic bases such as tripotassium phosphate, potassium carbonate, cesium carbonate, and sodium hydroxide.

The amount of the aminating agent to be used in the reaction is usually 1 to 5 moles based on 1 mole of Compound (M20). The amount of the copper compound to be used in the reaction is usually 0.02 to 0.5 moles based on 1 mole of Compound (M20). The amount of the ligand to be used in the reaction is 0.02 to 2 moles based on 1 mole of Compound (M20) as necessary. The amount of the base to be used in the reaction is 1 to 5 moles based on 1 mole of Compound (M20) as necessary.

The reaction temperature of the reaction is usually within a range of 30 to 200° C. The reaction time of the reaction is usually within a range of 0.1 to 48 hours.

After the completion of the reaction, Compound (M21) can be isolated by pouring the reaction mixture into water, extracting with an organic solvent, and concentrating the organic layer; pouring the reaction mixture into water, and collecting the generated solids by filtration; or collecting the solids generated in the reaction mixture by filtration. The isolated Compound (M21) can be further purified by recrystallization, chromatography, and the like.

(Production Method of Intermediate 21) (Step (A-2))

Compound (35) can be produced by reacting Compound (11) with Compound (5) in the presence of a dehydration-condensing agent:

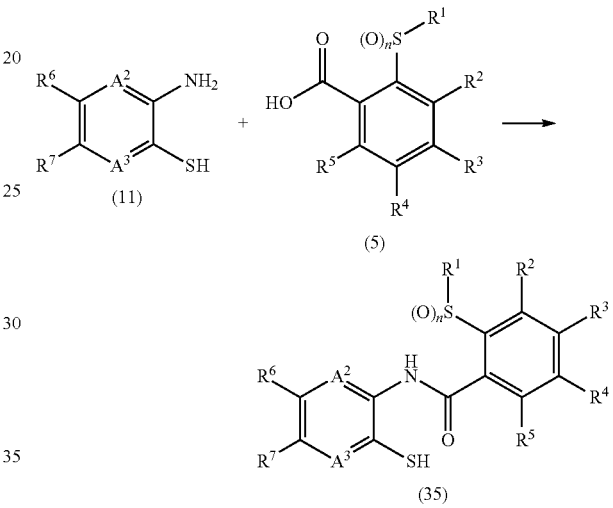

wherein, $R^1$, $R^2$, $R^4$, $R^5$, $R^6$, $R^7$, $A^2$, $A^3$, and n are as defined above.

The reaction is usually performed in the presence of a solvent.

Examples of the solvent to be used in the reaction include ethers such as THF, ethylene glycol dimethyl ether, tert-butyl methyl ether, and 1,4-dioxane; aliphatic hydrocarbons such as hexane, heptane, and octane; aromatic hydrocarbons such as toluene and xylene; halogenated hydrocarbons such as chlorobenzene; esters such as ethyl acetate and butyl acetate; nitriles such as acetonitrile; acid amides such as DMF and NMP; sulfoxides such as DMSO; nitrogen-containing aromatic compounds such as pyridine and quinoline; and mixtures thereof.

Examples of the dehydration-condensing agent to be used in the reaction include carbodiimides such as WSC and 1,3-dicyclohexylcarbodiimide, and BOP reagent.

The amount of Compound (5) to be used in the reaction is usually 1 to 3 moles based on 1 mole of Compound (11). The amount of the dehydration-condensing agent to be used in the reaction is usually 1 to 5 moles based on 1 mole of Compound (11).

The reaction temperature of the reaction is usually within a range of 0 to 140° C. The reaction time of the reaction is usually within a range of 0.1 to 24 hours.

After the completion of the reaction, Compound (35) can be isolated by post-treatments, for example, pouring water into the reaction mixture and then extracting the mixture with an organic solvent, followed by drying and concentrating the organic layer. The isolated Compound (35) can be further purified by chromatography, recrystallization, and the like.

(Production Method of Intermediate 22) (Step (B-2))

Compound (35) can be produced by reacting Compound (11) with Compound (M3) in the presence of a base:

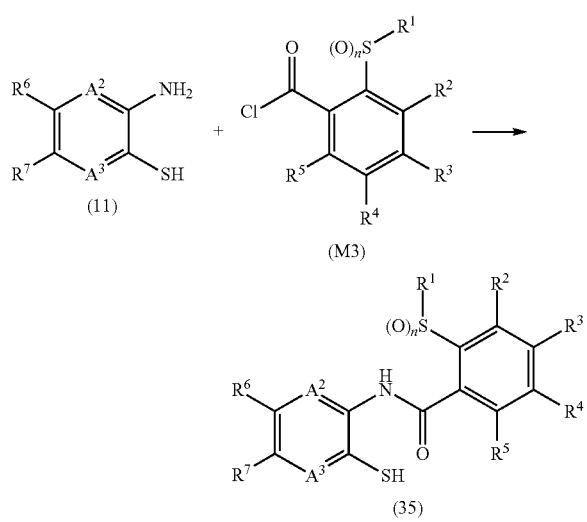

wherein, $R^1$, $R^2$, $R^3$, $R^4$, $R^5$, $R^6$, $R^7$, $A^2$, $A^3$, and n are as defined above.

The reaction is usually performed in the presence of a solvent.

Examples of the solvent to be used in the reaction include ethers such as THF, ethylene glycol dimethyl ether, tert-butyl methyl ether, and 1,4-dioxane; aliphatic hydrocarbons such as hexane, heptane, and octane; aromatic hydrocarbons such as toluene and xylene; halogenated hydrocarbons such as chlorobenzene; esters such as ethyl acetate and butyl acetate; nitriles such as acetonitrile; acid amides such as DMF and NMP; sulfoxides such as DMSO; and mixtures thereof.

Examples of the base include alkali metal carbonates such as sodium carbonate and potassium carbonate; tertiary amines such as triethylamine and diisopropylethylamine; and nitrogen-containing aromatic compounds such as pyridine and 4-dimethylaminopyridine.

The amount of Compound (M3) to be used in the reaction is usually 1 to 3 moles based on 1 mole of Compound (11). The amount of the base to be used in the reaction is usually 1 to 10 moles based on 1 mole of Compound (11).

The reaction temperature of the reaction is usually within a range of −20 to 100° C. The reaction time of the reaction is usually within a range of 0.1 to 24 hours.

After the completion of the reaction, Compound (35) can be isolated by post-treatments, for example, pouring water into the reaction mixture and then extracting the mixture with an organic solvent, followed by drying and concentrating the organic layer. The isolated Compound (35) can be further purified by chromatography, recrystallization, and the like.

(Production Method of Intermediate 23) (Step (E-1))

Compound (M24) of Compound (21) wherein $A^1$ is an oxygen atom can be produced by reacting Compound (7) with Compound (M9):

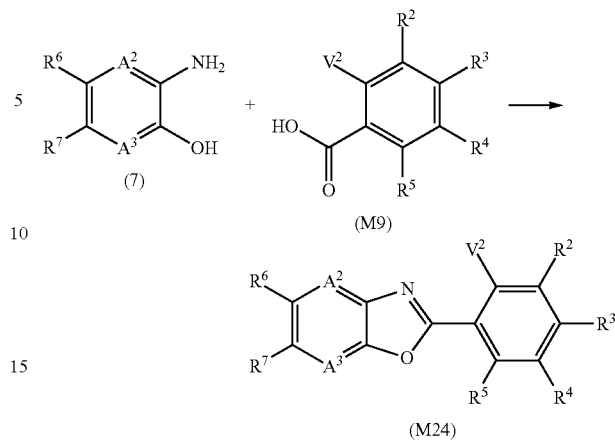

wherein, $R^2$, $R^3$, $R^4$, $R^5$, $R^6$, $R^7$, $A^2$, $A^3$, n, and $V^2$ are as defined above.

Compound (M24) can be produced according to the method described in (Production method 6) using Compound (M9) instead of Compound (5).

(Production Method of Intermediate 24) (Step (E-2))

Compound (M25) of Compound (1E) wherein $A^1$ is an oxygen atom can be produced by reacting Compound (7) with Compound (M9). Additionally, Compound (M26) of Compound (1E) wherein $A^1$ is a sulfur atom can be produced by reacting Compound (11) with Compound (M9):

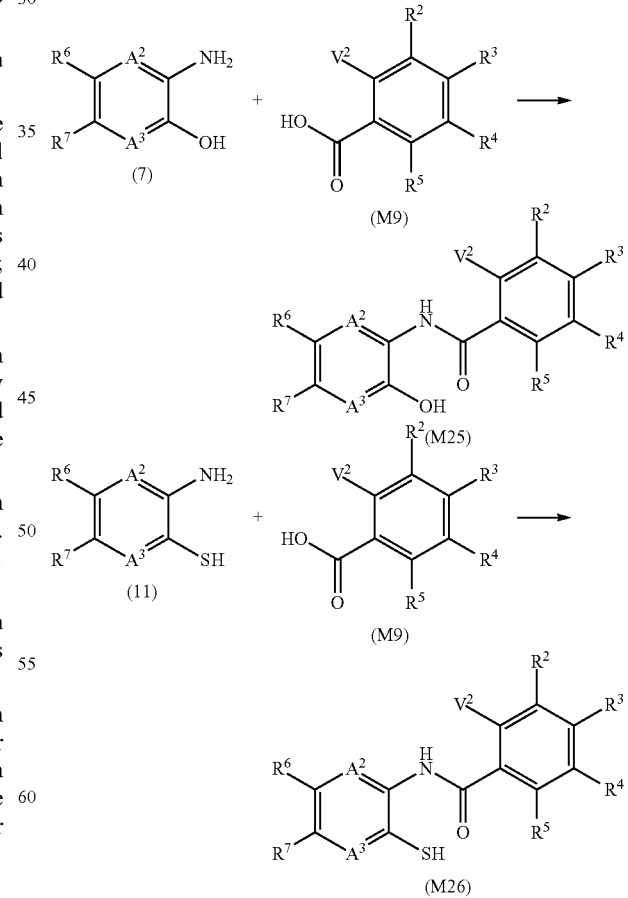

wherein, $R^2$, $R^3$, $R^4$, $R^5$, $R^6$, $R^7$, $A^2$, $A^3$, n, and $V^2$ are as defined above.

Compound (M25) can be produced according to the method described in Production method of intermediate 6 using Compound (M9) instead of Compound (5).

Compound (M26) can be produced according to the method described in Production method of intermediate 21 using Compound (11) instead of Compound (5).

(Production Method of Intermediate 25) (Step (E-3))

Compound (M27) of Compound (21) wherein $A^1$ is an oxygen atom can be produced by cyclizing Compound (M25). Additionally, Compound (M28) of Compound (21) wherein $A^1$ is a sulfur atom can be produced by cyclizing Compound (M26):

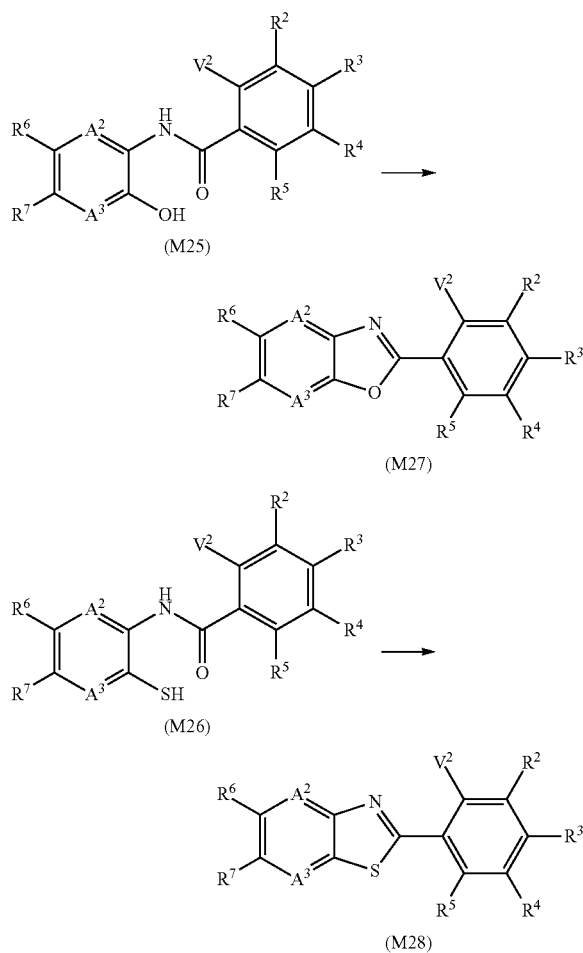

wherein, $R^2$, $R^3$, $R^4$, $R^5$, $R^6$, $R^7$, $A^2$, $A^3$, n, and $V^2$ are as defined above.

Compound (M27) can be produced according to the method described in Production method 8 or Production method 9 using Compound (M25) instead of Compound (10).

Compound (M28) can be produced according to the method described in Production method 21 using Compound (M26) instead of Compound (35).

(Production Method of Intermediate 26) (Step (F-1))

Compound (24) can be produced by reacting Compound (21) with sodium sulfide, sodium hydrogen sulfide, or hydrogen sulfide:

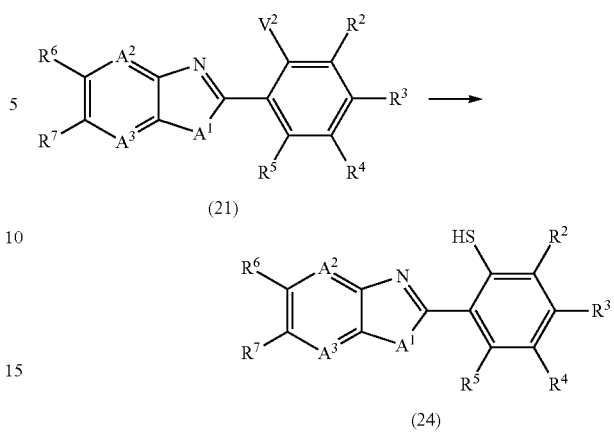

wherein, $R^2$, $R^3$, $R^4$, $R^5$, $R^6$, $R^7$, $A^1$, $A^2$, $A^3$, n, and $V^2$ are as defined above.

Compound (24) can be produced according to the method described in Production method 16 using sodium sulfide, sodium hydrogen sulfide, or hydrogen sulfide instead of Compound (22).

When sodium sulfide or sodium hydrogen sulfide is used, a reaction is usually performed without a base.

(Production Method of Intermediate 27) (Production Method D)

Compound (1K) can be produced by reacting Compound (M30) with Compound (5):

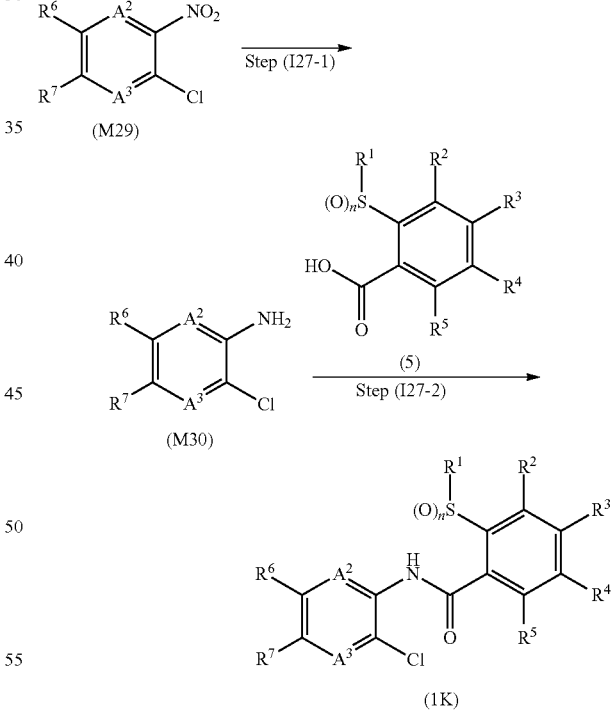

wherein, $R^1$, $R^2$, $R^3$, $R^4$, $R^5$, $R^6$, $R^7$, $A^2$, $A^3$, and n are as defined above.

(Step I27-1)

Compound (M30) can be produced by reducing Compound (M29).

The reduction reaction can be performed in the presence of a reducing agent such as iron powder and zinc powder; acids such as hydrochloric acid and acetic acid; and water.

The reaction can be usually performed in the presence of a solvent.

Examples of the solvent to be used in the reaction include ethers such as THF, ethylene glycol dimethyl ether, tert-butyl methyl ether, and 1,4-dioxane; esters such as ethyl acetate and butyl acetate; alcohols such as methanol and ethanol; acid amides such as DMF and NMP; and mixtures thereof.

The amount of the reducing agent to be used in the reaction is usually 3 to 10 moles based on 1 mole of Compound (M29).

The reaction temperature of the reaction is usually within a range of 0 to 100° C. The reaction time of the reaction is usually within a range of 0.1 to 24 hours.

After the completion of the reaction, Compound (M30) can be isolated by post-treatments, for example, adding water to the reaction mixture and then extracting the mixture with an organic solvent, followed by drying and concentrating the organic layer. The isolated Compound (M30) can be further purified by chromatography, recrystallization, and the like.

(Step I27-2)

The reaction is usually performed in the presence or absence of a solvent.

Examples of the solvent to be used in the reaction include ethers such as THF, ethylene glycol dimethyl ether, tert-butyl methyl ether, and 1,4-dioxane; aliphatic hydrocarbons such as hexane, heptane, and octane; aromatic hydrocarbons such as toluene and xylene; halogenated hydrocarbons such as chlorobenzene; esters such as ethyl acetate and butyl acetate; nitriles such as acetonitrile; acid amides such as DMF and NMP; sulfoxides such as DMSO; nitrogen-containing aromatic compounds such as pyridine and quinoline; and mixtures thereof.

Examples of the dehydration-condensing agent to be used in the reaction include carbodiimides such as WSC and 1,3-dicyclohexylcarbodiimide, and BOP reagent.

The amount of Compound (5) to be used in the reaction is usually 1 to 3 moles based on 1 mole of Compound (M30). The amount of the dehydration-condensing agent to be used in the reaction is usually 1 to 5 moles based on 1 mole of Compound (M30).

The reaction temperature of the reaction is usually within a range of 0 to 140° C. The reaction time of the reaction is usually within a range of 0.1 to 24 hours.

After the completion of the reaction, Compound (1K) can be isolated by post-treatments, for example, pouring water into the reaction mixture and then extracting the mixture with an organic solvent, followed by drying and concentrating the organic layer. The isolated Compound (1K) can be further purified by chromatography, recrystallization, and the like.

Alternatively, Compound (1K) can be produced according to the above method using Compound (M3) instead of Compound (5).

When Compound (M3) is used, the reaction is usually performed without a dehydration-condensing agent A base can be added to the reaction as necessary.

Examples of the base include carbonates of alkali metal such as sodium carbonate and potassium carbonate; tertiary amines such as triethylamine and diisopropylethylamine; and nitrogen-containing aromatic compounds such as pyridine and 4-dimethylaminopyridine.

The amount of Compound (M3) to be used in the reaction is usually 1 to 3 moles based on 1 mole of Compound (M30). The amount of the base to be used in the reaction is usually 1 to 10 moles based on 1 mole of Compound (M30).

(Production Method of Intermediate 28)

Compound (F) can be produced by reacting Compound (G) with an aminating agent:

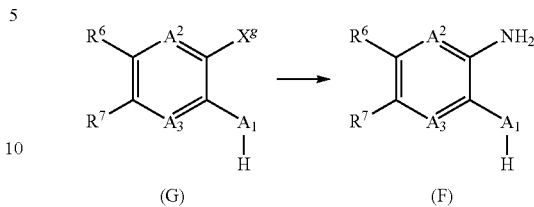

wherein, $X^g$, $R^6$, $R^7$, $A^1$, $A^2$, and $A^3$ are as defined the above.

Compound (F) can be produced according to the method described in Step (I20-3) of Production method of intermediate 20 using Compound (G) instead of Compound (M20).

Examples of Compound (B) include the following compounds:

An amide compound of the formula (6):

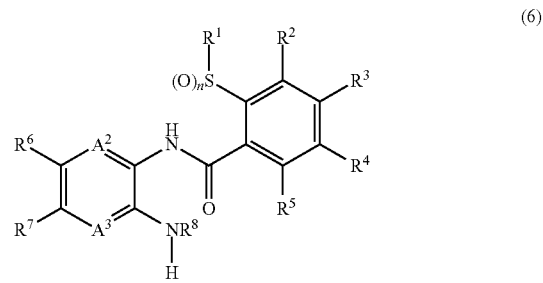

wherein, $R^1$, $R^2$, $R^3$, $R^9$, $R^5$, $R^6$, $R^7$, $R^8$, $A^2$, $A^3$, and n are as defined above (referred to as Compound (6));

An amide compound of the formula (10):

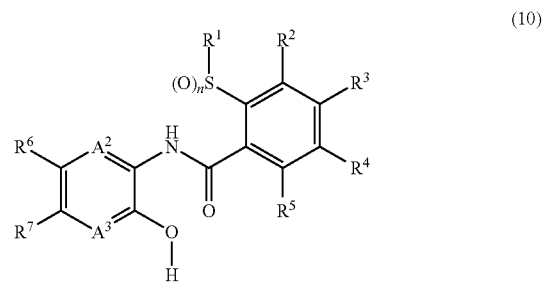

wherein, $R^1$, $R^2$, $R^3$, $R^4$, $R^5$, $R^6$, $R^7$, $A^2$, $A^3$, and n are as defined above (referred to as Compound (10));

An amide compound of the formula (35):

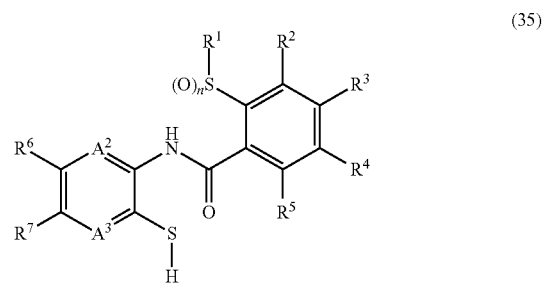

wherein, $R^1$, $R^2$, $R^3$, $R^4$, $R^5$, $R^6$, $R^7$, $A^2$, $A^3$, and n are as defined above (referred to as Compound (35));

An amide compound of the formula (1B):

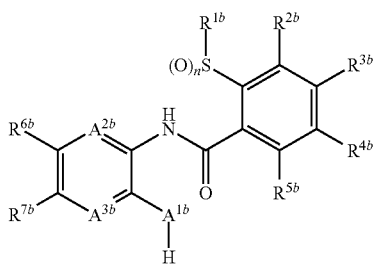

(1B)

wherein:
$A^{1b}$ represents —$NR^{8b}$—, an oxygen atom or a sulfur atom;
$A^{2b}$ represents a nitrogen atom or =$CR^{9b}$—;
$A^{3b}$ represents a nitrogen atom or =$CR^{10b}$—.
$R^{1b}$ represents a C1-C6 chain hydrocarbon group optionally having one or more halogen atoms or a C3-C6 alicyclic hydrocarbon group optionally having one or more halogen atoms;
$R^{2b}$, $R^{3b}$, $R^{4b}$, and $R^{5b}$ are same or different and represent independently a C1-C6 chain hydrocarbon group optionally having one or more halogen atoms, a phenyl group optionally having one or more halogen atoms or C1-C3 alkyl groups optionally having one or more halogen atoms, a 5-membered heterocyclic group optionally having one or more halogen atoms or C1-C3 alkyl groups optionally having one or more halogen atoms, a 6-membered heterocyclic group optionally having one or more halogen atoms or C1-C3 alkyl groups optionally having one or more halogen atoms, —$OR^{11b}$, —$S(O)_mR^{11b}$, —$SF_5$, a cyano group, a nitro group, a halogen atom, or a hydrogen atom: provided that at least two of $R^{2b}$, $R^{3b}$, $R^{4b}$, and $R^{5b}$ represent a hydrogen atom;
$R^{6b}$ represents a C1-C6 chain hydrocarbon group optionally having one or more halogen atoms, a phenyl group optionally having one or more halogen atoms or C1-C3 alkyl groups optionally having one or more halogen atoms, a 5-membered heterocyclic group optionally having one or more halogen atoms or C1-C3 alkyl groups optionally having one or more halogen atoms, a 6-membered heterocyclic group optionally having one or more halogen atoms or C1-C3 alkyl groups optionally having one or more halogen atoms, —$OR^{11b}$, —$S(O)_mR^{11b}$, —$SF_5$, a cyano group, a nitro group, or a halogen atom;
$R^{7b}$ represents a C1-C6 chain hydrocarbon group optionally having one or more halogen atoms, a phenyl group optionally having one or more halogen atoms or C1-C3 alkyl groups optionally having one or more halogen atoms, a 5-membered heterocyclic group optionally having one or more halogen atoms or C1-C3 alkyl groups optionally having one or more halogen atoms, a 6-membered heterocyclic group optionally having one or more halogen atoms or C1-C3 alkyl groups optionally having one or more halogen atoms, —$OR^{11b}$, —$S(O)_mR^{11b}$, —$SF_5$, a cyano group, a nitro group, a halogen atom, or a hydrogen atom;
$R^{8b}$ represents a C1-C6 chain hydrocarbon group optionally having one or more halogen atoms, a C1-C6 chain hydrocarbon group having one C1-C6 alkoxy group, a C3-C6 alicyclic hydrocarbon group optionally having one or more halogen atoms, or a hydrogen atom;
$R^{9b}$ and $R^{10b}$ are same or different and represent independently a C1-C6 chain hydrocarbon group optionally having one or more halogen atoms, —$OR^{11b}$, —$S(O)_mR^{11b}$, a cyano group, a nitro group, a halogen atom, or a hydrogen atom;
$R^{11b}$ and $R^{12b}$ are same or different and represent independently a C1-C6 chain hydrocarbon group optionally having one or more halogen atoms, or a hydrogen atom; and
m represents 0, 1, or 2, and n represents 0, 1, or 2;
provided that: in —$S(O)_mR^{11b}$, when m is 1 or 2, $R^{11b}$ is not a hydrogen atom; and when $A^{1b}$ is an oxygen atom, and $A^{2b}$ is a methine group, any one of $R^{2b}$, $R^{3b}$, $R^{4b}$, and $R^{5b}$ are a C1-C6 chain hydrocarbon group optionally having one or more halogen atoms, a phenyl group optionally having one or more halogen atoms or C1-C3 alkyl groups optionally having one or more halogen atoms, a 5-membered heterocyclic group optionally having one or more halogen atoms or C1-C3 alkyl groups optionally having one or more halogen atoms, a 6-membered heterocyclic group optionally having one or more halogen atoms or C1-C3 alkyl groups optionally having one or more halogen atoms, —$OR^{11b}$, —$S(O)_mR^{11b}$, a cyano group, a nitro group, or a halogen atom (hereinafter, referred to as Compound (1B));

And examples of Compound (1B) include the following compounds:
An amide compound of the formula (1B) wherein $A^{1b}$ is —$NR^{8b}$—;
An amide compound of the formula (1B) wherein $A^{1b}$ is —$NR^{8b}$—, and $R^{8b}$ is a C1-C6 chain hydrocarbon group optionally having one or more halogen atoms;
An amide compound of the formula (1B) wherein $A^{1b}$ is —$NR^{8b}$—, and $R^{8b}$ is a C1-C6 chain hydrocarbon group;
An amide compound of the formula (1B) wherein $A^{1b}$ is —$NR^{8b}$—, and $R^{8b}$ is a C1-C6 alkyl group;
An amide compound of the formula (1B) wherein $A^{1b}$ is —$NR^{8b}$—, and $R^{8b}$ is a C1-C3 alkyl group;
An amide compound of the formula (1B) wherein $A^{1b}$ is —$NR^{8b}$—, and $R^{8b}$ is a methyl group, an ethyl group, a propyl group, or an isopropyl group;
An amide compound of the formula (1B) wherein $A^{1b}$ is —$NR^{8b}$—, and $R^{8b}$ is a methyl group;
An amide compound of the formula (1B) wherein $A^{1b}$ is —$NR^{8b}$—, and $R^{8b}$ is an ethyl group;
An amide compound of the formula (1B) wherein $A^{1b}$ is —$NR^{8b}$—, and $R^{8b}$ is a propyl group;
An amide compound of the formula (1B) wherein $A^{1b}$ is —$NR^{8b}$—, and $R^{8b}$ is an isopropyl group;
An amide compound of the formula (1B) wherein $A^{1b}$ is —$NR^{8b}$—, and $R^{8b}$ is a C1-C6 chain hydrocarbon group having one C1-C6 alkoxy group;
An amide compound of the formula (1B) wherein $A^{1b}$ is —$NR^{8b}$—, and $R^{8b}$ is a methoxymethyl group or an ethoxymethyl group;
An amide compound of the formula (1B) wherein $A^{1b}$ is —$NR^{8b}$—, and $R^{8b}$ is a C3-C6 alicyclic hydrocarbon group optionally having one or more halogen atoms;
An amide compound of the formula (1B) wherein $A^{1b}$ is —$NR^{8b}$—, and $R^{8b}$ is a cyclopropyl group, a cyclobutyl group, a cyclopentyl group, or a cyclohexyl group;
An amide compound of the formula (1B) wherein $A^{1b}$ is —$NR^{8b}$—, and $R^{8b}$ is a hydrogen atom;
An amide compound of the formula (1B) wherein $A^{1b}$ is an oxygen atom;
An amide compound of the formula (1B) wherein $A^{1b}$ is a sulfur atom;
An amide compound of the formula (1B) wherein $A^{1b}$ is —$NR^{8b}$— or a sulfur atom;
An amide compound of the formula (1B) wherein $A^{1b}$ is —$NR^{8b}$— or a sulfur atom, and $R^{8b}$ is a methyl group, an ethyl group, a propyl group, or an isopropyl group;

An amide compound of the formula (1B) wherein $A^{1b}$ is $-NR^{8b}-$ or a sulfur atom, and $R^{8b}$ is a methoxymethyl group, an ethoxymethyl group, or a hydrogen atom;

An amide compound of the formula (1B) wherein $A^{2b}$ is $=CR^{9b}-$, and $A^{3b}$ is $=CR^{10b}-$;

An amide compound of the formula (1B) wherein $A^{2b}$ is $=CR^{9b}-$, $A^{3b}$ is $=CR^{10b}-$, and $R^{9b}$ and $R^{10b}$ are same or different and are independently a halogen atom or a hydrogen atom;

An amide compound of the formula (1B) wherein $A^{2b}$ is $=CR^{9b}-$, $A^{3b}$ is $=CR^{10b}-$, and $R^{9b}$ and $R^{10b}$ are a hydrogen atom;

An amide compound of the formula (1B) wherein $A^{2b}$ is a nitrogen atom, and $A^{3b}$ is $=CR^{10b}-$;

An amide compound of the formula (1B) wherein $A^{2b}$ is $=CR^{9b}-$, and $A^{3b}$ is a nitrogen atom;

An amide compound of the formula (1B) wherein $A^{2b}$ is $=CR^{9b}-$, $R^{9b}$ is a halogen atom or a hydrogen atom, and $A^{3b}$ is a nitrogen atom;

An amide compound of the formula (1B) wherein $A^{2b}$ is $=CR^{9b}-$, $R^{9b}$ is a hydrogen atom, and $A^{3b}$ is a nitrogen atom;

An amide compound of the formula (1B) wherein $A^{2b}$ is a nitrogen atom, and $A^{3b}$ is a nitrogen atom;

An amide compound of the formula (1B) wherein $A^{1b}$ is $-NR^{8b}-$, $A^{2b}$ is $=CR^{9b}-$, and $A^{3b}$ is $=CR^{10b}-$;

An amide compound of the formula (1B) wherein $A^{1b}$ is $-NR^{8b}-$, $A^{2b}$ is $=CR^{9b}-$, $A^{3b}$ is $=CR^{10b}-$, and $R^{9b}$ and $R^{10b}$ are a hydrogen atom;

An amide compound of the formula (1B) wherein $A^{1b}$ is an oxygen atom, $A^{2b}$ is $=CR^{9b}-$, and $A^{3b}$ is $=CR^{10b}-$;

An amide compound of the formula (1B) wherein $A^{1b}$ is a sulfur atom, $A^{2b}$ is $=CR^{9b}-$, and $A^{3b}$ is $=CR^{10b}-$.

An amide compound of the formula (1B) wherein $A^{1b}$ is a sulfur atom, $A^{2b}$ is $=CR^{9b}-$, $A^{3b}$ is $=CR^{10b}-$, and $R^{9b}$ and $R^{10b}$ are a hydrogen atom;

An amide compound of the formula (1B) wherein $A^{1b}$ is $-NR^{8b}-$, $A^{2b}$ is $=CR^{9b}-$, and $A^{3b}$ is a nitrogen atom;

An amide compound of the formula (1B) wherein $A^{1b}$ is $-NR^{8b}-$, $A^{2b}$ is $=CR^{9b}-$, $R^{9b}$ is a hydrogen atom, and $A^{3b}$ is a nitrogen atom;

An amide compound of the formula (1B) wherein $A^{1b}$ is an oxygen atom, $A^{2b}$ is $=CR^{9b}-$, and $A^{3b}$ is a nitrogen atom;

An amide compound of the formula (1B) wherein $A^{1b}$ is a sulfur atom, $A^{2b}$ is $=CR^{9b}-$, and $A^{3b}$ is a nitrogen atom;

An amide compound of the formula (1B) wherein $A^{1b}$ is a sulfur atom, $A^{2b}$ is $=CR^{9b}-$, $R^{9b}$ is a hydrogen atom, and $A^{3b}$ is a nitrogen atom;

An amide compound of the formula (1B) wherein $A^{1b}$ is $-NR^{8b}-$ or a sulfur atom, $R^{8b}$ is a methyl group, an ethyl group, a propyl group, or an isopropyl group, $A^{2b}$ is $=CR^{9b}-$, $A^{3b}$ is $=CR^{10b}-$, and $R^{9b}$ and $R^{10b}$ are a hydrogen atom;

An amide compound of the formula (1B) wherein $A^{1b}$ is $-NR^{8b}-$ or a sulfur atom, $R^{8b}$ is a methyl group, $A^{2b}$ is $=CR^{9b}-$, $A^{3b}$ is $=CR^{10b}-$, and $R^{9b}$ and $R^{10b}$ are a hydrogen atom;

An amide compound of the formula (1B) wherein $A^{1b}$ is $-NR^{8b}-$ or a sulfur atom, $R^{8b}$ is a methyl group, an ethyl group, a propyl group or an isopropyl group, $A^{2b}$ is $=CR^{9b}-$, $R^{9b}$ is a hydrogen atom, and $A^{3b}$ is a nitrogen atom;

An amide compound of the formula (1B) wherein $A^{1b}$ is $-NR^{8b}-$ or a sulfur atom, $R^{8b}$ is a methyl group, $A^{2b}$ is $=CR^{9b}-$, $R^{9b}$ is a hydrogen atom, and $A^{3b}$ is a nitrogen atom;

An amide compound of the formula (1B) wherein $A^{1b}$ is $-NR^{8b}-$ or a sulfur atom, and $R^{8b}$ is a methoxymethyl group, an ethoxymethyl group, or a hydrogen atom;

An amide compound of the formula (1B) wherein $R^{1b}$ is a C1-C6 chain hydrocarbon group optionally having one or more halogen atoms;

An amide compound of the formula (1B) wherein $R^{1b}$ is a C1-C6 chain hydrocarbon group optionally having one or more fluorine atoms;

An amide compound of the formula (1B) wherein $R^{1b}$ is a C1-C6 chain hydrocarbon group;

An amide compound of the formula (1B) wherein $R^{1b}$ is a C1-C6 alkyl group;

An amide compound of the formula (1B) wherein $R^{1b}$ is a C1-C6 alkyl group optionally having one or more fluorine atoms;

An amide compound of the formula (1B) wherein $R^{1b}$ is a C1-C3 alkyl group;

An amide compound of the formula (1B) wherein $R^{1b}$ is a C1-C3 alkyl group optionally having one or more fluorine atoms;

An amide compound of the formula (1B) wherein $R^{1b}$ is a methyl group, an ethyl group, a propyl group, an isopropyl group, a trifluoromethyl group, or a 2,2,2-trifluoroethyl group;

An amide compound of the formula (1B) wherein $R^{1b}$ is a methyl group;

An amide compound of the formula (1B) wherein $R^{1b}$ is an ethyl group;

An amide compound of the formula (1B) wherein $R^{1b}$ is a propyl group;

An amide compound of the formula (1B) wherein $R^{1b}$ is an isopropyl group;

An amide compound of the formula (1B) wherein $R^{1b}$ is a trifluoromethyl group;

An amide compound of the formula (1B) wherein $R^{1b}$ is a 2,2,2-trifluoroethyl group;

An amide compound of the formula (1B) wherein $R^{1b}$ is a C3-C6 alicyclic hydrocarbon group optionally having one or more halogen atoms;

An amide compound of the formula (1B) wherein $R^{1b}$ is a C3-C6 alicyclic hydrocarbon group;

An amide compound of the formula (1B) wherein $R^{1b}$ is a cyclopropyl group, a cyclobutyl group, or a cyclopentyl group;

An amide compound of the formula (1B) wherein $R^{2b}$, $R^{3b}$, $R^{4b}$, and $R^{5b}$ are same or different and are independently a C1-C6 chain hydrocarbon group optionally having one or more halogen atoms, or a hydrogen atom;

An amide compound of the formula (1B) wherein $R^{2b}$, $R^{3b}$, $R^{4b}$, and $R^{5b}$ are same or different and are independently a phenyl group optionally having one or more halogen atoms or C1-C3 alkyl groups optionally having one or more halogen atoms, a 5-membered heterocyclic group optionally having one or more halogen atoms or C1-C3 alkyl groups optionally having one or more halogen atoms, a 6-membered heterocyclic group optionally having one or more halogen atoms or C1-C3 alkyl groups optionally having one or more halogen atoms, or a hydrogen atom;

An amide compound of the formula (1B) wherein $R^{2b}$, $R^{3b}$, $R^{4b}$, and $R^{5b}$ are same or different and are independently $-OR^{11b}$ or a hydrogen atom;

An amide compound of the formula (1B) wherein $R^{2b}$, $R^{3b}$, $R^{4b}$, and $R^{5b}$ are same or different and are independently $-S(O)_mR^{11b}$ or a hydrogen atom;

An amide compound of the formula (1B) wherein $R^{2b}$, $R^{3b}$, $R^{4b}$, and $R^{5b}$ are same or different and are independently a cyano group, a nitro group, or a hydrogen atom;

An amide compound of the formula (1B) wherein $R^{2b}$, $R^{3b}$, $R^{4b}$, and $R^{5b}$ are same or different and are independently a halogen atom or a hydrogen atom;

An amide compound of the formula (1B) wherein $R^{2b}$, $R^{3b}$, $R^{4b}$, and $R^{5b}$ are a hydrogen atom;

An amide compound of the formula (1B) wherein $R^{2b}$, $R^{4b}$, and $R^{5b}$ are a hydrogen atom, and $R^{3b}$ is a 2-pyridyl group, a 2-pyrimidyl group, a 3-chloro-2-pyridyl group, or a 3-chloro-5-trifluoromethyl-2-pyridyl group;

An amide compound of the formula (1B) wherein $R^{2b}$, $R^{4b}$, and $R^{5b}$ are a hydrogen atom, and $R^{3b}$ is a 2-pyridyl group;

An amide compound of the formula (1B) wherein $R^{2b}$, $R^{4b}$, and $R^{5b}$ are a hydrogen atom, and $R^{3b}$ is a 2-pyrimidyl group;

An amide compound of the formula (1B) wherein $R^{2b}$, $R^{4b}$, and $R^{5b}$ are a hydrogen atom, and $R^{3b}$ is a 3-chloro-2-pyridyl group;

An amide compound of the formula (1B) wherein $R^{2b}$, $R^{4b}$, and $R^{5b}$ are a hydrogen atom, and $R^{3b}$ is a 3-chloro-5-trifluoromethyl-2-pyridyl group;

An amide compound of the formula (1B) wherein $R^{2b}$, $R^{4b}$, and $R^{5b}$ are a hydrogen atom, and $R^{3b}$ is a C1-C6 chain hydrocarbon group optionally having one or more halogen atoms;

An amide compound of the formula (1B) wherein $R^{2b}$, $R^{4b}$, and $R^{5b}$ are a hydrogen atom, and $R^{3b}$ is a C1-C6 alkyl group;

An amide compound of the formula (1B) wherein $R^{2b}$, $R^{4b}$, and $R^{5b}$ are a hydrogen atom, and $R^{3b}$ is a C1-C6 alkyl group optionally having one or more fluorine atoms;

An amide compound of the formula (1B) wherein $R^{2b}$, $R^{4b}$, and $R^{5b}$ are a hydrogen atom, and $R^{3b}$ is a C1-C3 alkyl group;

An amide compound of the formula (1B) wherein $R^{2b}$, $R^{4b}$, and $R^{5b}$ are a hydrogen atom, and $R^{3b}$ is a C1-C3 alkyl group optionally having one or more fluorine atoms;

An amide compound of the formula (1B) wherein $R^{2b}$, and $R^{5b}$ are a hydrogen atom, and $R^{3b}$ is a methyl group, an ethyl group, a propyl group, an isopropyl group, a trifluoromethyl group, a pentafluoroethyl group, a heptafluoropropyl group, or a heptafluoroisopropyl group;

An amide compound of the formula (1B) wherein $R^{2b}$, $R^{4b}$, and $R^{5b}$ are a hydrogen atom, and $R^{3b}$ is a methyl group;

An amide compound of the formula (1B) wherein $R^{2b}$, $R^{4b}$, and $R^{5b}$ are a hydrogen atom, and $R^{3b}$ is an ethyl group;

An amide compound of the formula (1B) wherein $R^{2b}$, $R^{4b}$, and $R^{5b}$ are a hydrogen atom, and $R^{3b}$ is a propyl group;

An amide compound of the formula (1B) wherein $R^{2b}$, $R^{4b}$, and $R^{5b}$ are a hydrogen atom, and $R^{3b}$ is an isopropyl group;

An amide compound of the formula (1B) wherein $R^{2b}$, $R^{4b}$, and $R^{5b}$ are a hydrogen atom, and $R^{3b}$ is a trifluoromethyl group;

An amide compound of the formula (1B) wherein $R^{2b}$, $R^{4b}$, and $R^{5b}$ are a hydrogen atom, and $R^{3b}$ is a pentafluoroethyl group;

An amide compound of the formula (1B) wherein $R^{2b}$, $R^{4b}$, and $R^{5b}$ are a hydrogen atom, and $R^{3b}$ is a heptafluoropropyl group;

An amide compound of the formula (1B) wherein $R^{2b}$, $R^{4b}$, and $R^{5b}$ are a hydrogen atom, and $R^{3b}$ is a heptafluoroisopropyl group;

An amide compound of the formula (1B) wherein $R^{2b}$, $R^{4b}$, and $R^{5b}$ are a hydrogen atom, and $R^{3b}$ is a halogen atom;

An amide compound of the formula (1B) wherein $R^{2b}$, $R^{4b}$, and $R^{5b}$ are a hydrogen atom, and $R^{3b}$ is a fluorine atom, a chlorine atom, or a bromine atom;

An amide compound of the formula (1B) wherein $R^{2b}$, $R^{4b}$, and $R^{5b}$ are a hydrogen atom, and $R^{3b}$ is a fluorine atom;

An amide compound of the formula (1B) wherein $R^{2b}$, $R^{4b}$, and $R^{5b}$ are a hydrogen atom, and $R^{3b}$ is a chlorine atom;

An amide compound of the formula (1B) wherein $R^{2b}$, $R^{4b}$, and $R^{5b}$ are a hydrogen atom, and $R^{3b}$ is a bromine atom;

An amide compound of the formula (1B) wherein $R^{2b}$, $R^{4b}$, and $R^{5b}$ are a hydrogen atom, and $R^{3b}$ is $—SF_5$;

An amide compound of the formula (1B) wherein $R^{2b}$, $R^{3b}$, $R^{4b}$, and $R^{5b}$ are same or different and are independently a C1-C6 chain hydrocarbon group optionally having one or more halogen atoms, a halogen atom, or a hydrogen atom;

An amide compound of the formula (1B) wherein $R^{2b}$, $R^{4b}$, and $R^{5b}$ are a hydrogen atom, and $R^{3b}$ is a 6-membered heterocyclic group optionally having one or more halogen atoms or C1-C3 alkyl groups optionally having one or more halogen atoms;

An amide compound of the formula (1B) wherein $R^{2b}$, $R^{4b}$, and $R^{5b}$ are a hydrogen atom, and $R^{3b}$ is a C1-C6 chain hydrocarbon group optionally having one or more halogen atoms or a halogen atom;

An amide compound of the formula (1B) wherein $R^{2b}$, $R^{4b}$, and $R^{5b}$ are a hydrogen atom, and $R^{3b}$ is a C1-C3 alkyl group optionally having one or more fluorine atoms or a halogen atom;

An amide compound of the formula (1B) wherein $R^{2b}$, $R^{4b}$, and $R^{5b}$ are a hydrogen atom, and $R^{3b}$ is a 2-pyridyl group, a 2-pyrimidyl group, a 3-chloro-2-pyridyl group, a 3-chloro-5-trifluoromethyl-2-pyridyl group, a methyl group, an ethyl group, a propyl group, an isopropyl group, a trifluoromethyl group, a pentafluoroethyl group, a heptafluoropropyl group, a heptafluoroisopropyl group, a fluorine atom, a chlorine atom, or a bromine atom;

An amide compound of the formula (1B) wherein $R^{2b}$, $R^{4b}$, and $R^{5b}$ are a hydrogen atom, $R^{3b}$ is a methyl group, an ethyl group, a propyl group, an isopropyl group, a trifluoromethyl group, a pentafluoroethyl group, a heptafluoropropyl group, a heptafluoroisopropyl group, a fluorine atom, a chlorine atom, or a bromine atom;

An amide compound of the formula (1B) wherein $R^{1b}$ is a C1-C6 alkyl group, $R^{2b}$, $R^{4b}$, and $R^{5b}$ are a hydrogen atom, and $R^{3b}$ is a C1-C6 chain hydrocarbon group optionally having one or more halogen atoms;

An amide compound of the formula (1B) wherein $R^{1b}$ is a C1-C6 alkyl group, $R^{2b}$, $R^{4b}$, and $R^{5b}$ are a hydrogen atom, and $R^{3b}$ is a halogen atom;

An amide compound of the formula (1B) wherein $R^{6b}$ is a C1-C6 chain hydrocarbon group optionally having one or more halogen atoms;

An amide compound of the formula (1B) wherein $R^{6b}$ is a C1-C6 chain hydrocarbon group;

An amide compound of the formula (1B) wherein $R^{6b}$ is a C1-C6 chain hydrocarbon group having one or more fluorine atoms;

An amide compound of the formula (1B) wherein $R^{6b}$ is a C1-C3 alkyl group having one or more fluorine atoms;

An amide compound of the formula (1B) wherein $R^{6b}$ is a trifluoromethyl group, a pentafluoroethyl group, a heptafluoropropyl group, or a heptafluoroisopropyl group;

An amide compound of the formula (1B) wherein $R^{6b}$ is a trifluoromethyl group;

An amide compound of the formula (1B) wherein $R^{6b}$ is a pentafluoroethyl group;

An amide compound of the formula (1B) wherein $R^{6b}$ is a heptafluoropropyl group;

An amide compound of the formula (1B) wherein $R^{6b}$ is a heptafluoroisopropyl group;

An amide compound of the formula (1B) wherein $R^{6b}$ is a phenyl group optionally having one or more halogen atoms or C1-C3 alkyl groups optionally having one or more halogen atoms, a 5-membered heterocyclic group optionally having one or more halogen atoms or C1-C3 alkyl groups optionally having one or more halogen atoms, or a 6-membered heterocyclic group optionally having one or more halogen atoms or a C1-C3 alkyl groups optionally having one or more halogen atoms;

An amide compound of the formula (1B) wherein $R^{6b}$ is —$OR^{11b}$;

An amide compound of the formula (1B) wherein $R^{6b}$ is a C1-C6 alkoxy group having one ore more fluorine atoms;

An amide compound of the formula (1B) wherein $R^{6b}$ is a C1-C3 alkoxy group having one or more fluorine atoms;

An amide compound of the formula (1B) wherein $R^{6b}$ is a trifluoromethoxy group;

An amide compound of the formula (1B) wherein $R^{6b}$ is —$S(O)_m R^{11b}$;

An amide compound of the formula (1B) wherein $R^{6b}$ is a C1-C6 alkylsulfanyl group having one or more fluorine atoms, a C1-C6 alkylsulfinyl group having one or more fluorine atoms, or a C1-C6 alkylsulfonyl group having one or more fluorine atoms;

An amide compound of the formula (13) wherein $R^{6b}$ is a C1-C3 alkylsulfanyl group having one or more fluorine atoms, a C1-C3 alkylsulfinyl group having one or more fluorine atoms, or a C1-C3 alkylsulfonyl group having one or more fluorine atoms;

An amide compound of the formula (1B) wherein $R^{6b}$ is a trifluoromethylsulfanyl group, a trifluoromethylsulfinyl group, or a trifluoromethylsulfonyl group;

An amide compound of the formula (1B) wherein $R^{6b}$ is a trifluoromethylsulfanyl group;

An amide compound of the formula (1B) wherein $R^{6b}$ is a trifluoromethylsulfinyl group;

An amide compound of the formula (1B) wherein $R^{6b}$ is a trifluoromethylsulfonyl group;

An amide compound of the formula (1B) wherein $R^{6b}$ is a cyano group or a nitro group;

An amide compound of the formula (1B) wherein $R^{6b}$ is a halogen atom;

An amide compound of the formula (1B) wherein $R^{6b}$ is a chlorine atom, a bromine atom, or an iodine atom;

An amide compound of the formula (1B) wherein $R^{6b}$ is a chlorine atom;

An amide compound of the formula (1B) wherein $R^{6b}$ is a bromine atom;

An amide compound of the formula (1B) wherein $R^{6b}$ is an iodine atom;

An amide compound of the formula (1B) wherein $R^{6b}$ is —$SF_5$;

An amide compound of the formula (1B) wherein $R^{6b}$ is a C1-C3 alkyl group having one or more fluorine atoms, a C1-C3 alkoxy group having one or more fluorine atoms, a C1-C3 alkylsulfanyl group having one or more fluorine atoms, a C1-C3 alkylsulfinyl group having one or more fluorine atoms, a C1-C3 alkylsulfonyl group having one or more fluorine atoms, or a halogen atom;

An amide compound of the formula (1B) wherein $R^{6b}$ is a trifluoromethyl group, a pentafluoroethyl group, a heptafluoropropyl group, a heptafluoroisopropyl group, a trifluoromethoxy group, a trifluoromethylsulfanyl group, a trifluoromethylsulfinyl group, a trifluoromethylsulfonyl group, a chlorine atom, a bromine atom, or an iodine atom;

An amide compound of the formula (1B) wherein $R^{7b}$ is a C1-C6 chain hydrocarbon group optionally having one or more halogen atoms;

An amide compound of the formula (1B) wherein $R^{7b}$ is a C1-C6 chain hydrocarbon group;

An amide compound of the formula (1B) wherein $R^{7b}$ is a C1-C6 chain hydrocarbon group having one or more fluorine atoms;

An amide compound of the formula (1B) wherein $R^{7b}$ is a C1-C3 alkyl group having one or more fluorine atoms;

An amide compound of the formula (1B) wherein $R^{7b}$ is a trifluoromethyl group, a pentafluoroethyl group, a heptafluoropropyl group, or a heptafluoroisopropyl group;

An amide compound of the formula (1B) wherein $R^{7b}$ is a trifluoromethyl group;

An amide compound of the formula (1B) wherein $R^{7b}$ is a pentafluoroethyl group;

An amide compound of the formula (1B) wherein $R^{7b}$ is a heptafluoropropyl group;

An amide compound of the formula (1B) wherein $R^{7b}$ is a heptafluoroisopropyl group;

An amide compound of the formula (1B) wherein $R^{7b}$ is a phenyl group optionally having one or more halogen atoms or C1-C3 alkyl groups optionally having one or more halogen atoms, a 5-membered heterocyclic group optionally having one or more halogen atoms or C1-C3 alkyl groups optionally having one or more halogen atoms, or a 6-membered heterocyclic group optionally having one or more halogen atoms or C1-C3 alkyl groups optionally having one or more halogen atoms;

An amide compound of the formula (1B) wherein $R^{7b}$ is —$OR^{11b}$;

An amide compound of the formula (1B) wherein $R^{7b}$ is a C1-C6 alkoxy group having one ore more fluorine atoms;

An amide compound of the formula (1B) wherein $R^{7b}$ is a C1-C3 alkoxy group having one or more fluorine atoms;

An amide compound of the formula (1B) wherein $R^{7b}$ is a trifluoromethoxy group;

An amide compound of the formula (1B) wherein $R^{7b}$ is —$S(O)_m R^{11b}$;

An amide compound of the formula (1B) wherein $R^{7b}$ is a C1-C6 alkylsulfanyl group having one or more fluorine atoms, a C1-C6 alkylsulfinyl group having one or more fluorine atoms, or a C1-C6 alkylsulfonyl group having one or more fluorine atoms;

An amide compound of the formula (1B) wherein $R^{7b}$ is a C1-C3 alkylsulfanyl group having one or more fluorine atoms, a C1-C3 alkylsulfinyl group having one or more fluorine atoms, or a C1-C3 alkylsulfonyl group having one or more fluorine atoms;

An amide compound of the formula (1B) wherein $R^{7b}$ is a trifluoromethylsulfanyl group, a trifluoromethylsulfinyl group, or a trifluoromethylsulfonyl group;

An amide compound of the formula (1B) wherein $R^{7b}$ is a trifluoromethylsulfanyl group;

An amide compound of the formula (1B) wherein $R^{7b}$ is a trifluoromethylsulfinyl group;

An amide compound of the formula (1B) wherein $R^{7b}$ is a trifluoromethylsulfonyl group;

An amide compound of the formula (1B) wherein $R^{7b}$ is a cyano group or a nitro group;

An amide compound of the formula (1B) wherein $R^{7b}$ is a halogen atom;

An amide compound of the formula (1B) wherein $R^{7b}$ is a chlorine atom, a bromine atom, or an iodine atom;

An amide compound of the formula (1B) wherein $R^{7b}$ is a chlorine atom;

An amide compound of the formula (1B) wherein $R^{7b}$ is a bromine atom;

An amide compound of the formula (1B) wherein $R^{7b}$ is an iodine atom;

An amide compound of the formula (1B) wherein $R^{7b}$ is a hydrogen atom;

An amide compound of the formula (1B) wherein $R^{7b}$ is —$SF_5$;

An amide compound of the formula (1B) wherein $R^{7b}$ is a C1-C3 alkyl group having one or more fluorine atoms, a C1-C3 alkoxy group having one or more fluorine atoms, a C1-C3 alkylsulfanyl group having one or more fluorine atoms, a C1-C3 alkylsulfinyl group having one or more fluorine atoms, a C1-C3 alkylsulfonyl group having one or more fluorine atoms, or a halogen atom;

An amide compound of the formula (1B) wherein $R^{7b}$ is a trifluoromethyl group, a pentafluoroethyl group, a heptafluoropropyl group, a heptafluoroisopropyl group, a trifluoromethoxy group, a trifluoromethylsulfanyl group, a trifluoromethylsulfinyl group, a trifluoromethylsulfonyl group, a chlorine atom, a bromine atom, or an iodine atom;

An amide compound of the formula (1B) wherein $R^{6b}$ is a C1-C3 alkyl group having one or more fluorine atoms, a C1-C3 alkoxy group having one or more fluorine atoms, a C1-C3 alkylsulfanyl group having one or more fluorine atoms, a C1-C3 alkylsulfinyl group having one or more fluorine atoms, a C1-C3 alkylsulfonyl group having one or more fluorine atoms, or a halogen atom, and $R^{7b}$ is a hydrogen atom;

An amide compound of the formula (1B) wherein $R^{6b}$ is a trifluoromethyl group, a pentafluoroethyl group, a heptafluoropropyl group, a heptafluoroisopropyl group, a trifluoromethoxy group, a trifluoromethylsulfanyl group, a trifluoromethylsulfinyl group, a trifluoromethylsulfonyl group, a chlorine atom, a bromine atom, or an iodine atom, and $R^{7b}$ is a hydrogen atom;

An amide compound of the formula (1B) wherein m is 0;
An amide compound of the formula (1B) wherein m is 1;
An amide compound of the formula (1B) wherein m is 2;
An amide compound of the formula (1B) wherein n is 0;
An amide compound of the formula (1B) wherein n is 1;
An amide compound of the formula (1B) wherein n is 2;

An amide compound of the formula (1B) wherein $A^{1b}$ is —$NR^{9b}$— or a sulfur atom, $R^{8b}$ is a C1-C6 alkyl group, $A^{1b}$ is =$CR^{9b}$—, $A^{3b}$ is =$CR^{10b}$—, $R^{9b}$ and $R^{10b}$ are a hydrogen atom, $R^{1b}$ is a C1-C3 alkyl group optionally having one or more fluorine atoms, $R^{2b}$, $R^{4b}$, and $R^{5b}$ are a hydrogen atom, $R^{3b}$ is a C1-C3 alkyl group optionally having one or more fluorine atoms or a halogen atom, $R^{6b}$ is a C1-C3 alkyl group having one or more fluorine atoms, a C1-C3 alkoxy group having one or more fluorine atoms, a C1-C3 alkylsulfanyl group having one or more fluorine atoms, a C1-C3 alkylsulfinyl group having one or more fluorine atoms, a C1-C3 alkylsulfonyl group having one or more fluorine atoms, or a halogen atom, and $R^{7b}$ is a hydrogen atom;

An amide compound of the formula (1B) wherein $A^{1b}$ is —$NR^{8b}$— or a sulfur atom, $R^{8b}$ is a C1-C6 alkyl group, $A^{2b}$ is =$CR^{9b}$—, $R^{9b}$ is a hydrogen atom, $A^{3b}$ is a nitrogen atom, $R^{1b}$ is a C1-C3 alkyl group optionally having one or more fluorine atoms, $R^{2b}$, $R^{4b}$, and $R^{5b}$ are a hydrogen atom, $R^{3b}$ is a C1-C3 alkyl group optionally having one or more fluorine atoms or a halogen atom, $R^{6b}$ is a C1-C3 alkyl group having one or more fluorine atoms, a C1-C3 alkoxy group having one or more fluorine atoms, a C1-C3 alkylsulfanyl group having one or more fluorine atoms, a C1-C3 alkylsulfinyl group having one or more fluorine atoms, a C1-C3 alkylsulfonyl group having one or more fluorine atoms, or a halogen atom, and $R^{7b}$ is a hydrogen atom;

An amide compound of the formula (1B) wherein $A^{1b}$ is —$NR^{8b}$—, $R^{8b}$ is a methyl group, an ethyl group, a propyl group, or an isopropyl group, $A^{2b}$ is =$CR^{9b}$—, $A^{3b}$ is =$CR^{10b}$—, $R^{9b}$ and $R^{10b}$ are a hydrogen atom, $R^{1b}$ is a methyl group, an ethyl group, a propyl group, an isopropyl group, a trifluoromethyl group or a 2,2,2-trifluoroethyl group, $R^{2b}$, $R^{4b}$, and $R^{5b}$ are a hydrogen atom, $R^{3b}$ is a methyl group, an ethyl group, a propyl group, an isopropyl group, a trifluoromethyl group, a pentafluoroethyl group, a heptafluoropropyl group, a heptafluoroisopropyl group, a fluorine atom, a chlorine atom, or a bromine atom, $R^{6b}$ is a trifluoromethyl group, a pentafluoroethyl group, a heptafluoropropyl group, a heptafluoroisopropyl group, a trifluoromethoxy group, a trifluoromethylsulfanyl group, a trifluoromethylsulfinyl group, a trifluoromethylsulfonyl group, a chlorine atom, a bromine atom, or an iodine atom, and $R^{7b}$ is a hydrogen atom;

An amide compound of the formula (1B) wherein $A^{1b}$ is a sulfur atom, $A^{1b}$ is =$CR^{9b}$—, $A^{3b}$ is =$CR^{10b}$—, $R^{9b}$ and $R^{10b}$ are a hydrogen atom, $R^{1b}$ is a methyl group, an ethyl group, a propyl group, an isopropyl group, a trifluoromethyl group or a 2,2,2-trifluoroethyl group, $R^{2b}$, $R^{4b}$, and $R^{5b}$ are a hydrogen atom, $R^{3b}$ is a methyl group, an ethyl group, a propyl group, an isopropyl group, a trifluoromethyl group, a pentafluoroethyl group, a heptafluoropropyl group, a heptafluoroisopropyl group, a fluorine atom, a chlorine atom or a bromine atom, $R^{6b}$ is a trifluoromethyl group, a pentafluoroethyl group, a heptafluoropropyl group, a heptafluoroisopropyl group, a trifluoromethoxy group, a trifluoromethylsulfanyl group, a trifluoromethylsulfinyl group, a trifluoromethylsulfonyl group, a chlorine atom, a bromine atom, or an iodine atom, and $R^{7b}$ is a hydrogen atom;

An amide compound of the formula (1B) wherein $A^{1b}$ is —$NR^{8b}$—, $R^{8b}$ is a methyl group, an ethyl group, a propyl group, or an isopropyl group, $A^{2b}$ is =$CR^{9b}$—, $R^{9b}$ is a hydrogen atom, $A^{3b}$ is a nitrogen atom, $R^{1b}$ is a methyl group, an ethyl group, a propyl group, an isopropyl group, a trifluoromethyl group, or a 2,2,2-trifluoroethyl group, $R^{2b}$, $R^{4b}$, and $R^{5b}$ are a hydrogen atom, $R^{3b}$ is a methyl group, an ethyl group, a propyl group, an isopropyl group, a trifluoromethyl group, a pentafluoroethyl group, a heptafluoropropyl group, a heptafluoroisopropyl group, a fluorine atom, a chlorine atom or a bromine atom, $R^{6b}$ is a trifluoromethyl group, a pentafluoroethyl group, a heptafluoropropyl group, a heptafluoroisopropyl group, a trifluoromethoxy group, a trifluoromethylsulfanyl group, a trifluoromethylsulfinyl group, a trifluoromethylsulfonyl group, a chlorine atom, a bromine atom, or an iodine atom, and $R^{7b}$ is a hydrogen atom;

An amide compound of the formula (1B) wherein $A^{1b}$ is a sulfur atom, $A^{2b}$ is =$CR^{9b}$—, $R^{9b}$ is a hydrogen atom, $A^{3b}$ is a nitrogen atom, $R^{1b}$ is a methyl group, an ethyl group, a propyl group, an isopropyl group, a trifluoromethyl group, or a 2,2,2-trifluoroethyl group, $R^{2b}$, $R^{4b}$, and $R^{5b}$ are a hydrogen atom, $R^{3b}$ is a methyl group, an ethyl group, a propyl group, an isopropyl group, a trifluoromethyl group, a pentafluoroethyl group, a heptafluoropropyl group, a heptafluoroisopropyl group, a fluorine atom, a chlorine atom or a bromine atom, $R^{6b}$ is a trifluoromethyl group, a pentafluoroethyl group, a heptafluoropropyl group, a heptafluoroisopropyl group, a trifluoromethoxy group, a trifluoromethylsulfanyl group, a trifluoromethylsulfinyl group, a trifluoromethylsulfonyl group, a chlorine atom, a bromine atom, or an iodine atom, and $R^{7b}$ is a hydrogen atom;

And examples of Compound (6) include the following compounds:

An amide compound of the formula (6) wherein $A^2$ is =CH—;

An amide compound of the formula (6) wherein $A^2$ is a nitrogen atom;

An amide compound of the formula (6) wherein $A^3$ is =CH—;

An amide compound of the formula (6) wherein $A^3$ is a nitrogen atom or =$CR^{10}$—, and $R^{10}$ is a halogen atom or a hydrogen atom;

An amide compound of the formula (6) wherein $A^3$ is a nitrogen atom;

An amide compound of the formula (6) wherein $A^2$ is =CH—, $A^3$ is a nitrogen atom or =$CR^{10}$—, and $R^{10}$ is a halogen atom or a hydrogen atom;

An amide compound of the formula (6) wherein $A^2$ is =CH—, and $A^3$ is a nitrogen atom;

An amide compound of the formula (6) wherein $A^2$ is =CH—, $A^3$ is =$CR^{10}$—, and $R^{10}$ is a halogen atom or a hydrogen atom;

An amide compound of the formula (6) wherein $R^1$ is a C1-C6 chain hydrocarbon group optionally having one or more atoms or groups selected from Group X;

An amide compound of the formula (6) wherein $R^1$ is a C1-C6 chain hydrocarbon group optionally having one or more halogen atoms;

An amide compound of the formula (6) wherein $R^1$ is a C1-C6 chain hydrocarbon group;

An amide compound of the formula (6) wherein $R^1$ is a C1-C3 alkyl group;

An amide compound of the formula (6) wherein $R^1$ is a methyl group;

An amide compound of the formula (6) wherein $R^1$ is an ethyl group;

An amide compound of the formula (6) wherein $R^1$ is a propyl group;

An amide compound of the formula (6) wherein $R^1$ is an isopropyl group;

An amide compound of the formula (6) wherein $R^2$, $R^3$, $R^4$, and $R^5$ are same or different and are independently a C1-C6 chain hydrocarbon group optionally having one or more halogen atoms, —$OR^{11}$, —$NR^{11}R^{12}$, a cyano group, a nitro group, a halogen atom, or a hydrogen atom;

An amide compound of the formula (6) wherein $R^2$, $R^4$ and $R^5$ are same or different and are independently a hydrogen atom or a halogen atom, $R^3$ is a C1-C6 chain hydrocarbon group optionally having one or more halogen atoms, —$OR^{11}$, a halogen atom, or a hydrogen atom;

An amide compound of the formula (6) wherein $R^2$, $R^4$, and $R^5$ are same or different and are independently a halogen atom or a hydrogen atom, and $R^3$ is a C1-C6 chain hydrocarbon group optionally having one or more halogen atoms, a halogen atom, or a hydrogen atom;

An amide compound of the formula (6) wherein $R^2$, $R^4$, and $R^5$ are same or different and are independently a halogen atom or a hydrogen atom, and $R^3$ is a methyl group, a trifluoromethyl group, a trifluoromethoxy group, a chlorine atom, a bromine atom, an iodine atom, or a hydrogen atom;

An amide compound of the formula (6) wherein $R^2$, $R^4$ and $R^5$ are same or different and are independently a halogen atom or a hydrogen atom, and $R^3$ is a methyl group;

An amide compound of the formula (6) wherein $R^2$, $R^4$, and $R^5$ are same or different and are independently a halogen atom or a hydrogen atom, and $R^3$ is a trifluoromethyl group;

An amide compound of the formula (6) wherein $R^2$, $R^4$, and $R^5$ are same or different and are independently a halogen atom or a hydrogen atom, and $R^3$ is a trifluoromethoxy group;

An amide compound of the formula (6) wherein $R^2$, $R^4$, and $R^5$ are same or different and are independently a halogen atom or a hydrogen atom, and $R^3$ is a chlorine atom;

An amide compound of the formula (6) wherein $R^2$, $R^4$, and $R^5$ are same or different and are independently a halogen atom or a hydrogen atom, and $R^3$ is a bromine atom;

An amide compound of the formula (6) wherein $R^2$, $R^4$, and $R^5$ are a hydrogen atom, and $R^3$ is a C1-C6 chain hydrocarbon group optionally having one or more halogen atoms;

An amide compound of the formula (6) wherein $R^2$, $R^4$, and $R^5$ are a hydrogen atom, and $R^3$ is a methyl group, a trifluoromethyl group, a trifluoromethoxy group, a chlorine atom, a bromine atom, an iodine atom, or a hydrogen atom;

An amide compound of the formula (6) wherein $R^2$, $R^4$, and $R^5$ are a hydrogen atom, $R^3$ is a methyl group, a trifluoromethyl group, a trifluoromethoxy group, a chlorine atom, a bromine atom, or an iodine atom;

An amide compound of the formula (6) wherein $R^2$, $R^4$, and $R^5$ are a hydrogen atom, and $R^3$ is a methyl group;

An amide compound of the formula (6) wherein $R^2$, $R^4$, and $R^5$ are a hydrogen atom, and $R^3$ is a trifluoromethyl group;

An amide compound of the formula (6) wherein $R^2$, $R^4$, and $R^5$ are a hydrogen atom, and $R^3$ is a trifluoromethoxy group;

An amide compound of the formula (6) wherein $R^2$, $R^4$, and $R^5$ are a hydrogen atom, and $R^3$ is a chlorine atom;

An amide compound of the formula (6) wherein $R^2$, $R^4$, and $R^5$ are a hydrogen atom, and $R^3$ is a bromine atom;

An amide compound of the formula (6) wherein $R^2$, $R^3$, $R^4$, and $R^5$ are a hydrogen atom;

An amide compound of the formula (6) wherein $R^1$ is a C1-C6 chain hydrocarbon group optionally having one or more halogen atoms, $R^2$, $R^4$, and $R^5$ are same or different and are independently a hydrogen atom or a halogen atom, and $R^3$ is a C1-C6 chain hydrocarbon group optionally having one or more halogen atoms, —$OR^{11}$, a halogen atom, or a hydrogen atom;

An amide compound of the formula (6) wherein $R^1$ is a C1-C6 chain hydrocarbon group optionally having one or more halogen atoms, $R^2$, $R^4$, and $R^5$ are same or different and are independently a halogen atom or a hydrogen atom, and $R^3$ is a methyl group, a trifluoromethyl group, a trifluoromethoxy group, a chlorine atom, a bromine atom, an iodine atom, or a hydrogen atom;

An amide compound of the formula (6) wherein $R^1$ is a methyl group, $R^2$, $R^4$, and $R^5$ are a hydrogen atom, and $R^3$ is a C1-C6 chain hydrocarbon group optionally having one or more halogen atoms;

An amide compound of the formula (6) wherein $R^1$ is a methyl group, $R^2$, $R^4$, and $R^5$ are a hydrogen atom, and $R^3$ is a methyl group or a hydrogen atom;

An amide compound of the formula (6) wherein $R^1$ is a methyl group, $R^2$, $R^4$, and $R^5$ are a hydrogen atom, and $R^3$ is a trifluoromethyl group or a hydrogen atom;

An amide compound of the formula (6) wherein $R^1$ is a methyl group, $R^2$, $R^4$, and $R^5$ are a hydrogen atom, and $R^3$ is a chlorine atom or a hydrogen atom;

An amide compound of the formula (6) wherein $R^1$ is a methyl group, $R^2$, $R^4$, and $R^5$ are a hydrogen atom, and $R^3$ is a bromine atom or a hydrogen atom;

An amide compound of the formula (6) wherein $R^1$ is a methyl group, $R^2$, $R^4$, and $R^5$ are a hydrogen atom, and $R^3$ is a methyl group, a trifluoromethyl group, a trifluoromethoxy group, a chlorine atom, a bromine atom, or an iodine atom;

An amide compound of the formula (6) wherein $R^1$ is a methyl group, and $R^2$, $R^3$, $R^4$, and $R^5$ are a hydrogen atom;

An amide compound of the formula (6) wherein $R^1$ is an ethyl group, $R^2$, $R^4$, and $R^5$ are a hydrogen atom, and $R^3$ is a C1-C6 chain hydrocarbon group optionally having one or more halogen atoms;

An amide compound of the formula (6) wherein $R^1$ is an ethyl group, $R^2$, $R^4$, and $R^5$ are a hydrogen atom, and $R^3$ is a methyl group or a hydrogen atom;

An amide compound of the formula (6) wherein $R^1$ is an ethyl group, $R^2$, $R^4$, and $R^5$ are a hydrogen atom, and $R^3$ is a trifluoromethyl group or a hydrogen atom;

An amide compound of the formula (6) wherein $R^1$ is an ethyl group, $R^2$, $R^4$, and $R^5$ are a hydrogen atom, and $R^3$ is a chlorine atom or a hydrogen atom;

An amide compound of the formula (6) wherein $R^1$ is an ethyl group, $R^2$, $R^4$, and $R^5$ are a hydrogen atom, and $R^3$ is a bromine atom or a hydrogen atom;

An amide compound of the formula (6) wherein $R^1$ is an ethyl group, $R^2$, $R^4$, and $R^5$ are a hydrogen atom, and $R^3$ is a methyl group, a trifluoromethyl group, a trifluoromethoxy group, a chlorine atom, a bromine atom, or an iodine atom;

An amide compound of the formula (6) wherein $R^1$ is an ethyl group, and $R^2$, $R^3$, $R^4$, and $R^5$ are a hydrogen atom;

An amide compound of the formula (6) wherein $R^1$ is a propyl group, $R^2$, $R^4$, and $R^5$ are a hydrogen atom, and $R^3$ is a C1-C6 chain hydrocarbon group optionally having one or more halogen atoms;

An amide compound of the formula (6) wherein $R^1$ is a propyl group, $R^2$, $R^4$, and $R^5$ are a hydrogen atom, and $R^3$ is a methyl group or a hydrogen atom;

An amide compound of the formula (6) wherein $R^1$ is a propyl group, $R^2$, $R^4$, and $R^5$ are a hydrogen atom, and $R^3$ is a trifluoromethyl group or a hydrogen atom;

An amide compound of the formula (6) wherein $R^1$ is a propyl group, $R^2$, $R^4$, and $R^5$ are a hydrogen atom, and $R^3$ is a chlorine atom or a hydrogen atom;

An amide compound of the formula (6) wherein $R^1$ is a propyl group, $R^2$, $R^4$, and $R^5$ are a hydrogen atom, and $R^3$ is a bromine atom or a hydrogen atom;

An amide compound of the formula (6) wherein $R^1$ is a propyl group, $R^2$, $R^4$, and $R^5$ are a hydrogen atom, and $R^3$ is a methyl group, a trifluoromethyl group, a trifluoromethoxy group, a chlorine atom, a bromine atom, or an iodine atom;

An amide compound of the formula (6) wherein $R^1$ is a propyl group, and $R^2$, $R^3$, $R^4$, and $R^5$ are a hydrogen atom;

An amide compound of the formula (6) wherein $R^6$ and $R^7$ are same or different and are independently a C1-C6 chain hydrocarbon group optionally having one or more halogen atoms, $-OR^{11}$, $-S(O)_mR^{11}$, $-NR^{11}R^{12}$, a cyano group, a nitro group, a halogen atom, or a hydrogen atom;

An amide compound of the formula (6) wherein $R^6$ and $R^7$ are same or different and are independently a C1-C6 chain hydrocarbon group optionally having one or more halogen atoms, $-OR^{11}$, $-S(O)_mR^{11}$, a halogen atom, or a hydrogen atom;

An amide compound of the formula (6) wherein $R^6$ is a C1-C6 chain hydrocarbon group optionally having one or more halogen atoms, $-OR^{11}$, $-S(O)_mR^{11}$, or a halogen atom, and $R^7$ is a hydrogen atom;

An amide compound of the formula (6) wherein $R^6$ is a C1-C6 chain hydrocarbon group optionally having one or more halogen atoms, and $R^7$ is a hydrogen atom;

An amide compound of the formula (6) wherein $R^6$ is a C1-C6 chain hydrocarbon group having one or more halogen atoms, and $R^7$ is a hydrogen atom;

An amide compound of the formula (6) wherein $R^6$ is a C1-C6 chain hydrocarbon group having one or more fluorine atoms, and $R^7$ is a hydrogen atom;

An amide compound of the formula (6) wherein $R^6$ is $-OR^{11}$, and $R^7$ is a hydrogen atom;

An amide compound of the formula (6) wherein $R^6$ is $-S(O)_mR^{11}$, and $R^7$ is a hydrogen atom;

An amide compound of the formula (6) wherein $R^6$ is a C1-C6 chain hydrocarbon group having one or more halogen atoms, $-OR^{11}$, $-S(O)_mR^{11}$, or a halogen atom, and $R^7$ is a hydrogen atom;

An amide compound of the formula (6) wherein $R^6$ is a trifluoromethyl group, a pentafluoroethyl group, a heptafluoroisopropyl group, a trifluoromethoxy group, a trifluoromethylsulfanyl group, a trifluoromethylsulfinyl group, a trifluoromethylsulfonyl group, a bromine atom, or an iodine atom, and $R^7$ is a hydrogen atom;

An amide compound of the formula (6) wherein $R^8$ is a C1-C6 chain hydrocarbon group having one C1-C6 alkoxy group optionally having one or more halogen atoms, a C1-C6 chain hydrocarbon group optionally having one or more halogen atoms, or a cyclopropyl group;

An amide compound of the formula (6) wherein $R^8$ is a methyl group, an ethyl group, a methoxymethyl group, or an ethoxymethyl group;

An amide compound of the formula (6) wherein $R^8$ is a methyl group;

An amide compound of the formula (6) wherein $A^2$ is $=CH-$, $A^3$ is a nitrogen atom or $=CR^{10}-$, $R^{10}$ is a hydrogen atom, $R^8$ is a C1-C6 chain hydrocarbon group optionally having one or more halogen atoms, $R^1$ is a C1-C6 chain hydrocarbon group optionally having one or more halogen atoms, $R^2$, $R^4$, and $R^5$ are same or different and are independently a hydrogen atom or a halogen atom, $R^3$ is a C1-C6 chain hydrocarbon group optionally having one or more halogen atoms, $-OR^{11}$, a halogen atom, or a hydrogen atom, and $R^6$ and $R^7$ are same or different and are independently a C1-C6 chain hydrocarbon group optionally having one or more halogen atoms, $-OR^{11}$, $-S(O)_mR^{11}$, a halogen atom, or a hydrogen atom;

An amide compound of the formula (6) wherein $A^2$ is $=CH-$, $A^3$ is a nitrogen atom, $R^8$ is a methyl group or a hydrogen atom, $R^1$ is a methyl group, an ethyl group or propyl group, $R^2$, $R^4$, and $R^5$ are same or different and are independently a halogen atom or a hydrogen atom, $R^3$ is a trifluoromethyl group, a halogen atom or a hydrogen atom, $R^6$ is a C1-C3 alkyl group having one or more fluorine atoms, a C1-C3 alkoxy group having one or more fluorine atoms, a C1-C3 alkylsulfanyl group having one or more fluorine atoms, a C1-C3 alkylsulfinyl group having one or more fluorine atoms, or a C1-C3 alkylsulfonyl group having one or more fluorine atoms, and $R^7$ is a hydrogen atom;

An amide compound of the formula (6) wherein $A^2$ is $=CH-$, $A^3$ is a nitrogen atom or $=CR^{10}-$, $R^{10}$ is a hydrogen atom, $R^8$ is a methyl group or a hydrogen atom, $R^1$ is a methyl group, an ethyl group, or propyl group, $R^2$, $R^4$, and $R^5$ are a hydrogen atom, $R^3$ is a methyl group, a trifluoromethyl group, a trifluoromethoxy group, a chlorine atom, a bromine atom, or an iodine atom, $R^6$ is a trifluoromethyl group, a pentafluoroethyl group, a heptafluoroisopropyl group, a trifluoromethoxy group, a trifluoromethylsulfanyl group, a trifluoromethylsulfinyl group, a trifluoromethylsulfonyl group, a bromine atom, or an iodine atom, and $R^7$ is a hydrogen atom.

Examples of Compound (C) include the following compounds:

An amide compound of the formula (M10):

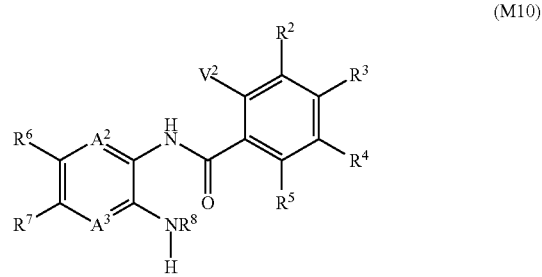

(M10)

wherein, $V^2$, $R^2$, $R^3$, $R^4$, $R^5$, $R^6$, $R^7$, $R^8$, $A^2$ and $A^3$ are as defined above (referred to as Compound (M10));

An amide compound of the formula (M25):

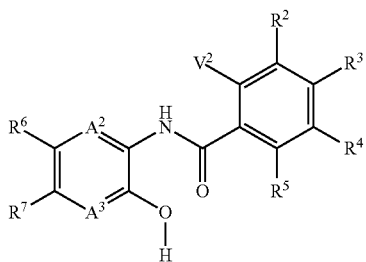

wherein, $V^2, R^2, R^3, R^4, R^5, R^6, R^7, A^2$ and $A^3$ are as defined above (referred to as Compound (M25));

An amide compound of the formula (M26):

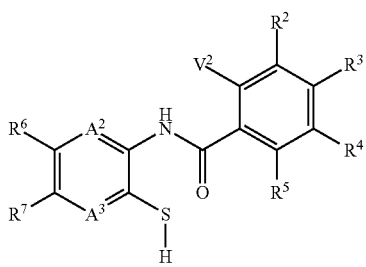

wherein, $V^2, R^2, R^3, R^4, R^5, R^6, R^7, A^2$ and $A^3$ are as defined above (referred to as Compound (M26));

A compound of the formula (1C):

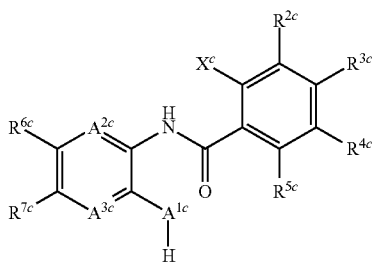

wherein, $X^c$ represents a fluorine atom or a chlorine atom;

$A^{1c}$ represents —$NR^{8c}$—, an oxygen atom, or a sulfur atom;

$A^{2c}$ represents a nitrogen atom or =$CR^{9c}$—;

$A^{3c}$ represents a nitrogen atom or =$CR^{10c}$—;

$R^{2c}, R^{3c}$, and $R^{5c}$ are same or different and represent independently a C1-C6 chain hydrocarbon group optionally having one or more halogen atoms, a phenyl group optionally having one or more halogen atoms or C1-C3 alkyl groups optionally having one or more halogen atoms, a 5-membered heterocyclic group optionally having one or more halogen atoms or C1-C3 alkyl groups optionally having one or more halogen atoms, a 6-membered heterocyclic group optionally having one or more halogen atoms or C1-C3 alkyl groups optionally having one or more halogen atoms —$OR^{11c}$, —$S(O)_mR^{11c}$, —$SF_5$, a cyano group, a halogen atom, or a hydrogen atom: provided that at least one of $R^{2c}, R^{3c}$, and $R^{5c}$ represent a hydrogen atom;

$R^{4c}$ represents a hydrogen atom;

$R^{6c}$ represents a C1-C3 alkyl group having one or more fluorine atoms, a C1-C3 alkylsulfanyl group having one or more fluorine atoms, a C1-C3 alkylsulfinyl group having one or more fluorine atoms, a C1-C3 alkylsulfonyl group having one or more fluorine atoms, or —$SF_5$;

$R^{7c}$ represents a C1-C6 chain hydrocarbon group optionally having one or more halogen atoms, a phenyl group optionally having one or more halogen atoms or C1-C3 alkyl groups optionally having one or more halogen atoms, a 5-membered heterocyclic group optionally having one or more halogen atoms or C1-C3 alkyl groups optionally having one or more halogen atoms, a 6-membered heterocyclic group optionally having one or more halogen atoms or C1-C3 alkyl groups optionally having one or more halogen atoms, —$OR^{11c}$, —$S(O)_mR^{11c}$, —$SF_5$, a cyano group, a halogen atom, or a hydrogen atom;

$R^{8c}$ represents a C1-C6 chain hydrocarbon group optionally having one or more halogen atoms, a C1-C6 chain hydrocarbon group having one C1-C6 alkoxy group, a C3-C6 alicyclic hydrocarbon group optionally having one or more halogen atoms, or a hydrogen atom;

$R^{9c}$ and $R^{10c}$ are same or different and represent independently a C1-C6 chain hydrocarbon group optionally having one or more halogen atoms, —$OR^{11c}$, —$S(O)_mR^{11c}$, a cyano group, a nitro group, a halogen atom, or a hydrogen atom;

$R^{11c}$ and $R^{12c}$ are same or different and represent independently a C1-C6 chain hydrocarbon group optionally having one or more halogen atoms or a hydrogen atom; and m represents 0, 1, or 2;

provided that: in —$S(O)_mR^{11c}$, when m is 1 or 2, $R^{11c}$ is not a hydrogen atom; and when $A^{1c}$ is —$NR^{8c}$—, and $A^{2c}$ and $A^{3c}$ are a methine group, $R^{8c}$ is a hydrogen atom or a methyl group (hereinafter, referred to as Compound (1C));

And examples of Compound (1C) include the following compounds:

An amide compound of the formula (1C) wherein $X^c$ is a fluorine atom;

An amide compound of the formula (1C) wherein $X^c$ is a chlorine atom;

An amide compound of the formula (1C) wherein $A^{1c}$ is —$NR^{8c}$—;

An amide compound of the formula (1C) wherein $A^{1c}$ is —$NR^{8c}$—, and $R^{8c}$ is a C1-C6 chain hydrocarbon group optionally having one or more halogen atoms;

An amide compound of the formula (1C) wherein $A^{1c}$ is —$NR^{8c}$—, and $R^{8c}$ is a C1-C6 chain hydrocarbon group;

An amide compound of the formula (1C) wherein $A^{1c}$ is —$NR^{8c}$—, and $R^{8c}$ is a C1-C6 alkyl group;

An amide compound of the formula (1C) wherein $A^{1c}$ is —$NR^{8c}$—, and $R^{8c}$ is a C1-C3 alkyl group;

An amide compound of the formula (1C) wherein $A^{1c}$ is —$NR^{8c}$—, and $R^{8c}$ is a methyl group, an ethyl group, a propyl group, or an isopropyl group;

An amide compound of the formula (1C) wherein $A^{1c}$ is —$NR^{8c}$—, and $R^{8c}$ is a methyl group;

An amide compound of the formula (1C) wherein $A^{1c}$ is —$NR^{8c}$—, and $R^{8c}$ is an ethyl group;

An amide compound of the formula (1C) wherein $A^{1c}$ is —$NR^{8c}$—, and $R^{8c}$ is a propyl group;

An amide compound of the formula (1C) wherein $A^{1c}$ is —$NR^{8c}$—, and $R^{8c}$ is an isopropyl group;

An amide compound of the formula (1C) wherein $A^{1c}$ is —$NR^{8c}$—, and $R^{8c}$ is a C1-C6 chain hydrocarbon group having one C1-C6 alkoxy group;

An amide compound of the formula (1C) wherein $A^{1c}$ is —$NR^{8c}$—, and $R^{8c}$ is a methoxymethyl group or an ethoxymethyl group;

An amide compound of the formula (1C) wherein $A^{1c}$ is —$NR^{8c}$—, and $R^{8c}$ is a C3-C6 alicyclic hydrocarbon group optionally having one or more halogen atoms;

An amide compound of the formula (1C) wherein $A^{1c}$ is —$NR^{8c}$—, and $R^{8c}$ is a cyclopropyl group, a cyclobutyl group, a cyclopentyl group, or a cyclohexyl group;

An amide compound of the formula (1C) wherein $A^{1c}$ is —$NR^{8c}$—, and $R^{8c}$ is a hydrogen atom;

An amide compound of the formula (1C) wherein $A^{1c}$ is an oxygen atom;

An amide compound of the formula (1C) wherein $A^{1c}$ is a sulfur atom;

An amide compound of the formula (1C) wherein $A^{1c}$ is —$NR^{8c}$— or a sulfur atom;

An amide compound of the formula (1C) wherein $A^{1c}$ is —$NR^{8c}$— or a sulfur atom, and $R^{8c}$ is a methyl group, an ethyl group, a propyl group, or an isopropyl group;

An amide compound of the formula (1C) wherein $A^{1c}$ is —$NR^{8c}$— or a sulfur atom, and $R^{8c}$ is a methoxymethyl group, an ethoxymethyl group, or a hydrogen atom;

An amide compound of the formula (1C) wherein $A^{2c}$ is =$CR^{9c}$—, and $A^{3c}$ is =$CR^{10c}$—;

An amide compound of the formula (1C) wherein $A^{2c}$ is =$CR^{9c}$—, $A^{3c}$ is =$CR^{10c}$—, and $R^{9c}$ and $R^{10c}$ are same or different and are independently a halogen atom or a hydrogen atom;

An amide compound of the formula (1C) wherein $A^{2c}$ is =$CR^{9c}$—, $A^{3c}$ is =$CR^{10c}$—, and $R^{9c}$ and $R^{10c}$ are a hydrogen atom;

An amide compound of the formula (1C) wherein $A^{2c}$ is a nitrogen atom, and $A^{3c}$ is =$CR^{10c}$—;

An amide compound of the formula (1C) wherein $A^{2c}$ is =$OR^{9c}$—, and $A^{3c}$ is a nitrogen atom;

An amide compound of the formula (1C) wherein $A^{2c}$ is =$CR^{9c}$—, $R^{9c}$ is a halogen atom or a hydrogen atom, and $A^{3c}$ is a nitrogen atom;

An amide compound of the formula (1C) wherein $A^{2c}$ is =$CR^{9c}$—, $R^{9c}$ is a hydrogen atom, and $A^{3c}$ is a nitrogen atom;

An amide compound of the formula (1C) wherein $A^{2c}$ is a nitrogen atom, and $A^{3c}$ is a nitrogen atom;

An amide compound of the formula (1C) wherein $A^{1c}$ is —$NR^{8c}$—, $A^{2c}$ is =$CR^{9c}$—, and $A^{3c}$ is =$CR^{10c}$—;

An amide compound of the formula (1C) wherein $A^{1c}$ is —$NR^{8c}$—, $A^{2c}$ is =$CR^{9c}$—, $A^{3c}$ is =$CR^{10c}$—, and $R^{9c}$ and $R^{10c}$ are a hydrogen atom;

An amide compound of the formula (1C) wherein $A^{1c}$ is an oxygen atom, $A^{2c}$ is =$OR^{9c}$—, and $A^{3c}$ is =$CR^{10c}$—;

An amide compound of the formula (1C) wherein $A^{1c}$ is a sulfur atom, $A^{2c}$ is =$OR^{9c}$—, and $A^{3c}$ is =$CR^{10c}$—;

An amide compound of the formula (1C) wherein $A^{1c}$ is a sulfur atom, $A^{2c}$ is =$CR^{9c}$—, $A^{3c}$ is =$CR^{10c}$—, and $R^{9c}$ and $R^{10c}$ are a hydrogen atom;

An amide compound of the formula (1C) wherein $A^{1c}$ is —$NR^{8c}$—, $A^{2c}$ is =$OR^{9c}$—, and $A^{3c}$ is a nitrogen atom;

An amide compound of the formula (1C) wherein $A^{1c}$ is —$NR^{8c}$—, $A^{2c}$ is =$CR^{9c}$—, $R^{9c}$ is a hydrogen atom, and $A^{3c}$ is a nitrogen atom;

An amide compound of the formula (1C) wherein $A^{1c}$ is an oxygen atom, $A^{2c}$ is =$CR^{9c}$—, and $A^{3c}$ is a nitrogen atom;

An amide compound of the formula (1C) wherein $A^{1c}$ is a sulfur atom, $A^{2c}$ is =$CR^{9c}$—, and $A^{3c}$ is a nitrogen atom;

An amide compound of the formula (1C) wherein $A^{1c}$ is a sulfur atom, $A^{2c}$ is =$CR^{9c}$—, $R^{9c}$ is a hydrogen atom, and $A^{3c}$ is a nitrogen atom;

An amide compound of the formula (1C) wherein $A^{1c}$ is —$NR^{8c}$— or a sulfur atom, $R^{8c}$ is a methyl group, an ethyl group, a propyl group or an isopropyl group, $A^{2c}$ is =$CR^{9c}$—, $A^{3c}$ is =$CR^{10c}$—, and $R^{9c}$ and $R^{10c}$ are a hydrogen atom;

An amide compound of the formula (1C) wherein $A^{1c}$ is —$NR^{8c}$— or a sulfur atom, $R^{8c}$ is a methyl group, $A^{2c}$ is =$CR^{9c}$—, $A^{3c}$ is =$CR^{10c}$—, and $R^{9c}$ and $R^{10c}$ are a hydrogen atom;

An amide compound of the formula (1C) wherein $A^{1c}$ is —$NR^{8c}$— or a sulfur atom, $R^{8c}$ is a methyl group, an ethyl group, a propyl group or an isopropyl group, $A^{2c}$ is =$CR^{9c}$—, $R^{9c}$ is a hydrogen atom, and $A^{3c}$ is a nitrogen atom;

An amide compound of the formula (1C) wherein $A^{1c}$ is —$NR^{8c}$— or a sulfur atom, $R^{8c}$ is a methyl group, $A^{2c}$ is =$CR^{9c}$—, $R^{9c}$ is a hydrogen atom, and $A^{3c}$ is a nitrogen atom;

An amide compound of the formula (1C) wherein $R^{2c}$, $R^{3c}$, and $R^{5c}$ are same or different and are independently a C1-C6 chain hydrocarbon group optionally having one or more halogen atoms, or a hydrogen atom;

An amide compound of the formula (1C) wherein $R^{2c}$, $R^{3c}$, and $R^{5c}$ are same or different and are independently a phenyl group optionally having one or more halogen atoms or C1-C3 alkyl groups optionally having one or more halogen atoms, a 5-membered heterocyclic group optionally having one or more halogen atoms or C1-C3 alkyl groups optionally having one or more halogen atoms, a 6-membered heterocyclic group optionally having one or more halogen atoms or C1-C3 alkyl groups optionally having one or more halogen atoms, or a hydrogen atom;

An amide compound of the formula (1C) wherein $R^{2c}$, $R^{3c}$, and $R^{5c}$ are same or different and are independently —$OR^{11c}$ or a hydrogen atom;

An amide compound of the formula (1C) wherein $R^{2c}$, $R^{3c}$, and $R^{5c}$ are same or different and are independently —$S(O)_m R^{11c}$ or a hydrogen atom;

An amide compound of the formula (1C) wherein $R^{2c}$, $R^{3c}$, and $R^{5c}$ are same or different and are independently a cyano group, a nitro group, or a hydrogen atom;

An amide compound of the formula (1C) wherein $R^{2c}$, $R^{3c}$, and $R^{5c}$ are same or different and are independently a halogen atom or a hydrogen atom;

An amide compound of the formula (1C) wherein $R^{2c}$, $R^{3c}$, and $R^{5c}$ is a hydrogen atom;

An amide compound of the formula (1C) wherein $R^{2c}$ and $R^{5c}$ are a hydrogen atom, and $R^{3c}$ is a 2-pyridyl group, a 2-pyrimidyl group, a 3-chloro-2-pyridyl group, or a 3-chloro-5-trifluoromethyl-2-pyridyl group;

An amide compound of the formula (1C) wherein $R^{2c}$ and $R^{5c}$ are a hydrogen atom, and $R^{3c}$ is a 2-pyridyl group;

An amide compound of the formula (1C) wherein $R^{2c}$ and $R^{5c}$ are a hydrogen atom, and $R^{3c}$ is a 2-pyrimidyl group;

An amide compound of the formula (1C) wherein $R^{2c}$ and $R^{5c}$ are a hydrogen atom, and $R^{3c}$ is a 3-chloro-2-pyridyl group;

An amide compound of the formula (1C) wherein $R^{2c}$ and $R^{5c}$ are a hydrogen atom, and $R^{3c}$ is a 3-chloro-5-trifluoromethyl-2-pyridyl group;

An amide compound of the formula (1C) wherein $R^{2c}$ and $R^{5c}$ are a hydrogen atom, and $R^{3c}$ is a C1-C6 chain hydrocarbon group optionally having one or more halogen atoms;

An amide compound of the formula (1C) wherein $R^{2c}$ and $R^{5c}$ are a hydrogen atom, and $R^{3c}$ is a C1-C6 alkyl group;

An amide compound of the formula (1C) wherein $R^{2c}$ and $R^{5c}$ are a hydrogen atom, and $R^{3c}$ is a C1-C6 alkyl group optionally having one or more fluorine atoms;

An amide compound of the formula (1C) wherein $R^{2c}$ and $R^{5c}$ are a hydrogen atom, and $R^{3c}$ is a C1-C3 alkyl group;

An amide compound of the formula (1C) wherein $R^{2c}$ and $R^{5c}$ are a hydrogen atom, and $R^{3c}$ is a C1-C3 alkyl group optionally having one or more fluorine atoms;

An amide compound of the formula (1C) wherein $R^{2c}$ and $R^{5c}$ are a hydrogen atom, and $R^{3c}$ is a methyl group, an ethyl group, a propyl group, an isopropyl group, a trifluoromethyl group, a pentafluoroethyl group, a heptafluoropropyl group, or a heptafluoroisopropyl group;

An amide compound of the formula (1C) wherein $R^{2c}$ and $R^{5c}$ are a hydrogen atom, and $R^{3c}$ is a methyl group;

An amide compound of the formula (1C) wherein $R^{2c}$ and $R^{5c}$ are a hydrogen atom, and $R^{3c}$ is an ethyl group;

An amide compound of the formula (1C) wherein $R^{2c}$ and $R^{5c}$ are a hydrogen atom, and $R^{3c}$ is a propyl group;

An amide compound of the formula (1C) wherein $R^{2c}$ and $R^{5c}$ are a hydrogen atom, and $R^{3c}$ is an isopropyl group;

An amide compound of the formula (1C) wherein $R^{2c}$ and $R^{5c}$ are a hydrogen atom, and $R^{3c}$ is a trifluoromethyl group;

An amide compound of the formula (1C) wherein $R^{2c}$ and $R^{5c}$ are a hydrogen atom, and $R^{3c}$ is a pentafluoroethyl group;

An amide compound of the formula (1C) wherein $R^{2c}$ and $R^{5c}$ are a hydrogen atom, and $R^{3c}$ is a heptafluoropropyl group;

An amide compound of the formula (1C) wherein $R^{2c}$ and $R^{5c}$ are a hydrogen atom, and $R^{3c}$ is a heptafluoroisopropyl group;

An amide compound of the formula (1C) wherein $R^{2c}$ and $R^{5c}$ are a hydrogen atom, and $R^{3c}$ is a halogen atom;

An amide compound of the formula (1C) wherein $R^{2c}$ and $R^{5c}$ are a hydrogen atom, and $R^{3c}$ is a fluorine atom, a chlorine atom, or a bromine atom;

An amide compound of the formula (1C) wherein $R^{2c}$ and $R^{5c}$ are a hydrogen atom, and $R^{3c}$ is a fluorine atom;

An amide compound of the formula (1C) wherein $R^{2c}$ and $R^{5c}$ are a hydrogen atom, and $R^{3c}$ is a chlorine atom;

An amide compound of the formula (1C) wherein $R^{2c}$ and $R^{5c}$ are a hydrogen atom, and $R^{3c}$ is a bromine atom;

An amide compound of the formula (1C) wherein $R^{2c}$ and $R^{5c}$ are a hydrogen atom, and $R^{3c}$ is —SF$_5$;

An amide compound of the formula (1C) wherein $R^{2c}$, $R^{3c}$, and $R^{5c}$ are same or different and are independently a C1-C6 chain hydrocarbon group optionally having one or more halogen atoms, a halogen atom, or a hydrogen atom;

An amide compound of the formula (1C) wherein $R^{2c}$ and $R^{5c}$ are a hydrogen atom, and $R^{3c}$ is a 6-membered heterocyclic group optionally having one or more halogen atoms or C1-C3 alkyl groups optionally having one or more halogen atoms;

An amide compound of the formula (1C) wherein $R^{2c}$ and $R^{5c}$ are a hydrogen atom, and $R^{3c}$ is a C1-C6 chain hydrocarbon group optionally having one or more halogen atoms or a halogen atom;

An amide compound of the formula (1C) wherein $R^{2c}$ and $R^{5c}$ are a hydrogen atom, and $R^{3c}$ is a C1-C3 alkyl group optionally having one or more fluorine atoms or a halogen atom;

An amide compound of the formula (1C) wherein $R^{2c}$ and $R^{5c}$ are a hydrogen atom, and $R^{3c}$ is a 2-pyridyl group, a 2-pyrimidyl group, a 3-chloro-2-pyridyl group, a 3-chloro-5-trifluoromethyl-2-pyridyl group, a methyl group, an ethyl group, a propyl group, an isopropyl group, a trifluoromethyl group, a pentafluoroethyl group, a heptafluoropropyl group, a heptafluoroisopropyl group, a fluorine atom, a chlorine atom, or a bromine atom;

An amide compound of the formula (1C) wherein $R^{2c}$ and $R^{5c}$ are a hydrogen atom, and $R^{3c}$ is a methyl group, an ethyl group, a propyl group, an isopropyl group, a trifluoromethyl group, a pentafluoroethyl group, a heptafluoropropyl group, a heptafluoroisopropyl group, a fluorine atom, a chlorine atom, or a bromine atom;

An amide compound of the formula (1C) wherein $R^{6c}$ is a C1-C3 alkyl group having one or more fluorine atoms;

An amide compound of the formula (1C) wherein $R^{6c}$ is a trifluoromethyl group, a pentafluoroethyl group, a heptafluoropropyl group, or a heptafluoroisopropyl group;

An amide compound of the formula (1C) wherein $R^{6c}$ is a trifluoromethyl group;

An amide compound of the formula (1C) wherein $R^{6c}$ is a pentafluoroethyl group;

An amide compound of the formula (1C) wherein $R^{6c}$ is a heptafluoropropyl group;

An amide compound of the formula (1C) wherein $R^{6c}$ is a heptafluoroisopropyl group;

An amide compound of the formula (1C) wherein $R^{6c}$ is a C1-C3 alkylsulfanyl group having one or more fluorine atoms, a C1-C3 alkylsulfinyl group having one or more fluorine atoms, or a C1-C3 alkylsulfonyl group having one or more fluorine atoms;

An amide compound of the formula (1C) wherein $R^{6c}$ is a trifluoromethylsulfanyl group, a trifluoromethylsulfinyl group, or a trifluoromethylsulfonyl group;

An amide compound of the formula (1C) wherein $R^{6c}$ is a trifluoromethylsulfanyl group;

An amide compound of the formula (1C) wherein $R^{6c}$ is a trifluoromethylsulfinyl group;

An amide compound of the formula (1C) wherein $R^{6c}$ is a trifluoromethylsulfonyl group;

An amide compound of the formula (1C) wherein $R^{6c}$ is —SF$_5$;

An amide compound of the formula (1C) wherein $R^{6c}$ is a C1-C3 alkyl group having one or more fluorine atoms, a C1-C3 alkoxy group having one or more fluorine atoms, a C1-C3 alkylsulfanyl group having one or more fluorine atoms, a C1-C3 alkylsulfinyl group having one or more fluorine atoms, or a C1-C3 alkylsulfonyl group having one or more fluorine atoms;

An amide compound of the formula (1C) wherein $R^{6c}$ is a trifluoromethyl group, a pentafluoroethyl group, a heptafluoropropyl group, a heptafluoroisopropyl group, a trifluoromethylsulfanyl group, a trifluoromethylsulfinyl group, or a trifluoromethylsulfonyl group;

An amide compound of the formula (1C) wherein $R^{7c}$ is a C1-C6 chain hydrocarbon group optionally having one or more halogen atoms;

An amide compound of the formula (1C) wherein $R^{7c}$ is a C1-C6 chain hydrocarbon group;

An amide compound of the formula (1C) wherein $R^{7c}$ is a C1-C6 chain hydrocarbon group having one or more fluorine atoms;

An amide compound of the formula (1C) wherein $R^{7c}$ is a C1-C3 alkyl group having one or more fluorine atoms;

An amide compound of the formula (1C) wherein $R^{7c}$ is a trifluoromethyl group, a pentafluoroethyl group, a heptafluoropropyl group, or a heptafluoroisopropyl group;

An amide compound of the formula (1C) wherein $R^{7c}$ is a trifluoromethyl group;

An amide compound of the formula (1C) wherein $R^{7c}$ is a pentafluoroethyl group;

An amide compound of the formula (1C) wherein $R^{7c}$ is a heptafluoropropyl group;

An amide compound of the formula (1C) wherein $R^{7c}$ is a heptafluoroisopropyl group;

An amide compound of the formula (1C) wherein $R^{7c}$ is a phenyl group optionally having one or more halogen atoms or C1-C3 alkyl groups optionally having one or more halogen atoms, a 5-membered heterocyclic group optionally having one or more halogen atoms or C1-C3 alkyl groups optionally having one or more halogen atoms, or a 6-membered heterocyclic group optionally having one or more halogen atoms or C1-C3 alkyl groups optionally having one or more halogen atoms;

An amide compound of the formula (1C) wherein $R^{7c}$ is $-OR^{11c}$;

An amide compound of the formula (1C) wherein $R^{7c}$ is a C1-C6 alkoxy group having one ore more fluorine atoms;

An amide compound of the formula (1C) wherein $R^{7c}$ is a C1-C3 alkoxy group having one or more fluorine atoms;

An amide compound of the formula (1C) wherein $R^{7c}$ is a trifluoromethoxy group;

An amide compound of the formula (1C) wherein $R^{7c}$ is $-S(O)_m R^{11c}$;

An amide compound of the formula (1C) wherein $R^{7c}$ is a C1-C6 alkylsulfanyl group having one or more fluorine atoms, a C1-C6 alkylsulfinyl group having one or more fluorine atoms, or a C1-C6 alkylsulfonyl group having one or more fluorine atoms;

An amide compound of the formula (1C) wherein $R^{7c}$ is a C1-C3 alkylsulfanyl group having one or more fluorine atoms, a C1-C3 alkylsulfinyl group having one or more fluorine atoms, or a C1-C3 alkylsulfonyl group having one or more fluorine atoms;

An amide compound of the formula (1C) wherein $R^{7c}$ is a trifluoromethylsulfanyl group, a trifluoromethylsulfinyl group, or a trifluoromethylsulfonyl group;

An amide compound of the formula (1C) wherein $R^{7c}$ is a trifluoromethylsulfanyl group;

An amide compound of the formula (1C) wherein $R^{7c}$ is a trifluoromethylsulfinyl group;

An amide compound of the formula (1C) wherein $R^{7c}$ is a trifluoromethylsulfonyl group;

An amide compound of the formula (1C) wherein $R^{7c}$ is a cyano group or a nitro group;

An amide compound of the formula (1C) wherein $R^{7c}$ is a halogen atom;

An amide compound of the formula (1C) wherein $R^{7c}$ is a chlorine atom, a bromine atom, or an iodine atom;

An amide compound of the formula (1C) wherein $R^{7c}$ is a chlorine atom;

An amide compound of the formula (1C) wherein $R^{7c}$ is a bromine atom;

An amide compound of the formula (1C) wherein $R^{7c}$ is an iodine atom;

An amide compound of the formula (1C) wherein $R^{7c}$ is a hydrogen atom;

An amide compound of the formula (1C) wherein $R^{7c}$ is $-SF_5$;

An amide compound of the formula (1C) wherein $R^{7c}$ is a C1-C3 alkyl group having one or more fluorine atoms, a C1-C3 alkoxy group having one or more fluorine atoms, a C1-C3 alkylsulfanyl group having one or more fluorine atoms, a C1-C3 alkylsulfinyl group having one or more fluorine atoms, a C1-C3 alkylsulfonyl group having one or more fluorine atoms, or a halogen atom;

An amide compound of the formula (1C) wherein $R^{7c}$ is a trifluoromethyl group, a pentafluoroethyl group, a heptafluoropropyl group, a heptafluoroisopropyl group, a trifluoromethoxy group, a trifluoromethylsulfanyl group, a trifluoromethylsulfinyl group, a trifluoromethylsulfonyl group, a chlorine atom, a bromine atom, or an iodine atom;

An amide compound of the formula (1C) wherein $R^{6c}$ is a C1-C3 alkyl group having one or more fluorine atoms, a C1-C3 alkoxy group having one or more fluorine atoms, a C1-C3 alkylsulfanyl group having one or more fluorine atoms, a C1-C3 alkylsulfinyl group having one or more fluorine atoms, or a C1-C3 alkylsulfonyl group having one or more fluorine atoms, and $R^{7c}$ is a hydrogen atom;

An amide compound of the formula (1C) wherein $R^{6c}$ is a trifluoromethyl group, a pentafluoroethyl group, a heptafluoropropyl group, a heptafluoroisopropyl group, a trifluoromethylsulfanyl group, a trifluoromethylsulfinyl group, or a trifluoromethylsulfonyl group, and $R^{7c}$ is a hydrogen atom;

An amide compound of the formula (1C) wherein m is 0;

An amide compound of the formula (1C) wherein m is 1;

An amide compound of the formula (1C) wherein m is 2;

An amide compound of the formula (1C) wherein $A^{1c}$ is $-NR^{8c}-$ or a sulfur atom, $R^{8c}$ is a C1-C6 alkyl group, $A^{2c}$ is $=CR^{9c}-$, $A^{3c}$ is $=CR^{10c}-$, $R^{9c}$ and $R^{10c}$ are a hydrogen atom, $R^{2c}$ and $R^{5c}$ are a hydrogen atom, $R^{3c}$ is a C1-C3 alkyl group optionally having one or more fluorine atoms or a halogen atom, $R^{6c}$ is a C1-C3 alkyl group having one or more fluorine atoms, a C1-C3 alkylsulfanyl group having one or more fluorine atoms, a C1-C3 alkylsulfinyl group having one or more fluorine atoms, or a C1-C3 alkylsulfonyl group having one or more fluorine atoms, and $R^{7c}$ is a hydrogen atom;

An amide compound of the formula (1C) wherein $A^{1c}$ is $-NR^{8c}-$ or a sulfur atom, $R^{8c}$ is a C1-C6 alkyl group, $A^{2c}$ is $=CR^{9c}-$, $R^{9c}$ is a hydrogen atom, $A^{3c}$ is a nitrogen atom, $R^{2c}$ and $R^{5c}$ are a hydrogen atom, $R^{3c}$ is a C1-C3 alkyl group optionally having one or more fluorine atoms or a halogen atom, $R^{6c}$ is a C1-C3 alkyl group having one or more fluorine atoms, a C1-C3 alkylsulfanyl group having one or more fluorine atoms, a C1-C3 alkylsulfinyl group having one or more fluorine atoms, or a C1-C3 alkylsulfonyl group having one or more fluorine atoms, and $R^{7c}$ is a hydrogen atom;

An amide compound of the formula (1C) wherein $A^{1c}$ is $-NR^{8c}-$, $R^{8c}$ is a methyl group, an ethyl group, a propyl group, or an isopropyl group, $A^{2c}$ is $=CR^{9c}-$, $A^{3c}$ is $=CR^{10c}-$, $R^{9c}$ and $R^{10c}$ are a hydrogen atom, $R^{2c}$ and $R^{5c}$ are a hydrogen atom, $R^{3c}$ is a methyl group, an ethyl group, a propyl group, an isopropyl group, a trifluoromethyl group, a pentafluoroethyl group, a heptafluoropropyl group, a heptafluoroisopropyl group, a fluorine atom, a chlorine atom, or a bromine atom, $R^{6c}$ is a trifluoromethyl group, a pentafluoroethyl group, a heptafluoropropyl group, a heptafluoroisopropyl group, a trifluoromethylsulfanyl group, a trifluoromethylsulfinyl group, or a trifluoromethylsulfonyl group, and $R^{7c}$ is a hydrogen atom;

An amide compound of the formula (1C) wherein $A^{1c}$ is a sulfur atom, $A^{2c}$ is $=CR^{9c}-$, $A^{3c}$ is $=CR^{10c}-$, $R^{9c}$ and $R^{10c}$ are a hydrogen atom, $R^{2c}$ and $R^{5c}$ are a hydrogen atom, $R^{3c}$ is a methyl group, an ethyl group, a propyl group, an isopropyl group, a trifluoromethyl group, a pentafluoroethyl group, a heptafluoropropyl group, a heptafluoroisopropyl group, a fluorine atom, a chlorine atom, or a bromine atom, $R^{6c}$ is a trifluoromethyl group, a pentafluoroethyl group, a heptafluoropropyl group, a heptafluoroisopropyl group, a trifluoromethylsulfanyl group, a trifluoromethylsulfinyl group, or a trifluoromethylsulfonyl group, and $R^{7c}$ is a hydrogen atom;

An amide compound of the formula wherein $A^{1c}$ is $-NR^{8c}-$, $R^{8c}$ is a methyl group, an ethyl group, a propyl group, or an isopropyl group, $A^{2c}$ is $=CR^{9c}-$, $R^{9c}$ is a hydrogen atom, $A^{3c}$ is a nitrogen atom, $R^{2c}$ and $R^{5c}$ are a hydrogen atom, $R^{3c}$ is a methyl group, an ethyl group, a propyl group, an isopropyl group, a trifluoromethyl group, a pentafluoroethyl group, a heptafluoropropyl group, a heptafluoroisopropyl group, a fluorine atom, a chlorine atom, or a bromine atom, $R^{6c}$ is a trifluoromethyl group, a pentafluoroethyl group, a heptafluoropropyl group, a heptafluoroisopropyl group, a trifluoromethylsulfanyl group, a trifluoromethylsulfinyl group, or a trifluoromethylsulfonyl group, and $R^{7c}$ is a hydrogen atom;

An amide compound of the formula (1C) wherein $A^{1c}$ is a sulfur atom, $A^{2c}$ is $=CR^{9c}$—, $R^{9c}$ is a hydrogen atom, $A^{3c}$ is a nitrogen atom, $R^2$ and $R^{5c}$ are a hydrogen atom, $R^{3c}$ is a methyl group, an ethyl group, a propyl group, an isopropyl group, a trifluoromethyl group, a pentafluoroethyl group, a heptafluoropropyl group, a heptafluoroisopropyl group, a fluorine atom, a chlorine atom or a bromine atom, $R^{6c}$ is a trifluoromethyl group, a pentafluoroethyl group, a heptafluoropropyl group, a heptafluoroisopropyl group, a trifluoromethylsulfanyl group, a trifluoromethylsulfinyl group, or a trifluoromethylsulfonyl group, and $R^{7c}$ is a hydrogen atom.

Examples of Compound (24) include the following compounds:

A compound of the formula (1D):

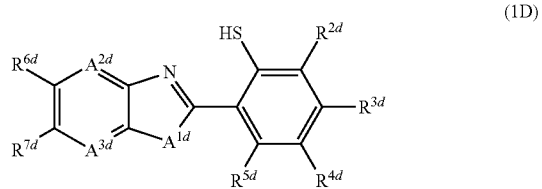

(1D)

wherein:

$A^{1d}$ represents —$NR^{8d}$—, an oxygen atom, or a sulfur atom;

$A^{2d}$ represents a nitrogen atom or $=CR^{9d}$—;

$A^{3d}$ represents a nitrogen atom or $=CR^{10d}$—;

$R^{2d}$, $R^{3d}$, $R^{4d}$, and $R^{5d}$ are same ore different and represent independently a C1-C6 chain hydrocarbon group optionally having one or more halogen atoms, a phenyl group optionally having one or more halogen atoms or C1-C3 alkyl groups optionally having one or more halogen atoms, a 5-membered heterocyclic group optionally having one or more halogen atoms or C1-C3 alkyl groups optionally having one or more halogen atoms, a 6-membered heterocyclic group optionally having one or more halogen atoms or C1-C3 alkyl groups optionally having one or more halogen atoms, —$OR^{11d}$, —$S(O)_mR^{11d}$, —$SF_5$, a cyano group, a nitro group, a halogen atom, or a hydrogen atom: provided that at least two of $R^{2d}$, $R^{3d}$, $R^{4d}$, and $R^{5d}$ represent a hydrogen atom;

$R^{6d}$ represents a C1-C6 chain hydrocarbon group optionally having one or more halogen atoms, a phenyl group optionally having one or more halogen atoms or C1-C3 alkyl groups optionally having one or more halogen atoms, a 5-membered heterocyclic group optionally having one or more halogen atoms or C1-C3 alkyl groups optionally having one or more halogen atoms, a 6-membered heterocyclic group optionally having one or more halogen atoms or C1-C3 alkyl groups optionally having one or more halogen atoms, —$OR^{11d}$, —$S(O)_mR^{11d}$, —$SF_5$, a cyano group, a nitro group, or a halogen atom;

$R^{7d}$ represents a C1-C6 chain hydrocarbon group optionally having one or more halogen atoms, a phenyl group optionally having one or more halogen atoms or C1-C3 alkyl groups optionally having one or more halogen atoms, a 5-membered heterocyclic group optionally having one or more halogen atoms or C1-C3 alkyl groups optionally having one or more halogen atoms, a 6-membered heterocyclic group optionally having one or more halogen atoms or C1-C3 alkyl groups optionally having one or more halogen atoms, —$S(O)_mR^{11d}$, —$SF_5$, a cyano group, a nitro group, a halogen atom, or a hydrogen atom;

$R^{8d}$ represents a C1-C6 chain hydrocarbon group optionally having one or more halogen atoms, a C1-C6 chain hydrocarbon group having one C1-C6 alkoxy group, a C3-C6 alicyclic hydrocarbon group optionally having one or more halogen atoms, or a hydrogen atom;

$R^{9d}$ and $R^{10d}$ are same ore different and represent independently a C1-C6 chain hydrocarbon group optionally having one or more halogen atoms, —$OR^{11}$, —$S(O)_mR^{11}$, a cyano group, a nitro group, a halogen atom, or a hydrogen atom;

$R^{11d}$ and $R^{12d}$ are same ore different and represent independently a C1-C6 chain hydrocarbon group optionally having one or more halogen atoms, or a hydrogen atom; and m represents 0, 1, or 2:

provided that in —$S(O)_mR^{11d}$, $R^{11d}$ is not a hydrogen atom (hereinafter, referred to as Compound (1D));

And examples of Compound (1D) include the following compounds:

A compound of the formula (1D) wherein $A^{1d}$ is —$NR^{8d}$—;

A compound of the formula (1D) wherein $A^{1d}$ is —$NR^{8d}$—, and $R^{8d}$ is a C1-C6 chain hydrocarbon group optionally having one or more halogen atoms;

A compound of the formula (1D) wherein $A^{1d}$ is —$NR^{8d}$—, and $R^{8d}$ is a C1-C6 chain hydrocarbon group;

A compound of the formula (1D) wherein $A^{1d}$ is —$NR^{8d}$—, and $R^{8d}$ is a C1-C6 alkyl group;

A compound of the formula (1D) wherein $A^{1d}$ is —$NR^{8d}$—, and $R^{8d}$ is a C1-C3 alkyl group;

A compound of the formula (1D) wherein $A^{1d}$ is —$NR^{8d}$—, and $R^{8d}$ is a methyl group, an ethyl group, a propyl group, or an isopropyl group;

A compound of the formula (1D) wherein $A^{1d}$ is —$NR^{8d}$—, and $R^{8d}$ is a methyl group;

A compound of the formula (1D) wherein $A^{1d}$ is —$NR^{8d}$—, and $R^{8d}$ is an ethyl group;

A compound of the formula (1D) wherein $A^{1d}$ is —$NR^{8d}$—, and $R^{8d}$ is a propyl group;

A compound of the formula (1D) wherein $A^{1d}$ is —$NR^{8d}$—, and $R^{8d}$ is an isopropyl group;

A compound of the formula (1D) wherein $A^{1d}$ is —$NR^{8d}$—, and $R^{8d}$ is a C1-C6 chain hydrocarbon group having one C1-C6 alkoxy group;

A compound of the formula (1D) wherein $A^{1d}$ is —$NR^{8d}$—, and $R^{8d}$ is a methoxymethyl group or an ethoxymethyl group;

A compound of the formula (1D) wherein $A^{1d}$ is —$NR^{8d}$—, and $R^{8d}$ is a C3-C6 alicyclic hydrocarbon group optionally having one or more halogen atoms;

A compound of the formula (1D) wherein $A^{1d}$ is —$NR^{8d}$—, and $R^{8d}$ is a cyclopropyl group, a cyclobutyl group, a cyclopentyl group, or a cyclohexyl group;

A compound of the formula (1D) wherein $A^{1d}$ is —$NR^{8d}$—, and $R^{8d}$ is a hydrogen atom;

A compound of the formula (1D) wherein $A^{1d}$ is an oxygen atom;

A compound of the formula (1D) wherein $A^{1d}$ is a sulfur atom;

A compound of the formula (1D) wherein $A^{1d}$ is —$NR^{8d}$— or a sulfur atom;

A compound of the formula (1D) wherein $A^{1d}$ is —$NR^{8d}$— or a sulfur atom, and $R^{8d}$ is a methyl group, an ethyl group, a propyl group, or an isopropyl group;

A compound of the formula (1D) wherein $A^{1d}$ is $-NR^{8d}-$ or a sulfur atom, and $R^{8d}$ is a methoxymethyl group, an ethoxymethyl group, or a hydrogen atom;

A compound of the formula (1D) wherein $A^{2d}$ is $=CR^{9d}-$, and $A^{3d}$ is $=CR^{10d}-$;

A compound of the formula (1D) wherein $A^{2d}$ is $=CR^{9d}-$, $A^{3d}$ is $=CR^{10d}-$, and $R^{9d}$ and $R^{10d}$ are same or different and are independently a halogen atom or a hydrogen atom;

A compound of the formula (1D) wherein $A^{2d}$ is $=CR^{9d}-$, $A^{3d}$ is $=CR^{10d}-$, and $R^{9d}$ and $R^{10d}$ are a hydrogen atom;

A compound of the formula (1D) wherein $A^{2d}$ is a nitrogen atom, and $A^{3d}$ is $=CR^{10d}-$;

A compound of the formula (1D) wherein $A^{2d}$ is $=CR^{9d}-$, and $A^{3d}$ is a nitrogen atom;

A compound of the formula (1D) wherein $A^{2d}$ is $=CR^{9d}-$, $R^{9d}$ is a halogen atom or a hydrogen atom, and $A^{3d}$ is a nitrogen atom;

A compound of the formula (1D) wherein $A^{2d}$ is $=CR^{9d}-$, $R^{9d}$ is a hydrogen atom, and $A^{3d}$ is a nitrogen atom;

A compound of the formula (1D) wherein $A^{2d}$ is a nitrogen atom, and $A^{3d}$ is a nitrogen atom;

A compound of the formula (1D) wherein $A^{1d}$ is $-NR^{8d}-$, $A^{2d}$ is $=CR^{9d}-$, and $A^{3d}$ is $=CR^{10d}-$;

A compound of the formula (1D) wherein $A^{1d}$ is $-NR^{8d}-$, $A^{2d}$ is $=CR^{9d}-$, $A^{3d}$ is $=CR^{10d}-$, and $R^{9d}$ and $R^{10d}$ are a hydrogen atom;

A compound of the formula (1D) wherein $A^{1d}$ is an oxygen atom, $A^{2d}$ is $=CR^{9d}-$, and $A^{3d}$ is $=CR^{10d}-$;

A compound of the formula (1D) wherein $A^{1d}$ is a sulfur atom, $A^{2d}$ is $=CR^{9d}-$, and $A^{3d}$ is $=CR^{10d}-$;

A compound of the formula (1D) wherein $A^{1d}$ is a sulfur atom, $A^{2d}$ is $=CR^{9d}-$, $A^{3d}$ is $=CR^{10d}-$, and $R^{9d}$ and $R^{10d}$ are a hydrogen atom;

A compound of the formula (1D) wherein $A^{1d}$ is $-NR^{8d}-$, $A^{2d}$ is $=CR^{9d}-$, and $A^{3d}$ is a nitrogen atom;

A compound of the formula (1D) wherein $A^{1d}$ is $-NR^{8d}-$, $A^{2d}$ is $=CR^{9d}-$, $R^{9d}$ is a hydrogen atom, and $A^{3d}$ is a nitrogen atom;

A compound of the formula (1D) wherein $A^{1d}$ is an oxygen atom, $A^{2d}$ is $=CR^{9d}-$, and $A^{3d}$ is a nitrogen atom;

A compound of the formula (1D) wherein $A^{1d}$ is a sulfur atom, $A^{2d}$ is $=CR^{9d}-$, and $A^{3d}$ is a nitrogen atom;

A compound of the formula (1D) wherein $A^{1d}$ is a sulfur atom, $A^{2d}$ is $=CR^{9d}-$, $R^{9d}$ is a hydrogen atom, and $A^{3d}$ is a nitrogen atom;

A compound of the formula (1D) wherein $A^{1d}$ is $-NR^{8d}-$ or a sulfur atom, $R^{8d}$ is a methyl group, an ethyl group, a propyl group or an isopropyl group, $A^{2d}$ is $=CR^{9d}-$, $A^{3d}$ is $=CR^{10d}-$, and $R^{9d}$ and $R^{10d}$ are a hydrogen atom;

A compound of the formula (1D) wherein $A^{1d}$ is $-NR^{8d}-$ or a sulfur atom, $R^{8d}$ is a methyl group, $A^{2d}$ is $=CR^{9d}-$, $A^{3d}$ is $=CR^{10d}-$, and $R^{9d}$ and $R^{10d}$ are a hydrogen atom;

A compound of the formula (1D) wherein $A^{1d}$ is $-NR^{8d}-$ or a sulfur atom, $R^{8d}$ is a methyl group, an ethyl group, a propyl group, or an isopropyl group, $A^{2d}$ is $=CR^{9d}-$, $R^{9d}$ is a hydrogen atom, and $A^{3d}$ is a nitrogen atom;

A compound of the formula (1D) wherein $A^{1d}$ is $-NR^{9d}-$ or a sulfur atom, $R^{8d}$ is a methyl group, $A^{2d}$ is $=CR^{9d}-$, $R^{9d}$ is a hydrogen atom, and $A^{3d}$ is a nitrogen atom;

A compound of the formula (1D) wherein $R^{2d}$, $R^{3d}$, $R^{4d}$, and $R^{5d}$ are same or different and are independently a C1-C6 chain hydrocarbon group optionally having one or more halogen atoms or a hydrogen atom;

A compound of the formula (1D) wherein $R^{2d}$, $R^{3d}$, $R^{4d}$, and $R^{5d}$ are same or different and are independently a phenyl group optionally having one or more halogen atoms or C1-C3 alkyl groups optionally having one or more halogen atoms, a 5-membered heterocyclic group optionally having one or more halogen atoms or C1-C3 alkyl groups optionally having one or more halogen atoms, a 6-membered heterocyclic group optionally having one or more halogen atoms or C1-C3 alkyl groups optionally having one or more halogen atoms, or a hydrogen atom;

A compound of the formula (1D) wherein $R^{2d}$, $R^{3d}$, $R^{4d}$, and $R^{5d}$ are same or different and are independently $-OR^{11d}$ or a hydrogen atom;

A compound of the formula (1D) wherein $R^{2d}$, $R^{3d}$, $R^{4d}$, and $R^{5d}$ are same or different and are independently $-S(O)_m R^{11d}$ or a hydrogen atom;

A compound of the formula (1D) wherein $R^{2d}$, $R^{3d}$, $R^{4d}$, and $R^{5d}$ are same or different and are independently a cyano group, a nitro group, or a hydrogen atom;

A compound of the formula (1D) wherein $R^{2d}$, $R^{3d}$, $R^{4d}$, and $R^{5d}$ are same or different and are independently a halogen atom or a hydrogen atom;

A compound of the formula (1D) wherein $R^{2d}$, $R^{3d}$, $R^{4d}$, and $R^{5d}$ are a hydrogen atom;

A compound of the formula (1D) wherein $R^{2d}$, $R^{4d}$, and $R^{5d}$ are a hydrogen atom, and $R^{3d}$ is a 2-pyridyl group, a 2-pyrimidyl group, a 3-chloro-2-pyridyl group, or a 3-chloro-5-trifluoromethyl-2-pyridyl group;

A compound of the formula (1D) wherein $R^{2d}$, $R^{4d}$, and $R^{5d}$ are a hydrogen atom, and $R^{3d}$ is a 2-pyridyl group;

A compound of the formula (1D) wherein $R^{2d}$, $R^{4d}$, and $R^{5d}$ are a hydrogen atom, and $R^{3d}$ is a 2-pyrimidyl group;

A compound of the formula (1D) wherein $R^{2d}$, $R^{4d}$, and $R^{5d}$ are a hydrogen atom, and $R^{3d}$ is a 3-chloro-2-pyridyl group;

A compound of the formula (1D) wherein $R^{2d}$, $R^{4d}$, and $R^{5d}$ are a hydrogen atom, and $R^{3d}$ is a 3-chloro-5-trifluoromethyl-2-pyridyl group;

A compound of the formula (1D) wherein $R^{2d}$, $R^{4d}$, and $R^{5d}$ are a hydrogen atom, and $R^{3d}$ is a C1-C6 chain hydrocarbon group optionally having one or more halogen atoms;

A compound of the formula (1D) wherein $R^{2d}$, $R^{4d}$, and $R^{5d}$ are a hydrogen atom, and $R^{3d}$ is a C1-C6 alkyl group;

A compound of the formula (1D) wherein $R^{2d}$, $R^{4d}$, and $R^{5d}$ are a hydrogen atom, and $R^{3d}$ is a C1-C6 alkyl group optionally having one or more fluorine atoms;

A compound of the formula (1D) wherein $R^{2d}$, $R^{4d}$, and $R^{5d}$ are a hydrogen atom, and $R^{3d}$ is a C1-C3 alkyl group;

A compound of the formula (1D) wherein $R^{2d}$, $R^{4d}$, and $R^{5d}$ are a hydrogen atom, and $R^{3d}$ is a C1-C3 alkyl group optionally having one or more fluorine atoms;

A compound of the formula (1D) wherein $R^{2d}$, $R^{4d}$, and $R^{5d}$ are a hydrogen atom, and $R^{3d}$ is a methyl group, an ethyl group, a propyl group, an isopropyl group, a trifluoromethyl group, a pentafluoroethyl group, a heptafluoropropyl group, or a heptafluoroisopropyl group;

A compound of the formula (1D) wherein $R^{2d}$, $R^{4d}$, and $R^{5d}$ are a hydrogen atom, and $R^{3d}$ is a methyl group;

A compound of the formula (1D) wherein $R^{2d}$, $R^{4d}$, and $R^{5d}$ are a hydrogen atom, and $R^{3d}$ is an ethyl group;

A compound of the formula (1D) wherein $R^{2d}$, $R^{4d}$, and $R^{5d}$ are a hydrogen atom, and $R^{3d}$ is a propyl group;

A compound of the formula (1D) wherein $R^{2d}$, $R^{4d}$, and $R^{5d}$ are a hydrogen atom, and $R^{3d}$ is an isopropyl group;

A compound of the formula (1D) wherein $R^{2d}$, $R^{4d}$, and $R^{5d}$ are a hydrogen atom, and $R^{3d}$ is a trifluoromethyl group;

A compound of the formula (1D) wherein $R^{2d}$, $R^{4d}$, and $R^{5d}$ are a hydrogen atom, and $R^{3d}$ is a pentafluoroethyl group;

A compound of the formula (1D) wherein $R^{2d}$, $R^{4d}$, and $R^{5d}$ are a hydrogen atom, and $R^{3d}$ is a heptafluoropropyl group;

A compound of the formula (1D) wherein $R^{2d}$, $R^{4d}$, and $R^{5d}$ are a hydrogen atom, and $R^{3d}$ is a heptafluoroisopropyl group;

A compound of the formula (1D) wherein $R^{2d}$, $R^{4d}$, and $R^{5d}$ are a hydrogen atom, and $R^{3d}$ is a halogen atom;

A compound of the formula (1D) wherein $R^{2d}$, $R^{4d}$, and $R^{5d}$ are a hydrogen atom, and $R^{3d}$ is a fluorine atom, a chlorine atom or a bromine atom;

A compound of the formula (1D) wherein $R^{2d}$, $R^{4d}$, and $R^{5d}$ are a hydrogen atom, and $R^{3d}$ is a fluorine atom;

A compound of the formula (1D) wherein $R^{2d}$, $R^{4d}$, and $R^{5d}$ are a hydrogen atom, and $R^{3d}$ is a chlorine atom; A compound of the formula (1D) wherein $R^{2d}$, $R^{4d}$, and $R^{5d}$ are a hydrogen atom, and $R^{3d}$ is a bromine atom;

A compound of the formula (1D) wherein $R^{2d}$, $R^{4d}$, and $R^{5d}$ are a hydrogen atom, and $R^{3d}$ is —SF$_5$;

A compound of the formula (1D) wherein $R^{2d}$, $R^{3d}$, $R^{4d}$, and $R^{5d}$ are same or different and are independently a C1-C6 chain hydrocarbon group optionally having one or more halogen atoms, a halogen atom, or a hydrogen atom;

A compound of the formula (1D) wherein $R^{2d}$, $R^{4d}$, and $R^{5d}$ are a hydrogen atom, and $R^{3d}$ is a 6-membered heterocyclic group optionally having one or more halogen atoms or C1-C3 alkyl groups optionally having one or more halogen atoms;

A compound of the formula (1D) wherein $R^{2d}$, $R^{4d}$, and $R^{5d}$ are a hydrogen atom, and $R^{3d}$ is a C1-C6 chain hydrocarbon group optionally having one or more halogen atoms or a halogen atom;

A compound of the formula (1D) wherein $R^{2d}$, $R^{4d}$, and $R^{5d}$ are a hydrogen atom, and $R^{3d}$ is a C1-C3 alkyl group optionally having one or more fluorine atoms or a halogen atom;

A compound of the formula (1D) wherein $R^{2d}$, $R^{4d}$, and $R^{5d}$ are a hydrogen atom, and $R^{3d}$ is a 2-pyridyl group, a 2-pyrimidyl group, a 3-chloro-2-pyridyl group, a 3-chloro-5-trifluoromethyl-2-pyridyl group, a methyl group, an ethyl group, a propyl group, an isopropyl group, a trifluoromethyl group, a pentafluoroethyl group, a heptafluoropropyl group, a heptafluoroisopropyl group, a fluorine atom, a chlorine atom, or a bromine atom;

A compound of the formula (1D) wherein $R^{2d}$, $R^{4d}$, and $R^{5d}$ are a hydrogen atom, and $R^{3d}$ is a methyl group, an ethyl group, a propyl group, an isopropyl group, a trifluoromethyl group, a pentafluoroethyl group, a heptafluoropropyl group, a heptafluoroisopropyl group, a fluorine atom, a chlorine atom, or a bromine atom;

A compound of the formula (1D) wherein $R^{6d}$ is a C1-C6 chain hydrocarbon group optionally having one or more halogen atoms;

A compound of the formula (1D) wherein $R^{6d}$ is a C1-C6 chain hydrocarbon group;

A compound of the formula (1D) wherein $R^{6d}$ is a C1-C6 chain hydrocarbon group having one or more fluorine atoms;

A compound of the formula (1D) wherein $R^{6d}$ is a C1-C3 alkyl group having one or more fluorine atoms;

A compound of the formula (1D) wherein $R^{6d}$ is a trifluoromethyl group, a pentafluoroethyl group, a heptafluoropropyl group, or a heptafluoroisopropyl group;

A compound of the formula (1D) wherein $R^{6d}$ is a trifluoromethyl group;

A compound of the formula (1D) wherein $R^{6d}$ is a pentafluoroethyl group;

A compound of the formula (1D) wherein $R^{6d}$ is a heptafluoropropyl group;

A compound of the formula (1D) wherein $R^{6d}$ is a heptafluoroisopropyl group;

A compound of the formula (1D) wherein $R^{6d}$ is a phenyl group optionally having one or more halogen atoms or C1-C3 alkyl groups optionally having one or more halogen atoms, a 5-membered heterocyclic group optionally having one or more halogen atoms or C1-C3 alkyl groups optionally having one or more halogen atoms, or a 6-membered heterocyclic group optionally having one or more halogen atoms or C1-C3 alkyl groups optionally having one or more halogen atoms;

A compound of the formula (1D) wherein $R^{6d}$ is —OR$^{11d}$;

A compound of the formula (1D) wherein $R^{6d}$ is a C1-C6 alkoxy group having one ore more fluorine atoms;

A compound of the formula (1D) wherein $R^{6d}$ is a C1-C3 alkoxy group having one or more fluorine atoms;

A compound of the formula (1D) wherein $R^{6d}$ is a trifluoromethoxy group;

A compound of the formula (1D) wherein $R^{6d}$ is $S(O)_m R^{11d}$;

A compound of the formula (1D) wherein $R^{6d}$ is a C1-C6 alkylsulfanyl group having one or more fluorine atoms, a C1-C6 alkylsulfinyl group having one or more fluorine atoms, or a C1-C6 alkylsulfonyl group having one or more fluorine atoms;

A compound of the formula (1D) wherein $R^{6d}$ is a C1-C3 alkylsulfanyl group having one or more fluorine atoms, a C1-C3 alkylsulfinyl group having one or more fluorine atoms, or a C1-C3 alkylsulfonyl group having one or more fluorine atoms;

A compound of the formula (1D) wherein $R^{6d}$ is a trifluoromethylsulfanyl group, a trifluoromethylsulfinyl group, or a trifluoromethylsulfonyl group;

A compound of the formula (1D) wherein $R^{6d}$ is a trifluoromethylsulfanyl group;

A compound of the formula (1D) wherein $R^{6d}$ is a trifluoromethylsulfinyl group;

A compound of the formula (1D) wherein $R^{6d}$ is a trifluoromethylsulfonyl group;

A compound of the formula (1D) wherein $R^{6d}$ is a cyano group or a nitro group;

A compound of the formula (1D) wherein $R^{6d}$ is a halogen atom;

A compound of the formula (1D) wherein $R^{6d}$ is a chlorine atom, a bromine atom, or an iodine atom;

A compound of the formula (1D) wherein $R^{6d}$ is a chlorine atom;

A compound of the formula (1D) wherein $R^{6d}$ is a bromine atom;

A compound of the formula (1D) wherein $R^{6d}$ is an iodine atom;

A compound of the formula (1D) wherein $R^{6d}$ is —SF$_5$;

A compound of the formula (1D) wherein $R^{6d}$ is a C1-C3 alkyl group having one or more fluorine atoms, a C1-C3 alkoxy group having one or more fluorine atoms, a C1-C3 alkylsulfanyl group having one or more fluorine atoms, a C1-C3 alkylsulfinyl group having one or more fluorine atoms, a C1-C3 alkylsulfonyl group having one or more fluorine atoms, or a halogen atom;

A compound of the formula (1D) wherein $R^{6d}$ is a trifluoromethyl group, a pentafluoroethyl group, a heptafluoropropyl group, a heptafluoroisopropyl group, a trifluoromethoxy group, a trifluoromethylsulfanyl group, a trifluoromethylsulfinyl group, a trifluoromethylsulfonyl group, a chlorine atom, a bromine atom, or an iodine atom;

A compound of the formula (1D) wherein $R^{7d}$ is a C1-C6 chain hydrocarbon group optionally having one or more halogen atoms;

A compound of the formula (1D) wherein $R^{7d}$ is a C1-C6 chain hydrocarbon group;

A compound of the formula (1D) wherein $R^{7d}$ is a C1-C6 chain hydrocarbon group having one or more fluorine atoms;

A compound of the formula (1D) wherein $R^{7d}$ is a C1-C3 alkyl group having one or more fluorine atoms;

A compound of the formula (1D) wherein $R^{7d}$ is a trifluoromethyl group, a pentafluoroethyl group, a heptafluoropropyl group, or a heptafluoroisopropyl group;

A compound of the formula (1D) wherein $R^{7d}$ is a trifluoromethyl group;

A compound of the formula (1D) wherein $R^{7d}$ is a pentafluoroethyl group;

A compound of the formula (1D) wherein $R^{7d}$ is a heptafluoropropyl group;

A compound of the formula (1D) wherein $R^{7d}$ is a heptafluoroisopropyl group;

A compound of the formula (1D) wherein $R^{7d}$ is a phenyl group optionally having one or more halogen atoms or C1-C3 alkyl groups optionally having one or more halogen atoms, a 5-membered heterocyclic group optionally having one or more halogen atoms or C1-C3 alkyl groups optionally having one or more halogen atoms, or a 6-membered heterocyclic group optionally having one or more halogen atoms or C1-C3 alkyl groups optionally having one or more halogen atoms;

A compound of the formula (1D) wherein $R^{7d}$ is —$OR^{11d}$;

A compound of the formula (1D) wherein $R^{7d}$ is a C1-C6 alkoxy group having one ore more fluorine atoms;

A compound of the formula (1D) wherein $R^{7d}$ is a C1-C3 alkoxy group having one or more fluorine atoms;

A compound of the formula (1D) wherein $R^{7d}$ is a trifluoromethoxy group;

A compound of the formula (1D) wherein $R^{7d}$ is —$S(O)_m R^{11d}$;

A compound of the formula (1D) wherein $R^{7d}$ is a C1-C6 alkylsulfanyl group having one or more fluorine atoms, a C1-C6 alkylsulfinyl group having one or more fluorine atoms, or a C1-C6 alkylsulfonyl group having one or more fluorine atoms;

A compound of the formula (1D) wherein $R^{7d}$ is a C1-C3 alkylsulfanyl group having one or more fluorine atoms, a C1-C3 alkylsulfinyl group having one or more fluorine atoms, or a C1-C3 alkylsulfonyl group having one or more fluorine atoms;

A compound of the formula (1D) wherein $R^{7d}$ is a trifluoromethylsulfanyl group, a trifluoromethylsulfinyl group, or a trifluoromethylsulfonyl group;

A compound of the formula (1D) wherein $R^{7d}$ is a trifluoromethylsulfanyl group;

A compound of the formula (1D) wherein $R^{7d}$ is a trifluoromethylsulfinyl group;

A compound of the formula (1D) wherein $R^{7d}$ is a trifluoromethylsulfonyl group;

A compound of the formula (1D) wherein $R^{7d}$ is a cyano group or a nitro group;

A compound of the formula (1D) wherein $R^{7d}$ is a halogen atom;

A compound of the formula (1D) wherein $R^{7d}$ is a chlorine atom, a bromine atom, or an iodine atom;

A compound of the formula (1D) wherein $R^{7d}$ is a chlorine atom;

A compound of the formula (1D) wherein $R^{7d}$ is a bromine atom;

A compound of the formula (1D) wherein $R^{7d}$ is an iodine atom;

A compound of the formula (1D) wherein $R^{7d}$ is a hydrogen atom;

A compound of the formula (1D) wherein $R^{7d}$ is —$SF_5$;

A compound of the formula (1D) wherein $R^{7d}$ is a C1-C3 alkyl group having one or more fluorine atoms, a C1-C3 alkoxy group having one or more fluorine atoms, a C1-C3 alkylsulfanyl group having one or more fluorine atoms, a C1-C3 alkylsulfinyl group having one or more fluorine atoms, a C1-C3 alkylsulfonyl group having one or more fluorine atoms, or a halogen atom;

A compound of the formula (1D) wherein $R^{7d}$ is a trifluoromethyl group, a pentafluoroethyl group, a heptafluoropropyl group, a heptafluoroisopropyl group, a trifluoromethoxy group, a trifluoromethylsulfanyl group, a trifluoromethylsulfinyl group, a trifluoromethylsulfonyl group, a chlorine atom, a bromine atom, or an iodine atom;

A compound of the formula (1D) wherein $R^{6d}$ is a C1-C3 alkyl group having one or more fluorine atoms, a C1-C3 alkoxy group having one or more fluorine atoms, a C1-C3 alkylsulfanyl group having one or more fluorine atoms, a C1-C3 alkylsulfinyl group having one or more fluorine atoms, a C1-C3 alkylsulfonyl group having one or more fluorine atoms, or a halogen atom, and $R^{7d}$ is a hydrogen atom;

A compound of the formula (1D) wherein $R^{6d}$ is a trifluoromethyl group, a pentafluoroethyl group, a heptafluoropropyl group, a heptafluoroisopropyl group, trifluoromethoxy group, a trifluoromethylsulfanyl group, a trifluoromethylsulfinyl group, a trifluoromethylsulfonyl group, a chlorine atom, a bromine atom, or an iodine atom, and $R^{7d}$ is a hydrogen atom;

A compound of the formula (1D) wherein m is 0;

A compound of the formula (1D) wherein m is 1;

A compound of the formula (1D) wherein m is 2;

A compound of the formula (1D) wherein $A^{1d}$ is —$NR^{8d}$— or a sulfur atom, $R^{8d}$ is a C1-C6 alkyl group, $A^{2d}$ is =$CR^{9d}$—, $A^{3d}$ is =$CR^{10d}$—, $R^{9d}$ and $R^{10d}$ are a hydrogen atom, $R^{2d}$, $R^{4d}$, $R^{5d}$ are a hydrogen atom, $R^{3d}$ is a C1-C3 alkyl group optionally having one or more fluorine atoms or a halogen atom, $R^{6d}$ is a C1-C3 alkyl group having one or more fluorine atoms, a C1-C3 alkoxy group having one or more fluorine atoms, a C1-C3 alkylsulfanyl group having one or more fluorine atoms, a C1-C3 alkylsulfinyl group having one or more fluorine atoms, a C1-C3 alkylsulfonyl group having one or more fluorine atoms, or a halogen atom, and $R^{7d}$ is a hydrogen atom;

A compound of the formula (1D) wherein $A^{1d}$ is —$NR^{8d}$— or a sulfur atom, $R^{8d}$ is a C1-C6 alkyl group, $A^{2d}$ is =$CR^{9d}$—, $R^{9d}$ is a hydrogen atom, $A^{3d}$ is a nitrogen atom, $R^{2d}$, $R^{4d}$, and $R^{5d}$ are a hydrogen atom, $R^{3d}$ is a C1-C3 alkyl group optionally having one or more fluorine atoms or a halogen atom, $R^{6d}$ is a C1-C3 alkyl group having one or more fluorine atoms, a C1-C3 alkoxy group having one or more fluorine atoms, a C1-C3 alkylsulfanyl group having one or more fluorine atoms, a C1-C3 alkylsulfinyl group having one or more fluorine atoms, a C1-C3 alkylsulfonyl group having one or more fluorine atoms, or a halogen atom, and $R^{7d}$ is a hydrogen atom;

A compound of the formula (1D) wherein $A^{1d}$ is —$NR^{8d}$—, $R^{8d}$ is a methyl group, an ethyl group, a propyl group, or an isopropyl group, $A^{2d}$ is =$CR^{9d}$—, $A^{3d}$ is =$CR^{10d}$—, $R^{9d}$ and $R^{10d}$ are a hydrogen atom, $R^{2d}$, $R^{4d}$, and $R^{5d}$ are a hydrogen atom, $R^{3d}$ is a methyl group, an ethyl group, a propyl group, an isopropyl group, a trifluoromethyl group, a pentafluoroethyl group, a heptafluoropropyl group, a heptafluoroisopropyl group, a fluorine atom, a chlorine atom, or a bromine atom, $R^{6d}$ is a trifluoromethyl group, a pentafluoroethyl group, a heptafluoropropyl group, a heptafluoroisopropyl group, a trifluoromethoxy group, a trifluoromethylsulfanyl group, a trifluoromethylsulfinyl group, a trifluoromethylsulfonyl group, a chlorine atom, a bromine atom, or an iodine atom, and $R^{7d}$ is a hydrogen atom;

A compound of the formula (1D) wherein $A^{1d}$ is a sulfur atom, $A^{2d}$ is $=CR^{9d}-$, $A^{3d}$ is $=CR^{10d}-$, $R^{9d}$ and $R^{10d}$ are a hydrogen atom, $R^{2d}$, $R^{4d}$, and $R^{5d}$ are a hydrogen atom, $R^{3d}$ is a methyl group, an ethyl group, a propyl group, an isopropyl group, a trifluoromethyl group, a pentafluoroethyl group, a heptafluoropropyl group, a heptafluoroisopropyl group, a fluorine atom, a chlorine atom, or a bromine atom, $R^{6d}$ is a trifluoromethyl group, a pentafluoroethyl group, a heptafluoropropyl group, a heptafluoroisopropyl group, a trifluoromethoxy group, a trifluoromethylsulfanyl group, a trifluoromethylsulfinyl group, a trifluoromethylsulfonyl group, a chlorine atom, a bromine atom, or an iodine atom, and $R^{7d}$ is a hydrogen atom;

A compound of the formula (1D) wherein $A^{1d}$ is $-NR^{8d}-$, $R^{8d}$ is a methyl group, an ethyl group, a propyl group, or an isopropyl group, $A^{2d}$ is $=CR^{9d}-$, $R^{9d}$ is a hydrogen atom, $A^{3d}$ is a nitrogen atom, $R^{2d}$, $R^{4d}$, and $R^{5d}$ are a hydrogen atom, $R^{3d}$ is a methyl group, an ethyl group, a propyl group, an isopropyl group, a trifluoromethyl group, a pentafluoroethyl group, a heptafluoropropyl group, a heptafluoroisopropyl group, a fluorine atom, a chlorine atom, or a bromine atom, $R^{6d}$ is a trifluoromethyl group, a pentafluoroethyl group, a heptafluoropropyl group, a heptafluoroisopropyl group, a trifluoromethoxy group, a trifluoromethylsulfanyl group, a trifluoromethylsulfinyl group, a trifluoromethylsulfonyl group, a chlorine atom, a bromine atom, or an iodine atom, and $R^{7d}$ is a hydrogen atom;

A compound of the formula (1D) wherein $A^{1d}$ is a sulfur atom, $A^{2d}$ is $=CR^{9d}-$, $R^{9d}$ is a hydrogen atom, $A^{3d}$ is a nitrogen atom, $R^{2d}$, $R^{4d}$, and $R^{5d}$ are a hydrogen atom, $R^{3d}$ is a methyl group, an ethyl group, a propyl group, an isopropyl group, a trifluoromethyl group, a pentafluoroethyl group, a heptafluoropropyl group, a heptafluoroisopropyl group, a fluorine atom, a chlorine atom, or a bromine atom, $R^{6d}$ is a trifluoromethyl group, a pentafluoroethyl group, a heptafluoropropyl group, a heptafluoroisopropyl group, a trifluoromethoxy group, a trifluoromethylsulfanyl group, a trifluoromethylsulfinyl group, a trifluoromethylsulfonyl group, a chlorine atom, a bromine atom, or an iodine atom, and $R^{7d}$ is a hydrogen atom.

Examples of Compound (21) include the following compounds:

A compound of the formula (1E):

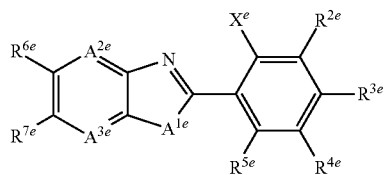

(1E)

wherein:

$X^e$ represents a fluorine atom or a chlorine atom;
$A^{1e}$ represents $-NR^{8e}-$, an oxygen atom or a sulfur atom;
$A^{2e}$ represents a nitrogen atom or $=CR^{9e}-$;

$R^{2e}$, $R^{3e}$, and $R^{5e}$ are same or different and represent independently a C1-C6 chain hydrocarbon group optionally having one or more halogen atoms, a phenyl group optionally having one or more halogen atoms or C1-C3 alkyl groups optionally having one or more halogen atoms, a 5-membered heterocyclic group optionally having one or more halogen atoms or C1-C3 alkyl groups optionally having one or more halogen atoms, a 6-membered heterocyclic group optionally having one or more halogen atoms or C1-C3 alkyl groups optionally having one or more halogen atoms $-OR^{11e}$, $-S(O)_m R^{11e}$, $-SF_5$, a cyano group, a halogen atom, or a hydrogen atom: provided that at least one of $R^{2e}$, $R^{3e}$, and $R^{5e}$ represent a hydrogen atom;

$R^{4e}$ represents a hydrogen atom;

$R^{6e}$ represents a C1-C3 alkyl group having one or more fluorine atoms, a C1-C3 alkylsulfanyl group having one or more fluorine atoms, a C1-C3 alkylsulfinyl group having one or more fluorine atoms, a C1-C3 alkylsulfonyl group having one or more fluorine atoms, or $-SF_5$;

$R^{7e}$ represents a C1-C6 chain hydrocarbon group optionally having one or more halogen atoms, $-OR^{11e}$, $-S(O)_m R^{11e}$, $-SF_5$, a cyano group, a halogen atom, or a hydrogen atom;

$R^{8e}$ represents a C1-C6 chain hydrocarbon group optionally having one or more halogen atoms, a C1-C6 chain hydrocarbon group having one C1-C6 alkoxy group, a C3-C6 alicyclic hydrocarbon group optionally having one or more halogen atoms, or a hydrogen atom;

$R^{9e}$ and $R^{10e}$ are same or different and represent independently a C1-C6 chain hydrocarbon group optionally having one or more halogen atoms, $-OR^{11e}$, $-S(O)_m R^{11e}$, a cyano group, a nitro group, a halogen atom, or a hydrogen atom;

$R^{11e}$ and $R^{12e}$ are same or different and represent independently a C1-C6 chain hydrocarbon group optionally having one or more halogen atoms, or a hydrogen atom; and m represents 0, 1, or 2:

provided that; in $-S(O)_m R^{11e}$, when m is 1 or 2, $R^{11e}$ is not a hydrogen atom; when $A^{1e}$ is an oxygen atom, and $A^{2e}$ and $A^{3e}$ are a methine group, one of $R^{2e}$, $R^{3e}$, and $R^{5e}$ are a C1-C6 chain hydrocarbon group optionally having one or more halogen atoms, a phenyl group optionally having one or more halogen atoms or C1-C3 alkyl groups optionally having one or more halogen atoms, a 5-membered heterocyclic group optionally having one or more halogen atoms or C1-C3 alkyl groups optionally having one or more halogen atoms, a 6-membered heterocyclic group optionally having one or more halogen atoms or C1-C3 alkyl groups optionally having one or more halogen atoms, $-OR^{11e}$, $-S(O)_m R^{11e}$, a cyano group, a nitro group, or a halogen atom, and two others are a hydrogen atom; and when $A^{1e}$ is $-NR^{8e}-$, and $A^{2e}$ is a methine group, $R^{8e}$ is a methyl group (hereinafter, referred to as Compound (1E));

Examples of Compound (1E) include the following compounds:

A compound of the formula (1E) wherein $X^e$ is a fluorine atom;

A compound of the formula (1E) wherein $X^e$ is a chlorine atom;

A compound of the formula (1E) wherein $A^{1e}$ is $-NR^{8e}-$;

A compound of the formula (1E) wherein $A^{1e}$ is $-NR^{8e}-$, and $R^{8e}$ is a C1-C6 chain hydrocarbon group optionally having one or more halogen atoms;

A compound of the formula (1E) wherein $A^{1e}$ is $-NR^{8e}-$, and $R^{8e}$ is a C1-C6 chain hydrocarbon group;

A compound of the formula (1E) wherein $A^{1e}$ is $-NR^{8e}-$, and $R^{8e}$ is a C1-C6 alkyl group;

A compound of the formula (1E) wherein $A^{1e}$ is —$NR^{8e}$—, and $R^{8e}$ is a C1-C3 alkyl group;

A compound of the formula (1E) wherein $A^{1e}$ is —$NR^{8e}$—, and $R^{8e}$ is a methyl group, an ethyl group, a propyl group, or an isopropyl group;

A compound of the formula (1E) wherein is —$NR^{8e}$—, and $R^{8e}$ is a methyl group;

A compound of the formula (1E) wherein $A^{1e}$ is —$NR^{8e}$—, and $R^{8e}$ is an ethyl group;

A compound of the formula (1E) wherein $A^{1e}$ is —$NR^{8e}$—, and $R^{8e}$ is a propyl group;

A compound of the formula (1E) wherein $A^{1e}$ is —$NR^{8e}$—, and $R^{8e}$ is an isopropyl group;

A compound of the formula (1E) wherein $A^{1e}$ is —$NR^{8e}$—, and $R^{8e}$ is a C1-C6 chain hydrocarbon group having one C1-C6 alkoxy group;

A compound of the formula (1E) wherein $A^{1e}$ is —$NR^{8e}$—, and $R^{8e}$ is a methoxymethyl group or an ethoxymethyl group;

A compound of the formula (1E) wherein $A^{1e}$ is —$NR^{8e}$—, and $R^{8e}$ is a C3-C6 alicyclic hydrocarbon group optionally having one or more halogen atoms;

A compound of the formula (1E) wherein $A^{1e}$ is —$NR^{8e}$—, and $R^{8e}$ is a cyclopropyl group, a cyclobutyl group, a cyclopentyl group, or a cyclohexyl group;

A compound of the formula (1E) wherein $A^{1e}$ is —$NR^{8e}$—, and $R^{8e}$ is a hydrogen atom;

A compound of the formula (1E) wherein $A^{1e}$ is an oxygen atom;

A compound of the formula (1E) wherein $A^{1e}$ is a sulfur atom;

A compound of the formula (1E) wherein $A^{1e}$ is —$NR^{8e}$— or a sulfur atom;

A compound of the formula (1E) wherein $A^{1e}$ is —$NR^{8e}$— or a sulfur atom, and $R^{8e}$ is a methyl group, an ethyl group, a propyl group, or an isopropyl group;

A compound of the formula (1E) wherein $A^{1e}$ is —$NR^{8e}$— or a sulfur atom, and $R^{8e}$ is a methoxymethyl group, an ethoxymethyl group, or a hydrogen atom;

A compound of the formula (1E) wherein $A^{2e}$ is =$CR^{9e}$—, and $A^{3e}$ is =$CR^{10e}$—;

A compound of the formula (1E) wherein $A^{2e}$ is =$CR^{9e}$—, $A^{3e}$ is =$CR^{10e}$—, and $R^{9e}$ and $R^{10e}$ are same or different and are independently a halogen atom or a hydrogen atom;

A compound of the formula (1E) wherein $A^{2e}$ is =$CR^{9e}$—, $A^{3e}$ is =$CR^{10e}$—, and $R^{9e}$ and $R^{10e}$ are a hydrogen atom;

A compound of the formula (1E) wherein $A^{2e}$ is a nitrogen atom, and $A^{3e}$ is =$CR^{10e}$—;

A compound of the formula (1E) wherein $A^{2e}$ is =$CR^{9e}$—, and $A^{3e}$ is a nitrogen atom;

A compound of the formula (1E) wherein $A^{2e}$ is =$CR^{9e}$—, $R^{9e}$ is a halogen atom or a hydrogen atom, and $A^{3e}$ is a nitrogen atom;

A compound of the formula (1E) wherein $A^{2e}$ is =$CR^{9e}$—, $R^{9e}$ is a hydrogen atom, and $A^{3e}$ is a nitrogen atom;

A compound of the formula (1E) wherein $A^{2e}$ is a nitrogen atom, and $A^{3e}$ is a nitrogen atom;

A compound of the formula (1E) wherein $A^{1e}$ is —$NR^{8e}$—, $A^{2e}$ is =$CR^{9e}$—, and $A^{3e}$ is =$CR^{10e}$—;

A compound of the formula (1E) wherein $A^{1e}$ is —$NR^{8e}$—, $A^{2e}$ is =$CR^{9e}$—, $A^{3e}$ is =$CR^{10e}$—, and $R^{9e}$ and $R^{10e}$ are a hydrogen atom;

A compound of the formula (1E) wherein $A^{1e}$ is an oxygen atom, $A^{2e}$ is =$CR^{9e}$—, and $A^{3e}$ is =$CR^{10e}$—;

A compound of the formula (1E) wherein $A^{1e}$ is a sulfur atom, $A^{2e}$ is =$CR^{9e}$—, and $A^{3e}$ is =$CR^{10e}$—;

A compound of the formula (1E) wherein $A^{1e}$ is a sulfur atom, $A^{2e}$ is =$CR^{9e}$—, $A^{3e}$ is =$CR^{10e}$—, and $R^{9e}$ and $R^{10e}$ are a hydrogen atom;

A compound of the formula (1E) wherein $A^{1e}$ is —$NR^{8e}$—, $A^{2e}$ is =$CR^{9e}$—, and $A^{3e}$ is a nitrogen atom;

A compound of the formula (1E) wherein $A^{1e}$ is —$NR^{8e}$—, $A^{2e}$ is =$CR^{9e}$—, $R^{9e}$ is a hydrogen atom, and $A^{3e}$ is a nitrogen atom;

A compound of the formula (1E) wherein $A^{1e}$ is an oxygen atom, $A^{2e}$ is =$CR^{9e}$—, and $A^{3e}$ is a nitrogen atom;

A compound of the formula (1E) wherein $A^{1e}$ is a sulfur atom, $A^{2e}$ is =$CR^{9e}$—, and $A^{3e}$ is a nitrogen atom;

A compound of the formula (1E) wherein $A^{1e}$ is a sulfur atom, $A^{2e}$ is =$CR^{9e}$—, $R^{9e}$ is a hydrogen atom, and $A^{3e}$ is a nitrogen atom;

A compound of the formula (1E) wherein $A^{1e}$ is —$NR^{8e}$— or a sulfur atom, $R^{8e}$ is a methyl group, an ethyl group, a propyl group, or an isopropyl group, $A^{2e}$ is =$CR^{9e}$—, $A^{3e}$ is =$CR^{10e}$—, and $R^{9e}$ and $R^{10e}$ are a hydrogen atom;

A compound of the formula (1E) wherein $A^{1e}$ is —$NR^{8e}$— or a sulfur atom, $R^{8e}$ is a methyl group, $A^{2e}$ is =$CR^{9e}$—, $A^{3e}$ is =$CR^{10e}$—, and $R^{9e}$ and $R^{10e}$ are a hydrogen atom;

A compound of the formula (1E) wherein $A^{1e}$ is —$NR^{8e}$— or a sulfur atom, $R^{8e}$ is a methyl group, an ethyl group, a propyl group, or an isopropyl group, $A^{2e}$ is =$CR^{9e}$—, $R^{9e}$ is a hydrogen atom, and $A^{3e}$ is a nitrogen atom;

A compound of the formula (1E) wherein $A^{1e}$ is —$NR^{8e}$— or a sulfur atom, $R^{8e}$ is a methyl group, $A^{2e}$ is =$CR^{9e}$—, $R^{9e}$ is a hydrogen atom, and $A^{3e}$ is a nitrogen atom;

A compound of the formula (1E) wherein $R^{2e}$, $R^{3e}$, and $R^{5e}$ are same or different and are independently a C1-C6 chain hydrocarbon group optionally having one or more halogen atoms, or a hydrogen atom;

A compound of the formula (1E) wherein $R^{2e}$, $R^{3e}$, and $R^{5e}$ are same or different and are independently a phenyl group optionally having one or more halogen atoms or C1-C3 alkyl groups optionally having one or more halogen atoms, a 5-membered heterocyclic group optionally having one or more halogen atoms or C1-C3 alkyl groups optionally having one or more halogen atoms, a 6-membered heterocyclic group optionally having one or more halogen atoms or C1-C3 alkyl groups optionally having one or more halogen atoms, or a hydrogen atom;

A compound of the formula (1E) wherein $R^{2e}$, $R^{3e}$, and $R^{5e}$ are same or different and are independently —$OR^{11e}$ or a hydrogen atom;

A compound of the formula (1E) wherein $R^{2e}$, $R^{3e}$, and $R^{5e}$ are same or different and are independently —$S(O)_m R^{11e}$ or a hydrogen atom;

A compound of the formula (1E) wherein $R^{2e}$, $R^{3e}$, and $R^{5e}$ are same or different and are independently a cyano group, a nitro group, or a hydrogen atom;

A compound of the formula (1E) wherein $R^{2e}$, $R^{3e}$, and $R^{5e}$ are same or different and are independently a halogen atom or a hydrogen atom;

A compound of the formula (1E) wherein $R^{2e}$, $R^{3e}$, and $R^{5e}$ are a hydrogen atom;

A compound of the formula (1E) wherein $R^{2e}$ and $R^{5e}$ are a hydrogen atom, $R^{3e}$ is a 2-pyridyl group, a 2-pyrimidyl group, a 3-chloro-2-pyridyl group, or a 3-chloro-5-trifluoromethyl-2-pyridyl group;

A compound of the formula (1E) wherein $R^{2e}$ and $R^{5e}$ are a hydrogen atom, and $R^{3e}$ is a 2-pyridyl group;

A compound of the formula (1E) wherein $R^{2e}$ and $R^{5e}$ are a hydrogen atom, and $R^{3e}$ is a 2-pyrimidyl group;

A compound of the formula (1E) wherein $R^{2e}$ and $R^{5e}$ are a hydrogen atom, and $R^{3e}$ is a 3-chloro-2-pyridyl group;

A compound of the formula (1E) wherein $R^{2e}$ and $R^{5e}$ are a hydrogen atom, and $R^{3e}$ is a 3-chloro-5-trifluoromethyl-2-pyridyl group;

A compound of the formula (1E) wherein $R^{2e}$ and $R^{5e}$ are a hydrogen atom, and $R^{3e}$ is a C1-C6 chain hydrocarbon group optionally having one or more halogen atoms;

A compound of the formula (1E) wherein $R^{2e}$ and $R^{5e}$ are a hydrogen atom, and $R^{3e}$ is a C1-C6 alkyl group; A compound of the formula (1E) wherein $R^{2e}$ and $R^{5e}$ are a hydrogen atom, and $R^{3e}$ is a C1-C6 alkyl group optionally having one or more fluorine atoms;

A compound of the formula (1E) wherein $R^{2e}$ and $R^{5e}$ are a hydrogen atom, and $R^{3e}$ is a C1-C3 alkyl group;

A compound of the formula (1E) wherein $R^{2e}$ and $R^{5e}$ are a hydrogen atom, and $R^{3e}$ is a C1-C3 alkyl group optionally having one or more fluorine atoms;

A compound of the formula (1E) wherein $R^{2e}$ and $R^{5e}$ are a hydrogen atom, and $R^{3e}$ is a methyl group, an ethyl group, a propyl group, an isopropyl group, a trifluoromethyl group, a pentafluoroethyl group, a heptafluoropropyl group, or a heptafluoroisopropyl group;

A compound of the formula (1E) wherein $R^{2e}$ and $R^{5e}$ are a hydrogen atom, and $R^{3e}$ is a methyl group;

A compound of the formula (1E) wherein $R^{2e}$ and $R^{5e}$ are a hydrogen atom, and $R^{3e}$ is an ethyl group;

A compound of the formula (1E) wherein $R^{2e}$ and $R^{5e}$ are a hydrogen atom, and $R^{3e}$ is a propyl group;

A compound of the formula (1E) wherein $R^{2e}$ and $R^{5e}$ are a hydrogen atom, and $R^{3e}$ is an isopropyl group;

A compound of the formula (1E) wherein $R^{2e}$ and $R^{5e}$ are a hydrogen atom, and $R^{3e}$ is a trifluoromethyl group;

A compound of the formula (1E) wherein $R^{2e}$ and $R^{5e}$ are a hydrogen atom, and $R^{3e}$ is a pentafluoroethyl group;

A compound of the formula (1E) wherein $R^{2e}$ and $R^{5e}$ are a hydrogen atom, and $R^{3e}$ is a heptafluoropropyl group;

A compound of the formula (1E) wherein $R^{2e}$ and $R^{5e}$ are a hydrogen atom, and $R^{3e}$ is a heptafluoroisopropyl group;

A compound of the formula (1E) wherein $R^{2e}$ and $R^{5e}$ are a hydrogen atom, and $R^{3e}$ is a halogen atom;

A compound of the formula (1E) wherein $R^{2e}$ and $R^{5e}$ are a hydrogen atom, and $R^{3e}$ is a fluorine atom, a chlorine atom, or a bromine atom;

A compound of the formula (1E) wherein $R^{2e}$ and $R^{5e}$ are a hydrogen atom, and $R^{3e}$ is a fluorine atom;

A compound of the formula (1E) wherein $R^{2e}$ and $R^{5e}$ are a hydrogen atom, and $R^{3e}$ is a chlorine atom;

A compound of the formula (1E) wherein $R^{2e}$ and $R^{5e}$ are a hydrogen atom, and $R^{3e}$ is a bromine atom;

A compound of the formula (1E) wherein $R^{2e}$ and $R^{5e}$ are a hydrogen atom, and $R^{3e}$ is —SF$_5$;

A compound of the formula (1E) wherein $R^{2e}$, $R^{3e}$, and $R^{5e}$ are same or different and are independently a C1-C6 chain hydrocarbon group optionally having one or more halogen atoms, a halogen atom, or a hydrogen atom;

A compound of the formula (1E) wherein $R^{2e}$ and $R^{5e}$ are a hydrogen atom, and $R^{3e}$ is a 6-membered heterocyclic group optionally having one or more halogen atoms or C1-C3 alkyl groups optionally having one or more halogen atoms;

A compound of the formula (1E) wherein $R^{2e}$ and $R^{5e}$ are a hydrogen atom, and $R^{3e}$ is a C1-C6 chain hydrocarbon group optionally having one or more halogen atoms or a halogen atom;

A compound of the formula (1E) wherein $R^{2e}$ and $R^{5e}$ are a hydrogen atom, and $R^{3e}$ is a C1-C3 alkyl group optionally having one or more fluorine atoms, or a halogen atom;

A compound of the formula (1E) wherein $R^{2e}$ and $R^{5e}$ are a hydrogen atom, and $R^{3e}$ is a 2-pyridyl group, a 2-pyrimidyl group, a 3-chloro-2-pyridyl group, a 3-chloro-5-trifluoromethyl-2-pyridyl group, a methyl group, an ethyl group, a propyl group, an isopropyl group, a trifluoromethyl group, a pentafluoroethyl group, a heptafluoropropyl group, a heptafluoroisopropyl group, a fluorine atom, a chlorine atom, or a bromine atom;

A compound of the formula (1E) wherein $R^{2e}$ and $R^{5e}$ are a hydrogen atom, and $R^{3e}$ is a methyl group, an ethyl group, a propyl group, an isopropyl group, a trifluoromethyl group, a pentafluoroethyl group, a heptafluoropropyl group, a heptafluoroisopropyl group, a fluorine atom, a chlorine atom, or a bromine atom;

A compound of the formula (1E) wherein $R^{6e}$ is a C1-C3 alkyl group having one or more fluorine atoms;

A compound of the formula (1E) wherein $R^{6e}$ is a trifluoromethyl group, a pentafluoroethyl group, a heptafluoropropyl group, or a heptafluoroisopropyl group;

A compound of the formula (1E) wherein $R^{6e}$ is a trifluoromethyl group;

A compound of the formula (1E) wherein $R^{6e}$ is a pentafluoroethyl group;

A compound of the formula (1E) wherein $R^{6e}$ is a heptafluoropropyl group;

A compound of the formula (1E) wherein $R^{6e}$ is a heptafluoroisopropyl group;

A compound of the formula (1E) wherein $R^{6e}$ is a C1-C3 alkylsulfanyl group having one or more fluorine atoms, a C1-C3 alkylsulfinyl group having one or more fluorine atoms, or a C1-C3 alkylsulfonyl group having one or more fluorine atoms;

A compound of the formula (1E) wherein $R^{6e}$ is a trifluoromethylsulfanyl group, a trifluoromethylsulfinyl group, or a trifluoromethylsulfonyl group;

A compound of the formula (1E) wherein $R^{6e}$ is a trifluoromethylsulfanyl group;

A compound of the formula (1E) wherein $R^{6e}$ is a trifluoromethylsulfinyl group;

A compound of the formula (1E) wherein $R^{6e}$ is a trifluoromethylsulfonyl group;

A compound of the formula (1E) wherein $R^{6e}$ is —SF$_5$;

A compound of the formula (1E) wherein $R^{6e}$ is a C1-C3 alkyl group having one or more fluorine atoms, a C1-C3 alkylsulfanyl group having one or more fluorine atoms, a C1-C3 alkylsulfinyl group having one or more fluorine atoms, or a C1-C3 alkylsulfonyl group having one or more fluorine atoms;

A compound of the formula (1E) wherein $R^{6e}$ is a trifluoromethyl group, a pentafluoroethyl group, a heptafluoropropyl group, a heptafluoroisopropyl group, a trifluoromethylsulfanyl group, a trifluoromethylsulfinyl group, or a trifluoromethylsulfonyl group;

A compound of the formula (1E) wherein $R^{7e}$ is a C1-C3 alkyl group having one or more fluorine atoms;

A compound of the formula (1E) wherein $R^{7e}$ is a trifluoromethyl group, a pentafluoroethyl group, a heptafluoropropyl group, or a heptafluoroisopropyl group;

A compound of the formula (1E) wherein $R^{7e}$ is a trifluoromethyl group;

A compound of the formula (1E) wherein $R^{7e}$ is a pentafluoroethyl group;

A compound of the formula (1E) wherein $R^{7e}$ is a heptafluoropropyl group;

A compound of the formula (1E) wherein $R^{7e}$ is a heptafluoroisopropyl group;

A compound of the formula (1E) wherein $R^{7e}$ is a C1-C3 alkylsulfanyl group having one or more fluorine atoms, a C1-C3 alkylsulfinyl group having one or more fluorine atoms, or a C1-C3 alkylsulfonyl group having one or more fluorine atoms;

A compound of the formula (1E) wherein $R^{7e}$ is a trifluoromethylsulfanyl group, a trifluoromethylsulfinyl group, or a trifluoromethylsulfonyl group;

A compound of the formula (1E) wherein $R^{7e}$ is a trifluoromethylsulfanyl group;

A compound of the formula (1E) wherein $R^{7e}$ is a trifluoromethylsulfinyl group;

A compound of the formula (1E) wherein $R^{7e}$ is a trifluoromethylsulfonyl group;

A compound of the formula (1E) wherein $R^{7e}$ is —SF$_5$;

A compound of the formula (1E) wherein $R^{7e}$ is a C1-C3 alkyl group having one or more fluorine atoms, a C1-C3 alkylsulfanyl group having one or more fluorine atoms, a C1-C3 alkylsulfinyl group having one or more fluorine atoms, or a C1-C3 alkylsulfonyl group having one or more fluorine atoms;

A compound of the formula (1E) wherein $R^{7e}$ is a trifluoromethyl group, a pentafluoroethyl group, a heptafluoropropyl group, a heptafluoroisopropyl group, a trifluoromethylsulfanyl group, a trifluoromethylsulfinyl group, or a trifluoromethylsulfonyl group;

A compound of the formula (1E) wherein $R^{6e}$ is a C1-C3 alkyl group having one or more fluorine atoms, a C1-C3 alkoxy group having one or more fluorine atoms, a C1-C3 alkylsulfanyl group having one or more fluorine atoms, a C1-C3 alkylsulfinyl group having one or more fluorine atoms, or a C1-C3 alkylsulfonyl group having one or more fluorine atoms, and $R^{7e}$ is a hydrogen atom;

A compound of the formula (1E) wherein $R^{6e}$ is a trifluoromethyl group, a pentafluoroethyl group, a heptafluoropropyl group, a heptafluoroisopropyl group, a trifluoromethylsulfanyl group, a trifluoromethylsulfinyl group, or a trifluoromethylsulfonyl group, and $R^{7e}$ is a hydrogen atom;

A compound of the formula (1E) wherein m is 0;
A compound of the formula (1E) wherein m is 1;
A compound of the formula (1E) wherein m is 2;

A compound of the formula (1E) wherein $A^{1e}$ is —NR$^{8e}$— or a sulfur atom, $R^{8e}$ is a C1-C6 alkyl group, $A^{2e}$ is =CR$^{9e}$—, $A^{3e}$ is =CR$^{10e}$—, $R^{9e}$ and $R^{10e}$ are a hydrogen atom, $R^{2e}$ and $R^{5e}$ are a hydrogen atom, $R^{3e}$ is a C1-C3 alkyl group optionally having one or more fluorine atoms or a halogen atom, $R^{6e}$ is a C1-C3 alkyl group having one or more fluorine atoms, a C1-C3 alkylsulfanyl group having one or more fluorine atoms, a C1-C3 alkylsulfinyl group having one or more fluorine atoms, or a C1-C3 alkylsulfonyl group having one or more fluorine atoms, and $R^{7e}$ is a hydrogen atom;

A compound of the formula (1E) wherein $A^{1e}$ is —NR$^{8e}$— or a sulfur atom, $R^{8e}$ is a C1-C6 alkyl group, $A^{2e}$ is =CR$^{9e}$—, $R^{9e}$ is a hydrogen atom, $A^{3e}$ is a nitrogen atom, $R^{2e}$ and $R^{5e}$ are a hydrogen atom, $R^{3e}$ is a C1-C3 alkyl group optionally having one or more fluorine atoms or a halogen atom, $R^{6e}$ is a C1-C3 alkyl group having one or more fluorine atoms, a C1-C3 alkylsulfanyl group having one or more fluorine atoms, a C1-C3 alkylsulfinyl group having one or more fluorine atoms, or a C1-C3 alkylsulfonyl group having one or more fluorine atoms, and $R^{7e}$ is a hydrogen atom;

A compound of the formula (1E) wherein $A^{1e}$ is —NR$^{8e}$—, $R^{8e}$ is a methyl group, an ethyl group, a propyl group, or an isopropyl group, $A^{2w}$ is =CR$^{9e}$—, $A^{3e}$ is =CR$^{10e}$—, $R^{9e}$ and $R^{10e}$ are a hydrogen atom, $R^{2e}$ and $R^{5e}$ are a hydrogen atom, $R^{3e}$ is a methyl group, an ethyl group, a propyl group, an isopropyl group, a trifluoromethyl group, a pentafluoroethyl group, a heptafluoropropyl group, a heptafluoroisopropyl group, a fluorine atom, a chlorine atom, or a bromine atom, $R^{6e}$ is a trifluoromethyl group, a pentafluoroethyl group, a heptafluoropropyl group, a heptafluoroisopropyl group, a trifluoromethylsulfanyl group, a trifluoromethylsulfinyl group, or a trifluoromethylsulfonyl group, and $R^{7e}$ is a hydrogen atom;

A compound of the formula (1E) wherein $A^{1e}$ is a sulfur atom, $A^{2e}$ is =CR$^{9e}$—, $A^{3e}$ is =CR$^{10e}$—, $R^{9e}$ and $R^{10e}$ are a hydrogen atom, $R^{2e}$ and $R^{5e}$ are a hydrogen atom, $R^{3e}$ is a methyl group, an ethyl group, a propyl group, an isopropyl group, a trifluoromethyl group, a pentafluoroethyl group, a heptafluoropropyl group, a heptafluoroisopropyl group, a fluorine atom, a chlorine atom, or a bromine atom, $R^{6e}$ is a trifluoromethyl group, a pentafluoroethyl group, a heptafluoropropyl group, a heptafluoroisopropyl group, a trifluoromethylsulfanyl group, a trifluoromethylsulfinyl group, or a trifluoromethylsulfonyl group, and $R^{7e}$ is a hydrogen atom;

A compound of the formula (1E) wherein $A^{1e}$ is —NR$^{8e}$—, $R^{8e}$ is a methyl group, an ethyl group, a propyl group, or an isopropyl group, $A^{2e}$ is =CR$^{9e}$—, $R^{9e}$ is a hydrogen atom, $A^{3e}$ is a nitrogen atom, $R^{2e}$ and $R^{5e}$ are a hydrogen atom, $R^{3e}$ is a methyl group, an ethyl group, a propyl group, an isopropyl group, a trifluoromethyl group, a pentafluoroethyl group, a heptafluoropropyl group, a heptafluoroisopropyl group, a fluorine atom, a chlorine atom, or a bromine atom, $R^{6e}$ is a trifluoromethyl group, a pentafluoroethyl group, a heptafluoropropyl group, a heptafluoroisopropyl group, a trifluoromethylsulfanyl group, a trifluoromethylsulfinyl group, or a trifluoromethylsulfonyl group, and $R^{7e}$ is a hydrogen atom;

A compound of the formula (1E) wherein $A^{1e}$ is a sulfur atom, $A^{2e}$ is =CR$^{9e}$—, $R^{9e}$ is a hydrogen atom, $A^{3e}$ is a nitrogen atom, $R^{2e}$, $R^{4e}$ and $R^{5e}$ are a hydrogen atom, $R^{3e}$ is a methyl group, an ethyl group, a propyl group, an isopropyl group, a trifluoromethyl group, a pentafluoroethyl group, a heptafluoropropyl group, a heptafluoroisopropyl group, a fluorine atom, a chlorine atom, or a bromine atom, $R^{6e}$ is a trifluoromethyl group, a pentafluoroethyl group, a heptafluoropropyl group, a heptafluoroisopropyl group, a trifluoromethylsulfanyl group, a trifluoromethylsulfinyl group, or a trifluoromethylsulfonyl group, and $R^{7e}$ is a hydrogen atom.

Examples of Compound (F) include the following compounds:

A compound of the formula (M21):

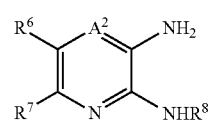

wherein, $R^6$, $R^7$, $R^8$ and $A^2$ are as defined above (referred to as Compound (M21));

A compound of the formula (1F):

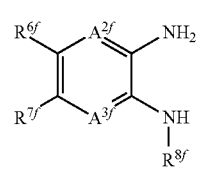

wherein:
$A^{2f}$ represents a nitrogen atom or =CR$^{9f}$—;
$A^{3f}$ represents a nitrogen atom or =CR$^{10f}$—;

$R^{6f}$ represents a C1-C6 chain hydrocarbon group optionally having one or more halogen atoms, $-OR^{11f}$, $-S(O)_m R^{11f}$, $-SF_5$, or a halogen atom;

$R^{7f}$ represents a C1-C6 chain hydrocarbon group optionally having one or more halogen atoms, $-OR^{11f}$, $-S(O)_m R^{11f}$, $-SF_5$, hydrogen atom, or a halogen atom;

$R^{8f}$ represents a C1-C6 chain hydrocarbon group optionally having one or more halogen atoms or a hydrogen atom;

$R^{9f}$ and $R^{10f}$ are same or different and represent independently a C1-C6 chain hydrocarbon group optionally having one or more halogen atoms, a halogen atom, or a hydrogen atom;

$R^{11f}$ and $R^{12f}$ are same or different and represent independently a C1-C6 chain hydrocarbon group optionally having one or more halogen atoms or a hydrogen atom;

m represents 0, 1, or 2:

provided that in $-S(O)_m R^{11f}$, when m is 1 or 2, $R^{11f}$ is not a hydrogen atom (hereinafter, referred to as Compound (1F));

And examples of Compound (1F) include the following compounds:

A compound of the formula (1F) wherein $A^{2f}$ is $=CR^{9f}-$, and $A^{3f}$ is $=CR^{10f}-$;

A compound of the formula (1F) wherein $A^{2f}$ is a nitrogen atom, and $A^{3f}$ is $=CR^{10f}-$;

A compound of the formula (1F) wherein $A^{2f}$ is $=CR^{9f}-$, and $A^{3f}$ is a nitrogen atom;

A compound of the formula (1F) wherein $A^{2f}$ is a nitrogen atom, and $A^{3f}$ is a nitrogen atom;

A compound of the formula (1F) wherein $A^{2f}$ is $=CR^{9f}-$, and $A^{3f}$ is $=CR^{10f}-$, $R^{9f}$ and $R^{10f}$ are a hydrogen atom;

A compound of the formula (1F) wherein $A^{2f}$ is $=CR^{9f}-$, $R^{9f}$ is a hydrogen atom, and $A^{3f}$ is a nitrogen atom;

A compound of the formula (1F) wherein $R^{6f}$ is a C2-C3 alkyl group having one or more fluorine atoms, a C1-C3 alkylsulfanyl group having one or more fluorine atoms, a C1-C3 alkylsulfinyl group having one or more fluorine atoms, or a C1-C3 alkylsulfonyl group having one or more fluorine atoms;

A compound of the formula (1F) wherein $R^{6f}$ is a C2-C3 alkyl group having one or more fluorine atoms;

A compound of the formula (1F) wherein $R^{6f}$ is a C1-C3 alkylsulfanyl group having one or more fluorine atoms, a C1-C3 alkylsulfinyl group having one or more fluorine atoms, or a C1-C3 alkylsulfonyl group having one or more fluorine atoms;

A compound of the formula (1F) wherein $R^{6f}$ is a pentafluoroethyl group, a trifluoromethylsulfanyl group, a trifluoromethylsulfinyl group, a trifluoromethylsulfonyl group, or an iodine atom;

A compound of the formula (1F) wherein $R^{6f}$ is a trifluoromethylsulfanyl group, a trifluoromethylsulfinyl group, or a trifluoromethylsulfonyl group;

A compound of the formula (1F) wherein $R^{6f}$ is a pentafluoroethyl group;

A compound of the formula (1F) wherein $R^{6f}$ is a trifluoromethylsulfanyl group;

A compound of the formula (1F) wherein $R^{6f}$ is a trifluoromethylsulfinyl group;

A compound of the formula (1F) wherein $R^{6f}$ is a trifluoromethylsulfonyl group;

A compound of the formula (1F) wherein $R^{6f}$ is an iodine atom;

A compound of the formula (1F) wherein $R^{6f}$ is $-SF_5$;

A compound of the formula (1F) wherein $R^{7f}$ is a hydrogen atom;

A compound of the formula (1F) wherein $R^{8f}$ is a C1-C3 alkyl group or a hydrogen atom;

A compound of the formula (1F) wherein $R^{8f}$ is a C1-C3 alkyl group;

A compound of the formula (1F) wherein $R^{8f}$ is a methyl group;

A compound of the formula (1F) wherein $R^{8f}$ is an ethyl group;

A compound of the formula (1F) wherein $R^{8f}$ is a propyl group;

A compound of the formula (1F) wherein $R^{8f}$ is a hydrogen atom;

A compound of the formula (1F) wherein $R^{8f}$ is a methyl group or a hydrogen atom;

A compound of the formula (1F) wherein $A^{2f}$ is $=CR^{9f}-$, $R^{9f}$ is a hydrogen atom, $A^{3f}$ is a nitrogen atom, $R^{6f}$ is a C2-C3 alkyl group having one or more fluorine atoms, a C1-C3 alkylsulfanyl group having one or more fluorine atoms, a C1-C3 alkylsulfinyl group having one or more fluorine atoms, a C1-C3 alkylsulfonyl group having one or more fluorine atoms, $R^{7f}$ is a hydrogen atom, and $R^{8f}$ is a C1-C3 alkyl group or a hydrogen atom;

A compound of the formula (1F) wherein $A^{2f}$ is $=CR^{9f}-$, $R^{9f}$ is a hydrogen atom, $A^{3f}$ is a nitrogen atom, $R^{6f}$ is a C2-C3 alkyl group having one or more fluorine atoms, $R^{7f}$ is a hydrogen atom, and $R^{8f}$ is a C1-C3 alkyl group or a hydrogen atom;

A compound of the formula (1F) wherein $A^{2f}$ is $=CR^{9f}-$, $R^{9f}$ is a hydrogen atom, $A^{3f}$ is a nitrogen atom, $R^{6f}$ is a C1-C3 alkylsulfanyl group having one or more fluorine atoms, a C1-C3 alkylsulfinyl group having one or more fluorine atoms, or a C1-C3 alkylsulfonyl group having one or more fluorine atoms, $R^{7f}$ is a hydrogen atom, and $R^{8f}$ is a C1-C3 alkyl group or a hydrogen atom;

A compound of the formula (1F) wherein $A^{2f}$ is $=CR^{9f}-$, $R^{9f}$ is a hydrogen atom, $A^{3f}$ is a nitrogen atom, $R^{6f}$ is a pentafluoroethyl group, a trifluoromethylsulfanyl group, a trifluoromethylsulfinyl group, or a trifluoromethylsulfonyl group or an iodine atom, $R^{7f}$ is a hydrogen atom, and $R^{8f}$ is a C1-C3 alkyl group or a hydrogen atom: provided that when $R^{6f}$ is an iodine atom, $R^{8f}$ is a C1-C3 alkyl group;

A compound of the formula (1F) wherein $A^{2f}$ is $=CR^{9f}-$, $R^{9f}$ is a hydrogen atom, $A^{3f}$ is a nitrogen atom, $R^{6f}$ is a pentafluoroethyl group, a trifluoromethylsulfanyl group, a trifluoromethylsulfinyl group, or a trifluoromethylsulfonyl group, $R^{7f}$ is a hydrogen atom, and $R^{8f}$ is a methyl group or a hydrogen atom;

A compound of the formula (1F) wherein $A^{2f}$ is $=CR^{9f}-$, $R^{9f}$ is a hydrogen atom, $A^{3f}$ is a nitrogen atom, $R^{6f}$ is a pentafluoroethyl group, $R^{7f}$ is a hydrogen atom, and $R^{8f}$ is a methyl group;

A compound of the formula (1F) wherein $A^{2f}$ is $=CR^{9f}-$, $R^{9f}$ is a hydrogen atom, $A^{3f}$ is a nitrogen atom, $R^{6f}$ is a trifluoromethylsulfanyl group, $R^{7f}$ is a hydrogen atom, and $R^{8f}$ is a methyl group;

A compound of the formula (1F) wherein $A^{2f}$ is $=CR^{9f}-$, $R^{9f}$ is a hydrogen atom, $A^{3f}$ is a nitrogen atom, $R^{6f}$ is a trifluoromethylsulfonyl group, $R^{7f}$ is a hydrogen atom, and $R^{8f}$ is a methyl group;

A compound of the formula (1F) wherein $A^{2f}$ is $=CR^{9f}-$, $R^{9f}$ is a hydrogen atom, $A^{3f}$ is a nitrogen atom, $R^{6f}$ is an iodine atom, $R^{7f}$ is a hydrogen atom, and $R^{8f}$ is a C1-C3 alkyl group;

A compound of the formula (1F) wherein $A^{2f}$ is $=CR^{9f}-$, $R^{9f}$ is a hydrogen atom, $A^{3f}$ is a nitrogen atom, $R^{6f}$ is an iodine atom, $R^{7f}$ is a hydrogen atom, and $R^{8f}$ is a methyl group;

A compound of the formula (1F) wherein $A^{2f}$ is $=CR^{9f}-$, $A^{3f}$ is $=CR^{10f}-$, $R^{9f}$ and $R^{10f}$ are a hydrogen atom, $R^{6f}$ is a C2-C3 alkyl group having one or more fluorine atoms, a C1-C3 alkylsulfanyl group having one or more fluorine atoms, a C1-C3 alkylsulfinyl group having one or more fluorine atoms, or a C1-C3 alkylsulfonyl group having one or more fluorine atoms, $R^{7f}$ is a hydrogen atom, and $R^{8f}$ is a C1-C3 alkyl group or a hydrogen atom;

A compound of the formula (1F) wherein $A^{2f}$ is =CR$^{9f}$—, $A^{3f}$ is =CR$^{10f}$—, $R^{9f}$ and $R^{10f}$ are a hydrogen atom, $R^{6f}$ is a C2-C3 alkyl group having one or more fluorine atoms, $R^{7f}$ is a hydrogen atom, and $R^{6f}$ is a C1-C3 alkyl group or a hydrogen atom;

A compound of the formula (1F) wherein $A^{2f}$ is =CR$^{9f}$—, $A^{3f}$ is =CR$^{10f}$—, $R^{9f}$ and $R^{10f}$ are a hydrogen atom, $R^{6f}$ is a C1-C3 alkylsulfanyl group having one or more fluorine atoms, a C1-C3 alkylsulfinyl group having one or more fluorine atoms, or a C1-C3 alkylsulfonyl group having one or more fluorine atoms, $R^{7f}$ is a hydrogen atom, and $R^{6f}$ is a C1-C3 alkyl group or a hydrogen atom;

A compound of the formula (1F) wherein $A^{2f}$ is =CR$^{9f}$—, $A^{3f}$ is =CR$^{10f}$—, $R^{9f}$ and $R^{10f}$ are a hydrogen atom, $R^{6f}$ is a pentafluoroethyl group, a trifluoromethylsulfanyl group, a trifluoromethylsulfinyl group, or a trifluoromethylsulfonyl group, $R^{7f}$ is a hydrogen atom, and $R^{6f}$ is a methyl group or a hydrogen atom;

A compound of the formula (1F) wherein $A^{2f}$ is =CR$^{9f}$—, $A^{3f}$ is =CR$^{10f}$—, $R^{9f}$ and $R^{10f}$ are a hydrogen atom, $R^{6f}$ is a pentafluoroethyl group, $R^{7f}$ is a hydrogen atom, and $R^{6f}$ is a methyl group;

A compound of the formula (1F) wherein $A^{2f}$ is =CR$^{9f}$—, $A^{3f}$ is =CR$^{10f}$—, $R^{9f}$ and $R^{10f}$ are a hydrogen atom, $R^{6f}$ is a trifluoromethylsulfanyl group, $R^{7f}$ is a hydrogen atom, and $R^{6f}$ is a methyl group;

A compound of the formula (1F) wherein $A^{2f}$ is =CR$^{9f}$—, $A^{3f}$ is =CR$^{10f}$—, $R^{9f}$ and $R^{10f}$ are a hydrogen atom, $R^{6f}$ is a trifluoromethylsulfonyl group, $R^{7f}$ is a hydrogen atom, and $R^{8f}$ is a methyl group;

A compound of the formula (1F) wherein $A^{2f}$ is =CR$^{9f}$—, $A^{3f}$ is =CR$^{10f}$—, $R^{9f}$ and $R^{10f}$ are a hydrogen atom, $R^{6f}$ is —SF$_5$, $R^{7f}$ is a hydrogen atom, and $R^{8f}$ is a methyl group;

And examples of Compound (M21) include the following compounds:

A compound of the formula (M21) wherein $A^2$ is =CH—;
A compound of the formula (M21) wherein $A^2$ is nitrogen;
A compound of the formula (M21) wherein $R^8$ is a C1-C6 chain hydrocarbon group optionally having one or more halogen atoms or hydrogen;
A compound of the formula (M21) wherein $R^8$ is a C1-C6 chain hydrocarbon group optionally having one or more halogen atoms;
A compound of the formula (M21) wherein $R^8$ is a C1-C3 alkyl group;
A compound of the formula (M21) wherein $R^8$ is a methyl group, an ethyl group, a propyl group, or hydrogen;
A compound of the formula (M21) wherein $R^8$ is a methyl group;
A compound of the formula (M21) wherein $R^8$ is an ethyl group;
A compound of the formula (M21) wherein $R^8$ is a propyl group;
A compound of the formula (M21) wherein $R^8$ is hydrogen;
A compound of the formula (M21) wherein $R^6$ is a C1-C6 chain hydrocarbon group optionally having one or more halogen atoms, a C1-C6 alkoxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a bromine atom, or an iodine atom;

A compound of the formula (M21) wherein $R^6$ is a C1-C6 chain hydrocarbon group optionally having one or more halogen atoms, a C1-C6 alkoxy group optionally having one or more halogen atoms, a C1-C6 alkylsulfanyl group optionally having one or more halogen atoms, a C1-C6 alkylsulfinyl group optionally having one or more halogen atoms, or a C1-C6 alkylsulfonyl group optionally having one or more halogen atoms;

A compound of the formula (M21) wherein $R^6$ is a C1-C6 chain hydrocarbon group optionally having one or more halogen atoms;

A compound of the formula (M21) wherein $R^6$ is a C1-C6 alkoxy group optionally having one or more halogen atoms;

A compound of the formula (M21) wherein $R^6$ is a C1-C6 alkylsulfanyl group optionally having one or more halogen atoms, a C1-C6 alkylsulfinyl group optionally having one or more halogen atoms, or a C1-C6 alkylsulfonyl group optionally having one or more halogen atoms;

A compound of the formula (M21) wherein $R^6$ is a bromine atom or an iodine atom;

A compound of the formula (M21) wherein $R^6$ is a trifluoromethyl group, a pentafluoroethyl group, a trifluoromethoxy group, a trifluoromethylsulfanyl group, a trifluoromethylsulfinyl group, or a trifluoromethylsulfonyl group;

A compound of the formula (M21) wherein $R^6$ is a pentafluoroethyl group, a trifluoromethoxy group, a trifluoromethylsulfanyl group, a trifluoromethylsulfinyl group, or a trifluoromethylsulfonyl group;

A compound of the formula (M21) wherein $R^6$ is a pentafluoroethyl group;

A compound of the formula (M21) wherein $R^6$ is a trifluoromethylsulfanyl group;

A compound of the formula (M21) wherein $R^6$ is a trifluoromethylsulfinyl group;

A compound of the formula (M21) wherein $R^6$ is a trifluoromethylsulfonyl group;

A compound of the formula (M21) wherein $R^6$ is a trifluoromethyl group, a pentafluoroethyl group, a trifluoromethoxy group, a trifluoromethylsulfanyl group, a trifluoromethylsulfinyl group, or a trifluoromethylsulfonyl group, and $R^7$ is hydrogen;

A compound of the formula (M21) wherein $R^6$ is a pentafluoroethyl group, a trifluoromethoxy group, a trifluoromethylsulfanyl group, a trifluoromethylsulfinyl group, or a trifluoromethylsulfonyl group, and $R^7$ is hydrogen;

A compound of the formula (M21) wherein $R^6$ is a pentafluoroethyl group, and $R^7$ is hydrogen;

A compound of the formula (M21) wherein $R^6$ is a trifluoromethylsulfanyl group, and $R^7$ is hydrogen;

A compound of the formula (M21) wherein $R^6$ is a trifluoromethylsulfinyl group, and $R^7$ is hydrogen;

A compound of the formula (M21) wherein $R^6$ is a trifluoromethylsulfonyl group, and $R^7$ is hydrogen;

A compound of the formula (M21) wherein $A^2$ is =CH—, $R^6$ is a C1-C6 chain hydrocarbon group optionally having one or more halogen atoms, $R^7$ is hydrogen, and $R^8$ is a C1-C6 chain hydrocarbon group optionally having one or more halogen atoms;

A compound of the formula (M21) wherein $A^2$ is =CH—, $R^6$ is a trifluoromethyl group, a difluoromethyl group, a fluoromethyl group, a pentafluoroethyl group, a trifluoromethoxy group, or a trifluoromethylsulfanyl group, $R^7$ is hydrogen, and $R^8$ is a methyl group, an ethyl group, a propyl group, or an isopropyl group;

A compound of the formula (M21) wherein $A^2$ is =CH—, $R^6$ is a trifluoromethyl group or pentafluoroethyl group, $R^7$ is hydrogen, and $R^8$ is a methyl group;

A compound of the formula (M21) wherein $A^2$ is =CH—, $R^6$ is a trifluoromethyl group, a pentafluoroethyl group, a trifluoromethoxy group, a trifluoromethylsulfanyl group, a trifluoromethylsulfinyl group, or a trifluoromethylsulfonyl group, $R^7$ is hydrogen, and $R^8$ is a methyl group;

A compound of the formula (M21) wherein $A^2$ is =CH—, $R^6$ is a pentafluoroethyl group, a trifluoromethoxy group, a trifluoromethylsulfanyl group, a trifluoromethylsulfinyl group, or a trifluoromethylsulfonyl group, $R^7$ is hydrogen, and $R^8$ is a methyl group;

A compound of the formula (M21) wherein $A^2$ is =CH—, $R^6$ is a pentafluoroethyl group, $R^7$ is hydrogen, and $R^8$ is a methyl group;

A compound of the formula (M21) wherein $A^2$ is =CH—, $R^6$ is a trifluoromethylsulfonyl group, $R^7$ is hydrogen, and $R^8$ is a methyl group.

Examples of Compound (G) include the following compounds:

A compound of the formula (M20):

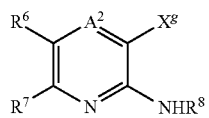

(M20)

wherein, $X^g$, $R^6$, $R^7$, $R^8$ and $A^2$ are as defined above (referred to as Compound (M20));

A compound of the formula (1G):

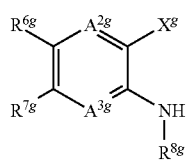

(1G)

wherein:

$X^g$ represents a chlorine atom, a bromine atom, or an iodine atom;

$A^{2g}$ represents a nitrogen atom or =CR$^{9g}$—;

$A^{3g}$ represents a nitrogen atom or =CR$^{10g}$—;

$R^{6g}$ represents a C1-C6 chain hydrocarbon group optionally having one or more halogen atoms, —OR$^{11g}$, —S(O)$_m$R$^{11g}$, —SF$_5$, or a halogen atom;

$R^{7g}$ represents a C1-C6 chain hydrocarbon group optionally having one or more halogen atoms, —OR$^{11g}$, —S(O)$_m$R$^{11g}$, —SF$_5$, or a halogen atom;

$R^{8g}$ represents a C1-C6 chain hydrocarbon group optionally having one or more halogen atoms or a hydrogen atom;

$R^{9g}$ and $R^{10g}$ are same or different and represent independently a C1-C6 chain hydrocarbon group optionally having one or more halogen atoms, a halogen atom or a hydrogen atom;

$R^{11g}$ and $R^{12g}$ are same or different and represent independently a C1-C6 chain hydrocarbon group optionally having one or more halogen atoms or a hydrogen atom;

m represents 0, 1, or 2;

provided that in —S(O)$_m$R$^{11g}$, when m is 1 or 2, $R^{11g}$ is not a hydrogen atom (hereinafter, referred to as Compound (1G));

And examples of Compound (1G) include the following compounds:

A compound of the formula (1G) wherein $X^g$ is a chlorine atom;

A compound of the formula (1G) wherein $X^g$ is a bromine atom;

A compound of the formula (1G) wherein $X^g$ is an iodine atom;

A compound of the formula (1G) wherein $A^{2g}$ is =CR$^{9g}$—, and $A^{3g}$ is =CR$^{10g}$—;

A compound of the formula (1G) wherein $A^{2g}$ is a nitrogen atom, and $A^{3g}$ is =CR$^{10g}$—;

A compound of the formula (1G) wherein $A^{2g}$ is =CR$^{9g}$—, and $A^{3g}$ is a nitrogen atom;

A compound of the formula (1G) wherein $A^{2g}$ is a nitrogen atom, and $A^{3g}$ is a nitrogen atom;

A compound of the formula (1G) wherein $A^{2g}$ is =CR$^{9g}$—, $A^{3g}$ is =CR$^{10g}$—, and $R^{9g}$ and $R^{10g}$ are a hydrogen atom;

A compound of the formula (1G) wherein $A^{2g}$ is =CR$^{9g}$—, $R^{9g}$ is a hydrogen atom, and $A^{3g}$ is a nitrogen atom;

A compound of the formula (1G) wherein $R^{6g}$ is a C2-C3 alkyl group having one or more fluorine atoms, a C1-C3 alkylsulfanyl group having one or more fluorine atoms, a C1-C3 alkylsulfinyl group having one or more fluorine atoms, or a C1-C3 alkylsulfonyl group having one or more fluorine atoms;

A compound of the formula (1G) wherein $R^{6g}$ is a C2-C3 alkyl group having one or more fluorine atoms;

A compound of the formula (1G) wherein $R^{6g}$ is a C1-C3 alkylsulfanyl group having one or more fluorine atoms, a C1-C3 alkylsulfinyl group having one or more fluorine atoms, or a C1-C3 alkylsulfonyl group having one or more fluorine atoms;

A compound of the formula (1G) wherein $R^{6g}$ is a pentafluoroethyl group, a trifluoromethylsulfanyl group, a trifluoromethylsulfinyl group, a trifluoromethylsulfonyl group, or an iodine atom;

A compound of the formula (1G) wherein $R^{6g}$ is a trifluoromethylsulfanyl group, a trifluoromethylsulfinyl group, or a trifluoromethylsulfonyl group;

A compound of the formula (1G) wherein $R^{6g}$ is a pentafluoroethyl group;

A compound of the formula (1G) wherein $R^{6g}$ is a trifluoromethylsulfanyl group;

A compound of the formula (1G) wherein $R^{6g}$ is a trifluoromethylsulfinyl group;

A compound of the formula (1G) wherein $R^{6g}$ is a trifluoromethylsulfonyl group;

A compound of the formula (1G) wherein $R^{6g}$ is an iodine atom;

A compound of the formula (1G) wherein $R^{6g}$ is —SF$_5$;

A compound of the formula (1G) wherein $R^{7g}$ is a hydrogen atom;

A compound of the formula (1G) wherein $R^{8g}$ is a C1-C3 alkyl group or a hydrogen atom;

A compound of the formula (1G) wherein $R^{8g}$ is a C1-C3 alkyl group;

A compound of the formula (1G) wherein $R^{8g}$ is a methyl group;

A compound of the formula (1G) wherein $R^{8g}$ is an ethyl group;

A compound of the formula (1G) wherein $R^{8g}$ is a propyl group;

A compound of the formula (1G) wherein $R^{8g}$ is a hydrogen atom;

A compound of the formula (1G) wherein $R^{8g}$ is a methyl group or a hydrogen atom;

A compound of the formula (1G) wherein $X^g$ is a chlorine atom or a bromine atom, $A^{2g}$ is =$CR^{9g}$—, $R^{9g}$ is a hydrogen atom, $A^{3g}$ is a nitrogen atom, $R^{6g}$ is a C2-C3 alkyl group having one or more fluorine atoms, a C1-C3 alkylsulfanyl group having one or more fluorine atoms, a C1-C3 alkylsulfinyl group having one or more fluorine atoms, or a C1-C3 alkylsulfonyl group having one or more fluorine atoms, $R^{7g}$ is a hydrogen atom, and $R^{8g}$ is a C1-C3 alkyl group or a hydrogen atom;

A compound of the formula (1G) wherein $X^g$ is a chlorine atom or a bromine atom, $A^{2g}$ is =$CR^{9g}$—, $R^{9g}$ is a hydrogen atom, $A^{3g}$ is a nitrogen atom, $R^{6g}$ is a C2-C3 alkyl group having one or more fluorine atoms, $R^{7g}$ is a hydrogen atom, and $R^{8g}$ is a C1-C3 alkyl group or a hydrogen atom;

A compound of the formula (1G) wherein $X^g$ is a chlorine atom or a bromine atom, $A^{2g}$ is =$CR^{9g}$—, $R^{9g}$ is a hydrogen atom, $A^{3g}$ is a nitrogen atom, $R^{6g}$ is a C1-C3 alkylsulfanyl group having one or more fluorine atoms, a C1-C3 alkylsulfinyl group having one or more fluorine atoms or a C1-C3 alkylsulfonyl group having one or more fluorine atoms, $R^{7g}$ is a hydrogen atom, and $R^{8g}$ is a C1-C3 alkyl group or a hydrogen atom;

A compound of the formula (1G) wherein $X^g$ is a chlorine atom or a bromine atom, $A^{2g}$ is =$CR^{9g}$—, $R^{9g}$ is a hydrogen atom, $A^{3g}$ is a nitrogen atom, $R^{6g}$ is a pentafluoroethyl group, a trifluoromethylsulfanyl group, a trifluoromethylsulfinyl group, a trifluoromethylsulfonyl group, or an iodine atom, $R^{7g}$ is a hydrogen atom, and $R^{8g}$ is a C1-C3 alkyl group or a hydrogen atom: provided that when $R^{6g}$ is an iodine atom, $R^{8g}$ is a C1-C3 alkyl group;

A compound of the formula (1G) wherein $A^{2g}$ is =$CR^{9g}$—, $R^{9g}$ is a hydrogen atom, $A^{3g}$ is a nitrogen atom, $R^{6g}$ is a pentafluoroethyl group, a trifluoromethylsulfanyl group, a trifluoromethylsulfinyl group, or a trifluoromethylsulfonyl group, $R^{7g}$ is a hydrogen atom, and $R^{8g}$ is a methyl group or a hydrogen atom;

A compound of the formula (1G) wherein $X^g$ is a chlorine atom or a bromine atom, $A^{2g}$ is =$CR^{9g}$—, $R^{9g}$ is a hydrogen atom, $A^{3g}$ is a nitrogen atom, $R^{6g}$ is a pentafluoroethyl group, $R^{7g}$ is a hydrogen atom, and $R^{8g}$ is a methyl group;

A compound of the formula (1G) wherein $X^g$ is a chlorine atom or a bromine atom, $A^{2g}$ is =$CR^{9g}$—, $R^{9g}$ is a hydrogen atom, $A^{3g}$ is a nitrogen atom, $R^{6g}$ is a trifluoromethylsulfanyl group, $R^{7g}$ is a hydrogen atom, and $R^{8g}$ is a methyl group;

A compound of the formula (1G) wherein $X^g$ is a chlorine atom or a bromine atom, $A^{2g}$ is =$CR^{9g}$—, $R^{9g}$ is a hydrogen atom, $A^{3g}$ is a nitrogen atom, $R^{6g}$ is a trifluoromethylsulfonyl group, $R^{7g}$ is a hydrogen atom, and $R^{8g}$ is a methyl group;

A compound of the formula (1G) wherein $X^g$ is a chlorine atom or a bromine atom, $A^{2g}$ is =$CR^{9g}$—, $R^{9g}$ is a hydrogen atom, $A^{3g}$ is a nitrogen atom, $R^{6g}$ is an iodine atom, $R^{7g}$ is a hydrogen atom, and $R^{8g}$ is a C1-C3 alkyl group;

A compound of the formula (1G) wherein $X^g$ is a chlorine atom or a bromine atom, $A^{2g}$ is =$CR^{9g}$—, $R^{9g}$ is a hydrogen atom, $A^{3g}$ is a nitrogen atom, $R^{6g}$ is an iodine atom, $R^{7g}$ is a hydrogen atom, and $R^{8g}$ is a methyl group;

A compound of the formula (1G) wherein $X^g$ is a chlorine atom or a bromine atom, $A^{2g}$ is =$CR^{9g}$—, $A^{3g}$ is =$CR^{10g}$—, $R^{9g}$ and $R^{10g}$ are a hydrogen atom, $R^{6g}$ is a C2-C3 alkyl group having one or more fluorine atoms, a C1-C3 alkylsulfanyl group having one or more fluorine atoms, a C1-C3 alkylsulfinyl group having one or more fluorine atoms, a C1-C3 alkylsulfonyl group having one or more fluorine atoms, $R^{7g}$ is a hydrogen atom, and $R^{8g}$ is a C1-C3 alkyl group or a hydrogen atom;

A compound of the formula (1G) wherein $X^g$ is a chlorine atom or a bromine atom, $A^{2g}$ is =$CR^{9g}$—, $A^{3g}$ is =$CR^{10g}$—, $R^{9g}$ and $R^{10g}$ are a hydrogen atom, $R^{6g}$ is a C2-C3 alkyl group having one or more fluorine atoms, $R^{7g}$ is a hydrogen atom, and $R^{8g}$ is a C1-C3 alkyl group or a hydrogen atom;

A compound of the formula (1G) wherein $X^g$ is a chlorine atom or a bromine atom, $A^{2g}$ is =$CR^{9g}$—, $A^{3g}$ is =$CR^{10g}$—, $R^{9g}$ and $R^{10g}$ are a hydrogen atom, $R^{6g}$ is a C1-C3 alkylsulfanyl group having one or more fluorine atoms, a C1-C3 alkylsulfinyl group having one or more fluorine atoms, or a C1-C3 alkylsulfonyl group having one or more fluorine atoms, $R^{7g}$ is a hydrogen atom, and $R^{8g}$ is a C1-C3 alkyl group or a hydrogen atom;

A compound of the formula (1G) wherein $X^g$ is a chlorine atom or a bromine atom, $A^{2g}$ is =$CR^{9g}$—, $A^{3g}$ is =$CR^{10g}$—, $R^{9g}$ and $R^{10g}$ are a hydrogen atom, $R^{6g}$ is a pentafluoroethyl group, a trifluoromethylsulfanyl group, a trifluoromethylsulfinyl group, or a trifluoromethylsulfonyl group, $R^{7g}$ is a hydrogen atom, and $R^{8g}$ is a methyl group or a hydrogen atom;

A compound of the formula (1G) wherein $X^g$ is a chlorine atom or a bromine atom, $A^{2g}$ is =$CR^{9g}$—, $A^{3g}$ is =$CR^{10g}$—, $R^{9g}$ and $R^{10g}$ are a hydrogen atom, $R^{6g}$ is a pentafluoroethyl group, $R^{7g}$ is a hydrogen atom, and $R^{8g}$ is a methyl group;

A compound of the formula (1G) wherein $X^g$ is a chlorine atom or a bromine atom, $A^{2g}$ is =$CR^{9g}$—, $A^{3g}$ is =$CR^{10g}$—, $R^{9g}$ and $R^{10g}$ are a hydrogen atom, $R^{6g}$ is a trifluoromethylsulfanyl group, $R^{7g}$ is a hydrogen atom, and $R^{8g}$ is a methyl group;

A compound of the formula (1G) wherein $X^g$ is a chlorine atom or a bromine atom, $A^{2g}$ is =$CR^{9g}$—, $A^{3g}$ is =$CR^{10g}$—, $R^{9g}$ and $R^{10g}$ are a hydrogen atom, $R^{6g}$ is a trifluoromethylsulfonyl group, $R^{7g}$ is a hydrogen atom, and $R^{8g}$ is a methyl group;

A compound of the formula (1G) wherein $X^g$ is a chlorine atom or a bromine atom, $A^{2g}$ is =$CR^{9g}$—, $A^{3g}$ is =$CR^{10g}$—, $R^{9g}$ and $R^{10g}$ are a hydrogen atom, $R^{6g}$ is —$SF_5$, $R^{7g}$ is a hydrogen atom, and $R^{8g}$ is a methyl group;

And examples of Compound (M20) include the following compounds:

A compound of the formula (M20) wherein $X^g$ is a chlorine atom;

A compound of the formula (M20) wherein $X^g$ is a bromine atom;

A compound of the formula (M20) wherein $X^g$ is an iodine atom;

A compound of the formula (M20) wherein $A^2$ is =CH—;

A compound of the formula (M20) wherein $A^2$ is nitrogen;

A compound of the formula (M20) wherein $R^8$ is a C1-C6 chain hydrocarbon group optionally having one or more halogen atoms or hydrogen;

A compound of the formula (M20) wherein $R^8$ is a C1-C6 chain hydrocarbon group optionally having one or more halogen atoms;

A compound of the formula (M20) wherein $R^8$ is a C1-C3 alkyl group;

A compound of the formula (M20) wherein $R^8$ is a methyl group, an ethyl group, a propyl group, or hydrogen;

A compound of the formula (M20) wherein $R^8$ is a methyl group;

A compound of the formula (M20) wherein $R^8$ is an ethyl group;

A compound of the formula (M20) wherein $R^8$ is a propyl group;

A compound of the formula (M20) wherein $R^8$ is hydrogen;

A compound of the formula (M20) wherein $R^6$ is a C1-C6 chain hydrocarbon group optionally having one or more halogen atoms, a C1-C6 alkoxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a bromine atom, or an iodine atom;

A compound of the formula (M20) wherein $R^6$ is a C1-C6 chain hydrocarbon group optionally having one or more halogen atoms, a C1-C6 alkoxy group optionally having one or more halogen atoms, a C1-C6 alkylsulfanyl group optionally having one or more halogen atoms, a C1-C6 alkylsulfinyl group optionally having one or more halogen atoms, or a C1-C6 alkylsulfonyl group optionally having one or more halogen atoms;

A compound of the formula (M20) wherein $R^6$ is a C1-C6 chain hydrocarbon group optionally having one or more halogen atoms;

A compound of the formula (M20) wherein $R^6$ is a C1-C6 alkoxy group optionally having one or more halogen atoms;

A compound of the formula (M20) wherein $R^6$ is a C1-C6 alkylsulfanyl group optionally having one or more halogen atoms, a C1-C6 alkylsulfinyl group optionally having one or more halogen atoms, or a C1-C6 alkylsulfonyl group optionally having one or more halogen atoms;

A compound of the formula (M20) wherein $R^6$ is a bromine atom or an iodine atom;

A compound of the formula (M20) wherein $R^6$ is a trifluoromethyl group, a pentafluoroethyl group, a trifluoromethoxy group, a trifluoromethylsulfanyl group, a trifluoromethylsulfinyl group, or a trifluoromethylsulfonyl group;

A compound of the formula (M20) wherein $R^6$ is a pentafluoroethyl group, a trifluoromethoxy group, a trifluoromethylsulfanyl group, a trifluoromethylsulfinyl group, or a trifluoromethylsulfonyl group;

A compound of the formula (M20) wherein $R^6$ is a pentafluoroethyl group;

A compound of the formula (M20) wherein $R^6$ is a trifluoromethylsulfanyl group;

A compound of the formula (M20) wherein $R^6$ is a trifluoromethylsulfinyl group;

A compound of the formula (M20) wherein $R^6$ is a trifluoromethylsulfonyl group;

A compound of the formula (M20) wherein $R^6$ is a trifluoromethyl group, a pentafluoroethyl group, a trifluoromethoxy group, a trifluoromethylsulfanyl group, a trifluoromethylsulfinyl group, or a trifluoromethylsulfonyl group, and $R^7$ is hydrogen;

A compound of the formula (M20) wherein $R^6$ is a pentafluoroethyl group, a trifluoromethoxy group, a trifluoromethylsulfanyl group, a trifluoromethylsulfinyl group, or a trifluoromethylsulfonyl group, and $R^7$ is hydrogen;

A compound of the formula (M20) wherein $R^6$ is a pentafluoroethyl group, and $R^7$ is hydrogen;

A compound of the formula (M20) wherein $R^6$ is a trifluoromethylsulfanyl group, and $R^7$ is hydrogen;

A compound of the formula (M20) wherein $R^6$ is a trifluoromethylsulfinyl group, and $R^7$ is hydrogen;

A compound of the formula (M20) wherein $R^6$ is a trifluoromethylsulfonyl group, and $R^7$ is hydrogen;

A compound of the formula (M20) wherein $A^2$ is =CH—, $R^6$ is a C1-C6 chain hydrocarbon group optionally having one or more halogen atoms, $R^7$ is hydrogen, and $R^8$ is a C1-C6 chain hydrocarbon group optionally having one or more halogen atoms;

A compound of the formula (M20) wherein $X^g$ is a bromine atom, $A^2$ is =CH—, $R^6$ is a C1-C6 chain hydrocarbon group optionally having one or more halogen atoms, $R^7$ is hydrogen, and $R^8$ is a C1-C6 chain hydrocarbon group optionally having one or more halogen atoms;

A compound of the formula (M20) wherein $A^2$ is =CH—, $R^6$ is a trifluoromethyl group, a difluoromethyl group, a fluoromethyl group, a pentafluoroethyl group, a trifluoromethoxy group, or a trifluoromethylsulfanyl group, $R^7$ is hydrogen, and $R^8$ is a methyl group, an ethyl group, a propyl group, or an isopropyl group;

A compound of the formula (M20) wherein $A^2$ is =CH—, $R^6$ is a trifluoromethyl group or a pentafluoroethyl group, $R^7$ is hydrogen, and $R^8$ is a methyl group;

A compound of the formula (M20) wherein $A^2$ is =CH—, $R^6$ is a trifluoromethyl group, a pentafluoroethyl group, a trifluoromethoxy group, a trifluoromethylsulfanyl group, a trifluoromethylsulfinyl group, or a trifluoromethylsulfonyl group, $R^7$ is hydrogen, and $R^8$ is a methyl group;

A compound of the formula (M20) wherein $A^2$ is =CH—, $R^6$ is a pentafluoroethyl group, a trifluoromethoxy group, a trifluoromethylsulfanyl group, a trifluoromethylsulfinyl group, or a trifluoromethylsulfonyl group, $R^7$ is hydrogen, and $R^8$ is a methyl group;

A compound of the formula (M20) wherein $X^g$ is a bromine atom, $A^2$ is =CH—, $R^6$ is a pentafluoroethyl group, a trifluoromethoxy group, a trifluoromethylsulfanyl group, a trifluoromethylsulfinyl group, or a trifluoromethylsulfonyl group, $R^7$ is hydrogen, and $R^8$ is a methyl group.

Examples of Compound (3), Compound (5), and Compound (M3) include the following compounds:

A compound of the formula (1H):

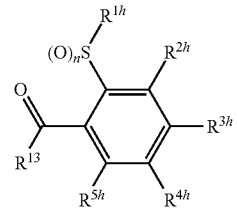

wherein:

$R^{1h}$ represents a C1-C6 alkyl group optionally having one or more halogen atoms;

$R^{13}$ represents a hydrogen atom, hydroxy group, or a chlorine atom;

$R^{2h}$, $R^{3h}$, $R^{4h}$, and $R^{5h}$ are same or different and represent independently a C1-C6 chain hydrocarbon group optionally having one or more halogen atoms, $-OR^{11h}$, $-S(O)_m R^{11h}$, $-SF_5$, a halogen atom, or a hydrogen atom;

$R^{11h}$ and $R^{12h}$ are same or different and represent independently a C1-C6 chain hydrocarbon group optionally having one or more halogen atoms or a hydrogen atom; and n represents 0, 1, or 2 (hereinafter, referred to as Compound (1H));

And examples of Compound (1H) include the following compounds:

A compound of the formula (1H) wherein $R^{1h}$ is a C1-C3 alkyl group optionally having one or more halogen atoms;

A compound of the formula (1H) wherein $R^{1h}$ is a C1-C3 alkyl group;

A compound of the formula (1H) wherein $R^{1h}$ is a methyl group;

A compound of the formula (1H) wherein $R^{1h}$ is an ethyl group;

A compound of the formula (1H) wherein $R^{1h}$ is a propyl group;

A compound of the formula (1H) wherein $R^{13}$ is a hydrogen atom;

A compound of the formula (1H) wherein $R^{13}$ is hydroxy group;

A compound of the formula (1H) wherein $R^{13}$ is a chlorine atom;

A compound of the formula (1H) wherein $R^{13}$ is a hydrogen atom or hydroxy group;

A compound of the formula (1H) wherein $R^{2h}$, $R^{3h}$, $R^{4h}$, and $R^{5h}$ are a hydrogen atom;

A compound of the formula (1H) wherein $R^{2h}$, $R^{3h}$, $R^{4h}$, and $R^{5h}$ are same or different and are independently a C1-C6 chain hydrocarbon group optionally having one or more halogen atoms or a hydrogen atom;

A compound of the formula (1H) wherein $R^{2h}$, $R^{3h}$, $R^{4h}$, and $R^{5h}$ are same or different and are independently $-OR^{11h}$ or a hydrogen atom;

A compound of the formula (1H) wherein $R^{2h}$, $R^{3h}$, $R^{4h}$, and $R^{5h}$ are same or different and are independently $-S(O)_m R^{11h}$ or a hydrogen atom;

A compound of the formula (1H) wherein $R^{2h}$, $R^{3h}$, $R^{4h}$, and $R^{5h}$ are same or different and are independently a halogen atom or a hydrogen atom;

A compound of the formula (1H) wherein $R^{2h}$, $R^{4h}$, and $R^{5h}$ are a hydrogen atom, and $R^{3h}$ is a C1-C6 chain hydrocarbon group optionally having one or more halogen atoms, $-OR^{11h}$, $-S(O)_m R^{11h}$ or a halogen atom;

A compound of the formula (1H) wherein $R^{2h}$, $R^{4h}$, and $R^{5h}$ are a hydrogen atom, and $R^{3h}$ is a C1-C3 alkyl group;

A compound of the formula (1H) wherein $R^{2h}$, $R^{4h}$, and $R^{5h}$ are a hydrogen atom, and $R^{3h}$ is a C1-C3 alkyl group optionally having one or more fluorine atoms;

A compound of the formula (1H) wherein $R^{2h}$, $R^{4h}$, and $R^{5h}$ are a hydrogen atom, and $R^{3h}$ is a C1-C3 alkyl group having one or more fluorine atoms;

A compound of the formula (1H) wherein $R^{2h}$, $R^{4h}$, and $R^{5h}$ are a hydrogen atom, and $R^{3h}$ is a methyl group, an ethyl group, a propyl group, an isopropyl group, a trifluoromethyl group, a pentafluoroethyl group, a heptafluoropropyl group, or a heptafluoroisopropyl group;

A compound of the formula (1H) wherein $R^{2h}$, $R^{4h}$, and $R^{5h}$ are a hydrogen atom, and $R^{3h}$ is a methyl group;

A compound of the formula (1H) wherein $R^{2h}$, $R^{4h}$, and $R^{5h}$ are a hydrogen atom, and $R^{3h}$ is an ethyl group;

A compound of the formula (1H) wherein $R^{2h}$, $R^{4h}$, and $R^{5h}$ are a hydrogen atom, and $R^{3h}$ is a propyl group;

A compound of the formula (1H) wherein $R^{2h}$, $R^{4h}$, and $R^{5h}$ are a hydrogen atom, and $R^{3h}$ is an isopropyl group;

A compound of the formula (1H) wherein $R^{2h}$, $R^{4h}$, and $R^{5h}$ are a hydrogen atom, and $R^{3h}$ is a trifluoromethyl group;

A compound of the formula (1H) wherein $R^{2h}$, $R^{4h}$, and $R^{5h}$ are a hydrogen atom, and $R^{3h}$ is a pentafluoroethyl group;

A compound of the formula (1H) wherein $R^{2h}$, $R^{4h}$, and $R^{5h}$ are a hydrogen atom, and $R^{3h}$ is a heptafluoropropyl group;

A compound of the formula (1H) wherein $R^{2h}$, $R^{4h}$, and $R^{5h}$ are a hydrogen atom, and $R^{3h}$ is a heptafluoroisopropyl group;

A compound of the formula (1H) wherein $R^{2h}$, $R^{4h}$, and $R^{5h}$ are a hydrogen atom, and $R^{3h}$ is $-OR^{11h}$;

A compound of the formula (1H) wherein $R^{2h}$, $R^{4h}$, and $R^{5h}$ are a hydrogen atom, and $R^{3h}$ is a C1-C3 alkoxy group optionally having one or more fluorine atoms;

A compound of the formula (1H) wherein $R^{2h}$, $R^{4h}$, and $R^{5h}$ are a hydrogen atom, and $R^{3h}$ is a trifluoromethoxy group;

A compound of the formula (1H) wherein $R^{2h}$, $R^{4h}$, and $R^{5h}$ are a hydrogen atom, and $R^{3h}$ is $-S(O)_m R^{11h}$;

A compound of the formula (1H) wherein $R^{2h}$, $R^{4h}$, and $R^{5h}$ are a hydrogen atom, and $R^{3h}$ is a C1-C3 alkylsulfanyl group optionally having one or more fluorine atoms, a C1-C3 alkylsulfinyl group optionally having one or more fluorine atoms, or a C1-C3 alkylsulfonyl group optionally having one or more fluorine atoms;

A compound of the formula (1H) wherein $R^{2h}$, $R^{4h}$, and $R^{5h}$ are a hydrogen atom, and $R^{3h}$ is a trifluoromethylsulfanyl group, a trifluoromethylsulfinyl group or a trifluoromethylsulfonyl group;

A compound of the formula (1H) wherein $R^{2h}$, $R^{4h}$, and $R^{5h}$ are a hydrogen atom, and $R^{3h}$ is a trifluoromethylsulfanyl group;

A compound of the formula (1H) wherein $R^{2h}$, $R^{4h}$, and $R^{5h}$ are a hydrogen atom, and $R^{3h}$ is a trifluoromethylsulfinyl group;

A compound of the formula (1H) wherein $R^{2h}$, $R^{4h}$, and $R^{5h}$ are a hydrogen atom, and $R^{3h}$ is a trifluoromethylsulfonyl group;

A compound of the formula (1H) wherein $R^{2h}$, $R^{4h}$, and $R^{5h}$ are a hydrogen atom, and $R^{3h}$ is a halogen atom;

A compound of the formula (1H) wherein $R^{2h}$, $R^{4h}$, and $R^{5h}$ are a hydrogen atom, and $R^{3h}$ is a fluorine atom, a chlorine atom, or a bromine atom;

A compound of the formula (1H) wherein $R^{2h}$, $R^{4h}$, and $R^{5h}$ are a hydrogen atom, and $R^{3h}$ is a fluorine atom;

A compound of the formula (1H) wherein $R^{2h}$, $R^{4h}$, and $R^{5h}$ are a hydrogen atom, and $R^{3h}$ is a chlorine atom;

A compound of the formula (1H) wherein $R^{2h}$, $R^{4h}$, and $R^{5h}$ are a hydrogen atom, and $R^{3h}$ is a bromine atom;

A compound of the formula (1H) wherein $R^{2h}$, $R^{4h}$, and $R^{5h}$ are a hydrogen atom, and $R^{3h}$ is $-SF_5$;

A compound of the formula (1H) wherein $R^{2h}$, $R^{4h}$, and $R^{5h}$ are a hydrogen atom, and $R^{3h}$ is a methyl group, an ethyl group, a propyl group, an isopropyl group, a trifluoromethyl group, a pentafluoroethyl group, a heptafluoropropyl group, a heptafluoroisopropyl group, a trifluoromethylsulfanyl group, a trifluoromethylsulfinyl group, a trifluoromethylsulfonyl group, a fluorine atom, a chlorine atom, a bromine atom, or $-SF_5$;

A compound of the formula (1H) wherein n is 0;

A compound of the formula (1H) wherein n is 1;

A compound of the formula (1H) wherein n is 2;

A compound of the formula (1H) wherein $R^{1h}$ is a methyl group, $R^{2h}$, $R^{4h}$, $R^{5h}$ are same or different and are independently a halogen atom or a hydrogen atom, and $R^{3h}$ a C1-C6 chain hydrocarbon group optionally having one or more halogen atoms, $-OR^{11h}$, $-S(O)_m R^{11h}$, a halogen atom, or a hydrogen atom;

A compound of the formula (1H) wherein $R^{1h}$ is a methyl group, $R^{2h}$, $R^{4h}$, and $R^{5h}$ are a hydrogen atom, and $R^{3h}$ is a C1-C3 alkyl group optionally having one or more fluorine atoms;

A compound of the formula (1H) wherein $R^{1h}$ is a methyl group, $R^{2h}$, $R^{4h}$, and $R^{5h}$ are a hydrogen atom, and $R^{3h}$ is a C1-C3 alkoxy group optionally having one or more fluorine atoms;

A compound of the formula (1H) wherein $R^{1h}$ is a methyl group, $R^{2h}$, $R^{4h}$, and $R^{5h}$ are a hydrogen atom, and $R^{3h}$ is a C1-C3 alkylsulfanyl group optionally having one or more fluorine atoms, a C1-C3 alkylsulfinyl group optionally having one or more fluorine atoms, or a C1-C3 alkylsulfonyl group optionally having one or more fluorine atoms;

A compound of the formula (1H) wherein $R^{1h}$ is a methyl group, $R^{2h}$, $R^{4h}$, and $R^{5h}$ are a hydrogen atom, and $R^{3h}$ is a halogen atom;

A compound of the formula (1H) wherein $R^{1h}$ is a methyl group, $R^{2h}$, $R^{4h}$, and $R^{5h}$ are a hydrogen atom, and $R^{3h}$ is a methyl group;

A compound of the formula (1H) wherein $R^{1h}$ is a methyl group, $R^{2h}$, $R^{4h}$, and $R^{5h}$ are a hydrogen atom, and $R^{3h}$ is an ethyl group;

A compound of the formula (1H) wherein $R^{1h}$ is a methyl group, $R^{2h}$, $R^{4h}$, and $R^{5h}$ are a hydrogen atom, and $R^{3h}$ is a trifluoromethyl group;

A compound of the formula (1H) wherein $R^{1h}$ is a methyl group, $R^{2h}$, $R^{4h}$, and $R^{5h}$ are a hydrogen atom, and $R^{3h}$ is a trifluoromethoxy group;

A compound of the formula (1H) wherein $R^{1h}$ is a methyl group, $R^{2h}$, $R^{4h}$, and $R^{5h}$ are a hydrogen atom, and $R^{3h}$ is a fluorine atom;

A compound of the formula (1H) wherein $R^{1h}$ is a methyl group, $R^{2h}$, $R^{4h}$, and $R^{5h}$ are a hydrogen atom, and $R^{3h}$ is a chlorine atom;

A compound of the formula (1H) wherein $R^{1h}$ is a methyl group, $R^{2h}$, $R^{4h}$, and $R^{5h}$ are a hydrogen atom, and $R^{3h}$ is a bromine atom;

A compound of the formula (1H) wherein $R^{1h}$ is a methyl group, $R^{2h}$, $R^{4h}$, and $R^{5h}$ are a hydrogen atom, and $R^{3h}$ is —$SF_5$;

A compound of the formula (1H) wherein $R^{1h}$ is an ethyl group, $R^{2h}$, $R^{4h}$, and $R^{5h}$ are same or different and are independently a halogen atom or a hydrogen atom, and $R^{3h}$ a C1-C6 chain hydrocarbon group optionally having one or more halogen atoms, —$OR^{11h}$, —$S(O)_m R^{11h}$, a halogen atom, or a hydrogen atom;

A compound of the formula (1H) wherein $R^{1h}$ is an ethyl group, $R^{2h}$, $R^{4h}$, and $R^{5h}$ are a hydrogen atom, and $R^{3h}$ is a C1-C3 alkyl group optionally having one or more fluorine atoms;

A compound of the formula (1H) wherein $R^{1h}$ is an ethyl group, $R^{2h}$, $R^{4h}$, and $R^{5h}$ are a hydrogen atom, and $R^{3h}$ is a C1-C3 alkoxy group optionally having one or more fluorine atoms;

A compound of the formula (1H) wherein $R^{1h}$ is an ethyl group, $R^{2h}$, $R^{4h}$, and $R^{5h}$ are a hydrogen atom, and $R^{3h}$ is a C1-C3 alkylsulfanyl group optionally having one or more fluorine atoms, a C1-C3 alkylsulfinyl group optionally having one or more fluorine atoms, or a C1-C3 alkylsulfonyl group optionally having one or more fluorine atoms;

A compound of the formula (1H) wherein $R^{1h}$ is an ethyl group, $R^{2h}$, $R^{4h}$, and $R^{5h}$ are a hydrogen atom, and $R^{3h}$ is a halogen atom;

A compound of the formula (1H) wherein $R^{1h}$ is an ethyl group, $R^{2h}$, $R^{4h}$, and $R^{5h}$ are a hydrogen atom, and $R^{3h}$ is a methyl group;

A compound of the formula (1H) wherein $R^{1h}$ is an ethyl group, $R^{2h}$, $R^{4h}$, and $R^{5h}$ are a hydrogen atom, $R^{3h}$ is a methyl group, and $R^{13}$ is hydroxy group;

A compound of the formula (1H) wherein $R^{1h}$ is an ethyl group, $R^{2h}$, $R^{4h}$, and $R^{5h}$ are a hydrogen atom, $R^{3h}$ is a methyl group, and $R^{13}$ is a chlorine atom;

A compound of the formula (1H) wherein $R^{1h}$ is an ethyl group, $R^{2h}$, $R^{4h}$, and $R^{5h}$ are a hydrogen atom, $R^{3h}$ is a methyl group, and $R^{13}$ is a hydrogen atom;

A compound of the formula (1H) wherein $R^{1h}$ is an ethyl group, $R^{2h}$, $R^{4h}$, and $R^{5h}$ are a hydrogen atom, and $R^{3h}$ is an ethyl group;

A compound of the formula (1H) wherein $R^{1h}$ is an ethyl group, $R^{2h}$, $R^{4h}$, and $R^{5h}$ are a hydrogen atom, and $R^{3h}$ is a trifluoromethyl group;

A compound of the formula (1H) wherein $R^{1h}$ is an ethyl group, $R^{2h}$, $R^{4h}$, and $R^{5h}$ are a hydrogen atom, $R^{3h}$ is a trifluoromethyl group, and $R^{13}$ is hydroxy group;

A compound of the formula (1H) wherein $R^{1h}$ is an ethyl group, $R^{2h}$, $R^{4h}$, and $R^{5h}$ are a hydrogen atom, $R^{3h}$ is a trifluoromethyl group, and $R^{13}$ is a chlorine atom;

A compound of the formula (1H) wherein $R^{1h}$ is an ethyl group, $R^{2h}$, $R^{4h}$, and $R^{5h}$ are a hydrogen atom, $R^{3h}$ is a trifluoromethyl group, and $R^{5h}$ is a hydrogen atom;

A compound of the formula (1H) wherein $R^{1h}$ is an ethyl group, $R^{2h}$, $R^{4h}$, and $R^{5h}$ are a hydrogen atom, and $R^{3h}$ is a trifluoromethoxy group;

A compound of the formula (1H) wherein $R^{1h}$ is an ethyl group, $R^{2h}$, $R^{4h}$, and $R^{5h}$ are a hydrogen atom, and $R^{3h}$ is a fluorine atom;

A compound of the formula (1H) wherein $R^{1h}$ is an ethyl group, $R^{2h}$, $R^{4h}$, and $R^{5h}$ are a hydrogen atom, and $R^{3h}$ is a chlorine atom;

A compound of the formula (1H) wherein $R^{1h}$ is an ethyl group, $R^{2h}$, $R^{4h}$, and $R^{5h}$ are a hydrogen atom, $R^{3h}$ is a chlorine atom, and $R^{13}$ is hydroxy group;

A compound of the formula (1H) wherein $R^{1h}$ is an ethyl group, $R^{2h}$, $R^{4h}$, and $R^{5h}$ are a hydrogen atom, $R^{3h}$ is a chlorine atom, and $R^{13}$ is a chlorine atom;

A compound of the formula (1H) wherein $R^{1h}$ is an ethyl group, $R^{2h}$, $R^{4h}$, $R^{5h}$ are a hydrogen atom, $R^{3h}$ is a chlorine atom, and $R^{13}$ is a hydrogen atom;

A compound of the formula (1H) wherein $R^{1h}$ is an ethyl group, $R^{2h}$, $R^{4h}$, and $R^{5h}$ are a hydrogen atom, and $R^{3h}$ is a bromine atom;

A compound of the formula (1H) wherein $R^{1h}$ is an ethyl group, $R^{2h}$, $R^{4h}$, and $R^{5h}$ are a hydrogen atom, $R^{3h}$ is a bromine atom, and $R^{13}$ is hydroxy group;

A compound of the formula (1H) wherein $R^{1h}$ is an ethyl group, $R^{2h}$, $R^{4h}$, and $R^{5h}$ are a hydrogen atom, $R^{3h}$ is a bromine atom, and $R^{13}$ is a chlorine atom;

A compound of the formula (1H) wherein $R^{1h}$ is an ethyl group, $R^{2h}$, $R^{4h}$, and $R^{5h}$ are a hydrogen atom, $R^{3h}$ is a bromine atom, and $R^{13}$ is a hydrogen atom;

A compound of the formula (1H) wherein $R^{1h}$ is an ethyl group, $R^{2h}$, $R^{4h}$, and $R^{5h}$ are a hydrogen atom, and $R^{3h}$ is —$SF_5$;

A compound of the formula (1H) wherein $R^{1h}$ is a propyl group, $R^{2h}$, $R^{4h}$, and $R^{5h}$ are same or different and are independently a halogen atom or a hydrogen atom, and $R^{3h}$ a C1-C6 chain hydrocarbon group optionally having one or more halogen atoms, —$OR^{1h}$, —$S(O)_m R^{11h}$, a halogen atom, or a hydrogen atom;

A compound of the formula (1H) wherein $R^{1h}$ is a propyl group, $R^{2h}$, $R^{4h}$, and $R^{5h}$ are a hydrogen atom, and $R^{3h}$ is a C1-C3 alkyl group optionally having one or more fluorine atoms;

A compound of the formula (1H) wherein $R^{1h}$ is a propyl group, and $R^{3h}$ is a C1-C3 alkoxy group optionally having one or more fluorine atoms;

A compound of the formula (1H) wherein $R^{1h}$ is a propyl group, and $R^{3h}$ is a C1-C3 alkylsulfanyl group optionally having one or more fluorine atoms, a C1-C3 alkylsulfinyl group optionally having one or more fluorine atoms, or a C1-C3 alkylsulfonyl group optionally having one or more fluorine atoms;

A compound of the formula (1H) wherein $R^{1h}$ is a propyl group, $R^{2h}$, $R^{4h}$, and $R^{5h}$ are a hydrogen atom, and $R^{3h}$ is a halogen atom;

A compound of the formula (1H) wherein $R^{1h}$ is a propyl group, $R^{2h}$, $R^{4h}$, and $R^{5h}$ are a hydrogen atom, and $R^{3h}$ is a methyl group;

A compound of the formula (1H) wherein $R^{1h}$ is a propyl group, $R^{2h}$, $R^{4h}$, and $R^{5h}$ are a hydrogen atom, and $R^{3h}$ is an ethyl group;

A compound of the formula (1H) wherein $R^{1h}$ is a propyl group, $R^{2h}$, $R^{4h}$, and $R^{5h}$ are a hydrogen atom, and $R^{3h}$ is a trifluoromethyl group;

A compound of the formula (1H) wherein $R^{1h}$ is a propyl group, $R^{2h}$, $R^{4h}$, and $R^{5h}$ are a hydrogen atom, and $R^{3h}$ is a trifluoromethoxy group;

A compound of the formula (1H) wherein $R^{1h}$ is a propyl group, $R^{2h}$, $R^{4h}$, and $R^{5h}$ are a hydrogen atom, and $R^{3h}$ is a fluorine atom;

A compound of the formula (1H) wherein $R^{1h}$ is a propyl group, $R^{2h}$, $R^{4h}$, and $R^{5h}$ are a hydrogen atom, and $R^{3h}$ is a chlorine atom;

A compound of the formula (1H) wherein $R^{1h}$ is a propyl group, $R^{2h}$, $R^{4h}$, and $R^{5h}$ are a hydrogen atom, and $R^{3h}$ is a bromine atom;

A compound of the formula (1H) wherein $R^{1h}$ is a propyl group, $R^{2h}$, $R^{4h}$, and $R^{5h}$ are a hydrogen atom, and $R^{3h}$ is $-SF_5$.

Examples of Compound (M22) include the following compounds:

A compound of the formula (1I):

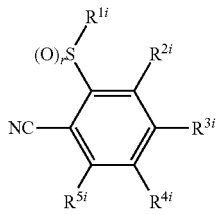

(1I)

wherein:

$R^{1i}$ represents a C1-C6 alkyl group optionally having one or more halogen atoms;

$R^{2i}$, $R^{3i}$, $R^{4i}$, and $R^{5i}$ are same or different and represent independently a C1-C6 chain hydrocarbon group optionally having one or more halogen atoms, $-OR^{11i}$, $-S(O)_mR^{11i}$, $-SF_5$, a halogen atom, or a hydrogen atom;

$R^{11i}$ and $R^{12i}$ are same or different and represent independently a C1-C6 chain hydrocarbon group optionally having one or more halogen atoms or a hydrogen atom; and r represents 1 or 2 (hereinafter, referred to as Compound (1I));

And examples of Compound (1I) include the following compounds:

A compound of the formula (1I) wherein $R^{1i}$ is a C1-C3 alkyl group optionally having one or more halogen atoms;

A compound of the formula (1I) wherein $R^{1i}$ is a C1-C3 alkyl group;

A compound of the formula (1I) wherein $R^{1i}$ is a methyl group;

A compound of the formula (1I) wherein $R^{1i}$ is an ethyl group;

A compound of the formula (1I) wherein $R^{1i}$ is a propyl group;

A compound of the formula (1I) wherein $R^{2i}$, $R^{3i}$, $R^{4i}$, and $R^{5i}$ are a hydrogen atom;

A compound of the formula (1I) wherein $R^{2i}$, $R^{3i}$, $R^{4i}$, and $R^{5i}$ are same or different and are independently a C1-C6 chain hydrocarbon group optionally having one or more halogen atoms or a hydrogen atom;

A compound of the formula (1I) wherein $R^{2i}$, $R^{3i}$, $R^{4i}$, and $R^{5i}$ are same or different and are independently $-OR^{11i}$ or a hydrogen atom;

A compound of the formula (1I) wherein $R^{2i}$, $R^{3i}$, $R^{4i}$, and $R^{5i}$ are same or different and are independently $-S(O)_mR^{11i}$ or a hydrogen atom;

A compound of the formula (1I) wherein $R^{2i}$, $R^{3i}$, $R^{4i}$, and $R^{5i}$ are same or different and are independently a halogen atom or a hydrogen atom;

A compound of the formula (1I) wherein $R^{2i}$, $R^{4i}$, and $R^{5i}$ are a hydrogen atom, and $R^{3i}$ is a C1-C6 chain hydrocarbon group optionally having one or more halogen atoms, $-OR^{11}$, $-S(O)_mR^{11i}$, or a halogen atom;

A compound of the formula (1I) wherein $R^{2i}$, $R^{4i}$, and $R^{5i}$ are a hydrogen atom, and $R^{3i}$ is a C1-C3 alkyl group;

A compound of the formula (1I) wherein $R^{2i}$, $R^{4i}$, and $R^{5i}$ are a hydrogen atom, and $R^{3i}$ is a C1-C3 alkyl group optionally having one or more fluorine atoms;

A compound of the formula (1I) wherein $R^{2i}$, $R^{4i}$, and $R^{5i}$ are a hydrogen atom, and $R^{3i}$ is a C1-C3 alkyl group having one or more fluorine atoms;

A compound of the formula (1I) wherein $R^{2i}$, $R^{4i}$, and $R^{5i}$ are a hydrogen atom, and $R^{3i}$ is a methyl group, an ethyl group, a propyl group, an isopropyl group, a trifluoromethyl group, a pentafluoroethyl group, a heptafluoropropyl group, or a heptafluoroisopropyl group;

A compound of the formula (1I) wherein $R^{2i}$, $R^{4i}$, and $R^{5i}$ are a hydrogen atom, and $R^{3i}$ is a methyl group;

A compound of the formula (1I) wherein $R^{2i}$, $R^{4i}$, and $R^{5i}$ are a hydrogen atom, and $R^{3i}$ is an ethyl group;

A compound of the formula (1I) wherein $R^{2i}$, $R^{4i}$, and $R^{5i}$ are a hydrogen atom, and $R^{3i}$ is a propyl group;

A compound of the formula (1I) wherein $R^{2i}$, $R^{4i}$, and $R^{5i}$ are a hydrogen atom, and $R^{3i}$ is an isopropyl group;

A compound of the formula (1I) wherein $R^{2i}$, $R^{4i}$, and $R^{5i}$ are a hydrogen atom, and $R^{3i}$ is a trifluoromethyl group;

A compound of the formula (1I) wherein $R^{2i}$, $R^{4i}$, and $R^{5i}$ are a hydrogen atom, and $R^{3i}$ is a pentafluoroethyl group;

A compound of the formula (1I) wherein $R^{2i}$, $R^{4i}$, and $R^{5i}$ are a hydrogen atom, and $R^{3i}$ is a heptafluoropropyl group;

A compound of the formula (1I) wherein $R^{2i}$, $R^{4i}$, and $R^{5i}$ are a hydrogen atom, and $R^{3i}$ is a heptafluoroisopropyl group;

A compound of the formula (1I) wherein $R^{2i}$, $R^{4i}$, and $R^{5i}$ are a hydrogen atom, and $R^{3i}$ is $-OR^{11i}$;

A compound of the formula (1I) wherein $R^{2i}$, $R^{4i}$, and $R^{5i}$ are a hydrogen atom, and $R^{3i}$ is a C1-C3 alkoxy group optionally having one or more fluorine atoms;

A compound of the formula (1I) wherein $R^{2i}$, $R^{4i}$, and $R^{5i}$ are a hydrogen atom, and $R^{3i}$ is a trifluoromethoxy group;

A compound of the formula (1I) wherein $R^{2i}$, $R^{4i}$, and $R^{5i}$ are a hydrogen atom, and $R^{3i}$ is $-S(O)_mR^{11i}$;

A compound of the formula (1I) wherein $R^{2i}$, $R^{4i}$, and $R^{5i}$ are a hydrogen atom, and $R^{3i}$ is a C1-C3 alkylsulfanyl group optionally having one or more fluorine atoms, a C1-C3 alkylsulfinyl group optionally having one or more fluorine atoms, or a C1-C3 alkylsulfonyl group optionally having one or more fluorine atoms;

A compound of the formula (1I) wherein $R^{2i}$, $R^{4i}$, and $R^{5i}$ are a hydrogen atom, and $R^{3i}$ is a trifluoromethylsulfanyl group, a trifluoromethylsulfinyl group, or a trifluoromethylsulfonyl group;

A compound of the formula (1I) wherein $R^{2i}$, $R^{4i}$, and $R^{5i}$ are a hydrogen atom, and $R^{3i}$ is a trifluoromethylsulfanyl group;

A compound of the formula (1I) wherein $R^{2i}$, $R^{4i}$, and $R^{5i}$ are a hydrogen atom, and $R^{3i}$ is a trifluoromethylsulfinyl group;

A compound of the formula (1I) wherein $R^{2i}$, $R^{4i}$, and $R^{5i}$ are a hydrogen atom, and $R^{3i}$ is a trifluoromethylsulfonyl group;

A compound of the formula (1I) wherein $R^{2i}$, $R^{4i}$, and $R^{5i}$ are a hydrogen atom, and $R^{3i}$ is a halogen atom;

A compound of the formula (1I) wherein $R^{2i}$, $R^{4i}$, and $R^{5i}$ are a hydrogen atom, and $R^{3i}$ is a fluorine atom, a chlorine atom, or a bromine atom;

A compound of the formula (1I) wherein $R^{2i}$, $R^{4i}$, and $R^{5i}$ are a hydrogen atom, and $R^{3i}$ is a fluorine atom;

A compound of the formula (I) wherein $R^{2i}$, $R^{4i}$, and $R^{5i}$ are a hydrogen atom, and $R^{3i}$ is a chlorine atom;

A compound of the formula (1I) wherein $R^{2i}$, $R^{4i}$, and $R^{5i}$ are a hydrogen atom, and $R^{3i}$ is a bromine atom;

A compound of the formula (1I) wherein $R^{2i}$, $R^{4i}$, and $R^{5i}$ are a hydrogen atom, and $R^{3i}$ is —$SF_5$;

A compound of the formula (1I) wherein $R^{2i}$, $R^{4i}$, and $R^{5i}$ are a hydrogen atom, and $R^{3i}$ is a methyl group, an ethyl group, a propyl group, an isopropyl group, a trifluoromethyl group, a pentafluoroethyl group, a heptafluoropropyl group, a heptafluoroisopropyl group, a trifluoromethylsulfanyl group, a trifluoromethylsulfinyl group, a trifluoromethylsulfonyl group, a fluorine atom, a chlorine atom, a bromine atom, or —$SF_5$;

A compound of the formula (1I) wherein r is 1;

A compound of the formula (1I) wherein r is 2;

A compound of the formula (1I) wherein $R^{1i}$ is a methyl group, $R^{2i}$, $R^{4i}$, and $R^{5i}$ are same or different and are independently a halogen atom or a hydrogen atom, and $R^{3i}$ a C1-C6 chain hydrocarbon group optionally having one or more halogen atoms, —$OR^{11i}$, —$S(O)_mR^{11i}$, a halogen atom, or a hydrogen atom;

A compound of the formula (1I) wherein $R^{1i}$ is a methyl group, $R^{2i}$, $R^{4i}$, and $R^{5i}$ are a hydrogen atom, and $R^{3i}$ is a C1-C3 alkyl group optionally having one or more fluorine atoms;

A compound of the formula (1I) wherein $R^{1i}$ is a methyl group, $R^{2i}$, $R^{4i}$, and $R^{5i}$ are a hydrogen atom, and $R^{3i}$ is a C1-C3 alkoxy group optionally having one or more fluorine atoms;

A compound of the formula (1I) wherein $R^{1i}$ is a methyl group, $R^{2i}$, $R^{4i}$, and $R^{5i}$ are a hydrogen atom, and $R^{3i}$ is a C1-C3 alkylsulfanyl group optionally having one or more fluorine atoms, a C1-C3 alkylsulfinyl group optionally having one or more fluorine atoms, or a C1-C3 alkylsulfonyl group optionally having one or more fluorine atoms;

A compound of the formula (1I) wherein $R^{1i}$ is a methyl group, $R^{2i}$, $R^{4i}$, and $R^{5i}$ are a hydrogen atom, and $R^{3i}$ is a halogen atom;

A compound of the formula (1I) wherein $R^{1i}$ is a methyl group, $R^{2i}$, $R^{4i}$, and $R^{5i}$ are a hydrogen atom, and $R^{3i}$ is a methyl group;

A compound of the formula (1I) wherein $R^{1i}$ is a methyl group, $R^{2i}$, $R^{4i}$, and $R^{5i}$ are a hydrogen atom, and $R^{3i}$ is an ethyl group;

A compound of the formula (1I) wherein $R^{1i}$ is a methyl group, $R^{2i}$, $R^{4i}$, and $R^{5i}$ are a hydrogen atom, and $R^{3i}$ is a trifluoromethyl group;

A compound of the formula (1I) wherein $R^{1i}$ is a methyl group, $R^{2i}$, $R^{4i}$, and $R^{5i}$ are a hydrogen atom, and $R^{3i}$ is a trifluoromethoxy group;

A compound of the formula (1I) wherein $R^{1i}$ is a methyl group, $R^{2i}$, $R^{4i}$, and $R^{5i}$ are a hydrogen atom, and $R^{3i}$ is a fluorine atom;

A compound of the formula (1I) wherein $R^{1i}$ is a methyl group, $R^{2i}$, $R^{4i}$, and $R^{5i}$ are a hydrogen atom, and $R^{3i}$ is a chlorine atom;

A compound of the formula (1I) wherein $R^{1i}$ is a methyl group, $R^{2i}$, $R^{4i}$, and $R^{5i}$ are a hydrogen atom, and $R^{3i}$ is a bromine atom;

A compound of the formula (1I) wherein $R^{1i}$ is a methyl group, $R^{2i}$, $R^{4i}$, and $R^{5i}$ are a hydrogen atom, and $R^{3i}$ is —$SF_5$;

A compound of the formula (1I) wherein $R^{1i}$ is an ethyl group, $R^{2i}$, $R^{4i}$, and $R^{5i}$ are same or different and are independently a halogen atom or a hydrogen atom, and $R^{3i}$ a C1-C6 chain hydrocarbon group optionally having one or more halogen atoms, —$OR^{11i}$, —$S(O)_mR^{11i}$, a halogen atom, or a hydrogen atom;

A compound of the formula (1I) wherein $R^{1i}$ is an ethyl group, $R^{2i}$, $R^{4i}$, and $R^{5i}$ are a hydrogen atom, and $R^{3i}$ is a C1-C3 alkyl group optionally having one or more fluorine atoms;

A compound of the formula (1I) wherein $R^{1i}$ is an ethyl group, $R^{2i}$, $R^{4i}$, and $R^{5i}$ are a hydrogen atom, and $R^{3i}$ is a C1-C3 alkoxy group optionally having one or more fluorine atoms;

A compound of the formula (1I) wherein $R^{1i}$ is an ethyl group, $R^{2i}$, $R^{4i}$, and $R^{5i}$ are a hydrogen atom, and $R^{3i}$ is a C1-C3 alkylsulfanyl group optionally having one or more fluorine atoms, a C1-C3 alkylsulfinyl group optionally having one or more fluorine atoms, or a C1-C3 alkylsulfonyl group optionally having one or more fluorine atoms;

A compound of the formula (1I) wherein $R^{1i}$ is an ethyl group, $R^{2i}$, $R^{4i}$, and $R^{5i}$ are a hydrogen atom, and $R^{3i}$ is a halogen atom;

A compound of the formula (1I) wherein $R^{1i}$ is an ethyl group, $R^{2i}$, $R^{4i}$, and $R^{5i}$ are a hydrogen atom, and $R^{3i}$ is a methyl group;

A compound of the formula (1I) wherein $R^{1i}$ is an ethyl group, $R^{2i}$, $R^{4i}$, and $R^{5i}$ are a hydrogen atom, and $R^{3i}$ is an ethyl group;

A compound of the formula (1I) wherein $R^{1i}$ is an ethyl group, $R^{2i}$, $R^{4i}$, and $R^{5i}$ are a hydrogen atom, and $R^{3i}$ is a trifluoromethyl group;

A compound of the formula (1I) wherein $R^{1i}$ is an ethyl group, $R^{2i}$, $R^{4i}$, and $R^{5i}$ are a hydrogen atom, and $R^{3i}$ is a trifluoromethoxy group;

A compound of the formula (1I) wherein $R^{1i}$ is an ethyl group, $R^{2i}$, $R^{4i}$, and $R^{5i}$ are a hydrogen atom, and $R^{3i}$ is a fluorine atom;

A compound of the formula (1I) wherein $R^{1i}$ is an ethyl group, $R^{2i}$, $R^{4i}$, and $R^{5i}$ are a hydrogen atom, and $R^{3i}$ is a chlorine atom;

A compound of the formula (1I) wherein $R^{1i}$ is an ethyl group, $R^{2i}$, $R^{4i}$, and $R^{5i}$ are a hydrogen atom, and $R^{3i}$ is a bromine atom;

A compound of the formula (1I) wherein $R^{1i}$ is an ethyl group, $R^{2i}$, $R^{4i}$, and $R^{5i}$ are a hydrogen atom, and $R^{3i}$ is —$SF_5$;

A compound of the formula (1I) wherein $R^{1i}$ is a propyl group, $R^{2i}$, $R^{4i}$, and $R^{5i}$ are same or different and are independently a halogen atom or a hydrogen atom, and $R^{3i}$ a C1-C6 chain hydrocarbon group optionally having one or more halogen atoms, —$OR^{11i}$, —$S(O)_mR^{11i}$, a halogen atom, or a hydrogen atom;

A compound of the formula (1I) wherein $R^{1i}$ is a propyl group, $R^{2i}$, $R^{4i}$, and $R^{5i}$ are a hydrogen atom, and $R^{3i}$ is a C1-C3 alkyl group optionally having one or more fluorine atoms;

A compound of the formula (1I) wherein $R^{1i}$ is a propyl group, $R^{2i}$, $R^{4i}$, and $R^{5i}$ are a hydrogen atom, and $R^{3i}$ is a C1-C3 alkoxy group optionally having one or more fluorine atoms;

A compound of the formula (1I) wherein $R^{1i}$ is a propyl group, $R^{2i}$, $R^{4i}$, and $R^{5i}$ are a hydrogen atom, and $R^{3i}$ is a C1-C3 alkylsulfanyl group optionally having one or more fluorine atoms, a C1-C3 alkylsulfinyl group optionally having one or more fluorine atoms, or a C1-C3 alkylsulfonyl group optionally having one or more fluorine atoms;

A compound of the formula (1I) wherein $R^{1i}$ is a propyl group, $R^{2i}$, $R^{4i}$, and $R^{5i}$ are a hydrogen atom, and $R^{3i}$ is a halogen atom;

A compound of the formula (1I) wherein $R^{1i}$ is a propyl group, $R^{2i}$, $R^{4i}$, and $R^{5i}$ are a hydrogen atom, and $R^{3i}$ is a methyl group;

A compound of the formula (1I) wherein $R^{1i}$ is a propyl group, $R^{2i}$, $R^{4i}$, and $R^{5i}$ are a hydrogen atom, and $R^{3i}$ is an ethyl group;

A compound of the formula (1I) wherein $R^{1i}$ is a propyl group, $R^{2i}$, $R^{4i}$, and $R^{5i}$ are a hydrogen atom, and $R^{3i}$ is a trifluoromethyl group;

A compound of the formula (1I) wherein $R^{1i}$ is a propyl group, $R^{2i}$, $R^{4i}$, and $R^{5i}$ are a hydrogen atom, and $R^{3i}$ is a trifluoromethoxy group;

A compound of the formula (1I) wherein $R^{1i}$ is a propyl group, $R^{2i}$, $R^{4i}$, and $R^{5i}$ are a hydrogen atom, and $R^{3i}$ is a fluorine atom;

A compound of the formula (1I) wherein $R^{1i}$ is a propyl group, $R^{2i}$, $R^{4i}$, and $R^{5i}$ are a hydrogen atom, and $R^{3i}$ is a chlorine atom;

A compound of the formula (1I) wherein $R^{1i}$ is a propyl group, $R^{2i}$, $R^{4i}$, and $R^{5i}$ are a hydrogen atom, and $R^{3i}$ is a bromine atom;

A compound of the formula (1I) wherein $R^{1i}$ is a propyl group, $R^{2i}$, $R^{4i}$, and $R^{5i}$ are a hydrogen atom, and $R^{3i}$ is —$SF_5$.

Examples of the present compound are shown bellow.

A compound of the formula (A):

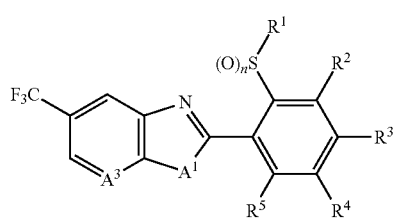

(A)

wherein $R^2$, $R^3$, $R^4$, and $R^5$ are a hydrogen atom, and $R^1$, $A^1$, $A^3$, and n are a combination shown in Tables 1-19:

TABLE 1

| $R^1$ | $A^1$ | $A^3$ | n |
|---|---|---|---|
| Me | —NMe— | =N— | 0 |
| Me | —NMe— | =N— | 1 |
| Me | —NMe— | =N— | 2 |
| Et | —NMe— | =N— | 0 |
| Et | —NMe— | =N— | 1 |
| Et | —NMe— | =N— | 2 |
| Pr | —NMe— | =N— | 0 |
| Pr | —NMe— | =N— | 1 |
| Pr | —NMe— | =N— | 2 |
| iPr | —NMe— | =N— | 0 |
| iPr | —NMe— | =N— | 1 |
| iPr | —NMe— | =N— | 2 |

TABLE 1-continued

| $R^1$ | $A^1$ | $A^3$ | n |
|---|---|---|---|
| tBu | —NMe— | =N— | 0 |
| tBu | —NMe— | =N— | 1 |
| tBu | —NMe— | =N— | 2 |
| $CF_3$ | —NMe— | =N— | 0 |
| $CF_3$ | —NMe— | =N— | 1 |
| $CF_3$ | —NMe— | =N— | 2 |
| $CH_2CF_3$ | —NMe— | =N— | 0 |
| $CH_2CF_3$ | —NMe— | =N— | 1 |
| $CH_2CF_3$ | —NMe— | =N— | 2 |
| CH=$CH_2$ | —NMe— | =N— | 0 |
| CH=$CH_2$ | —NMe— | =N— | 1 |
| CH=$CH_2$ | —NMe— | =N— | 2 |

TABLE 2

| $R^1$ | $A^1$ | $A^3$ | n |
|---|---|---|---|
| $CH_2CH$=$CH_2$ | —NMe— | =N— | 0 |
| $CH_2CH$=$CH_2$ | —NMe— | =N— | 1 |
| $CH_2CH$=$CH_2$ | —NMe— | =N— | 2 |
| C≡CH | —NMe— | =N— | 0 |
| C≡CH | —NMe— | =N— | 1 |
| C≡CH | —NMe— | =N— | 2 |
| $CH_2C$≡CH | —NMe— | =N— | 0 |
| $CH_2C$≡CH | —NMe— | =N— | 1 |
| $CH_2C$≡CH | —NMe— | =N— | 2 |
| CyPr | —NMe— | =N— | 0 |
| CyPr | —NMe— | =N— | 1 |
| CyPr | —NMe— | =N— | 2 |
| Me | —NMe— | =CH— | 0 |
| Me | —NMe— | =CH— | 1 |
| Me | —NMe— | =CH— | 2 |
| Et | —NMe— | =CH— | 0 |
| Et | —NMe— | =CH— | 1 |
| Et | —NMe— | =CH— | 2 |
| Pr | —NMe— | =CH— | 0 |
| Pr | —NMe— | =CH— | 1 |
| Pr | —NMe— | =CH— | 2 |
| iPr | —NMe— | =CH— | 0 |
| iPr | —NMe— | =CH— | 1 |
| iPr | —NMe— | =CH— | 2 |

TABLE 3

| $R^1$ | $A^1$ | $A^3$ | n |
|---|---|---|---|
| tBu | —NMe— | =CH— | 0 |
| tBu | —NMe— | =CH— | 1 |
| tBu | —NMe— | =CH— | 2 |
| $CF_3$ | —NMe— | =CH— | 0 |
| $CF_3$ | —NMe— | =CH— | 1 |
| $CF_3$ | —NMe— | =CH— | 2 |
| $CH_2CF_3$ | —NMe— | =CH— | 0 |
| $CH_2CF_3$ | —NMe— | =CH— | 1 |
| $CH_2CF_3$ | —NMe— | =CH— | 2 |
| CH=$CH_2$ | —NMe— | =CH— | 0 |
| CH=$CH_2$ | —NMe— | =CH— | 1 |
| CH=$CH_2$ | —NMe— | =CH— | 2 |
| $CH_2CH$=$CH_2$ | —NMe— | =CH— | 0 |
| $CH_2CH$=$CH_2$ | —NMe— | =CH— | 1 |
| $CH_2CH$=$CH_2$ | —NMe— | =CH— | 2 |
| C≡CH | —NMe— | =CH— | 0 |
| C≡CH | —NMe— | =CH— | 1 |
| C≡CH | —NMe— | =CH— | 2 |
| $CH_2C$≡CH | —NMe— | =CH— | 0 |
| $CH_2C$≡CH | —NMe— | =CH— | 1 |
| $CH_2C$≡CH | —NMe— | =CH— | 2 |
| CyPr | —NMe— | =CH— | 0 |
| CyPr | —NMe— | =CH— | 1 |
| CyPr | —NMe— | =CH— | 2 |

TABLE 4

| R¹ | A¹ | A³ | n |
|---|---|---|---|
| Me | —NMe— | =CBr— | 0 |
| Me | —NMe— | =CBr— | 1 |
| Me | —NMe— | =CBr— | 2 |
| Et | —NMe— | =CBr— | 0 |
| Et | —NMe— | =CBr— | 1 |
| Et | —NMe— | =CBr— | 2 |
| Pr | —NMe— | =CBr— | 0 |
| Pr | —NMe— | =CBr— | 1 |
| Pr | —NMe— | =CBr— | 2 |
| iPr | —NMe— | =CBr— | 0 |
| iPr | —NMe— | =CBr— | 1 |
| iPr | —NMe— | =CBr— | 2 |
| tBu | —NMe— | =CBr— | 0 |
| tBu | —NMe— | =CBr— | 1 |
| tBu | —NMe— | =CBr— | 2 |
| CF₃ | —NMe— | =CBr— | 0 |
| CF₃ | —NMe— | =CBr— | 1 |
| CF₃ | —NMe— | =CBr— | 2 |
| CH₂CF₃ | —NMe— | =CBr— | 0 |
| CH₂CF₃ | —NMe— | =CBr— | 1 |
| CH₂CF₃ | —NMe— | =CBr— | 2 |
| CH=CH₂ | —NMe— | =CBr— | 0 |
| CH=CH₂ | —NMe— | =CBr— | 1 |
| CH=CH₂ | —NMe— | =CBr— | 2 |

TABLE 5

| R¹ | A¹ | A³ | n |
|---|---|---|---|
| CH₂CH=CH₂ | —NMe— | =CBr— | 0 |
| CH₂CH=CH₂ | —NMe— | =CBr— | 1 |
| CH₂CH=CH₂ | —NMe— | =CBr— | 2 |
| C≡CH | —NMe— | =CBr— | 0 |
| C≡CH | —NMe— | =CBr— | 1 |
| C≡CH | —NMe— | =CBr— | 2 |
| CH₂C≡CH | —NMe— | =CBr— | 0 |
| CH₂C≡CH | —NMe— | =CBr— | 1 |
| CH₂C≡CH | —NMe— | =CBr— | 2 |
| CyPr | —NMe— | =CBr— | 0 |
| CyPr | —NMe— | =CBr— | 1 |
| CyPr | —NMe— | =CBr— | 2 |
| Me | —N(CH₂OMe)— | =N— | 0 |
| Me | —N(CH₂OMe)— | =N— | 1 |
| Me | —N(CH₂OMe)— | =N— | 2 |
| Et | —N(CH₂OMe)— | =N— | 0 |
| Et | —N(CH₂OMe)— | =N— | 1 |
| Et | —N(CH₂OMe)— | =N— | 2 |
| Pr | —N(CH₂OMe)— | =N— | 0 |
| Pr | —N(CH₂OMe)— | =N— | 1 |
| Pr | —N(CH₂OMe)— | =N— | 2 |
| iPr | —N(CH₂OMe)— | =N— | 0 |
| iPr | —N(CH₂OMe)— | =N— | 1 |
| iPr | —N(CH₂OMe)— | =N— | 2 |

TABLE 6

| R¹ | A¹ | A³ | n |
|---|---|---|---|
| tBu | —N(CH₂OMe)— | =N— | 0 |
| tBu | —N(CH₂OMe)— | =N— | 1 |
| tBu | —N(CH₂OMe)— | =N— | 2 |
| CF₃ | —N(CH₂OMe)— | =N— | 0 |
| CF₃ | —N(CH₂OMe)— | =N— | 1 |
| CF₃ | —N(CH₂OMe)— | =N— | 2 |
| CH₂CF₃ | —N(CH₂OMe)— | =N— | 0 |
| CH₂CF₃ | —N(CH₂OMe)— | =N— | 1 |
| CH₂CF₃ | —N(CH₂OMe)— | =N— | 2 |
| CH=CH₂ | —N(CH₂OMe)— | =N— | 0 |
| CH=CH₂ | —N(CH₂OMe)— | =N— | 1 |
| CH=CH₂ | —N(CH₂OMe)— | =N— | 2 |
| CH₂CH=CH₂ | —N(CH₂OMe)— | =N— | 0 |
| CH₂CH=CH₂ | —N(CH₂OMe)— | =N— | 1 |
| CH₂CH=CH₂ | —N(CH₂OMe)— | =N— | 2 |

TABLE 6-continued

| R¹ | A¹ | A³ | n |
|---|---|---|---|
| C≡CH | —N(CH₂OMe)— | =N— | 0 |
| C≡CH | —N(CH₂OMe)— | =N— | 1 |
| C≡CH | —N(CH₂OMe)— | =N— | 2 |
| CH₂C≡CH | —N(CH₂OMe)— | =N— | 0 |
| CH₂C≡CH | —N(CH₂OMe)— | =N— | 1 |
| CH₂C≡CH | —N(CH₂OMe)— | =N— | 2 |
| CyPr | —N(CH₂OMe)— | =N— | 0 |
| CyPr | —N(CH₂OMe)— | =N— | 1 |
| CyPr | —N(CH₂OMe)— | =N— | 2 |

TABLE 7

| R¹ | A¹ | A³ | n |
|---|---|---|---|
| Me | —N(CH₂OMe)— | =CH— | 0 |
| Me | —N(CH₂OMe)— | =CH— | 1 |
| Me | —N(CH₂OMe)— | =CH— | 2 |
| Et | —N(CH₂OMe)— | =CH— | 0 |
| Et | —N(CH₂OMe)— | =CH— | 1 |
| Et | —N(CH₂OMe)— | =CH— | 2 |
| Pr | —N(CH₂OMe)— | =CH— | 0 |
| Pr | —N(CH₂OMe)— | =CH— | 1 |
| Pr | —N(CH₂OMe)— | =CH— | 2 |
| iPr | —N(CH₂OMe)— | =CH— | 0 |
| iPr | —N(CH₂OMe)— | =CH— | 1 |
| iPr | —N(CH₂OMe)— | =CH— | 2 |
| tBu | —N(CH₂OMe)— | =CH— | 0 |
| tBu | —N(CH₂OMe)— | =CH— | 1 |
| tBu | —N(CH₂OMe)— | =CH— | 2 |
| CF₃ | —N(CH₂OMe)— | =CH— | 0 |
| CF₃ | —N(CH₂OMe)— | =CH— | 1 |
| CF₃ | —N(CH₂OMe)— | =CH— | 2 |
| CH₂CF₃ | —N(CH₂OMe)— | =CH— | 0 |
| CH₂CF₃ | —N(CH₂OMe)— | =CH— | 1 |
| CH₂CF₃ | —N(CH₂OMe)— | =CH— | 2 |
| CH=CH₂ | —N(CH₂OMe)— | =CH— | 0 |
| CH=CH₂ | —N(CH₂OMe)— | =CH— | 1 |
| CH=CH₂ | —N(CH₂OMe)— | =CH— | 2 |

TABLE 8

| R¹ | A¹ | A³ | n |
|---|---|---|---|
| CH₂CH=CH₂ | —N(CH₂OMe)— | =CH— | 0 |
| CH₂CH=CH₂ | —N(CH₂OMe)— | =CH— | 1 |
| CH₂CH=CH₂ | —N(CH₂OMe)— | =CH— | 2 |
| C≡CH | —N(CH₂OMe)— | =CH— | 0 |
| C≡CH | —N(CH₂OMe)— | =CH— | 1 |
| C≡CH | —N(CH₂OMe)— | =CH— | 2 |
| CH₂C≡CH | —N(CH₂OMe)— | =CH— | 0 |
| CH₂C≡CH | —N(CH₂OMe)— | =CH— | 1 |
| CH₂C≡CH | —N(CH₂OMe)— | =CH— | 2 |
| CyPr | —N(CH₂OMe)— | =CH— | 0 |
| CyPr | —N(CH₂OMe)— | =CH— | 1 |
| CyPr | —N(CH₂OMe)— | =CH— | 2 |
| Me | —N(CH₂OMe)— | =CBr— | 0 |
| Me | —N(CH₂OMe)— | =CBr— | 1 |
| Me | —N(CH₂OMe)— | =CBr— | 2 |
| Et | —N(CH₂OMe)— | =CBr— | 0 |
| Et | —N(CH₂OMe)— | =CBr— | 1 |
| Et | —N(CH₂OMe)— | =CBr— | 2 |
| Pr | —N(CH₂OMe)— | =CBr— | 0 |
| Pr | —N(CH₂OMe)— | =CBr— | 1 |
| Pr | —N(CH₂OMe)— | =CBr— | 2 |
| iPr | —N(CH₂OMe)— | =CBr— | 0 |
| iPr | —N(CH₂OMe)— | =CBr— | 1 |
| iPr | —N(CH₂OMe)— | =CBr— | 2 |

TABLE 9

| R¹ | A¹ | A³ | n |
|---|---|---|---|
| tBu | —N(CH$_2$OMe)— | =CBr— | 0 |
| tBu | —N(CH$_2$OMe)— | =CBr— | 1 |
| tBu | —N(CH$_2$OMe)— | =CBr— | 2 |
| CF$_3$ | —N(CH$_2$OMe)— | =CBr— | 0 |
| CF$_3$ | —N(CH$_2$OMe)— | =CBr— | 1 |
| CF$_3$ | —N(CH$_2$OMe)— | =CBr— | 2 |
| CH$_2$CF$_3$ | —N(CH$_2$OMe)— | =CBr— | 0 |
| CH$_2$CF$_3$ | —N(CH$_2$OMe)— | =CBr— | 1 |
| CH$_2$CF$_3$ | —N(CH$_2$OMe)— | =CBr— | 2 |
| CH=CH$_2$ | —N(CH$_2$OMe)— | =CBr— | 0 |
| CH=CH$_2$ | —N(CH$_2$OMe)— | =CBr— | 1 |
| CH=CH$_2$ | —N(CH$_2$OMe)— | =CBr— | 2 |
| CH$_2$CH=CH$_2$ | —N(CH$_2$OMe)— | =CBr— | 0 |
| CH$_2$CH=CH$_2$ | —N(CH$_2$OMe)— | =CBr— | 1 |
| CH$_2$CH=CH$_2$ | —N(CH$_2$OMe)— | =CBr— | 2 |
| C≡CH | —N(CH$_2$OMe)— | =CBr— | 0 |
| C≡CH | —N(CH$_2$OMe)— | =CBr— | 1 |
| C≡CH | —N(CH$_2$OMe)— | =CBr— | 2 |
| CH$_2$C≡CH | —N(CH$_2$OMe)— | =CBr— | 0 |
| CH$_2$C≡CH | —N(CH$_2$OMe)— | =CBr— | 1 |
| CH$_2$C≡CH | —N(CH$_2$OMe)— | =CBr— | 2 |
| CyPr | —N(CH$_2$OMe)— | =CBr— | 0 |
| CyPr | —N(CH$_2$OMe)— | =CBr— | 1 |
| CyPr | —N(CH$_2$OMe)— | =CBr— | 2 |

TABLE 10

| R¹ | A¹ | A³ | n |
|---|---|---|---|
| Me | O | =N— | 0 |
| Me | O | =N— | 1 |
| Me | O | =N— | 2 |
| Et | O | =N— | 0 |
| Et | O | =N— | 1 |
| Et | O | =N— | 2 |
| Pr | O | =N— | 0 |
| Pr | O | =N— | 1 |
| Pr | O | =N— | 2 |
| iPr | O | =N— | 0 |
| iPr | O | =N— | 1 |
| iPr | O | =N— | 2 |
| tBu | O | =N— | 0 |
| tBu | O | =N— | 1 |
| tBu | O | =N— | 2 |
| CF$_3$ | O | =N— | 0 |
| CF$_3$ | O | =N— | 1 |
| CF$_3$ | O | =N— | 2 |
| CH$_2$CF$_3$ | O | =N— | 0 |
| CH$_2$CF$_3$ | O | =N— | 1 |
| CH$_2$CF$_3$ | O | =N— | 2 |
| CH=CH$_2$ | O | =N— | 0 |
| CH=CH$_2$ | O | =N— | 1 |
| CH=CH$_2$ | O | =N— | 2 |

TABLE 11

| R¹ | A¹ | A³ | n |
|---|---|---|---|
| CH$_2$CH=CH$_2$ | O | =N— | 0 |
| CH$_2$CH=CH$_2$ | O | =N— | 1 |
| CH$_2$CH=CH$_2$ | O | =N— | 2 |
| C≡CH | O | =N— | 0 |
| C≡CH | O | =N— | 1 |
| C≡CH | O | =N— | 2 |
| CH$_2$C≡CH | O | =N— | 0 |
| CH$_2$C≡CH | O | =N— | 1 |
| CH$_2$C≡CH | O | =N— | 2 |
| CyPr | O | =N— | 0 |
| CyPr | O | =N— | 1 |
| CyPr | O | =N— | 2 |
| Me | O | =CH— | 0 |
| Me | O | =CH— | 1 |
| Me | O | =CH— | 2 |

TABLE 11-continued

| R¹ | A¹ | A³ | n |
|---|---|---|---|
| Et | O | =CH— | 0 |
| Et | O | =CH— | 1 |
| Et | O | =CH— | 2 |
| Pr | O | =CH— | 0 |
| Pr | O | =CH— | 1 |
| Pr | O | =CH— | 2 |
| iPr | O | =CH— | 0 |
| iPr | O | =CH— | 1 |
| iPr | O | =CH— | 2 |

TABLE 12

| R¹ | A¹ | A³ | n |
|---|---|---|---|
| tBu | O | =CH— | 0 |
| tBu | O | =CH— | 1 |
| tBu | O | =CH— | 2 |
| CF$_3$ | O | =CH— | 0 |
| CF$_3$ | O | =CH— | 1 |
| CF$_3$ | O | =CH— | 2 |
| CH$_2$CF$_3$ | O | =CH— | 0 |
| CH$_2$CF$_3$ | O | =CH— | 1 |
| CH$_2$CF$_3$ | O | =CH— | 2 |
| CH=CH$_2$ | O | =CH— | 0 |
| CH=CH$_2$ | O | =CH— | 1 |
| CH=CH$_2$ | O | =CH— | 2 |
| CH$_2$CH=CH$_2$ | O | =CH— | 0 |
| CH$_2$CH=CH$_2$ | O | =CH— | 1 |
| CH$_2$CH=CH$_2$ | O | =CH— | 2 |
| C≡CH | O | =CH— | 0 |
| C≡CH | O | =CH— | 1 |
| C≡CH | O | =CH— | 2 |
| CH$_2$C≡CH | O | =CH— | 0 |
| CH$_2$C≡CH | O | =CH— | 1 |
| CH$_2$C≡CH | O | =CH— | 2 |
| CyPr | O | =CH— | 0 |
| CyPr | O | =CH— | 1 |
| CyPr | O | =CH— | 2 |

TABLE 13

| R¹ | A¹ | A³ | n |
|---|---|---|---|
| Me | O | =CBr— | 0 |
| Me | O | =CBr— | 1 |
| Me | O | =CBr— | 2 |
| Et | O | =CBr— | 0 |
| Et | O | =CBr— | 1 |
| Et | O | =CBr— | 2 |
| Pr | O | =CBr— | 0 |
| Pr | O | =CBr— | 1 |
| Pr | O | =CBr— | 2 |
| iPr | O | =CBr— | 0 |
| iPr | O | =CBr— | 1 |
| iPr | O | =CBr— | 2 |
| tBu | O | =CBr— | 0 |
| tBu | O | =CBr— | 1 |
| tBu | O | =CBr— | 2 |
| CF$_3$ | O | =CBr— | 0 |
| CF$_3$ | O | =CBr— | 1 |
| CF$_3$ | O | =CBr— | 2 |
| CH$_2$CF$_3$ | O | =CBr— | 0 |
| CH$_2$CF$_3$ | O | =CBr— | 1 |
| CH$_2$CF$_3$ | O | =CBr— | 2 |
| CH=CH$_2$ | O | =CBr— | 0 |
| CH=CH$_2$ | O | =CBr— | 1 |
| CH=CH$_2$ | O | =CBr— | 2 |

TABLE 14

| R¹ | A¹ | A³ | n |
|---|---|---|---|
| CH₂CH=CH₂ | O | =CBr— | 0 |
| CH₂CH=CH₂ | O | =CBr— | 1 |
| CH₂CH=CH₂ | O | =CBr— | 2 |
| C≡CH | O | =CBr— | 0 |
| C≡CH | O | =CBr— | 1 |
| C≡CH | O | =CBr— | 2 |
| CH₂C≡CH | O | =CBr— | 0 |
| CH₂C≡CH | O | =CBr— | 1 |
| CH₂C≡CH | O | =CBr— | 2 |
| CyPr | O | =CBr— | 0 |
| CyPr | O | =CBr— | 1 |
| CyPr | O | =CBr— | 2 |

TABLE 15

| R¹ | A¹ | A³ | n |
|---|---|---|---|
| Me | S | =N— | 0 |
| Me | S | =N— | 1 |
| Me | S | =N— | 2 |
| Et | S | =N— | 0 |
| Et | S | =N— | 1 |
| Et | S | =N— | 2 |
| Pr | S | =N— | 0 |
| Pr | S | =N— | 1 |
| Pr | S | =N— | 2 |
| iPr | S | =N— | 0 |
| iPr | S | =N— | 1 |
| iPr | S | =N— | 2 |
| tBu | S | =N— | 0 |
| tBu | S | =N— | 1 |
| tBu | S | =N— | 2 |
| CF₃ | S | =N— | 0 |
| CF₃ | S | =N— | 1 |
| CF₃ | S | =N— | 2 |
| CH₂CF₃ | S | =N— | 0 |
| CH₂CF₃ | S | =N— | 1 |
| CH₂CF₃ | S | =N— | 2 |
| CH=CH₂ | S | =N— | 0 |
| CH=CH₂ | S | =N— | 1 |
| CH=CH₂ | S | =N— | 2 |

TABLE 16

| R¹ | A¹ | A³ | n |
|---|---|---|---|
| CH₂CH=CH₂ | S | =N— | 0 |
| CH₂CH=CH₂ | S | =N— | 1 |
| CH₂CH=CH₂ | S | =N— | 2 |
| C≡CH | S | =N— | 0 |
| C≡CH | S | =N— | 1 |
| C≡CH | S | =N— | 2 |
| CH₂C≡CH | S | =N— | 0 |
| CH₂C≡CH | S | =N— | 1 |
| CH₂C≡CH | S | =N— | 2 |
| CyPr | S | =N— | 0 |
| CyPr | S | =N— | 1 |
| CyPr | S | =N— | 2 |
| Me | S | =CH— | 0 |
| Me | S | =CH— | 1 |
| Me | S | =CH— | 2 |
| Et | S | =CH— | 0 |
| Et | S | =CH— | 1 |
| Et | S | =CH— | 2 |
| Pr | S | =CH— | 0 |
| Pr | S | =CH— | 1 |
| Pr | S | =CH— | 2 |
| iPr | S | =CH— | 0 |
| iPr | S | =CH— | 1 |
| iPr | S | =CH— | 2 |

TABLE 17

| R¹ | A¹ | A³ | n |
|---|---|---|---|
| tBu | S | =CH— | 0 |
| tBu | S | =CH— | 1 |
| tBu | S | =CH— | 2 |
| CF₃ | S | =CH— | 0 |
| CF₃ | S | =CH— | 1 |
| CF₃ | S | =CH— | 2 |
| CH₂CF₃ | S | =CH— | 0 |
| CH₂CF₃ | S | =CH— | 1 |
| CH₂CF₃ | S | =CH— | 2 |
| CH=CH₂ | S | =CH— | 0 |
| CH=CH₂ | S | =CH— | 1 |
| CH=CH₂ | S | =CH— | 2 |
| CH₂CH=CH₂ | S | =CH— | 0 |
| CH₂CH=CH₂ | S | =CH— | 1 |
| CH₂CH=CH₂ | S | =CH— | 2 |
| C≡CH | S | =CH— | 0 |
| C≡CH | S | =CH— | 1 |
| C≡CH | S | =CH— | 2 |
| CH₂C≡CH | S | =CH— | 0 |
| CH₂C≡CH | S | =CH— | 1 |
| CH₂C≡CH | S | =CH— | 2 |
| CyPr | S | =CH— | 0 |
| CyPr | S | =CH— | 1 |
| CyPr | S | =CH— | 2 |

TABLE 18

| R¹ | A¹ | A³ | n |
|---|---|---|---|
| Me | S | =CBr— | 0 |
| Me | S | =CBr— | 1 |
| Me | S | =CBr— | 2 |
| Et | S | =CBr— | 0 |
| Et | S | =CBr— | 1 |
| Et | S | =CBr— | 2 |
| Pr | S | =CBr— | 0 |
| Pr | S | =CBr— | 1 |
| Pr | S | =CBr— | 2 |
| iPr | S | =CBr— | 0 |
| iPr | S | =CBr— | 1 |
| iPr | S | =CBr— | 2 |
| tBu | S | =CBr— | 0 |
| tBu | S | =CBr— | 1 |
| tBu | S | =CBr— | 2 |
| CF₃ | S | =CBr— | 0 |
| CF₃ | S | =CBr— | 1 |
| CF₃ | S | =CBr— | 2 |
| CH₂CF₃ | S | =CBr— | 0 |
| CH₂CF₃ | S | =CBr— | 1 |
| CH₂CF₃ | S | =CBr— | 2 |
| CH=CH₂ | S | =CBr— | 0 |
| CH=CH₂ | S | =CBr— | 1 |
| CH=CH₂ | S | =CBr— | 2 |

TABLE 19

| R¹ | A¹ | A³ | n |
|---|---|---|---|
| CH₂CH=CH₂ | S | =CBr— | 0 |
| CH₂CH=CH₂ | S | =CBr— | 1 |
| CH₂CH=CH₂ | S | =CBr— | 2 |
| C≡CH | S | =CBr— | 0 |
| C≡CH | S | =CBr— | 1 |
| C≡CH | S | =CBr— | 2 |
| CH₂C≡CH | S | =CBr— | 0 |
| CH₂C≡CH | S | =CBr— | 1 |
| CH₂C≡CH | S | =CBr— | 2 |
| CyPr | S | =CBr— | 0 |
| CyPr | S | =CBr— | 1 |
| CyPr | S | =CBr— | 2 |

In the above Tables 1 to 19, Me represents a methyl group, Et represents an ethyl group, Pr represents a propyl group, iPr represents an isopropyl group, tBu represents a tert-butyl group, and CyPr represents a cyclopropyl group.

A compound of the formula (A) wherein $R^2$ is a fluorine atom, $R^3$, $R^4$, and $R^5$ are a hydrogen atom, and $R^1$, $A^1$, $A^3$, and n are a combination shown in Tables 1-19.

A compound of the formula (A) wherein $R^2$, $R^4$, and $R^5$ are a hydrogen atom, $R^3$ is a fluorine atom, and $R^1$, $A^1$, $A^3$, and n are a combination shown in Tables 1-19.

A compound of the formula (A) wherein $R^2$, $R^3$, and $R^5$ are a hydrogen atom, $R^4$ is a fluorine atom, and $R^1$, $A^1$, $A^3$, and n are a combination shown in Tables 1-19.

A compound of the formula (A) wherein $R^2$, $R^3$, and $R^4$ are a hydrogen atom, $R^5$ is a fluorine atom, and $R^1$, $A^1$, $A^3$, and n are a combination shown in Tables 1-19.

A compound of the formula (A) wherein $R^2$ is a chlorine atom, $R^3$, $R^4$, and $R^5$ are a hydrogen atom, and $R^1$, $A^1$, $A^3$, and n are a combination shown in Tables 1-19.

A compound of the formula (A) wherein $R^2$, $R^4$, and $R^5$ are a hydrogen atom, $R^3$ is a chlorine atom, and $R^1$, $A^1$, $A^3$, and n are a combination shown in Tables 1-19.

A compound of the formula (A) wherein $R^2$, $R^3$, and $R^5$ are a hydrogen atom, $R^4$ is a chlorine atom, and $R^1$, $A^1$, $A^3$, and n are a combination shown in Tables 1-19.

A compound of the formula (A) wherein $R^2$, $R^3$, and $R^4$ are a hydrogen atom, $R^5$ is a chlorine atom, and $R^1$, $A^1$, $A^3$, and n are a combination shown in Tables 1-19.

A compound of the formula (A) wherein $R^2$ is a methyl group, $R^3$, $R^4$, and $R^5$ are a hydrogen atom, and $R^1$, $A^1$, $A^3$, and n are a combination shown in Tables 1-19.

A compound of the formula (A) wherein $R^2$, $R^4$, and $R^5$ are a hydrogen atom, $R^3$ is a methyl group, and $R^1$, $A^1$, $A^3$, and n are a combination shown in Tables 1-19.

A compound of the formula (A) wherein $R^2$, $R^3$, and $R^5$ are a hydrogen atom, $R^4$ is a methyl group, and $R^1$, $A^1$, $A^3$, and n are a combination shown in Tables 1-19.

A compound of the formula (A) wherein $R^2$, $R^3$, and $R^4$ are a hydrogen atom, $R^5$ is a methyl group, and $R^1$, $A^1$, $A^3$, and n are a combination shown in Tables 1-19.

A compound of the formula (A) wherein $R^2$ is a trifluoromethyl group, $R^3$, $R^4$, and $R^5$ are a hydrogen atom, and $R^1$, $A^1$, $A^3$, and n are a combination shown in Tables 1-19.

A compound of the formula (A) wherein $R^2$, $R^4$, and $R^5$ are a hydrogen atom, $R^3$ is a trifluoromethyl group, and $R^1$, $A^1$, $A^3$, and n are a combination shown in Tables 1-19.

A compound of the formula (A) wherein $R^2$, $R^3$, and $R^5$ are a hydrogen atom, $R^4$ is a trifluoromethyl group, and $R^1$, $A^1$, $A^3$, and n are a combination shown in Tables 1-19.

A compound of the formula (A) wherein $R^2$, $R^3$, and $R^4$ are a hydrogen atom, $R^5$ is a trifluoromethyl group, and $R^1$, $A^1$, $A^3$, and n are a combination shown in Tables 1-19.

A compound of the formula (A) wherein $R^2$ is a bromine atom, $R^3$, $R^4$, and $R^5$ are a hydrogen atom, and $R^1$, $A^1$, $A^3$, and n are a combination shown in Tables 1-19.

A compound of the formula (A) wherein $R^2$, $R^4$, and $R^5$ are a hydrogen atom, $R^3$ is a bromine atom, and $R^1$, $A^1$, $A^3$, and n are a combination shown in Tables 1-19.

A compound of the formula (A) wherein $R^2$, $R^3$, and $R^5$ are a hydrogen atom, $R^4$ is a bromine atom, and $R^1$, $A^1$, $A^3$, and n are a combination shown in Tables 1-19.

A compound of the formula (A) wherein $R^2$, $R^3$ and $R^4$ are a hydrogen atom, $R^5$ is a bromine atom, and $R^1$, $A^1$, $A^3$, and n are a combination shown in Tables 1-19.

A compound of the formula (A) wherein $R^2$ is a pentafluoroethyl group, $R^3$, $R^4$, and $R^5$ are a hydrogen atom, and $R^1$, $A^1$, $A^3$, and n are a combination shown in Tables 1-19.

A compound of the formula (A) wherein $R^2$, $R^4$, and $R^5$ are a hydrogen atom, $R^3$ is a pentafluoroethyl group, and $R^1$, $A^1$, $A^3$, and n are a combination shown in Tables 1-19.

A compound of the formula (A) wherein $R^2$, $R^3$, and $R^5$ are a hydrogen atom, $R^4$ is a pentafluoroethyl group, and $R^1$, $A^1$, $A^3$, and n are a combination shown in Tables 1-19.

A compound of the formula (A) wherein $R^2$, $R^3$ and $R^4$ are a hydrogen atom, $R^5$ is a pentafluoroethyl group, and $R^1$, $A^1$, $A^3$, and n are a combination shown in Tables 1-19.

A compound of the formula (A) wherein $R^2$ is a trifluoromethoxy group, $R^3$, $R^4$, and $R^5$ are a hydrogen atom, and $R^1$, $A^1$, $A^3$, and n are a combination shown in Tables 1-19.

A compound of the formula (A) wherein $R^2$, $R^4$, and $R^5$ are a hydrogen atom, $R^3$ is a trifluoromethoxy group, and $R^1$, $A^1$, $A^3$, and n are a combination shown in Tables 1-19.

A compound of the formula (A) wherein $R^2$, $R^3$, and $R^5$ are a hydrogen atom, $R^4$ is a trifluoromethoxy group, and $R^1$, $A^1$, $A^3$, and n are a combination shown in Tables 1-19.

A compound of the formula (A) wherein $R^2$, $R^3$, and $R^4$ are a hydrogen atom, $R^5$ is a trifluoromethoxy group, and $R^1$, $A^1$, $A^3$, and n are a combination shown in Tables 1-19.

A compound of the formula (A) wherein $R^2$, $R^4$, and $R^5$ are a hydrogen atom, $R^3$ is a 2-pyridyl group, and $R^1$, $A^1$, $A^3$, and n are a combination shown in Tables 1-19.

A compound of the formula (A) wherein $R^2$, $R^4$, and $R^5$ are a hydrogen atom, $R^3$ is a 3-chloro-2-pyridyl group, and $R^1$, $A^1$, $A^3$, and n are a combination shown in Tables 1-19.

A compound of the formula (A) wherein $R^2$, $R^4$, and $R^5$ are a hydrogen atom, $R^3$ is a 2-pyrimidyl group, and $R^1$, $A^1$, $A^3$, and n are a combination shown in Tables 1-19.

A compound of the formula (A) wherein $R^2$, $R^4$, and $R^5$ are a hydrogen atom, $R^3$ is —$SF_5$, and $R^1$, $A^1$, $A^3$, and n are a combination shown in Tables 1-19.

A compound of the formula (A) wherein $A^2$ is =CH—, $R^2$, $R^3$, $R^4$, and $R^5$ are a hydrogen atom, $R^6$ is a hydrogen atom, $R^7$ is a trifluoromethyl group, and $R^1$, $A^1$, $A^3$, and n are a combination shown in Tables 1-19.

A compound of the formula (A) wherein $A^2$ is =CH—, $R^2$, $R^3$, $R^4$, and $R^5$ are a hydrogen atom, $R^6$ is a pentafluoroethyl group, $R^7$ is a hydrogen atom, and $R^1$, $A^1$, $A^3$, and n are a combination shown in Tables 1-19.

A compound of the formula (A) wherein $A^2$ is =CH—, $R^2$, $R^3$, $R^4$, and $R^5$ are a hydrogen atom, $R^6$ is a heptafluoroisopropyl group, $R^7$ is a hydrogen atom, and $R^1$, $A^1$, $A^3$, and n are a combination shown in Tables 1-19.

A compound of the formula (A) wherein $A^2$ is =CH—, $R^2$, $R^4$, and $R^5$ are a hydrogen atom, $R^3$ is a fluorine atom, $R^6$ is a pentafluoroethyl group, $R^7$ is a hydrogen atom, and $R^1$, $A^1$, $A^3$, and n are a combination shown in Tables 1-19.

A compound of the formula (A) wherein $A^2$ is =CH—, $R^2$, $R^4$, and $R^5$ are a hydrogen atom, $R^3$ is a chlorine atom, $R^6$ is a pentafluoroethyl group, $R^7$ is a hydrogen atom, and $R^1$, $A^1$, $A^3$, and n are a combination shown in Tables 1-19.

A compound of the formula (A) wherein $A^2$ is =CH—, $R^2$, $R^4$, and $R^5$ are a hydrogen atom, $R^3$ is a bromine atom, $R^6$ is a pentafluoroethyl group, $R^7$ is a hydrogen atom, and $R^1$, $A^1$, $A^3$, and n are a combination shown in Tables 1-19.

A compound of the formula (A) wherein $A^2$ is =CH—, $R^2$, $R^4$, and $R^5$ are a hydrogen atom, $R^3$ is a methyl group, $R^6$ is a pentafluoroethyl group, $R^7$ is a hydrogen atom, and $R^1$, $A^1$, $A^3$, and n are a combination shown in Tables 1-19.

A compound of the formula (A) wherein $A^2$ is =CH—, $R^2$, $R^4$, and $R^5$ are a hydrogen atom, $R^3$ is a trifluoromethyl group, $R^6$ is a pentafluoroethyl group, $R^7$ is a hydrogen atom, and $R^1$, $A^1$, $A^3$, and n are a combination shown in Tables 1-19.

A compound of the formula (A) wherein $A^2$ is =CH—, $R^4$, and $R^5$ are a hydrogen atom, $R^3$ is a pentafluoroethyl group, $R^6$ is a pentafluoroethyl group, $R^7$ is a hydrogen atom, and $R^1, A^1, A^3$, and n are a combination shown in Tables 1-19.

A compound of the formula (A) wherein $A^2$ is =CH—, $R^2$, $R^4$, and $R^5$ are a hydrogen atom, $R^3$ is a trifluoromethoxy group, $R^6$ is a pentafluoroethyl group, $R^7$ is a hydrogen atom, and $R^1, A^1, A^3$, and n are a combination shown in Tables 1-19.

A compound of the formula (A) wherein $A^2$ is =CH—, $R^2$, $R^3$, $R^4$, and $R^5$ are a hydrogen atom, $R^6$ is a difluoromethyl group, $R^7$ is a hydrogen atom, and $R^1, A^1, A^3$, and n are a combination shown in Tables 1-19.

A compound of the formula (A) wherein $A^2$ is =CH—, $R^2$, $R^3$, $R^4$, and $R^5$ are a hydrogen atom, $R^6$ is a trifluoromethoxy group, $R^7$ is a hydrogen atom, and $R^1, A^1, A^3$, and n are a combination shown in Tables 1-19.

A compound of the formula (A) wherein $A^2$ is =CH—, $R^2$, $R^4$, and $R^5$ are a hydrogen atom, $R^3$ is a fluorine atom, $R^6$ is a trifluoromethoxy group, $R^7$ is a hydrogen atom, and $R^1, A^1, A^3$, and n are a combination shown in Tables 1-19.

A compound of the formula (A) wherein $A^2$ is =CH—, $R^2$, $R^4$, and $R^5$ are a hydrogen atom, $R^3$ is a chlorine atom, $R^6$ is a trifluoromethoxy group, $R^7$ is a hydrogen atom, and $R^1, A^1, A^3$, and n are a combination shown in Tables 1-19.

A compound of the formula (A) wherein $A^2$ is =CH—, $R^2$, $R^4$, and $R^5$ are a hydrogen atom, $R^3$ is a bromine atom, $R^6$ is a trifluoromethoxy group, $R^7$ is a hydrogen atom, and $R^1, A^1, A^3$, and n are a combination shown in Tables 1-19.

A compound of the formula (A) wherein $A^2$ is =CH—, $R^2$, $R^4$, and $R^5$ are a hydrogen atom, $R^3$ is a methyl group, $R^6$ is a trifluoromethoxy group, $R^7$ is a hydrogen atom, and $R^1, A^1, A^3$, and n are a combination shown in Tables 1-19.

A compound of the formula (A) wherein $A^2$ is =CH—, $R^2$, $R^4$, and $R^5$ are a hydrogen atom, $R^3$ is a trifluoromethyl group, $R^6$ is a trifluoromethoxy group, $R^7$ is a hydrogen atom, and $R^1, A^1, A^3$, and n are a combination shown in Tables 1-19.

A compound of the formula (A) wherein $A^2$ is =CH—, $R^2$, $R^4$, and $R^5$ are a hydrogen atom, $R^3$ is a pentafluoroethyl group, $R^6$ is a trifluoromethoxy group, $R^7$ is a hydrogen atom, and $R^1, A^1, A^3$, and n are a combination shown in Tables 1-19.

A compound of the formula (A) wherein $A^2$ is =CH—, $R^2$, $R^4$, and $R^5$ are a hydrogen atom, $R^3$ is a trifluoromethoxy group, $R^6$ is a trifluoromethoxy group, $R^7$ is a hydrogen atom, and $R^1, A^1, A^3$, and n are a combination shown in Tables 1-19.

A compound of the formula (A) wherein $A^2$ is =CH—, $R^2$, $R^3$, $R^4$, and $R^5$ are a hydrogen atom, $R^6$ is a trifluoromethylsulfanyl group, $R^7$ is a hydrogen atom, and $R^1, A^1, A^3$, and n are a combination shown in Tables 1-19.

A compound of the formula (A) wherein $A^2$ is =CH—, $R^2$, $R^4$, and $R^5$ are a hydrogen atom, $R^3$ is a fluorine atom, $R^6$ is a trifluoromethylsulfanyl group, $R^7$ is a hydrogen atom, and $R^1, A^1, A^3$, and n are a combination shown in Tables 1-19.

A compound of the formula (A) wherein $A^2$ is =CH—, $R^2$, $R^4$, and $R^5$ are a hydrogen atom, $R^3$ is a chlorine atom, $R^6$ is a trifluoromethylsulfanyl group, $R^7$ is a hydrogen atom, and $R^1, A^1, A^3$, and n are a combination shown in Tables 1-19.

A compound of the formula (A) wherein $A^2$ is =CH—, $R^2$, $R^4$, and $R^5$ are a hydrogen atom, $R^3$ is a bromine atom, $R^6$ is a trifluoromethylsulfanyl group, $R^7$ is a hydrogen atom, and $R^1, A^1, A^3$, and n are a combination shown in Tables 1-19.

A compound of the formula (A) wherein $A^2$ is =CH—, $R^2$, $R^4$, and $R^5$ are a hydrogen atom, $R^3$ is a methyl group, $R^6$ is a trifluoromethylsulfanyl group, $R^7$ is a hydrogen atom, and $R^1, A^1, A^3$, and n are a combination shown in Tables 1-19.

A compound of the formula (A) wherein $A^2$ is =CH—, $R^2$, $R^4$, and $R^5$ are a hydrogen atom, $R^3$ is a trifluoromethyl group, $R^6$ is a trifluoromethylsulfanyl group, $R^7$ is a hydrogen atom, and $R^1, A^1, A^3$, and n are a combination shown in Tables 1-19.

A compound of the formula (A) wherein $A^2$ is =CH—, $R^2$, $R^4$, and $R^5$ are a hydrogen atom, $R^3$ is a pentafluoroethyl group, $R^6$ is a trifluoromethylsulfanyl group, $R^7$ is a hydrogen atom, and $R^1, A^1, A^3$, and n are a combination shown in Tables 1-19.

A compound of the formula (A) wherein $A^2$ is =CH—, $R^2$, $R^4$, and $R^5$ are a hydrogen atom, $R^3$ is a trifluoromethoxy group, $R^6$ is a trifluoromethylsulfanyl group, $R^7$ is a hydrogen atom, and $R^1, A^1, A^3$, and n are a combination shown in Tables 1-19.

A compound of the formula (A) wherein $A^2$ is =CH—, $R^2$, $R^3$, $R^4$, and $R^5$ are a hydrogen atom, $R^6$ is a trifluoromethylsulfinyl group, $R^7$ is a hydrogen atom, and $R^1, A^1, A^3$, and n are a combination shown in Tables 1-19.

A compound of the formula (A) wherein $A^2$ is =CH—, $R^2$, $R^4$, and $R^5$ are a hydrogen atom, $R^3$ is a fluorine atom, $R^6$ is a trifluoromethylsulfinyl group, $R^7$ is a hydrogen atom, and $R^1, A^1, A^3$, and n are a combination shown in Tables 1-19.

A compound of the formula (A) wherein $A^2$ is =CH—, $R^2$, $R^4$, and $R^5$ are a hydrogen atom, $R^3$ is a chlorine atom, $R^6$ is a trifluoromethylsulfinyl group, $R^7$ is a hydrogen atom, and $R^1, A^1, A^3$, and n are a combination shown in Tables 1-19.

A compound of the formula (A) wherein $A^2$ is =CH—, $R^2$, $R^4$, and $R^5$ are a hydrogen atom, $R^3$ is a bromine atom, $R^6$ is a trifluoromethylsulfinyl group, $R^7$ is a hydrogen atom, and $R^1, A^1, A^3$, and n are a combination shown in Tables 1-19.

A compound of the formula (A) wherein $A^2$ is =CH—, $R^2$, $R^4$, and $R^5$ are a hydrogen atom, $R^3$ is a methyl group, $R^6$ is a trifluoromethylsulfinyl group, $R^7$ is a hydrogen atom, and $R^1, A^1, A^3$, and n are a combination shown in Tables 1-19.

A compound of the formula (A) wherein $A^2$ is =CH—, $R^2$, $R^4$, and $R^5$ are a hydrogen atom, $R^3$ is a trifluoromethyl group, $R^6$ is a trifluoromethylsulfinyl group, $R^7$ is a hydrogen atom, and $R^1, A^1, A^3$, and n are a combination shown in Tables 1-19.

A compound of the formula (A) wherein $A^2$ is =CH—, $R^2$, $R^4$, and $R^5$ are a hydrogen atom, $R^3$ is a pentafluoroethyl group, $R^6$ is a trifluoromethylsulfinyl group, $R^7$ is a hydrogen atom, and $R^1, A^1, A^3$, and n are a combination shown in Tables 1-19.

A compound of the formula (A) wherein $A^2$ is =CH—, $R^2$, $R^4$, and $R^5$ are a hydrogen atom, $R^3$ is a trifluoromethoxy group, $R^6$ is a trifluoromethylsulfinyl group, $R^7$ is a hydrogen atom, and $R^1, A^1, A^3$, and n are a combination shown in Tables 1-19.

A compound of the formula (A) wherein $A^2$ is =CH—, $R^2$, $R^3$, $R^4$, and $R^5$ are a hydrogen atom, $R^6$ is a trifluoromethylsulfonyl group, $R^7$ is a hydrogen atom, and $R^1, A^1, A^3$, and n are a combination shown in Tables 1-19.

A compound of the formula (A) wherein $A^2$ is =CH—, $R^2$, $R^4$, and $R^5$ are a hydrogen atom, $R^3$ is a fluorine atom, $R^6$ is a trifluoromethylsulfonyl group, $R^7$ is a hydrogen atom, and $R^1, A^1, A^3$, and n are a combination shown in Tables 1-19.

A compound of the formula (A) wherein $A^2$ is =CH—, $R^2$, $R^4$, and $R^5$ are a hydrogen atom, $R^3$ is a chlorine atom, $R^6$ is a trifluoromethylsulfonyl group, $R^7$ is a hydrogen atom, and $R^1, A^1, A^3$, and n are a combination shown in Tables 1-19.

A compound of the formula (A) wherein $A^2$ is =CH—, $R^2$, $R^4$, and $R^5$ are a hydrogen atom, $R^3$ is a bromine atom, $R^6$ is a trifluoromethylsulfonyl group, $R^7$ is a hydrogen atom, and $R^1, A^1, A^3$, and n are a combination shown in Tables 1-19.

A compound of the formula (A) wherein $A^2$ is =CH—, $R^2$, $R^4$, and $R^5$ are a hydrogen atom, $R^3$ is a methyl group, $R^6$ is a trifluoromethylsulfonyl group, $R^7$ is a hydrogen atom, and $R^1, A^1, A^3$, and n are a combination shown in Tables 1-19.

A compound of the formula (A) wherein $A^2$ is =CH—, $R^2$, $R^4$, and $R^5$ are a hydrogen atom, $R^3$ is a trifluoromethyl group, $R^6$ is a trifluoromethylsulfonyl group, $R^7$ is a hydrogen atom, and $R^1$, $A^1$, $A^3$, and n are a combination shown in Tables 1-19.

A compound of the formula (A) wherein $A^2$ is =CH—, $R^2$, $R^4$, and $R^5$ are a hydrogen atom, $R^3$ is a pentafluoroethyl group, $R^6$ is a trifluoromethylsulfonyl group, $R^7$ is a hydrogen atom, and $R^1$, $A^1$, $A^3$, and n are a combination shown in Tables 1-19.

A compound of the formula (A) wherein $A^2$ is =CH—, $R^2$, $R^4$, and $R^5$ are a hydrogen atom, $R^3$ is a trifluoromethoxy group, $R^6$ is a trifluoromethylsulfonyl group, $R^7$ is a hydrogen atom, and $R^1$, $A^1$, $A^3$, and n are a combination shown in Tables 1-19.

A compound of the formula (A) wherein $A^2$ is =CH—, $R^2$, $R^3$, $R^4$, and $R^5$ are a hydrogen atom, $R^6$ is a bromine atom, $R^7$ is a hydrogen atom, and $R^1$, $A^1$, $A^3$, and n are a combination shown in Tables 1-19.

A compound of the formula (A) wherein $A^2$ is =CH—, $R^2$, $R^4$, and $R^5$ are a hydrogen atom, $R^3$ is a fluorine atom, $R^6$ is a bromine atom, $R^7$ is a hydrogen atom, and $R^1$, $A^1$, $A^3$, and n are a combination shown in Tables 1-19.

A compound of the formula (A) wherein $A^2$ is =CH—, $R^2$, $R^4$, and $R^5$ are a hydrogen atom, $R^3$ is a chlorine atom, $R^6$ is a bromine atom, $R^7$ is a hydrogen atom, and $R^1$, $A^1$, $A^3$, and n are a combination shown in Tables 1-19.

A compound of the formula (A) wherein $A^2$ is =CH—, $R^2$, $R^4$, and $R^5$ are a hydrogen atom, $R^3$ is a bromine atom, $R^6$ is a bromine atom, $R^7$ is a hydrogen atom, and $R^1$, $A^1$, $A^3$, and n are a combination shown in Tables 1-19.

A compound of the formula (A) wherein $A^2$ is =CH—, $R^2$, $R^4$, and $R^5$ are a hydrogen atom, $R^3$ is a methyl group, $R^6$ is a bromine atom, $R^7$ is a hydrogen atom, and $R^1$, $A^1$, $A^3$, and n are a combination shown in Tables 1-19.

A compound of the formula (A) wherein $A^2$ is =CH—, $R^2$, $R^4$, and $R^5$ are a hydrogen atom, $R^3$ is a trifluoromethyl group, $R^6$ is a bromine atom, $R^7$ is a hydrogen atom, and $R^1$, $A^1$, $A^3$, and n are a combination shown in Tables 1-19.

A compound of the formula (A) wherein $A^2$ is =CH—, $R^2$, $R^4$, and $R^5$ are a hydrogen atom, $R^3$ is a pentafluoroethyl group, $R^6$ is a bromine atom, $R^7$ is a hydrogen atom, and $R^1$, $A^1$, $A^3$, and n are a combination shown in Tables 1-19.

A compound of the formula (A) wherein $A^2$ is =CH—, $R^2$, $R^4$, and $R^5$ are a hydrogen atom, $R^3$ is a trifluoromethoxy group, $R^6$ is a bromine atom, $R^7$ is a hydrogen atom, and $R^1$, $A^1$, $A^3$, and n are a combination shown in Tables 1-19.

A compound of the formula (A) wherein $A^2$ is =CH—, $R^2$, $R^3$, $R^4$, and $R^5$ are a hydrogen atom, $R^6$ is an iodine atom, $R^7$ is a hydrogen atom, and $R^1$, $A^1$, $A^3$, and n are a combination shown in Tables 1-19.

A compound of the formula (A) wherein $A^2$ is =CH—, $R^2$, $R^4$, and $R^5$ are a hydrogen atom, $R^3$ is a fluorine atom, $R^6$ is an iodine atom, $R^7$ is a hydrogen atom, and $R^1$, $A^1$, $A^3$, and n are a combination shown in Tables 1-19.

A compound of the formula (A) wherein $A^2$ is =CH—, $R^2$, $R^4$, and $R^5$ are a hydrogen atom, $R^3$ is a chlorine atom, $R^6$ is an iodine atom, $R^7$ is a hydrogen atom, and $R^1$, $A^1$, $A^3$, and n are a combination shown in Tables 1-19.

A compound of the formula (A) wherein $A^2$ is =CH—, $R^2$, $R^4$, and $R^5$ are a hydrogen atom, $R^3$ is a bromine atom, $R^6$ is an iodine atom, $R^7$ is a hydrogen atom, and $R^1$, $A^1$, $A^3$, and n are a combination shown in Tables 1-19.

A compound of the formula (A) wherein $A^2$ is =CH—, $R^2$, $R^4$, and $R^5$ are a hydrogen atom, $R^3$ is a methyl group, $R^6$ is an iodine atom, $R^7$ is a hydrogen atom, and $R^1$, $A^1$, $A^3$, and n are a combination shown in Tables 1-19.

A compound of the formula (A) wherein $A^2$ is =CH—, $R^2$, $R^4$, and $R^5$ are a hydrogen atom, $R^3$ is a trifluoromethyl group, $R^6$ is an iodine atom, $R^7$ is a hydrogen atom, and $R^1$, $A^1$, $A^3$, and n are a combination shown in Tables 1-19.

A compound of the formula (A) wherein $A^2$ is =CH—, $R^2$, $R^4$, and $R^5$ are a hydrogen atom, $R^3$ is a pentafluoroethyl group, $R^6$ is an iodine atom, $R^7$ is a hydrogen atom, and $R^1$, $A^1$, $A^3$, and n are a combination shown in Tables 1-19.

A compound of the formula (A) wherein $A^2$ is =CH—, $R^2$, $R^4$, and $R^5$ are a hydrogen atom, $R^3$ is a trifluoromethoxy group, $R^6$ is an iodine atom, $R^7$ is a hydrogen atom, and $R^1$, $A^1$, $A^3$, and n are a combination shown in Tables 1-19.

A compound of the formula (A) wherein $A^2$ is =CH—, $R^2$, $R^3$, $R^4$, and $R^5$ are a hydrogen atom, $R^6$ is —$SF_5$, $R^7$ is a hydrogen atom, and $R^1$, $A^1$, $A^3$, and n are a combination shown in Tables 1-19.

A compound of the formula (A) wherein $A^2$ is =CH—, $R^2$, $R^4$, and $R^5$ are a hydrogen atom, $R^3$ is a fluorine atom, $R^6$ is —$SF_5$, $R^7$ is a hydrogen atom, and $R^1$, $A^1$, $A^3$, and n are a combination shown in Tables 1-19.

A compound of the formula (A) wherein $A^2$ is =CH—, $R^2$, $R^4$, and $R^5$ are a hydrogen atom, $R^3$ is a chlorine atom, $R^6$ is —$SF_5$, $R^7$ is a hydrogen atom, and $R^1$, $A^1$, $A^3$, and n are a combination shown in Tables 1-19.

A compound of the formula (A) wherein $A^2$ is =CH—, $R^2$, $R^4$, and $R^5$ are a hydrogen atom, $R^3$ is a bromine atom, $R^6$ is —$SF_5$, $R^7$ is a hydrogen atom, and $R^1$, $A^1$, $A^3$, and n are a combination shown in Tables 1-19.

A compound of the formula (A) wherein $A^2$ is =CH—, $R^2$, $R^4$, and $R^5$ are a hydrogen atom, $R^3$ is a methyl group, $R^6$ is —$SF_5$, $R^7$ is a hydrogen atom, and $R^1$, $A^1$, $A^3$, and n are a combination shown in Tables 1-19.

A compound of the formula (A) wherein $A^2$ is =CH—, $R^2$, $R^4$, and $R^5$ are a hydrogen atom, $R^3$ is a trifluoromethyl group, $R^6$ is —$SF_5$, $R^7$ is a hydrogen atom, and $R^1$, $A^1$, $A^3$, and n are a combination shown in Tables 1-19.

A compound of the formula (A) wherein $A^2$ is =CH—, $R^2$, $R^4$, and $R^5$ are a hydrogen atom, $R^3$ is a pentafluoroethyl group, $R^6$ is —$SF_5$, $R^7$ is a hydrogen atom, and $R^1$, $A^1$, $A^3$, and n are a combination shown in Tables 1-19.

A compound of the formula (A) wherein $A^2$ is =CH—, $R^2$, $R^4$, and $R^5$ are a hydrogen atom, $R^3$ is a trifluoromethoxy group, $R^6$ is —$SF_5$, $R^7$ is a hydrogen atom, and $R^1$, $A^1$, $A^3$, and n are a combination shown in Tables 1-19.

Examples of pests against which the present compound has an activity include noxious arthropods such as noxious insects and noxious acarines, and nematodes. In particular, examples of the pests include the following.

Hemiptera: Delphacidae such as *Laodelphax striatellus*, *Nilaparvata lugens*, and *Sogatella furcifera*; Deltocephalidae such as *Nephotettix cincticeps*, *Nephotettix virescens*, and *Empoasca onukii*; Aphididae such as *Aphis gossypii*, *Myzus persicae*, *Brevicoryne brassicae*, *Aphis spiraecola*, *Macrosiphum euphorbiae*, *Aulacorthum solani*, *Rhopalosiphum padi*, *Toxoptera citricidus*, and *Hyalopterus pruni*; Pentatomidae such as *Nezara antennata*, *Riptortus clavetus*, *Leptocorisa chinensis*, *Eysarcoris parvus*, and *Halyomorpha mista*; Aleyrodidae such as *Trialeurodes vaporariorum*, *Bemisia tabaci*, *Dialeurodes citri*, and *Aleurocanthus spiniferus*; Coccidae such as *Aonidiella aurantii*, *Comstockaspis perniciosa*, *Unaspis citri*, *Ceroplastes rubens*, *Icerya purchasi*, *Planococcus kraunhiae*, *Pseudococcus longispinis*, and *Pseudaulacaspis pentagona*; Tingidae; Cimices such as *Cimex lectularius*; and Psyllidae.

Lepidoptera: Pyralidae such as *Chilo suppressalis*, *Tryporyza incertulas*, *Cnaphalocrocis medinalis*, *Notarcha derogata*, *Plodia interpunctella*, *Ostrinia furnacalis*, *Hellula undalis*, and *Pediasia teterrellus*; Noctuidae such as *Spodoptera litura*, *Spodoptera exigua*, *Pseudaletia separata*,

*Mamestra brassicae, Agrotis ipsilon, Plusia nigrisigna, Thoricoplusia* spp., *Heliothis* spp., and *Helicoverpa* spp.; Pieridae such as *Pieris rapae*; Tortricidae such as *Adoxophyes* spp., *Grapholita molesta, Leguminivora glycinivorella, Matsumuraeses azukivora, Adoxophyes orana fasciata, Adoxophyes honmai, Homona magnanima, Archips fuscocupreanus*, and *Cydia pomonella*; Gracillariidae such as *Caloptilia theivora* and *Phyllonorycter ringoneella*; Carposimidae such as *Carposina niponensis*; Lyonetiidae such as *Lyonetia* spp.; Lymantriidae such as *Lymantria* spp. and *Euproctis* spp; Yponomeutidae such as *Plutella xylostella*; Gelechiidae such as *Pectinophora gossypiella* and *Phthorimaea operculella*; Arctiidae such as *Hyphantria cunea*; and Tineidae such as *Tinea translucens* and *Tineola bisselliella*.

Thysanoptera: Thripidae such as *Frankliniella occidentalis, Thrips palmi, Scirtothrips dorsalis, Thrips tabaci*, and *Frankliniella intonsa*.

Diptera: Culices such as *Culex pipiens pallens, Culex tritaeniorhynchus*, and *Culex* quinquefasciatus; *Aedes* spp. such as *Aedes aegypti* and *Aedes albopictus; Anopheles* spp. such as *Anopheles sinensis*; Chironomidae; Muscidae such as *Musca domestica* and *Muscina stabulans*; Calliphoridae; Sarcophagidae; Fanniidae; Anthomyiidae such as *Delia platura* and *Delia antiqua*; Agromyzidae such as *Agromyza oryzae, Hydrellia griseola, Liriomyza sativae, Liriomyza trifolii*, and *Chromatomyia horticol*; Chloropidae such as *Chlorops oryzae*; Tephritidae such as *Dacus cucurbitae* and *Ceratitis capitata*; Drosophilidae; Phoridae such as *Megaselia spiracularis*; Psychodidae such as *Clogmia albipunctata*; Simuliidae; Tabanidae such as *Tabanus trigonus*; and stable flies.

Coleoptera: *Diabrotica* spp. such as *Diabrotica virgifera* virgifera and *Diabrotica undecimpunctata howardi*; Scarabaeidae such as *Anomala cuprea, Anomala rufocuprea*, and *Popillia japonica*; weevils such as *Sitophilus zeamais, Lissorhoptrus oryzophilus, Callosobruchuys chienensis, Echinocnemus squameus, Anthonomus grandis*, and *Sphenophorus venatus*; Tenebrionidae such as *Tenebrio molitor* and *Tribolium castaneum*; Chrysomelidae such as *Oulema oryzae, Aulacophora femoralis, Phyllotreta striolata*, and *Leptinotarsa decemlineata*; Dermestidae such as *Anthrenus verbasci* and *Dermestes maculates*; Anobiidae such as *Lasioderma serricorne*; Epilachna such as *Epilachna vigintioctopunctata*; Scolytidae such as *Lyctus brunneus* and *Tomicus piniperda*; Bostrychidae; Ptinidae; Cerambycidae such as *Anoplophora malasiaca; Agriotes* spp., and *Paederus fuscipes*.

Orthoptera: *Locusta migratoria, Gryllotalpa africana, Oxya yezoensis, Oxya japonica*, and Gryllidae.

Hymenoptera: Formicidae such as *Monomorium pharaosis, Formica fusca japonica, Ochetellus glaber, Pristomyrmex pungens, Pheidole noda, Acromyrmex* spp., and *Solenopsis* spp.; Vespidae; Betylidae; and Tenthredimidae such as *Athalia rosae* and *Athalia* japonica.

Nematoda: *Aphelenchoides besseyi, Nothotylenchus acris, Meloidogyne incognita, Meloidogyne hapla, Meloidogyne javanica, Heterodera glycines, Globodera rostochiensis, Pratylenchus coffeae*, and *Pratylenchus neglectus*.

Blattodea: *Blattella germanica, Periplaneta fuliginosa, Periplaneta americana, Periplaneta brunnea*, and *Blatta orientalis*.

Acarina: Tetranychidae such as *Tetranychus urticae, Tetranychus kanzawai, Panonychus citri, Panonychus ulmi*, and *Oligonychus* spp.; Eriophyidae such as *Aculops pelekassi, Phyllocoptruta citri, Aculops lycopersici, Calacarus carinatus, Acaphylla theavagrans, Eriophyes chibaensis*, and *Aculus schlechtendali*; Tarsonemidae such as *Polyphagotarsonemus latus*; Tenuipalpidae such as *Brevipalpus phoenicis*; Tuckerellidae; Ixodidae such as *Haemaphysalis longicornis, Haemaphysalis flava, Dermacentor taiwanicus, Ixodes ovatus, Ixodes persulcatus, Ixodes scapularis, Boophilus microplus*, and *Rhipicephalus sanguineus*; Acaridae such as *Tyrophagus putrescentiae* and *Tyrophagus similis*; Pyroglyphidae such as *Dermatophagoides farinae* and *Dermatophagoides ptrenyssnus*; Cheyletidae such as *Cheyletus eruditus, Cheyletus malaccensis*, and *Cheyletus moorei*; Dermanyssidae such as *Ornithonyssus bacoti, Ornithonyssus sylvairum*, and *Dermanyssus gallinae*; Trombiculidae such as *Leptotrombidium akamushi*; and Araneae such as *Chiracanthium japonicum* and *Latrodectus hasseltii*.

The pest controlling agent of the present invention contains the present compound and an inert carrier. Generally, the pest controlling agent of the present invention is a formulation such as an emulsion, an oil solution, a powder, a granule, a wettable powder, a flowable formulation, a microcapsule, an aerosol, a smoking agent, a poison bait, and a resin formulation which are obtained by mixing the present compound and an inert carrier such as a solid carrier, a liquid carrier and a gaseous carrier, and further adding a surfactant and other adjuvant for formulation, if necessary.

The pest controlling agent of the present invention usually contains the present compound in an amount of 0.01% to 95% by weight.

Examples of the solid carrier to be used for formulation include a fine power and a granule of clays (such as kaolin clay, diatomite, bentonite, Fubasami clay, and acid clay), synthetic hydrated silicon oxide, talc, ceramic, other inorganic minerals (such as sericite, quartz, sulfur, activated carbon, calcium carbonate, and hydrated silica), and chemical fertilizers (such as ammonium sulfate, ammonium phosphate, ammonium nitrate, urea, and ammonium chloride) as well as synthetic resins (such as polypropylene, polyacrylonitrile, polyester resins such as methyl polymethacrylate and polyethylene terephthalate, nylon resins such as nylon-6, nylon-11, and nylon-66, polyamide resins, polyvinyl chloride, polyvinylidene chloride, and vinyl chloride-propylene copolymer).

Examples of the liquid carrier include water, alcohols (such as methanol, ethanol, isopropyl alcohol, butanol, hexanol, benzyl alcohol, ethylene glycol, propylene glycol, and phenoxyethanol), ketones (such as acetone, methyl ethyl ketone, and cyclohexanone), aromatic hydrocarbons (such as toluene, xylene, ethylbenzene, dodecylbenzene, phenylxylylethane, and methylnaphthalene), aliphatic hydrocarbons (such as hexane, cyclohexane, kerosine, and light oil), esters (such as ethyl acetate, butyl acetate, isopropyl mylistate, ethyl oleate, diisopropyl adipate, diisobutyl adipate, and propyleneglycol monomethyl ether acetate), nitriles (such as acetonitrile and isobutyronitrile), ethers (such as diisopropyl ether, 1,4-dioxane, ethylene glycol dimethyl ether, diethylene glycol dimethyl ether, diethylene glycol monomethyl ether, propylene glycol monomethyl ether, dipropylene glycol monomethyl ether, and 3-methoxy-3-methyl-1-butanol), acid amides (such as N,N-dimethylformamide and N,N-dimethylacetamide), halogenated hydrocarbons (such as dichloromethane, trichloroethane, and tetrachlorocarbon), sulfoxides (such as dimethylsulfoxide), propylene carbonate, and vegetable oils (such as soy bean oil and cotton seed oil).

Examples of the gaseous carrier include fluorocarbons, butane gas, liquefied petroleum gas (LPG), dimethyl ether, and carbon dioxide.

Examples of the surfactant include nonionic surfactant such as polyoxyethylene alkyl ether, polyoxyethylene alkylaryl ether, and polyethyleneglycol fatty acid ester; and anionic surfactant such as alkylsulfonic acid salts, alkylbenzenesulfonic acid salts, and alkylsurfic acid salts.

Examples of the other adjuvant for formulation include binders, dispersants, colorants and stabilizers, and particularly for example, casein, gelatin, polysaccharides (such as starch, gum arabic, cellulose derivatives, and alginic acid), lignin derivatives, synthetic water-soluble polymers (such as polyvinyl alcohol, polyvinylpyrrolidone, and polyacrylic acid), PAP (acidic isopropyl phosphate), BHT (2,6-di-t-butyl-4-methylphenol), and BHA (a mixture of 2-t-butyl-4-methoxyphenol and 3-t-butyl-4-methoxyphenol).

The method for controlling pests of the present invention is applying an effective amount of the present compound to pests directly and/or habitats of pests (such as plant, soil, indoor, and in-body of animals). The present compound is usually used as the pest controlling agent of the present invention in the method for controlling pests of the present invention.

When the pest controlling agent of the present invention is used for a control of pests in agriculture, the application amount is usually 1 to 10,000 g as the present compound per 10,000 $m^2$. When the pest controlling agent of the present invention is a formulation of emulsions, wettable powders or flowables, they are usually applied after a dilution with water to have an active ingredient concentration of 0.01 to 10,000 ppm. When the pest controlling agent of the present invention is a formulation of granules or powders, they are usually applied as such.

The formulations and the dilute aqueous solutions of the formulation may be sprayed directly to the plant to be protected from pests, or may be applied to the soil to control the pests living in a soil.

Furthermore, the resin formulations of sheets or strip form can be applied by a method such as winding around plants, stretching in the vicinity of plants, and laying on the soil surface at the plant bottom.

When the pest controlling agent of the present invention is used for a control of pests in indoor, the application amount is usually 0.01 to 1,000 mg as the present compound per 1 $m^2$ in case of application for plane surface, and 0.01 to 500 mg as the present compound per 1 $m^3$ in case of application for space. When the pest controlling agent of the present invention is a formulation of emulsions, wettable powders or flowables, they are usually applied after a dilution with water to have an active ingredient concentration of 0.1 to 1,000 ppm. When the pest controlling agent of the present invention is a formulation of oil solutions, aerosols, smoking agents and poison baits, they are usually applied as such.

The pest controlling agent of the present invention could be used in farmlands on which "crops" shown below are cultivated.

Agricultural crops: corn, rice, wheat, barley, rye, oat, sorghum, cotton, soybean, peanut, sarrazin, sugar beet, rapeseed, sunflower, sugar cane, and tobacco;

Vegetables: Solanaceae vegetables (such as eggplant, tomato, green pepper, hot pepper, and potato), Cucurbitaceae vegetables (such as cucumber, pumpkin, zucchini, watermelon, and melon), Cruciferae vegetables (such as Japanese radish, turnip, horseradish, kohlrabi, Chinese cabbage, cabbage, brown mustard, broccoli, and cauliflower), Compositae vegetables (such as burdock, garland chrysanthemum, artichoke, and lettuce), Liliaceae vegetables (such as Welsh onion, onion, garlic, and asparagus), Umbelliferae vegetables (such as carrot, parsley, celery, and parsnip), Chenopodiaceae vegetables (such as spinach, and Swiss chard), Labiatae vegetables (such as Japanese basil, mint, and basil), strawberry, sweat potato, yam, and aroid;

Fruit trees: pomaceous fruits (such as apple, common pear, Japanese pear, Chinese quince, and quince), stone fleshy fruits (such as peach, plum, nectarine, Japanese plum, cherry, apricot, and prune), citrus plants (such as Satsuma mandarin, orange, lemon, lime, and grapefruit), nuts (such as chestnut, walnut, hazel nut, almond, pistachio, cashew nut, and *macadamia* nut), berry fruits (such as blueberry, cranberry, blackberry, and raspberry), grape, persimmon, olive, loquat, banana, coffee, date, coconut palm, and oil palm;

Trees other fruit trees: tea, mulberry, flowering trees (such as azalea, japonica, hydrangea, sasanqua, *Illicium anisatum*, cherry tree, tulip poplar, crepe myetle, and orange osmanthus), street trees (such as ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, yew, elm, and horse-chestnut), sweet viburnum, *Podocarpus macrophyllus*, Japanese cedar, Japanese cypress, croton, spindle tree, and Chainese howthorn.

Lawn: zoysia (such as Japanese lawn grass and mascarene grass), Bermuda grass (such as *Cynodon dactylon*), bent grass (such as creeping bent grass, *Agrostis stolonifera*, and *Agrostis tenuis*), bluegrass (such as Kentucky bluegrass and rough bluegrass), fescue (such as tall fescue, chewing fescue, and creeping fescue), ryegrass (such as darnel and perennial ryegrass), cocksfoot, and timothy grass;

Others: flowers (such as rose, carnation, chrysanthemum, *Eustoma grandiflorum* Shinners, gypsophila, gerbera, pot marigold, salvia, petunia, verbena, tulip, aster, gentian, lily, pansy, cyclamen, orchid, lily of the valley, lavender, stock, ornamental kale, primula, poinsttia, gladiolus, cattleya, daisy, cymbidium, and begonia), biofuel plants (such as Jatropha, curcas, safflower, Camelina alyssum, switchgrass, miscanthus, reed canary grass, Arundo donax, kenaf, cassava, willow, and algae), and foliage plant.

The "crops" include genetically modified crops.

The pest controlling agent of the present invention can be used as a mixture with or together with other insecticides, acaricides, nematocides, fungicides, plant growth regulators, herbicides, and synergists. Examples of active ingredients of the insecticide, the acaricide, the nematocide, the fungicide, the herbicide, and the synergist are shown below.

Active Ingredients of Insecticides:
(1) Organic Phosphorus Compounds:

Acephate, Aluminium phosphide, butathiofos, cadusafos, chlorethoxyfos, chlorfenvinphos, chlorpyrifos, chlorpyrifos-methyl, cyanophos: CYAP, DCIP (diazinon, dichlorodiisopropyl ether), dichlofenthion: ECP, dichlorvos: DDVP, dimethoate, dimethylvinphos, disulfoton, EPN, ethion, ethoprophos, etrimfos, fenthion: MPP, fenitrothion: MEP, fosthiazate, formothion, Hydrogen phosphide, isofenphos, isoxathion, malathion, mesulfenfos, methidathion: DMTP, monocrotophos, naled: BRP, oxydeprofos: ESP, parathion, phosalone, phosmet: PMP, pirimiphos-methyl, pyridafenthion, quinalphos, phenthoate: PAP, profenofos, propaphos, prothiofos, pyraclorfos, salithion, sulprofos, tebupirimfos, temephos, tetrachlorvinphos, terbufos, thiometon, trichlorphon: DEP, vamidothion, phorate, and cadusafos.

(2) Carbamate Compounds:

Alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb: MIPC, metolcarb, methomyl, methiocarb, NAC, oxamyl, pirimicarb, propoxur: PHC, XMC, thiodicarb, xylylcarb, and aldicarb.

(3) Pyrethroid Compounds:

Acrinathrin, allethrin, benfluthrin, beta-cyfluthrin, bifenthrin, cycloprothrin, cyfluthrin, cyhalothrin, cypermethrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, lambda-cyhalothrin, gamma-cyhalothrin, furamethrin, tau-fluvalinate, metofluthrin, profluthrin, dimefluthrin, 2,3,5,6-tetrafluoro-4-(methoxymethyl)benzyl (EZ)-(1RS,3RS;1RS, 3SR)-2,2-dimethyl-3-prop-1-enylcyclopropanecarboxylate, 2,3,5,6-tetrafluoro-4-methylbenzyl (EZ)-(1RS,3RS;1RS, 3SR)-2,2-dimethyl-3-prop-1-enylcyclopropanecarboxylate, and 2,3,5,6-tetrafluoro-4-(methoxymethyl)benzyl (1RS, 3RS;1RS,3SR)-2,2-dimethyl-3-(2-methyl-1-propenyl)cyclopropanecarboxylate.

(4) Nereistoxin Compounds:

Cartap, bensultap, thiocyclam, monosultap, and bisultap.

(5) Neonicotinoid Compounds:

Imidacloprid, nitenpyram, acetamiprid, thiamethoxam, thiacloprid, dinotefuran, and clothianidin.

(6) Benzoylurea Compounds:

Chlorfluazuron, bistrifluoron, diafenthiuron, diflubenzuron, fluazuron, flucycloxuron, flufenoxuron, hexaflumuron, lufenuron, novaluron, noviflumuron, teflubenzuron, triflumuron, and triazuron.

(7) Phenylpyrazole Compounds:

Acetoprole, ethiprole, fipronil, vaniliprole, pyriprole, and pyrafluprole.

(8) Bt Toxines:

Live spores derived from and crystal toxins produced from *Bacillus thuringiesis* and a mixture thereof;

(9) Hydrazine Compounds:

Chromafenozide, halofenozide, methoxyfenozide, and tebufenozide.

(10) Organic Chlorine Compounds:

Aaldrin, dieldrin, dienochlor, endosulfan, and methoxychlor.

(11) Other Insecticidal Active Ingredients:

Mmachine oil, nicotine-sulfate; avermectin-B, bromopropylate, buprofezin, chlorphenapyr, cyantraniliprole, cyromazine, D-D (1,3-Dichloropropene), emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, lepimectin, arsenic acid, benclothiaz, calcium cyanamide, calcium polysulfide, chlordane, DDT, DSP, flufenerim, flonicamid, flurimfen, formetanate, metam-ammonium, metam-sodium, Methyl bromide, Potassium oleate, protrifenbute, spiromesifen, sulfoxaflor, sulfur, metaflumizone, spirotetramat, pyrifluquinazone, spinetoram, chlorantraniliprole, tralopyril, cyantraniliprole, a compound of the following formula (K):

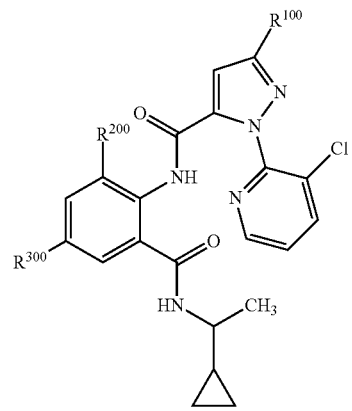

wherein:
$R^{100}$ is chlorine, bromine, or a trifluoromethyl group,
$R^{200}$ is chlorine, bromine, or a methyl group, and
$R^{300}$ is chlorine, bromine, or a cyano group,
and a compound of the following formula (L):

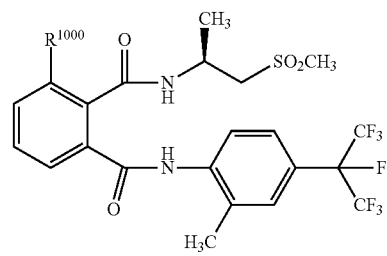

wherein:
$R^{1000}$ is chlorine, bromine, or iodine.

Active Ingredients of Acardides:

Acequinocyl, amitraz, benzoximate, bifenaate, bromopropylate, chinomethionat, chlorobenzilate, CPCBS (chlorfenson), clofentezine, cyflumetofen, Kelthane (dicofol), etoxazole, fenbutatin oxide, fenothiocarb, fenpyroximate, fluacrypyrim, fluproxyfen, hexythiazox, propargite: BPPS, polynactins, pyridaben, Pyrimidifen, tebufenpyrad, tetradifon, spirodiclofen, spiromesifen, spirotetramat, amidoflumet, and cyenopyrafen.

Active Ingredients of Nematocides:

DCIP, fosthiazate, levamisole hydrochloride (levamisole), methylsothiocyanate, morantel tartarate, and imicyafos.

Active Ingredients of Fungicides:

Azole fungicidal compounds such as propiconazole, prothioconazole, triadimenol, prochloraz, penconazole, tebuconazole, flusilazole, diniconazole, bromuconazole, epoxiconazole, difenoconazole, cyproconazole, metconazole, triflumizole, tetraconazole, myclobutanil, fenbuconazole, hexaconazole, fluquinconazole, triticonazole, bitertanol, imazalil, and flutriafol;

Cyclic amine fungicidal compounds such as fenpropimorph, tridemorph, and fenpropidin;

Benzimidazole fungicidal compounds such as carbendezim, benomyl, thiabendazole, and thiophanate-methyl;

Procymidone; cyprodinil; pyrimethanil; diethofencarb; thiuram; fluazinam; mancozeb; iprodione; vinclozolin; chlorothalonil; captan; mepanipyrim; fenpiclonil; fludioxonil;

dichlofluanid; folpet; kresoxim-methyl; azoxystrobin; trifloxystrobin; fluoxastrobin; picoxystrobin; pyraclostrobin; dimoxystrobin; pyribencarb; spiroxamine; quinoxyfen; fenhexamid; famoxadone; fenamidone; zoxamide; ethaboxam; amisulbrom; iprovalicarb; benthiavalicarb; cyazofamid; mandipropamid; boscalid; penthiopyrad; metrafenone; fluopiran; bixafen; cyflufenamid; proquinazid; isotianil, and tiadinil.

Active Ingredients of Herbicides:

(1) Phenoxyfatty Acid Herbicidal Compounds:

2,4-PA, MCP, MCPB, phenothiol, mecoprop, fluoroxypyr, triclopyr, clomeprop, and naproanilide.

(2) Benzoic Acid Herbicidal Compounds:

2,3,6-TBA, dicamba, clopyralid, picloram, aminopyralid, quinclorac, and quinmerac.

(3) Urea Herbicidal Compounds:

Diuron, linuron, chlortoluron, isoproturon, fluometuron, isouron, tebuthiuron, methabenzthiazuron, cumyluron, daimuron, and methyl-daimuron.

(4) Triazine Herbicidal Compounds:

Atrazine, ametoryn, cyanazine, simazine, propazine, simetryn, dimethametryn, prometryn, metribuzin, triaziflam, and indaziflam.

(5) Bipyridinium Herbicidal Compounds:

Paraquat and diquat.

(6) Hydroxybenzonitrile Herbicidal Compounds:

Bromoxynil and ioxynil.

(7) Dinitroaniline Herbicidal Compounds:

Pendimethalin, prodiamine, and trifluralin.

(8) Organic Phosphorus Herbicidal Compounds:

Amiprofos-methyl, butamifos, bensulide, piperophos, anilofos, glyphosate, glufosinate, glufosinate-P, and bialaphos.

(9) Carbamate Herbicidal Compounds:

Di-allate, tri-allate, EPTC, butylate, benthiocarb, esprocarb, molinate, dimepiperate, swep, chlorpropham, phenmedipham, phenisopham, pyributicarb, and asulam.

(10) Acid Amide Herbicidal Compounds:

Propanil, propyzamide, bromobutide, and etobenzanid.

(11) Chloroacetanilide Herbicidal Compounds:

Acetochlor, alachlor, butachlor, dimethenamid, propachlor, metazachlor, metolachlor, pretilachlor, thenylchlor, and pethoxamid.

(12) Diphenylether Herbicidal Compounds:

Acifluorfen-sodium, bifenox, oxyfluorfen, lactofen, fomesafen, chlomethoxynil, and aclonifen.

(13) Cyclic Imide Herbicidal Compounds:

Oxadiazon, cinidon-ethyl, carfentrazone-ethyl, surfentrazone, flumiclorac-pentyl, flumioxazin, pyraflufen-ethyl, oxadiargyl, pentoxazone, fluthiacet-methyl, butafenacil, benzfendizone, bencarbazone, and saflufenacil.

(14) Pyrazole Herbicidal Compounds:

Benzofenap, pyrazolate, pyrazoxyfen, topramezone, and pyrasulfotole.

(15) Triketone Herbicidal Compounds:

Isoxaflutole, benzobicyclon, sulcotrione, mesotrione, tembotrione, and tefuryltrione.

(16) Aryloxyphenoxypropionic Acid Herbicidal Compounds:

Clodinafop-propargyl, cyhalofop-butyl, diclofop-methyl, fenoxaprop-ethyl, fluazifop-butyl, haloxyfop-methyl, quizalofop-ethyl, and metamifop.

(17) Trioneoxime Herbicidal Compounds:

Alloxydim-sodium, sethoxydim, butroxydim, clethodim, cloproxydim, cycloxydim, tepraloxydim, tralkoxydim, and profoxydim.

(18) Sulfonylurea Herbicidal Compounds:

Chlorsulfuron, sulfometuron-methyl, metsulfuron-methyl, chlorimuron-ethyl, tribenuron-methyl, triasulfuron, bensulfuron-methyl, thifensulfuron-methyl, pyrazosulfuron-ethyl, primisulfuron-methyl, nicosulfuron, amidosulfuron, cinosulfuron, imazosulfuron, rimsulfuron, halosulfuron-methyl, prosulfuron, ethametsulfuron-methyl, triflusulfuron-methyl, flazasulfuron, cyclosulfamuron, flupyrsulfuron, sulfosulfuron, azimsulfuron, ethoxysulfuron, oxasulfuron, iodosulfuron-methyl-sodium, foramsulfuron, mesosulfuron-methyl, trifloxysulfuron, tritosulfuron, orthosulfamuron, flucetosulfuron, and propyrisulfuron.

(19) Imidazolinone Herbicidal Compounds:

Imazamethabenz-methyl, imazamethapyr, imazamox, imazapyr, imazaquin, and imazethapyr.

(20) Sulfonamide Herbicidal Compounds:

Flumetsulam, metosulam, diclosulam, florasulam, cloransulam-methyl, penoxsulam, and pyroxsulam.

(21) Pyrimidinyloxybenzoic Acid Herbicidal Compounds:

Pyrithiobac-sodium, bispyribac-sodium, pyriminobac-methyl, pyribenzoxim, pyriftalid, and pyrimisulfan.

(22) Other Herbicidal Compounds:

Bentazon, bromacil, terbacil, chlorthiamid, isoxaben, dinoseb, amitrole, cinmethylin, tridiphane, dalapon, diflufenzopyr-sodium, dithiopyr, thiazopyr, flucarbazone-sodium, propoxycarbazone-sodium, mefenacet, flufenacet, fentrazamide, cafenstrole, indanofan, oxaziclomefone, benfuresate, ACN, pyridate, chloridazon, norflurazon, flurtamone, diflufenican, picolinafen, beflubutamid, clomazone, amicarbazone, pinoxaden, pyraclonil, pyroxasulfone, thiencarbazone-methyl, aminocyclopyrachlor, ipfencarbazone, and methiozolin.

Active Ingredients of Synergists:

Piperonyl butoxide, sesamex, sulfoxide, N-(2-ethylhexyl)-8,9,10-trinorborn-5-ene-2,3-dicarboxylmide (MGK 264), N-declyimidazole, WARF-antiresistant, TBPT, TPP, IBP, PSCP, methyl iodide ($CH_3I$), t-phenylbutenone, diethylmaleate, DMC, FDMC, ETP, and ETN.

EXAMPLES

The present invention is described in more detail by Production Examples, Formulation Examples, and Test Examples, but the present invention is not limited to these Examples.

First, Production Examples of the present compound are shown below.

Production Example 1

A mixture of $N^2$-methyl-5-trifluoromethylpyridin-2,3-diamine (1.34 g), 2-methylsulfanylbenzaldehyde (1.28 g), sodium hydrogen sulfite (2.19 g), and DMF (14 ml) was stirred with heating at 80° C. for 1 hour, and then heated to 120° C., and stirred with heating for further 3 hours. Into the reaction mixture cooled to room temperature, saturated aqueous ammonium chloride solution was poured, and extracted with ethyl acetate 3 times. The combined organic layer was dried over magnesium sulfate, and concentrated under reduced pressure. The resulting residue was subjected to silica gel column chromatography to give 0.74 g of 3-methyl- 2-(2-methylsulfanylphenyl)-6-trifluoromethyl-3H-imidazo[4,5-b]pyridine (hereinafter referred to as Present Compound 1).

Present Compound 1

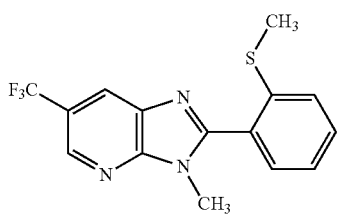 [SMILES: CSc1ccccc1-c1nc2cc(C(F)(F)F)cnc2n1C]

$^1$H-NMR (CDCl$_3$) δ: 8.72-8.71 (1H, m), 8.33-8.32 (1H, m), 7.58-7.53 (1H, m), 7.45-7.42 (2H, m), 7.36-7.31 (1H, m), 3.79 (3H, s), 2.44 (3H, s)

Production Example 2

To a mixture of 3-methyl-2-(2-methylsulfanylphenyl)-6-trifluoromethyl-3H-imidazo[4,5-b]pyridine (0.32 g), methanol (4 ml) and water (6 ml), sodium periodate (0.42 g) was added under ice-cooling. The mixture was heated to room temperature, and stirred for 1 hour, and then heated to 40° C., and stirred with heating for further 1 hour. Into the reaction mixture cooled to room temperature saturated aqueous sodium hydrogen carbonate solution and saturated aqueous sodium thiosulfate solution were poured, and extracted with chloroform 2 times. The combined organic layer was dried over magnesium sulfate, and concentrated under reduced pressure. The resulting residue was subjected to silica gel column chromatography to give 0.32 g of 2-(2-methylsulfinylphenyl)-3-methyl-6-trifluoromethyl-3H-imidazo[4,5-b]pyridine (hereinafter referred to as Present Compound 2).

Present Compound 2

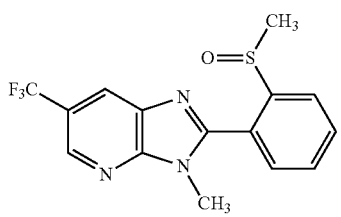

$^1$H-NMR (CDCl$_3$) δ: 8.76-8.74 (1H, m), 8.38-8.35 (1H, m), 8.33-8.32 (1H, m), 7.89-7.84 (1H, m), 7.73-7.69 (1H, m), 7.62-7.59 (1H, m), 3.92 (3H, s), 3.03 (3H, s)

Production Example 3

To a mixture of 3-methyl-2-(2-methylsulfanylphenyl)-6-trifluoromethyl-3H-imidazo[4,5-b]pyridine (0.30 g) and chloroform (9 ml), 69% of 3-chloroperbenzoic acid (0.70 g) was added under ice-cooling, and then heated to room temperature, and stirred for 2 hours. Then, into the mixture, saturated aqueous sodium hydrogen carbonate solution and saturated aqueous sodium thiosulfate solution were poured, and extracted with chloroform 2 times. The combined organic layer was dried over magnesium sulfate, and concentrated under reduced pressure. The resulting residue was subjected to silica gel column chromatography to give 0.32 g of 2-(2-methylsulfonylphenyl)-3-methyl-6-trifluoromethyl-3H-imidazo[4,5-b]pyridine (hereinafter referred to as Present Compound 3).

Present Compound 3

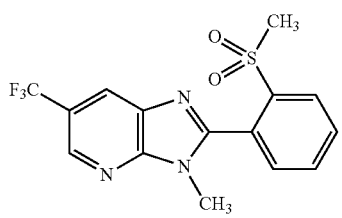 [SMILES: Cn1c(-c2ccccc2S(C)(=O)=O)nc2cc(C(F)(F)F)cnc21]

$^1$H-NMR (CDCl$_3$) δ: 8.76-8.74 (1H, m), 8.31-8.27 (2H, m), 7.88-7.80 (2H, m), 7.59-7.55 (1H, m), 3.72 (3H, s), 3.29 (3H, s)

Production Example 4-1

A mixture of N$^2$-methyl-5-trifluoromethylpyridin-2,3-diamine (1.0 g), 2-ethylsulfanylbenzaldehyde (0.96 g), sodium hydrogen sulfite (1.80 g), sodium hydrogen sulfite (1.80 g) and DMF (10 ml) was stirred with heating at 160° C. for 5 hours. The reaction mixture was ice-cooled, and water was added thereto. The precipitated crystal was collected by filtration, and washed with water, then hexane. The obtained crystal was dried under reduced pressure to give 1.09 g of 2-(2-ethylsulfanylphenyl)-3-methyl-6-trifluoromethyl-3H-imidazo[4,5-b]pyridine (hereinafter referred to as Present Compound 4).

Present Compound 4

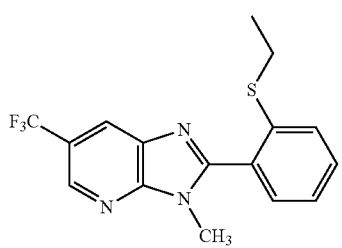

$^1$H-NMR (CDCl$_3$) δ: 8.72-8.70 (1H, m), 8.33-8.31 (1H, m), 7.56-7.49 (2H, m), 7.47-7.43 (1H, m), 7.39-7.34 (1H, m), 3.77 (3H, s), 2.87 (2H, q), 1.24 (3H, t)

Alternatively, Present Compound 4 can be synthesized by the following method.

Production Example 4-2

To a mixture of N-(2-methylamino-5-trifluoromethylpyridine-3-yl)-2-ethylsulfanyl-benzamide (6.0 g) and xylene (170 ml), p-toluenesulfonic acid monohydrate (5.47 g) was added, and stirred under reflux for 9 hours. After the reaction mixture was allowed to stand to cool to room temperature, the mixture was concentrated under reduced pressure, and then saturated aqueous sodium hydrogen carbonate solution was poured, and extracted with ethyl acetate. The organic layer was dried over magnesium sulfate, and concentrated under reduced pressure. The resulting residue was subjected to silica gel column chromatography to give 5.17 g of Present Compound 4.

Production Example 5

A mixture of 2-(2-ethylsulfanylphenyl)-3-methyl-6-trifluoromethyl-3H-imidazo[4,5-b]pyridine (0.25 g), sodium periodate (0.24 g), methanol (6 ml), water (2 ml), and THF (0.8 ml) was stirred at room temperature for 20 minutes, and then heated to 50° C., and stirred with heating for further 1.5 hours. To the ice-cooled reaction mixture, water was added. The precipitated crystal was collected by filtration. The obtained crystal was dissolved in ethyl acetate, and washed with saturated aqueous sodium thiosulfate solution, saturated aqueous sodium hydrogen carbonate solution, then saturated brine, sequentially. The organic layer was dried over magnesium sulfate, and concentrated under reduced pressure. The resulting residue was washed with hexane to give 0.20 g of 2-(2-ethylsulfinylphenyl)-3-methyl-6-trifluoromethyl-3H-imidazo[4,5-b]pyridine (hereinafter referred to as Present Compound 5).

Present Compound 5

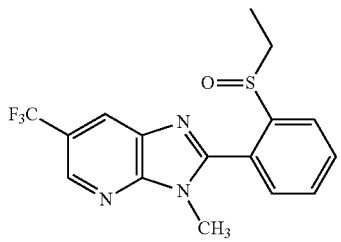 [SMILES: CCS(=O)c1ccccc1-c1nc2cc(C(F)(F)F)cnc2n1C]

$^1$H-NMR (CDCl$_3$) δ: 8.76-8.74 (1H, m), 8.32-8.30 (1H, m), 8.27-8.24 (1H, m), 7.86-7.81 (1H, m), 7.72-7.68 (1H, m), 7.62-7.59 (1H, m), 3.89 (3H, s), 3.42-3.31 (1H, m), 3.02-2.92 (1H, m), 1.31 (3H, t)

Production Example 6

To a mixture of 2-(2-ethylsulfanylphenyl)-3-methyl-6-trifluoromethyl-3H-imidazo[4,5-b]pyridine (0.25 g) and chloroform (3 ml), 3-chloroperbenzoic acid (purity: not less than 65%, 0.43 g) was added under ice-cooling, and then heated to room temperature, and stirred for 1 hour. To the reaction mixture, chloroform was added under ice-cooling, and then saturated aqueous sodium thiosulfate solution was poured, and extracted with ethyl acetate. The organic layer was washed with saturated aqueous sodium hydrogen carbonate solution, then saturated brine, dried over sodium sulfate, and concentrated under reduced pressure. The obtained crystal was washed with hexane, then methyl-tert-butyl ether to give 0.27 g of 2-(2-ethylsulfonylphenyl)-3-methyl-6-trifluoromethyl-3H-imidazo[4,5-b]pyridine (hereinafter referred to as Present Compound 6).

Present Compound 6

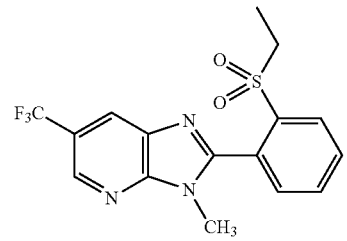 [SMILES: CCS(=O)(=O)c1ccccc1-c1nc2cc(C(F)(F)F)cnc2n1C]

$^1$H-NMR (CDCl$_3$) δ: 8.75-8.73 (1H, m), 8.29-8.27 (1H, m), 8.25-8.21 (1H, m), 7.87-7.79 (2H, m), 7.58-7.55 (1H, m), 3.72 (3H, s), 3.42 (2H, q), 1.26 (3H, t)

Production Example 7

A mixture of N$^2$-methyl-5-trifluoromethylpyridin-2,3-diamine (0.96 g), 2-propylsulfanylbenzoic acid (1.08 g), WSC (0.78 g), and pyridine (10 ml) was stirred with heating at 120° C. for 1.5 hours. To the reaction mixture, HOBt (0.74 g) was added, and stirred with heating for 1.5 hours. WSC (0.38 g) was added thereto, and stirred with heating for further 2 hours. Into the reaction mixture cooled to room temperature, water was poured, and extracted with ethyl acetate. The organic layer was dried over magnesium sulfate, and concentrated under reduced pressure. The resulting residue was subjected to silica gel column chromatography to give 0.23 g of 3-methyl-2-(2-propylsulfanylphenyl)-6-trifluoromethyl-3H-imidazo[4,5-b]pyridine (hereinafter referred to as Present Compound 7).

Present Compound 7

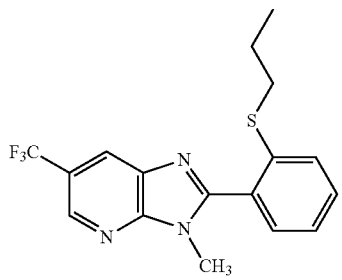 [SMILES: CCCSc1ccccc1-c1nc2cc(C(F)(F)F)cnc2n1C]

$^1$H-NMR (CDCl$_3$) δ: 8.72-8.71 (1H, m), 8.33-8.31 (1H, m), 7.53-7.51 (2H, m), 7.46-7.43 (1H, m), 7.38-7.33 (1H, m), 3.77 (3H, s), 2.81 (2H, t), 1.65-1.54 (2H, m), 0.93 (3H, t)

Production Example 8

A mixture of 3-methyl-2-(2-propylsulfanylphenyl)-6-trifluoromethyl-3H-imidazo[4,5-b]pyridine (0.22 g), sodium periodate (0.27 g), methanol (2 ml), and water (4 ml) was stirred with heating at 40° C. for 1.5 hours. To the reaction mixture cooled to room temperature, saturated aqueous sodium hydrogen carbonate solution and saturated aqueous sodium thiosulfate solution were added, and extracted with ethyl acetate. The organic layer was dried over magnesium sulfate, and concentrated under reduced pressure. The resulting residue was subjected to silica gel column chromatography to give 0.17 g of 3-methyl-2-(2-propylsulfinylphenyl)-6-trifluoromethyl-3H-imidazo[4,5-b]pyridine (hereinafter referred to as Present Compound 8).

Present Compound 8

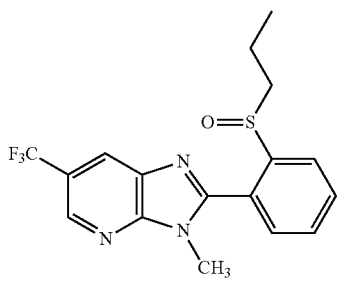 [SMILES: CCCS(=O)c1ccccc1-c1nc2cc(C(F)(F)F)cnc2n1C]

¹H-NMR (CDCl₃) δ: 8.77-8.74 (1H, m), 8.31-8.27 (2H, m), 7.86-7.80 (1H, m), 7.72-7.66 (1H, m), 7.63-7.59 (1H, m), 3.90 (3H, s), 3.44-3.36 (1H, m), 2.94-2.85 (1H, m), 2.02-1.87 (1H, m), 1.85-1.72 (1H, m), 1.06 (3H, t)

Production Example 9

To a mixture of 2-(2-propylsulfanylphenyl)-3-methyl-6-trifluoromethyl-3H-imidazo[4,5-b]pyridine (0.22 g) and chloroform (3 ml), 3-chloroperbenzoic acid (purity: not less than 65%, 0.33 g) was added under ice-cooling, and then heated to room temperature, and stirred for 1.5 hours. Into the reaction mixture, saturated aqueous sodium hydrogen carbonate solution and saturated aqueous sodium thiosulfate solution were poured, and extracted with ethyl acetate. The organic layer was dried over sodium sulfate, and concentrated under reduced pressure. The resulting residue was subjected to silica gel column chromatography to give 0.24 g of 2-(2-ethylsulfonylphenyl)-3-methyl-6-trifluoromethyl-3H-imidazo[4,5-b]pyridine (hereinafter referred to as Present Compound 9).

Present Compound 9

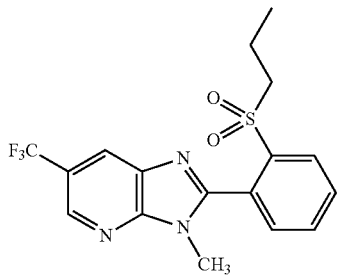 [SMILES: CCCS(=O)(=O)c1ccccc1-c1nc2cc(C(F)(F)F)cnc2n1C]

¹H-NMR (CDCl₃) δ: 8.75-8.73 (1H, m), 8.29-8.27 (1H, m), 8.24-8.21 (1H, m), 7.86-7.78 (2H, m), 7.58-7.54 (1H, m), 3.71 (3H, s), 3.41-3.33 (2H, m), 1.76-1.65 (2H, m), 1.00 (3H, t)

Production Example 10

A mixture of N²-methyl-5-trifluoromethylpyridin-2,3-diamine (0.96 g), 2-allylsulfanylbenzoic acid (1.46 g), WSC (1.06 g), and xylene (10 ml) was stirred with heating at 145° C. for 3 hours. After the mixture was evaporated to remove xylene, acetic acid (10 ml) was added thereto, and stirred with heating at 120° C. for further 1 hour. To the reaction mixture cooled to room temperature, 5 mol/l of aqueous sodium hydroxide solution was added to neutralize, and extracted with ethyl acetate. The organic layer was dried over magnesium sulfate, and concentrated under reduced pressure. The resulting residue was subjected to silica gel column chromatography to give 0.83 g of 2-(2-allylsulfanylphenyl)-3-methyl-6-trifluoromethyl-3H-imidazo[4,5-b]pyridine (hereinafter referred to as Present Compound 10).

Present Compound 10

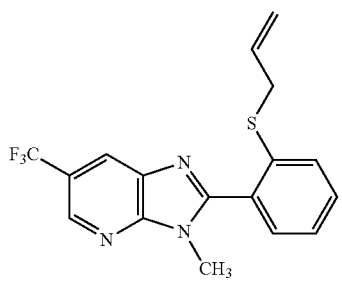 [SMILES: C=CCSc1ccccc1-c1nc2cc(C(F)(F)F)cnc2n1C]

¹H-NMR (CDCl₃) δ: 8.73-8.71 (1H, m), 8.34-8.32 (1H, m), 7.55-7.49 (2H, m), 7.48-7.45 (1H, m), 7.42-7.36 (1H, m), 5.81-5.70 (1H, m), 5.15-5.04 (2H, m), 3.77 (3H, s), 3.49-3.45 (2H, m)

Production Example 11

The procedure was performed according to the method described in Production Example 9 using 2-(2-allylsulfanylphenyl)-3-methyl-6-trifluoromethyl-3H-imidazo[4,5-b]pyridine instead of 3-methyl-2-(2-propylsulfanylphenyl)-6-trifluoromethyl-3H-imidazo[4,5-b]pyridine to give 2-(2-allylsulfonylphenyl)-3-methyl-6-trifluoromethyl-3H-imidazo[4,5-b]pyridine (hereinafter referred to as Present Compound 11).

Present Compound 11

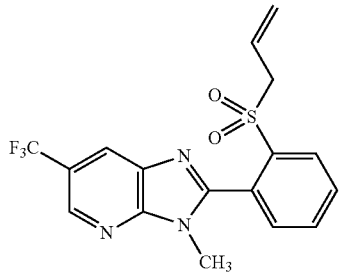 [SMILES: C=CCS(=O)(=O)c1ccccc1-c1nc2cc(C(F)(F)F)cnc2n1C]

¹H-NMR (CDCl₃) δ: 8.76-8.74 (1H, m), 8.31-8.29 (1H, m), 8.17-8.14 (1H, m), 7.86-7.76 (2H, m), 7.58-7.55 (1H, m), 5.81-5.69 (1H, m), 5.37-5.28 (2H, m), 4.21-4.14 (2H, m), 3.72 (3H, s)

Production Example 12

A mixture of N²-methyl-5-trifluoromethylpyridin-2,3-diamine (0.96 g), 2-isopropylsulfanylbenzoic acid (1.47 g), WSC (1.06 g), and pyridine (10 ml) was stirred with heating at 120° C. for 2 hours. Into the reaction mixture cooled to room temperature, water was poured, and extracted with ethyl acetate. The organic layer was dried over magnesium sulfate, and concentrated under reduced pressure.

A mixture of the resulting residue and acetic acid (10 ml) was stirred with heating at 118° C. for 1.5 hours, and then acetic anhydride (10 ml) was poured thereinto, and stirred with heating at 118° C. for 1.5 hours. Into the reaction mixture cooled to room temperature, water was poured, and extracted with tert-butyl methyl ether. The organic layer was dried over magnesium sulfate, and concentrated under reduced pressure. The resulting residue was subjected to silica gel column chromatography to give 1.05 g of 2-(2-isopropylsulfanylphenyl)-3-methyl-6-trifluoromethyl-3H-imidazo[4,5-b]pyridine (hereinafter referred to as Present Compound 12).

Present Compound 12

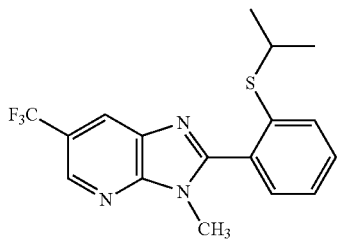 [SMILES: CC(C)Sc1ccccc1-c1nc2cc(C(F)(F)F)cnc2n1C]

$^1$H-NMR (CDCl$_3$) δ: 8.72-8.71 (1H, m), 8.32-8.30 (1H, m), 7.61-7.58 (1H, m), 7.56-7.51 (1H, m), 7.49-7.46 (1H, m), 7.43-7.38 (1H, m), 3.75 (3H, s), 3.38-3.27 (1H, m), 1.18 (6H, d)

Production Example 13

The procedure was performed according to the method described in Production Example 8 using 2-(2-isopropylsulfanylphenyl)-3-methyl-6-trifluoromethyl-3H-imidazo[4,5-b]pyridine instead of 3-methyl-2-(2-propylsulfanylphenyl)-6-trifluoromethyl-3H-imidazo[4,5-b]pyridine to give 2-(2-isopropylsulfinylphenyl)-3-methyl-6-trifluoromethyl-3H-imidazo[4,5-b]pyridine (hereinafter referred to as Present Compound 13).

Present Compound 13

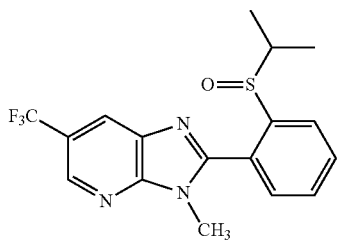 [SMILES: CC(C)S(=O)c1ccccc1-c1nc2cc(C(F)(F)F)cnc2n1C]

$^1$H-NMR (CDCl$_3$) δ: 8.76-8.75 (1H, m), 8.31-8.30 (1H, m), 8.18-8.15 (1H, m), 7.84-7.80 (1H, m), 7.72-7.67 (1H, m), 7.62-7.59 (1H, m), 3.87 (3H, s), 3.50-3.39 (1H, m), 1.33 (3H, d), 1.09 (3H, d)

Production Example 14

The procedure was performed according to the method described in Production Example 9 using 2-(2-isopropylsulfanylphenyl)-3-methyl-6-trifluoromethyl-3H-imidazo[4,5-b]pyridine instead of 3-methyl-2-(2-propylsulfanylphenyl)-6-trifluoromethyl-3H-imidazo[4,5-b]pyridine to give 2-(2-isopropylsulfonylphenyl)-3-methyl-6-trifluoromethyl-3H-imidazo[4,5-b]pyridine (hereinafter referred to as Present Compound 14).

Present Compound 14

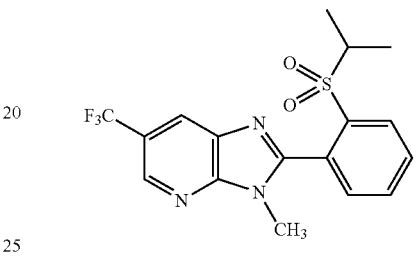

$^1$H-NMR (CDCl$_3$) δ: 8.75-8.74 (1H, m), 8.28-8.27 (1H, m), 8.22-8.19 (1H, m), 7.86-7.78 (2H, m), 7.57-7.54 (1H, m), 3.85-3.74 (1H, m), 3.71 (3H, s), 1.24 (6H, d)

Production Example 15

To a mixture of tert-butylthiol (0.67 g) and DMF (12 ml), sodium hydride (60% in oil) was added under ice-cooling. The mixture was stirred under ice-cooling for 10 minutes, and then 2-(2-fluorophenyl)-3-methyl-6-trifluoromethyl-3H-imidazo[4,5-b]pyridine (1.09 g) was added. The mixture was stirred at room temperature for 1 hour, and then stirred with heating at 60° C. for 1.5 hours, then at 80° C. for 2 hours. Into the reaction mixture cooled to room temperature, saturated aqueous sodium hydrogen carbonate solution was poured, and extracted with ethyl acetate. The organic layer was dried over magnesium sulfate, and concentrated under reduced pressure. The resulting residue was subjected to silica gel column chromatography to give 1.19 g of 2-(2-tert-butylsulfanylphenyl)-3-methyl-6-trifluoromethyl-3H-imidazo[4,5-b]pyridine (hereinafter referred to as Present Compound 15).

Present Compound 15

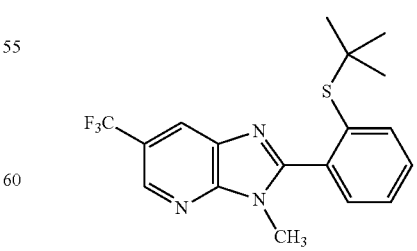

$^1$H-NMR (CDCl$_3$) δ: 8.73-8.70 (1H, m), 8.31-8.29 (1H, m), 7.78-7.75 (1H, m), 7.62-7.52 (3H, m), 3.72 (3H, s), 1.12 (9H, s)

Production Examples 16 and 17

To a mixture of 2-(2-tert-butylsulfanylphenyl)-3-methyl-6-trifluoromethyl-3H-imidazo[4,5-b]pyridine (0.87 g) and chloroform (12 ml), 3-chloroperbenzoic acid (purity: not less than 65%) (0.95 g) was added under ice-cooling, heated to room temperature, and stirred for 2 hours. Into the reaction mixture, saturated aqueous sodium hydrogen carbonate solution and saturated aqueous sodium thiosulfate solution were poured, and extracted with chloroform. The organic layer was dried over magnesium sulfate, and concentrated under reduced pressure. The resulting residue was subjected to silica gel column chromatography to give 0.33 g of 2-(2-tert-butylsulfinylphenyl)-3-methyl-6-trifluoromethyl-3H-imidazo[4,5-b]pyridine (hereinafter referred to as Present Compound 16) and 0.52 g of 2-(2-tert-butylsulfonylphenyl)-3-methyl-6-trifluoromethyl-3H-imidazo[4,5-b]pyridine (hereinafter referred to as Present Compound 17).

Present Compound 16

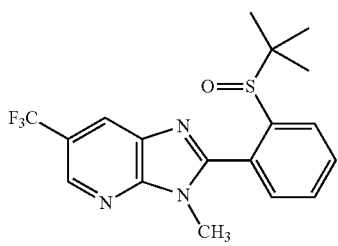 [SMILES: Cn1c(-c2ccccc2S(=O)C(C)(C)C)nc2cc(C(F)(F)F)cnc21]

¹H-NMR (CDCl₃) δ: 8.76-8.74 (1H, m), 8.33-8.31 (1H, m), 8.19-8.15 (1H, m), 7.85-7.80 (1H, m), 7.75-7.70 (1H, m), 7.63-7.59 (1H, m), 3.84 (3H, s), 1.05 (9H, s)

Present Compound 17

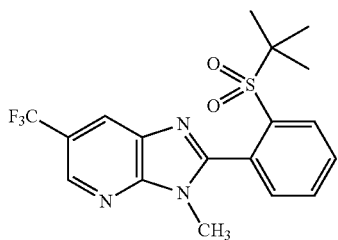 [SMILES: Cn1c(-c2ccccc2S(=O)(=O)C(C)(C)C)nc2cc(C(F)(F)F)cnc21]

¹H-NMR (CDCl₃) δ: 8.73-8.71 (1H, m), 8.28-8.26 (1H, m), 8.17-8.12 (1H, m), 7.86-7.80 (2H, m), 7.57-7.53 (1H, m), 3.66 (3H, s), 1.31 (9H, s)

Production Example 18

A mixture of N²-methyl-5-trifluoromethylpyridin-2,3-diamine (0.86 g), 2-trifluoromethylsulfanylbenzoic acid (1.00 g), WSC (0.76 g), and pyridine (9 ml) was stirred with heating at 120° C. for 3.5 hours. Into the reaction mixture cooled to room temperature, water was poured, and extracted with ethyl acetate. The organic layer was dried over magnesium sulfate, and concentrated under reduced pressure.

A mixture of the resulting residue, tripotassium phosphate (2.87 g), and 1-pentanol (9 ml) was stirred with heating at 135° C. for 3.5 hours. Into the reaction mixture cooled to room temperature, water was poured, and extracted with ethyl acetate. The organic layer was dried over magnesium sulfate, and concentrated under reduced pressure. The resulting residue was subjected to silica gel column chromatography to give 0.98 g of 3-methyl-6-trifluoromethyl-2-(2-trifluoromethylsulfanylphenyl)-3H-imidazo[4,5-b]pyridine (hereinafter referred to as Present Compound 18).

Present Compound 18

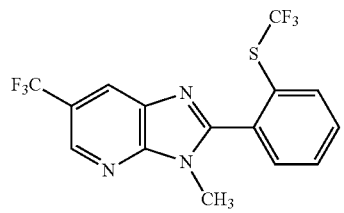 [SMILES: Cn1c(-c2ccccc2SC(F)(F)F)nc2cc(C(F)(F)F)cnc21]

¹H-NMR (CDCl₃) δ: 8.76-8.74 (1H, m), 8.35-8.33 (1H, m), 7.98-7.93 (1H, m), 7.71-7.59 (3H, m), 3.77 (3H, s)

Production Example 19

To a mixture of 3-methyl-6-trifluoromethyl-2-(2-trifluoromethylsulfanylphenyl)-3H-imidazo[4,5-b]pyridine (0.80 g) and chloroform (7 ml), 3-chloroperbenzoic acid (purity: not less than 65%) (0.49 g) was added under ice-cooling. The mixture was heated to room temperature, stirred for 20 minutes, and then heated to 62° C., and stirred under reflux for 2 hours. Into the reaction mixture cooled to room temperature, saturated aqueous sodium hydrogen carbonate solution and saturated aqueous sodium thiosulfate solution were poured, and extracted with chloroform. The organic layer was dried over magnesium sulfate, and concentrated under reduced pressure. The resulting residue was subjected to silica gel column chromatography to give 0.44 g of 3-methyl-6-trifluoromethyl-2-(2-trifluoromethylsulfinylphenyl)-3H-imidazo[4,5-b]pyridine (hereinafter referred to as Present Compound 19).

Present Compound 19

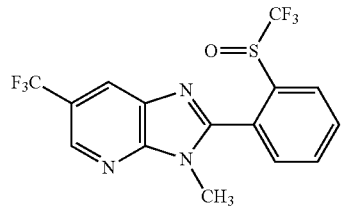 [SMILES: Cn1c(-c2ccccc2S(=O)C(F)(F)F)nc2cc(C(F)(F)F)cnc21]

¹H-NMR (CDCl₃) δ: 8.77-8.74 (1H, m), 8.46-8.41 (1H, m), 8.36-8.33 (1H, m), 7.92-7.83 (3H, m), 4.04 (3H, s)

Production Example 20

A mixture of 3-methyl-6-trifluoromethyl-2-(2-trifluoromethylsulfanylphenyl)-3H-imidazo[4,5-b]pyridine (0.25 g) and acetic acid (7 ml) was heated to 80° C., and 30% of an aqueous solution of hydrogen peroxide (3 ml) was added dropwise thereto. The mixture was heated to 100° C., and then stirred with heating for 5 hours. Into the reaction mixture cooled to room temperature, water was poured, and extracted with ethyl acetate. The organic layer was dried over magnesium sulfate, and concentrated under reduced pressure. The resulting residue was subjected to silica gel column chromatography to give 76 mg of 3-methyl-6-trifluoromethyl-2-(2-trifluoromethylsulfonylphenyl)-3H-imidazo[4,5-b]pyridine (hereinafter referred to as Present Compound 20).

Present Compound 20

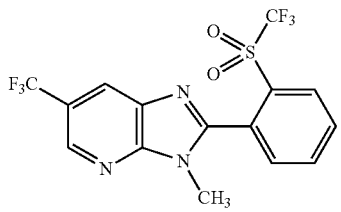 [SMILES: Cn1c(-c2ccccc2S(=O)(=O)C(F)(F)F)nc2cc(C(F)(F)F)cnc21]

$^1$H-NMR (CDCl$_3$) δ: 8.76-8.74 (1H, m), 8.35-8.32 (2H, m), 8.05-8.01 (1H, m), 7.97-7.93 (1H, m), 7.72-7.70 (1H, m), 3.71 (3H, s)

Production Example 21

To a mixture of N$^2$-ethyl-5-trifluoromethylpyridin-2,3-diamine (700 mg), 2-ethylsulfanylbenzoic acid (690 mg), and pyridine (20 ml), WSC (720 mg) was added at room temperature, and heated to 95° C., and then stirred with heating for 10 hours. Into the reaction mixture cooled to room temperature, saturated aqueous sodium carbonate solution was poured, and extracted with ethyl acetate. The organic layer was dried over sodium sulfate, and concentrated under reduced pressure.

The resulting residue was dissolved in xylene (20 ml), and p-toluenesulfonic acid monohydrate (1.6 g) was added thereto. The mixture was heated to 170° C., and stirred with heating for 9.5 hours. Into the reaction mixture cooled to room temperature, saturated aqueous sodium hydrogen carbonate solution was poured, and extracted with ethyl acetate. The organic layer was dried over sodium sulfate, and concentrated under reduced pressure. The resulting residue was subjected to silica gel column chromatography to give 295 mg of 3-ethyl-2-(2-ethylsulfanylphenyl)-6-trifluoromethyl-3H-imidazo[4,5-b]pyridine (hereinafter referred to as Present Compound 21).

Present Compound 21

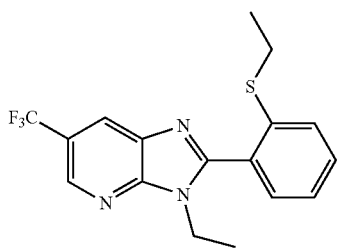 [SMILES: CCSc1ccccc1-c1nc2cc(C(F)(F)F)cnc2n1CC]

$^1$H-NMR (CDCl$_3$) δ: 8.70 (1H, s), 8.32 (1H, s), 7.60-7.30 (4H, m), 4.25 (2H, q), 2.89 (2H, q), 1.35-1.30 (3H, m), 1.27-1.21 (3H, m)

Production Examples 22 and 23

The procedure was performed according to the method described in Production Examples 16 and 17 using 3-ethyl-2-(2-ethylsulfanylphenyl)-6-trifluoromethyl-3H-imidazo[4,5-b]pyridine instead of 2-(2-tert-butylsulfanylphenyl)-3-methyl-6-trifluoromethyl-3H-imidazo[4,5-b]pyridine to give 140 mg of 2-(2-ethylsulfinylphenyl)-3-ethyl-6-trifluoromethyl-3H-imidazo[4,5-b]pyridine (hereinafter referred to as Present Compound 22) and 60 mg of 2-(2-ethylsulfonylphenyl)-3-ethyl-6-trifluoromethyl-3H-imidazo[4,5-b]pyridine (hereinafter referred to as Present Compound 23).

Present Compound 22

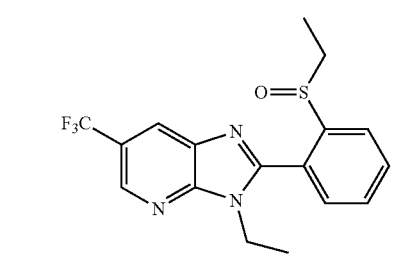 [SMILES: CCn1c(-c2ccccc2S(=O)CC)nc2cc(C(F)(F)F)cnc21]

$^1$H-NMR (CDCl$_3$) δ: 8.75 (1H, d), 8.31 (1H, d), 8.24 (1H, dd), 7.84 (1H, dt), 7.70 (1H, dt), 7.58 (1H, dd), 4.35 (2H, q), 3.43-3.30 (1H, m), 3.06-2.94 (1H, m), 1.41 (3H, t), 1.30 (3H, t)

Present Compound 23

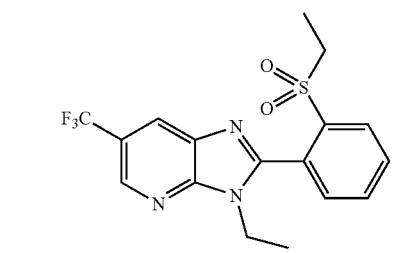 [SMILES: CCn1c(-c2ccccc2S(=O)(=O)CC)nc2cc(C(F)(F)F)cnc21]

$^1$H-NMR (CDCl$_3$) δ: 8.71 (1H, d), 8.32 (1H, d), 7.56-7.47 (2H, m), 7.43 (1H, dd), 7.39-7.31 (1H, m), 4.25 (2H, q), 2.89 (2H, q), 1.32 (3H, t), 1.25 (3H, t)

Production Example 24

A mixture of 2-ethylsulfanyl-N-(2-propylamino-5-toluenesulfonic acid monohydrate (1.1 g), and xylene (10 ml) was stirred with heating at 160° C. for 10 hours. Into the reaction mixture cooled to room temperature, saturated aqueous sodium hydrogen carbonate solution was poured, and extracted with ethyl acetate. The organic layer was dried over sodium sulfate, and concentrated under reduced pressure. The resulting residue was subjected to silica gel column chromatography to give 522 mg of 2-(2-ethylsulfanylphenyl)-3-propyl-6-trifluoromethyl-3H-imidazo[4,5-b]pyridine (hereinafter referred to as Present Compound 24).

Present Compound 24

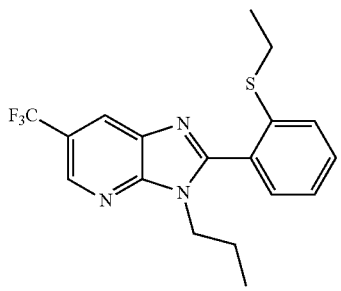 [SMILES: CCCn1c(-c2ccccc2SCC)nc2cc(C(F)(F)F)cnc21]

¹H-NMR (CDCl₃) δ: 8.70 (1H, d), 8.31 (1H, d), 7.56-7.32 (4H, m), 4.18 (2H, t), 2.89 (2H, q), 1.78-1.73 (2H, m), 1.28-1.21 (3H, m), 0.79 (3H, t)

Production Examples 25 and 26

The procedure was performed according to the method described in Production Examples 16 and 17 using 2-(2-ethylsulfanylphenyl)-3-propyl-6-trifluoromethyl-3H-imidazo[4,5-b]pyridine instead of 2-(2-tert-butylsulfanylphenyl)-3-methyl-6-trifluoromethyl-3H-imidazo[4,5-b]pyridine to give 100 mg of 2-(2-ethylsulfinylphenyl)-3-propyl-6-trifluoromethyl-3H-imidazo[4,5-b]pyridine (hereinafter referred to as Present Compound 25) and 42 mg of 2-(2-ethylsulfonylphenyl)-3-propyl-6-trifluoromethyl-3H-imidazo[4,5-b]pyridine (hereinafter referred to as Present Compound 26).

Present Compound 25

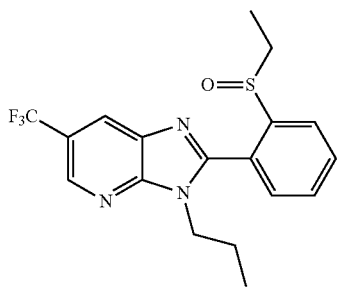 [SMILES: CCCn1c(-c2ccccc2S(=O)CC)nc2cc(C(F)(F)F)cnc21]

¹H-NMR (CDCl₃) δ: 8.74 (1H, d), 8.31 (1H, d), 8.24 (1H, dd), 7.84 (1H, td), 7.70 (1H, td), 7.58 (1H, dd), 4.33-4.24 (2H, m), 3.40-3.35 (1H, m), 3.03-2.98 (1H, m), 1.84-1.71 (2H, m), 1.29 (3H, t), 0.81 (3H, t)

Present Compound 26

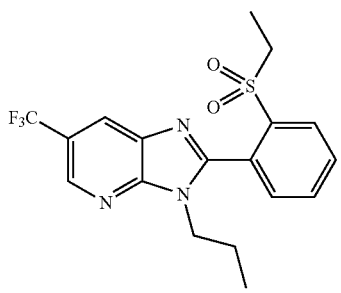 [SMILES: CCCn1c(-c2ccccc2S(=O)(=O)CC)nc2cc(C(F)(F)F)cnc21]

¹H-NMR (CDCl₃) δ: 8.65 (1H, s), 8.21-8.13 (2H, m), 7.79-7.70 (2H, m), 7.52-7.49 (1H, m), 4.12-3.92 (2H, m), 3.50-3.30 (2H, m), 1.81-1.70 (2H, m), 1.22-1.16 (3H, m), 0.84-0.76 (3H, m)

Production Example 27

The procedure was performed according to the method described in Production Example 21 using N²-isopropyl-5-trifluoromethyl-pyridin-2,3-diamine instead of N²-ethyl-5-trifluoromethyl-pyridin-2,3-diamine to give 130 mg of 2-(2-ethylsulfanylphenyl)-3-isopropyl-6-trifluoromethyl-3H-imidazo[4,5-b]pyridine (hereinafter referred to as Present Compound 27).

Present Compound 27

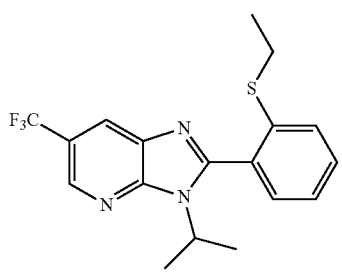 [SMILES: CCSc1ccccc1-c1nc2cc(C(F)(F)F)cnc2n1C(C)C]

¹H-NMR (CDCl₃) δ: 8.68 (1H, d), 8.28 (1H, d), 7.55-7.47 (2H, m), 7.39-7.31 (2H, m), 4.40-4.33 (1H, m), 2.91 (2H, q), 1.77-1.66 (6H, m), 1.25 (3H, t)

Production Examples 28 and 29

The procedure was performed according to the method described in Production Examples 16 and 17 using 2-(2-ethylsulfanylphenyl)-3-isopropyl-6-trifluoromethyl-3H-imidazo[4,5-b]pyridine instead of 2-(2-tert-butylsulfanylphenyl)-3-methyl-6-trifluoromethyl-3H-imidazo[4,5-b]pyridine to give 60 mg of 2-(2-ethylsulfinylphenyl)-3-isopropyl-6-trifluoromethyl-3H-imidazo[4,5-b]pyridine (hereinafter referred to as Present Compound 28) and 55 mg of 2-(2-ethylsulfonylphenyl)-3-isopropyl-6-trifluoromethyl-3H-imidazo[4,5-b]pyridine (hereinafter referred to as Present Compound 29).

Present Compound 28

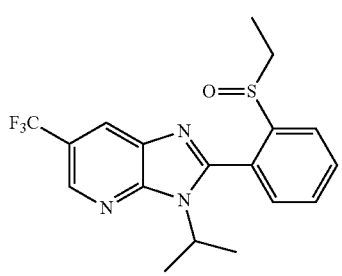 [SMILES: CCS(=O)c1ccccc1-c1nc2cc(C(F)(F)F)cnc2n1C(C)C]

¹H-NMR (CDCl₃) δ: 8.73 (1H, d), 8.28 (1H, d), 8.22 (1H, dd), 7.83 (1H, td), 7.69 (1H, td), 7.50 (1H, dd), 4.60-4.48 (1H, m), 3.38-3.26 (1H, m), 3.05-2.95 (1H, m), 1.77-1.71 (6H, m), 1.27 (3H, t)

Present Compound 29

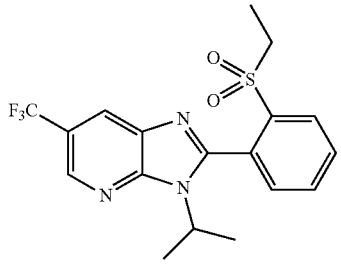 [SMILES: CCS(=O)(=O)c1ccccc1-c1nc2cc(C(F)(F)F)cnc2n1C(C)C]

¹H-NMR (CDCl₃) δ: 8.71 (1H, d), 8.24-8.22 (2H, m), 7.85-7.78 (2H, m), 7.55-7.52 (1H, m), 4.33-4.26 (1H, m), 3.72-3.62 (1H, m), 3.44-3.34 (1H, m), 1.77-1.69 (6H, m), 1.28 (3H, t)

Production Example 30

The procedure was performed according to the method described in Production Example 21 using N²-cyclopropyl-5-trifluoromethyl-pyridin-2,3-diamine instead of N²-ethyl-5-trifluoromethyl-pyridin-2,3-diamine to give 280 mg of 3-cyclopropyl-2-(2-ethylsulfanylphenyl)-6-trifluoromethyl-3H-imidazo[4,5-b]pyridine (hereinafter referred to as Present Compound 30).

Present Compound 30

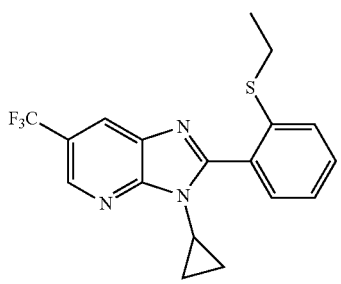 [SMILES: CCSc1ccccc1-c1nc2cc(C(F)(F)F)cnc2n1C1CC1]

¹H-NMR (CDCl₃) δ: 8.74 (1H, s), 8.31 (1H, s), 7.53-7.47 (3H, m), 7.39-7.31 (1H, m), 3.55-3.49 (1H, m), 2.90 (2H, q), 1.25 (3H, t), 1.01-0.94 (2H, m), 0.93-0.86 (2H, m)

Production Examples 31 and 32

The procedure was performed according to the method described in Production Examples 16 and 17 using 3-cyclopropyl-2-(2-ethylsulfanylphenyl)-6-trifluoromethyl-3H-imidazo[4,5-b]pyridine instead of 2-(2-tert-butylsulfanylphenyl)-3-methyl-6-trifluoromethyl-3H-imidazo[4,5-b]pyridine to give 114 mg of 3-cyclopropyl-2-(2-ethylsulfinylphenyl)-6-trifluoromethyl-3H-imidazo[4,5-b]pyridine (hereinafter referred to as Present Compound 31) and 109 mg of 3-cyclopropyl-2-(2-ethylsulfonylphenyl)-6-trifluoromethyl-3H-imidazo[4,5-b]pyridine (hereinafter referred to as Present Compound 32).

Present Compound 31

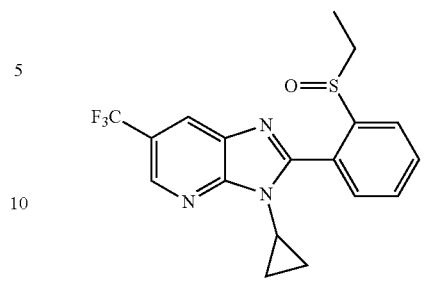

¹H-NMR (CDCl₃) δ: 8.77 (1H, d), 8.29-8.26 (2H, m), 7.85-7.79 (2H, m), 7.72-7.67 (1H, m), 3.57-3.51 (1H, m), 3.49-3.39 (1H, m), 3.09-2.95 (1H, m), 1.34 (3H, t), 1.29-1.16 (1H, m), 1.09-0.92 (2H, m), 0.80-0.65 (1H, m)

Present Compound 32

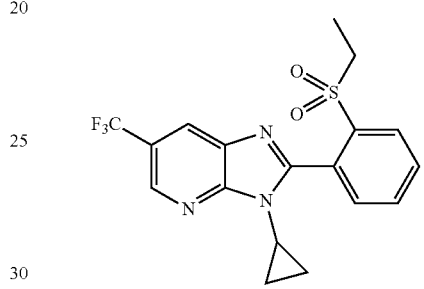

¹H-NMR (CDCl₃) δ: 8.76 (1H, s), 8.27-8.22 (2H, m), 7.87-7.78 (2H, m), 7.65 (1H, dd), 3.60 (2H, brs), 3.39-3.33 (1H, m), 1.29 (3H, t), 1.11-1.11 (2H, m), 0.93 (2H, brs).

Production Examples 33 and 34

To a mixture of 2-(2-ethylsulfanylphenyl)-6-trifluoromethyl-3H-imidazo[4,5-b]pyridine (270 mg) and DMF (10 ml), 60% of sodium hydride (in oil) (80 mg) and chloromethyl ethyl ether (118 μl) were sequentially added under ice-cooling. The mixture was heated to room temperature, and stirred for 5 hours. Into the reaction mixture, water was poured, and extracted with ethyl acetate. The organic layer was dried over sodium sulfate, and concentrated under reduced pressure. The resulting residue was subjected to silica gel column chromatography to give 180 mg of 3-ethoxymethyl-2-(2-ethylsulfanylphenyl)-6-trifluoromethyl-3H-imidazo[4,5-b]pyridine (hereinafter referred to as Present Compound 33) and 70 mg of 1-ethoxymethyl-2-(2-ethylsulfanylphenyl)-6-trifluoromethyl-1H-imidazo[4,5-b]pyridine (hereinafter referred to as Present Compound 34)).

Present Compound 33

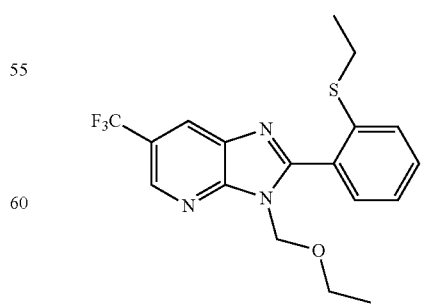

¹H-NMR (CDCl₃) δ: 8.73 (1H, d), 8.35 (1H, d), 7.58-7.47 (3H, m), 7.35 (1H, td), 5.60 (2H, s), 3.50 (2H, q), 2.89 (2H, q), 1.25 (3H, t), 1.10 (3H, t)

Present Compound 34

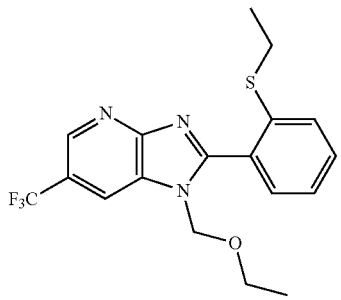 [SMILES: CCOCn1c(-c2ccccc2SCC)nc2ncc(C(F)(F)F)cc21]

¹H-NMR (CDCl₃) δ: 8.90 (1H, d), 8.19 (1H, d), 7.56-7.50 (3H, m), 7.40-7.36 (1H, m), 5.45 (2H, s), 3.25 (2H, q), 2.85 (2H, q), 1.22 (3H, t), 1.04 (3H, t)

Production Examples 35 and 36

The procedure was performed according to the method described in Production Examples 16 and 17 using 3-ethoxymethyl-2-(2-ethylsulfanylphenyl)-6-trifluoromethyl-3H-imidazo[4,5-b]pyridine instead of 2-(2-tert-butylsulfanylphenyl)-3-methyl-6-trifluoromethyl-3H-imidazo[4,5-b]pyridine to give 86 mg of 2-(2-ethylsulfinylphenyl)-3-ethoxymethyl-6-trifluoromethyl-3H-imidazo[4,5-b]pyridine (hereinafter referred to as Present Compound 35) and 96 mg of 2-(2-ethylsulfonylphenyl)-3-ethoxymethyl-6-trifluoromethyl-3H-imidazo[4,5-b]pyridine (hereinafter referred to as Present Compound 36).

Present Compound 35

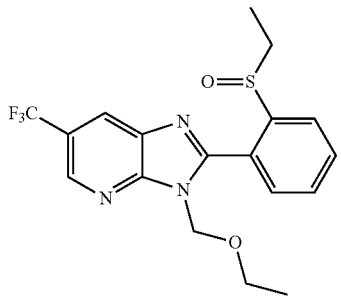 [SMILES: CCOCn1c(-c2ccccc2S(=O)CC)nc2cc(C(F)(F)F)cnc21]

¹H-NMR (CDCl₃) δ: 8.75 (1H, d), 8.32 (1H, d), 8.29 (1H, dd), 8.04 (1H, dd), 7.82 (1H, td), 7.70 (1H, td), 5.83 (1H, d), 5.47 (1H, d), 3.80-3.70 (2H, m), 3.61-3.49 (1H, m), 3.10-3.01 (1H, m), 1.40 (3H, t), 1.25 (3H, t)

Present Compound 36

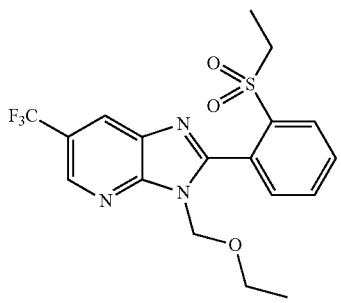 [SMILES: CCOCn1c(-c2ccccc2S(=O)(=O)CC)nc2cc(C(F)(F)F)cnc21]

¹H-NMR (CDCl₃) δ: 8.75 (1H, d), 8.29 (1H, d), 8.21 (1H, dd), 7.86-7.78 (2H, m), 7.72 (1H, dd), 5.51 (2H, brs), 3.64 (2H, q), 3.49 (2H, q), 1.28 (3H, t), 1.17 (3H, t)

Production Example 37

To a mixture of 2-(2-ethylsulfanylphenyl)-6-trifluoromethyl-3H-imidazo[4,5-b]pyridine (98 mg) and DMF (6 ml), 60% of sodium hydride (in oil) (29 mg) and chloromethyl methyl ether (25 μl) were sequentially added under ice-cooling. The mixture was heated room temperature, and stirred for 4 hours. Then, water was poured thereinto, and extracted with ethyl acetate. The organic layer was dried over sodium sulfate, and concentrated under reduced pressure. The resulting residue was subjected to silica gel column chromatography to give 72 mg of 3-methoxymethyl-2-(2-ethylsulfanylphenyl)-6-trifluoromethyl-3H-imidazo[4,5-b]pyridine (hereinafter referred to as Present Compound 37).

Present Compound 37

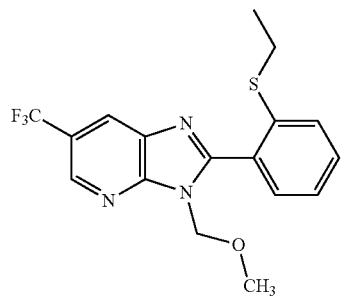 [SMILES: CCSc1ccccc1-c1nc2cc(C(F)(F)F)cnc2n1COC]

¹H-NMR (CDCl₃) δ: 8.74 (1H, d), 8.36 (1H, d), 7.58-7.47 (3H, m), 7.35 (1H, td), 5.55 (2H, s), 3.31 (3H, s), 2.90 (2H, q), 1.25 (3H, t)

Production Example 38

The procedure was performed according to the method described in Production Example 37 using 2-(2-ethylsulfonylphenyl)-6-trifluoromethyl-3H-imidazo[4,5-b]pyridine instead of 2-(2-ethylsulfanylphenyl)-6-trifluoromethyl-3H-imidazo[4,5-b]pyridine to give 79 mg of 2-(2-ethylsulfonylphenyl)-3-methoxymethyl-6-trifluoromethyl-3H-imidazo[4,5-b]pyridine (hereinafter referred to as Present Compound 38).

Present Compound 38

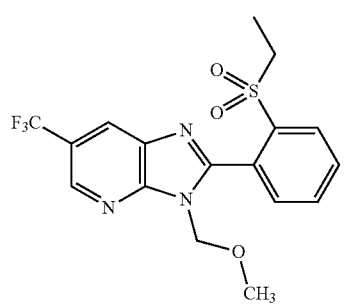 [SMILES: CCS(=O)(=O)c1ccccc1-c1nc2cc(C(F)(F)F)cnc2n1COC]

¹H-NMR (CDCl₃) δ: 8.76 (1H, d), 8.31 (1H, d), 8.21 (1H, dd), 7.87-7.78 (2H, m), 7.72 (1H, dd), 5.48 (2H, brs), 3.50 (2H, q), 3.43 (3H, s), 1.28 (3H, t)

Production Example 39

A mixture of 2-ethylsulfanyl-N-(5-methyl-2-methylaminopyridin-3-yl)-benzamide (1.40 g), tripotassium phosphate (1.97 g), and tert-butanol (10 ml) was stirred under reflux at 82° C. for 2 hours. Into the reaction mixture cooled to room temperature, water was poured, and extracted with ethyl acetate. The organic layer was dried over magnesium sulfate, and concentrated under reduced pressure. The resulting residue was subjected to silica gel column chromatography to give 0.27 g of 2-(2-ethylsulfanylphenyl)-3,6-dimethyl-3H-imidazo[4,5-b]pyridine (hereinafter referred to as Present Compound 39).

Present Compound 39

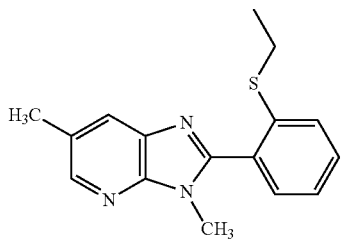 [SMILES: CCSc1ccccc1-c1nc2cc(C)cnc2n1C]

$^1$H-NMR (CDCl$_3$) δ: 8.28-8.26 (1H, m), 7.89-7.88 (1H, m), 7.50-7.43 (3H, m), 7.35-7.30 (1H, m), 3.72 (3H, s), 2.85 (2H, q), 2.51 (3H, s), 1.22 (3H, t)

Production Examples 40 and 41

The procedure was performed according to the method described in Production Examples 16 and 17 using 2-(2-ethylsulfanylphenyl)-3,6-dimethyl-3H-imidazo[4,5-b]pyridine instead of 2-(2-tert-butylsulfanylphenyl)-3-methyl-6-trifluoromethyl-3H-imidazo[4,5-b]pyridine to give 2-(2-ethylsulfinylphenyl)-3,6-dimethyl-3H-imidazo[4,5-b]pyridine (hereinafter referred to as Present Compound 40) and 2-(2-ethylsulfonylphenyl)-3,6-dimethyl-3H-imidazo[4,5-b]pyridine (hereinafter referred to as Present Compound 41).

Present Compound 40

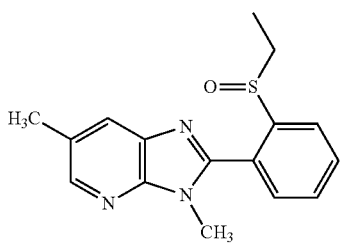

$^1$H-NMR (CDCl$_3$) δ: 8.32-8.31 (1H, m), 8.24-8.21 (1H, m), 7.88-7.86 (1H, m), 7.81-7.77 (1H, m), 7.69-7.64 (1H, m), 7.60-7.57 (1H, m), 3.83 (3H, s), 3.38-3.28 (1H, m), 2.97-2.87 (1H, m), 2.52 (3H, s), 1.27 (3H, t)

Present Compound 41

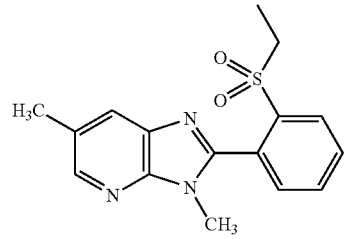

$^1$H-NMR (CDCl$_3$) δ: 8.31-8.29 (1H, m), 8.23-8.20 (1H, m), 7.84-7.75 (3H, m), 7.57-7.54 (1H, m), 3.66 (3H, s), 3.45 (2H, q), 2.51 (3H, s), 1.24 (3H, t)

Production Example 42

A mixture of 5-bromo-N$^2$-methylpyridin-2,3-diamine (0.70 g), 2-ethylsulfanylbenzoic acid (0.66 g), WSC (0.80 g), HOBt (23 mg), and pyridine (20 ml) was stirred under reflux at 120° C. for 30 minutes. After the reaction mixture was allowed to stand overnight, the mixture was stirred under reflux at 120° C. for 9.5 hours again. Into the reaction mixture cooled to room temperature, water was poured under ice-cooling, and extracted with ethyl acetate. The organic layer was washed with water and saturated brine, dried over sodium sulfate, and concentrated under reduced pressure. A mixture of the resulting residue and acetic anhydride (7 ml) was stirred under reflux at 140° C. for 1 hour. Aqueous sodium hydroxide solution was added to the reaction mixture cooled to room temperature to neutralize, and extracted with ethyl acetate. The organic layer was washed with water and saturated brine, dried over sodium sulfate, and concentrated under reduced pressure. The resulting residue was subjected to silica gel column chromatography to give 0.60 g of 6-bromo-2-(2-ethylsulfanylphenyl)-3-methyl-3H-imidazo[4,5-b]pyridine (hereinafter referred to as Present Compound 42).

Present Compound 42

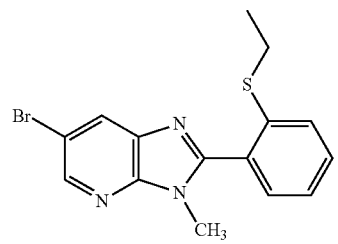 [SMILES: CCSc1ccccc1-c1nc2cc(Br)cnc2n1C]

$^1$H-NMR (CDCl$_3$) δ: 8.47 (1H, d), 8.22 (1H, d), 7.54-7.48 (2H, m), 7.45-7.42 (1H, m), 7.37-7.32 (1H, m), 3.71 (3H, s), 2.86 (2H, q), 1.23 (3H, t)

Production Example 43

A mixture of 6-bromo-2-(2-ethylsulfanylphenyl)-3-methyl-3H-imidazo[4,5-b]pyridine (0.20 g), sodium periodate (0.18 g), methanol (3 ml), water (1 ml), and THF (0.4 ml) was stirred at room temperature for 3.5 hours. Water was poured thereinto under ice-cooling, and then the precipitated solid was collected by filtration. The obtained solid was washed with water and hexane, and dried to give 0.19 g of 6-bromo- 2-(2-ethylsulfinylphenyl)-3-methyl-3H-imidazo[4,5-b]pyridine (hereinafter referred to as Present Compound 43).

Present Compound 43

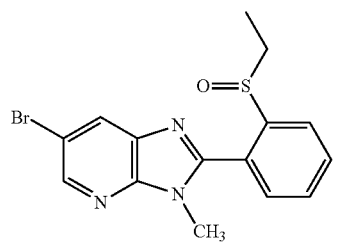

¹H-NMR (CDCl₃) δ: 8.52-8.51 (1H, m), 8.26-8.22 (1H, m), 8.21-8.20 (1H, m), 7.84-7.78 (1H, m), 7.71-7.65 (1H, m), 7.60-7.57 (1H, m), 3.83 (3H, s), 3.39-3.28 (1H, m), 2.99-2.88 (1H, m), 1.29 (3H, t)

Production Example 44

To a mixture of 6-bromo-2-(2-ethylsulfanylphenyl)-3-methyl-3H-imidazo[4,5-b]pyridine (0.20 g) and chloroform (3 ml), 3-chloroperbenzoic acid (purity: not less than 65%) (0.34 g) was added under ice-cooling, and then heated to room temperature, and stirred for 3.5 hours. Chloroform and saturated aqueous sodium thiosulfate solution were poured thereinto under ice-cooling, and stirred, and then, water was poured, and extracted with ethyl acetate. The organic layer was washed with saturated aqueous sodium hydrogen carbonate solution and saturated brine, dried over sodium sulfate, and concentrated under reduced pressure. The resulting solid was washed with hexane, and dried to give 0.20 g of 6-bromo-2-(2-ethylsulfonylphenyl)-3-methyl-3H-imidazo[4,5-b]pyridine (hereinafter referred to as Present Compound 44).

Present Compound 44

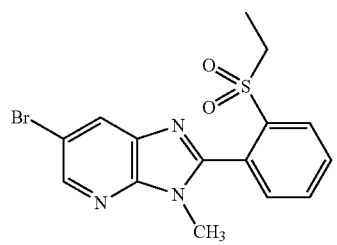 [SMILES: CCS(=O)(=O)c1ccccc1-c1nc2cc(Br)cnc2n1C]

¹H-NMR (CDCl₃) δ: 8.50 (1H, d), 8.23-8.20 (1H, m), 8.17 (1H, d), 7.86-7.77 (2H, m), 7.57-7.54 (1H, m), 3.66 (3H, s), 3.42 (2H, q), 1.24 (3H, t)

Production Example 45

The procedure was performed according to the method described in Production Example 21 using 5-iodo-N²-methyl-pyridin-2,3-diamine instead of N²-ethyl-5-trifluoromethyl-pyridin-2,3-diamine to give 435 mg of 2-(2-ethylsulfanylphenyl)-6-iodo-3-methyl-3H-imidazo[4,5-b]pyridine (hereinafter referred to as Present Compound 45).

Present Compound 45

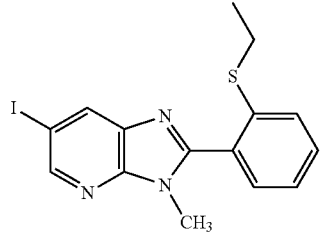 [SMILES: CCSc1ccccc1-c1nc2cc(I)cnc2n1C]

¹H-NMR (CDCl₃) δ: 8.60 (1H, d), 8.39 (1H, d), 7.54-7.41 (3H, m), 7.38-7.31 (1H, m), 3.71 (3H, s), 2.85 (2H, q), 1.23 (3H, t)

Production Examples 46 and 47

The procedure was performed according to the method described in Production Examples 16 and 17 using 2-(2-ethylsulfanylphenyl)-6-iodo-3-methyl-3H-imidazo[4,5-b]pyridine instead of 2-(2-tert-butylsulfanylphenyl)-3-methyl-6-trifluoromethyl-3H-imidazo[4,5-b]pyridine to give 136 mg of 2-(2-ethylsulfinylphenyl)-6-iodo-3-methyl-3H-imidazo[4,5-b]pyridine (hereinafter referred to as Present Compound 46) and 107 mg of 2-(2-ethylsulfonylphenyl)-6-iodo-3-methyl-3H-imidazo[4,5-b]pyridine (hereinafter referred to as Present Compound 47).

Present Compound 46

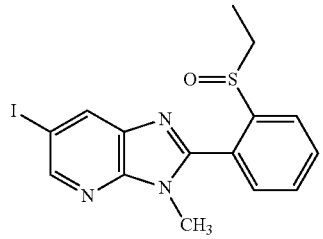 [SMILES: CCS(=O)c1ccccc1-c1nc2cc(I)cnc2n1C]

¹H-NMR (CDCl₃) δ: 8.63 (1H, d), 8.38 (1H, d), 8.24 (1H, dd), 7.81 (1H, td), 7.68 (1H, td), 7.59 (1H, dd), 3.83 (3H, s), 3.39-3.29 (1H, m), 2.99-2.88 (1H, m), 1.29 (3H, t)

Present Compound 47

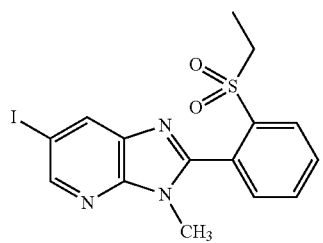 [SMILES: CCS(=O)(=O)c1ccccc1-c1nc2cc(I)cnc2n1C]

¹H-NMR (CDCl₃) δ: 8.63 (1H, d), 8.37 (1H, d), 8.21 (1H, dd), 7.85-7.77 (2H, m), 7.56 (1H, dd), 3.65 (3H, s), 3.41 (2H, q), 1.24 (3H, t)

Production Example 48

A mixture of zinc cyanide (0.47 g), tetrakis(triphenylphosphine)palladium (0.12 g), 6-bromo-2-(2-ethylsulfanylphenyl)-3-methyl-3H-imidazo[4,5-b]pyridine (0.70 g), and N-methylpyrrolidone (hereinafter referred to as NMP) (4 ml) was stirred at 90° C. for 2 hours. Into the reaction mixture cooled to room temperature, saturated aqueous ammonium chloride solution was poured, and extracted with ethyl acetate. The organic layer was dried over sodium sulfate, and concentrated under reduced pressure. The resulting residue was subjected to silica gel column chromatography to give 0.59 g of 6-cyano-2-(2-ethylsulfanylphenyl)-3-methyl-3H-imidazo[4,5-b]pyridine (hereinafter referred to as Present Compound 48).

Present Compound 48

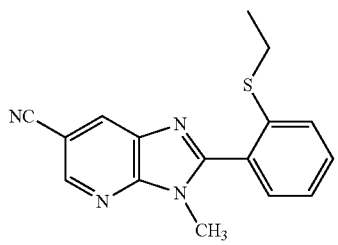 [SMILES: CCSc1ccccc1-c1nc2cc(C#N)cnc2n1C]

¹H-NMR (CDCl₃) δ: 8.70 (1H, d), 8.35 (1H, d), 7.49-7.58 (2H, m), 7.42-7.47 (1H, m), 7.34-7.40 (1H, m), 3.77 (3H, s), 2.88 (2H, q), 1.24 (3H, t)

Production Example 49

To a mixture of 6-cyano-2-(2-ethylsulfanylphenyl)-3-methyl-3H-imidazo[4,5-b]pyridine (0.40 g) and chloroform (5 ml), 70% of 3-chloroperbenzoic acid (0.35 g) was added under ice-cooling, and stirred at room temperature for 2 hours. To the reaction mixture, saturated aqueous sodium hydrogen carbonate solution was added, and extracted with ethyl acetate. The organic layer was dried over sodium sulfate, and concentrated under reduced pressure to give 0.40 g of 6-cyano-2-(2-ethylsulfinylphenyl)-3-methyl-3H-imidazo[4,5-b]pyridine (hereinafter referred to as Present Compound 49).

Present Compound 49

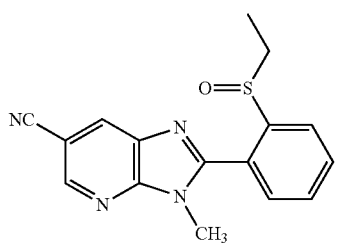 [SMILES: CCS(=O)c1ccccc1-c1nc2cc(C#N)cnc2n1C]

¹H-NMR (CDCl₃) δ: 8.74 (1H, d), 8.35 (1H, d), 8.26 (1H, d), 7.84 (1H, t), 7.71 (1H, t), 7.56-7.64 (1H, m), 3.89 (3H, s), 3.28-3.41 (1H, m), 2.91-3.04 (1H, m), 1.26-1.35 (3H, m)

Production Example 50

To a mixture of 6-cyano-2-(2-ethylsulfinylphenyl)-3-methyl-3H-imidazo[4,5-b]pyridine (0.25 g) and chloroform (5 ml), 70% of 3-chloroperbenzoic acid (0.35 g) was added, and stirred at 50° C. for 2 hours. To the reaction mixture, saturated aqueous sodium hydrogen carbonate solution and sodium sulfite were added, and extracted with ethyl acetate. The organic layer was dried over sodium sulfate, and concentrated under reduced pressure. The resulting residue was subjected to silica gel column chromatography to give 0.27 g of 6-cyano-2-(2-ethylsulfinylphenyl)-3-methyl-3H-imidazo[4,5-b]pyridine (hereinafter referred to as Present Compound 50).

Present Compound 50

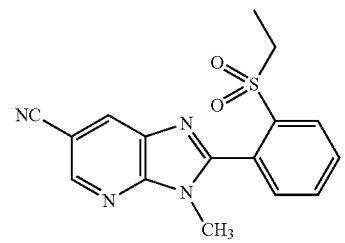 [SMILES: CCS(=O)(=O)c1ccccc1-c1nc2cc(C#N)cnc2n1C]

¹H-NMR (CDCl₃) δ: 8.73 (1H, d), 8.32 (1H, d), 8.20-8.26 (1H, m), 7.80-7.89 (2H, m), 7.54-7.60 (1H, m), 3.71 (3H, s), 3.33-3.45 (2H, m), 1.25 (3H, t)

Production Example 51

To a mixture of 6-bromo-2-(2-ethylsulfanylphenyl)-3-methyl-3H-imidazo[4,5-b]pyridine (2 g) and THF (60 ml), n-butyllithium (1.6 M in hexane) (4.3 ml) was added dropwise with cooling in dry-ice-acetone bath. The mixture was stirred for 30 minutes, and then DMF (2.2 ml) was poured. The mixture was heated to room temperature, and then saturated aqueous ammonium chloride solution was poured, and extracted with ethyl acetate. The organic layer was dried over sodium sulfate, and concentrated under reduced pressure. The resulting residue was subjected to silica gel column chromatography to give 189 mg of 2-(2-ethylsulfanylphenyl)-3-methyl-3H-imidazo[4,5-b]pyridin-6-carbaldehyde (hereinafter referred to as Present Compound 51).

Present Compound 51

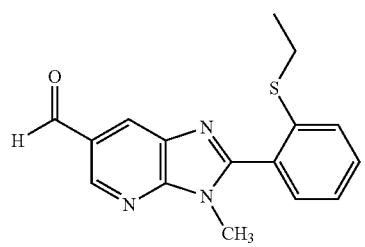 [SMILES: CCSc1ccccc1-c1nc2cc(C=O)cnc2n1C]

¹H-NMR (CDCl₃) δ: 10.20 (1H, s), 8.96 (1H, d), 8.55 (1H, d), 7.56-7.24 (4H, m), 3.79 (3H, s), 2.90-2.83 (2H, m), 1.25-1.21 (3H, m)

Production Example 52

To a mixture of 2-(2-ethylsulfanylphenyl)-3-methyl-3H-imidazo[4,5-b]pyridin-6-carbaldehyde (122 mg) and chloroform (3 ml), bis(2-methoxyethyl)aminosulfur trifluoride (700 μl) was added under ice-cooling. The mixture was heated to room temperature, and stirred for 3 hours. Into the reaction mixture, saturated aqueous sodium hydrogen carbonate solution was poured, and extracted with chloroform and ethyl acetate, sequentially. The organic layer was dried over sodium sulfate, and concentrated under reduced pressure. The resulting residue was subjected to silica gel column chromatography to give 49 mg of 6-difluoromethyl-2-(2-ethylsulfanylphenyl)-3-methyl-3H-imidazo[4,5-b]pyridine.

Present Compound 52

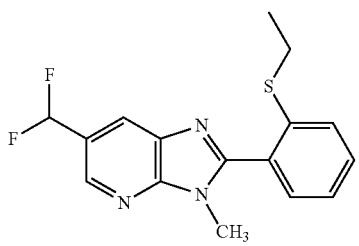 [SMILES: CCSc1ccccc1-c1nc2cc(C(F)F)cnc2n1C]

¹H-NMR (CDCl₃) δ: 8.59 (1H, s), 8.23 (1H, s), 7.56-7.43 (3H, m), 7.38-7.33 (1H, m), 6.88 (1H, t), 3.77 (3H, s), 2.87 (2H, q), 1.23 (3H, t)

Production Examples 53 and 54

The procedure was performed according to the method described in Production Examples 16 and 17 using 6-difluoromethyl-2-(2-ethylsulfanylphenyl)-3-methyl-3H-imidazo[4,5-b]pyridine instead of 2-(2-tert-butylsulfanylphenyl)-3-methyl-6-trifluoromethyl-3H-imidazo[4,5-b]pyridine to give 110 mg of 6-difluoromethyl-2-(2-ethylsulfinylphenyl)-3-methyl-3H-imidazo[4,5-b]pyridine (hereinafter referred to as Present Compound 53) and 101 mg of 6-difluoromethyl-2-(2-ethylsulfonylphenyl)-3-methyl-3H-imidazo[4,5-b]pyridine (hereinafter referred to as Present Compound 54).

Present Compound 53

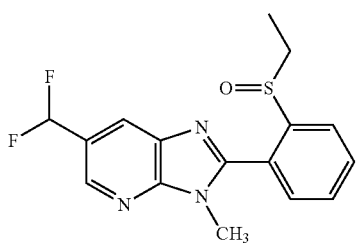 [SMILES: CCS(=O)c1ccccc1-c1nc2cc(C(F)F)cnc2n1C]

¹H-NMR (CDCl₃) δ: 8.62 (1H, s), 8.26-8.23 (2H, m), 7.83 (1H, td), 7.70 (1H, td), 7.62 (1H, dd), 6.90 (1H, t), 3.89 (3H, s), 3.42-3.32 (1H, m), 3.02-2.92 (1H, m), 1.30 (3H, t)

Present Compound 54

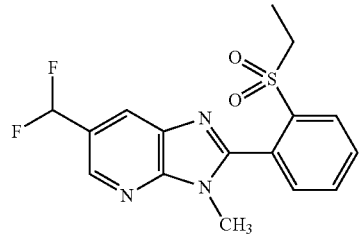

¹H-NMR (CDCl₃) δ: 8.61 (1H, s), 8.24-8.19 (2H, m), 7.87-7.78 (2H, m), 7.58 (1H, dd), 6.89 (1H, t), 3.71 (3H, s), 3.43 (2H, q), 1.25 (3H, t)

Production Example 55

A mixture of 6-bromo-2-(2-ethylsulfanylphenyl)-3-methyl-3H-imidazo[4,5-b]pyridine (500 mg), NMP (24 ml), xylene (10 ml), copper iodide (1.1 g), and sodium pentafluoropropionate (1.1 g) was heated to 170° C., and stirred with heating for 3 days. Into the reaction mixture cooled to room temperature, saturated aqueous sodium hydrogen carbonate solution was poured, and extracted with tert-butyl methyl ether. The organic layer was dried over sodium sulfate, and concentrated under reduced pressure. The resulting residue was subjected to silica gel column chromatography to give 43 mg of 2-(2-ethylsulfanylphenyl)-3-methyl-6-pentafluoroethyl-3H-imidazo[4,5-b]pyridine (hereinafter referred to as Present Compound 55).

Present Compound 55

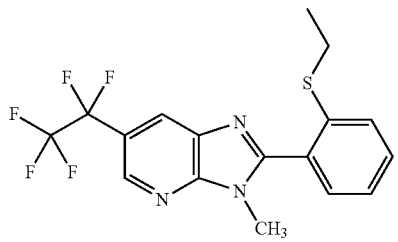 [SMILES: CCSc1ccccc1-c1nc2cc(C(F)(F)C(F)(F)F)cnc2n1C]

¹H-NMR (CDCl₃) δ: 8.66 (1H, d), 8.30 (1H, d), 7.56-7.49 (2H, m), 7.47-7.43 (1H, m), 7.38-7.34 (1H, m), 3.78 (3H, s), 2.88 (2H, q), 1.24 (3H, t)

Production Example 56

A mixture of 6-bromo-2-(2-ethylsulfanylphenyl)-3-methyl-3H-imidazo[4,5-b]pyridine (0.35 g), tripotassium phosphate (0.42 g), phenylboronic acid (0.13 g), 2-dicyclohexylphosphino-2',6'-dimethoxybiphenyl (0.03 g), tris(dibenzylideneacetone)dipalladium(0) (0.01 g), and 1,4-dioxane (3 ml) was stirred with heating at 70° C. for 2 hours, and then heated to 90° C., and stirred with heating for further 2 hours. Into the reaction mixture cooled to room temperature, saturated aqueous ammonium chloride solution was poured, and extracted with ethyl acetate. The organic layer was dried over sodium sulfate, and concentrated under reduced pressure. The resulting residue was subjected to silica gel column chromatography to give 0.37 g of 2-(2-ethylsulfanylphenyl)-3-methyl-6-phenyl-3H-imidazo[4,5-b]pyridine (hereinafter referred to as Present Compound 56).

Present Compound 56

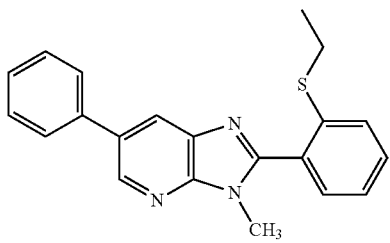 [SMILES: CCSc1ccccc1-c1nc2cc(-c3ccccc3)cnc2n1C]

¹H-NMR (CDCl₃) δ: 8.67 (1H, d), 8.26 (1H, d), 7.63-7.69 (2H, m), 7.45-7.54 (5H, m), 7.38-7.43 (1H, m), 7.32-7.37 (1H, m), 3.77 (3H, s), 2.88 (2H, q), 1.25 (3H, t)

Production Example 57

The procedure was performed according to the method described in Production Example 3 using 2-(2-ethylsulfanylphenyl)-3-methyl-6-phenyl-3H-imidazo[4,5-b]pyridine instead of 3-methyl-2-(2-methylsulfanylphenyl)-6-trifluoromethyl-3H-imidazo[4,5-b]pyridine to give 0.04 g of 2-(2-ethylsulfonylphenyl)-3-methyl-6-phenyl-3H-imidazo[4,5-b]pyridine (hereinafter referred to as Present Compound 57).

Present Compound 57

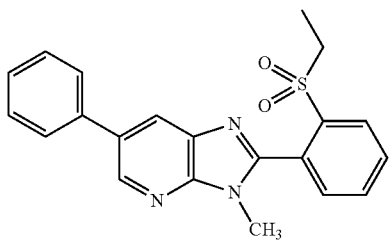 [SMILES: CCS(=O)(=O)c1ccccc1-c1nc2cc(-c3ccccc3)cnc2n1C]

¹H-NMR (CDCl₃) δ: 8.70 (1H, d), 8.22-8.25 (1H, m), 8.20 (1H, d), 7.77-7.86 (2H, m), 7.64-7.68 (2H, m), 7.57-7.60 (1H, m), 7.48-7.54 (2H, m), 7.38-7.44 (1H, m), 3.72 (3H, s), 3.40-3.53 (2H, m), 1.23-1.29 (3H, m)

Production Example 58

To a mixture of 6-bromo-2-(2-ethylsulfanylphenyl)-3-methyl-3H-imidazo[4,5-b]pyridine (350 mg) and 1,4-dioxane (5 ml), 2-fluorophenylboronic acid (150 mg), tripotassium phosphate (600 mg), 2-dicyclohexylphosphino-2',6'-dimethoxybiphenyl (25 mg), and tris(dibenzylideneacetone)palladium(0) (14 mg) were sequentially added, heated to 80° C., and stirred with heating for 8 hours. The reaction mixture was cooled to room temperature, and then water was poured into the reaction mixture, and extracted with ethyl acetate. The organic layer was dried over sodium sulfate, and concentrated under reduced pressure. The resulting residue was subjected to silica gel column chromatography to give 349 mg of 2-(2-ethylsulfanylphenyl)-6-(2-fluorophenyl)-3-methyl-3H-imidazo[4,5-b]pyridine (hereinafter referred to as Present Compound 58).

Present Compound 58

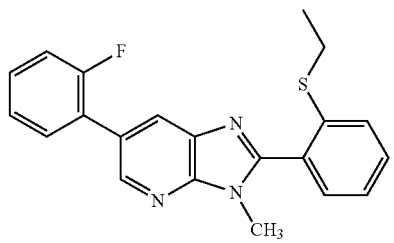 [SMILES: CCSc1ccccc1-c1nc2cc(-c3ccccc3F)cnc2n1C]

¹H-NMR (CDCl₃) δ: 8.63-8.61 (1H, m), 8.27-8.25 (1H, m), 7.54-7.46 (4H, m), 7.41-7.18 (4H, m), 3.78 (3H, s), 2.88 (2H, q), 1.28-1.22 (3H, m)

Production Examples 59 and 60

The procedure was performed according to the method described in Production Examples 16 and 17 using 2-(2-ethylsulfanylphenyl)-6-(2-fluorophenyl)-3-methyl-3H-imidazo[4,5-b]pyridine instead of 2-(2-tert-butylsulfanylphenyl)-3-methyl-6-trifluoromethyl-3H-imidazo[4,5-b]pyridine to give 150 mg of 2-(2-ethylsulfinylphenyl)-6-(2-fluorophenyl)-3-methyl-3H-imidazo[4,5-b]pyridine (hereinafter referred to as Present Compound 59) and 140 mg of 2-(2-ethylsulfonylphenyl)-6-(2-fluorophenyl)-3-methyl-3H-imidazo[4,5-b]pyridine (hereinafter referred to as Present Compound 60).

Present Compound 59

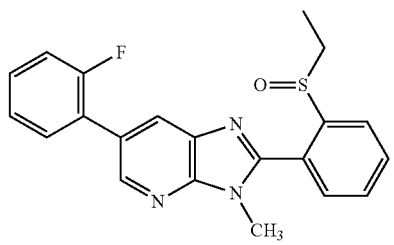 [SMILES: CCS(=O)c1ccccc1-c1nc2cc(-c3ccccc3F)cnc2n1C]

¹H-NMR (CDCl₃) δ: 8.67-8.65 (1H, m), 8.27-8.23 (2H, m), 7.81 (1H, td), 7.69 (1H, t), 7.62 (1H, dd), 7.53 (1H, td), 7.43-7.37 (1H, m), 7.31-7.21 (2H, m), 3.89 (3H, s), 3.42-3.32 (1H, m), 3.02-2.92 (1H, m), 1.29 (3H, t)

Present Compound 60

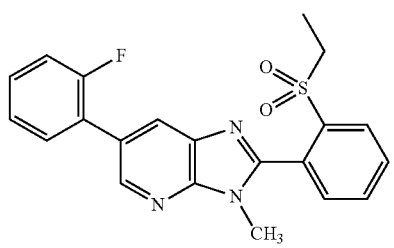 [SMILES: CCS(=O)(=O)c1ccccc1-c1nc2cc(-c3ccccc3F)cnc2n1C]

¹H-NMR (CDCl₃) δ: 8.64 (1H, d), 8.24-8.20 (2H, m), 7.84-7.76 (2H, m), 7.60-7.57 (1H, m), 7.55-7.49 (1H, m), 7.40-7.33 (1H, m), 7.29-7.18 (2H, m), 3.72 (3H, s), 3.48 (2H, q), 1.28-1.22 (3H, m)

Production Example 61

To a mixture of 6-bromo-2-(2-ethylsulfanylphenyl)-3-methyl-3H-imidazo[4,5-b]pyridine (350 mg) and 1,4-dioxane (5 ml), 3-fluorophenylboronic acid (150 mg), sodium carbonate (320 mg), and dichloro[1,1'-bis(diphenylphosphino)ferrocene]palladium(II) (22 mg) were sequentially added. The mixture was heated to 80° C., and stirred with heating for 8 hours. Into the mixture cooled to room temperature, water was poured, and extracted with ethyl acetate. The organic layer was dried over sodium sulfate, and concentrated under reduced pressure. The resulting residue was subjected to silica gel column chromatography to give 240 mg of 2-(2-ethylsulfanylphenyl)-6-(3-fluorophenyl)-3-methyl-3H-imidazo[4,5-b]pyridine (hereinafter referred to as Present Compound 61).

Present Compound 61

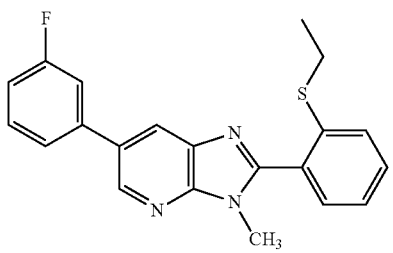 [SMILES: CCSc1ccccc1-c1nc2cc(-c3cccc(F)c3)cnc2n1C]

$^1$H-NMR (CDCl$_3$) δ: 8.65 (1H, d), 8.29 (1H, d), 7.55-7.41 (5H, m), 7.38-7.32 (2H, m), 7.15-7.05 (1H, m), 3.77 (3H, s), 2.86 (2H, q), 1.24 (3H, t)

Production Examples 62 and 63

The procedure was performed according to the method described in Production Examples 16 and 17 using 2-(2-ethylsulfanylphenyl)-6-(3-fluorophenyl)-3-methyl-3H-imidazo[4,5-b]pyridine instead of 2-(2-tert-butylsulfanylphenyl)-3-methyl-6-trifluoromethyl-3H-imidazo[4,5-b]pyridine to give 120 mg of 2-(2-ethylsulfinylphenyl)-6-(3-fluorophenyl)-3-methyl-3H-imidazo[4,5-b]pyridine (hereinafter referred to as Present Compound 62) and 34 mg of 2-(2-ethylsulfonylphenyl)-6-(3-fluorophenyl)-3-methyl-3H-imidazo[4,5-b]pyridine (hereinafter referred to as Present Compound 63).

Present Compound 62

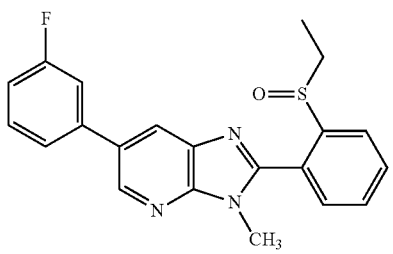 [SMILES: CCS(=O)c1ccccc1-c1nc2cc(-c3cccc(F)c3)cnc2n1C]

$^1$H-NMR (CDCl$_3$) δ: 8.69 (1H, d), 8.26 (1H, dd), 8.22 (1H, d), 7.82 (1H, td), 7.69 (1H, td), 7.62 (1H, dd), 7.51-7.42 (2H, m), 7.39-7.34 (1H, m), 7.15-7.08 (1H, m), 3.89 (3H, s), 3.43-3.33 (1H, m), 3.02-2.92 (1H, m), 1.30 (3H, t)

Present Compound 63

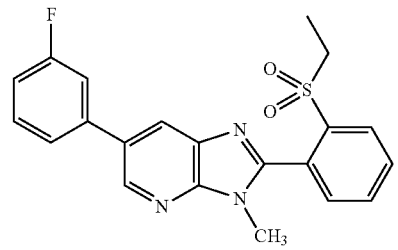 [SMILES: CCS(=O)(=O)c1ccccc1-c1nc2cc(-c3cccc(F)c3)cnc2n1C]

$^1$H-NMR (CDCl$_3$) δ: 8.60 (1H, d), 8.16 (1H, dd), 8.11 (1H, d), 7.78-7.71 (2H, m), 7.51 (1H, dd), 7.42-7.34 (2H, m), 7.28 (1H, dd), 7.06-6.99 (1H, m), 3.65 (3H, s), 3.40 (2H, q), 1.19 (3H, t)

Production Example 64

The procedure was performed according to the method described in Production Example 61 using 4-fluorophenylboronic acid instead of 3-fluorophenylboronic acid to give 140 mg of 2-(2-ethylsulfanylphenyl)-6-(4-fluorophenyl)-3-methyl-3H-imidazo[4,5-b]pyridine (hereinafter referred to as Present Compound 64).

Present Compound 64

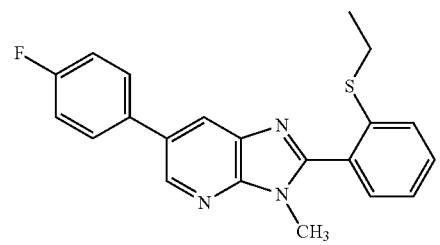 [SMILES: CCSc1ccccc1-c1nc2cc(-c3ccc(F)cc3)cnc2n1C]

$^1$H-NMR (CDCl$_3$) δ: 8.61 (1H, d), 8.22 (1H, d), 7.63-7.57 (2H, m), 7.54-7.45 (3H, m), 7.38-7.33 (1H, m), 7.23-7.16 (2H, m), 3.77 (3H, s), 2.88 (2H, q), 1.24 (3H, t)

Production Example 65

The procedure was performed according to the method described in Production Example 3 using 2-(2-ethylsulfanylphenyl)-6-(4-fluorophenyl)-3-methyl-3H-imidazo[4,5-b]pyridine instead of 3-methyl-2-(2-methylsulfanylphenyl)-6-trifluoromethyl-3H-imidazo[4,5-b]pyridine to give 58 mg of 2-(2-ethylsulfonylphenyl)-6-(4-fluorophenyl)-3-methyl-3H-imidazo[4,5-b]pyridine (hereinafter referred to as Present Compound 65).

Present Compound 65

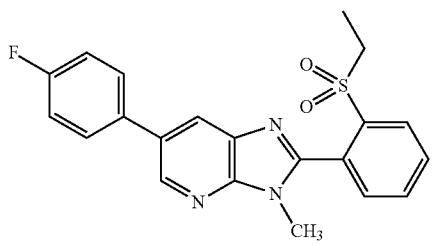 [SMILES: CCS(=O)(=O)c1ccccc1-c1nc2cc(-c3ccc(F)cc3)cnc2n1C]

¹H-NMR (CDCl₃) δ: 8.64 (1H, d), 8.24-8.22 (1H, m), 8.15 (1H, d), 7.86-7.78 (2H, m), 7.62-7.58 (3H, m), 7.22-7.18 (2H, m), 3.72 (3H, s), 3.47 (2H, q), 1.26 (3H, t)

Production Example 66

The procedure was performed according to the method described in Production Example 21 using N³-methyl-5-trifluoromethyl-pyridin-2,3-diamine instead of N²-ethyl-5-trifluoromethylpyridin-2,3-diamine to give 67 mg of 2-(2-ethylsulfanylphenyl)-1-methyl-6-trifluoromethyl-1H-imidazo[4,5-b]pyridine (hereinafter referred to as Present Compound 66).

Present Compound 66

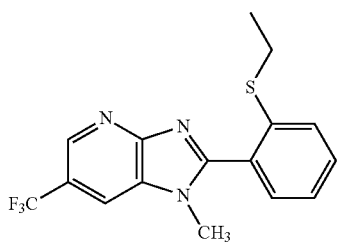 [SMILES: CCSc1ccccc1-c1nc2ncc(C(F)(F)F)cc2n1C]

¹H-NMR (CDCl₃) δ: 8.87 (1H, d), 7.99 (1H, d), 7.54-7.48 (3H, m), 7.41-7.34 (1H, m), 3.73 (3H, s), 2.84 (2H, q), 1.21 (3H, t)

Production Example 67

The procedure was performed according to the method described in Production Example 1 using N¹-methyl-4-trifluoromethylbenzene-1,2-diamine instead of N²-methyl-5-trifluoromethylpyridin-2,3-diamine to give 0.28 g of 1-methyl-2-(2-methylsulfanylphenyl)-5-trifluoromethyl-1H-benzimidazole (hereinafter referred to as Present Compound 67).

Present Compound 67

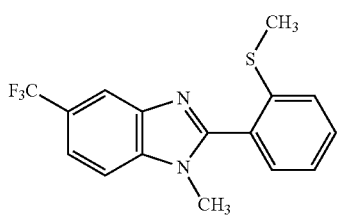

¹H-NMR (CDCl₃) δ: 8.12 (1H, brs), 7.62-7.58 (1H, m), 7.55-7.48 (2H, m), 7.45-7.39 (2H, m), 7.34-7.29 (1H, m), 3.70 (3H, s), 2.41 (3H, s)

Production Example 68

A mixture of 2-ethylsulfanyl-N-(2-methylamino-5-trifluoromethylphenyl)-benzamide (1.64 g), p-toluenesulfonic acid monohydrate (1.76 g), and xylene (50 ml) was stirred under reflux at 150° C. for 1 hour. Into the reaction mixture cooled to room temperature, saturated aqueous sodium hydrogen carbonate solution was poured, and extracted with ethyl acetate. The organic layer was washed with saturated aqueous sodium hydrogen carbonate solution and saturated brine, dried over sodium sulfate, and concentrated under reduced pressure. The resulting residue was subjected to silica gel column chromatography to give 1.40 g of 2-(2-ethylsulfanylphenyl)-1-methyl-5-trifluoromethyl-1H-benzimidazole (hereinafter referred to as Present Compound 68).

Present Compound 68

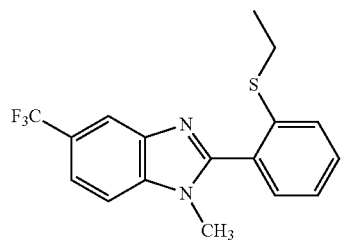

¹H-NMR (CDCl₃) δ: 8.12-8.10 (1H, m), 7.61-7.58 (1H, m), 7.53-7.44 (4H, m), 7.38-7.32 (1H, m), 3.69 (3H, s), 2.84 (2H, q), 1.22 (3H, t)

Production Example 69

The procedure was performed according to the method described in Production Example 2 using 2-(2-ethylsulfanylphenyl)-1-methyl-5-trifluoromethyl-1H-benzimidazole instead of 3-methyl-2-(2-methylsulfanylphenyl)-6-trifluoromethyl-3H-imidazo[4,5-b]pyridine to give 0.30 g of 2-(2-ethylsulfinylphenyl)-1-methyl-5-trifluoromethyl-1H-benzimidazole (hereinafter referred to as Present Compound 69).

Present Compound 69

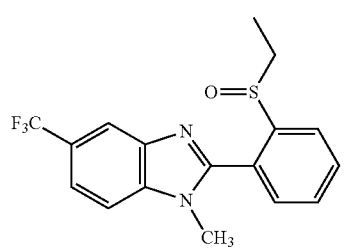

¹H-NMR (CDCl₃) δ: 8.24-8.20 (1H, m), 8.10-8.07 (1H, m), 7.83-7.78 (1H, m), 7.70-7.62 (2H, m), 7.57-7.51 (2H, m), 3.79 (3H, s), 3.36-3.26 (1H, m), 2.98-2.88 (1H, m), 1.26 (3H, t)

Production Example 70

The procedure was performed according to the method described in Production Example 3 using 2-(2-ethylsulfanylphenyl)-1-methyl-5-trifluoromethyl-1H-benzimidazole instead of 3-methyl-2-(2-methylsulfanylphenyl)-6-trifluoromethyl-3H-imidazo[4,5-b]pyridine to give 0.24 g of 2-(2-ethylsulfonylphenyl)-1-methyl-5-trifluoromethyl-1H-benzimidazole (hereinafter referred to as Present Compound 70).

Present Compound 70

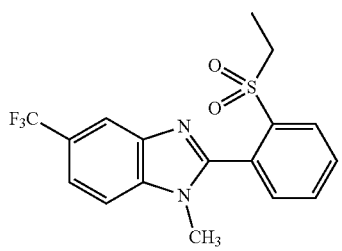

$^1$H-NMR (CDCl$_3$) δ: 8.24-8.20 (1H, m), 8.07-8.05 (1H, m), 7.84-7.77 (2H, m), 7.64-7.61 (1H, m), 7.57-7.54 (1H, m), 7.53-7.49 (1H, m), 3.63 (3H, s), 3.46-3.34 (2H, m), 1.23 (3H, t)

Production Example 71

To a mixture of 3-chloro-N$^2$-methyl-5-trifluoromethylbenzene-1,2-diamine (1.12 g) and THF (5 ml), 2-ethylsulfanylbenzoic acid hydrochloride (1.00 g) was added under ice-cooling, heated to room temperature, and stirred for 1 hour. Sodium hydrogen carbonate (0.46 g) was added thereto, and then the reaction mixture was allowed to stand overnight. The reaction mixture was heated to 66° C., and stirred under reflux for 1.5 hours. After the mixture was cooled to room temperature, 2-ethylsulfanylbenzoic acid hydrochloride (0.5 g) was added at room temperature. After the reaction mixture was allowed to stand at room temperature overnight, sodium hydrogen carbonate (1.00 g) was added, and stirred. The reaction mixture was ice-cooled, and then water was added under ice-cooling, and extracted with ethyl acetate. The organic layer was washed with saturated aqueous sodium hydrogen carbonate solution and saturated brine, dried over sodium sulfate, and concentrated under reduced pressure. The resulting residue was subjected to silica gel column chromatography to give 0.48 g of 7-chloro-2-(2-ethylsulfanylphenyl)-1-methyl-5-trifluoromethyl-1H-benzimidazole (hereinafter referred to as Present Compound 71).

Present Compound 71

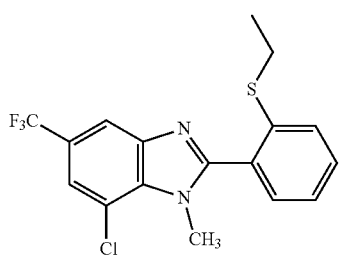 [SMILES: CCSc1ccccc1-c1nc2cc(C(F)(F)F)cc(Cl)c2n1C]

$^1$H-NMR (CDCl$_3$) δ: 7.99-7.98 (1H, m), 7.54-7.48 (3H, m), 7.44-7.41 (1H, m), 7.37-7.32 (1H, m), 3.94 (3H, s), 2.86 (2H, q), 1.24 (3H, t)

Production Example 72

The procedure was performed according to the method described in Production Example 2 using 7-chloro-2-(2-ethylsulfanylphenyl)-1-methyl-5-trifluoromethyl-1H-benzimidazole instead of 3-methyl-2-(2-methylsulfanylphenyl)-6-trifluoromethyl-3H-imidazo[4,5-b]pyridine to give 0.13 g of 7-chloro-2-(2-ethylsulfinylphenyl)-1-methyl-5-trifluoromethyl-1H-benzimidazole (hereinafter referred to as Present Compound 72).

Present Compound 72

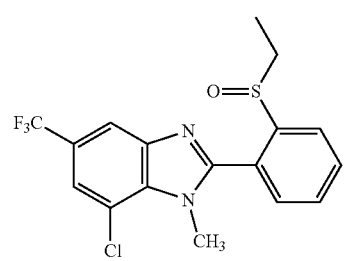 [SMILES: CCS(=O)c1ccccc1-c1nc2cc(C(F)(F)F)cc(Cl)c2n1C]

$^1$H-NMR (CDCl$_3$) δ: 8.23-8.20 (1H, m), 7.97-7.95 (1H, m), 7.85-7.80 (1H, m), 7.71-7.66 (1H, m), 7.58-7.51 (2H, m), 4.04 (3H, s), 3.32-3.21 (1H, m), 2.96-2.87 (1H, m), 1.25 (3H, t)

Production Example 73

The procedure was performed according to the method described in Production Example 3 using 7-chloro-2-(2-ethylsulfanylphenyl)-1-methyl-5-trifluoromethyl-1H-benzimidazole instead of 3-methyl-2-(2-methylsulfanylphenyl)-6-trifluoromethyl-3H-imidazo[4,5-b]pyridine to give 0.16 g of 7-chloro-2-(2-ethylsulfonylphenyl)-1-methyl-5-trifluoromethyl-1H-benzimidazole (hereinafter referred to as Present Compound 73).

Present Compound 73

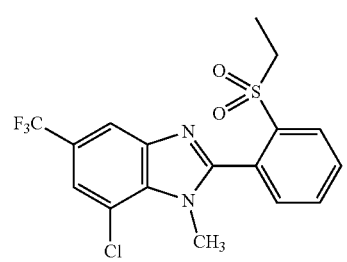

$^1$H-NMR (CDCl$_3$) δ: 8.24-8.20 (1H, m), 7.94-7.92 (1H, m), 7.86-7.78 (2H, m), 7.58-7.52 (2H, m), 3.90 (3H, s), 3.60-3.16 (2H, m), 1.24 (3H, t)

Production Example 74

A mixture of 3-bromo-N$^2$-methyl-5-trifluoromethylbenzene-1,2-diamine (2.22 g), 2-ethylsulfanylbenzoic acid (1.80 g), WSC (1.40 g), and pyridine (10 ml) was stirred under reflux at 115° C. for 6 hours. Into the reaction mixture cooled to room temperature, water was poured, and extracted with ethyl acetate. The organic layer was dried over magnesium sulfate, and concentrated under reduced pressure. The resulting residue was subjected to silica gel column chromatography to give 1.48 g of 7-bromo-2-(2-ethylsulfanylphenyl)-1- methyl-5-trifluoromethyl-1H-benzimidazole (hereinafter referred to as Present Compound 74).

Present Compound 74

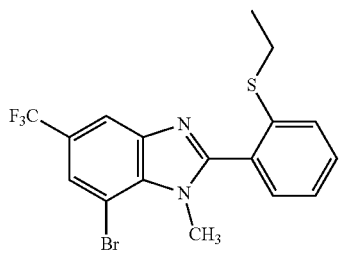 [SMILES: CCSc1ccccc1-c1nc2cc(C(F)(F)F)cc(Br)c2n1C]

¹H-NMR (CDCl₃) δ: 8.03-8.02 (1H, m), 7.71-7.70 (1H, m), 7.54-7.47 (2H, m), 7.44-7.41 (1H, m), 7.37-7.32 (1H, m), 3.95 (3H, s), 2.86 (2H, q), 1.24 (3H, t)

Production Examples 75 and 76

The procedure was performed according to the method described in Production Examples 16 and 17 using 7-bromo-2-(2-ethylsulfanylphenyl)-1-methyl-5-trifluoromethyl-1H-benzimidazole instead of 2-(2-tert-butylsulfanylphenyl)-3-methyl-6-trifluoromethyl-3H-imidazo[4,5-b]pyridine to give 7-bromo-2-(2-ethylsulfinylphenyl)-1-methyl-5-trifluoromethyl-1H-benzimidazole (hereinafter referred to as Present Compound 75) and 7-bromo-2-(2-ethylsulfonylphenyl)-1-methyl-5-trifluoromethyl-1H-benzimidazole (hereinafter referred to as Present Compound 76).

Present Compound 75

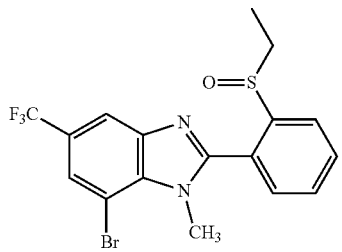 [SMILES: CCS(=O)c1ccccc1-c1nc2cc(C(F)(F)F)cc(Br)c2n1C]

¹H-NMR (CDCl₃) δ: 8.24-8.20 (1H, m), 8.03-7.99 (1H, m), 7.86-7.80 (1H, m), 7.77-7.75 (1H, m), 7.72-7.66 (1H, m), 7.56-7.52 (1H, m), 4.05 (3H, s), 3.33-3.23 (1H, m), 2.98-2.88 (1H, m), 1.26 (3H, t)

Present Compound 76

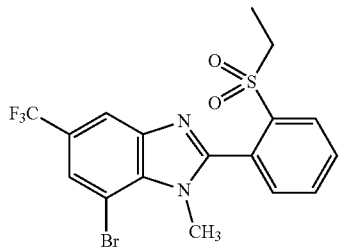 [SMILES: CCS(=O)(=O)c1ccccc1-c1nc2cc(C(F)(F)F)cc(Br)c2n1C]

¹H-NMR (CDCl₃) δ: 8.24-8.20 (1H, m), 7.99-7.96 (1H, m), 7.86-7.78 (2H, m), 7.75-7.73 (1H, m), 7.57-7.53 (1H, m), 3.90 (3H, s), 3.58-3.19 (2H, m), 1.25 (3H, t)

Production Example 77

To a mixture of N-(2-hydroxy-5-trifluoromethylphenyl)-2-methylsulfanylbenzamide (0.33 g), triphenylphosphine (0.34 g), and THF (7 ml), diethyl azodicarboxylate (40% in toluene) (0.57 g) was added dropwise, and stirred at room temperature for 1.5 hours. Triphenylphosphine (79 mg) and diethyl azodicarboxylate (40% in toluene, 0.13 g) were added to the mixture, and stirred for further 1 hour. The mixture was heated to 50° C., and stirred for 1.5 hours. The reaction mixture was cooled to room temperature, and then the mixture was allowed to stand at room temperature overnight. The reaction mixture was subjected to silica gel column chromatography to give 0.28 g of 2-(2-methylsulfanylphenyl)-5-trifluoromethylbenzoxazole (hereinafter referred to as Present Compound 77).

Present Compound 77

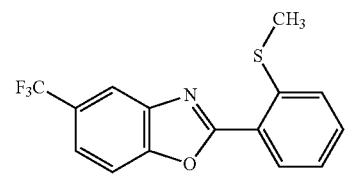 [SMILES: CSc1ccccc1-c1nc2cc(C(F)(F)F)ccc2o1]

¹H-NMR (CDCl₃) δ: 8.22-8.19 (1H, m), 8.17-8.15 (1H, m), 7.71-7.67 (1H, m), 7.66-7.63 (1H, m), 7.55-7.50 (1H, m), 7.41-7.37 (1H, m), 7.32-7.27 (1H, m), 2.57 (3H, s)

Production Example 78

A mixture of 2-amino-4-trifluoromethyl-phenol (0.97 g), 2-ethylsulfanylbenzoic acid (1.10 g), WSC (1.27 g), HOBt (37 mg), and pyridine (5 ml) was stirred under reflux at 115° C. for 2.5 hours. After the mixture was allowed to stand overnight, the mixture was stirred under reflux at 115° C. for 6 hours. Into the reaction mixture cooled to room temperature, water was poured, and extracted with ethyl acetate. The organic layer was washed with water, saturated aqueous sodium hydrogen carbonate solution, and saturated brine, sequentially, dried over sodium sulfate, and concentrated under reduced pressure.

A mixture of the resulting residue, p-toluenesulfonic acid monohydrate (2.09 g), and xylene (50 ml) was stirred under reflux at 153° C. for 2 hours. Into the reaction mixture cooled to room temperature, saturated aqueous sodium hydrogen carbonate solution was poured, and extracted with ethyl acetate. The organic layer was washed with saturated aqueous sodium hydrogen carbonate solution, water, 10% aqueous citric acid solution, water, saturated aqueous sodium hydrogen carbonate solution, and saturated brine, sequentially, dried over sodium sulfate, and concentrated under reduced pressure. The resulting residue was subjected to silica gel column chromatography to give 0.98 g of 2-(2-ethylsulfanylphenyl)-5-trifluoromethylbenzoxazole (hereinafter referred to as Present Compound 78).

Present Compound 78

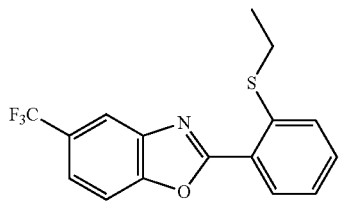

¹H-NMR (CDCl₃) δ: 8.19-8.15 (2H, m), 7.71-7.67 (1H, m), 7.66-7.63 (1H, m), 7.52-7.47 (1H, m), 7.45-7.42 (1H, m), 7.31-7.27 (1H, m), 3.06 (2H, q), 1.44 (3H, t)

Production Example 79

The procedure was performed according to the method described in Production Example 2 using 2-(2-ethylsulfanylphenyl)-5-trifluoromethylbenzoxazole instead of 3-methyl-2-(2-methylsulfanylphenyl)-6-trifluoromethyl-3H-imidazo[4,5-b]pyridine to give 0.27 g of 2-(2-ethylsulfinylphenyl)-5-trifluoromethylbenzoxazole (hereinafter referred to as Present Compound 79).

Present Compound 79

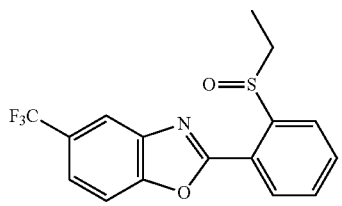

¹H-NMR (CDCl₃) δ: 8.35-8.30 (2H, m), 8.12-8.10 (1H, m), 7.85-7.79 (1H, m), 7.75-7.66 (3H, m), 3.48-3.38 (1H, m), 3.00-2.90 (1H, m), 1.41 (3H, t)

Production Example 80

The procedure was performed according to the method described in Production Example 3 using 2-(2-ethylsulfanylphenyl)-5-trifluoromethylbenzoxazole instead of 3-methyl-2-(2-methylsulfanylphenyl)-6-trifluoromethyl-3H-imidazo[4,5-b]pyridine to give 0.24 g of 2-(2-ethylsulfonylphenyl)-5-trifluoromethylbenzoxazole (hereinafter referred to as Present Compound 80).

Present Compound 80

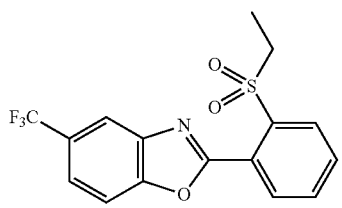 [SMILES: CCS(=O)(=O)c1ccccc1-c1nc2cc(C(F)(F)F)ccc2o1]

¹H-NMR (CDCl₃) δ: 8.28-8.24 (1H, m), 8.11-8.09 (1H, m), 7.99-7.95 (1H, m), 7.85-7.77 (2H, m), 7.72-7.70 (2H, m), 3.82 (2H, q), 1.40 (3H, t)

Production Example 81

A mixture of 2-ethylsulfanylphenyl-N-(2-hydroxy-5-trifluoromethylpyridin-3-yl)-benzamide (0.92 g) and phosphorous oxychloride (5 ml) was heated to 120° C., and stirred under reflux. The reaction mixture cooled to room temperature was allowed to stand overnight. The mixture was heated to 120° C. again, and stirred under reflux for 2 hours. Into the reaction mixture cooled to room temperature, water was poured, and then the precipitated solid was collected by filtration, washed with water and hexane, and dried to give 0.53 g of 2-(2-ethylsulfanylphenyl)-6-trifluoromethyloxazolo[5,4-b]pyridine (hereinafter referred to as Present Compound 81).

Present Compound 81

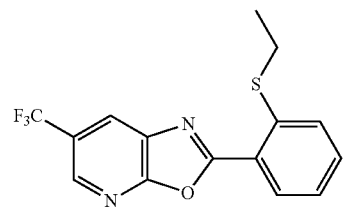 [SMILES: CCSc1ccccc1-c1nc2cc(C(F)(F)F)cnc2o1]

¹H-NMR (CDCl₃) δ: 8.67 (1H, s), 8.40 (1H, s), 8.25 (1H, d), 7.53 (1H, t), 7.45 (1H, d), 7.32 (1H, t), 3.08 (2H, q), 1.45 (3H, t)

Production Example 82

The procedure was performed according to the method described in Production Example 2 using 2-(2-ethylsulfanylphenyl)-6-trifluoromethyloxazolo[5,4-b]pyridine instead of 3-methyl-2-(2-methylsulfanylphenyl)-6-trifluoromethyl-3H-imidazo[4,5-b]pyridine to give 0.17 g of 2-(2-ethylsulfinylphenyl)-6-trifluoromethyloxazolo[5,4-b]pyridine (hereinafter referred to as Present Compound 82).

Present Compound 82

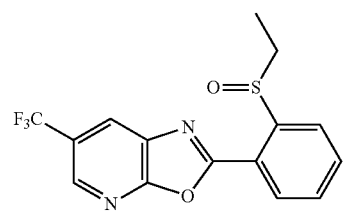 [SMILES: CCS(=O)c1ccccc1-c1nc2cc(C(F)(F)F)cnc2o1]

¹H-NMR (CDCl₃) δ: 8.73-8.72 (1H, m), 8.41-8.38 (2H, m), 8.36-8.33 (1H, m), 7.90-7.84 (1H, m), 7.74-7.69 (1H, m), 3.45-3.35 (1H, m), 3.00-2.90 (1H, m), 1.40 (3H, t)

Production Example 83

The procedure was performed according to the method described in Production Example 3 using 2-(2-ethylsulfanylphenyl)-6-trifluoromethyloxazolo[5,4-b]pyridine instead of 3-methyl-2-(2-methylsulfanylphenyl)-6-trifluoromethyl-3H-imidazo[4,5-b]pyridine to give 0.19 g of 2-(2-ethylsulfonylphenyl)-6-trifluoromethyloxazolo[5,4-b]pyridine (hereinafter referred to as Present Compound 83).

Present Compound 83

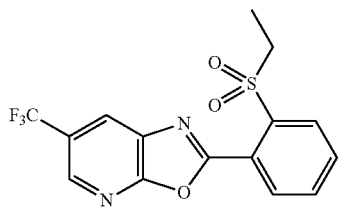 [SMILES: CCS(=O)(=O)c1ccccc1-c1nc2cc(C(F)(F)F)cnc2o1]

¹H-NMR (CDCl₃) δ: 8.75-8.73 (1H, m), 8.40-8.37 (1H, m), 8.29-8.26 (1H, m), 8.05-8.02 (1H, m), 7.89-7.81 (2H, m), 3.81 (2H, q), 1.43 (3H, t)

Production Example 84

A mixture of 2-amino-4-trifluoromethylbenzenethiol hydrochloride (0.50 g), 2-methylsulfanylbenzaldehyde (0.33 g), diisopropylethylamine (0.28 g), and DMSO (4 ml) was heated to 170-180° C., and stirred with heating for 3 hours. Into the reaction mixture cooled to room temperature, water was poured, and extracted with ethyl acetate. The organic layer was washed with water and saturated brine, dried over magnesium sulfate, and concentrated under reduced pressure. The resulting residue was subjected to silica gel column chromatography to give 0.42 g of 2-(2-methylsulfanylphenyl)-5-trifluoromethylbenzothiazole (hereinafter referred to as Present Compound 84).

Present Compound 84

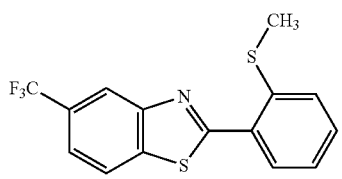

¹H-NMR (CDCl₃) δ: 8.42-8.40 (1H, m), 8.05-8.02 (1H, m), 7.92-7.89 (1H, m), 7.66-7.63 (1H, m), 7.50-7.42 (2H, m), 7.32-7.27 (1H, m), 2.51 (3H, s)

Production Example 85

The procedure was performed according to the method described in Production Example 71 using 2-amino-4-trifluoromethylbenzenethiol hydrochloride instead of 3-chloro-N²-methyl-5-trifluoromethylbenzene-1,2-diamine to give 0.50 g of 2-(2-ethylsulfanylphenyl)-5-trifluoromethylbenzothiazole (hereinafter referred to as Present Compound 85).

Present Compound 85

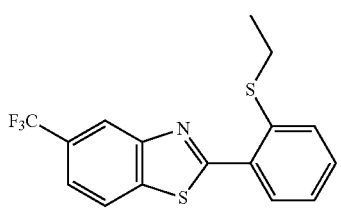 [SMILES: CCSc1ccccc1-c1nc2cc(C(F)(F)F)ccc2s1]

¹H-NMR (CDCl₃) δ: 8.41-8.39 (1H, m), 8.06-8.00 (2H, m), 7.66-7.62 (1H, m), 7.55-7.51 (1H, m), 7.48-7.42 (1H, m), 7.37-7.32 (1H, m), 2.96 (2H, q), 1.33 (3H, t)

Production Example 86

The procedure was performed according to the method described in Production Example 2 using 2-(2-ethylsulfanylphenyl)-5-trifluoromethylbenzothiazole instead of 3-methyl-2-(2-methylsulfanylphenyl)-6-trifluoromethyl-3H-imidazo[4,5-b]pyridine to give 0.25 g of 2-(2-ethylsulfinylphenyl)-5-trifluoromethylbenzothiazole (hereinafter referred to as Present Compound 86).

Present Compound 86

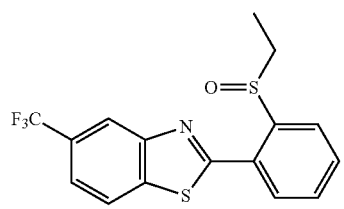 [SMILES: CCS(=O)c1ccccc1-c1nc2cc(C(F)(F)F)ccc2s1]

¹H-NMR (CDCl₃) δ: 8.36-8.32 (1H, m), 8.32-8.30 (1H, m), 8.08-8.05 (1H, m), 7.97-7.94 (1H, m), 7.80-7.75 (1H, m), 7.71-7.68 (1H, m), 7.66-7.61 (1H, m), 3.56-3.45 (1H, m), 3.02-2.93 (1H, m), 1.46 (3H, t)

Production Example 87

The procedure was performed according to the method described in Production Example 3 using 2-(2-ethylsulfanylphenyl)-5-trifluoromethylbenzothiazole instead of 3-methyl-2-(2-methylsulfanylphenyl)-6-trifluoromethyl-3H-imidazo[4,5-b]pyridine to give 0.30 g of 2-(2-ethylsulfonylphenyl)-5-trifluoromethylbenzothiazole (hereinafter referred to as Present Compound 87).

Present Compound 87

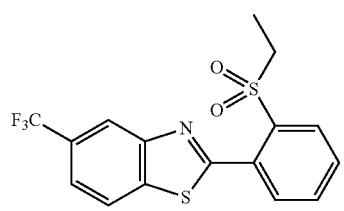

¹H-NMR (CDCl₃) δ: 8.33-8.31 (1H, m), 8.26-8.23 (1H, m), 8.10-8.06 (1H, m), 7.81-7.69 (4H, m), 3.75 (2H, q), 1.36 (3H, t)

Production Example 88

A mixture of N²-methyl-5-trifluoromethylpyridin-2,3-diamine (1.14 g), 3-chloro-2-ethylsulfanylbenzoic acid (1.56 g), WSC (1.02 g), and pyridine (12 ml) was stirred under reflux at 115° C. for 3 hours. Into the reaction mixture cooled to room temperature, water was poured, and extracted with ethyl acetate. The organic layer was washed with water and saturated brine, dried over magnesium sulfate, and concentrated under reduced pressure.

To the resulting residue, tripotassium phosphate (3.82 g) and pyridine (12 ml) were added, and stirred under reflux at 115° C. for 2.5 hours. The reaction mixture was cooled to room temperature, and then the solvent was evaporated. Tripotassium phosphate (3.82 g) and DMSO (12 ml) were added to the resulting residue, and stirred with heating at 150° C. for 1 hour. The mixture was heated to 165° C., and stirred with heating for further 2 hours. Into the reaction mixture cooled to room temperature, water was poured, and extracted with ethyl acetate. The organic layer was washed with water and saturated brine, dried over magnesium sulfate, and concentrated under reduced pressure. The resulting residue was subjected to silica gel column chromatography to give 0.96 g of 2-(3-chloro-2-ethylsulfanylphenyl)-3-methyl-6-trifluoromethyl-3H-imidazo[4,5-b]pyridine (hereinafter referred to as Present Compound 88).

Present Compound 88

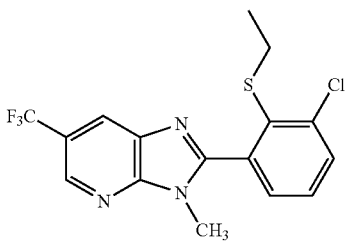 [SMILES: CCSc1c(Cl)cccc1-c1nc2cc(C(F)(F)F)cnc2n1C]

$^1$H-NMR (CDCl$_3$) δ: 8.74-8.72 (1H, m), 8.32-8.30 (1H, m), 7.71 (1H, dd), 7.48-7.42 (2H, m), 3.73 (3H, s), 2.73 (2H, q), 1.05 (3H, t)

Production Example 89

To a mixture of 2-(3-chloro-2-ethylsulfanylphenyl)-3-methyl-6-trifluoromethyl-3H-imidazo[4,5-b]pyridine (0.72 g) and chloroform (10 ml), 3-chloroperbenzoic acid (purity: 69-75%, 0.66 g) was added under ice-cooling, and then heated to room temperature, and stirred for 20 minutes. Into the reaction mixture, saturated aqueous sodium hydrogen carbonate solution and saturated aqueous sodium thiosulfate solution were poured, and extracted with chloroform 2 times. The combined organic layer was dried over magnesium sulfate, and concentrated under reduced pressure. The resulting residue was subjected to silica gel column chromatography to give 0.67 g of 2-(3-chloro-2-ethylsulfinylphenyl)-3-methyl-6-trifluoromethyl-3H-imidazo[4,5-b]pyridine (hereinafter referred to as Present Compound 89).

Present Compound 89

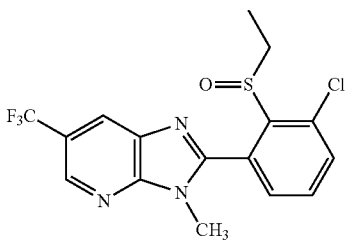 [SMILES: CCS(=O)c1c(Cl)cccc1-c1nc2cc(C(F)(F)F)cnc2n1C]

$^1$H-NMR (CDCl$_3$) δ: 8.69 (1H, d), 8.25 (1H, d), 7.64 (1H, dd), 7.58 (1H, t), 7.39 (1H, dd), 3.71 (3H, s), 3.60-3.49 (1H, m), 3.33-3.23 (1H, m), 1.33 (3H, t)

Production Example 90

A mixture of 2-(3-chloro-2-ethylsulfinylphenyl)-3-methyl-6-trifluoromethyl-3H-imidazo[4,5-b]pyridine (0.48 g) and acetic acid (12 ml) was stirred with heating at 80° C., and then 30% of an aqueous solution of hydrogen peroxide (6 ml) was added dropwise. The mixture was heated to 100° C., and stirred with heating for 3 hours. Into the reaction mixture cooled to room temperature, water was poured, and extracted with ethyl acetate. The organic layer was washed with saturated aqueous sodium hydrogen carbonate solution, dried over magnesium sulfate, and concentrated under reduced pressure. The resulting residue was subjected to silica gel column chromatography to give 0.21 g of 2-(3-chloro-2-ethylsulfonylphenyl)-3-methyl-6-trifluoromethyl-3H-imidazo[4,5-b]pyridine (hereinafter referred to as Present Compound 90).

Present Compound 90

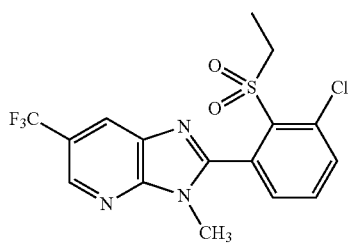 [SMILES: CCS(=O)(=O)c1c(Cl)cccc1-c1nc2cc(C(F)(F)F)cnc2n1C]

$^1$H-NMR (CDCl$_3$) δ: 8.73-8.71 (1H, m), 8.25 (1H, d), 7.85-7.81 (1H, m), 7.71 (1H, t), 7.46-7.43 (1H, m), 3.75 (3H, s), 3.59-3.41 (2H, m), 1.33 (3H, t)

Production Examples 91 and 92

The procedure was performed according to the method described in Production Examples 16 and 17 using 2-(2-ethylsulfanyl-phenyl)-3-methyl-6-pentafluoroethyl-3H-imidazo[4,5-b]pyridine instead of 2-(2-tert-butylsulfanylphenyl)-3-methyl-6-trifluoromethyl-3H-imidazo[4,5-b]pyridine to give 27 mg of 2-(2-ethylsulfinyl-phenyl)-3-methyl-6-pentafluoroethyl-3H-imidazo[4,5-b]pyridine (hereinafter referred to as Present Compound 112) and 31 mg of 2-(2-ethylsulfonylphenyl)-3-methyl-6-pentafluoroethyl-3H-imidazo[4,5-b]pyridine (hereinafter referred to as Present Compound 113).

Present Compound 112

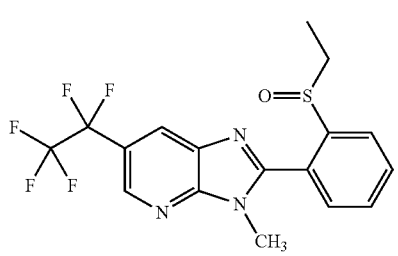 [SMILES: CCS(=O)c1ccccc1-c1nc2cc(C(F)(F)C(F)(F)F)cnc2n1C]

$^1$H-NMR (CDCl$_3$) δ: 8.70 (1H, d), 8.29 (1H, d), 8.27 (1H, d), 7.84 (1H, t), 7.71 (1H, t), 7.60 (1H, d), 3.90 (3H, s), 3.43-3.33 (1H, m), 3.04-2.94 (1H, m), 1.31 (3H, t)

Present Compound 113

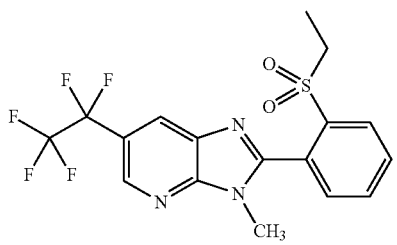

¹H-NMR (CDCl₃) δ: 8.69 (1H, s), 8.25 (1H, s), 8.23-8.22 (1H, m), 7.88-7.79 (2H, m), 7.59-7.52 (1H, m), 3.72 (3H, s), 3.43 (2H, q), 1.26 (3H, t)

Production Example 93

A mixture of N²-methyl-5-trifluoromethylpyridin-2,3-diamine (1.14 g), 2-ethylsulfanyl-4-fluorobenzoic acid (1.44 g), WSC (1.02 g), and pyridine (12 ml) was stirred with heating at 120° C. for 1.5 hours. Into the reaction mixture cooled to room temperature, water was poured, and extracted with ethyl acetate. The organic layer was dried over magnesium sulfate, and concentrated under reduced pressure.

To the resulting residue, p-toluenesulfonic acid (3.42 g), xylene (10 ml) and NMP (2 ml) were added, and stirred under reflux at 150° C. for 4.5 hours with removing water with Dean-Stark apparatus. Into the reaction mixture cooled to room temperature, water was poured, and extracted with ethyl acetate. The organic layer was dried over magnesium sulfate, and concentrated under reduced pressure. The resulting residue was subjected to silica gel column chromatography to give 1.05 g of 2-(2-ethylsulfanyl-4-fluorophenyl)-3-methyl-6-trifluoromethyl-3H-imidazo[4,5-b]pyridine (hereinafter referred to as Present Compound 116).

Present Compound 116

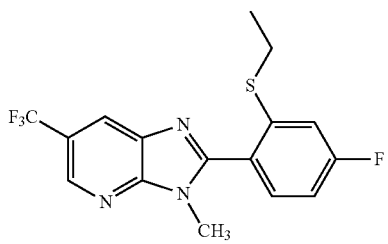 [SMILES: CCSc1cc(F)ccc1-c1nc2cc(C(F)(F)F)cnc2n1C]

¹H-NMR (CDCl₃) δ: 8.70-8.68 (1H, m), 8.31-8.28 (1H, m), 7.43-7.38 (1H, m), 7.17-7.13 (1H, m), 7.04-6.98 (1H, m), 3.75 (3H, s), 2.89 (2H, q), 1.26 (3H, t)

Production Examples 94 and 95

To a mixture of 2-(2-ethylsulfanyl-4-fluorophenyl)-3-methyl-6-trifluoromethyl-3H-imidazo[4,5-b]pyridine (0.85 g) and chloroform (12 ml), 3-chloroperbenzoic acid (purity: not less than 65%, 0.81) was added under ice-cooling, heated to room temperature, and stirred for 30 minutes. Into the reaction mixture, saturated aqueous sodium hydrogen carbonate solution and saturated aqueous sodium thiosulfate solution were poured, and extracted with chloroform. The organic layer was dried over magnesium sulfate, and concentrated under reduced pressure. The resulting residue was subjected to silica gel column chromatography to give 0.33 g of 2-(2-ethylsulfinyl-4-fluorophenyl)-3-methyl-6-trifluoromethyl-3H-imidazo[4,5-b]pyridine (hereinafter referred to as Present Compound 117) and 0.52 g of 2-(2-ethylsulfonyl-4-fluorophenyl)-3-methyl-6-trifluoromethyl-3H-imidazo[4,5-b]pyridine (hereinafter referred to as Present Compound 118).

Present Compound 117

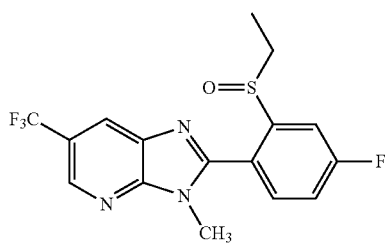

¹H-NMR (CDCl₃) δ: 8.76-8.75 (1H, m), 8.31-8.30 (1H, m), 8.01-7.98 (1H, m), 7.65-7.61 (1H, m), 7.41-7.36 (1H, m), 3.90 (3H, s), 3.47-3.37 (1H, m), 3.04-2.94 (1H, m), 1.33 (3H, t)

Present Compound 118

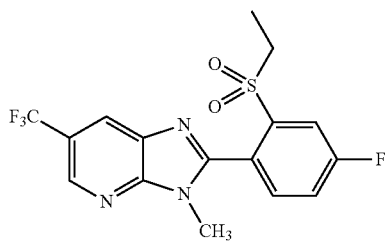

¹H-NMR (CDCl₃) δ: 8.76-8.74 (1H, m), 8.29-8.27 (1H, m), 7.97-7.94 (1H, m), 7.60-7.51 (2H, m), 3.72 (3H, s), 3.44 (2H, q), 1.28 (3H, t)

Production Example 96

To a pressure-resistant reaction container, 6-bromo-2-(2-ethylsulfanylphenyl)-3-methyl-3H-imidazo[4,5-b]pyridine (1.74 g), copper (II) acetylacetone (0.26 g), acetylacetone (0.50 g), cesium carbonate (3.25 g), NMP (9 ml), and 28% of aqueous ammonia (4 ml) were added, and stirred at 120° C. for 6 hours. The mixture was cooled to room temperature, and then saturated aqueous ammonium chloride solution was poured, and extracted with ethyl acetate. The organic layer was dried over sodium sulfate, and concentrated under reduced pressure. The resulting residue was subjected to silica gel column chromatography to give 1.20 g of 6-amino-2-(2-ethylsulfanylphenyl)-3-methyl-3H-imidazo[4,5-b]pyridine (hereinafter referred to as Present Compound 125).

Present Compound 125

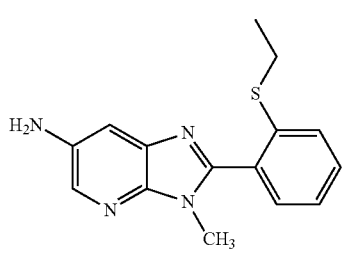 [SMILES: CCSc1ccccc1-c1nc2cc(N)cnc2n1C]

¹H-NMR (CDCl₃) δ: 7.99 (1H, d), 7.40-7.49 (4H, m), 7.28-7.34 (1H, m), 3.61-3.70 (5H, m), 2.85 (2H, q), 1.22 (3H, t)

Production Example 97

A mixture of 2-(2-ethylsulfanyl-phenyl)-6-iodo-3-methyl-3H-imidazo[4,5-b]pyridine (311 mg), copper iodide (1.5 g), sodium heptafluorobutyrate (1.8 g), NMP (5 ml), and xylene (25 ml) was stirred with heating at 150° C. for 12 hours. Into the reaction mixture cooled to room temperature, saturated aqueous sodium hydrogen carbonate solution and 28% aqueous ammonia were poured, and extracted with tert-butyl methyl ether. The combined organic layer was dried over sodium sulfate, and concentrated under reduced pressure. The residue was subjected to silica gel column chromatography to give 118 mg of 2-(2-ethylsulfanyl-phenyl)-6-heptafluoropropyl-3-methyl-3H-imidazo[4,5-b]pyridine (hereinafter referred to as Present Compound 128).

Present Compound 128

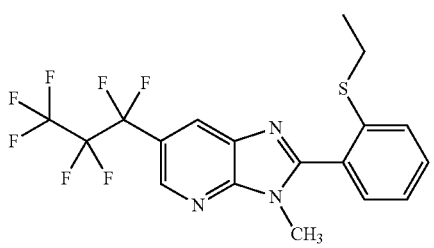

¹H-NMR (CDCl₃) δ: 8.65 (1H, d), 8.29 (1H, d), 7.56-7.51 (2H, m), 7.48-7.43 (1H, m), 7.38-7.34 (1H, m), 3.78 (3H, s), 2.89 (2H, q), 1.25 (3H, t)

Production Examples 98 and 99

The procedure was performed according to the method described in Production Examples 16 and 17 using 2-(2-ethylsulfanyl-phenyl)-6-heptafluoropropyl-3-methyl-3H-imidazo[4,5-b]pyridine instead of 2-(2-tert-butylsulfanylphenyl)-3-methyl-6-trifluoromethyl-3H-imidazo[4,5-b]pyridine to give 2-(2-ethylsulfinyl-phenyl)-6-heptafluoropropyl-3-methyl-3H-imidazo[4,5-b]pyridine (hereinafter referred to as Present Compound 129) and 2-(2-ethylsulfonylphenyl)-6-heptafluoropropyl-3-methyl-3H-imidazo[4,5-b]pyridine (hereinafter referred to as Present Compound 130).

Present Compound 129

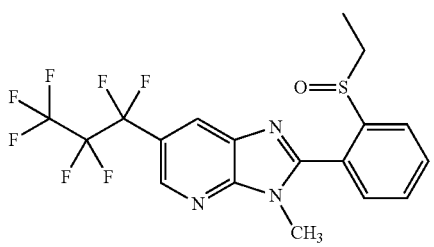 [SMILES: CCS(=O)c1ccccc1-c1nc2cc(C(F)(F)C(F)(F)C(F)(F)F)cnc2n1C]

¹H-NMR (CDCl₃) δ: 8.68 (1H, d), 8.29-8.24 (2H, m), 7.87-7.81 (1H, m), 7.74-7.68 (1H, m), 7.61 (1H, dd), 3.91 (3H, s), 3.43-3.32 (1H, m), 3.05-2.94 (1H, m), 1.31 (3H, t)

Present Compound 130

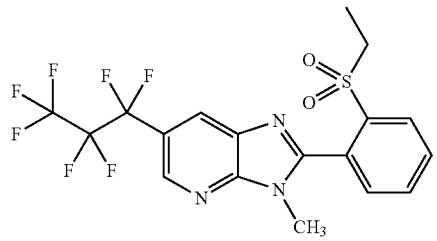 [SMILES: CCS(=O)(=O)c1ccccc1-c1nc2cc(C(F)(F)C(F)(F)C(F)(F)F)cnc2n1C]

¹H-NMR (CDCl₃) δ: 8.67 (1H, d), 8.26-8.22 (2H, m), 7.87-7.81 (2H, m), 7.59-7.55 (1H, m), 3.73 (3H, s), 3.43 (2H, q), 1.26 (3H, t).

Production Example 100

To a mixture of 2-(4-chloro-2-fluorophenyl)-3-methyl-6-trifluoromethyl-3H-imidazo[4,5-b]pyridine (0.83 g) and DMF (5 ml), a suspension of sodium ethylmercaptide (80%, 0.26 g) was added dropwise in DMF under ice-cooling, and stirred for 1 hour under ice-cooling. Into the reaction mixture, saturated aqueous sodium hydrogen carbonate solution was poured under ice-cooling, and extracted with ethyl acetate. The organic layer was dried over magnesium sulfate, and concentrated under reduced pressure. The resulting residue was subjected to silica gel column chromatography. 0.20 g of the resulting product was subjected to recycle preparation liquid chromatography to give 0.12 g of 2-(2-ethylsulfanyl-4-chlorophenyl)-3-methyl-6-trifluoromethyl-3H-imidazo[4,5-b]pyridine (hereinafter referred to as Present Compound 133).

Present Compound 133

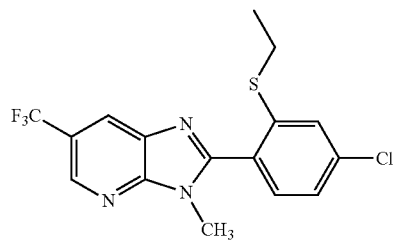

¹H-NMR (CDCl₃) δ: 8.73-8.71 (1H, m), 8.33-8.31 (1H, m), 7.44 (1H, d), 7.38 (1H, d), 7.34-7.30 (1H, m), 3.77 (3H, s), 2.91 (2H, q), 1.27 (3H, t)

Production Examples 101 and 102

The procedure was performed according to the method described in Production Examples 16 and 17 using 2-(2-ethylsulfanyl-4-chlorophenyl)-3-methyl-6-trifluoromethyl-3H-imidazo[4,5-b]pyridine instead of 2-(2-tert-butylsulfanylphenyl)-3-methyl-6-trifluoromethyl-3H-imidazo[4,5-b]pyridine to give 0.34 g of 2-(2-ethylsulfinyl-4-chlorophenyl)-3-methyl-6-trifluoromethyl-3H-imidazo[4,5-b]pyridine (hereinafter referred to as Present Compound 134) and 0.17 g of 2-(2-ethylsulfanyl-4-chlorophenyl)-3-methyl-6-trifluoromethyl-3H-imidazo[4,5-b]pyridine (hereinafter referred to as Present Compound 135).

Present Compound 134

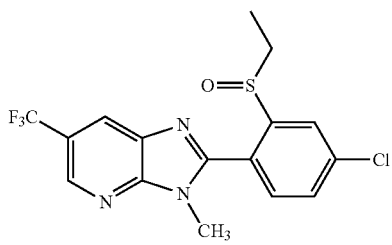 [SMILES: CCS(=O)c1cc(Cl)ccc1-c1nc2cc(C(F)(F)F)cnc2n1C]

¹H-NMR (CDCl₃) δ: 8.76-8.75 (1H, m), 8.32-8.30 (1H, m), 8.25 (1H, d), 7.68-7.65 (1H, m), 7.56 (1H, d), 3.91 (3H, s), 3.49-3.39 (1H, m), 3.05-2.95 (1H, m), 1.35 (3H, t)

Present Compound 135

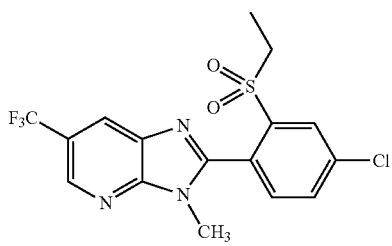 [SMILES: CCS(=O)(=O)c1cc(Cl)ccc1-c1nc2cc(C(F)(F)F)cnc2n1C]

¹H-NMR (CDCl₃) δ: 8.76-8.74 (1H, m), 8.29-8.27 (1H, m), 8.23-8.21 (1H, m), 7.83-7.80 (1H, m), 7.51 (1H, d), 3.72 (3H, s), 3.45 (2H, q), 1.28 (3H, t)

Production Example 103

To a mixture of 2-(2-ethylsulfanyl-phenyl)-6-iodo-3-methyl-3H-imidazo[4,5-b]pyridine (430 mg), copper iodide (229 mg), and DMF (3 ml), sodium sulfide nonahydrate (721 mg) was added at room temperature. The mixture was stirred with heating at 110° C. for 6 hours. Into the reaction mixture cooled to room temperature, saturated aqueous ammonium chloride water solution was poured, and extracted with ethyl acetate. The combined organic layer was dried over sodium sulfate, and concentrated under reduced pressure. The residue was subjected to silica gel column chromatography to give 85 mg of 2-(2-ethylsulfanyl-phenyl)-3-methyl-3H-imidazo[4,5-b]pyridin-6-thiol (hereinafter referred to as Present Compound 145):

Present Compound 145

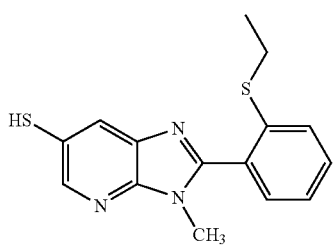

¹H-NMR (CDCl₃) δ: 8.41 (1H, d), 8.11 (1H, d), 7.53-7.47 (2H, m), 7.46-7.42 (1H, m), 7.37-7.31 (1H, m), 3.71 (3H, s), 3.56 (1H, s), 2.85 (2H, q), 1.22 (3H, t);

and 98 mg of a compound of the following formula (hereinafter referred to as Compound (145A).

Compound (145A)

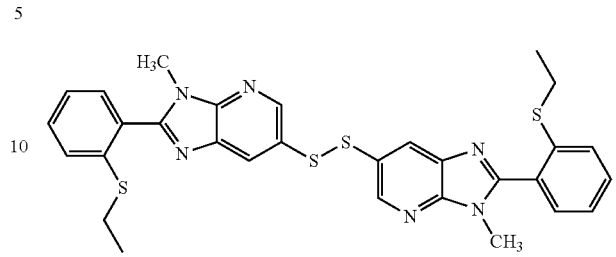

¹H-NMR (CDCl₃) δ: 8.48 (2H, d), 8.25 (2H, d), 7.53-7.47 (4H, m), 7.47-7.43 (2H, m), 7.36-7.32 (2H, m), 3.73 (6H, s), 2.86 (4H, q), 1.23 (6H, t)

Production Example 104

To a mixture of 6-bromo-2-(2-ethylsulfanyl-phenyl)-3-methyl-3H-imidazo[4,5-b]pyridine (348 mg), [1,1-bis(diphenylphosphino)ferrocene]palladium(II) dichloride dichloromethane adduct (41 mg), and THF (5 mL), diisopropyl zinc (1 M in toluene, 2 mL) was added at room temperature. The mixture was stirred at room temperature for 4 hours, washed with water, and extracted with ethyl acetate. The combined organic layer was dried over sodium sulfate, and concentrated under reduced pressure. The residue was subjected to silica gel column chromatography to give 290 mg of 2-(2-ethylsulfanyl-phenyl)-6-isopropyl-3-methyl-3H-imidazo[4,5-b]pyridine (hereinafter referred to as Present Compound 147).

Present Compound 147

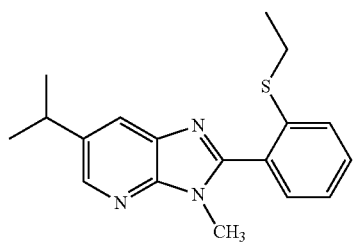 [SMILES: CCSc1ccccc1-c1nc2cc(C(C)C)cnc2n1C]

¹H-NMR (CDCl₃) δ: 8.35 (1H, s), 7.97 (1H, s), 7.51-7.42 (3H, m), 7.32-7.26 (1H, m), 3.73 (3H, s), 3.15-3.08 (1H, m), 2.83 (2H, q), 1.35 (6H, d), 1.20 (3H, t).

Production Example 105

To a mixture of copper cyanide (514 mg) and THF (20 ml), tert-butylmagnesium chloride (1 M in THF) was added with cooling at −78° C., and stirred at the temperature for hours. To the mixture, a mixture of 6-bromo-2-(2-ethylsulfanyl-phenyl)-3-methyl-3H-imidazo[4,5-b]pyridine (1 g) and THF (10 ml) was added dropwise with cooling at −78° C.

The reaction mixture was stirred for 16 hours with warming to room temperature gradually, and then saturated aqueous ammonium chloride solution was poured, and extracted with ethyl acetate. The combined organic layer was dried over sodium sulfate, and concentrated under reduced pressure. The residue was subjected to silica gel column chromatography to 111 mg of 6-tert-butyl-2-(2-ethylsulfanyl-phenyl)-3-methyl-3H-imidazo[4,5-b]pyridine (hereinafter referred to as Present Compound 150).

Present Compound 150

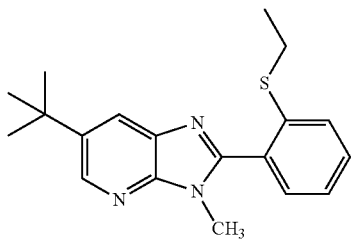 [SMILES: CCSc1ccccc1-c1nc2cc(C(C)(C)C)cnc2n1C]

$^1$H-NMR (CDCl$_3$) δ: 8.53 (1H, d), 8.11 (1H, d), 7.51-7.46 (2H, m), 7.45-7.40 (1H, m), 7.36-7.29 (1H, m), 3.72 (3H, s), 2.86 (2H, q), 1.45 (9H, s), 1.24 (3H, t)

Production Example 106

A mixture of N$^2$-methyl-6-trifluoromethylpyridin-2,3-diamine (0.96 g), 2-ethylsulfanylbenzoic acid (1.01 g), WSC (1.06 g), and pyridine (5 ml) was stirred under reflux for hours. Into the reaction mixture cooled to room temperature, water was poured, and extracted with ethyl acetate. The organic layer was dried over sodium sulfate, and concentrated under reduced pressure. To the resulting residue, a mixture of tripotassium phosphate (2.65 g) and 1-propanol (10 ml) was added, and stirred under reflux for hours. Into the reaction mixture cooled to room temperature, water was poured, and extracted with ethyl acetate. The organic layer was dried over sodium sulfate, and concentrated under reduced pressure. The resulting residue was subjected to silica gel column chromatography to give 0.98 g of 2-(2-ethylsulfanylphenyl)-3-methyl-5-trifluoromethyl-3H-imidazo[4,5-b]pyridine (hereinafter referred to as Present Compound 151).

Present Compound 151

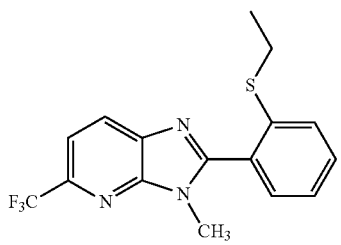 [SMILES: CCSc1ccccc1-c1nc2ccc(C(F)(F)F)nc2n1C]

$^1$H-NMR (CDCl$_3$) δ: 8.20 (1H, d), 7.67 (1H, d), 7.56-7.48 (2H, m), 7.47-7.42 (1H, m), 7.40-7.33 (1H, m), 3.78 (3H, s), 2.87 (2H, q), 1.24 (3H, t)

Production Examples 107 and 108

The procedure was performed according to the method described in Production Examples 16 and 17 using 2-(2-ethylsulfanylphenyl)-3-methyl-5-trifluoromethyl-3H-imidazo[4,5-b]pyridine instead of 2-(2-tert-butylsulfanylphenyl)-3-methyl-6-trifluoromethyl-3H-imidazo[4,5-b]pyridine to give 0.23 g of 2-(2-ethylsulfinylphenyl)-3-methyl-5-trifluoromethyl-3H-imidazo[4,5-b]pyridine (hereinafter referred to as Present Compound 159) and 0.42 g of 2-(2-ethylsulfonylphenyl)-3-methyl-5-trifluoromethyl-3H-imidazo[4,5-b]pyridine (hereinafter referred to as Present Compound 160).

Present Compound 159

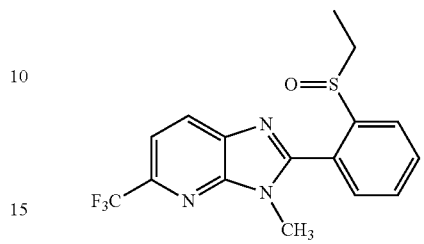

$^1$H-NMR (CDCl$_3$) δ: 8.26 (1H, dd), 8.19 (1H, dd), 7.86-7.80 (1H, m), 7.74-7.67 (2H, m), 7.60 (1H, dd), 3.90 (3H, s), 3.41-3.27 (1H, m), 3.02-2.89 (1H, m), 1.31-1.26 (3H, m)

Present Compound 160

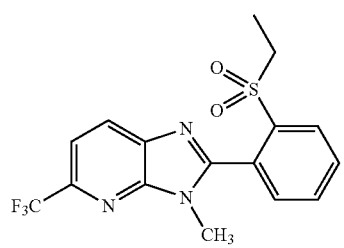 [SMILES: CCS(=O)(=O)c1ccccc1-c1nc2ccc(C(F)(F)F)nc2n1C]

$^1$H-NMR (CDCl$_3$) δ: 8.25-8.21 (1H, m), 8.15 (1H, d), 7.88-7.78 (2H, m), 7.69 (1H, d), 7.59-7.54 (1H, m), 3.73 (3H, s), 3.43 (2H, q), 1.25 (3H, t)

Production Example 109

A mixture of Compound (145A) (3.3 g) and DMF (60m) was cooled to −50° C., and bubbled with trifluoroiodomethane (17 g). The mixture was kept at −50° C., and tetrakis(dimethylamino)ethylene (3.8 ml) was added dropwise. The reaction mixture was stirred for 5 hours with warming gradually. The mixture was diluted with water, and extracted with ethyl acetate. The combined organic layer was dried over sodium sulfate, and concentrated under reduced pressure. The residue was subjected to silica gel column chromatography to give 3.2 g of 2-(2-ethylsulfanyl-phenyl)-3-methyl-6-trifluoromethylsulfanyl-3H-imidazo[4,5-b]pyridine (hereinafter referred to as Present Compound 161).

Present Compound 161

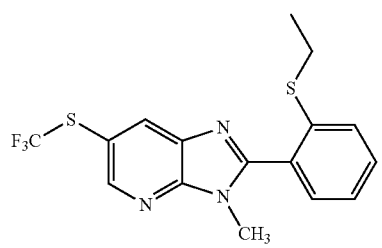 [SMILES: CCSc1ccccc1-c1nc2cc(SC(F)(F)F)cnc2n1C]

¹H-NMR (CDCl₃) δ: 8.66 (1H, d), 8.39 (1H, d), 7.57-7.49 (2H, m), 7.48-7.42 (1H, m), 7.39-7.33 (1H, m), 3.76 (3H, s), 2.88 (2H, q), 1.24 (3H, t)

Production Example 110-a

To a mixture of 6-bromo-2-(2-ethylsulfanyl-phenyl)-3-methyl-3H-imidazo[4,5-b]pyridine (1 g) and THF (20 ml), n-butyllithium (1.5 M in hexane, 2.1 ml) was added dropwise at −78° C. The mixture was stirred at −78° C. for 30 minutes, and then methyl trifluoroacetate (577 μl) was added dropwise. The mixture was heated to room temperature, and then saturated aqueous ammonium chloride solution was poured, and extracted with ethyl acetate. The combined organic layer was dried over sodium sulfate, and concentrated under reduced pressure to give 778 mg of crude 1-[2-(2-ethylsulfanyl-phenyl)-3-methyl-3H-imidazo[4,5-b]pyridin-6-yl]-2,2,2-trifluoro-ethanone (hereinafter referred to as Present Compound 91).

Present Compound 91

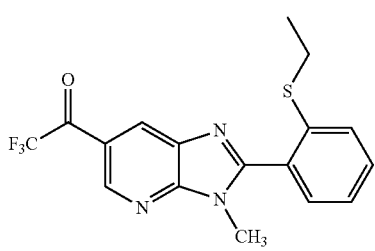 [SMILES: CCSc1ccccc1-c1nc2cc(C(=O)C(F)(F)F)cnc2n1C]

Production Example 110-b

To a mixture of the crude 1-[2-(2-ethylsulfanyl-phenyl)-3-methyl-3H-imidazo[4,5-b]pyridin-6-yl]-2,2,2-trifluoro-ethanone from Production Example 110-a (778 mg), methanol (5 ml), and THF (20 ml), sodium borohydride (109 mg) was added under ice-cooling. The mixture was stirred at room temperature for 12 hours, and then 1N aqueous sodium hydroxide solution was poured, and extracted with ethyl acetate. The combined organic layer was dried over sodium sulfate, and concentrated under reduced pressure. The residue was subjected to silica gel column chromatography to give 170 mg of 1-[2-(2-ethylsulfanyl-phenyl)-3-methyl-3H-imidazo[4,5-b]pyridin-6-yl]-2,2,2-trifluoro-ethanol (hereinafter referred to as Present Compound 265).

Present Compound 265

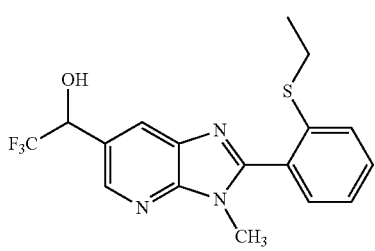 [SMILES: CCSc1ccccc1-c1nc2cc(C(O)C(F)(F)F)cnc2n1C]

¹H-NMR (CDCl₃) δ: 8.56 (1H, s), 8.25 (1H, s), 7.58-7.35 (4H, m), 5.24 (1H, brs), 3.77 (3H, s), 2.90 (2H, q), 1.27-1.19 (3H, m)

Production Example 110-c

To a mixture of 1-[2-(2-ethylsulfanyl-phenyl)-3-methyl-3H-imidazo[4,5-b]pyridin-6-yl]-2,2,2-trifluoro-ethanol (98 mg), toluene (10 ml), and pyridine (50 μl), thionyl chloride (1 ml) was added. The mixture was stirred with heating at 50° C. for 5 hours, and then saturated aqueous sodium hydrogen carbonate solution was poured, and extracted with ethyl acetate. The combined organic layer was dried over sodium sulfate, and concentrated under reduced pressure. The residue was subjected to silica gel column chromatography to give 66 mg of 6-(1-chloro-2,2,2-trifluoro-ethyl)-2-(2-ethylsulfanyl-phenyl)-3-methyl-3H-imidazo[4,5-b]pyridine (hereinafter referred to as Present Compound 266).

Present Compound 266

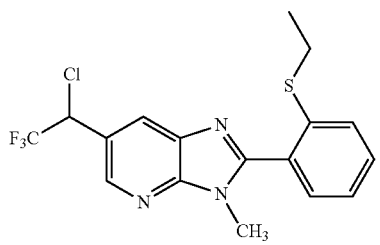 [SMILES: CCSc1ccccc1-c1nc2cc(C(Cl)C(F)(F)F)cnc2n1C]

¹H-NMR (CDCl₃) δ: 8.52 (1H, d), 8.29 (1H, d), 7.52-7.49 (2H, m), 7.44 (1H, dd), 7.37-7.33 (1H, m), 5.36 (1H, q), 3.75 (3H, s), 2.88 (2H, q), 1.24 (3H, t)

Production Example 110-d

To a mixture of 6-(1-chloro-2,2,2-trifluoro-ethyl)-2-(2-ethylsulfanyl-phenyl)-3-methyl-3H-imidazo[4,5-b]pyridine (61 mg) and methanol (5 ml), sodium borohydride (20 mg) was added under ice-cooling. The mixture was stirred at room temperature for 3 hours, and then 1N aqueous sodium hydroxide solution was poured, and extracted with ethyl acetate. The combined organic layer was dried over sodium sulfate, and concentrated under reduced pressure. The residue was subjected to silica gel column chromatography to give 40 mg of 2-(2-ethylsulfanyl-phenyl)-3-methyl-6-(2,2,2-trifluoro-ethyl)-3H-imidazo[4,5-b]pyridine (hereinafter referred to as Present Compound 165).

Present Compound 165

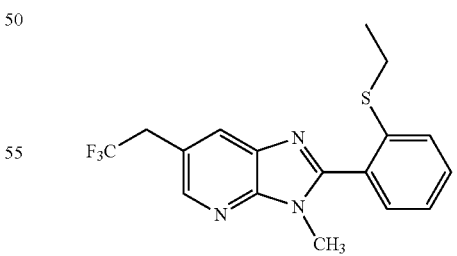

¹H-NMR (CDCl₃) δ: 8.53 (1H, s), 8.45-8.37 (1H, m), 7.78-7.31 (4H, m), 3.84 (3H, s), 3.60-3.50 (2H, m), 2.91-2.82 (2H, m), 1.23-1.16 (3H, m)

Production Example 111

A mixture of N³-methyl-6-trifluoromethylpyridin-2,3-diamine (0.38 g), 2-ethylsulfanylbenzoic acid (0.40 g), WSC (0.42 g), and pyridine (3 ml) was stirred under reflux for hours. Into the reaction mixture cooled to room temperature, water was poured, and extracted with ethyl acetate. The organic layer was dried over sodium sulfate, and concentrated under reduced pressure. To the resulting residue, tripotassium phosphate (1.06 g) and 1-propanol (4 ml) were added, and stirred under reflux for 4 hours. Into the reaction mixture cooled to room temperature, water was poured, and extracted with ethyl acetate. The organic layer was dried over sodium sulfate, and concentrated under reduced pressure. The resulting residue was subjected to silica gel column chromatography to give 0.33 g of 2-(2-ethylsulfanylphenyl)-1-methyl-5-trifluoromethyl-1H-imidazo[4,5-b]pyridine (hereinafter referred to as Present Compound 166).

Present Compound 166

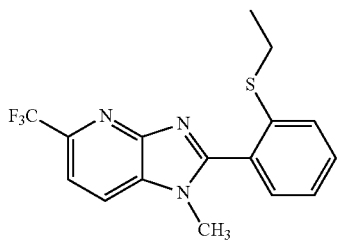 [SMILES: CCSc1ccccc1-c1nc2nc(C(F)(F)F)ccc2n1C]

$^1$H-NMR (CDCl$_3$) δ: 7.85 (1H, d), 7.68 (1H, d), 7.58-7.47 (3H, m), 7.43-7.33 (1H, m), 3.71 (3H, s), 2.83 (2H, q), 1.20 (3H, t)

Production Examples 112 and 113

The procedure was performed according to the method described in Production Examples 16 and 17 using 2-(2-ethylsulfanylphenyl)-1-methyl-5-trifluoromethyl-1H-imidazo[4,5-b]pyridine instead of 2-(2-tert-butylsulfanylphenyl)-3-methyl-6-trifluoromethyl-3H-imidazo[4,5-b]pyridine to give 0.23 g of 2-(2-ethylsulfinylphenyl)-1-methyl-5-trifluoromethyl-1H-imidazo[4,5-b]pyridine (hereinafter referred to as Present Compound 167) and 0.42 g of 2-(2-ethylsulfonylphenyl)-1-methyl-5-trifluoromethyl-1H-imidazo[4,5-b]pyridine (hereinafter referred to as Present Compound 168).

Present Compound 167

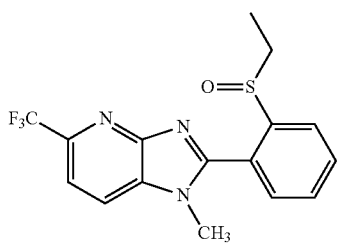 [SMILES: CCS(=O)c1ccccc1-c1nc2nc(C(F)(F)F)ccc2n1C]

$^1$H-NMR (CDCl$_3$) δ: 8.25 (1H, dd), 7.91 (1H, d), 7.83 (1H, td), 7.74 (1H, d), 7.69 (1H, td), 7.56 (1H, dd), 3.83 (3H, s), 3.53-3.37 (1H, m), 3.18-3.05 (1H, m), 1.30 (3H, t)

Present Compound 168

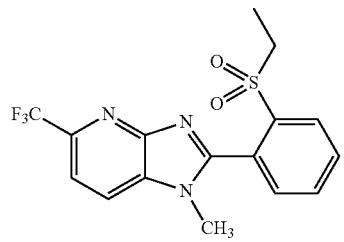 [SMILES: CCS(=O)(=O)c1ccccc1-c1nc2nc(C(F)(F)F)ccc2n1C]

$^1$H-NMR (CDCl$_3$) δ: 8.26-8.19 (1H, m), 7.90-7.86 (1H, m), 7.85-7.80 (2H, m), 7.72 (1H, d), 7.59-7.53 (1H, m), 3.66 (3H, s), 3.60-3.30 (2H, m), 1.24 (3H, t)

Production Example 114

To a mixture of ethylmercaptide (80%, 0.35 g) and DMF (9 ml), a solution of 2-(2-fluoro-4-trifluoromethylphenyl)-3-methyl-6-trifluoromethyl-3H-imidazo[4,5-b]pyridine (1.0 g) in DMF was added dropwise under ice-cooling, heated to room temperature, and stirred at room temperature for 30 minutes. To the reaction mixture, saturated aqueous sodium hydrogen carbonate solution was poured, and extracted with ethyl acetate. The organic layer was dried over magnesium sulfate, and concentrated under reduced pressure. The resulting residue was subjected to silica gel column chromatography to give 1.10 g of 2-(2-ethylsulfanyl-4-trifluoromethylphenyl)-3-methyl-6-trifluoromethyl-3H-imidazo[4,5-b]pyridine (hereinafter referred to as Present Compound 174).

Present Compound 174

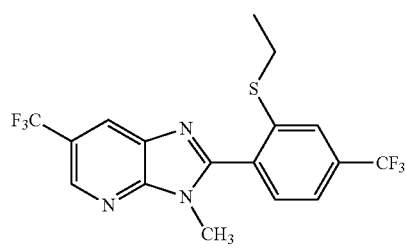

$^1$H-NMR (CDCl$_3$) δ: 8.75-8.73 (1H, m), 8.35-8.33 (1H, m), 7.70-7.68 (1H, m), 7.62-7.56 (2H, m), 3.79 (3H, s), 2.95 (2H, q), 1.28 (3H, t)

Production Examples 115 and 116

The procedure was performed according to the method described in Production Examples 16 and 17 using 2-(2-ethylsulfanyl-4-trifluoromethylphenyl)-3-methyl-6-trifluoromethyl-3H-imidazo[4,5-b]pyridine instead of 2-(2-tert-butylsulfanylphenyl)-3-methyl-6-trifluoromethyl-3H-imidazo[4,5-b]pyridine to give 0.51 g of 2-(2-ethylsulfinyl-4-trifluoromethylphenyl)-3-methyl-6-trifluoromethyl-3H-imidazo[4,5-b]pyridine (hereinafter referred to as Present Compound 175) and 0.26 g of 2-(2-ethylsulfonyl-4-trifluoromethylphenyl)-3-methyl-6-trifluoromethyl-3H-imidazo[4,5-b]pyridine (hereinafter referred to as Present Compound 176).

Present Compound 175

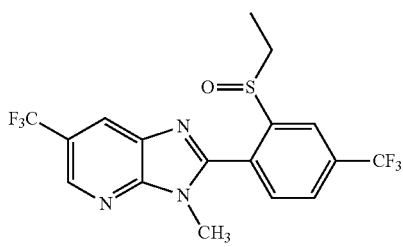

¹H-NMR (CDCl₃) δ: 8.79-8.78 (1H, m), 8.57-8.55 (1H, m), 8.35-8.34 (1H, m), 7.97-7.94 (1H, m), 7.77 (1H, d), 3.94 (3H, s), 3.53-3.43 (1H, m), 3.07-2.98 (1H, m), 1.36 (3H, t)

Present Compound 176

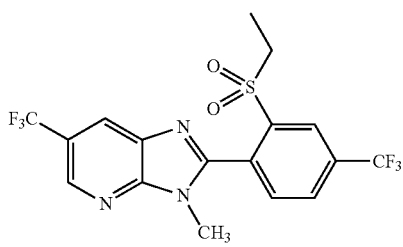

¹H-NMR (CDCl₃) δ: 8.78-8.76 (1H, m), 8.51-8.49 (1H, m), 8.31-8.30 (1H, m), 8.12-8.09 (1H, m), 7.74 (1H, d), 3.74 (3H, s), 3.48 (2H, q), 1.29 (3H, t)

Production Example 117

A mixture of 3-amino-5-(trifluoromethyl)pyridin-2-thiol 0.56 g, 2-ethylsulfanylbenzoic acid (0.52 g), WSC (0.80 g), HOBt (39 mg), and pyridine (6 ml) was stirred at 60° C. for 2 hours. After the reaction mixture was allowed to stand to cool, water was poured thereinto, and extracted with ethyl acetate. The organic layer was washed with water, dried over anhydrous magnesium sulfate, and concentrated under reduced pressure.

A mixture of the resulting residue, p-toluenesulfonic acid monohydrate (0.65 g), and N-methylpyrrolidinone (5 ml) was stirred with heating at 150° C. for 2 hours. After the reaction mixture was allowed to cool, water was poured thereinto, and extracted with ethyl acetate. The organic layer was washed with water, dried over anhydrous magnesium sulfate, and concentrated under reduced pressure. The resulting residue was subjected to silica gel column chromatography to give 0.38 g of 2-(2-ethylsulfanylphenyl)-6-(trifluoromethyl)thiazolo[5,4-b]pyridine (hereinafter referred to as Present Compound 183).

Present Compound 183

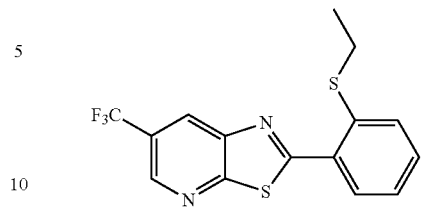

¹H-NMR (CDCl₃) δ: 8.86 (1H, d), 8.57 (1H, d), 8.03 (1H, dd), 7.55 (1H, dd), 7.48 (1H, td), 7.36 (1H, td), 2.98 (2H, q), 1.34 (3H, t).

Production Examples 118 and 119

The procedure was performed according to the method described in Production Examples 16 and 17 using 2-(2-ethylsulfanylphenyl)-6-(trifluoromethyl)thiazolo[5,4-b]pyridine instead of 2-(2-tert-butylsulfanylphenyl)-3-methyl-6-trifluoromethyl-3H-imidazo[4,5-b]pyridine to give 0.13 g of 2-(2-ethylsulfinylphenyl)-6-(trifluoromethyl)thiazolo[5,4-b]pyridine (hereinafter referred to as Present Compound 184) and 0.14 g of 2-(2-ethylsulfonylphenyl)-6-(trifluoromethyl)thiazolo[5,4-b]pyridine (hereinafter referred to as Present Compound 185).

Present Compound 184

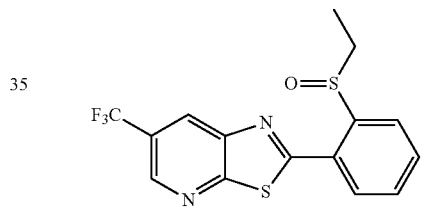

¹H-NMR (CDCl₃) δ: 8.90 (1H, d), 8.49 (1H, d), 8.37 (1H, dd), 7.99 (1H, dd), 7.81 (1H, td), 7.67 (1H, td), 3.52-3.42 (1H, m), 3.01-2.92 (1H, m), 1.45 (3H, t).

Present Compound 185

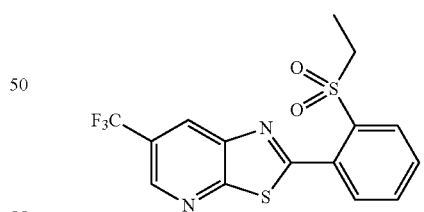

¹H-NMR (CDCl₃) δ: 8.92 (1H, d), 8.52 (1H, d), 8.25 (1H, dd), 7.84-7.71 (3H, m), 3.73 (2H, q), 1.37 (3H, t).

Production Example 120-1

A mixture of 2-(2-fluorophenyl)-3-methyl-6-trifluoromethyl-3H-imidazo[4,5-b]pyridine (7.83 g), sodium sulfide (6.20 g), and NMP (27 ml) was stirred with heating at 150° C. for 2 hours. Into the reaction mixture cooled to room temperature, water and 12N hydrochloric acid were poured, and extracted with ethyl acetate. The organic layer was dried over magnesium sulfate, and concentrated under reduced pressure.

The resulting residue was subjected to silica gel column chromatography to give 1.74 g of a compound of the following formula:

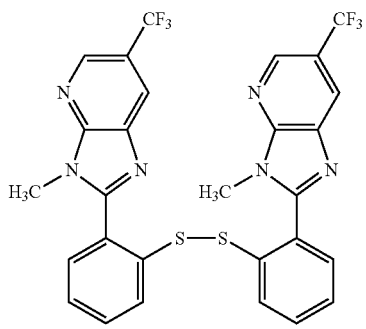 [SMILES: Cn1c(-c2ccccc2SSc2ccccc2-c2nc3cc(C(F)(F)F)cnc3n2C)nc2cc(C(F)(F)F)cnc21]

(hereinafter referred to as Compound (186A)).

$^1$H-NMR (CDCl$_3$) δ: 8.73-8.71 (2H, m), 8.31-8.29 (2H, m), 7.77-7.73 (2H, m), 7.47-7.37 (6H, m), 3.77 (6H, s)

Production Example 120-2

To a solution of sodium hydride (60% in oil, 0.12 g) in DMF, Compound (186A) (0.80 g) of the following formula:

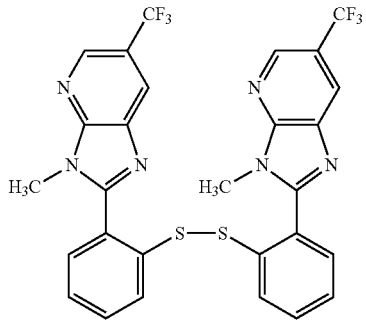 [SMILES: Cn1c(-c2ccccc2SSc2ccccc2-c2nc3cc(C(F)(F)F)cnc3n2C)nc2cc(C(F)(F)F)cnc21]

was added under ice-cooling, and stirred for 10 minutes under ice-cooling. To the mixture, 2,2,2-trifluoroethyl iodide (0.65 g) was added under ice-cooling, heated to room temperature, and stirred for 15 minutes. Then, the mixture was heated to 60° C., and stirred with heating for 1 hour. Into the reaction mixture cooled to room temperature, water was poured, and extracted with ethyl acetate. The organic layer was dried over magnesium sulfate, and concentrated under reduced pressure. The resulting residue was subjected to silica gel column chromatography to give 0.23 g of 3-methyl-2-[2-(2,2,2-trifluoroethylsulfanylphenyl)]-6-trifluoromethyl-3H-imidazo[4,5-b]pyridine (hereinafter referred to as Present Compound 186).

Present Compound 186

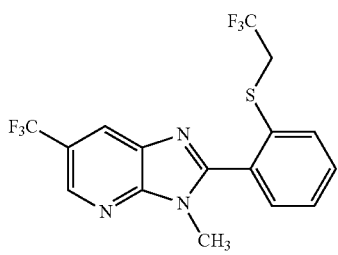 [SMILES: Cn1c(-c2ccccc2SCC(F)(F)F)nc2cc(C(F)(F)F)cnc21]

$^1$H-NMR (CDCl$_3$) δ: 8.75-8.73 (1H, m), 8.34-8.32 (1H, m), 7.77-7.74 (1H, m), 7.61-7.48 (3H, m), 3.75 (3H, s), 3.37 (2H, q)

Production Examples 121 and 122

The procedure was performed according to the method described in Production Examples 16 and 17 using 3-methyl-2-[2-(2,2,2-trifluoroethylsulfanylphenyl)]-6-trifluoromethyl-3H-imidazo[4,5-b]pyridine instead of 2-(2-tert-butylsulfanylphenyl)-3-methyl-6-trifluoromethyl-3H-imidazo[4,5-b]pyridine to give 73 mg of 3-methyl-2-[2-(2,2,2-trifluoroethylsulfinylphenyl)]-6-trifluoromethyl-3H-imidazo[4,5-b]pyridine (hereinafter referred to as Present Compound 187) and 68 mg of 3-methyl-2-[2-(2,2,2-trifluoroethylsulfanylphenyl)]-6-trifluoromethyl-3H-imidazo[4,5-b]pyridine (hereinafter referred to as Present Compound 188).

Present Compound 187

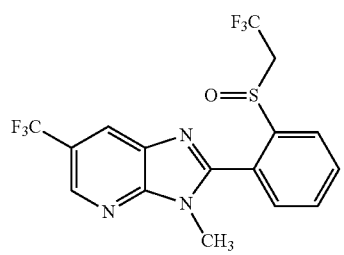 [SMILES: Cn1c(-c2ccccc2S(=O)CC(F)(F)F)nc2cc(C(F)(F)F)cnc21]

$^1$H-NMR (CDCl$_3$) δ: 8.77-8.75 (1H, m), 8.47-8.44 (1H, m), 8.29-8.26 (1H, m), 7.91-7.87 (1H, m), 7.80-7.74 (2H, m), 4.85-4.73 (1H, m), 4.03 (3H, s), 3.55-3.43 (1H, m)

Present Compound 187

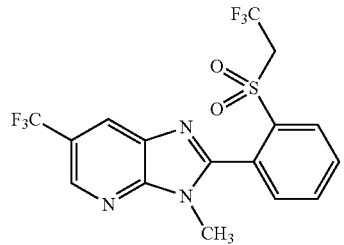 [SMILES: Cn1c(-c2ccccc2S(=O)(=O)CC(F)(F)F)nc2cc(C(F)(F)F)cnc21]

$^1$H-NMR (CDCl$_3$) δ: 8.77-8.75 (1H, m), 8.35-8.31 (2H, m), 7.95-7.84 (2H, m), 7.63-7.60 (1H, m), 4.61-4.47 (2H, m), 3.75 (3H, s)

Production Examples 123 and 124

The procedure was performed according to the method described in Production Examples 16 and 17 using 2-(2-ethylsulfanyl-phenyl)-3-methyl-6-trifluoromethylsulfanyl-3H-imidazo[4,5-b]pyridine instead of 2-(2-tert-butylsulfanylphenyl)-3-methyl-6-trifluoromethyl-3H-imidazo[4,5-b]pyridine to give 2-(2-ethylsulfonylphenyl)-6-trifluoromethylsulfanyl-3-methyl-3H-imidazo[4,5-b]pyridine (hereinafter referred to as Present Compound 209) and 2-(2-ethylsulfinyl-phenyl)-6-trifluoromethylsulfanyl-3-methyl-3H-imidazo[4,5-b]pyridine (hereinafter referred to as Present Compound 210).

Present Compound 209

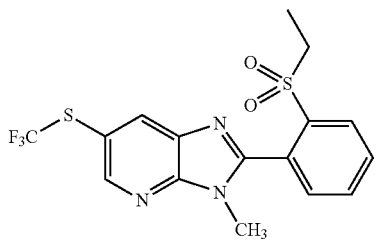 [SMILES: CCS(=O)(=O)c1ccccc1-c1nc2cc(SC(F)(F)F)cnc2n1C]

¹H-NMR (CDCl₃) δ: 8.68 (1H, d), 8.36 (1H, d), 8.21 (1H, dd), 7.87-7.77 (2H, m), 7.59 (1H, dd), 3.71 (3H, s), 3.44 (2H, q), 1.24 (3H, t)

Present Compound 210

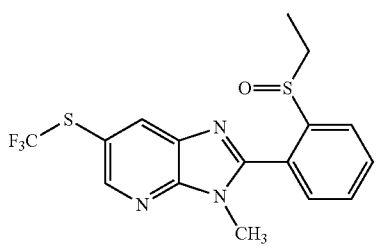 [SMILES: CCS(=O)c1ccccc1-c1nc2cc(SC(F)(F)F)cnc2n1C]

¹H-NMR (CDCl₃) δ: 8.69 (1H, d), 8.38 (1H, d), 8.25 (1H, dd), 7.86-7.80 (1H, m), 7.72-7.67 (1H, m), 7.60 (1H, dd), 3.88 (3H, s), 3.43-3.31 (1H, m), 3.03-2.92 (1H, m), 1.31 (3H, t)

Production Examples 125 and 126

The procedure was performed according to the method described in Production Examples 16 and 17 using 2-(2-ethylsulfonylphenyl)-6-trifluoromethylsulfanyl-3-methyl-3H-imidazo[4,5-b]pyridine instead of 2-(2-tert-butylsulfanylphenyl)-3-methyl-6-trifluoromethyl-3H-imidazo[4,5-b]pyridine to give 2-(2-ethylsulfonylphenyl)-6-trifluoromethylsulfinyl-3-methyl-3H-imidazo[4,5-b]pyridine (hereinafter referred to as Present Compound 214) and 2-(2-ethylsulfonylphenyl)-6-trifluoromethylsulfonyl3-methyl-3H-imidazo[4,5-b]pyridine (hereinafter referred to as Present Compound 215).

Present Compound 214

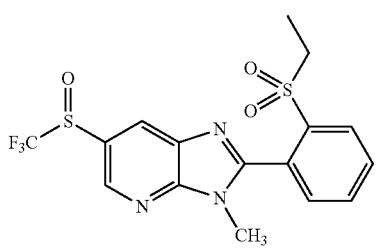 [SMILES: CCS(=O)(=O)c1ccccc1-c1nc2cc(S(=O)C(F)(F)F)cnc2n1C]

¹H-NMR (CDCl₃) δ: 8.77 (1H, d), 8.55 (1H, d), 8.24 (1H, dd), 7.90-7.83 (2H, m), 7.61 (1H, dd), 3.75 (3H, s), 3.43 (2H, q), 1.26 (3H, t)

Present Compound 215

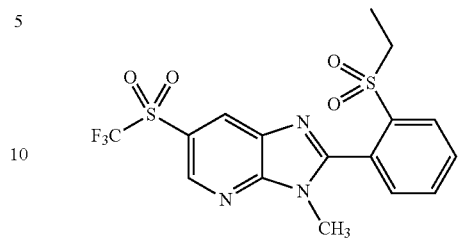

¹H-NMR (CDCl₃) δ: 9.05 (1H, d), 8.65 (1H, d), 8.26-8.23 (1H, m), 7.90-7.85 (2H, m), 7.61-7.57 (1H, m), 3.77 (3H, s), 3.41 (2H, q), 1.27 (3H, t)

Production Example 127

To a mixture of 2-[2-fluoro-4-(trifluoromethyl)phenyl]-6-(trifluoromethyl)thiazolo[5,4-b]pyridine (0.18 g) and DMF (2 ml), sodium thiomethoxide (63 mg) was added under ice-cooling, and stirred at room temperature for 4 hours. Into the reaction mixture, water was poured, and extracted with ethyl acetate. The organic layer was washed with water, dried over anhydrous magnesium sulfate, and concentrated under reduced pressure. The resulting residue was subjected to silica gel column chromatography to give 0.11 g of 2-[2-ethylsulfanyl-4-(trifluoromethyl)phenyl]-6-(trifluoromethyl)thiazolo[5,4-b]pyridine (hereinafter referred to as Present Compound 267).

Present Compound 267

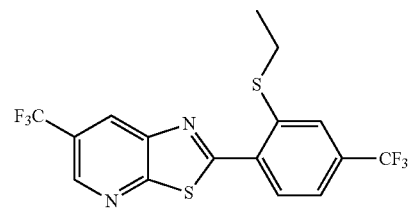 [SMILES: CCSc1cc(C(F)(F)F)ccc1-c1nc2cc(C(F)(F)F)cnc2s1]

¹H-NMR (CDCl₃) δ: 8.90 (1H, d), 8.61 (1H, d), 8.14 (1H, d), 7.75 (1H, s), 7.58 (1H, d), 3.04 (2H, q), 1.38 (3H, t).

Production Example 128

To a mixture of 2-[2-ethylsulfanyl-4-(trifluoromethyl)phenyl]-6-(trifluoromethyl)thiazolo[5,4-b]pyridine (0.11 g) and chloroform (3 ml), 3-chloroperbenzoic acid (purity: not less than 65%) (0.13 g) was added, and stirred at room temperature for 12 hours. The reaction mixture was diluted with chloroform, washed with 10% aqueous sodium thiosulfate solution and saturated aqueous sodium hydrogen carbonate solution, sequentially, dried over anhydrous magnesium sulfate, and concentrated under reduced pressure. The resulting residue was subjected to silica gel column chromatography to give 0.11 g of 2-[2-ethylsulfonyl-4-(trifluoromethyl)phenyl]-6-(trifluoromethyl)thiazolo[5,4-b]pyridine (hereinafter referred to as Present Compound 251).

Present Compound 251

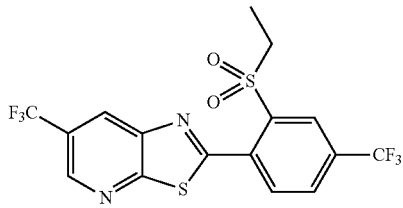 [SMILES: CCS(=O)(=O)c1cc(C(F)(F)F)ccc1-c1nc2cc(C(F)(F)F)cnc2s1]

¹H-NMR (CDCl₃) δ: 8.95 (1H, s), 8.55 (1H, s), 8.52 (1H, s), 8.07 (1H, d), 7.88 (1H, d), 3.77 (2H, q), 1.40 (3H, t).

Production Example 129

To a mixture of 2-(2-ethylsulfanyl-phenyl)-3-methyl-3H-imidazo[4,5-b]pyridin-6-thiol (535 mg), iodomethane (166 µl), and ethanol (5 ml), potassium hydroxide (200 mg) was added at room temperature, and stirred for 5 hours. To the reaction mixture, saturated aqueous ammonium chloride solution was added, and extracted with ethyl acetate. The combined organic layer was dried over sodium sulfate, and concentrated under reduced pressure. The residue was subjected to silica gel column chromatography to give 515 mg of 2-(2-ethylsulfanyl-phenyl)-3-methyl-6-methylsulfanyl-3H-imidazo[4,5-b]pyridine (hereinafter referred to as Present Compound 253).

Present Compound 253

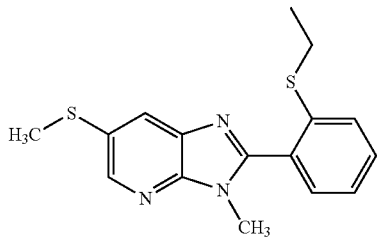 [SMILES: CCSc1ccccc1-c1nc2cc(SC)cnc2n1C]

¹H-NMR (CDCl₃) δ: 8.46 (1H, d), 8.10 (1H, d), 7.52-7.42 (3H, m), 7.37-7.26 (1H, m), 3.73 (3H, s), 2.86 (2H, q), 2.54 (3H, s), 1.22 (3H, t)

Production Example 130

To a mixture of 2-(2-ethylsulfanyl-phenyl)-3-methyl-6-methylsulfanyl-3H-imidazo[4,5-b]pyridine (363 mg) and chloroform (5 ml), 69-75% of 3-chloroperbenzoic acid (1.13 g) was added under ice-cooling. The mixture was heated to room temperature, and stirred for 5 hours, and then saturated aqueous sodium hydrogen carbonate solution and saturated aqueous sodium thiosulfate solution were poured, and extracted with chloroform. The combined organic layer was dried over sodium sulfate, and concentrated under reduced pressure. The residue was subjected to silica gel column chromatography to give 356 mg of 2-(2-ethylsulfonylphenyl)-6-methylsulfonyl3-methyl-3H-imidazo[4,5-b]pyridine (hereinafter referred to as Present Compound 254).

Present Compound 254

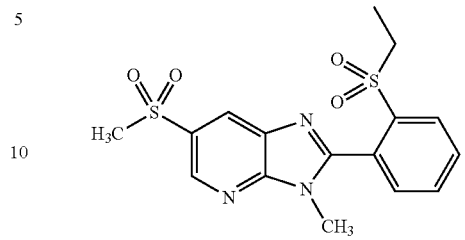

¹H-NMR (CDCl₃) δ: 9.02 (1H, d), 8.58 (1H, d), 8.23 (1H, dd), 7.90-7.81 (2H, m), 7.59 (1H, dd), 3.74 (3H, s), 3.42 (2H, q), 3.19 (3H, s), 1.26 (3H, t).

Production Example 131-1

A mixture of 6-bromo-2-(2-ethylsulfanyl-phenyl)-3-methyl-3H-imidazo[4,5-b]pyridine (1.02 mg), copper iodide (280 mg), 1,10-phenanthroline (268 mg), benzyl alcohol (456 µL), cesium carbonate (1.9 g), NMP (4 mL), and xylene (20 mL) was stirred with heating at 150° C. for 8 hours. After the mixture was allowed to stand to cool to room temperature, into the mixture, 28% of aqueous ammonia and saturated aqueous sodium hydrogen carbonate solution were poured, extracted with tert-butyl methyl ether. The combined organic layer was dried over sodium sulfate, and concentrated under reduced pressure. The residue was subjected to silica gel column chromatography to give 402 mg of 6-benzyloxy-2-(2-ethylsulfanyl-phenyl)-3-methyl-3H-imidazo[4,5-b]pyridine (hereinafter referred to as Compound 268A).

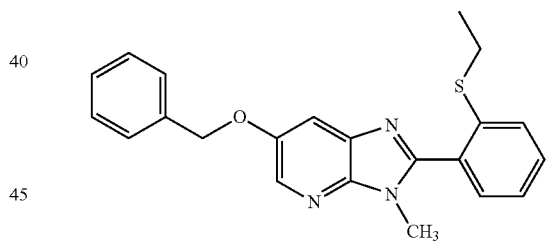

¹H-NMR (CDCl₃) δ: 8.27 (1H, d), 7.67 (1H, d), 7.45-7.33 (9H, m), 5.16 (2H, s), 3.70 (3H, s), 2.85 (2H, q), 1.22 (3H, t).

Production Example 131-2

To a mixture of 6-benzyloxy-2-(2-ethylsulfanyl-phenyl)-3-methyl-3H-imidazo[4,5-b]pyridine 262 mg, and chloroform (3 mL), boron tribromide (1M in dichloromethane) (698 µL) was added under ice-cooling, and stirred for 3 hours. Into the mixture, saturated aqueous sodium hydrogen carbonate solution was poured, and extracted with chloroform then ethyl acetate. The combined organic layer was dried over sodium sulfate, and concentrated under reduced pressure. The residue was subjected to silica gel column chromatography to give 168 mg of 2-(2-ethylsulfanyl-phenyl)-3-methyl-3H-imidazo[4,5-b]pyridine-6-ol (hereinafter, Present Compound 268).

Present Compound 268

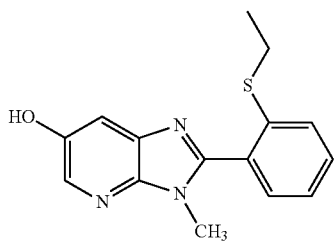

¹H-NMR (DMSO-D₆) δ: 9.58 (1H, brs), 8.02 (1H, d), 7.60-7.54 (2H, m), 7.47 (1H, d), 7.41 (1H, d), 7.38-7.33 (1H, m), 3.54 (3H, s), 2.94 (2H, q), 1.16 (3H, t).

Production Example 132

To a mixture of 2-(2-ethylsulfanyl-phenyl)-3-methyl-3H-imidazo[4,5-b]pyridine-6-ol (579 mg), chloroform (20 mL), and acetonitrile (6 mL), 69% of 3-chloroperbenzoic acid (1.05 g) was added under ice-cooling. The mixture was heated to room temperature, stirred for 3 hours, and filtered. The resulting filtered substance was washed with chloroform to give 566 mg of 2-(2-ethylsulfonyl-phenyl)-3-methyl-3H-imidazo[4,5-b]pyridine-6-ol (hereinafter, Present Compound 269).

Present Compound 269

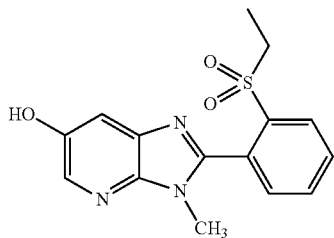 [SMILES: CCS(=O)(=O)c1ccccc1-c1nc2cc(O)cnc2n1C]

Production Example 133-1

To a mixture of 2-(2-ethylsulfonyl-phenyl)-3-methyl-3H-imidazo[4,5-b]pyridine-6-ol (566 mg) and DMF (5 mL), 60% of sodium hydride (in oil, 129 mg) was added, and stirred with heating at 50° C. for 1 hour. After the mixture was allowed to stand to cool to room temperature, to the mixture, carbon disulfide (1.08 mL) was added, and stirred at room temperature (2.5 hours). To a mixture, iodomethane (446 µL) was added, and stirred at room temperature for 1.5 hours. Into the mixture, saturated aqueous sodium hydrogen carbonate solution was poured, and extracted with ethyl acetate. The combined organic layer was dried over sodium sulfate, and concentrated under reduced pressure. The residue was subjected to silica gel column chromatography to give 681 mg of S-methyl O-[2-(2-ethylsulfonyl-phenyl)-3-methyl-3H-imidazo[4,5-b]pyridine-6-yl]dithiocarboxylate (hereinafter referred to as Compound 270A).

Compound 270A

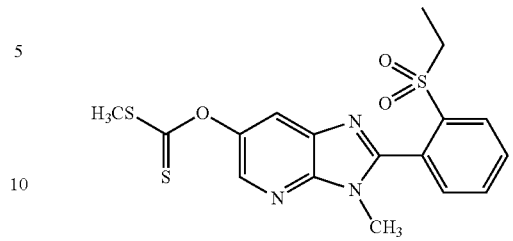

¹H-NMR (CDCl₃) δ: 8.30-8.25 (1H, m), 8.24-8.18 (1H, m), 7.85-7.76 (3H, m), 7.58-7.53 (1H, m), 3.69 (3H, brs), 3.44 (2H, q), 2.71 (3H, brs), 1.26-1.22 (3H, m).

Production Example 133-2

To a mixture of S-methyl O-[2-(2-ethylsulfonyl-phenyl)-3-methyl-3H-imidazo[4,5-b]pyridine-6-yl]dithiocarboxylate (371 mg) and chloroform (3 mL), HF-pyridine complex (1.25 mL) and 1,3-dibromo-5,5-dimethylhydantoin (1.58 g) were added with cooling at −55° C. The mixture was stirred for 7 hours with heating to room temperature gradually, and then saturated aqueous sodium hydrogen carbonate solution was poured, and extracted with chloroform. The combined organic layer was washed with aqueous sodium thiosulfate solution, dried over sodium sulfate, and concentrated under reduced pressure. The residue was subjected to reversed-phase silica gel column chromatography to give 29 mg of 6-(bromo-difluoro-methoxy)-2-(2-ethylsulfonyl-phenyl)-3-methyl-3H-imidazo[4,5-b]pyridine (hereinafter, Present Compound 270) and 76 mg of 2-(2-ethylsulfonyl-phenyl)-3-methyl-6-trifluoromethoxy-3H-imidazo[4,5-b]pyridine (hereinafter, Present Compound 271).

Present Compound 270

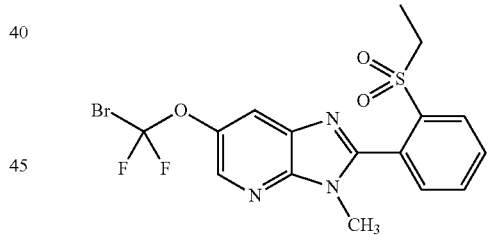

¹H-NMR (CDCl₃) δ: 8.43 (1H, d), 8.26-8.21 (1H, m), 7.97-7.97 (1H, m), 7.87-7.80 (2H, m), 7.56 (1H, dd), 3.70 (3H, s), 3.45 (2H, q), 1.26 (3H, t).

Present Compound 271

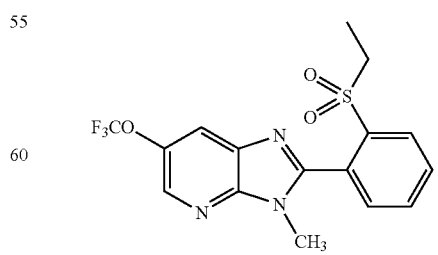

¹H-NMR (CDCl₃) δ: 8.42 (1H, d), 8.22 (1H, dd), 7.94-7.94 (1H, m), 7.87-7.79 (2H, m), 7.56 (1H, dd), 3.70 (3H, s), 3.44 (2H, q), 1.25 (3H, t).

Production Example 134

The procedure was performed according to the method described in Production Example 103 using 2-(2-ethylsulfanyl-4-trifluoromethylphenyl)-6-iodo-3-methyl-3H-imidazo[4,5-b]pyridine instead of 2-(2-ethylsulfanyl-phenyl)-6-iodo-3-methyl-3H-imidazo[4,5-b]pyridine to give Compound 301A.

A mixture of Compound 301A (0.94 g) and DMF (13 ml) was cooled to −50° C., and bubbled with excessive amounts of $CF_3I$ gas to dissolve the compound in DMF. To the mixture, tetrakis(dimethylamino)ethylenediamine (1.2 ml) was added dropwise at a rate that the internal temperature did not exceed −40° C. Then, the mixture was heated to −10° C. over 1 hour, and stirred at −10° C. for 1 hour. Into the reaction mixture, water was poured, heated to room temperature, and extracted with ethyl acetate. The combined organic layer was dried over magnesium sulfate, and concentrated under reduced pressure. The resulting residue was subjected to silica gel column chromatography to give 0.68 g of 2-(2-ethylsulfanyl-4-trifluoromethylphenyl)-3-methyl-6-trifluoromethylsulfanyl-3H-imidazo[4,5-b]pyridine (hereinafter, Present Compound 301).

Present Compound 301

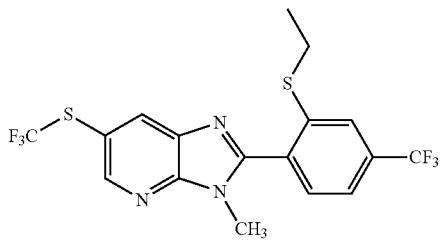 [SMILES: CCSc1cc(C(F)(F)F)ccc1-c1nc2cc(SC(F)(F)F)cnc2n1C]

$^1$H-NMR (CDCl$_3$) δ: 8.66 (1H, d) 8.39 (1H, d), 7.67-7.64 (1H, m), 7.59-7.52 (2H, m), 3.75 (3H, s), 2.94 (2H, q), 1.27 (3H, t).

Production Example 135

To a mixture of 2-(2-ethylsulfanyl-4-trifluoromethylphenyl)-3-methyl-6-trifluoromethylsulfanyl-3H-imidazo[4,5-b]pyridine and chloroform (5 ml), 69% of 3-chloroperbenzoic acid (1.05 g) was added under ice-cooling, and then heated to room temperature, and stirred for 1.5 hours. Then, saturated aqueous sodium hydrogen carbonate solution and saturated aqueous sodium thiosulfate solution was poured, and extracted with chloroform. The combined organic layer was dried over magnesium sulfate, and concentrated under reduced pressure. The resulting residue was subjected to silica gel column chromatography to give 0.20 g of 2-(2-ethylsulfonyl-4-trifluoromethylphenyl)-3-methyl-6-trifluoromethylsulfanyl-3H-imidazo[4,5-b]pyridine (hereinafter, Present Compound 306).

Present Compound 306

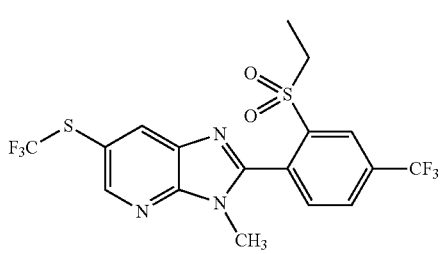 [SMILES: CCS(=O)(=O)c1cc(C(F)(F)F)ccc1-c1nc2cc(SC(F)(F)F)cnc2n1C]

$^1$H-NMR (CDCl$_3$) δ: 8.71-8.70 (1H, m), 8.50-8.49 (1H, m), 8.38-8.36 (1H, m), 8.12-8.08 (1H, m), 7.74-7.71 (1H, m), 3.72 (3H, s), 3.49 (2H, q), 1.29 (3H, t).

Production Example 136

A mixture of 2-(2-ethylsulfonyl-4-trifluoromethylphenyl)-3-methyl-6-trifluoromethylsulfinyl-3H-imidazo[4,5-b]pyridine (0.26 g), sodium tungstate dihydrate (36 mg), 30% of aqueous hydrogen peroxide solution (1 ml) and acetonitrile (5 ml) was stirred under reflux for 4.5 hours. The mixture was cooled to room temperature. Into the reaction mixture, water was poured, and extracted with ethyl acetate. The combined organic layer was dried over magnesium sulfate, and concentrated under reduced pressure. The resulting residue was subjected to silica gel column chromatography to give 0.24 g of 2-(2-ethylsulfonyl-4-trifluoromethylphenyl)-3-methyl-6-trifluoromethylsulfonyl-3H-imidazo[4,5-b]pyridine (hereinafter, Present Compound 302).

Present Compound 302

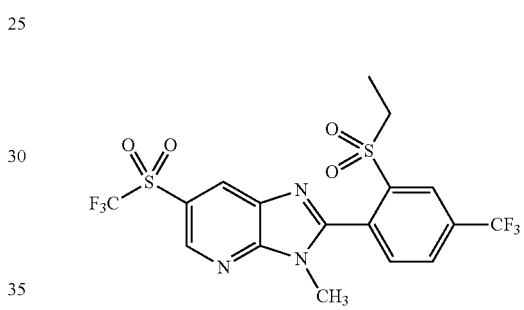

$^1$H-NMR (CDCl$_3$) δ: 9.08-9.07 (1H, m), 8.68-8.66 (1H, m), 8.52-8.50 (1H, m), 8.16-8.12 (1H, m), 7.76-7.73 (1H, m), 3.78 (3H, s), 3.46 (2H, q), 1.30 (3H, t)

Production Example 137-1

To a mixture of 4-(1,2,2,2-tetrafluoro-1-trifluoromethyl-ethyl)-benzene-1,2-diamine (552 mg), 2-ethylsulfanylbenzoic acid (401 mg), and pyridine (27 mL), 1-ethyl-3-(3-dimethylaminopropyl)carbodiimide hydrochloride (422 mg) and 1-hydroxybenzotriazole (27 mg) were added at room temperature. The reaction mixture was stirred at room temperature for 5 hours, diluted with water, and extracted with ethyl acetate. The combined organic layer was dried over sodium sulfate, and concentrated under reduced pressure. The resulting residue was dissolved in a mixed solution of DMF (7.5 mL) and toluene (30 mL), and then p-toluenesulfonic acid (837 mg) was added at room temperature. The mixture was stirred with heating at 130° C. for 8 hours, and allowed to stand to cool to room temperature. Into the reaction mixture, saturated aqueous sodium hydrogen carbonate solution was poured, and extracted with ethyl acetate. The combined organic layer was dried over sodium sulfate, and concentrated under reduced pressure. The residue was subjected to silica gel column chromatography to give 97 mg of 2-(2-ethylsulfanyl-phenyl)-5-(1,2,2,2-tetrafluoro-1-trifluoromethyl-ethyl)-1H-benzimidazole (hereinafter, Present Compound 346).

Present Compound 346

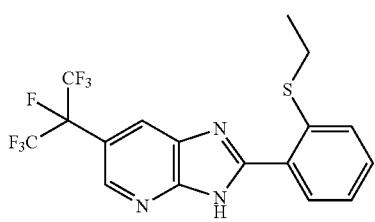 [SMILES: CCSc1ccccc1-c1nc2cc(C(F)(C(F)(F)F)C(F)(F)F)cnc2[nH]1]

¹H-NMR (CDCl₃) δ: 12.08-11.87 (1H, m), 8.31 (1H, s), 8.12-7.44 (4H, m), 7.42-7.30 (2H, m), 2.86 (2H, q), 1.22 (3H, t).

Production Example 137-2

To a mixture of 2-(2-ethylsulfanyl-phenyl)-5-(1,2,2,2-tetrafluoro-1-trifluoromethyl-ethyl)-1H-benzimidazole (97 mg) and DMF (10 mL), sodium hydride (11 mg) and iodomethane (16 μL) were added under ice-cooling. The mixture was heated to room temperature, and stirred for 5 hours. The reaction mixture was diluted with water, and extracted with ethyl acetate. The combined organic layer was dried over sodium sulfate, and concentrated under reduced pressure. The residue was subjected to silica gel column chromatography to give 35 mg of 2-(2-ethylsulfanyl-phenyl)-1-methyl-6-(1,2,2,2-tetrafluoro-1-trifluoromethyl-ethyl)-1H-benzimidazole (hereinafter, Present Compound 304) and 80 mg of 2-(2-ethylsulfanyl-phenyl)-1-methyl-5-(1,2,2,2-tetrafluoro-1-trifluoromethyl-ethyl)-1H-benzimidazole (hereinafter, Present Compound 305).

Present Compound 304

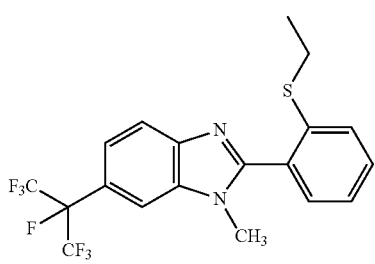 [SMILES: CCSc1ccccc1-c1nc2ccc(C(F)(C(F)(F)F)C(F)(F)F)cc2n1C]

¹H-NMR (CDCl₃) δ: 7.93 (1H, d), 7.68 (1H, s), 7.55-7.44 (4H, m), 7.37-7.29 (1H, m), 3.71 (3H, s), 2.87 (2H, q), 1.24 (3H, t).

Present Compound 305

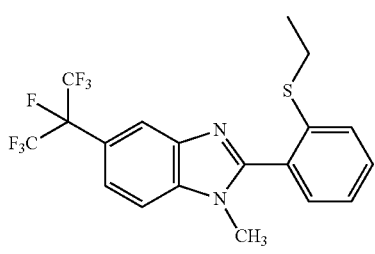 [SMILES: CCSc1ccccc1-c1nc2cc(C(F)(C(F)(F)F)C(F)(F)F)ccc2n1C]

¹H-NMR (CDCl₃) δ: 8.12 (1H, s), 7.61-7.41 (5H, m), 7.36-7.30 (1H, m), 3.68 (3H, s), 2.86 (2H, q), 1.23 (3H, t).

Production Example 138-1

To a mixture of 2-nitro-4-(pentafluorosulphur)-phenylamine (2.0 g) and DMF (15 mL), sodium hydride (313 mg) and iodomethane (447 μL) were added under ice-cooling. The mixture was heated to room temperature, and stirred for 5 hours. The reaction mixture was diluted with water, and then the precipitated powder was collected by filtration. The resulting powder was washed with hexane to give 2.0 g of methyl-(2-nitro-4-(pentafluorosulphur)-phenyl)-amine.

methyl-[2-nitro-4-(pentafluorosulphur)-phenyl]-amine

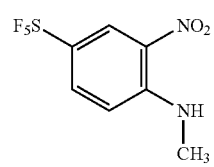

¹H-NMR (CDCl₃) δ: 8.60 (1H, d), 8.29 (1H, brs), 7.78 (1H, dd), 6.89 (1H, d), 3.10 (3H, d).

Production Example 138-2

To a mixture of methyl-[2-nitro-4-(pentafluorosulphur)-phenyl]-amine (2.0 g), acetic acid (1.9 mL), ethanol (80 mL), and water (20 mL), iron powder (1.5 g) was added with stirring with heating at 80° C. The reaction mixture was stirred with heating at 80° C. for 6 hours, and filtered through Celite®. The resulting filtrate was concentrated under reduced pressure, and diluted with 1N aqueous sodium hydroxide solution. The mixed solution was extracted with ethyl acetate. The combined organic layer was dried over sodium sulfate, and concentrated under reduced pressure. The residue was subjected to silica gel column chromatography to give 1.6 g of N¹-methyl-4-(pentafluorosulphur)-benzene-1,2-diamine (Compound (1F)-35). N¹-methyl-4-(pentafluorosulphur)-benzene-1,2-diamine

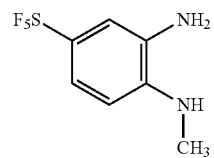

Production Example 138-3

To a mixture of W-methyl-4-(pentafluorosulphur)-benzene-1,2-diamine (575 mg), 2-fluoro-4-trifluoromethyl-benzaldehyde (348 μL), and DMF (5 mL), sodium hydrogen sulfite (290 mg) was added at room temperature. The mixture was heated to 100° C., and stirred with heating for 10 hours. After the mixture was allowed to stand to cool to room temperature, the mixture was diluted with water, and extracted with ethyl acetate. The combined organic layer was dried over sodium sulfate, and concentrated under reduced pressure. The residue was dissolved in DMF, and then and sodium ethanethiolate (175 mg) was added at room temperature thereto. The mixture was stirred at room temperature for 8 hours, and then into the mixture, saturated aqueous sodium hydrogen carbonate solution was poured, and extracted with ethyl acetate. The combined organic layer was dried over sodium sulfate, and concentrated under reduced pressure. The residue was subjected to silica gel column chromatography to give 537 mg of 2-(2-ethylsulfanyl-4-trifluoromethyl-phenyl)-1-methyl-5-(pentafluorosulphur)-1H-benzimidazole (hereinafter, Present Compound 314).

Present Compound 314

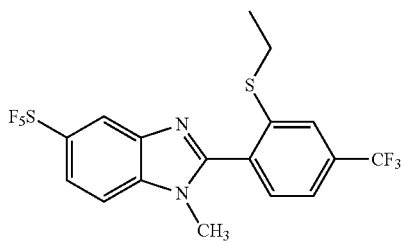

¹H-NMR (CDCl₃) δ: 8.28 (1H, d), 7.79 (1H, dd), 7.67 (1H, s), 7.57 (2H, s), 7.46 (1H, d), 3.70 (3H, s), 2.93 (2H, q), 1.27 (3H, t).

Production Example 139

To a mixture of 2-(2-ethylsulfanyl-4-trifluoromethyl-phenyl)-1-methyl-5-(pentafluorosulphur)-1H-benzimidazole (370 mg) and chloroform (10 mL), 69-75% of 3-chloroperbenzoic acid (335 mg) was added under ice-cooling. The mixture was heated to room temperature, and stirred for 0.5 hours. Into the mixture, saturated aqueous sodium hydrogen carbonate solution and saturated aqueous sodium thiosulfate solution were poured, and extracted with chloroform. The combined organic layer was dried over magnesium sulfate, and concentrated under reduced pressure. The residue was subjected to silica gel column chromatography to give 115 mg of 2-(2-ethylsulfinyl-4-trifluoromethyl-phenyl)-1-methyl-5-(pentafluorosulphur)-1H-benzimidazole (hereinafter, Present Compound 315) and 244 mg of 2-(2-ethylsulfonyl-4-trifluoromethyl-phenyl)-1-methyl-5-(pentafluorosulphur)-1H-benzimidazole (hereinafter, Present Compound 316).

Present Compound 315

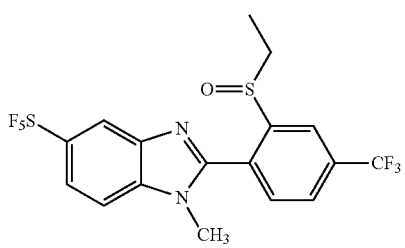

¹H-NMR (CDCl₃) δ: 8.54-8.49 (1H, m), 8.26-8.21 (1H, m), 7.95-7.89 (1H, m), 7.85-7.80 (1H, m), 7.74-7.68 (1H, m), 7.52-7.47 (1H, m), 3.82 (3H, s), 3.48-3.36 (1H, m), 3.06-2.94 (1H, m), 1.35-1.27 (3H, m).

Present Compound 316

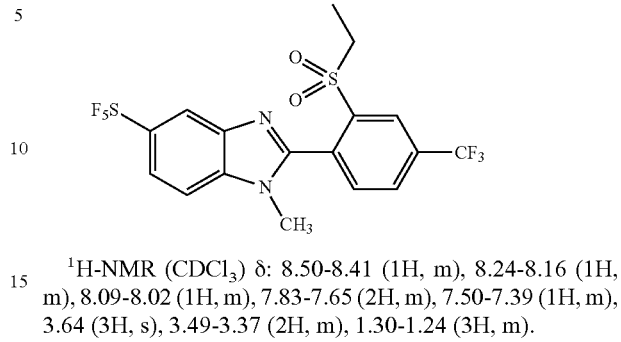

¹H-NMR (CDCl₃) δ: 8.50-8.41 (1H, m), 8.24-8.16 (1H, m), 8.09-8.02 (1H, m), 7.83-7.65 (2H, m), 7.50-7.39 (1H, m), 3.64 (3H, s), 3.49-3.37 (2H, m), 1.30-1.24 (3H, m).

Production Example 140

A mixture of 2-ethylsulfanylbenzoic acid (1.0 g), oxalyl chloride (0.7 ml), DMF (1 drop) and chloroform (4 ml) was stirred at room temperature for 1 hour, and concentrated under reduced pressure.

A mixture of the resulting residue, 2-amino-3-chloro-5-trifluoromethylpyridine (1.08 g) and N-ethyldiisopropylamine (0.85 g) was stirred at 140° C. for 2 hours. After the reaction mixture was allowed to stand to cool, into the mixture, water was poured, and extracted with ethyl acetate. The organic layer was washed with water, dried over anhydrous magnesium sulfate, and concentrated under reduced pressure.

A mixture of the resulting residue, Lawesson's reagent (2.1 g), and chlorobenzene (10 ml) was refluxed for 3 hours. After the reaction mixture was allowed to stand to cool, the reaction mixture was concentrated under reduced pressure. The resulting residue was subjected to silica gel column chromatography to give 0.14 g of 2-(2-ethylsulfanylphenyl)-6-(trifluoromethyl)thiazolo[4,5-b]pyridine (hereinafter, Present Compound 328).

Present Compound 328

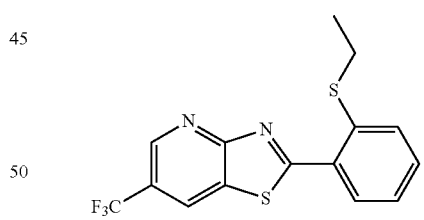

¹H-NMR (CDCl₃) δ: 9.02 (1H, d), 8.55 (1H, d), 8.35 (1H, dd), 7.60 (1H, dd), 7.49 (1H, td), 7.40 (1H, td), 2.99 (2H, q), 1.33 (3H, t).

Production Example 141

To a mixture of 2-(2-ethylsulfanylphenyl)-6-(trifluoromethyl)thiazolo[4,5-b]pyridine (0.14 g) and chloroform (3 ml), 3-chloroperbenzoic acid (purity: not less than 65%, 0.21 g) was added, and stirred at room temperature for 12 hours. The reaction mixture was diluted with chloroform, washed with 10% of aqueous sodium thiosulfate solution then saturated aqueous sodium hydrogen carbonate solution, dried over anhydrous magnesium sulfate, and concentrated under reduced pressure. The resulting residue was subjected to silica gel column chromatography to give 57 mg of 2-(2-ethylsulfonylphenyl)-6-(trifluoromethyl)thiazolo[4,5-b]pyridine (hereinafter, Present Compound 329).

Present Compound 329

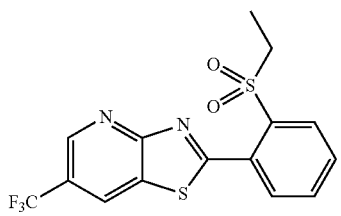 [SMILES: CCS(=O)(=O)c1ccccc1-c1nc2ncc(C(F)(F)F)cc2s1]

$^1$H-NMR (CDCl$_3$) δ: 9.04 (1H, d), 8.62 (1H, d), 8.26 (1H, dd), 7.84-7.77 (2H, m), 7.71 (1H, dd), 3.81 (2H, q), 1.36 (3H, t).

Production Example 142

To a mixture of sodium ethyl mercaptide (80%, 0.63 g) and DMF (10 ml), a solution of 2-(4-bromo-2-fluorophenyl)-3-methyl-6-trifluoromethyl-3H-imidazo[4,5-b]pyridine (2.08 g) in DMF was added dropwise under ice-cooling, then heated to room temperature, and stirred for 30 minutes. Into the reaction mixture, saturated aqueous sodium hydrogen carbonate solution was poured, and extracted with ethyl acetate. The combined organic layer was dried over magnesium sulfate, and concentrated under reduced pressure. The resulting residue was subjected to silica gel column chromatography to give 1.57 g of 2-(4-bromo-2-ethylsulfanylphenyl)-3-methyl-6-trifluoromethyl-3H-imidazo[4,5-b]pyridine (hereinafter, Present Compound 238).

Present Compound 238

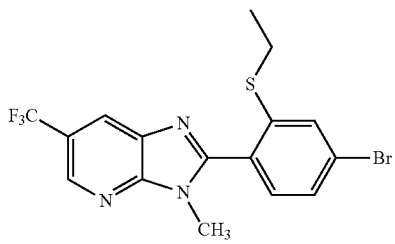 [SMILES: CCSc1cc(Br)ccc1-c1nc2cc(C(F)(F)F)cnc2n1C]

Production Example 143

To a mixture of 2-(4-bromo-2-ethylsulfanylphenyl)-3-methyl-6-trifluoromethyl-3H-imidazo[4,5-b]pyridine (0.40 g) and chloroform (5 ml), 3-chloroperbenzoic acid (purity: not less than 65%, 0.29 g) was added under ice-cooling, then heated to room temperature, and stirred for 2 hours. Into the reaction mixture, saturated aqueous sodium hydrogen carbonate solution and saturated aqueous sodium thiosulfate solution were poured, and extracted with chloroform. The combined organic layer was dried over magnesium sulfate, and concentrated under reduced pressure. The resulting residue was subjected to silica gel column chromatography to give 0.26 g of 2-(4-bromo-2-ethylsulfinylphenyl)-3-methyl-6-trifluoromethyl-3H-imidazo[4,5-b]pyridine (hereinafter, Present Compound 239) and 0.17 g of 2-(4-bromo-2-ethylsulfonylphenyl)-3-methyl-6-trifluoromethyl-3H-imidazo[4,5-b]pyridine (hereinafter, Present Compound 240).

Present Compound 239

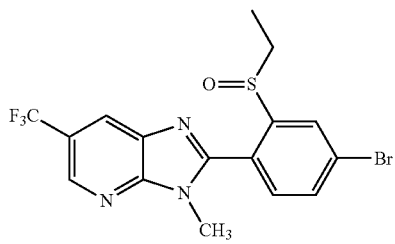 [SMILES: CCS(=O)c1cc(Br)ccc1-c1nc2cc(C(F)(F)F)cnc2n1C]

Present Compound 240

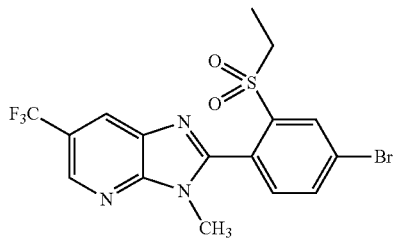

Production Example 144

A mixture of 2-(4-bromo-2-ethylsulfonylphenyl)-3-methyl-6-trifluoromethyl-3H-imidazo[4,5-b]pyridine (0.20 g), 2-tributylstannylpyrimidine (0.17 g), tetrakis(triphenylphosphine)palladium (27 mg) and toluene (5 ml) was heated at reflux under nitrogen atmosphere for 5.5 hours. After the mixture was cooled to room temperature, to the mixture, 2-tributylstannylpyrimidine (0.17 g) and tetrakis(triphenylphosphine)palladium (27 mg) were added, and stirred under reflux for further 8 hours. After the mixture was cooled to room temperature, water was poured thereinto, and extracted with ethyl acetate. The combined organic layer was dried over magnesium sulfate, and concentrated under reduced pressure. The resulting residue was subjected to silica gel column chromatography to give 0.20 g of 2-[2-ethylsulfonyl-4-(pyrimidine-2-yl)-phenyl)-3-methyl-6-trifluoromethyl-3H-imidazo[4,5-b]pyridine (hereinafter, Present Compound 333).

Present Compound 333

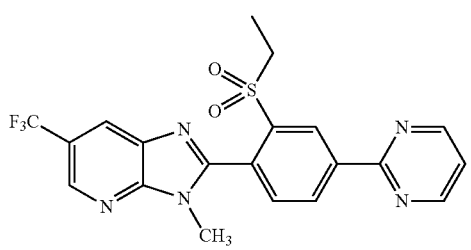 [SMILES: CCS(=O)(=O)c1cc(-c2ncccn2)ccc1-c1nc2cc(C(F)(F)F)cnc2n1C]

¹H-NMR (CDCl₃) δ: 8.77-8.74 (1H, m), 8.38-8.36 (1H, m), 8.30-8.27 (1H, m), 8.00-7.95 (1H, m), 7.63-7.55 (1H, m), 7.43 (1H, d), 7.41-7.30 (2H, m), 3.72 (3H, s), 3.44 (2H, q), 1.28 (3H, t).

Production Example 145-1

To a mixture of 2-chloro-1,3-dinitro-5-trifluoromethyl-benzene (20 g) and DMF (30 mL), 40% of aqueous methylamine solution (15 mL) was added dropwise under ice-cooling. The mixture was stirred for 6 hours under ice-cooling, and then the reaction mixture was added to iced water. The precipitated powder was collected by filtration, and washed with water to give 20 g of (2,6-dinitro-4-trifluoromethyl-phenyl)-methyl-amine.

(2,6-dinitro-4-trifluoromethyl-phenyl)-methyl-amine

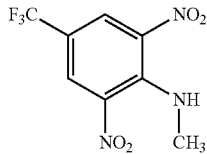

Production Example 145-2

To a mixture of (2,6-dinitro-4-trifluoromethyl-phenyl)-methyl-amine (5.0 g), acetic acid (11 mL), ethanol (100 mL), and ice (20 g), iron powder (6.4 g) was added under ice-cooling. The reaction mixture was stirred at 0° C. for 3.5 hours, and filtered through Celite®. The resulting filtrate was concentrated under reduced pressure, and diluted with 1N aqueous sodium hydroxide solution. The solution was extracted with ethyl acetate. The combined organic layer was dried over sodium sulfate, and concentrated under reduced pressure to give 3.1 g of N'-methyl-5-trifluoromethyl-benzene-1,2,3-triamine. N'-methyl-5-trifluoromethyl-benzene-1,2,3-triamine

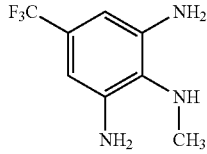

Production Example 145-3

To a mixture of N'-methyl-5-trifluoromethyl-benzene-1,2,3-triamine (1.3 g), 2-ethylsulfanylbenzoic acid (1.3 g), and pyridine (12 mL), 1-ethyl-3-(3-dimethylaminopropyl)carbodiimide hydrochloride (1.4 g) and 1-hydroxybenzotriazole (86 mg) were added at room temperature. The mixture was stirred at room temperature for 5 hours, then heated to 110° C., and stirred with heating for 8 hours. After the reaction mixture was allowed to cool to room temperature, the reaction mixture was diluted with water, and extracted with ethyl acetate. The combined organic layer was dried over sodium sulfate, and concentrated under reduced pressure. The residue was subjected to silica gel column chromatography to give 339 mg of 2-(2-ethylsulfanyl-phenyl)-3-methyl-6-trifluoromethyl-3H-benzimidazole-4-ylamine (hereinafter, Present Compound 336).

Present Compound 336

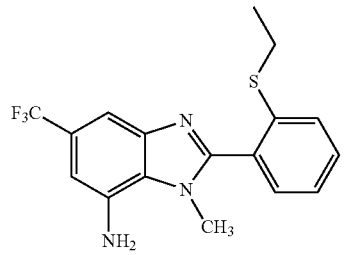 [SMILES: CCSc1ccccc1-c1nc2cc(C(F)(F)F)cc(N)c2n1C]

¹H-NMR (CDCl₃) δ: 7.55 (1H, s), 7.50-7.36 (3H, m), 7.33-7.28 (1H, m), 6.77 (1H, d), 4.04 (2H, brs), 3.91 (3H, s), 2.83 (2H, q), 1.21 (3H, t).

Production Example 146

To a mixture of sodium ethyl mercaptide (80%, 0.33 g) and DMF (4 ml), a solution of 2-(2-fluoro-4-(pentafluorosulphur)phenyl)-3-methyl-6-trifluoromethyl-3H-imidazo[4,5-b]pyridine (1.19 g) in DMF was added dropwise under ice-cooling, then heated to room temperature, and stirred at room temperature for 2 hours. Into the reaction mixture, saturated aqueous sodium hydrogen carbonate solution was poured, and extracted with ethyl acetate. The combined organic layer was dried over magnesium sulfate, and concentrated under reduced pressure. The resulting residue was subjected to silica gel column chromatography to give 1.21 g of 2-(2-ethylsulfanyl-4-(pentafluorosulphur)phenyl)-3-methyl-6-trifluoromethyl-3H-imidazo[4,5-b]pyridine (hereinafter, Present Compound 341).

Present Compound 341

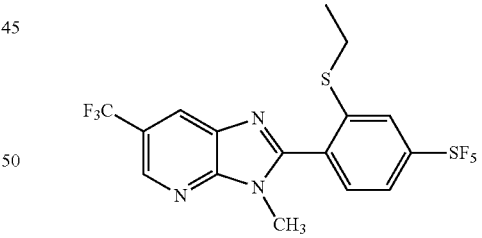

¹H-NMR (CDCl₃) δ: 8.75-8.74 (1H, m), 8.36-8.34 (1H, m), 7.81 (1H, d), 7.73 (1H, dd), 7.58-7.54 (1H, m), 3.80 (3H, s), 2.95 (2H, q), 1.29 (3H, t).

Production Example 147

To a mixture of 2-(2-ethylsulfanyl-4-(pentafluorosulphur)phenyl)-3-methyl-6-trifluoromethyl-3H-imidazo[4,5-b]pyridine (0.90 g) and chloroform (6 ml), 3-chloroperbenzoic acid (purity: not less than 65%, 0.68 g) was added under ice-cooling, then heated to room temperature, and stirred for 1 hour. Into the reaction mixture, saturated aqueous sodium hydrogen carbonate solution and saturated aqueous sodium thiosulfate solution were poured, and extracted with chloroform. The combined organic layer was dried over magnesium sulfate, and concentrated under reduced pressure. The resulting residue was subjected to silica gel column chromatography to give 0.45 g of 2-(2-ethylsulfinyl-4-(pentafluorosulphur)phenyl)-3-methyl-6-trifluoromethyl-3H-imidazo[4,5-b]pyridine (hereinafter, Present Compound 342) and 0.44 g of 2-(2-ethylsulfonyl-4-(pentafluorosulphur)phenyl)-3-methyl-6-trifluoromethyl-3H-imidazo[4,5-b]pyridine (hereinafter, Present Compound 343).

Present Compound 342

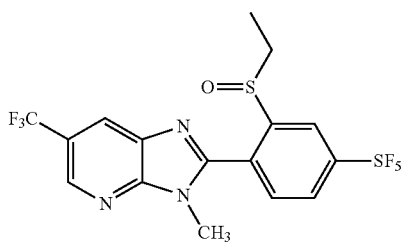

¹H-NMR (CDCl₃) δ: 8.80-8.78 (1H, m), 8.65 (1H, d), 8.35-8.34 (1H, m), 8.07 (1H, dd), 7.78-7.75 (1H, m), 3.95 (3H, s), 3.55-3.45 (1H, m), 3.10-3.00 (1H, m), 1.36 (3H, t).

Present Compound 343

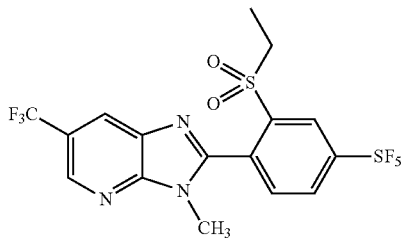

¹H-NMR (CDCl₃) δ: 8.78-8.76 (1H, m), 8.61 (1H, d), 8.32-8.30 (1H, m), 8.22 (1H, dd), 7.74-7.70 (1H, m), 3.75 (3H, s), 3.50 (2H, q), 1.30 (3H, t).

Production Example 148-1

To a mixture of 5-trifluoromethyl-pyridine-2-ylamine (65 g) and chloroform (100 mL), N-bromosuccinimide (71 g) was added in 5 parts under ice-cooling. The mixture was heated to room temperature, and stirred for 1 hour, then heated to 80° C., and stirred with heating for 30 minutes. After the mixture was allowed to cool to room temperature, into the mixture, saturated aqueous sodium thiosulfate solution and saturated aqueous sodium hydrogen carbonate solution were poured, and extracted with chloroform. The combined organic layer was dried over sodium sulfate, and concentrated under reduced pressure. The residue was subjected to silica gel column chromatography to give 96 g of 3-bromo-5-trifluoromethyl-pyridine-2-ylamine.

3-bromo-5-trifluoromethyl-pyridine-2-ylamine

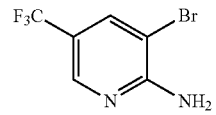 [SMILES: Nc1ncc(C(F)(F)F)cc1Br]

¹H-NMR (CDCl₃) δ: 8.27 (1H, d), 7.86 (1H, d), 5.38 (2H, brs).

Production Example 148-2

To an autoclave reactor, 3-bromo-5-trifluoromethyl-pyridine-2-ylamine (40 g), acetylacetone copper(II) (2.2 g), acetylacetone (6.6 g), cesium carbonate (59 g), and NMP (105 mL) were added, and then 28% of aqueous ammonia solution (25 mL) was added under ice-cooling. After the reactor was sealed, the mixture heated to 110° C., and stirred with heating for 12 hours. The mixture was ice-cooled to room temperature, then diluted with water, and extracted with ethyl acetate. The combined organic layer was dried over sodium sulfate, and concentrated under reduced pressure. The residue was subjected to silica gel column chromatography to give 15 g 5-trifluoromethyl-pyridine-2,3-diamine (Compound (1F)-22).

5-trifluoromethyl-pyridine-2,3-diamine

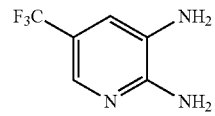 [SMILES: Nc1cc(C(F)(F)F)cnc1N]

¹H-NMR (CDCl₃) δ: 7.93 (1H, d), 7.04 (1H, d), 4.71 (2H, brs), 3.46 (2H, brs).

Production Example 148-3

To a mixture of 5-trifluoromethyl-pyridine-2,3-diamine (8.6 g), 2-formyl-5-trifluoromethylphenylethylsulfide (11 g), and DMF (67 mL), sodium hydrogen sulfite (6.1 g) was added at room temperature. After the mixture was stirred with heating at 100° C. for 3 hours, to the mixture, copper (II) chloride dihydrate (1 g) was added, and stirred at 100° C. for further 1 hour. After the reaction mixture was allowed to cool to room temperature, the reaction mixture was added to water, and extracted with ethyl acetate. The combined organic layer was dried over sodium sulfate, and concentrated under reduced pressure. The residue was subjected to silica gel column chromatography to give a yellow powdered solid. The solid was washed with hot hexane to give 12 g of 2-(2-ethylsulfanyl-4-trifluoromethyl-phenyl)-6-trifluoromethyl-3H-imidazo[4,5-b]pyridine (hereinafter, Present Compound 344).

Present Compound 344

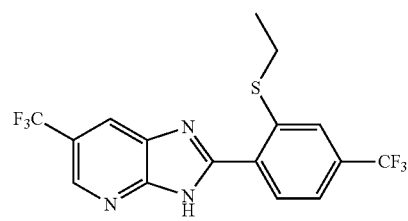 [SMILES: CCSc1cc(C(F)(F)F)ccc1-c1nc2cc(C(F)(F)F)cnc2[nH]1]

¹H-NMR (CDCl₃) δ: 12.79 (1H, brs), 8.72 (1H, brs), 8.49-8.34 (2H, m), 7.79 (1H, s), 7.64 (1H, d), 3.00 (2H, q), 1.31 (3H, t).

Production Example 149

To a mixture of 2-(2-ethylsulfanyl-4-trifluoromethyl-phenyl)-6-trifluoromethyl-3H-imidazo[4,5-b]pyridine (12 g) and chloroform (111 mL), 69-75% of 3-chloroperbenzoic acid (8.0 g) was added under ice-cooling. The mixture was heated to room temperature, and stirred for 0.5 hours. Into the mixture, saturated aqueous sodium hydrogen carbonate solution and saturated aqueous sodium thiosulfate solution were poured, and extracted with chloroform. The combined organic layer was dried over magnesium sulfate, and concentrated under reduced pressure. The residue was subjected to silica gel column chromatography to give 9.1 g of 2-(2-ethylsulfonyl-4-trifluoromethyl-phenyl)-6-trifluoromethyl-3H-imidazo[4,5-b]pyridine (hereinafter, Present Compound 345).

Present Compound 345

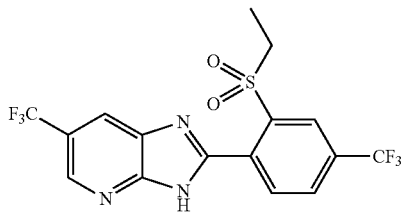 [SMILES: CCS(=O)(=O)c1cc(C(F)(F)F)ccc1-c1nc2cc(C(F)(F)F)cnc2[nH]1]

$^1$H-NMR (DMSO-D$_6$) δ: 14.15 (1H, brs), 8.83 (1H, s), 8.58 (1H, s), 8.41 (1H, d), 8.37 (1H, s), 8.19 (1H, d), 3.97 (2H, q), 1.23 (3H, t).

Production Example 150

A mixture of N-(2-amino-5-trifluoromethylpyridine-3-yl)-2-ethylsulfanyl-benzamide (200 mg), tert-butylalcohol (1 ml), and THF (9 ml) was stirred with heating at 80° C., then 60% of sodium hydride (in oil, 56 mg) was added thereto. The mixture was stirred with heating at 80° C. for 2 hours, and then 60% of sodium hydride (in oil, 56 mg) was added. The mixture was further stirred with heating at the same temperature for 2 hours, and then to the mixture, 60% of sodium hydride (in oil, 56 mg) was added, and stirred with heating at the same temperature for 2 hours. The reaction mixture was cooled to room temperature, and evaporated to remove the solvent, and then to the mixture, saturated ammonium chloride solution was added, and extracted with ethyl acetate. The organic layer was dried over sodium sulfate, and concentrated under reduced pressure. The resulting residue was subjected to silica gel column chromatography to give 132 mg of 2-(2-ethylsulfanylphenyl)-6-trifluoromethyl-3H-imidazo[4,5-b]pyridine (hereinafter, Present Compound 351).

Present Compound 351

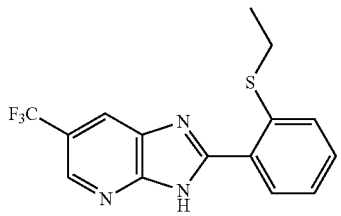 [SMILES: CCSc1ccccc1-c1nc2cc(C(F)(F)F)cnc2[nH]1]

$^1$H-NMR (CDCl$_3$) δ: 8.67 (1H, d), 8.51-8.48 (1H, m), 8.33 (1H, d), 7.66-7.61 (1H, m), 7.51-7.46 (2H, m), 2.93 (2H, q), 1.27 (3H, t)

The above present compounds and present compounds produced by a similar production method to those of the above present compounds are shown in the following tables.

The compound of the formula (1-2):

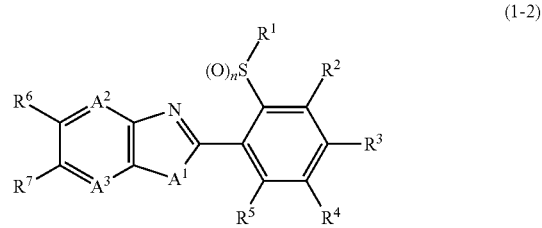

wherein, $R^1$, $R^2$, $R^3$, $R^4$, $R^5$, $R^6$, $R^7$, $A^1$, $A^2$, $A^3$, and n represent a combination shown in Tables 20-34.

TABLE 20

| Present Compound | $R^1$ | $R^2$ | $R^3$ | $R^4$ | $R^5$ | $R^6$ | $R^7$ | $A^1$ | $A^2$ | $A^3$ | n |
|---|---|---|---|---|---|---|---|---|---|---|---|
| 1 | Me | H | H | H | H | CF$_3$ | H | NMe | CH | N | 0 |
| 2 | Me | H | H | H | H | CF$_3$ | H | NMe | CH | N | 1 |
| 3 | Me | H | H | H | H | CF$_3$ | H | NMe | CH | N | 2 |
| 4 | Et | H | H | H | H | CF$_3$ | H | NMe | CH | N | 0 |
| 5 | Et | H | H | H | H | CF$_3$ | H | NMe | CH | N | 1 |
| 6 | Et | H | H | H | H | CF$_3$ | H | NMe | CH | N | 2 |
| 7 | Pr | H | H | H | H | CF$_3$ | H | NMe | CH | N | 0 |
| 8 | Pr | H | H | H | H | CF$_3$ | H | NMe | CH | N | 1 |
| 9 | Pr | H | H | H | H | CF$_3$ | H | NMe | CH | N | 2 |
| 10 | CH$_2$=CHCH$_2$ | H | H | H | H | CF$_3$ | H | NMe | CH | N | 0 |
| 11 | CH$_2$=CHCH$_2$ | H | H | H | H | CF$_3$ | H | NMe | CH | N | 2 |
| 12 | iPr | H | H | H | H | CF$_3$ | H | NMe | CH | N | 0 |
| 13 | iPr | H | H | H | H | CF$_3$ | H | NMe | CH | N | 1 |
| 14 | iPr | H | H | H | H | CF$_3$ | H | NMe | CH | N | 2 |
| 15 | tBu | H | H | H | H | CF$_3$ | H | NMe | CH | N | 0 |
| 16 | tBu | H | H | H | H | CF$_3$ | H | NMe | CH | N | 1 |
| 17 | tBu | H | H | H | H | CF$_3$ | H | NMe | CH | N | 2 |
| 18 | CF$_3$ | H | H | H | H | CF$_3$ | H | NMe | CH | N | 0 |
| 19 | CF$_3$ | H | H | H | H | CF$_3$ | H | NMe | CH | N | 1 |
| 20 | CF$_3$ | H | H | H | H | CF$_3$ | H | NMe | CH | N | 2 |
| 21 | Et | H | H | H | H | CF$_3$ | H | NEt | CH | N | 0 |
| 22 | Et | H | H | H | H | CF$_3$ | H | NEt | CH | N | 1 |
| 23 | Et | H | H | H | H | CF$_3$ | H | NEt | CH | N | 2 |
| 24 | Et | H | H | H | H | CF$_3$ | H | NPr | CH | N | 0 |
| 25 | Et | H | H | H | H | CF$_3$ | H | NPr | CH | N | 1 |

TABLE 21

| Present Compound | $R^1$ | $R^2$ | $R^3$ | $R^4$ | $R^5$ | $R^6$ | $R^7$ | $A^1$ | $A^2$ | $A^3$ | n |
|---|---|---|---|---|---|---|---|---|---|---|---|
| 26 | Et | H | H | H | H | CF$_3$ | H | NPr | CH | N | 2 |
| 27 | Et | H | H | H | H | CF$_3$ | H | NiPr | CH | N | 0 |
| 28 | Et | H | H | H | H | CF$_3$ | H | NiPr | CH | N | 1 |
| 29 | Et | H | H | H | H | CF$_3$ | H | NiPr | CH | N | 2 |
| 30 | Et | H | H | H | H | CF$_3$ | H | NCycPr | CH | N | 0 |
| 31 | Et | H | H | H | H | CF$_3$ | H | NCycPr | CH | N | 1 |
| 32 | Et | H | H | H | H | CF$_3$ | H | NCycPr | CH | N | 2 |
| 33 | Et | H | H | H | H | CF$_3$ | H | NCH$_2$OEt | CH | N | 0 |
| 34 | Et | H | H | H | H | H | CF$_3$ | NCH$_2$OEt | N | CH | 0 |
| 35 | Et | H | H | H | H | CF$_3$ | H | NCH$_2$OEt | CH | N | 1 |
| 36 | Et | H | H | H | H | CF$_3$ | H | NCH$_2$OEt | CH | N | 2 |
| 37 | Et | H | H | H | H | CF$_3$ | H | NCH$_2$OMe | CH | N | 0 |
| 38 | Et | H | H | H | H | CF$_3$ | H | NCH$_2$OMe | CH | N | 2 |
| 39 | Et | H | H | H | H | Me | H | NMe | CH | N | 0 |
| 40 | Et | H | H | H | H | Me | H | NMe | CH | N | 1 |
| 41 | Et | H | H | H | H | Me | H | NMe | CH | N | 2 |
| 42 | Et | H | H | H | H | Br | H | NMe | CH | N | 0 |
| 43 | Et | H | H | H | H | Br | H | NMe | CH | N | 1 |
| 44 | Et | H | H | H | H | Br | H | NMe | CH | N | 2 |

TABLE 21-continued

| Present Compound | R¹ | R² | R³ | R⁴ | R⁵ | R⁶ | R⁷ | A¹ | A² | A³ | n |
|---|---|---|---|---|---|---|---|---|---|---|---|
| 45 | Et | H | H | H | H | I | H | NMe | CH | N | 0 |
| 46 | Et | H | H | H | H | I | H | NMe | CH | N | 1 |
| 47 | Et | H | H | H | H | I | H | NMe | CH | N | 2 |
| 48 | Et | H | H | H | H | CN | H | NMe | CH | N | 0 |
| 49 | Et | H | H | H | H | CN | H | NMe | CH | N | 1 |
| 50 | Et | H | H | H | H | CN | H | NMe | CH | N | 2 |

TABLE 22

| Present Compound | R¹ | R² | R³ | R⁴ | R⁵ | R⁶ | R⁷ | A¹ | A² | A³ | n |
|---|---|---|---|---|---|---|---|---|---|---|---|
| 51 | Et | H | H | H | H | CHO | H | NMe | CH | N | 0 |
| 52 | Et | H | H | H | H | CF$_2$H | H | NMe | CH | N | 0 |
| 53 | Et | H | H | H | H | CF$_2$H | H | NMe | CH | N | 1 |
| 54 | Et | H | H | H | H | CF$_2$H | H | NMe | CH | N | 2 |
| 55 | Et | H | H | H | H | C$_2$F$_5$ | H | NMe | CH | N | 0 |
| 56 | Et | H | H | H | H | Ph | H | NMe | CH | N | 0 |
| 57 | Et | H | H | H | H | Ph | H | NMe | CH | N | 2 |
| 58 | Et | H | H | H | H | 2-F-Ph | H | NMe | CH | N | 0 |
| 59 | Et | H | H | H | H | 2-F-Ph | H | NMe | CH | N | 1 |
| 60 | Et | H | H | H | H | 2-F-Ph | H | NMe | CH | N | 2 |
| 61 | Et | H | H | H | H | 3-F-Ph | H | NMe | CH | N | 0 |
| 62 | Et | H | H | H | H | 3-F-Ph | H | NMe | CH | N | 1 |
| 63 | Et | H | H | H | H | 3-F-Ph | H | NMe | CH | N | 2 |
| 64 | Et | H | H | H | H | 4-F-Ph | H | NMe | CH | N | 0 |
| 65 | Et | H | H | H | H | 4-F-Ph | H | NMe | CH | N | 2 |
| 66 | Et | H | H | H | H | H | CF$_3$ | NMe | N | CH | 0 |
| 67 | Me | H | H | H | H | CF$_3$ | H | NMe | CH | CH | 0 |
| 68 | Et | H | H | H | H | CF$_3$ | H | NMe | CH | CH | 0 |
| 69 | Et | H | H | H | H | CF$_3$ | H | NMe | CH | CH | 1 |
| 70 | Et | H | H | H | H | CF$_3$ | H | NMe | CH | CH | 2 |
| 71 | Et | H | H | H | H | CF$_3$ | H | NMe | CH | CCl | 0 |
| 72 | Et | H | H | H | H | CF$_3$ | H | NMe | CH | CCl | 1 |
| 73 | Et | H | H | H | H | CF$_3$ | H | NMe | CH | CCl | 2 |
| 74 | Et | H | H | H | H | CF$_3$ | H | NMe | CH | CBr | 0 |
| 75 | Et | H | H | H | H | CF$_3$ | H | NMe | CH | CBr | 1 |

TABLE 23

| Present Compound | R¹ | R² | R³ | R⁴ | R⁵ | R⁶ | R⁷ | A¹ | A² | A³ | n |
|---|---|---|---|---|---|---|---|---|---|---|---|
| 76 | Et | H | H | H | H | CF$_3$ | H | NMe | CH | CBr | 2 |
| 77 | Me | H | H | H | H | CF$_3$ | H | O | CH | CH | 0 |
| 78 | Et | H | H | H | H | CF$_3$ | H | O | CH | CH | 0 |
| 79 | Et | H | H | H | H | CF$_3$ | H | O | CH | CH | 1 |
| 80 | Et | H | H | H | H | CF$_3$ | H | O | CH | CH | 2 |
| 81 | Et | H | H | H | H | CF$_3$ | H | O | CH | N | 0 |
| 82 | Et | H | H | H | H | CF$_3$ | H | O | CH | N | 1 |
| 83 | Et | H | H | H | H | CF$_3$ | H | O | CH | N | 2 |
| 84 | Me | H | H | H | H | CF$_3$ | H | S | CH | CH | 0 |
| 85 | Et | H | H | H | H | CF$_3$ | H | S | CH | CH | 0 |
| 86 | Et | H | H | H | H | CF$_3$ | H | S | CH | CH | 1 |
| 87 | Et | H | H | H | H | CF$_3$ | H | S | CH | CH | 2 |
| 88 | Et | Cl | H | H | H | CF$_3$ | H | NMe | CH | N | 0 |
| 89 | Et | Cl | H | H | H | CF$_3$ | H | NMe | CH | N | 1 |
| 90 | Et | Cl | H | H | H | CF$_3$ | H | NMe | CH | N | 2 |
| 91 | Et | H | H | H | H | C(O)CF$_3$ | H | NMe | CH | N | 0 |
| 92 | Me | H | H | H | SMe | CF$_3$ | H | NMe | CH | N | 0 |
| 93 | Me | H | H | H | SOMe | CF$_3$ | H | NMe | CH | N | 1 |
| 94 | Me | H | H | H | SO$_2$Me | CF$_3$ | H | NMe | CH | N | 2 |
| 95 | Et | H | H | H | SEt | CF$_3$ | H | NMe | CH | N | 0 |
| 96 | Et | H | H | H | SOEt | CF$_3$ | H | NMe | CH | N | 1 |
| 97 | Et | H | H | H | SO$_2$Et | CF$_3$ | H | NMe | CH | N | 2 |
| 98 | Et | H | H | H | H | Cl | H | NMe | CH | N | 0 |
| 99 | Et | H | H | H | H | Cl | H | NMe | CH | N | 1 |
| 100 | Et | H | H | H | H | Cl | H | NMe | CH | N | 2 |

TABLE 24

| Present Compound | R¹ | R² | R³ | R⁴ | R⁵ | R⁶ | R⁷ | A¹ | A² | A³ | n |
|---|---|---|---|---|---|---|---|---|---|---|---|
| 101 | Et | H | H | H | H | Br | H | NMe | CCHO | N | 0 |
| 102 | Et | H | H | SEt | H | CF$_3$ | H | NMe | CH | N | 0 |
| 103 | Et | H | H | H | H | CF$_3$ | H | NCH$_2$OEt | CH | CH | 0 |
| 104 | Et | H | H | H | H | H | CF$_3$ | NCH$_2$OEt | N | CH | 0 |
| 105 | Et | H | H | H | H | CF$_3$ | H | NCH$_2$CO$_2$Me | CH | N | 0 |
| 106 | Et | H | H | H | H | CF$_3$ | H | NCH$_2$CO$_2$Et | CH | N | 0 |
| 107 | Et | H | H | H | H | CF$_3$ | H | N(CH$_2$)$_2$OMe | CH | N | 0 |
| 108 | Et | H | H | H | H | CF$_3$ | H | NCH$_2$SMe | CH | N | 0 |
| 109 | Et | H | H | H | H | CF$_3$ | H | N(CH$_2$)$_2$SMe | CH | N | 0 |
| 110 | Et | H | H | H | H | CF$_3$ | H | NBu | CH | N | 0 |
| 111 | Et | H | H | H | H | CF$_3$ | H | NCO$_2$tBu | CH | N | 0 |
| 112 | Et | H | H | H | H | C$_2$F$_5$ | H | NMe | CH | N | 1 |
| 113 | Et | H | H | H | H | C$_2$F$_5$ | H | NMe | CH | N | 2 |
| 114 | Et | H | H | H | H | CH(OH)CF$_3$ | H | NMe | CH | N | 0 |
| 115 | Et | H | H | H | H | CHFCF$_3$ | H | NMe | CH | N | 0 |
| 116 | Et | H | F | H | H | CF$_3$ | H | NMe | CH | N | 0 |
| 117 | Et | H | F | H | H | CF$_3$ | H | NMe | CH | N | 1 |
| 118 | Et | H | F | H | H | CF$_3$ | H | NMe | CH | N | 2 |
| 119 | Et | OMe | H | H | H | CF$_3$ | H | NMe | CH | N | 0 |
| 120 | Et | OMe | H | H | H | CF$_3$ | H | NMe | CH | N | 1 |
| 121 | Et | H | OMe | H | H | CF$_3$ | H | NMe | CH | N | 0 |
| 122 | Et | H | OMe | H | H | CF$_3$ | H | NMe | CH | N | 1 |
| 123 | Et | H | OMe | H | H | CF$_3$ | H | NMe | CH | N | 2 |
| 124 | Et | H | OH | H | H | CF$_3$ | H | NMe | CH | N | 0 |
| 125 | Et | H | H | H | H | NH$_2$ | H | NMe | CH | N | 0 |

TABLE 25

| Present Compound | R¹ | R² | R³ | R⁴ | R⁵ | R⁶ | R⁷ | A¹ | A² | A³ | n |
|---|---|---|---|---|---|---|---|---|---|---|---|
| 126 | Et | H | H | H | H | CHFCF$_3$ | H | NMe | CH | N | 1 |
| 127 | Et | H | H | H | H | CHFCF$_3$ | H | NMe | CH | N | 2 |
| 128 | Et | H | H | H | H | C$_3$F$_7$ | H | NMe | CH | N | 0 |
| 129 | Et | H | H | H | H | C$_3$F$_7$ | H | NMe | CH | N | 1 |
| 130 | Et | H | H | H | H | C$_3$F$_7$ | H | NMe | CH | N | 2 |
| 131 | Et | Cl | H | H | H | C$_2$F$_5$ | H | NMe | CH | N | 1 |
| 132 | Et | Cl | H | H | H | C$_2$F$_5$ | H | NMe | CH | N | 2 |
| 133 | Et | H | Cl | H | H | CF$_3$ | H | NMe | CH | N | 0 |
| 134 | Et | H | Cl | H | H | CF$_3$ | H | NMe | CH | N | 1 |
| 135 | Et | H | Cl | H | H | CF$_3$ | H | NMe | CH | N | 2 |
| 136 | Et | H | H | Cl | H | CF$_3$ | H | NMe | CH | N | 0 |
| 137 | Et | H | H | Cl | H | CF$_3$ | H | NMe | CH | N | 1 |
| 138 | Et | H | H | Cl | H | CF$_3$ | H | NMe | CH | N | 2 |
| 139 | Et | H | H | H | Cl | CF$_3$ | H | NMe | CH | N | 0 |
| 140 | Et | H | H | H | Cl | CF$_3$ | H | NMe | CH | N | 1 |
| 141 | Et | H | H | H | Cl | CF$_3$ | H | NMe | CH | N | 2 |
| 142 | Et | H | H | OMe | H | CF$_3$ | H | NMe | CH | N | 0 |
| 143 | Et | H | H | OMe | H | CF$_3$ | H | NMe | CH | N | 1 |
| 144 | Et | H | H | OMe | H | CF$_3$ | H | NMe | CH | N | 2 |
| 145 | Et | H | H | H | H | SH | H | NMe | CH | N | 0 |
| 146 | Et | H | H | H | H | Et | H | NMe | CH | N | 0 |
| 147 | Et | H | H | H | H | iPr | H | NMe | CH | N | 0 |
| 148 | Et | H | H | H | H | NHEt | H | NMe | CH | N | 0 |
| 149 | Et | H | H | H | H | NEt$_2$ | H | NMe | CH | N | 0 |
| 150 | Et | H | H | H | H | tBu | H | NMe | CH | N | 0 |

TABLE 26

| Present Compound | R¹ | R² | R³ | R⁴ | R⁵ | R⁶ | R⁷ | A¹ | A² | A³ | n |
|---|---|---|---|---|---|---|---|---|---|---|---|
| 151 | Et | H | H | H | H | H | CF$_3$ | NMe | CH | N | 0 |
| 152 | Et | H | H | H | OMe | CF$_3$ | H | NMe | CH | N | 0 |
| 153 | Et | H | H | H | OMe | CF$_3$ | H | NMe | CH | N | 1 |
| 154 | Et | H | H | H | OMe | CF$_3$ | H | NMe | CH | N | 2 |
| 155 | Et | H | H | H | OH | CF$_3$ | H | NMe | CH | N | 0 |
| 156 | Et | F | H | H | H | CF$_3$ | H | NMe | CH | N | 0 |
| 157 | Et | F | H | H | H | CF$_3$ | H | NMe | CH | N | 1 |
| 158 | Et | F | H | H | H | CF$_3$ | H | NMe | CH | N | 2 |
| 159 | Et | H | H | H | H | H | CF$_3$ | NMe | CH | N | 1 |
| 160 | Et | H | H | H | H | H | CF$_3$ | NMe | CH | N | 2 |
| 161 | Et | H | H | H | H | SCF$_3$ | H | NMe | CH | N | 0 |
| 162 | Et | H | H | H | H | NMe$_2$ | H | NMe | CH | N | 0 |
| 163 | Et | H | H | H | H | pyrrolidin-1-yl | H | NMe | CH | N | 0 |
| 164 | Et | H | H | H | H | NHCOMe | H | NMe | CH | N | 0 |
| 165 | Et | H | H | H | H | CH$_2$CF$_3$ | H | NMe | CH | N | 0 |
| 166 | Et | H | H | H | H | CF$_3$ | H | NMe | N | CH | 0 |
| 167 | Et | H | H | H | H | CF$_3$ | H | NMe | N | CH | 1 |
| 168 | Et | H | H | H | H | CF$_3$ | H | NMe | N | CH | 2 |
| 169 | Et | H | H | H | F | CF$_3$ | H | NMe | CH | N | 0 |
| 170 | Et | H | H | H | F | CF$_3$ | H | NMe | CH | N | 1 |
| 171 | Et | H | H | H | F | CF$_3$ | H | NMe | CH | N | 2 |
| 172 | Et | H | H | H | H | N(Me)COMe | H | NMe | CH | N | 0 |
| 173 | Et | H | H | H | H | NH2 | H | NMe | CH | N | 1 |
| 174 | Et | H | CF$_3$ | H | H | CF$_3$ | H | NMe | CH | N | 0 |
| 175 | Et | H | CF$_3$ | H | H | CF$_3$ | H | NMe | CH | N | 1 |

TABLE 27

| Present Compound | R¹ | R² | R³ | R⁴ | R⁵ | R⁶ | R⁷ | A¹ | A² | A³ | n |
|---|---|---|---|---|---|---|---|---|---|---|---|
| 176 | Et | H | CF$_3$ | H | H | CF$_3$ | H | NMe | CH | N | 2 |
| 177 | Et | H | H | H | H | NHCOCF$_3$ | H | NMe | CH | N | 0 |
| 178 | Et | H | H | H | H | NHCOCF$_3$ | H | NMe | CH | N | 1 |
| 179 | Et | H | H | H | H | NHCOCF$_3$ | H | NMe | CH | N | 2 |
| 180 | Et | H | H | H | H | 2-CF$_3$-Ph | H | NMe | CH | N | 0 |
| 181 | Et | H | H | H | H | 3-CF$_3$-Ph | H | NMe | CH | N | 0 |
| 182 | Et | H | H | H | H | 4-CF$_3$-Ph | H | NMe | CH | N | 0 |
| 183 | Et | H | H | H | H | CF$_3$ | H | S | CH | N | 0 |
| 184 | Et | H | H | H | H | CF$_3$ | H | S | CH | N | 1 |
| 185 | Et | H | H | H | H | CF$_3$ | H | S | CH | N | 2 |
| 186 | CH$_2$CF$_3$ | H | H | H | H | CF$_3$ | H | NMe | CH | N | 0 |
| 187 | CH$_2$CF$_3$ | H | H | H | H | CF$_3$ | H | NMe | CH | N | 1 |
| 188 | CH$_2$CF$_3$ | H | H | H | H | CF$_3$ | H | NMe | CH | N | 2 |
| 189 | Et | Me | H | H | H | CF$_3$ | H | NMe | CH | N | 0 |
| 190 | Et | Me | H | H | H | CF$_3$ | H | NMe | CH | N | 1 |
| 191 | Et | Me | H | H | H | CF$_3$ | H | NMe | CH | N | 2 |
| 192 | Et | H | Me | H | H | CF$_3$ | H | NMe | CH | N | 0 |
| 193 | Et | H | Me | H | H | CF$_3$ | H | NMe | CH | N | 1 |
| 194 | Et | H | Me | H | H | CF$_3$ | H | NMe | CH | N | 2 |
| 195 | Et | H | H | H | H | 2-CF$_3$-Ph | H | NMe | CH | N | 1 |
| 196 | Et | H | H | H | H | 2-CF$_3$-Ph | H | NMe | CH | N | 2 |
| 197 | Et | H | H | H | H | 3-CF$_3$-Ph | H | NMe | CH | N | 1 |
| 198 | Et | H | H | H | H | 3-CF$_3$-Ph | H | NMe | CH | N | 2 |
| 199 | Et | H | H | H | H | 4-CF$_3$-Ph | H | NMe | CH | N | 1 |
| 200 | Et | H | H | H | H | 4-CF$_3$-Ph | H | NMe | CH | N | 2 |

TABLE 28

| Present Compound | R¹ | R² | R³ | R⁴ | R⁵ | R⁶ | R⁷ | A¹ | A² | A³ | n |
|---|---|---|---|---|---|---|---|---|---|---|---|
| 201 | Et | H | H | CF$_3$ | H | CF$_3$ | H | NMe | CH | N | 0 |
| 202 | Et | H | H | CF$_3$ | H | CF$_3$ | H | NMe | CH | N | 1 |
| 203 | Et | H | H | CF$_3$ | H | CF3 | H | NMe | CH | N | 2 |
| 204 | Et | H | H | H | H | 2-Cl-Ph | H | NMe | CH | N | 0 |
| 205 | Et | H | H | H | H | 3-Cl-Ph | H | NMe | CH | N | 0 |
| 206 | Et | H | H | H | H | 4-Cl-Ph | H | NMe | CH | N | 0 |
| 207 | Et | H | H | H | H | 6-Cl-3-Py | H | NMe | CH | N | 0 |
| 208 | Et | H | H | H | H | 5-F-3-Py | H | NMe | CH | N | 0 |

TABLE 28-continued

| Present Compound | R¹ | R² | R³ | R⁴ | R⁵ | R⁶ | R⁷ | A¹ | A² | A³ | n |
|---|---|---|---|---|---|---|---|---|---|---|---|
| 209 | Et | H | H | H | H | SCF₃ | H | NMe | CH | N | 2 |
| 210 | Et | H | H | H | H | SCF₃ | H | NMe | CH | N | 1 |
| 211 | Et | H | H | H | H | 3-Py | H | NMe | CH | N | 0 |
| 212 | Et | H | H | H | H | 4-Py | H | NMe | CH | N | 0 |
| 213 | Et | H | H | H | H | 4-Cl-Pyrazole | H | NMe | CH | N | 0 |
| 214 | Et | H | H | H | H | SOCF₃ | H | NMe | CH | N | 2 |
| 215 | Et | H | H | H | H | SO₂CF₃ | H | NMe | CH | N | 2 |
| 216 | Et | H | H | H | H | 2-Cl-Ph | H | NMe | CH | N | 1 |
| 217 | Et | H | H | H | H | 2-Cl-Ph | H | NMe | CH | N | 2 |
| 218 | Et | H | H | H | H | 3-Cl-Ph | H | NMe | CH | N | 1 |
| 219 | Et | H | H | H | H | 3-Cl-Ph | H | NMe | CH | N | 2 |
| 220 | Et | H | H | H | H | 4-Cl-Ph | H | NMe | CH | N | 2 |
| 221 | Et | H | H | H | H | 4-Py | H | NMe | CH | N | 1 |
| 222 | Et | H | H | H | H | 4-Py | H | NMe | CH | N | 2 |
| 223 | Et | H | H | H | H | 6-Cl-3-Py | H | NMe | CH | N | 2 |
| 224 | Et | H | H | H | H | 5-F-3-Py | H | NMe | CH | N | 1 |
| 225 | Et | H | H | H | H | 5-F-3-Py | H | NMe | CH | N | 2 |

TABLE 29

| Present Compound | R¹ | R² | R³ | R⁴ | R⁵ | R⁶ | R⁷ | A¹ | A² | A³ | n |
|---|---|---|---|---|---|---|---|---|---|---|---|
| 226 | Et | H | H | H | H | 4-Cl-Pyrazole | H | NMe | CH | N | 2 |
| 227 | Et | H | H | H | H | 3-Cl-triazole | H | NMe | CH | N | 0 |
| 228 | Et | H | H | H | H | 4-CF₃-imidazole | H | NMe | CH | N | 0 |
| 229 | Et | H | H | H | H | 2-NO₂—Ph | H | NMe | CH | N | 0 |
| 230 | Et | H | H | H | H | 3-NO₂—Ph | H | NMe | CH | N | 0 |
| 231 | Et | H | H | H | H | 2-CN—Ph | H | NMe | CH | N | 0 |
| 232 | Et | H | H | H | H | 3-CN—Ph | H | NMe | CH | N | 0 |
| 233 | Et | H | H | H | H | 4-CN—Ph | H | NMe | CH | N | 0 |
| 234 | Et | H | H | H | H | 3-CF₃-triazole | H | NMe | CH | N | 0 |
| 235 | Et | H | H | H | H | 3-CF₃-5-Me-triazole | H | NMe | CH | N | 0 |
| 236 | Et | H | H | H | H | 3-Cl-triazole | H | NMe | CH | N | 2 |
| 237 | Et | H | H | H | H | 4-CF₃-imidazole | H | NMe | CH | N | 1 |
| 238 | Et | H | Br | H | H | CF₃ | H | NMe | CH | N | 0 |
| 239 | Et | H | Br | H | H | CF₃ | H | NMe | CH | N | 1 |
| 240 | Et | H | Br | H | H | CF₃ | H | NMe | CH | N | 2 |
| 241 | Et | H | CN | H | H | CF₃ | H | NMe | CH | N | 0 |
| 242 | Et | H | CN | H | H | CF₃ | H | NMe | CH | N | 1 |
| 243 | Et | H | CN | H | H | CF₃ | H | NMe | CH | N | 2 |
| 246 | Et | H | C₂F₅ | H | H | CF₃ | H | NMe | CH | N | 0 |
| 247 | Et | H | C₂F₅ | H | H | CF₃ | H | NMe | CH | N | 1 |
| 248 | Et | H | C₂F₅ | H | H | CF₃ | H | NMe | CH | N | 2 |
| 249 | Et | H | CHO | H | H | CF₃ | H | NMe | CH | N | 0 |
| 250 | Et | H | Ph | H | H | CF₃ | H | NMe | CH | N | 0 |

TABLE 30

| Present Compound | R¹ | R² | R³ | R⁴ | R⁵ | R⁶ | R⁷ | A¹ | A² | A³ | n |
|---|---|---|---|---|---|---|---|---|---|---|---|
| 251 | Et | H | CF₃ | H | H | CF₃ | H | S | CH | N | 2 |
| 253 | Et | H | H | H | H | SMe | H | NMe | CH | N | 0 |
| 254 | Et | H | H | H | H | SO₂Me | H | NMe | CH | N | 2 |
| 255 | Et | H | H | H | H | SEt | H | NMe | CH | N | 0 |
| 256 | Et | H | H | H | H | SO₂Et | H | NMe | CH | N | 2 |
| 257 | Et | H | H | H | H | SiPr | H | NMe | CH | N | 0 |
| 258 | Et | H | H | H | H | SO₂iPr | H | NMe | CH | N | 2 |
| 259 | Et | H | H | H | H | SCH₂CF₃ | H | NMe | CH | N | 0 |
| 260 | Et | H | H | H | H | SO₂CH2CF₃ | H | NMe | CH | N | 2 |
| 261 | Et | H | H | H | H | SCH₂CH=CH₂ | H | NMe | CH | N | 0 |
| 262 | Et | H | H | H | H | SCF₂CF₃ | H | NMe | CH | N | 0 |
| 263 | Et | H | H | H | H | SCF₂CF₂CF₃ | H | NMe | CH | N | 0 |
| 264 | Et | H | H | H | H | SCF(CF₃)₂ | H | NMe | CH | N | 0 |
| 265 | Et | H | H | H | H | CH(OH)CF₃ | H | NMe | CH | N | 0 |
| 266 | Et | H | H | H | H | CH(Cl)CF₃ | H | NMe | CH | N | 0 |
| 267 | Et | H | CF₃ | H | H | CF₃ | H | S | CH | N | 0 |
| 268 | Et | H | H | H | H | OH | H | NMe | CH | N | 0 |
| 269 | Et | H | H | H | H | OH | H | NMe | CH | N | 2 |
| 270 | Et | H | H | H | H | OCF₂Br | H | NMe | CH | N | 2 |
| 271 | Et | H | H | H | H | OCF₃ | H | NMe | CH | N | 2 |
| 272 | Et | H | H | H | H | SCF₂CF₃ | H | NMe | CH | N | 1 |
| 273 | Et | H | H | H | H | SCF₂CF₃ | H | NMe | CH | N | 2 |
| 274 | Et | H | H | H | H | SCF₂CF₂CF₃ | H | NMe | CH | N | 1 |
| 275 | Et | H | H | H | H | SCF₂CF₂CF₃ | H | NMe | CH | N | 2 |

TABLE 31

| Present Compound | R¹ | R² | R³ | R⁴ | R⁵ | R⁶ | R⁷ | A¹ | A² | A³ | n |
|---|---|---|---|---|---|---|---|---|---|---|---|
| 276 | Et | H | H | H | H | SC(CH₃)₃ | H | NMe | CH | N | 0 |
| 277 | Et | H | H | H | H | SO₂C(CH₃)₃ | H | NMe | CH | N | 2 |
| 278 | Et | H | CF₃ | H | H | Br | H | NMe | CH | N | 0 |
| 279 | Et | H | CF₃ | H | H | Br | H | NMe | CH | N | 1 |
| 280 | Et | H | CF₃ | H | H | Br | H | NMe | CH | N | 2 |
| 281 | Et | H | H | H | H | SCH=C=CH₂ | H | NMe | CH | N | 0 |

TABLE 31-continued

| Present Compound | R¹ | R² | R³ | R⁴ | R⁵ | R⁶ | R⁷ | A¹ | A² | A³ | n |
|---|---|---|---|---|---|---|---|---|---|---|---|
| 282 | Et | H | H | H | H | SO$_2$CH=C=CH$_2$ | H | NMe | CH | N | 2 |
| 283 | Et | H | H | H | H | SO$_2$CH$_2$CH=CH$_2$ | H | NMe | CH | N | 2 |
| 284 | Et | H | H | H | H | NHSO$_2$CH$_3$ | H | NMe | CH | N | 2 |
| 285 | Et | H | NO$_2$ | H | H | CF$_3$ | H | NMe | CH | N | 0 |
| 286 | Et | H | NO$_2$ | H | H | CF$_3$ | H | NMe | CH | N | 1 |
| 287 | Et | H | NO$_2$ | H | H | CF$_3$ | H | NMe | CH | N | 2 |
| 289 | Et | H | H | H | H | NHSO$_2$CF$_3$ | H | NMe | CH | N | 2 |
| 290 | Et | H | H | H | H | NCH$_3$SO$_2$CF$_3$ | H | NMe | CH | N | 2 |
| 291 | Et | H | H | H | H | NCH$_3$SO$_2$CH$_3$ | H | NMe | CH | N | 2 |
| 292 | Et | H | CF$_3$ | H | H | CF$_2$CF$_3$ | H | NMe | CH | N | 0 |
| 293 | Et | H | Cl | H | H | CF$_3$ | H | S | CH | N | 0 |
| 294 | Et | H | Cl | H | H | CF$_3$ | H | S | CH | N | 2 |
| 295 | Et | H | H | H | H | C(OH)(CF$_3$)$_2$ | H | NMe | CH | N | 0 |
| 296 | Et | H | H | H | H | C(Cl)(CF$_3$)$_2$ | H | NMe | CH | N | 0 |
| 297 | Et | H | H | H | H | C(Cl)(CF$_3$)$_2$ | H | NMe | CH | N | 1 |
| 298 | Et | H | H | H | H | C(Cl)(CF$_3$)$_2$ | H | NMe | CH | N | 2 |
| 299 | Et | H | CF$_3$ | H | H | CF$_2$CF$_3$ | H | NMe | CH | N | 2 |
| 300 | Et | H | CF$_3$ | H | H | I | H | NMe | CH | N | 0 |

TABLE 32

| Present Compound | R¹ | R² | R³ | R⁴ | R⁵ | R⁶ | R⁷ | A¹ | A² | A³ | n |
|---|---|---|---|---|---|---|---|---|---|---|---|
| 301 | Et | H | CF$_3$ | H | H | SCF$_3$ | H | NMe | CH | N | 0 |
| 302 | Et | H | CF$_3$ | H | H | SO$_2$CF$_3$ | H | NMe | CH | N | 2 |
| 303 | Et | H | H | H | H | I | H | NMe | CH | CH | 0 |
| 304 | Et | H | H | H | H | H | CF(CF$_3$)$_2$ | NMe | CH | CH | 0 |
| 305 | Et | H | H | H | H | CF(CF$_3$)$_2$ | H | NMe | CH | CH | 0 |
| 306 | Et | H | CF$_3$ | H | H | SCF$_3$ | H | NMe | CH | N | 2 |
| 307 | Et | H | CF$_3$ | H | H | I | H | NMe | CH | N | 2 |
| 308 | Et | H | H | H | H | CF$_2$CF$_3$ | H | NMe | CH | CH | 0 |
| 309 | Et | H | H | H | H | CF$_2$CF$_3$ | H | NMe | CH | CH | 1 |
| 310 | Et | H | H | H | H | CF$_2$CF$_3$ | H | NMe | CH | CH | 2 |
| 311 | Et | H | H | H | H | SF$_5$ | H | NMe | CH | CH | 0 |
| 312 | Et | H | H | H | H | SF$_5$ | H | NMe | CH | CH | 1 |
| 313 | Et | H | H | H | H | SF$_5$ | H | NMe | CH | CH | 2 |
| 314 | Et | H | CF$_3$ | H | H | SF$_5$ | H | NMe | CH | CH | 0 |
| 315 | Et | H | CF$_3$ | H | H | SF$_5$ | H | NMe | CH | CH | 1 |
| 316 | Et | H | CF$_3$ | H | H | SF$_5$ | H | NMe | CH | CH | 2 |
| 317 | Et | H | Me | H | H | CF$_2$CF$_3$ | H | NMe | CH | N | 0 |
| 318 | Et | H | Me | H | H | CF$_2$CF$_3$ | H | NMe | CH | N | 1 |
| 319 | Et | H | Me | H | H | CF$_2$CF$_3$ | H | NMe | CH | N | 2 |
| 320 | Et | H | H | H | H | I | H | S | CH | N | 0 |
| 321 | Et | H | CF$_3$ | H | H | I | H | S | CH | N | 0 |
| 322 | Et | H | H | H | H | CF$_2$CF$_3$ | H | S | CH | N | 0 |
| 323 | Et | H | CF$_3$ | H | H | CF$_2$CF$_3$ | H | S | CH | N | 0 |
| 324 | Et | H | H | H | H | CF$_2$CF$_3$ | H | S | CH | N | 2 |
| 325 | Et | H | CF$_3$ | H | H | CF$_2$CF$_3$ | H | S | CH | N | 2 |

TABLE 33

| Present Compound | R¹ | R² | R³ | R⁴ | R⁵ | R⁶ | R⁷ | A¹ | A² | A³ | n |
|---|---|---|---|---|---|---|---|---|---|---|---|
| 326 | Et | H | H | H | Cl | CF$_3$ | H | S | CH | N | 0 |
| 327 | Et | H | H | H | Cl | CF$_3$ | H | S | CH | N | 2 |
| 328 | Et | H | H | H | H | H | CF$_3$ | S | N | CH | 0 |
| 329 | Et | H | H | H | H | H | CF$_3$ | S | N | CH | 2 |
| 330 | Et | H | CH=CH$_2$ | H | H | CF$_3$ | H | NMe | CH | N | 2 |
| 331 | Et | H | Et | H | H | CF$_3$ | H | NMe | CH | N | 2 |
| 332 | Et | H | CF$_2$CF$_2$CF$_3$ | H | H | CF$_3$ | H | NMe | CH | N | 2 |
| 333 | Et | H | 2-pyrimidyl | H | H | CF$_3$ | H | NMe | CH | N | 2 |
| 334 | Et | H | H | H | H | SO$_2$NMe$_2$ | H | NMe | CH | N | 1 |
| 335 | Et | H | H | H | H | SO$_2$NMe$_2$ | H | NMe | CH | N | 2 |
| 336 | Et | H | H | H | H | CF$_3$ | H | NMe | CH | CNH$_2$ | 0 |
| 337 | Et | H | H | H | H | CF$_3$ | H | NMe | CH | CNHCOCH$_3$ | 0 |
| 338 | Et | H | H | H | H | CF$_3$ | H | NMe | CH | CNMe$_2$ | 0 |
| 339 | Et | H | CF$_3$ | H | H | CF$_3$ | H | NMe | CH | CNH$_2$ | 0 |
| 340 | Et | H | CF$_3$ | H | H | CF$_3$ | H | NMe | CH | CNMe$_2$ | 0 |
| 341 | Et | H | SF$_5$ | H | H | CF$_3$ | H | NMe | CH | N | 0 |

TABLE 33-continued

| Present Compound | $R^1$ | $R^2$ | $R^3$ | $R^4$ | $R^5$ | $R^6$ | $R^7$ | $A^1$ | $A^2$ | $A^3$ | n |
|---|---|---|---|---|---|---|---|---|---|---|---|
| 342 | Et | H | $SF_5$ | H | H | $CF_3$ | H | NMe | CH | N | 1 |
| 343 | Et | H | $SF_5$ | H | H | $CF_3$ | H | NMe | CH | N | 0 |
| 344 | Et | H | $CF_3$ | H | H | $CF_3$ | H | NH | CH | N | 0 |
| 345 | Et | H | $CF_3$ | H | H | $CF_3$ | H | NH | CH | N | 2 |
| 346 | Et | H | H | H | H | $CF(CF_3)_2$ | H | NH | CH | CH | 0 |
| 347 | Et | H | H | H | H | Br | H | NMe | $CCF_2H$ | N | 0 |
| 348 | Et | H | H | H | H | Br | H | NMe | $CCF_2H$ | N | 1 |
| 349 | Et | H | H | H | H | Br | H | NMe | $CCF_2H$ | N | 2 |
| 350 | Et | H | H | H | H | Br | H | NMe | $CCH(CH_3)_2$ | N | 0 |

TABLE 34

| Present Compound | $R^1$ | $R^2$ | $R^3$ | $R^4$ | $R^5$ | $R^6$ | $R^7$ | $A^1$ | $A^2$ | $A^3$ | n |
|---|---|---|---|---|---|---|---|---|---|---|---|
| 351 | Et | H | H | H | H | $CF_3$ | H | NH | CH | N | 0 |
| 352 | Et | H | H | H | H | $CF_3$ | H | NH | CH | N | 1 |
| 353 | Et | H | H | H | H | $CF_3$ | H | NH | CH | N | 2 |
| 354 | Et | H | H | H | H | $CF_3$ | H | NH | CH | CH | 0 |
| 355 | Et | H | $CF_3$ | H | H | $CF_3$ | H | NEt | CH | N | 2 |
| 356 | Et | H | $CF_3$ | H | H | $CF_3$ | H | $NCH_2CH=CH_2$ | CH | N | 2 |
| 357 | Et | H | $CF_3$ | H | H | $CF_3$ | H | $NCH_2CCH$ | CH | N | 2 |
| 358 | Et | H | $CF_3$ | H | H | $CF_3$ | H | $NCH_2CN$ | CH | N | 2 |
| 359 | Et | H | $CF_3$ | H | H | H | $CF_3$ | $NCH_2CN$ | N | CH | 2 |
| 360 | Et | H | $CF_3$ | H | H | $CF_3$ | H | $NCH_2OEt$ | CH | N | 2 |
| 361 | Et | H | $CF_3$ | H | H | H | $CF_3$ | $NCH_2OEt$ | N | CH | 2 |
| 362 | Et | H | $CF_3$ | H | H | $CF_3$ | H | $NCH_2SMe$ | CH | N | 2 |
| 363 | Et | H | $CF_3$ | H | H | $CF_3$ | H | NPr | CH | N | 2 |
| 364 | Et | H | $CF_3$ | H | H | $CF_3$ | H | $N(CH_2)_3CH_3$ | CH | N | 2 |
| 365 | Et | H | $CF_3$ | H | H | $CF_3$ | H | $NCH_2CO_2Me$ | CH | N | 2 |
| 366 | Et | H | $CF_3$ | H | H | H | $CF_3$ | $NCH_2CO_2Me$ | N | CH | 2 |
| 367 | Et | H | $CF_3$ | H | H | $CF_3$ | H | $NCH_2CH=CCl_2$ | CH | N | 2 |
| 368 | Et | H | $CF_3$ | H | H | $CF_3$ | H | $NCO_2tBu$ | CH | N | 2 |
| 369 | Et | H | $CF_3$ | H | H | $CF_3$ | H | NMe | CH | CH | 0 |
| 370 | Et | H | $CF_3$ | H | H | $CF_3$ | H | NMe | CH | CH | 1 |
| 371 | Et | H | $CF_3$ | H | H | $CF_3$ | H | NMe | CH | CH | 2 |
| 372 | Et | H | $CF_3$ | H | H | $CF_3$ | H | $NCO_2Me$ | CH | N | 2 |
| 373 | Et | H | $CF_3$ | H | H | $CF_3$ | H | NCOMe | CH | N | 2 |
| 374 | Et | H | $OCF_3$ | H | H | $CF_3$ | H | NMe | CH | N | 0 |
| 375 | Et | H | $OCF_3$ | H | H | $CF_3$ | H | NMe | CH | N | 1 |

TABLE 35

| Present Compound | $R^1$ | $R^2$ | $R^3$ | $R^4$ | $R^5$ | $R^6$ | $R^7$ | $A^1$ | $A^2$ | $A^3$ | n |
|---|---|---|---|---|---|---|---|---|---|---|---|
| 376 | Et | H | $OCF_3$ | H | H | $CF_3$ | H | NMe | CH | N | 2 |
| 377 | Et | H | $CF_2CF_2CF_2CF_3$ | H | H | $CF_3$ | H | NMe | CH | N | 2 |
| 378 | Et | H | 2-pyridyl | H | H | $CF_3$ | H | NMe | CH | N | 2 |
| 379 | Et | H | $NH_2$ | H | H | $CF_3$ | H | NMe | CH | N | 2 |
| 380 | Et | H | $NHCOCF_3$ | H | H | $CF_3$ | H | NMe | CH | N | 2 |
| 381 | Et | H | iPr | H | H | $CF_3$ | H | NMe | CH | N | 2 |
| 382 | Et | H | CHO | H | H | $CF_3$ | H | NMe | CH | N | 2 |
| 383 | $CH_2CH_2CH_2CH_3$ | H | H | H | H | $CF_3$ | H | NMe | CH | N | 0 |
| 384 | $CH_2CO_2CH_3$ | H | H | H | H | $CF_3$ | H | NMe | CH | N | 0 |
| 385 | $CH_2CH=CCl_2$ | H | H | H | H | $CF_3$ | H | NMe | CH | N | 0 |
| 386 | $CH_2CCCH_3$ | H | H | H | H | $CF_3$ | H | NMe | CH | N | 0 |
| 387 | $CH_2CN$ | H | H | H | H | $CF_3$ | H | NMe | CH | N | 0 |
| 388 | $CH_2C(CH_3)_3$ | H | H | H | H | $CF_3$ | H | NMe | CH | N | 0 |
| 389 | $CH_2CH_2CN$ | H | H | H | H | $CF_3$ | H | NMe | CH | N | 0 |
| 390 | $CH_2CyBu$ | H | H | H | H | $CF_3$ | H | NMe | CH | N | 0 |
| 391 | $CF_2Br$ | H | H | H | H | $CF_3$ | H | NMe | CH | N | 0 |
| 392 | Et | H | $CF_2H$ | H | H | $CF_3$ | H | NMe | CH | N | 2 |
| 393 | Et | H | $CH_2OH$ | H | H | $CF_3$ | H | NMe | CH | N | 2 |
| 394 | $(CH_2)_3CH_3$ | H | H | H | H | $CF_3$ | H | NMe | CH | N | 2 |
| 395 | $CH_2CO_2CH_3$ | H | H | H | H | $CF_3$ | H | NMe | CH | N | 2 |
| 396 | $CH_2CH=CCl_2$ | H | H | H | H | $CF_3$ | H | NMe | CH | N | 2 |
| 397 | $CH_2CCCH_3$ | H | H | H | H | $CF_3$ | H | NMe | CH | N | 2 |
| 398 | $CH_2CN$ | H | H | H | H | $CF_3$ | H | NMe | CH | N | 2 |

TABLE 35-continued

| Present Compound | R¹ | R² | R³ | R⁴ | R⁵ | R⁶ | R⁷ | A¹ | A² | A³ | n |
|---|---|---|---|---|---|---|---|---|---|---|---|
| 399 | CH₂C(CH₃)₃ | H | H | H | H | CF₃ | H | NMe | CH | N | 2 |
| 400 | CH₂CH₂CN | H | H | H | H | CF₃ | H | NMe | CH | N | 2 |

TABLE 36

| Present Compound | R¹ | R² | R³ | R⁴ | R⁵ | R⁶ | R⁷ | A¹ | A² | A³ | n |
|---|---|---|---|---|---|---|---|---|---|---|---|
| 401 | CH₂CyBu | H | H | H | H | CF₃ | H | NMe | CH | N | 2 |
| 402 | CF₂Br | H | H | H | H | CF₃ | H | NMe | CH | N | 2 |
| 403 | Et | H | CH₂F | H | H | CF₃ | H | NMe | CH | N | 2 |
| 404 | CH=CH₂ | H | H | H | H | CF₃ | H | NMe | CH | N | 0 |
| 405 | CH=CH₂ | H | H | H | H | CF₃ | H | NMe | CH | N | 1 |
| 406 | CH=CH₂ | H | H | H | H | CF₃ | H | NMe | CH | N | 2 |
| 407 | Et | H | H | H | H | H | CF₃ | S | CH | N | 0 |
| 408 | Et | H | H | H | H | H | CF₃ | S | CH | N | 2 |
| 409 | Et | H | OCF₃ | H | H | CF₂CF₃ | H | NMe | CH | N | 0 |
| 410 | Et | H | OCF₃ | H | H | CF₂CF₃ | H | NMe | CH | N | 1 |
| 411 | Et | H | OCF₃ | H | H | CF₂CF₃ | H | NMe | CH | N | 2 |
| 412 | Et | H | CF₃ | H | H | CF₃ | H | NMe | CH | CCH₃ | 0 |
| 413 | Et | H | CF₃ | H | H | CF₃ | H | NMe | CH | CCH₃ | 1 |
| 414 | Et | H | CF₃ | H | H | CF₃ | H | NMe | CH | CCH₃ | 2 |
| 415 | Et | H | CF₃ | H | H | CF₃ | H | NMe | CH | CF | 0 |
| 416 | Et | H | CF₃ | H | H | CF₃ | H | NMe | CH | CF | 1 |
| 417 | Et | H | CF₃ | H | H | CF₃ | H | NMe | CH | CF | 2 |
| 418 | Et | H | CF₃ | H | H | CF₂CF₃ | H | NMe | CH | CH | 0 |
| 419 | Et | H | CF₃ | H | H | CF₂CF₃ | H | NMe | CH | CH | 1 |
| 420 | Et | H | CF₃ | H | H | CF₂CF₃ | H | NMe | CH | CH | 2 |
| 421 | CH₂CyPr | H | H | H | H | CF₃ | H | NMe | CH | N | 0 |
| 422 | CH₂CyPr | H | H | H | H | CF₃ | H | NMe | CH | N | 1 |
| 423 | CH₂CyPr | H | H | H | H | CF₃ | H | NMe | CH | N | 2 |
| 424 | Et | H | CF₃ | H | H | CF₃ | H | O | CH | CH | 0 |
| 425 | Et | H | CF₃ | H | H | CF₃ | H | O | CH | CH | 2 |

TABLE 37

| Present Compound | R¹ | R² | R³ | R⁴ | R⁵ | R⁶ | R⁷ | A¹ | A² | A³ | n |
|---|---|---|---|---|---|---|---|---|---|---|---|
| 426 | Et | H | CF₃ | H | H | CF₃ | H | NMe | CH | CBr | 0 |
| 427 | Et | H | CF₃ | H | H | CF₃ | H | NMe | CH | CSCH₂CH₃ | 0 |

In the above Tables 20-37, Me represents a methyl group, Et represents an ethyl group, Pr represents a propyl group, iPr represents an isopropyl group, tBu represents a tert-butyl group, CyPr represents a cyclopropyl group, CyBu represents a cyclobutyl group, 2-F-Ph represents a 2-fluorophenyl group, 3-F-Ph represents a 3-fluorophenyl group, 4-F-Ph represents a 4-fluorophenyl group, 2-CF₃-Ph represents a 2-trifluoromethylphenyl group, 3-CF₃-Ph represents a 3-trifluoromethylphenyl group, 4-CF₃-Ph represents a 4-trifluoromethylphenyl group, 2-Cl-Ph represents a 2-chlorophenyl group, 3-Cl-Ph represents a 3-chlorophenyl group, 4-Cl-Ph represents a 4-chlorophenyl group, 2-NO₂-Ph represents a 2-nitrophenyl group, 3-NO₂-Ph represents a 3-nitrophenyl group, 2-CN-Ph represents a 2-cyanophenyl group, 3-CN-Ph represents a 3-cyanophenyl group, 4-CN-Ph represents a 4-cyanophenyl group, 3-Py represents a pyridin-3-yl group, 4-Py represents a pyridin-4-yl group, 6-Cl-3-Py represents a 6-chloropyridin-3-yl group, 5-F-3-Py represents a 6-fluoropyridin-3-yl group, 4-Cl-pyrazole represents a 4-chloropyrazol-1-yl group, 3-Cl-triazole represents a 3-chloro-(1H-1,2,4-triazol)-1-yl group, 3-CF₃-triazole represents a 3-trifluoromethyl-(1H-1,2,4-triazol)-1-yl group, 3-CF₃-5-Me-triazole represents a 3-trifluoromethyl-5-methyl-(1H-1,2,4-triazol)-1-yl group, and 4-CF₃-imidazole represents a 4-trifluoromethylimidazol-1-yl group.

The ¹H-NMR data of the present compounds listed in Tables 20-37 are shown below.

Present Compound 92

¹H-NMR (CDCl₃) δ: 8.73-8.71 (1H, m), 8.36-8.35 (1H, m), 7.49 (1H, t), 7.17 (2H, d), 3.70 (3H, s), 2.41 (6H, s).

Present Compound 94

¹H-NMR (CDCl₃) δ: 8.80-8.78 (1H, m), 8.60 (2H, d), 8.30-8.28 (1H, m), 8.08 (1H, t), 3.70 (3H, s), 3.09 (6H, s).

Present Compound 95

¹H-NMR (CDCl₃) δ: 8.73-8.71 (1H, m), 8.35-8.34 (1H, m), 7.47-7.43 (1H, m), 7.28-7.25 (2H, m), 3.69 (3H, s), 2.97-2.79 (4H, m), 1.24 (6H, t).

Present Compound 96

¹H-NMR (CDCl₃) δ: 8.85-8.75 (1H, m), 8.38-7.96 (4H, m), 3.81-3.71 (3H, m), 3.15-2.65 (4H, m), 1.22-1.03 (6H, m).

Present Compound 97

¹H-NMR (CDCl₃) δ: 8.79 (1H, d), 8.54 (2H, d), 8.27 (1H, d), 8.06 (1H, t), 3.71 (3H, s), 3.32-3.07 (4H, m), 1.19 (6H, t).

Present Compound 98

¹H-NMR (CDCl₃) δ: 8.39 (1H, d), 8.07 (1H, d), 7.54-7.48 (2H, m), 7.45-7.43 (1H, m), 7.37-7.32 (1H, m), 3.72 (3H, s), 2.86 (2H, q), 1.23 (3H, t).

Present Compound 99

¹H-NMR (CDCl₃) δ: 8.43 (1H, d), 8.26-8.22 (1H, m), 8.06 (1H, d), 7.84-7.79 (1H, m), 7.71-7.65 (1H, m), 7.60-7.57 (1H, m), 3.84 (3H, s), 3.39-3.29 (1H, m), 2.99-2.89 (1H, m), 1.29 (3H, t).

Present Compound 100

¹H-NMR (CDCl₃) δ: 8.42 (1H, d), 8.23-8.20 (1H, m), 8.02 (1H, d), 7.86-7.77 (2H, m), 7.57-7.54 (1H, m), 3.67 (3H, s), 3.42 (2H, q), 1.25 (3H, t).

Present Compound 101

¹H-NMR (CDCl₃) δ: 10.83 (1H, s), 8.63 (1H, s), 7.55-7.43 (3H, m), 7.38-7.32 (1H, m), 3.76 (3H, s), 2.89 (2H, q), 1.24 (3H, t).

Present Compound 102

¹H-NMR (CDCl₃) δ: 8.73-8.71 (1H, m), 8.33-8.31 (1H, m), 7.47-7.42 (2H, m), 7.39-7.38 (1H, m), 3.77 (3H, s), 2.97 (2H, q), 2.82 (2H, q), 1.34 (3H, t), 1.21 (3H, t).

Present Compound 103

¹H-NMR (CDCl₃) δ: 8.12 (1H, s), 7.69 (1H, d), 7.62-7.57 (1H, m), 7.53-7.45 (3H, m), 7.36-7.31 (1H, m), 5.43 (2H, s), 3.26 (2H, q), 2.84 (2H, q), 1.22 (3H, t), 1.04 (3H, t).

Present Compound 104

¹H-NMR (CDCl₃) δ: 7.94-7.88 (2H, m), 7.61-7.56 (1H, m), 7.54-7.44 (3H, m), 7.37-7.30 (1H, m), 5.44 (2H, s), 3.27 (2H, q), 2.84 (2H, q), 1.22 (3H, t), 1.05 (3H, t).

Present Compound 107

¹H-NMR (CDCl₃) δ: 8.72-8.69 (1H, m), 8.33-8.30 (1H, m), 7.55-7.45 (3H, m), 7.37-7.32 (1H, m), 4.40 (2H, t), 3.65 (2H, t), 3.14 (3H, s), 2.87 (2H, q), 1.24 (3H, t).

Present Compound 108

¹H-NMR (CDCl₃) δ: 8.65 (1H, d), 8.26 (1H, d), 7.50-7.39 (3H, m), 7.33-7.26 (1H, m), 5.23 (2H, s), 2.81 (2H, q), 1.98 (3H, s), 1.17 (3H, t).

Present Compound 109

¹H-NMR (CDCl₃) δ: 8.70 (1H, d), 8.32 (1H, d), 7.56-7.46 (3H, m), 7.39-7.33 (1H, m), 4.40 (2H, t), 2.92-2.80 (4H, m), 1.85 (3H, s), 1.24 (3H, t).

Present Compound 110

¹H-NMR (CDCl₃) δ: 8.71 (1H, d), 8.31 (1H, d), 7.55-7.47 (2H, m), 7.45-7.41 (1H, m), 7.38-7.32 (1H, m), 4.21 (2H, t), 2.89 (2H, q), 1.75-1.63 (2H, m), 1.28-1.11 (5H, m), 0.78 (3H, t).

Present Compound 111

¹H-NMR (CDCl₃) δ: 8.84-8.81 (1H, m), 8.65-8.61 (1H, m), 7.48-7.37 (3H, m), 7.35-7.27 (1H, m), 2.74-2.64 (2H, m), 1.26 (9H, s), 1.10-1.04 (3H, m).

Present Compound 114

¹H-NMR (CDCl₃) δ: 8.59-8.52 (1H, m), 8.31-8.17 (1H, m), 7.61-7.32 (4H, m), 5.24 (1H, brs), 3.77 (3H, s), 2.97-2.82 (2H, m), 1.31-1.15 (3H, m).

Present Compound 115

¹H-NMR (CDCl₃) δ: 8.51 (1H, s), 8.22 (1H, s), 7.55-7.50 (2H, m), 7.47-7.43 (1H, m), 7.38-7.32 (1H, m), 5.81 (1H, dq), 3.76 (3H, s), 2.88 (2H, q), 1.24 (3H, t).

Present Compound 119

¹H-NMR (CDCl₃) δ: 8.71-8.70 (1H, m), 8.31-8.29 (1H, m), 7.49-7.45 (1H, m), 7.14-7.09 (2H, m), 4.00 (3H, s), 3.71 (3H, s), 2.74 (2H, q), 1.04 (3H, t).

Present Compound 121

¹H-NMR (CDCl₃) δ: 8.68-8.66 (1H, m), 8.28-8.27 (1H, m), 7.35 (1H, d), 6.99 (1H, d), 6.86-6.83 (1H, m), 3.88 (3H, s), 3.74 (3H, s), 2.84 (2H, q), 1.22 (3H, t).

Present Compound 122

¹H-NMR (CDCl₃) δ: 8.73-8.72 (1H, m), 8.29-8.27 (1H, m), 7.77 (1H, d), 7.53 (1H, d), 7.19-7.15 (1H, m), 4.00 (3H, s), 3.89 (3H, s), 3.46-3.36 (1H, m), 3.00-2.90 (1H, m), 1.33 (3H, t).

Present Compound 123

¹H-NMR (CDCl₃) δ: 8.73-8.72 (1H, m), 8.27-8.25 (1H, m), 7.71 (1H, d), 7.46 (1H, d), 7.32-7.28 (1H, m), 3.99 (3H, s), 3.70 (3H, s), 3.43 (2H, q), 1.26 (3H, t).

Present Compound 124

¹H-NMR (CDCl₃) δ: 9.12 (1H, brs), 8.72-8.70 (1H, m), 8.33-8.30 (1H, m), 7.15 (1H, d), 6.88 (1H, d), 6.63-6.60 (1H, m), 3.77 (3H, s), 2.77 (2H, q), 1.19 (3H, t).

Present Compound 126

¹H-NMR (CDCl₃) δ: 8.55 (1H, d), 8.26 (1H, d), 8.21 (1H, d), 7.83 (1H, t), 7.69 (1H, t), 7.60 (1H, d), 5.84 (1H, dq), 3.88 (3H, s), 3.42-3.30 (1H, m), 3.03-2.91 (1H, m), 1.33-1.25 (3H, m).

Present Compound 127

¹H-NMR (CDCl₃) δ: 8.53 (1H, s), 8.26-8.16 (2H, m), 7.88-7.78 (2H, m), 7.59-7.53 (1H, m), 5.82 (1H, dq), 3.70 (3H, s), 3.44 (2H, q), 1.26 (3H, t).

Present Compound 131

¹H-NMR (CDCl₃) δ: 8.68 (1H, d), 8.29 (1H, d), 7.74-7.68 (1H, m), 7.49-7.40 (2H, m), 3.73 (3H, s), 2.74 (2H, q), 1.06 (3H, t).

Present Compound 132

¹H-NMR (CDCl₃) δ: 8.64 (1H, s), 8.24 (1H, s), 7.65 (1H, d), 7.58 (1H, t), 7.39 (1H, d), 3.72 (3H, s), 3.63-3.47 (1H, m), 3.37-3.22 (1H, m), 1.38-1.30 (3H, m).

Present Compound 136

¹H-NMR (CDCl₃) δ: 8.74-8.72 (1H, m), 8.33-8.32 (1H, m), 7.52-7.49 (1H, m), 7.47-7.43 (2H, m), 3.79 (3H, s), 2.85 (2H, q), 1.23 (3H, t).

Present Compound 137

¹H-NMR (CDCl₃) δ: 8.78-8.76 (1H, m), 8.33-8.31 (1H, m), 8.20 (1H, d), 7.81-7.78 (1H, m), 7.60 (1H, d), 3.93 (3H, s), 3.42-3.32 (1H, m), 3.02-2.92 (1H, m), 1.31 (3H, t).

Present Compound 138

¹H-NMR (CDCl₃) δ: 8.76-8.75 (1H, m), 8.29-8.28 (1H, m), 8.16 (1H, d), 7.80-7.77 (1H, m), 7.57 (1H, d), 3.75 (3H, s), 3.40 (2H, q), 1.26 (3H, t).

Present Compound 139

¹H-NMR (CDCl₃) δ: 8.75-8.73 (1H, m), 8.37-8.35 (1H, m), 7.48-7.44 (1H, m), 7.38-7.34 (2H, m), 3.72 (3H, s), 3.00-2.83 (2H, m), 1.26 (3H, t).

Present Compound 140

¹H-NMR (CDCl₃) δ: 8.80-8.78 (1H, m), 8.35-8.34 (1H, m), 8.11-8.08 (1H, m), 7.79 (1H, t), 7.73-7.71 (1H, m), 3.77 (3H, s), 3.37-3.27 (1H, m), 3.09-2.99 (1H, m), 1.25 (3H, t).

Present Compound 141

¹H-NMR (CDCl₃) δ: 8.77-8.76 (1H, m), 8.32-8.30 (1H, m), 8.16-8.13 (1H, m), 7.89-7.87 (1H, m), 7.77 (1H, t), 3.73 (3H, s), 3.61-3.49 (1H, m), 3.34-3.24 (1H, m), 1.26 (3H, t).

Present Compound 142

¹H-NMR (CDCl₃) δ: 8.72-8.71 (1H, m), 8.32-8.30 (1H, m), 7.54 (1H, d), 7.10-7.06 (1H, m), 7.03 (1H, d), 3.85 (3H, s), 3.77 (3H, s), 2.68 (2H, q), 1.12 (3H, t).

Present Compound 143

¹H-NMR (CDCl₃) δ: 8.76-8.74 (1H, m), 8.31-8.30 (1H, m), 8.14 (1H, d), 7.34-7.30 (1H, m), 7.08 (1H, d), 3.93 (3H, s), 3.89 (3H, s), 3.29-3.19 (1H, m), 2.97-2.86 (1H, m), 1.26 (3H, t).

Present Compound 144

¹H-NMR (CDCl₃) δ: 8.74-8.73 (1H, m), 8.28-8.27 (1H, m), 8.13 (1H, d), 7.25-7.21 (1H, m), 7.03 (1H, d), 3.94 (3H, s), 3.74 (3H, s), 3.34 (2H, q), 1.24 (3H, t).

Present Compound 146

¹H-NMR (CDCl₃) δ: 8.30 (1H, s), 7.93 (1H, s), 7.49-7.42 (3H, m), 7.33-7.27 (1H, m), 3.72 (3H, s), 2.89-2.78 (4H, m), 1.33 (3H, t), 1.22 (3H, t).

Present Compound 148

¹H-NMR (CDCl₃) δ: 7.94 (1H, d), 7.48-7.39 (3H, m), 7.34-7.25 (2H, m), 3.67 (3H, s), 3.26-3.16 (2H, m), 2.89-2.80 (2H, m), 1.34-1.27 (3H, m), 1.26-1.19 (3H, m).

Present Compound 149

¹H-NMR (CDCl₃) δ: 8.09 (1H, d), 7.50-7.41 (4H, m), 7.34-7.27 (1H, m), 3.68 (3H, s), 3.38 (4H, q), 2.86 (2H, q), 1.23 (3H, t), 1.17 (6H, t).

Present Compound 152

¹H-NMR (CDCl₃) δ: 8.71-8.69 (1H, m), 8.33-8.31 (1H, m), 7.47 (1H, t), 7.06 (1H, d), 6.86 (1H, d), 3.76 (3H, s), 3.69 (3H, s), 2.98-2.82 (2H, m), 1.25 (3H, t).

Present Compound 153

¹H-NMR (CDCl₃) δ: 8.75-8.73 (1H, m), 8.30-8.29 (1H, m), 7.79-7.76 (2H, m), 7.22-7.18 (1H, m), 3.86 (3H, s), 3.73 (3H, s), 3.42-3.30 (1H, m), 3.09-2.97 (1H, m), 1.29 (3H, t).

Present Compound 154

¹H-NMR (CDCl₃) δ: 8.73-8.71 (1H, m), 8.27-8.25 (1H, m), 7.82-7.73 (2H, m), 7.37-7.34 (1H, m), 3.83 (3H, s), 3.68 (3H, s), 3.67-3.56 (1H, m), 3.36-3.26 (1H, m), 1.26 (3H, t).

Present Compound 155

¹H-NMR (CDCl₃) δ: 8.73-8.72 (1H, m), 8.29-8.27 (1H, m), 7.93 (1H, brs), 7.36 (1H, t), 7.09-7.06 (1H, m), 6.95-6.92 (1H, m), 3.85 (3H, s), 2.87-2.78 (2H, m), 1.21 (3H, t).

Present Compound 156

¹H-NMR (CDCl₃) δ: 8.74-8.72 (1H, m), 8.33-8.31 (1H, m), 7.51-7.45 (1H, m), 7.36-7.31 (2H, m), 3.75 (3H, s), 2.78 (2H, q), 1.10 (3H, t).

Present Compound 157

¹H-NMR (CDCl₃) δ: 8.73-8.71 (1H, m), 8.29-8.27 (1H, m), 7.70-7.64 (1H, m), 7.44-7.38 (1H, m), 7.33 (1H, d), 3.81 (3H, s), 3.53-3.43 (1H, m), 3.42-3.31 (1H, m), 1.33 (3H, t).

Present Compound 158

¹H-NMR (CDCl₃) δ: 8.73-8.72 (1H, m), 8.28-8.26 (1H, m), 7.84-7.78 (1H, m), 7.55-7.49 (1H, m), 7.38-7.35 (1H, m), 3.77 (3H, s), 3.50-3.34 (2H, m), 1.34 (3H, t).

Present Compound 162

¹H-NMR (CDCl₃) δ: 8.14 (1H, d), 7.51-7.40 (4H, m), 7.35-7.27 (1H, m), 3.69 (3H, s), 3.00 (6H, s), 2.90-2.81 (2H, m), 1.26-1.19 (3H, m).

Present Compound 163

¹H-NMR (CDCl₃) δ: 7.92 (1H, d), 7.48-7.43 (3H, m), 7.34-7.28 (1H, m), 7.26 (1H, d), 3.68 (3H, s), 3.40-3.32 (4H, m), 2.84 (2H, q), 2.08-2.05 (4H, m), 1.22 (3H, t).

Present Compound 164

¹H-NMR (CDCl₃) δ: 9.72 (1H, s), 8.41 (1H, d), 8.23 (1H, d), 7.37-7.28 (3H, m), 7.18-7.13 (1H, m), 3.58 (3H, s), 2.74 (2H, q), 2.02 (3H, s), 1.09 (3H, t).

Present Compound 169

¹H-NMR (CDCl₃) δ: 8.74-8.72 (1H, m), 8.37-8.35 (1H, m), 7.54-7.48 (1H, m), 7.27-7.24 (1H, m), 7.09-7.03 (1H, m), 3.77 (3H, d), 2.93 (2H, q), 1.28 (3H, t).

Present Compound 170

¹H-NMR (CDCl₃) δ: 8.79-8.76 (1H, m), 8.35-8.32 (1H, m), 8.03 (1H, d), 7.87-7.80 (1H, m), 7.43 (1H, t), 3.84 (3H, d), 3.51-3.40 (1H, m), 3.13-3.02 (1H, m), 1.33 (3H, t).

Present Compound 171

¹H-NMR (CDCl₃) δ: 8.77-8.75 (1H, m), 8.32-8.30 (1H, m), 8.07-8.04 (1H, m), 7.86-7.80 (1H, m), 7.62-7.57 (1H, m), 3.76 (3H, s), 3.69-3.58 (1H, m), 3.41-3.31 (1H, m), 1.29 (3H, t).

Present Compound 172

¹H-NMR (CDCl₃) δ: 8.32 (1H, d), 7.94 (1H, d), 7.57-7.48 (2H, m), 7.47-7.43 (1H, m), 7.39-7.33 (1H, m), 3.77 (3H, s), 3.36 (3H, s), 2.91 (2H, q), 1.93 (3H, s), 1.27 (3H, t).

Present Compound 173

¹H-NMR (CDCl₃) δ: 8.21 (1H, dd), 8.03 (1H, d), 7.77 (1H, td), 7.65 (1H, td), 7.57 (1H, dd), 7.37 (1H, d), 3.78 (3H, s), 3.36-3.24 (1H, m), 2.96-2.83 (1H, m), 1.26 (3H, t).

Present Compound 177

¹H-NMR (CDCl₃) δ: 8.55 (1H, d), 8.39 (1H, d), 8.21 (1H, brs), 7.55-7.42 (3H, m), 7.38-7.31 (1H, m), 3.74 (3H, s), 2.86 (2H, q), 1.23 (3H, t).

Present Compound 178

¹H-NMR (DMSO-D₆) δ: 11.57 (1H, brs), 8.68-8.64 (1H, m), 8.45-8.42 (1H, m), 8.10 (1H, d), 7.90 (2H, dd), 7.78 (1H, t), 3.83 (3H, s), 3.41-3.30 (1H, m), 2.94-2.81 (1H, m), 1.16 (3H, t).

Present Compound 179

¹H-NMR (CDCl₃) δ: 9.18 (1H, brs), 8.52-8.48 (1H, m), 8.38-8.34 (1H, m), 8.25-8.17 (1H, m), 7.87-7.76 (2H, m), 7.59-7.52 (1H, m), 3.65 (3H, s), 3.47 (2H, q), 1.26 (3H, t).

Present Compound 180

¹H-NMR (CDCl₃) δ: 8.40 (1H, d), 8.06 (1H, d), 7.82 (1H, d), 7.66-7.59 (1H, m), 7.58-7.46 (4H, m), 7.44-7.39 (1H, m), 7.38-7.31 (1H, m), 3.79 (3H, s), 2.90 (2H, q), 1.26 (3H, t).

Present Compound 181

¹H-NMR (CDCl₃) δ: 8.65 (1H, d), 8.26 (1H, d), 7.89 (1H, s), 7.83 (1H, d), 7.69-7.60 (2H, m), 7.53-7.46 (3H, m), 7.38-7.33 (1H, m), 3.78 (3H, s), 2.88 (2H, q), 1.25 (3H, t).

Present Compound 182

¹H-NMR (CDCl₃) δ: 8.67 (1H, d), 8.27 (1H, d), 7.78-7.75 (4H, m), 7.56-7.44 (3H, m), 7.39-7.32 (1H, m), 3.78 (3H, s), 2.89 (2H, q), 1.25 (3H, t).

Present Compound 189

¹H-NMR (CDCl₃) δ: 8.72-8.70 (1H, m), 8.30-8.28 (1H, m), 7.50-7.47 (1H, m), 7.40 (1H, t), 7.35-7.32 (1H, m), 3.71 (3H, s), 2.64 (3H, s), 2.53 (2H, q), 1.00 (3H, t).

Present Compound 190

¹H-NMR (CDCl₃) δ: 8.71-8.70 (1H, m), 8.26-8.24 (1H, m), 7.53 (1H, t), 7.47-7.44 (1H, m), 7.31-7.28 (1H, m), 3.73 (3H, s), 3.54-3.43 (1H, m), 3.27-3.17 (1H, m), 2.66 (3H, s), 1.29 (3H, t).

Present Compound 191

¹H-NMR (CDCl₃) δ: 8.72-8.70 (1H, m), 8.24-8.22 (1H, m), 7.65 (1H, t), 7.60-7.56 (1H, m), 7.34-7.31 (1H, m), 3.73 (3H, s), 3.52-3.32 (2H, m), 2.85 (3H, s), 1.32 (3H, t).

Present Compound 192

¹H-NMR (CDCl₃) δ: 8.71-8.69 (1H, m), 8.31-8.30 (1H, m), 7.35-7.31 (2H, m), 7.19-7.15 (1H, m), 3.76 (3H, s), 2.85 (2H, q), 2.46 (3H, s), 1.22 (3H, t).

Present Compound 193

¹H-NMR (CDCl₃) δ: 8.74-8.73 (1H, m), 8.30-8.28 (1H, m), 8.06-8.05 (1H, m), 7.49-7.48 (2H, m), 3.88 (3H, s), 3.42-3.32 (1H, m), 3.00-2.90 (1H, m), 2.58 (3H, s), 1.32 (3H, t).

Present Compound 194

¹H-NMR (CDCl₃) δ: 8.74-8.72 (1H, m), 8.27-8.26 (1H, m), 8.03-8.02 (1H, m), 7.64-7.61 (1H, m), 7.44 (1H, d), 3.70 (3H, s), 3.41 (2H, q), 2.59 (3H, s), 1.26 (3H, t).

Present Compound 195

¹H-NMR (CDCl₃) δ: 8.45 (1H, d), 8.26 (1H, d), 8.05 (1H, d), 7.85-7.78 (2H, m), 7.73-7.61 (3H, m), 7.56 (1H, t), 7.44 (1H, d), 3.91 (3H, s), 3.46-3.32 (1H, m), 3.03-2.91 (1H, m), 1.29 (3H, t).

Present Compound 196

¹H-NMR (CDCl₃) δ: 8.43 (1H, d), 8.28-8.20 (1H, m), 8.06-8.00 (1H, m), 7.90-7.75 (3H, m), 7.67-7.59 (2H, m), 7.54 (1H, t), 7.44 (1H, d), 3.74 (3H, s), 3.49 (2H, q), 1.25 (3H, t).

Present Compound 197

¹H-NMR (CDCl₃) δ: 8.70 (1H, d), 8.29-8.23 (2H, m), 7.92-7.78 (3H, m), 7.74-7.60 (4H, m), 3.90 (3H, s), 3.47-3.33 (1H, m), 3.06-2.93 (1H, m), 1.32 (3H, t).

Present Compound 198

¹H-NMR (CDCl₃) δ: 8.69 (1H, d), 8.26-8.19 (2H, m), 7.92-7.89 (1H, m), 7.87-7.76 (3H, m), 7.69-7.57 (3H, m), 3.73 (3H, s), 3.50 (2H, q), 1.27 (3H, t).

Present Compound 199

¹H-NMR (CDCl₃) δ: 8.71 (1H, d), 8.29-8.23 (2H, m), 7.85-7.79 (1H, m), 7.78-7.75 (4H, m), 7.70 (1H, td), 7.63 (1H, dd), 3.90 (3H, s), 3.44-3.32 (1H, m), 3.05-2.92 (1H, m), 1.31 (3H, t).

Present Compound 200

¹H-NMR (CDCl₃) δ: 8.70 (1H, d), 8.27-8.19 (2H, m), 7.87-7.78 (2H, m), 7.77-7.75 (4H, m), 7.62-7.57 (1H, m), 3.73 (3H, s), 3.48 (2H, d), 1.26 (3H, t).

Present Compound 201

¹H-NMR (CDCl₃) δ: 8.75-8.74 (1H, m), 8.35-8.34 (1H, m), 7.78-7.74 (1H, m), 7.71-7.69 (1H, m), 7.54 (1H, d), 3.80 (3H, s), 2.98 (2H, q), 1.31 (3H, t).

Present Compound 202

¹H-NMR (CDCl₃) δ: 8.79-8.78 (1H, m), 8.44-8.41 (1H, m), 8.35-8.33 (1H, m), 8.10-8.06 (1H, m), 7.89-7.87 (1H, m), 3.94 (3H, s), 3.50-3.40 (1H, m), 3.07-2.97 (1H, m), 1.34 (3H, t).

Present Compound 203

¹H-NMR (CDCl₃) δ: 8.78-8.77 (1H, m), 8.40-8.37 (1H, m), 8.31-8.30 (1H, m), 8.10-8.06 (1H, m), 7.86-7.84 (1H, m), 3.75 (3H, s), 3.45 (2H, q), 1.28 (3H, t).

Present Compound 204

¹H-NMR (CDCl₃) δ: 8.53 (1H, d), 8.19 (1H, d), 7.56-7.26 (8H, m), 3.79 (3H, s), 2.88 (2H, q), 1.24 (3H, t).

Present Compound 205

¹H-NMR (CDCl₃) δ: 8.63 (1H, d), 8.23 (1H, d), 7.65-7.29 (8H, m), 3.77 (3H, s), 2.87 (2H, q), 1.23 (3H, t).

Present Compound 206

¹H-NMR (CDCl₃) δ: 8.62 (1H, d), 8.22 (1H, d), 7.59-7.53 (2H, m), 7.51-7.40 (5H, m), 7.36-7.29 (1H, m), 3.77 (3H, s), 2.87 (2H, q), 1.23 (3H, t).

Present Compound 207

¹H-NMR (CDCl₃) δ: 8.68 (1H, d), 8.62 (1H, d), 8.24 (1H, d), 7.93 (1H, dd), 7.56-7.42 (4H, m), 7.40-7.34 (1H, m), 3.79 (3H, s), 2.89 (2H, q), 1.25 (3H, t).

Present Compound 208

¹H-NMR (CDCl₃) δ: 8.78-8.74 (1H, m), 8.67-8.64 (1H, m), 8.52 (1H, d), 8.27 (1H, d), 7.73-7.65 (1H, m), 7.57-7.46 (3H, m), 7.41-7.34 (1H, m), 3.79 (3H, s), 2.89 (2H, q), 1.25 (3H, t).

Present Compound 211

¹H-NMR (CDCl₃) δ: 8.93 (1H, d), 8.69-8.62 (2H, m), 8.27 (1H, d), 8.00-7.92 (1H, m), 7.55-7.31 (5H, m), 3.79 (3H, s), 2.89 (2H, q), 1.25 (3H, t).

Present Compound 212

¹H-NMR (CDCl₃) δ: 8.75-8.69 (3H, m), 8.33 (1H, d), 7.63-7.57 (2H, m), 7.56-7.44 (3H, m), 7.40-7.32 (1H, m), 3.79 (3H, s), 2.89 (2H, q), 1.25 (3H, t).

Present Compound 213

¹H-NMR (CDCl₃) δ: 8.79 (1H, d), 8.28 (1H, d), 7.97 (1H, s), 7.70 (1H, s), 7.55-7.43 (3H, m), 7.40-7.30 (1H, m), 3.77 (3H, s), 2.87 (2H, q), 1.23 (3H, t).

Present Compound 216

¹H-NMR (CDCl₃) δ: 8.56 (1H, d), 8.26 (1H, dd), 8.16 (1H, d), 7.84-7.78 (1H, m), 7.69 (1H, td), 7.62 (1H, dd), 7.56-7.52 (1H, m), 7.46-7.43 (1H, m), 7.42-7.33 (2H, m), 3.90 (3H, s), 3.44-3.31 (1H, m), 3.03-2.91 (1H, m), 1.30 (3H, t).

Present Compound 217

¹H-NMR (CDCl₃) δ: 8.55 (1H, d), 8.24-8.20 (1H, m), 8.14 (1H, d), 7.85-7.76 (2H, m), 7.59 (1H, dd), 7.53 (1H, dd), 7.44 (1H, dd), 7.40-7.29 (2H, m), 3.73 (3H, s), 3.49 (2H, q), 1.25 (3H, t).

Present Compound 218

¹H-NMR (CDCl₃) δ: 8.68-8.64 (1H, m), 8.28-8.23 (1H, m), 8.22-8.19 (1H, m), 7.84-7.78 (1H, m), 7.71-7.66 (1H, m), 7.65-7.59 (2H, m), 7.56-7.49 (1H, m), 7.46-7.41 (1H, m), 7.40-7.34 (1H, m), 3.89 (3H, s), 3.45-3.33 (1H, m), 3.04-2.92 (1H, m), 1.31 (3H, t).

Present Compound 219

¹H-NMR (CDCl₃) δ: 8.65 (1H, d), 8.22 (1H, dd), 8.18 (1H, d), 7.86-7.76 (2H, m), 7.64-7.62 (1H, m), 7.59 (1H, dd), 7.52 (1H, dt), 7.42 (1H, t), 7.36 (1H, dt), 3.72 (3H, s), 3.48 (2H, q), 1.26 (3H, t).

Present Compound 220

¹H-NMR (CDCl₃) δ: 8.66-8.62 (1H, m), 8.24-8.20 (1H, m), 8.19-8.17 (1H, m), 7.86-7.75 (2H, m), 7.62-7.54 (3H, m), 7.48-7.42 (2H, m), 3.71 (3H, s), 3.56-3.41 (2H, m), 1.25 (3H, t).

Present Compound 221

¹H-NMR (CDCl₃) δ: 8.76 (1H, d), 8.74 (2H, dd), 8.30 (1H, d), 8.26 (1H, dd), 7.83 (1H, td), 7.71 (1H, td), 7.65-7.59 (3H, m), 3.91 (3H, s), 3.44-3.32 (1H, m), 3.05-2.93 (1H, m), 1.31 (3H, t).

Present Compound 222

¹H-NMR (CDCl₃) δ: 9.07-8.56 (3H, m), 8.28 (1H, d), 8.25-8.20 (1H, m), 7.89-7.78 (2H, m), 7.66-7.56 (3H, m), 3.73 (3H, s), 3.47 (2H, q), 1.26 (3H, t).

Present Compound 223

¹H-NMR (CDCl₃) δ: 8.68 (1H, d), 8.64 (1H, d), 8.26-8.21 (1H, m), 8.18 (1H, d), 7.92 (1H, dd), 7.89-7.78 (2H, m), 7.60 (1H, dd), 7.47 (1H, d), 3.73 (3H, s), 3.52-3.41 (2H, m), 1.26 (3H, t).

Present Compound 224

¹H-NMR (CDCl₃) δ: 8.77-8.74 (1H, m), 8.69 (1H, d), 8.53 (1H, d), 8.29-8.23 (2H, m), 7.87-7.80 (1H, m), 7.74-7.67 (2H, m), 7.66-7.61 (1H, m), 3.91 (3H, s), 3.45-3.31 (1H, m), 3.05-2.93 (1H, m), 1.31 (3H, t).

Present Compound 225

¹H-NMR (CDCl₃) δ: 8.77-8.74 (1H, m), 8.67 (1H, d), 8.53 (1H, d), 8.26-8.23 (1H, m), 8.22-8.20 (1H, m), 7.89-7.79 (2H, m), 7.71-7.66 (1H, m), 7.64-7.59 (1H, m), 3.74 (3H, s), 3.48 (2H, q), 1.27 (3H, t).

Present Compound 226

¹H-NMR (DMSO-D₆) δ: 8.96 (1H, d), 8.89 (1H, s), 8.54 (1H, d), 8.14 (1H, dd), 8.02-7.87 (4H, m), 3.60 (3H, s), 3.55 (2H, q), 1.12 (3H, t).

Present Compound 227

¹H-NMR (CDCl₃) δ: 8.74 (1H, d), 8.48 (1H, s), 8.28 (1H, d), 7.57-7.50 (2H, m), 7.49-7.45 (1H, m), 7.40-7.34 (1H, m), 3.79 (3H, s), 2.88 (2H, q), 1.24 (3H, t).

Present Compound 228

¹H-NMR (CDCl₃) δ: 8.51 (1H, d), 8.10 (1H, d), 7.89 (1H, s), 7.66-7.63 (1H, m), 7.58-7.43 (3H, m), 7.41-7.33 (1H, m), 3.80 (3H, s), 2.90 (2H, q), 1.25 (3H, t).

Present Compound 229

¹H-NMR (CDCl₃) δ: 8.38 (1H, d), 8.05 (1H, d), 7.98 (1H, dd), 7.70 (1H, td), 7.60-7.43 (5H, m), 7.39-7.31 (1H, m), 3.78 (3H, s), 2.89 (2H, q), 1.26 (3H, t).

Present Compound 230

¹H-NMR (CDCl₃) δ: 8.69 (1H, d), 8.54-8.51 (1H, m), 8.31-8.29 (1H, m), 8.27 (1H, dd), 7.98 (1H, d), 7.69 (1H, t), 7.57-7.46 (3H, m), 7.40-7.34 (1H, m), 3.79 (3H, s), 2.89 (2H, q), 1.26 (3H, t).

Present Compound 231

¹H-NMR (CDCl₃) δ: 8.62 (1H, d), 8.25 (1H, d), 7.83 (1H, dd), 7.71 (1H, td), 7.59 (1H, dd), 7.55-7.46 (4H, m), 7.39-7.32 (1H, m), 3.79 (3H, s), 2.89 (2H, q), 1.25 (3H, t).

Present Compound 232

¹H-NMR (CDCl₃) δ: 8.63 (1H, d), 8.24 (1H, d), 7.93 (1H, s), 7.89 (1H, d), 7.74-7.58 (2H, m), 7.56-7.45 (3H, m), 7.40-7.33 (1H, m), 3.79 (3H, s), 2.89 (2H, q), 1.25 (3H, t).

Present Compound 233

¹H-NMR (CDCl₃) δ: 8.66 (1H, d), 8.27 (1H, d), 7.83-7.73 (4H, m), 7.56-7.45 (3H, m), 7.40-7.32 (1H, m), 3.79 (3H, s), 2.89 (2H, q), 1.25 (3H, t).

Present Compound 234

¹H-NMR (CDCl₃) δ: 8.78 (1H, d), 8.68 (1H, s), 8.34 (1H, d), 7.54-7.26 (4H, m), 3.80 (3H, s), 2.93-2.82 (2H, m), 1.28-1.19 (3H, m).

Present Compound 235

¹H-NMR (CDCl₃) δ: 8.55 (1H, d), 8.17 (1H, d), 7.57-7.24 (4H, m), 3.81 (3H, s), 2.93-2.86 (2H, m), 2.60 (3H, s), 1.28-1.23 (3H, m).

Present Compound 236

¹H-NMR (CDCl₃) δ: 8.75 (1H, d), 8.49 (1H, s), 8.27 (1H, d), 8.25-8.22 (1H, m), 7.89-7.78 (2H, m), 7.63-7.57 (1H, m), 3.73 (3H, s), 3.43 (2H, q), 1.26 (3H, t).

Present Compound 237

¹H-NMR (CDCl₃) δ: 8.57 (1H, d), 8.27 (1H, d), 8.11 (1H, d), 7.92 (1H, s), 7.88-7.82 (1H, m), 7.75-7.68 (2H, m), 7.65 (1H, d), 3.93 (3H, s), 3.46-3.32 (1H, m), 3.06-2.94 (1H, m), 1.32 (3H, t).

Present Compound 238

¹H-NMR (CDCl₃) δ: 8.73-8.71 (1H, m), 8.33-8.32 (1H, m), 7.59 (1H, d), 7.50-7.47 (1H, m), 7.30 (1H, d), 3.77 (3H, s), 2.91 (2H, q), 1.27 (3H, t).

Present Compound 239

¹H-NMR (CDCl₃) δ: 8.77-8.75 (1H, m), 8.39 (1H, d), 8.32-8.31 (1H, m), 7.84-7.81 (1H, m), 7.49 (1H, d), 3.91 (3H, s), 3.50-3.40 (1H, m), 3.06-2.96 (1H, m), 1.35 (3H, t).

Present Compound 240

¹H-NMR (CDCl₃) δ: 8.77-8.75 (1H, m), 8.37 (1H, d), 8.31-8.29 (1H, m), 7.99-7.96 (1H, m), 7.44 (1H, d), 3.72 (3H, s), 3.44 (2H, q), 1.28 (3H, t).

Present Compound 241

¹H-NMR (CDCl₃) δ: 8.76-8.74 (1H, m), 8.35-8.34 (1H, m), 7.70-7.69 (1H, m), 7.63-7.60 (1H, m), 7.57-7.54 (1H, m), 3.79 (3H, s), 2.95 (2H, q), 1.30 (3H, t).

Present Compound 242

¹H-NMR (CDCl₃) δ: 8.80-8.78 (1H, m), 8.59-8.57 (1H, m), 8.36-8.34 (1H, m), 7.99-7.96 (1H, m), 7.78 (1H, d), 3.96 (3H, s), 3.57-3.46 (1H, m), 3.10-3.00 (1H, m), 1.37 (3H, t).

Present Compound 243

¹H-NMR (CDCl₃) δ: 8.79-8.77 (1H, m), 8.53-8.51 (1H, m), 8.32-8.30 (1H, m), 8.14-8.10 (1H, m), 7.74-7.71 (1H, m), 3.74 (3H, s), 3.49 (2H, q), 1.29 (3H, t).

Present Compound 246

¹H-NMR (CDCl₃) δ: 8.75-8.74 (1H, m), 8.35-8.34 (1H, m), 7.66-7.65 (1H, m), 7.61-7.55 (2H, m), 3.80 (3H, s), 2.95 (2H, q), 1.28 (3H, t).

Present Compound 247

¹H-NMR (CDCl₃) δ: 8.80-8.78 (1H, m), 8.54-8.53 (1H, m), 8.35-8.34 (1H, m), 7.95-7.91 (1H, m), 7.79 (1H, d), 3.95 (3H, s), 3.52-3.41 (1H, m), 3.09-2.99 (1H, m), 1.33 (3H, t).

Present Compound 248

$^1$H-NMR (CDCl$_3$) δ: 8.78-8.76 (1H, m), 8.47-8.46 (1H, m), 8.31-8.30 (1H, m), 8.10-8.07 (1H, m), 7.76 (1H, d), 3.76 (3H, s), 3.48 (2H, q), 1.28 (3H, t).

Present Compound 249

$^1$H-NMR (CDCl$_3$) δ: 10.12 (1H, s), 8.75-8.74 (1H, m), 8.36-8.34 (1H, m), 7.97-7.96 (1H, m), 7.83-7.81 (1H, m), 7.64 (1H, d), 3.80 (3H, s), 3.00 (2H, q), 1.30 (3H, t).

Present Compound 250

$^1$H-NMR (CDCl$_3$) δ: 8.74-8.71 (1H, m), 8.35-8.33 (1H, m), 7.72-7.64 (3H, m), 7.59-7.42 (5H, m), 3.83 (3H, s), 2.92 (2H, q), 1.27 (3H, t).

Present Compound 255

$^1$H-NMR (CDCl$_3$) δ: 8.51 (1H, d), 8.19 (1H, d), 7.53-7.42 (3H, m), 7.38-7.29 (1H, m), 3.73 (3H, s), 2.97-2.83 (4H, m), 1.33-1.19 (6H, m).

Present Compound 256

$^1$H-NMR (CDCl$_3$) δ: 8.96 (1H, d), 8.54 (1H, d), 8.28-8.18 (1H, m), 7.91-7.80 (2H, m), 7.63-7.55 (1H, m), 3.74 (3H, s), 3.43 (2H, q), 3.24 (2H, q), 1.38 (3H, t), 1.26 (3H, t).

Present Compound 257

$^1$H-NMR (CDCl$_3$) δ: 8.53 (1H, d), 8.23 (1H, d), 7.54-7.42 (3H, m), 7.38-7.29 (1H, m), 3.74 (3H, s), 3.33-3.22 (1H, m), 2.87 (2H, q), 1.30 (6H, d), 1.24 (3H, t).

Present Compound 258

$^1$H-NMR (CDCl$_3$) δ: 8.92 (1H, d), 8.51 (1H, d), 8.22 (1H, dd), 7.92-7.81 (2H, m), 7.62 (1H, dd), 3.75 (3H, s), 3.43 (2H, q), 3.36-3.26 (1H, m), 1.38 (6H, d), 1.26 (3H, t).

Present Compound 259

$^1$H-NMR (CDCl$_3$) δ: 8.64-8.58 (1H, m), 8.33-8.29 (1H, m), 7.53-7.30 (4H, m), 3.75-3.73 (3H, m), 3.45-3.38 (2H, m), 2.89-2.82 (2H, m), 1.27-1.21 (3H, m).

Present Compound 260

$^1$H-NMR (CDCl$_3$) δ: 9.01 (1H, d), 8.59 (1H, d), 8.25-8.21 (1H, m), 7.91-7.82 (2H, m), 7.63-7.58 (1H, m), 4.07 (2H, q), 3.75 (3H, s), 3.41 (2H, q), 1.26 (3H, t).

Present Compound 261

$^1$H-NMR (CDCl$_3$) δ: 8.48 (1H, d), 8.18 (1H, d), 7.53-7.41 (3H, m), 7.38-7.28 (1H, m), 5.95-5.81 (1H, m), 5.06-4.92 (2H, m), 3.73 (3H, s), 3.51 (2H, d), 2.86 (2H, q), 1.23 (3H, t).

Present Compound 262

$^1$H-NMR (CDCl$_3$) δ: 8.65-8.60 (1H, m), 8.40-8.35 (1H, m), 7.55-7.48 (2H, m), 7.47-7.41 (1H, m), 7.37-7.31 (1H, m), 3.76 (3H, s), 2.92-2.83 (2H, m), 1.27-1.18 (3H, m).

Present Compound 263

$^1$H-NMR (CDCl$_3$) δ: 8.64 (1H, d), 8.39 (1H, d), 7.56-7.49 (2H, m), 7.47-7.43 (1H, m), 7.38-7.32 (1H, m), 3.76 (3H, s), 2.89 (2H, q), 1.24 (3H, t).

Present Compound 264

$^1$H-NMR (CDCl$_3$) δ: 8.63 (1H, d), 8.37 (1H, d), 7.56-7.42 (3H, m), 7.38-7.32 (1H, m), 3.76 (3H, s), 2.88 (2H, q), 1.24 (3H, t).

Present Compound 272

$^1$H-NMR (CDCl$_3$) δ: 8.67 (1H, d), 8.37 (1H, d), 8.26 (1H, dd), 7.83 (1H, td), 7.70 (1H, td), 7.61 (1H, dd), 3.88 (3H, s), 3.40-3.35 (1H, m), 3.01-2.95 (1H, m), 1.31 (3H, t).

Present Compound 273

$^1$H-NMR (CDCl$_3$) δ: 8.66 (1H, d), 8.34 (1H, d), 8.24-8.22 (1H, m), 7.89-7.78 (2H, m), 7.59-7.56 (1H, m), 3.71 (3H, s), 3.43 (2H, q), 1.25 (3H, t).

Present Compound 274

$^1$H-NMR (CDCl$_3$) δ: 8.68 (1H, d), 8.37 (1H, d), 8.26 (1H, dd), 7.83 (1H, td), 7.70 (1H, td), 7.61 (1H, dd), 3.89 (3H, s), 3.43-3.32 (1H, m), 3.04-2.93 (1H, m), 1.31 (3H, t).

Present Compound 275

$^1$H-NMR (CDCl$_3$) δ: 8.67 (1H, d), 8.35 (1H, d), 8.23 (1H, dd), 7.89-7.77 (2H, m), 7.57 (1H, dd), 3.71 (3H, s), 3.43 (2H, q), 1.25 (3H, t).

Present Compound 276

$^1$H-NMR (CDCl$_3$) δ: 8.56 (1H, d), 8.27 (1H, d), 7.53-7.41 (3H, m), 7.39-7.25 (1H, m), 3.74 (3H, s), 2.89 (2H, q), 1.33 (9H, s), 1.24 (3H, t).

Present Compound 277

$^1$H-NMR (CDCl$_3$) δ: 8.92 (1H, d), 8.52 (1H, d), 8.25-8.20 (1H, m), 7.89-7.84 (2H, m), 7.63-7.58 (1H, m), 3.75 (3H, s), 3.41 (2H, q), 1.43 (9H, s), 1.26 (3H, t).

Present Compound 278

$^1$H-NMR (CDCl$_3$) δ: 8.50 (1H, d), 8.24 (1H, d), 7.68-7.66 (1H, m), 7.60-7.54 (2H, m), 3.73 (3H, s), 2.94 (2H, q), 1.28 (3H, t).

Present Compound 279

$^1$H-NMR (CDCl$_3$) δ: 8.56-8.54 (2H, m), 8.23 (1H, d), 7.95-7.91 (1H, m), 7.77-7.74 (1H, m), 3.88 (3H, s), 3.50-3.40 (1H, m), 3.04-2.94 (1H, m), 1.34 (3H, t).

Present Compound 280

$^1$H-NMR (CDCl$_3$) δ: 8.53 (1H, d), 8.49-8.48 (1H, m), 8.19 (1H, d), 8.10-8.07 (1H, m), 7.74-7.71 (1H, m), 3.68 (3H, s), 3.48 (2H, q), 1.28 (3H, t).

Present Compound 281

¹H-NMR (CDCl₃) δ: 8.50 (1H, d), 8.20 (1H, d), 7.51-7.48 (2H, m), 7.46-7.43 (1H, m), 7.37-7.31 (1H, m), 5.96 (1H, t), 4.97 (2H, d), 3.73 (3H, s), 2.90-2.83 (2H, m), 1.23 (3H, t).

Present Compound 282

¹H-NMR (CDCl₃) δ: 8.99 (1H, d), 8.54 (1H, d), 8.26-8.20 (1H, m), 7.88-7.80 (2H, m), 7.58-7.11 (1H, m), 6.36 (1H, t), 5.53 (2H, d), 3.76-3.68 (3H, m), 3.46-3.35 (2H, m), 1.30-1.21 (3H, m).

Present Compound 283

¹H-NMR (CDCl₃) δ: 8.93 (1H, d), 8.51 (1H, d), 8.25-8.22 (1H, m), 7.88-7.81 (2H, m), 7.59-7.57 (1H, m), 5.95-5.84 (1H, m), 5.42 (1H, d), 5.23 (1H, dd), 3.93 (2H, d), 3.73 (3H, s), 3.42 (2H, q), 1.26 (3H, t).

Present Compound 284

¹H-NMR (CDCl₃) δ: 8.26-8.15 (1H, m), 8.05-7.97 (1H, m), 7.87-7.74 (2H, m), 7.62-7.55 (1H, m), 7.40-7.32 (1H, m), 3.70-3.57 (6H, m), 3.54-3.42 (2H, m), 1.30-1.19 (3H, m).

Present Compound 285

¹H-NMR (CDCl₃) δ: 8.77-8.75 (1H, m), 8.37-8.35 (1H, m), 8.28-8.27 (1H, m), 8.18-8.14 (1H, m), 7.65-7.62 (1H, m), 3.81 (3H, s), 3.04 (2H, q), 1.34 (3H, t).

Present Compound 286

¹H-NMR (CDCl₃) δ: 9.13-9.11 (1H, m), 8.81-8.79 (1H, m), 8.54-8.51 (1H, m), 8.37-8.34 (1H, m), 7.87 (1H, d), 3.98 (3H, s), 3.60-3.49 (1H, m), 3.13-3.02 (1H, m), 1.40 (3H, t).

Present Compound 287

¹H-NMR (CDCl₃) δ: 9.08-9.05 (1H, m), 8.80-8.77 (1H, m), 8.68 (1H, dd), 8.34-8.31 (1H, m), 7.81 (1H, d), 3.75 (3H, s), 3.52 (2H, q), 1.32 (3H, t).

Present Compound 289

¹H-NMR (CDCl₃) δ: 8.19 (1H, dd), 8.01 (1H, d), 7.83-7.73 (2H, m), 7.55 (1H, dd), 7.35 (1H, d), 3.61 (3H, s), 3.46 (2H, q), 1.23 (3H, t).

Present Compound 290

¹H-NMR (CDCl₃) δ: 8.51 (1H, d), 8.21 (1H, dd), 8.07 (1H, d), 7.90-7.81 (2H, m), 7.59 (1H, dd), 3.69 (3H, s), 3.50-3.42 (5H, m), 1.25 (3H, t).

Present Compound 291

¹H-NMR (CDCl₃) δ: 8.21 (1H, dd), 8.16 (1H, d), 7.83-7.72 (2H, m), 7.55 (1H, dd), 7.40 (1H, d), 3.63 (3H, s), 3.48 (2H, q), 3.01 (6H, s), 1.24 (3H, t).

Present Compound 292

¹H-NMR (CDCl₃) δ: 8.69-8.68 (1H, m), 8.33-8.31 (1H, m), 7.70-7.68 (1H, m), 7.62-7.55 (2H, m), 3.79 (3H, s), 2.97 (2H, q), 1.29 (3H, t).

Present Compound 293

¹H-NMR (CDCl₃) δ: 8.86 (1H, d), 8.56 (1H, d), 7.96 (1H, d), 7.48 (1H, d), 7.32 (1H, dd), 3.02 (2H, t), 1.37 (3H, d).

Present Compound 294

¹H-NMR (CDCl₃) δ: 8.93 (1H, d), 8.52 (1H, d), 8.25 (1H, d), 7.78 (1H, dd), 7.67 (1H, d), 3.76 (2H, q), 1.40 (3H, t).

Present Compound 295

¹H-NMR (CDCl₃) δ: 8.74 (1H, s), 8.59 (1H, d), 7.56-7.49 (2H, m), 7.41 (1H, dd), 7.37-7.31 (1H, m), 6.84 (1H, brs), 3.75 (3H, s), 2.88 (2H, q), 1.23 (3H, t).

Present Compound 296

¹H-NMR (CDCl₃) δ: 8.89 (1H, d), 8.56 (1H, d), 7.56-7.42 (3H, m), 7.39-7.33 (1H, m), 3.77 (3H, s), 2.89 (2H, q), 1.25 (3H, t).

Present Compound 297

¹H-NMR (CDCl₃) δ: 8.93 (1H, d), 8.53 (1H, d), 8.26 (1H, dd), 7.84 (1H, td), 7.71 (1H, td), 7.60 (1H, dd), 3.89 (3H, s), 3.42-3.32 (1H, m), 3.05-2.96 (1H, m), 1.31 (3H, t).

Present Compound 298

¹H-NMR (CDCl₃) δ: 8.91 (1H, d), 8.50 (1H, d), 8.23 (1H, dd), 7.87-7.80 (2H, m), 7.56 (1H, dd), 3.71 (3H, s), 3.45 (2H, q), 1.26 (3H, t).

Present Compound 299

¹H-NMR (CDCl₃) δ: 8.72-8.70 (1H, m), 8.51-8.49 (1H, m), 8.29-8.27 (1H, m), 8.13-8.09 (1H, m), 7.74-7.71 (1H, m), 3.74 (3H, s), 3.49 (2H, q), 1.29 (3H, t).

Present Compound 300

¹H-NMR (CDCl₃) δ: 8.60 (1H, d), 8.39 (1H, d), 7.65-7.64 (1H, m), 7.58-7.51 (2H, m), 3.70 (3H, s), 2.91 (2H, q), 1.25 (3H, t).

Present Compound 303

¹H-NMR (CDCl₃) δ: 8.09 (1H, s), 7.52 (1H, d), 7.46-7.35 (3H, m), 7.25 (1H, t), 7.12 (1H, d), 3.56 (3H, s), 2.78 (2H, q), 1.17 (3H, t).

Present Compound 307

¹H-NMR (CDCl₃) δ: 8.65 (1H, d), 8.49-8.47 (1H, m), 8.37 (1H, d), 8.10-8.06 (1H, m), 7.74-7.71 (1H, m), 3.67 (3H, s), 3.47 (2H, q), 1.28 (3H, t).

Present Compound 308

¹H-NMR (CDCl₃) δ: 8.09 (1H, s), 7.59-7.42 (5H, m), 7.37-7.31 (1H, m), 3.69 (3H, s), 2.85 (2H, q), 1.23 (3H, t).

Present Compound 309

¹H-NMR (CDCl₃) δ: 8.22 (1H, d), 8.07 (1H, s), 7.80 (1H, t), 7.67 (1H, t), 7.62-7.52 (3H, m), 3.79 (3H, s), 3.37-3.26 (1H, m), 3.01-2.89 (1H, m), 1.27 (3H, t).

Present Compound 310

¹H-NMR (CDCl₃) δ: 8.20-8.18 (1H, m), 8.06 (1H, s), 7.82-7.74 (2H, m), 7.59-7.52 (3H, m), 3.61 (3H, s), 3.43 (2H, brs), 1.22 (3H, t).

Present Compound 311

¹H-NMR (CDCl₃) δ: 7.83 (1H, d), 7.69 (1H, d), 7.60 (1H, dd), 7.54-7.49 (1H, m), 7.48-7.42 (1H, m), 7.41-7.35 (1H, m), 6.69 (1H, d), 3.00 (2H, q), 2.93 (3H, s), 1.32 (3H, t).

Present Compound 312

¹H-NMR (CDCl₃) δ: 8.25-8.19 (2H, m), 7.83-7.78 (2H, m), 7.68 (1H, t), 7.55 (1H, d), 7.47 (1H, d), 3.79 (3H, s), 3.36-3.26 (1H, m), 3.00-2.90 (1H, m), 1.27 (3H, t).

Present Compound 313

¹H-NMR (CDCl₃) δ: 8.23-8.20 (2H, m), 7.85-7.76 (3H, m), 7.57-7.53 (1H, m), 7.46 (1H, d), 3.62 (3H, s), 3.39 (2H, brs), 1.24 (3H, t).

Present Compound 317

¹H-NMR (CDCl₃) δ: 8.65-8.64 (1H, m), 8.29-8.28 (1H, m), 7.35-7.31 (2H, m), 7.18-7.15 (1H, m), 3.76 (3H, s), 2.86 (2H, q), 2.46 (3H, s), 1.23 (3H, t).

Present Compound 318

¹H-NMR (CDCl₃) δ: 8.69-8.68 (1H, m), 8.28-8.26 (1H, m), 8.07-8.05 (1H, m), 7.50-7.48 (2H, m), 3.89 (3H, s), 3.44-3.33 (1H, m), 3.01-2.92 (1H, m), 2.58 (3H, s), 1.32 (3H, t).

Present Compound 319

¹H-NMR (CDCl₃) δ: 8.68-8.66 (1H, m), 8.25-8.23 (1H, m), 8.04-8.02 (1H, m), 7.65-7.61 (1H, m), 7.45-7.42 (1H, m), 3.71 (3H, s), 3.47-3.38 (2H, m), 2.59 (3H, s), 1.26 (3H, t).

Present Compound 320

¹H-NMR (CDCl₃) δ: 8.77 (1H, d), 8.68 (1H, d), 8.00-7.94 (1H, m), 7.55-7.51 (1H, m), 7.48-7.43 (1H, m), 7.36-7.31 (1H, m), 2.97 (2H, q), 1.33 (3H, t).

Present Compound 321

¹H-NMR (CDCl₃) δ: 8.81 (1H, d), 8.71 (1H, d), 8.08 (1H, d), 7.72 (1H, s), 7.56 (1H, d), 3.03 (2H, q), 1.37 (3H, t).

Present Compound 322

¹H-NMR (CDCl₃) δ: 8.81 (1H, d), 8.55 (1H, d), 8.07-8.00 (1H, m), 7.59-7.53 (1H, m), 7.52-7.45 (1H, m), 7.41-7.33 (1H, m), 2.99 (2H, q), 1.35 (3H, t).

Present Compound 323

¹H-NMR (CDCl₃) δ: 8.85 (1H, d), 8.59 (1H, d), 8.15 (1H, d), 7.75 (1H, s), 7.59 (1H, d), 3.05 (2H, q), 1.38 (3H, t).

Present Compound 324

¹H-NMR (CDCl₃) δ: 8.87 (1H, d), 8.50 (1H, d), 8.28-8.22 (1H, m), 7.85-7.76 (2H, m), 7.74-7.70 (1H, m), 3.74 (2H, q), 1.37 (3H, t).

Present Compound 325

¹H-NMR (CDCl₃) δ: 8.90 (1H, s), 8.57-8.49 (2H, m), 8.07 (1H, d), 7.88 (1H, d), 3.77 (2H, q), 1.40 (3H, t).

Present Compound 326

¹H-NMR (CDCl₃) δ: 8.93 (1H, d), 8.61 (1H, d), 7.45-7.34 (3H, m), 2.91 (2H, q), 1.27 (3H, t).

Present Compound 327

¹H-NMR (CDCl₃) δ: 8.95 (1H, d), 8.55 (1H, d), 8.14 (1H, dd), 7.86 (1H, dd), 7.73 (1H, t), 3.40 (2H, q), 1.28 (3H, t).

Present Compound 330

¹H-NMR (CDCl₃) δ: 8.74-8.73 (1H, m), 8.28-8.27 (1H, m), 8.22 (1H, d), 7.82 (1H, dd), 7.51 (1H, d), 6.86 (1H, dd), 6.03 (1H, d), 5.58 (1H, d), 3.72 (3H, s), 3.44 (2H, q), 1.27 (3H, t).

Present Compound 331

¹H-NMR (CDCl₃) δ: 8.74-8.72 (1H, m), 8.28-8.26 (1H, m), 8.05-8.03 (1H, m), 7.67-7.64 (1H, m), 7.46 (1H, d), 3.71 (3H, s), 3.41 (2H, q), 2.88 (2H, q), 1.37 (3H, t), 1.26 (3H, t).

Present Compound 332

¹H-NMR (CDCl₃) δ: 8.78-8.76 (1H, m), 8.46-8.44 (1H, m), 8.31-8.30 (1H, m), 8.09-8.05 (1H, m), 7.76 (1H, d), 3.75 (3H, s), 3.48 (2H, q), 1.27 (3H, t).

Present Compound 334

¹H-NMR (CDCl₃) δ: 8.89 (1H, d), 8.46 (1H, d), 8.27 (1H, dd), 7.85 (1H, td), 7.71 (1H, td), 7.62 (1H, dd), 3.92 (3H, s), 3.45-3.34 (1H, m), 3.04-2.94 (1H, m), 2.18 (6H, s), 1.32 (3H, t).

Present Compound 335

¹H-NMR (CDCl₃) δ: 8.87 (1H, d), 8.44 (1H, d), 8.26-8.19 (1H, m), 7.93-7.81 (2H, m), 7.64-7.60 (1H, m), 3.74 (3H, s), 3.43 (2H, q), 2.80 (6H, s), 1.26 (3H, t).

Present Compound 337

¹H-NMR (CDCl₃) δ: 9.26 (1H, s), 7.80 (1H, s), 7.43-7.36 (1H, m), 7.34-7.30 (1H, m), 7.27-7.21 (2H, m), 7.17 (1H, td), 3.66 (3H, s), 2.77 (2H, q), 2.12 (3H, s), 1.15 (3H, t).

Present Compound 338

¹H-NMR (CDCl₃) δ: 7.82-7.80 (1H, m), 7.50-7.43 (3H, m), 7.37-7.30 (1H, m), 7.19 (1H, s), 3.93 (3H, s), 2.87-2.82 (8H, m), 1.22 (3H, t).

Present Compound 339

¹H-NMR (CDCl₃) δ: 7.65 (1H, s), 7.60-7.53 (3H, m), 6.82 (1H, s), 4.01 (2H, brs), 3.94 (3H, s), 2.92 (2H, q), 1.27 (3H, t).

Present Compound 340

¹H-NMR (CDCl₃) δ: 7.82 (1H, s), 7.67 (1H, s), 7.61-7.53 (2H, m), 7.23 (1H, s), 3.96 (3H, s), 2.93 (2H, q), 2.86 (6H, s), 1.28 (3H, t).

Present Compound 347

¹H-NMR (CDCl₃) δ: 8.58 (1H, s), 7.56-7.29 (5H, m), 3.73 (3H, s), 2.88 (2H, q), 1.24 (3H, t).

Present Compound 348

¹H-NMR (CDCl₃) δ: 8.61 (1H, s), 8.28 (1H, dd), 7.81 (1H, td), 7.68 (1H, td), 7.62 (1H, dd), 7.27 (1H, t), 3.91 (3H, s), 3.68-3.58 (1H, m), 3.12-3.02 (1H, m), 1.37 (3H, t).

Present Compound 349

¹H-NMR (CDCl₃) δ: 8.59 (1H, s), 8.21 (1H, dd), 7.86-7.77 (2H, m), 7.60 (1H, dd), 7.27 (1H, t), 3.71 (3H, s), 3.54 (2H, q), 1.27 (3H, t).

Present Compound 350

¹H-NMR (CDCl₃) δ: 8.46 (1H, s), 7.51-7.32 (4H, m), 3.86-3.71 (1H, m), 3.68 (3H, s), 2.86 (2H, q), 1.61 (3H, s), 1.59 (3H, s), 1.22 (3H, t).

Present Compound 352

¹H-NMR (CDCl₃) δ: 8.69 (1H, s), 8.33 (1H, s), 8.25 (1H, dd), 8.21 (1H, dd), 7.73-7.58 (2H, m), 3.47-3.36 (1H, m), 3.13-3.01 (1H, m), 1.57-0.71 (3H, m).

Present Compound 355

¹H-NMR (CDCl₃) δ: 8.76 (1H, d), 8.51 (1H, d), 8.29 (1H, d), 8.10 (1H, dd), 7.74 (1H, d), 4.22 (2H, q), 3.55 (2H, q), 1.42 (3H, t), 1.30 (3H, t).

Present Compound 356

¹H-NMR (CDCl₃) δ: 8.77 (1H, d), 8.48 (1H, s), 8.31 (1H, d), 8.05 (1H, d), 7.73 (1H, d), 6.02-5.90 (1H, m), 5.19 (1H, d), 4.96 (1H, d), 4.79 (2H, s), 3.51 (2H, q), 1.29 (3H, t).

Present Compound 357

¹H-NMR (CDCl₃) δ: 8.81 (1H, d), 8.49 (1H, s), 8.33 (1H, d), 8.11 (1H, d), 7.94 (1H, d), 4.95 (2H, brs), 3.46 (2H, q), 2.34-2.31 (1H, m), 1.29 (3H, t).

Present Compound 358

¹H-NMR (CDCl₃) δ: 8.83 (1H, d), 8.50 (1H, d), 8.37 (1H, d), 8.18 (1H, dd), 7.93 (1H, d), 5.10 (2H, brs), 3.35 (2H, q), 1.27 (3H, t).

Present Compound 359

¹H-NMR (CDCl₃) δ: 8.98 (1H, d), 8.50 (1H, d), 8.21-8.17 (2H, m), 7.89 (1H, d), 4.97 (1H, brs), 4.85 (1H, brs), 3.47 (1H, brs), 3.34 (1H, brs), 1.28-1.20 (3H, m).

Present Compound 360

¹H-NMR (CDCl₃) δ: 8.77 (1H, d), 8.47 (1H, d), 8.32 (1H, d), 8.08 (1H, dd), 7.90 (1H, d), 5.53 (2H, s), 3.67 (2H, q), 3.58 (2H, q), 1.31 (3H, t), 1.18 (3H, t).

Present Compound 361

¹H-NMR (CDCl₃) δ: 8.91 (1H, d), 8.48 (1H, d), 8.21 (1H, d), 8.09 (1H, dd), 7.81 (1H, d), 5.36 (2H, s), 3.60-3.49 (4H, m), 1.28 (3H, t), 1.19 (3H, t).

Present Compound 362

¹H-NMR (CDCl₃) δ: 8.76 (1H, d), 8.47 (1H, d), 8.31 (1H, d), 8.10 (1H, dd), 7.98 (1H, d), 5.23 (2H, brs), 3.45 (2H, q), 2.26 (3H, s), 1.28 (3H, t).

Present Compound 363

¹H-NMR (CDCl₃) δ: 8.75 (1H, d), 8.50 (1H, d), 8.29 (1H, d), 8.09 (1H, dd), 7.74 (1H, d), 4.12 (2H, q), 3.53 (2H, q), 1.89-1.79 (2H, m), 1.29 (3H, t), 0.90 (3H, t).

Present Compound 364

¹H-NMR (CDCl₃) δ: 8.75 (1H, d), 8.51 (1H, d), 8.29 (1H, d), 8.09 (1H, dd), 7.74 (1H, d), 4.17-4.10 (2H, m), 3.53 (2H, q), 1.82-1.75 (2H, m), 1.34-1.24 (5H, m), 0.86 (3H, t).

Present Compound 365

¹H-NMR (CDCl₃) δ: 8.75 (1H, d), 8.46 (1H, d), 8.33 (1H, d), 8.05 (1H, dd), 7.87 (1H, d), 4.91 (2H, brs), 3.77 (3H, s), 3.41 (2H, q), 1.27 (3H, t).

Present Compound 366

¹H-NMR (CDCl₃) δ: 8.92 (1H, d), 8.47 (1H, d), 8.07 (1H, dd), 7.96 (1H, d), 7.83 (1H, d), 4.82 (1H, brs), 4.69 (1H, brs), 3.81 (3H, s), 3.54 (1H, brs), 3.40 (1H, brs), 1.26 (3H, t).

Present Compound 367

¹H-NMR (CDCl₃) δ: 8.77 (1H, d), 8.50 (1H, d), 8.32 (1H, d), 8.11 (1H, dd), 7.73 (1H, d), 6.12 (1H, t), 4.92 (2H, d), 3.48 (2H, q), 1.29 (3H, t).

Present Compound 368

¹H-NMR (CDCl₃) δ: 8.76 (1H, d), 8.42 (1H, d), 8.21 (1H, d), 7.99 (1H, dd), 7.67 (1H, d), 3.60-3.50 (1H, m), 3.40-3.30 (1H, m), 1.70 (9H, s), 1.28 (3H, t).

Present Compound 369

¹H-NMR (CDCl₃) δ: 8.13 (1H, s), 7.67 (1H, s), 7.62 (1H, d), 7.59-7.57 (2H, m), 7.52 (1H, d), 3.70 (3H, s), 2.92 (2H, q), 1.27 (3H, t).

Present Compound 370

¹H-NMR (CDCl₃) δ: 8.53 (1H, s), 8.10 (1H, s), 7.93 (1H, d), 7.75 (1H, d), 7.65 (1H, d), 7.57 (1H, d), 3.85 (3H, s), 3.52-3.41 (1H, m), 3.05-2.95 (1H, m), 1.32 (3H, t).

Present Compound 371

¹H-NMR (CDCl₃) δ: 8.48 (1H, s), 8.10-8.05 (2H, m), 7.74 (1H, d), 7.62 (1H, d), 7.53 (1H, d), 3.63 (3H, s), 3.47 (2H, q), 1.25 (3H, t).

Present Compound 372

¹H-NMR (CDCl₃) δ: 8.77 (1H, d), 8.50 (1H, d), 8.30 (1H, d), 8.10 (1H, dd), 7.73 (1H, d), 3.74 (3H, s), 3.48 (2H, q), 1.29 (3H, t).

Present Compound 373

¹H-NMR (CDCl₃) δ: 8.83 (1H, d), 8.37-8.34 (2H, m), 8.04 (1H, dd), 7.72 (1H, d), 3.30-3.11 (2H, brm), 3.04 (3H, s), 1.24 (3H, t).

Present Compound 374

¹H-NMR (CDCl₃) δ: 8.74-8.72 (1H, m), 8.33-8.32 (1H, m), 7.48 (1H, d), 7.29-7.27 (1H, m), 7.21-7.17 (1H, m), 3.79 (3H, s), 2.92 (2H, q), 1.29 (3H, t).

Present Compound 375

¹H-NMR (CDCl₃) δ: 8.78-8.76 (1H, m), 8.33-8.31 (1H, m), 8.14-8.12 (1H, m), 7.68 (1H, d), 7.54-7.50 (1H, m), 3.93 (3H, s), 3.49-3.39 (1H, m), 3.06-2.96 (1H, m), 1.33 (3H, t).

Present Compound 376

¹H-NMR (CDCl₃) δ: 8.77-8.75 (1H, m), 8.30-8.28 (1H, m), 8.09-8.07 (1H, m), 7.70-7.66 (1H, m), 7.63 (1H, d), 3.74 (3H, s), 3.46 (2H, q), 1.28 (3H, t).

Present Compound 377

¹H-NMR (CDCl₃) δ: 8.78-8.77 (1H, m), 8.47-8.45 (1H, m), 8.32-8.30 (1H, m), 8.09-8.06 (1H, m), 7.76 (1H, d), 3.75 (3H, s), 3.48 (2H, q), 1.27 (3H, t).

Present Compound 378

¹H-NMR (CDCl₃) δ: 8.83-8.74 (3H, m), 8.54 (1H, dd), 8.31-8.29 (1H, m), 7.95-7.86 (2H, m), 7.68 (1H, d), 7.41-7.37 (1H, m), 3.75 (3H, s), 3.49 (2H, q), 1.30 (3H, t).

Present Compound 379

¹H-NMR (CDCl₃) δ: 8.72-8.70 (1H, m), 8.27-8.25 (1H, m), 7.43 (1H, d), 7.29 (1H, d), 6.99 (1H, dd), 4.28 (2H, brs), 3.70 (3H, s), 3.40 (2H, q), 1.26 (3H, t).

Present Compound 380

¹H-NMR (DMSO-D₆) δ: 11.94 (1H, brs), 8.86-8.84 (1H, m), 8.62-8.60 (1H, m), 8.53 (1H, d), 8.28 (1H, dd), 7.95 (1H, d), 3.64 (3H, s), 3.56 (2H, q), 1.14 (3H, t).

Present Compound 381

¹H-NMR (CDCl₃) δ: 8.74-8.72 (1H, m), 8.28-8.25 (1H, m), 8.07-8.05 (1H, m), 7.69-7.66 (1H, m), 7.47 (1H, d), 3.72 (3H, s), 3.41 (2H, q), 3.18-3.10 (1H, m), 1.37 (6H, d), 1.26 (3H, t).

Present Compound 382

¹H-NMR (CDCl₃) δ: 10.23 (1H, s), 8.78-8.76 (1H, m), 8.71 (1H, d), 8.35 (1H, dd), 8.31 (1H, d), 7.77 (1H, d), 3.74 (3H, s), 3.49 (2H, q), 1.30 (3H, t).

Present Compound 383

¹H-NMR (CDCl₃) δ: 8.72-8.70 (1H, m), 8.32-8.31 (1H, m), 7.55-7.49 (2H, m), 7.46-7.43 (1H, m), 7.38-7.33 (1H, m), 3.77 (3H, s), 2.84 (2H, t), 1.58-1.50 (2H, m), 1.39-1.29 (2H, m), 0.85 (3H, t).

Present Compound 384

¹H-NMR (CDCl₃) δ: 8.73-8.72 (1H, m), 8.33-8.31 (1H, m), 7.66-7.63 (1H, m), 7.58-7.53 (1H, m), 7.49-7.41 (2H, m), 3.79 (3H, s), 3.66 (3H, s), 3.60 (2H, s).

Present Compound 385

¹H-NMR (CDCl₃) δ: 8.74-8.72 (1H, m), 8.34-8.32 (1H, m), 7.61-7.55 (2H, m), 7.52-7.44 (2H, m), 5.85 (1H, t), 3.77 (3H, s), 3.54 (2H, d).

Present Compound 386

¹H-NMR (CDCl₃) δ: 8.72-8.71 (1H, m), 8.32-8.31 (1H, m), 7.68-7.65 (1H, m), 7.59-7.54 (1H, m), 7.47 (1H, dd), 7.44-7.39 (1H, m), 3.78 (3H, s), 3.55 (2H, q), 1.75 (3H, t).

Present Compound 387

¹H-NMR (CDCl₃) δ: 8.75-8.73 (1H, m), 8.33-8.31 (1H, m), 7.87-7.84 (1H, m), 7.70-7.64 (1H, m), 7.63-7.58 (1H, m), 7.56 (1H, dd), 3.78 (3H, s), 3.61 (2H, s).

Present Compound 388

¹H-NMR (CDCl₃) δ: 8.72-8.71 (1H, m), 8.33-8.31 (1H, m), 7.57-7.48 (2H, m), 7.45-7.42 (1H, m), 7.37-7.32 (1H, m), 3.78 (3H, s), 2.82 (2H, s), 0.91 (9H, s).

Present Compound 389

¹H-NMR (CDCl₃) δ: 8.75-8.73 (1H, m), 8.33-8.31 (1H, m), 7.71-7.68 (1H, m), 7.63-7.58 (1H, m), 7.55-7.51 (2H, m), 3.76 (3H, s), 2.97 (2H, t), 2.52 (2H, t).

Present Compound 390

¹H-NMR (CDCl₃) δ: 8.72-8.70 (1H, m), 8.33-8.31 (1H, m), 7.53-7.49 (2H, m), 7.46-7.42 (1H, m), 7.39-7.33 (1H, m), 3.76 (3H, s), 2.90 (2H, d), 2.50-2.37 (1H, m), 2.06-1.96 (2H, m), 1.87-1.71 (2H, m), 1.67-1.56 (2H, m).

Present Compound 391

¹H-NMR (CDCl₃) δ: 8.76-8.74 (1H, m), 8.35-8.34 (1H, m), 7.98-7.94 (1H, m), 7.71-7.67 (2H, m), 7.63-7.60 (1H, m), 3.78 (3H, s).

Present Compound 392

$^1$H-NMR (CDCl$_3$) δ: 8.77-8.75 (1H, m), 8.38-8.36 (1H, m), 8.31-8.29 (1H, m), 8.02-7.99 (1H, m), 7.69 (1H, d), 6.85 (1H, t), 3.73 (3H, s), 3.54-3.33 (2H, m), 1.28 (3H, t).

Present Compound 393

$^1$H-NMR (CDCl$_3$) δ: 8.75-8.73 (1H, m), 8.29-8.27 (1H, m), 8.21-8.19 (1H, m), 7.88-7.84 (1H, m), 7.56 (1H, d), 4.97-4.93 (2H, m), 3.71 (3H, s), 3.43 (2H, q), 1.26 (3H, t).

Present Compound 394

$^1$H-NMR (CDCl$_3$) δ: 8.75-8.73 (1H, m), 8.28-8.26 (1H, m), 8.25-8.22 (1H, m), 7.87-7.79 (2H, m), 7.58-7.55 (1H, m), 3.72 (3H, s), 3.43-3.37 (2H, m), 1.70-1.60 (2H, m), 1.45-1.35 (2H, m), 0.90 (3H, t).

Present Compound 395

$^1$H-NMR (CDCl$_3$) δ: 8.76-8.74 (1H, m), 8.33-8.29 (2H, m), 7.91-7.81 (2H, m), 7.60-7.57 (1H, m), 4.68 (2H, br s), 3.74 (3H, s), 3.72 (3H, s).

Present Compound 396

$^1$H-NMR (CDCl$_3$) δ: 8.75-8.74 (1H, m), 8.29-8.27 (1H, m), 8.22-8.20 (1H, m), 7.92-7.82 (2H, m), 7.61-7.58 (1H, m), 5.92 (1H, t), 4.40 (2H, d), 3.73 (3H, s).

Present Compound 397

$^1$H-NMR (CDCl$_3$) δ: 8.75-8.73 (1H, m), 8.32-8.28 (2H, m), 7.89-7.80 (2H, m), 7.60-7.57 (1H, m), 4.35 (2H, br s), 3.73 (3H, s), 1.78 (3H, t).

Present Compound 398

$^1$H-NMR (CDCl$_3$) δ: 8.78-8.76 (1H, m), 8.43-8.40 (1H, m), 8.30-8.29 (1H, m), 8.00-7.95 (1H, m), 7.94-7.89 (1H, m), 7.68-7.65 (1H, m), 4.83 (2H, br s), 3.78 (3H, s).

Present Compound 399

$^1$H-NMR (CDCl$_3$) δ: 8.75-8.74 (1H, m), 8.27-8.24 (2H, m), 7.83-7.80 (2H, m), 7.55-7.52 (1H, m), 3.71 (3H, s), 3.45 (2H, br s), 1.06 (9H, s).

Present Compound 400

$^1$H-NMR (CDCl$_3$) δ: 8.77-8.75 (1H, m), 8.33-8.32 (1H, m), 8.29-8.26 (1H, m), 7.95-7.90 (1H, m), 7.89-7.84 (1H, m), 7.64-7.61 (1H, m), 3.87 (2H, t), 3.73 (3H, s), 2.78 (2H, t).

Present Compound 401

$^1$H-NMR (CDCl$_3$) δ: 8.75-8.73 (1H, m), 8.32-8.30 (1H, m), 8.22-8.19 (1H, m), 7.86-7.78 (2H, m), 7.57-7.54 (1H, m), 3.70 (3H, s), 3.51 (2H, d), 2.75-2.63 (1H, m), 2.06-1.96 (2H, m), 1.94-1.70 (4H, m).

Present Compound 402

$^1$H-NMR (CDCl$_3$) δ: 8.75-8.73 (1H, m), 8.33-8.30 (2H, m), 8.03-7.98 (2H, m), 7.95-7.90 (1H, m), 7.70-7.68 (1H, m), 3.70 (3H, s).

Present Compound 403

$^1$H-NMR (CDCl$_3$) δ: 8.76-8.74 (1H, m), 8.29-8.28 (1H, m), 8.21-8.19 (1H, m), 7.87-7.84 (1H, m), 7.63-7.60 (1H, m), 5.61 (2H, d), 3.72 (3H, s), 3.54-3.32 (2H, m), 1.27 (3H, t).

Present Compound 404

$^1$H-NMR (CDCl$_3$) δ: 8.72-8.71 (1H, m), 8.33-8.31 (1H, m), 7.61-7.50 (3H, m), 7.47-7.42 (1H, m), 6.42 (1H, dd), 5.37 (1H, d), 5.35 (1H, d), 3.79 (3H, s).

Present Compound 405

$^1$H-NMR (CDCl$_3$) δ: 8.76-8.75 (1H, m), 8.35-8.33 (1H, m), 8.17-8.14 (1H, m), 7.82-7.77 (1H, m), 7.69-7.61 (2H, m), 7.42 (1H, dd), 6.17 (1H, d), 5.86 (1H, d), 3.97 (3H, s).

Present Compound 406

$^1$H-NMR (CDCl$_3$) δ: 8.75-8.74 (1H, m), 8.30-8.29 (1H, m), 8.25-8.22 (1H, m), 7.84-7.80 (2H, m), 7.57-7.54 (1H, m), 7.10 (1H, dd), 6.31 (1H, d), 6.03 (1H, d), 3.74 (3H, s).

Present Compound 407

$^1$H-NMR (CDCl$_3$) δ: 8.47 (1H, d), 8.04 (1H, dd), 7.84 (1H, d), 7.56 (1H, dd), 7.48 (1H, td), 7.37 (1H, td), 2.98 (2H, q), 1.34 (3H, t).

Present Compound 408

$^1$H-NMR (CDCl$_3$) δ: 8.44 (1H, d), 8.25 (1H, dd), 7.89 (1H, d), 7.84-7.71 (3H, m), 3.72 (2H, q), 1.37 (3H, t).

Present Compound 409

$^1$H-NMR (CDCl$_3$) δ: 8.68-8.66 (1H, m), 8.31-8.30 (1H, m), 7.48 (1H, d), 7.29-7.26 (1H, m), 7.21-7.17 (1H, m), 3.80 (3H, s), 2.93 (2H, q), 1.29 (3H, t).

Present Compound 410

$^1$H-NMR (CDCl$_3$) δ: 8.72-8.71 (1H, m), 8.30-8.29 (1H, m), 8.14-8.12 (1H, m), 7.68 (1H, d), 7.55-7.51 (1H, m), 3.93 (3H, s), 3.50-3.40 (1H, m), 3.08-2.98 (1H, m), 1.33 (3H, t).

Present Compound 411

$^1$H-NMR (CDCl$_3$) δ: 8.71-8.69 (1H, m), 8.27-8.26 (1H, m), 8.09-8.07 (1H, m), 7.70-7.66 (1H, m), 7.62 (1H, d), 3.74 (3H, s), 3.47 (2H, q), 1.28 (3H, t).

Present Compound 412

$^1$H-NMR (DMSO-D$_6$) δ: 7.88 (1H, s), 7.81 (1H, s), 7.73 (1H, d), 7.69 (1H, d), 7.39 (1H, s), 3.84 (3H, s), 3.09 (2H, q), 2.84 (3H, s), 1.19 (3H, t).

Present Compound 413

$^1$H-NMR (CDCl$_3$) δ: 8.50 (1H, s), 7.94-7.89 (2H, m), 7.69 (1H, d), 7.35 (1H, s), 3.99 (3H, s), 3.42-3.32 (1H, m), 3.01-2.90 (1H, m), 2.85 (3H, s), 1.28 (3H, t).

Present Compound 414

$^1$H-NMR (CDCl$_3$) δ: 8.48 (1H, d), 8.07 (1H, dd), 7.88 (1H, s), 7.72 (1H, d), 7.32 (1H, s), 3.82 (3H, s), 3.45 (2H, br s), 2.82 (3H, s), 1.26 (3H, t).

Present Compound 415

$^1$H-NMR (DMSO-D$_6$) δ: 8.13 (1H, d), 7.96 (1H, d), 7.82 (1H, s), 7.77-7.71 (2H, m), 3.65 (3H, s), 3.09 (2H, q), 1.18 (3H, t).

Present Compound 416

$^1$H-NMR (CDCl$_3$) δ: 8.52 (1H, d), 8.06 (1H, d), 7.93 (1H, dd), 7.72 (1H, d), 7.28 (1H, d), 3.80 (3H, s), 3.49-3.39 (1H, m), 3.05-2.95 (1H, m), 1.33 (3H, t).

Present Compound 417

$^1$H-NMR (CDCl$_3$) δ: 8.48 (1H, d), 8.09 (1H, dd), 8.02 (1H, d), 7.74 (1H, d), 7.25 (1H, d), 3.60 (3H, s), 3.45 (2H, q), 1.26 (3H, t).

Present Compound 418

$^1$H-NMR (CDCl$_3$) δ: 8.11 (1H, s), 7.67 (1H, s), 7.61-7.56 (3H, m), 7.53 (1H, d), 3.70 (3H, s), 2.93 (2H, q), 1.28 (3H, t).

Present Compound 419

$^1$H-NMR (CDCl$_3$) δ: 8.53 (1H, d), 8.09 (1H, s), 7.93 (1H, dd), 7.74 (1H, d), 7.64 (1H, d), 7.59 (1H, d), 3.85 (3H, s), 3.51-3.40 (1H, m), 3.06-2.97 (1H, m), 1.32 (3H, t).

Present Compound 420

$^1$H-NMR (CDCl$_3$) δ: 8.49 (1H, d), 8.10-8.04 (2H, m), 7.73 (1H, d), 7.60 (1H, d), 7.55 (1H, d), 3.64 (3H, s), 3.47 (2H, q), 1.25 (3H, t).

Present Compound 421

$^1$H-NMR (CDCl$_3$) δ: 8.72-8.71 (1H, m), 8.32-8.31 (1H, m), 7.57-7.49 (2H, m), 7.47-7.44 (1H, m), 7.39-7.34 (1H, m), 3.78 (3H, s), 2.78 (2H, d), 0.99-0.89 (1H, m), 0.54-0.48 (2H, m), 0.18-0.14 (2H, m).

Present Compound 422

$^1$H-NMR (CDCl$_3$) δ: 8.76-8.75 (1H, m), 8.34-8.31 (1H, m), 8.28-8.26 (1H, m), 7.85-7.80 (1H, m), 7.71-7.67 (1H, m), 7.61-7.58 (1H, m), 3.91 (3H, s), 3.27 (1H, dd), 3.04 (1H, dd), 1.33-1.22 (1H, m), 0.71-0.62 (2H, m), 0.43-0.31 (2H, m).

Present Compound 423

$^1$H-NMR (CDCl$_3$) δ: 8.75-8.73 (1H, m), 8.31-8.26 (2H, m), 7.88-7.79 (2H, m), 7.57-7.54 (1H, m), 3.72 (3H, s), 3.34 (2H, d), 1.05-0.94 (1H, m), 0.57-0.50 (2H, m), 0.26-0.20 (2H, m).

Present Compound 424

$^1$H-NMR (CDCl$_3$) δ: 8.30 (1H, d), 8.20 (1H, s), 7.78-7.67 (2H, m), 7.63 (1H, s), 7.52 (1H, d), 3.11 (2H, q), 1.47 (3H, t).

Present Compound 425

$^1$H-NMR (CDCl$_3$) δ: 8.53 (1H, s), 8.18-8.12 (2H, m), 8.08 (1H, d), 7.77-7.72 (2H, m), 3.91 (2H, q), 1.44 (3H, t).

Present Compound 426

$^1$H-NMR (CDCl$_3$) δ: 8.12 (1H, s), 7.66 (1H, s), 7.62 (1H, dd), 7.57 (1H, br s), 7.52 (1H, d), 3.70 (3H, s), 2.92 (2H, q), 1.26 (3H, t).

Present Compound 427

$^1$H-NMR (CDCl$_3$) δ: 7.95 (1H, d), 7.64 (1H, s), 7.57-7.51 (3H, m), 4.03 (3H, s), 3.04 (2H, q), 2.93 (2H, q), 1.37 (3H, t), 1.29-1.20 (3H, m).

The productions of the intermediates of the present compound are shown in the following Reference Production Examples.

Reference Production Example 1

A mixture of N$^2$-methyl-5-trifluoromethylpyridin-2,3-diamine (1.91 g), 2-fluorobenzaldehyde (1.86 g), sodium hydrogen sulfite (1.56 g), and DMF (10 ml) was stirred with heating under reflux at 153° C. for 3 hours. Into the reaction mixture cooled to room temperature, water was poured, and extracted with ethyl acetate. The organic layer was dried over magnesium sulfate, and concentrated under reduced pressure. The resulting residue was subjected to silica gel column chromatography to give 0.89 g of 2-(2-fluorophenyl)-3-methyl-6-trifluoromethyl-3H-imidazo[4,5-b]pyridine (Compound (1E)-F1).

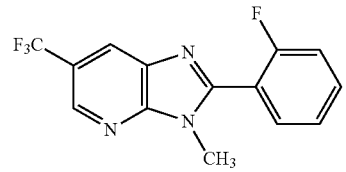 [SMILES: Cn1c(-c2ccccc2F)nc2cc(C(F)(F)F)cnc21]

$^1$H-NMR (CDCl$_3$) δ: 8.73-8.72 (1H, m), 8.33-8.32 (1H, m), 7.76-7.72 (1H, m), 7.64-7.58 (1H, m), 7.41-7.36 (1H, m), 7.32-7.27 (1H, m), 3.89 (3H, d)

Reference Production Example 2-a

To a mixture of 2-chloro-5-trifluoromethylpyridine (18.2) and N-methylpyrrolidone (100 ml), 40% of aqueous methylamine solution (23.3 g) was added, and stirred at room temperature for 3 hours. Water was poured thereinto, and extracted with ethyl acetate 3 times. The combined organic layer was dried over magnesium sulfate, and concentrated under reduced pressure. The residue was subjected to silica gel column chromatography to give 17.3 g of N-methyl-(5-trifluoromethyl-pyridin-2-yl)-amine.

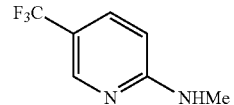

¹H-NMR (CDCl₃) δ: 8.34 (s, 1H), 7.60 (dd, 1H), 6.40 (d, 1H), 4.89 (brs, 1H), 2.97 (d, 3H)

Reference Production Example 2-b

To a mixture of N-methyl-(5-trifluoromethyl-pyridin-2-yl)-amine (17.3 g) and sulfuric acid (100 ml), nitric acid (12.3 g) was added dropwise, and stirred with heating at 80° C. for 2 hours. The mixture was cooled to room temperature, and then the reaction mixture was poured into water. The precipitate was collected by filtration, washed with water, and dried under reduced pressure to give 18.8 g of N-methyl-(3-nitro-5-trifluoromethyl-pyridin-2-yl)-amine.

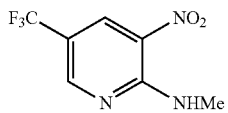

¹H-NMR (CDCl₃) δ: 8.66-8.64 (m, 2H), 8.43 (brs, 1H), 3.23 (d, 3H)

Reference Production Example 2-c

A mixture of N-methyl-(3-nitro-5-trifluoromethyl-pyridin-2-yl)-amine (6.93 g), 5% of palladium-carbon (0.69 g), and ethanol was stirred under about 1 atm of hydrogen at room temperature for 10 hours. The reaction mixture was filtered through Celite®, and then the filtrate was concentrated under reduced pressure to give 5.02 g of $N^2$-methyl-5-trifluoromethylpyridin-2,3-diamine (Compound (1F)-1).

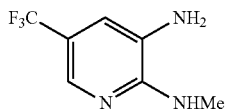

¹H-NMR (CDCl₃) δ: 8.04 (s, 1H), 6.98 (d, 1H), 4.56 (brs, 1H), 3.25 (brs, 2H), 3.06 (d, 3H)

The compound of Reference Production Example 2-c can also be produced by the following production method.

Reference Production Example 2-d

To a mixture of N-methyl-(5-trifluoromethyl-pyridin-2-yl)-amine (3.48 g) and DMF (20 ml), N-bromosuccinimide (4.27 g) was added, and stirred at room temperature for 1 hour. Into the reaction mixture, saturated aqueous ammonium chloride solution was poured, and extracted with ethyl acetate. The organic layer was dried over sodium sulfate, and concentrated under reduced pressure. The resulting residue was subjected to silica gel column chromatography to give 4.8 g of N-methyl-(3-bromo-5-trifluoromethyl-pyridin-2-yl)-amine.

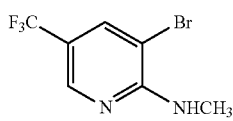

¹H-NMR (CDCl₃) δ: 3.08 (3H, d), 5.40 (1H, brs), 7.78 (1H, d), 8.34 (1H, s).

Reference Production Example 2-e

To a pressure-resistant reaction container, N-methyl-(3-bromo-5-trifluoromethyl-pyridin-2-yl)-amine (0.51 g), copper (II) acetylacetone (0.11 g), acetylacetone (0.20 g), cesium carbonate (1.30 g), NMP (2 ml), and 28% of aqueous ammonia (1 ml) were added, and stirred at 120° C. for 7 hours, then at 130° C. for 3 hours. The mixture was allowed to cool to room temperature, and then saturated aqueous ammonium chloride solution was poured, and extracted with ethyl acetate. The organic layer was dried over sodium sulfate, and concentrated under reduced pressure. The resulting residue was subjected to silica gel column chromatography to give 0.28 g of $N^2$-methyl-5-trifluoromethylpyridin-2,3-diamin.

Reference Production Example 3-a

A mixture of 2-chloro-5-trifluoromethylpyridine (12 g), 70% of aqueous ethylamine solution (16 ml), and NMP (7 ml) was stirred with heating at 70° C. for 1 day. Into the reaction mixture cooled to room temperature, water was poured, and then the precipitated solid was collected by filtration. The obtained solid was washed with water, and dried to give 6.3 g of N-ethyl-(5-trifluoromethylpyridin-2-yl)-amine.

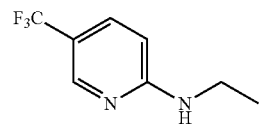

¹H-NMR (CDCl₃) δ: 8.25 (1H, s), 7.51 (1H, d), 6.31 (1H, d), 4.84 (1H, brs), 3.32-3.25 (2H, m), 1.27-1.11 (3H, m)

Reference Production Example 3-b

A mixture of N-[[m]]ethyl-(5-trifluoromethylpyridin-2-yl)-amine (1.0 g) and sulfuric acid (7 ml) was stirred with heating at 95° C., and then a mixture of fuming nitric acid (0.45 ml) and sulfuric acid (3 ml) were added thereto, and stirred with heating for 1 hour. The reaction mixture cooling to room temperature was poured into ice, and then saturated aqueous sodium hydrogen carbonate solution was poured, and extracted with ethyl acetate. The organic layer was dried over sodium sulfate, and concentrated under reduced pressure. The resulting residue was subjected to silica gel chromatography to give 600 mg of N-ethyl-(3-nitro-5-trifluoromethylpyridin-2-yl)-amine.

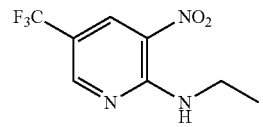 [SMILES: CCNc1ncc(C(F)(F)F)cc1[N+](=O)[O-]]

Reference Production Example 3-c

A mixture of iron powder (700 mg), acetic acid (60 μl), ethanol (5 ml), and water (3 ml) was stirred with heating at 70° C., and then a mixture of N-ethyl-(3-nitro-5-trifluoromethylpyridin-2-yl)-amine (490 mg) and ethanol (10 ml) was added dropwise. The mixture was stirred with heating at 70° C. for 3 hours. The reaction mixture cooled to room temperature was filtered through Celite®, and the resulting filtrate was concentrated under reduced pressure. The resulting residue was diluted with saturated aqueous sodium hydrogen carbonate solution, and extracted with ethyl acetate. The organic layer was dried over sodium sulfate, and concentrated under reduced pressure. The resulting residue was subjected to silica gel column chromatography to give 0.29 g of $N^2$-ethyl-5-trifluoromethylpyridin-2,3-diamine (Compound (1F)-8).

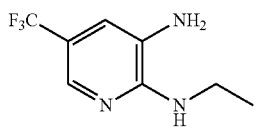

$^1$H-NMR (CDCl$_3$) δ: 8.01 (1H, d), 6.97 (1H, d), 3.51 (2H, q), 1.27 (3H, t)

Reference Production Example 4-a

The procedure was performed according to the method described in Reference Production Example 3-a using n-propylamine instead of 70% of aqueous ethylamine solution to give 10 g of N-propyl-(5-trifluoromethylpyridin-2-yl)-amine.

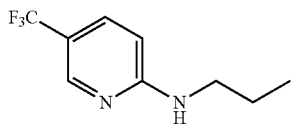

Reference Production Example 4-b

A mixture of N-propyl-(5-trifluoromethylpyridin-2-yl)-amine (3.0 g) and sulfuric acid (20 ml) was stirred with heating at 95° C., and then a mixture of fuming nitric acid (1.3 ml) and sulfuric acid (10 ml) was added dropwise, and stirred with heating for 1 hour. The reaction mixture was poured into ice, and then saturated aqueous sodium hydrogen carbonate solution was poured, and extracted with ethyl acetate. The organic layer was dried over sodium sulfate, and concentrated under reduced pressure.

To a mixture of the resulting residue, ethanol (12 ml) and water (8 ml), iron powder (2.5 g) and acetic acid (0.5 ml) were added, heated to 70° C., and stirred with heating for 2 hours. The reaction mixture cooled to room temperature was filtered through Celite®, and then the resulting filtrate was concentrated under reduced pressure. The resulting residue was subjected to silica gel column chromatography to give 1.5 g of $N^2$-propyl-5-trifluoromethylpyridin-2,3-diamine.

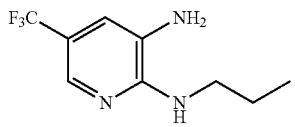

Reference Production Example 4-c

A mixture of N-propyl-5-trifluoromethylpyridin-2,3-diamine (770 mg), 2-ethylsulfanyl-benzoic acid (700 mg), WSC (740 mg), and pyridine (20 ml) was stirred with heating at 95° C. for 7 hours. Into the reaction mixture cooled to room temperature, saturated aqueous sodium carbonate solution was poured, and extracted with ethyl acetate. The organic layer was dried over sodium sulfate, and concentrated under reduced pressure. The resulting residue was subjected to silica gel column chromatography to give 422 mg of 2-ethyl-sulfanyl-N-(2-propylamino-5-trifluoromethylpyridin-3-yl)-benzamide (Compound (1B)-513).

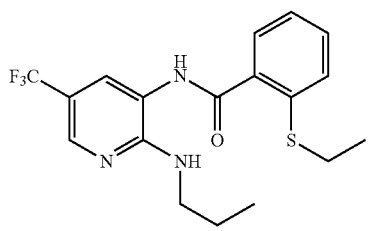 [SMILES: CCCNc1ncc(C(F)(F)F)cc1NC(=O)c1ccccc1SCC]

Reference Production Example 5-a

The procedure was performed according to the method described in Reference Production Example 3-b using 5-trifluoromethylpyridin-2-ol instead of N-methyl-(5-trifluoromethylpyridin-2-yl)-amine to give 3.3 g of 3-nitro-5-trifluoromethylpyridin-2-ol.

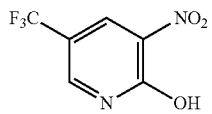

$^1$H-NMR (DMSO-d$_6$) δ: 13.54 (1H, brs), 8.67 (1H, d), 8.46 (1H, d)

Reference Production Example 5-b

To a mixture of 3-nitro-5-trifluoromethylpyridin-2-ol (3.2 g) and DMF (1 drop), phosphorous oxychloride (8.2 ml) was added at room temperature. The mixture was heated to 105° C., and stirred with heating for 2 days. The reaction mixture was cooled to room temperature, and then the reaction mixture was poured into ice, and extracted with ethyl acetate. The organic layer was dried over sodium sulfate, and concentrated under reduced pressure to give 2.5 g of 2-chloro-3-nitro-5-trifluoromethylpyridine.

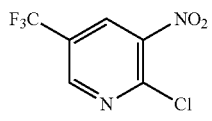

Reference Production Example 5-c

To a mixture of 2-chloro-3-nitro-5-trifluoromethylpyridine (1.5 g) and ethanol (15 ml), isopropylamine (1.8 ml) was added under ice-cooling, heated to room temperature, and stirred with heating for 3 hours. Into the reaction mixture, 2 mol/l of aqueous solution of hydrochloric acid was poured, and extracted with ethyl acetate. The organic layer was dried over sodium sulfate, and concentrated under reduced pressure.

To the resulting residue, ethanol (30 ml), water (20 ml), ammonium chloride (0.7 g), iron powder (445 mg), and ammonium chloride (0.7 g) were sequentially added at room temperature. The mixture was heated to 70° C., and stirred with heating for 1 day. Into the reaction mixture cooled to room temperature, aqueous sodium hydroxide solution was poured, and extracted with ethyl acetate. The organic layer was dried over sodium sulfate, and concentrated under reduced pressure to give 970 mg of $N^2$-isopropyl-5-trifluoromethylpyridin-2,3-diamine (Compound (1F)-15).

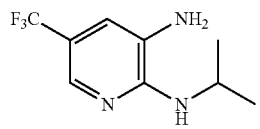

Reference Production Example 6

The procedure was performed according to the method described in Reference Production Example 5-c using cyclopropylamine instead of isopropylamine to give 750 mg of $N^2$-cyclopropyl-5-trifluoromethylpyridin-2,3-diamine.

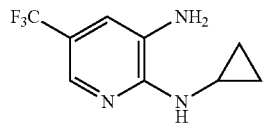 [SMILES: Nc1cc(C(F)(F)F)cnc1NC1CC1]

Reference Production Example 7

The procedure was performed according to the method described in Reference Production Example 3-c using 5-trifluoromethyl-pyridin-2,3-diamine instead of $N^2$-propyl-5-trifluoromethylpyridin-2,3-diamine to give 4.7 g of N-(2-amino-5-trifluoromethylpyridin-3-yl)-2-ethylsulfanyl-benzamide (Compound (1B)-512).

$^1$H-NMR (DMSO-D$_6$) δ: 9.75 (1H, s), 8.17 (1H, s), 8.09 (1H, s), 7.64 (1H, d), 7.53-7.45 (2H, m), 7.34-7.28 (1H, m), 6.71 (2H, s), 2.97 (2H, q), 1.22 (3H, t)

Reference Production Example 8

A mixture of 5,$N^2$-dimethylpyridin-2,3-diamine (1.13 g), 2-ethylsulfanylbenzoic acid (1.79 g), WSC (1.38 g), and pyridine (20 ml) was stirred with heating under reflux at 120° C. for 2 hours. Into the reaction mixture cooled to room temperature, water was poured, and extracted with ethyl acetate. The organic layer was dried over magnesium sulfate, and concentrated under reduced pressure. The resulting residue was subjected to silica gel column chromatography to give 1.58 g of 2-ethylsulfanylphenyl-N-(5-methyl-2-methylaminopyridin-3-yl)-benzamide (Compound (1B)-514).

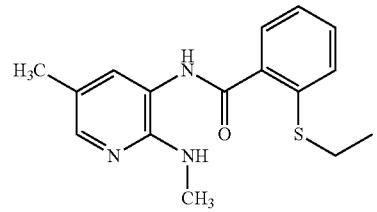 [SMILES: CCSc1ccccc1C(=O)Nc1cc(C)cnc1NC]

$^1$H-NMR (CDCl$_3$) δ: 8.18 (1H, brs), 7.97-7.93 (1H, m), 7.85-7.80 (1H, m), 7.54-7.42 (3H, m), 7.39-7.33 (1H, m), 3.03-2.93 (5H, m), 1.32 (3H, t)

Reference Production Example 9

To a mixture of 5-iodo-3-nitropyridin-2-ylamine (1.0 g) and DMF (20 ml), 60% of sodium hydride (in oil, 180 mg) and methyl iodide (240 μl) were sequentially added under ice-cooling. The mixture was heated to room temperature, and stirred for 1 hour. Into the reaction mixture, water was poured, and then the precipitated solid was collected by filtration, and dried.

The obtained solid was dissolved in THF. The solution was added dropwise to a mixture of iron powder (633 mg), acetic acid (1 ml), ethanol (30 ml), and water (20 ml) with heating at 70° C. The mixture was stirred with heating at 70° C. for 3.5 hours. The reaction mixture cooled to room temperature was filtered through Celite®. The resulting filtrate was concentrated under reduced pressure. The resulting residue was subjected to silica gel column chromatography to give 980 mg of 5-iodo-$N^2$-methylpyridin-2,3-diamine (Compound (1F)-6).

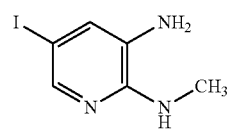

Reference Production Example 10-a

To a mixture of 5-trifluoromethylpyridin-2,3-diamine (1.2 g) and pyridine (20 ml), methyl chloroformate (0.63 ml) was added under ice-cooling. The mixture was heated to room temperature, stirred for 8 hours, and concentrated under reduced pressure. The resulting residue was subjected to silica gel column chromatography to give 628 mg of methyl (2-amino-5-trifluoromethylpyridin-3-yl)-carbamate.

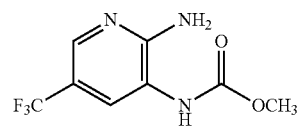 [SMILES: COC(=O)Nc1cc(C(F)(F)F)cnc1N]

$^1$H-NMR (CDCl$_3$) δ: 8.65 (1H, brs), 8.18-7.99 (2H, m), 5.75 (2H, brs), 3.79 (3H, s)

Reference Production Example 10-b

To a mixture of methyl (2-amino-5-trifluoromethylpyridin-3-yl)-carbamate (100 mg) and THF (15 ml), lithium aluminum hydride (26 mg) was added under ice-cooling. The mixture was stirred for 15 minutes under ice-cooling, heated to 90° C., and stirred with heating for 1.5 hours. Into the reaction mixture cooled to room temperature, aqueous sodium hydroxide solution was poured, and extracted with tert-butyl methyl ether. The organic layer was dried over sodium sulfate, and concentrated under reduced pressure. The resulting residue was subjected to silica gel column chromatography to give 77 mg of $N^3$-methyl-5-trifluoromethylpyridin-2,3-diamine.

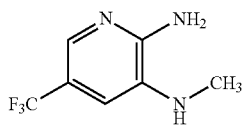

Reference Production Example 11-a

To a mixture of methyl-(2-nitro-4-trifluoromethylphenyl)-amine (4.40 g) and DMF (20 ml), N-chlorosuccinimide (3.67 g) was added under ice-cooling, and stirred for 3 hours. The mixture was heated to room temperature, and allowed to stand. Water was poured thereinto under ice-cooling, and then the precipitated solid was collected by filtration. The obtained solid was washed with water, and dried to give 3.96 g of (2-chloro-6-nitro-4-trifluoromethylphenyl)-methylamine.

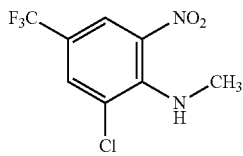 [SMILES: CNc1c(Cl)cc(C(F)(F)F)cc1[N+](=O)[O-]]

$^1$H-NMR (CDCl$_3$) δ: 8.19 (1H, d), 7.68 (1H, d), 7.17 (1H, brs), 3.19 (3H, d)

Reference Production Example 11-b

To a mixture of (2-chloro-6-nitro-4-trifluoromethylphenyl)-methylamine (3.70 g) and ethanol (60 ml), Raney® nickel (slurry in water, 0.5 ml) was added, and stirred under about 1 atm of hydrogen at room temperature for 1.5 hours. The reaction mixture was filtered. The filtrate was concentrated under reduced pressure. The resulting residue was subjected to silica gel column chromatography to give 2.95 g of 3-chloro-$N^2$-methyl-5-trifluoromethylbenzene-1,2-diamine.

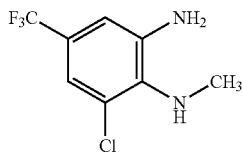

$^1$H-NMR (CDCl$_3$) δ: 7.02 (1H, d), 6.82 (1H, d), 4.09 (2H, brs), 3.49 (1H, brs), 2.74 (3H, d)

Reference Production Example 12

A mixture of 2-amino-4-trifluoromethylphenol (1.00 g), 2-methylsulfanylbenzoic acid (0.95 g), WSC (1.41 g), and pyridine (10 ml) was stirred with heating at 80° C. for 2.5 hours. Into the reaction mixture cooled to room temperature, 1 mol/l of hydrochloric acid was poured, and extracted with ethyl acetate. The organic layer was washed with saturated aqueous sodium hydrogen carbonate solution, water, and saturated brine, sequentially, dried over sodium sulfate, and concentrated under reduced pressure. The resulting residue was subjected to silica gel column chromatography to give 0.33 g of N-(2-hydroxy-5-trifluoromethylphenyl)-2-methylsulfanyl-benzamide (Compound (1B)-515).

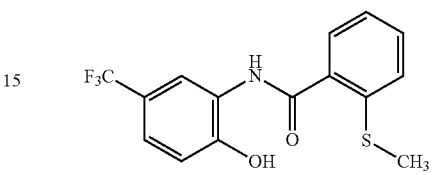

$^1$H-NMR (DMSO-D$_6$) δ: 9.50 (1H, brs), 8.24 (1H, s), 7.61 (1H, d), 7.50 (1H, t), 7.42 (1H, d), 7.37 (1H, dd), 7.27 (1H, t), 7.06 (1H, d), 2.45 (3H, s)

Reference Production Example 13

To a mixture of 3-amino-5-trifluoromethylpyridin-2-ol (0.75 g) and THF (5 ml), 2-ethylsulfanylbenzoic acid hydrochloride (0.93 g) was added under ice-cooling, heated to room temperature, and stirred for 2 hours. After the mixture was allowed to stand overnight, the mixture was heated to 50° C., and stirred with heating for 6 hours. To the mixture, sodium hydrogen carbonate (0.35 g) was added, and stirred with heating for further 2.5 hours. After the mixture was allowed to stand, water was poured thereinto, and the precipitated solid was collected by filtration. The obtained solid was washed with water, and dried to give 1.37 g of 2-ethylsulfanyl-N-(2-hydroxy-5-trifluoromethylpyridin-3-yl)-benzamide (Compound (1B)-506).

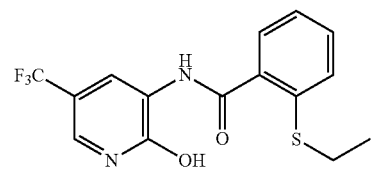 [SMILES: CCSc1ccccc1C(=O)Nc1cc(C(F)(F)F)cnc1O]

$^1$H-NMR (CDCl$_3$) δ: 11.68 (1H, brs), 9.35 (1H, brs), 8.87 (1H, d), 7.75-7.71 (1H, m), 7.49-7.43 (3H, m), 7.33-7.29 (1H, m), 2.99 (2H, q), 1.34 (3H, t)

Reference Production Example 14

To a mixture of 3-chloroanthranilic acid (3.43 g) and 1 mol/l of hydrochloric acid (20 ml), sodium nitrite (1.38 g) was added portionwise at room temperature, and stirred for 10 minutes. The reaction mixture was added dropwise to a mixture of potassium butylxanthogenate (5.65 g) and water (20 ml) at room temperature, and stirred for 1 hour. 3N aqueous sodium hydroxide solution (20 ml) and diethylsulfuric acid (2.9 ml) were added thereto, heated to 100° C., and stirred under reflux for 1 hour. To the reaction mixture cooled to room temperature, 12 mol/l of hydrochloric acid was added dropwise under ice-cooling until the reaction mixture reached pH 1-2. The precipitated solid was collected by filtration, and dried under reduced pressure.

To the obtained solid, 3N aqueous sodium hydroxide solution (10 ml), ethanol (10 ml), and ethyl iodide (6.86 g) were added, heated to 80° C., and stirred under reflux for 2 hours. To the reaction mixture cooled to room temperature, 12 mol/l of hydrochloric acid was added dropwise under ice-cooling until the reaction mixture reached pH 1-2, and extracted with ethyl acetate. The organic layer was dried over sodium sulfate, and concentrated under reduced pressure. The resulting residue was subjected to silica gel column chromatography to give 2.79 g of 3-chloro-2-ethylsulfanylbenzoic acid.

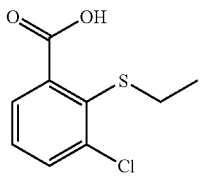

$^1$H-NMR (CDCl$_3$) δ: 8.10-8.05 (1H, m), 7.68 (1H, dd), 7.43 (1H, t), 3.00 (2H, q), 1.26 (3H, t)

Reference Production Example 15

To a pressure-resistant reaction container, 3-amino-2-chloro-5-trifluoromethylpyridine (5 g), copper (II) acetylacetone (1.31 g), acetylacetone (2.50 g), cesium carbonate (16.25 g), NMP (20 ml), and 40% of aqueous methylamine solution (15 ml) were added, and stirred at 100° C. for 3 hours, at 120° C. for 3 hours, then at 140° C. for 5 hours. After the mixture was allowed to cool to room temperature, saturated aqueous ammonium chloride solution was poured thereinto, and extracted with ethyl acetate. The organic layer was dried over sodium sulfate, and concentrated under reduced pressure. The resulting residue was subjected to silica gel column chromatography to give 2.09 g of N$^2$-methyl-6-trifluoromethylpyridin-2,3-diamine.

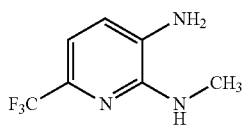

$^1$H-NMR (CDCl$_3$) δ: 3.04 (3H, s), 3.41 (2H, brs), 4.22 (1H, brs), 6.84 (1H, d), 6.91 (1H, d).

Reference Production Example 16-a

To a mixture of 3-amino-2-chloro-6-trifluoromethylpyridine (3.93 g) and chloroform (30 ml), pivaloyl chloride (2.65 g) and triethylamine (4.04 g) were added under ice-cooling, and stirred at room temperature for 2 hours, then at 60° C. for 2 hours. Into the reaction mixture cooled to room temperature, water was poured, and extracted with ethyl acetate. The organic layer was dried over sodium sulfate, and concentrated under reduced pressure. The resulting residue was subjected to silica gel column chromatography to give 6.59 g of N-(2-chloro-6-trifluoromethylpyridin-3-yl)-2,2-dimethylpropionamide.

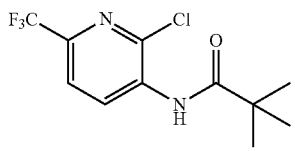 [SMILES: CC(C)(C)C(=O)Nc1ccc(C(F)(F)F)nc1Cl]

$^1$H-NMR (CDCl$_3$) δ: 1.36 (9H, s), 7.65 (1H, d), 8.17 (1H, brs), 8.97 (1H, d).

Reference Production Example 16-b

To a mixture of N-(2-chloro-6-trifluoromethylpyridin-3-yl)-2,2-dimethylpropionamide (6.59 g) and THF (30 ml), sodium hydride (60% in oily, 1 g) was added under ice-cooling, and stirred at room temperature for 30 minutes. The reaction mixture was ice-cooled, and then methyl iodide (10 g) was added, and stirred at room temperature for 4 hours. Into the reaction mixture, water was poured, and extracted with ethyl acetate. The organic layer was dried over sodium sulfate, and concentrated under reduced pressure. To the resulting residue, acetonitrile (40 ml), concentrated hydrochloric acid (40 ml), and isopropanol (40 ml) were added, and stirred at room temperature for 2 hours, at 60° C. for 2 hours, then at 80° C. for 2 hours. Into the reaction mixture cooled to room temperature, saturated aqueous sodium hydrogen carbonate solution was poured, and extracted with ethyl acetate. The organic layer was dried over sodium sulfate, and concentrated under reduced pressure. The resulting residue was subjected to silica gel column chromatography to give 2.60 g of (2-chloro-6-trifluoromethylpyridin-3-yl)-methylamine.

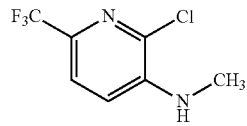

$^1$H-NMR (CDCl$_3$) δ: 7.49 (1H, d), 6.89 (1H, d), 4.82 (1H, brs), 2.96 (3H, d).

Reference Production Example 16-c

To a pressure-resistant reaction container, (2-chloro-6-trifluoromethylpyridin-3-yl)-methylamine (2.60 g), copper (II) acetylacetone (0.64 g), acetylacetone (1.23 g), cesium carbonate (7.99 g), NMP (10 ml), and 28% of aqueous ammonia (7 ml) were added, and stirred at 140° C. for 8 hours. After the mixture was allowed to cool to room temperature, saturated aqueous ammonium chloride solution was poured thereinto, and extracted with ethyl acetate. The organic layer was dried over sodium sulfate, and concentrated under reduced pressure. The resulting residue was subjected to silica gel column chromatography to give 2.09 g of N$^3$-methyl-6-trifluoromethylpyridin-2,3-diamine.

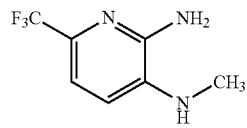

$^1$H-NMR (CDCl$_3$) δ: 2.89 (3H, d), 3.56 (1H, brs), 4.29 (2H, brs), 6.77 (1H, d), 7.13 (1H, d).

Reference Production Example 17

A mixture of 3-amino-5-(trifluoromethyl)pyridin-2-thiol (0.20 g), 2-ethylsulfanylbenzaldehyde (0.20 g), sodium hydrogen sulfite (0.13 g), copper (II) chloride (0.41 g), and DMF (2.5 ml) was stirred at 120° C. for 8 hours. After the reaction mixture was allowed to cool, water was added thereto, and ethyl acetate was poured. The mixture was filtered, and the resulting filtrate was extracted with ethyl acetate. The organic layer was washed with water, dried over anhydrous magnesium sulfate, and concentrated under reduced pressure. The residue was subjected to silica gel column chromatography to give 0.18 g of 2-[2-fluoro-4-(trifluoromethyl)phenyl]-6-(trifluoromethyl)thiazolo[5,4-b]pyridine ((1E)-F57).

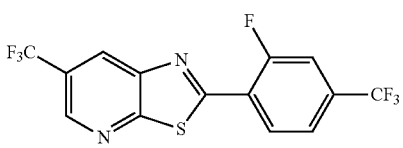 [SMILES: Fc1cc(C(F)(F)F)ccc1-c1nc2cc(C(F)(F)F)cnc2s1]

¹H-NMR (CDCl₃) δ: 7.58 (1H, d), 7.64 (1H, d), 8.57-8.63 (2H, m), 8.92 (1H, s).

Reference Production Example 18

A mixture of N²-methyl-5-trifluoromethylpyridin-2,3-diamine (5.37 g), 2-fluoro-4-trifluorobenzaldehyde (6.92 g), sodium hydrogen sulfite (3.75 g), and DMF (30 ml) was stirred at 150° C. for 3 hours. Into the reaction mixture cooled to room temperature, water was poured, and extracted with ethyl acetate. The organic layer was dried over magnesium sulfate, and concentrated under reduced pressure. The resulting residue was subjected to silica gel column chromatography to give 7.83 g of 2-(2-fluoro-4-trifluoromethylphenyl)-3-methyl-6-trifluoromethyl-3H-imidazo[4,5-b]pyridine ((1E)-F6).

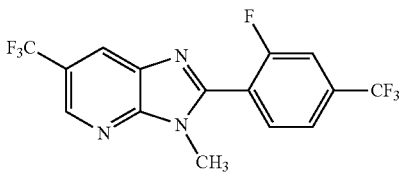

¹H-NMR (CDCl₃) δ: 8.75 (1H, d), 8.35 (1H, d), 7.91 (1H, t), 7.67 (1H, d), 7.59 (1H, d), 3.92 (3H, d).

Reference Production Example 19-a

To a mixture of 2-chloro-5-iodppyridine (7.2 g), NMP (75 mL), and xylene (75 mL), pentafluorosodium propionate (28 g) and copper iodide (14 g) were added at room temperature, heated to 150° C., and stirred with heating for 5.5 hours. After the mixture was cooled to 80° C., to the mixture, 40% of aqueous methylamine solution (180 mL) was added in parts 4 every 2 hours, and stirred with heating for 8.5 hours. The mixture was ice-cooled to 0° C., and then 28% of aqueous ammonia and saturated aqueous sodium hydrogen carbonate solution were poured thereinto, and extracted with MTBE. The combined organic layer was dried over sodium sulfate, and concentrated under reduced pressure. The residue was subjected to silica gel column chromatography to give 4.6 g of methyl-(5-pentafluoroethyl-pyridine-2-yl)-amine.

methyl-(5-pentafluoroethyl-pyridine-2-yl)-amine

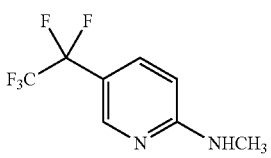

¹H-NMR (CDCl₃) δ: 8.28 (1H, d), 7.56 (1H, dd), 6.41 (1H, d), 5.74 (1H, brs), 2.95 (3H, d).

Reference Production Example 19-b

To a mixture of methyl-(5-pentafluoroethyl-pyridine-2-yl)-amine (4.6 g) and acetonitrile (70 mL), N-bromosuccinimide (5.0 g) was added under ice-cooling, and stirred at room temperature for 8 hours. Into a mixture, saturated aqueous sodium thiosulfate solution and aqueous sodium hydrogen carbonate solution were poured, and extracted with ethyl acetate. The combined organic layer was dried over sodium sulfate, and concentrated under reduced pressure. The residue was subjected to silica gel column chromatography to give 6.3 g of (3-bromo-5-pentafluoroethyl-pyridine-2-yl)-methylamine.

(3-bromo-5-pentafluoroethyl-pyridine-2-yl)-methylamine

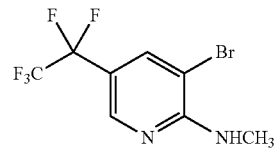 [SMILES: CNc1ncc(C(F)(F)C(F)(F)F)cc1Br]

¹H-NMR (CDCl₃) δ: 8.29 (1H, d), 7.74 (1H, d), 5.45 (1H, brs), 3.09 (3H, d).

Reference Production Example 19-c

To an autoclave reactor, (3-bromo-5-pentafluoroethyl-pyridine-2-yl)-methyl-amine (2.0 g), acetylacetone copper(II) (86 mg), acetylacetone (263 mg), cesium carbonate (3.2 g), and NMP (13 mL) were added, and then 28% of aqueous ammonia (5 mL) was added under ice-cooling. After the reactor was sealed, the mixture was heated to 110° C., and stirred with heating for 15 hours. After the mixture was cooled to room temperature, the reaction mixture was diluted with water, and extracted with MTBE. The combined organic layer was dried over sodium sulfate, and concentrated under reduced pressure. The residue was subjected to silica gel column chromatography to give 623 mg of N²-methyl-5-pentafluoroethyl-2,3-diamine (Compound (1F)-2).

N²-methyl-5-pentafluoroethyl-2,3-diamine

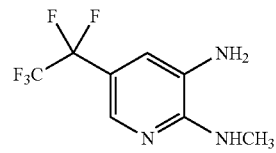 [SMILES: CNc1ncc(C(F)(F)C(F)(F)F)cc1N]

¹H-NMR (CDCl₃) δ: 7.99 (1H, d), 6.94 (1H, d), 4.64 (1H, brs), 3.30 (2H, brs), 3.06 (3H, d).

Reference Production Example 20-a

A mixture of 2-chloro-5-iodppyridine (23.9 g), thiobenzoic acid (14 ml), copper iodide (1.90 g), 1,10-phenanthroline (3.60 g), diisopropylethylamine (35 ml), and toluene (200 ml) was stirred at 110° C. for 4 hours. After the reaction mixture was cooled to room temperature, water was poured thereinto. The insoluble material was filtered through Celite®, and then the filtered material was washed with ethyl acetate, and the filtrate was extracted with ethyl acetate. The combined organic layer was dried over magnesium sulfate, and concentrated under reduced pressure. The resulting residue was subjected to silica gel column chromatography to give 21.2 g of S-(6-chloropyridine-3-yl)thiobenzoate.

S-(6-chloropyridine-3-yl)thiobenzoate

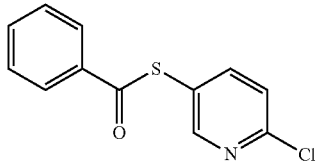 [SMILES: O=C(Sc1ccc(Cl)nc1)c1ccccc1]

$^1$H-NMR (CDCl$_3$) δ: 8.43-8.42 (1H, m), 8.01-7.98 (2H, m), 7.79-7.76 (1H, m), 7.66-7.61 (1H, m), 7.52-7.47 (2H, m), 7.44-7.41 (1H, m).

Reference Production Example 20-b

A mixture of S-(6-chloropyridine-3-yl)thiobenzoate (21.2 g), potassium carbonate (17.6 g), and methanol (170 ml) was stirred at room temperature for 2 hours. The reaction mixture was filtered, and then the filtered material was washed with methanol, and filtrate was concentrated under reduced pressure. To the resulting crude, 1N aqueous sodium hydroxide solution (170 ml) was added, and then an aqueous solution of potassium ferricyanide (56.0 g) was added dropwise, and stirred at room temperature for 2 hours. The reaction mixture was extracted with methyl-tert-butyl ether. The combined organic layer was dried over magnesium sulfate, and concentrated under reduced pressure. The residue was subjected to silica gel column chromatography to give 11.5 g of a compound of the following formula:

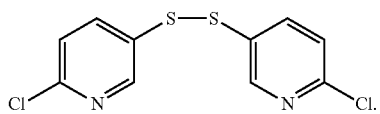 [SMILES: Clc1ccc(SSc2ccc(Cl)nc2)cn1]

$^1$H-NMR (CDCl$_3$) δ: 8.41 (2H, d), 7.74 (2H, dd), 7.29 (2H, d).

Reference Production Example 20-c

A mixture of a compound (11.5 g) of the following formula:

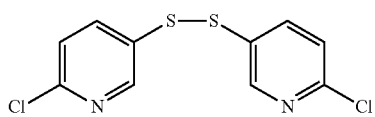 [SMILES: Clc1ccc(SSc2ccc(Cl)nc2)cn1]

and
DMF (133 ml) was cooled to −50° C., and bubbled with excessive amounts of CF$_3$I gas to dissolve the compound in DMF. To the mixture, tetrakis(dimethylamino)ethylenediamine (37.0 ml) was added dropwise at a rate that the internal temperature did not exceed −40° C. Then, the mixture was heated to −10° C. over 1 hour, and stirred at −10° C. for 2 hour. Into the reaction mixture, water was poured, heated to room temperature, and extracted with ethyl acetate. The combined organic layer was dried over magnesium sulfate, and concentrated under reduced pressure. The resulting residue was subjected to silica gel column chromatography to give 7.25 g of 2-chloro-5-trifluoromethylsulfanylpyridine.

2-chloro-5-trifluoromethylsulfanylpyridine

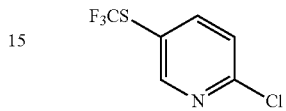

$^1$H-NMR (CDCl$_3$) δ: 8.62 (1H, d), 7.93 (1H, dd), 7.43 (1H, d).

Reference Production Example 20-d

To a mixture of 2-chloro-5-trifluoromethylsulfanylpyridine (1.71 g) and NMP (16 ml), 40% of aqueous methylamine solution (1.86 g) was added dropwise, and then the mixture was heated to 60° C., and stirred with heating for 2 hours. After the mixture was cooled to room temperature, potassium carbonate (1.66 g) was added thereto, and 40% of aqueous methylamine solution (1.86 g) was added dropwise. The mixture was heated to 60° C., and stirred with heating for further 2 hours. After the mixture was cooled to room temperature, water was poured, and extracted with ethyl acetate. The combined organic layer was dried over magnesium sulfate, and concentrated under reduced pressure. The resulting residue was subjected to silica gel column chromatography to give 1.52 g of methyl-(5-trifluoromethylsulfanylpyridine-2-yl)-amine.

methyl-(5-trifluoromethylsulfanylpyridine-2-yl)-amine

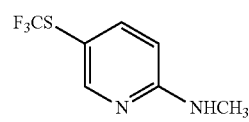

$^1$H-NMR (CDCl$_3$) δ: 8.28 (1H, d), 7.63 (1H, dd), 6.41-6.38 (1H, m), 4.90 (1H, brs), 2.96 (3H, d,).

Reference Production Example 20-e

To a mixture of methyl-(5-trifluoromethylsulfanylpyridine-2-yl)-amine (1.52 g) and chloroform (24 mL), N-bromosuccinimide (1.43 g) was added, and stirred at room temperature for 1 hour. Into the reaction mixture, water was poured, and extracted with chloroform. The combined organic layer was dried over sodium sulfate, and concentrated under reduced pressure. The resulting residue was subjected to silica gel column chromatography to give 1.96 g of (3-bromo-5-trifluoromethylsulfanylpyridine-2-yl)-methylamine.

(3-bromo-5-trifluoromethylsulfanylpyridine-2-yl)-methylamine

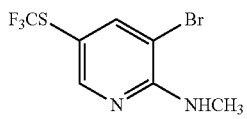

$^1$H-NMR (CDCl$_3$) δ: 8.28 (1H, d), 7.83 (1H, d), 5.40 (1H, brs), 3.07 (3H, d).

Reference Production Example 20-f

To a pressure-resistant reaction container, (3-bromo-5-trifluoromethylsulfanylpyridine-2-yl)-methylamine (1.96 g), acetylacetone copper (II) (89 mg), acetylacetone (0.27 g), cesium carbonate (2.34 g), and NMP (7 ml), 28% of aqueous ammonia (5 ml) was added, and stirred at 110° C. for 8.5 hours. After the mixture was cooled to room temperature, into the reaction mixture, water was poured. The insoluble material was filtered through Celite®, and then the filtered material was washed with ethyl acetate, and filtrate was extracted with ethyl acetate. The combined organic layer was dried over sodium sulfate, and concentrated under reduced pressure. The resulting residue was subjected to silica gel column chromatography to give 1.18 g of N$^2$-methyl-5-trifluoromethylsulfanylpyridine-2,3-diamine (Compound (1F)-3).

N$^2$-methyl-5-trifluoromethylsulfanylpyridine-2,3-diamine

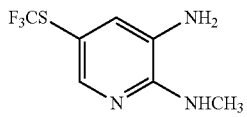

$^1$H-NMR (CDCl$_3$) δ: 8.01-7.99 (1H, m), 7.07-7.05 (1H, m), 4.60 (1H, brs), 3.22 (2H, brs), 3.05 (3H, d).

Reference Production Example 21-a

To a mixture of 2-ethylsulfanylbenzoic acid (9.11 g), chloroform (100 ml), and oxalyl chloride (9.72 g), DMF (2 drops) was added, and stirred at room temperature for 6 hours. The reaction mixture was concentrated under reduced pressure to give 10.03 g of 2-ethylsulfanylbenzoic acid chloride (Compound (1H)-241).

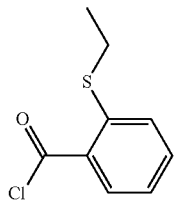

$^1$H-NMR (CDCl$_3$) δ: 8.31 (1H, dd), 7.57-7.50 (1H, m), 7.42-7.32 (1H, m), 7.28-7.21 (1H, m), 3.00 (2H, q), 1.41 (3H, t).

Reference Production Example 21-b

To a mixture of N$^2$-methyl-5-trifluoromethylpyridine-2,3-diamine (3.82 g) and THF (40 ml), 2-ethylsulfanylbenzoic acid chloride (4.42 g) was added, stirred at 50° C. for 2 hours, then stirred under reflux for hours. After the mixture was allowed to cool to room temperature, sodium hydrogen carbonate (1.85 g) was added thereto, and stirred at 50° C. for 2 hours. After the mixture was allowed to cool to room temperature, water was poured thereinto, and then the precipitated solid was collected by the filtration. The resulting solid was washed with water and hexane, and dried to give 7.15 g of N-(2-methylamino-5-trifluoromethylpyridine-3-yl)-2-ethylsulfanyl-benzamide (Compound ((1B)-19).

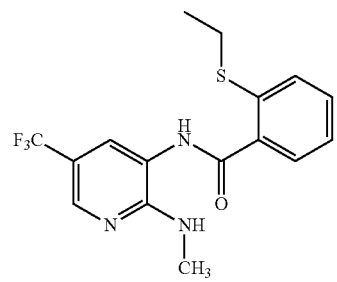 [SMILES: CCSc1ccccc1C(=O)Nc1cc(C(F)(F)F)cnc1NC]

$^1$H-NMR (CDCl$_3$) δ: 8.36 (1H, S), 8.26 (1H, S), 7.85 (1H, d), 7.76 (1H, S), 7.53 (1H, d), 7.47 (1H, t), 7.39 (1H, t), 5.55 (1H, brs), 3.08 (3H, d), 3.01 (2H, q), 1.32 (3H, t).

The above intermediate, Compounds (1B)-(1E) are shown in the following tables.

A compound of the formula (1B):

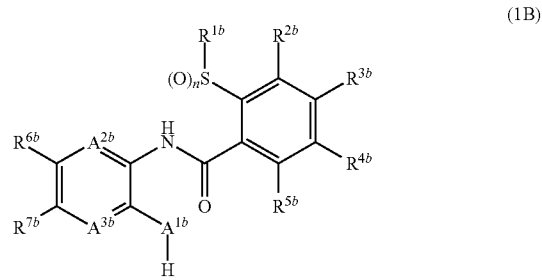

(1B)

wherein, A$^{2b}$ represents =CH—, R$^{2b}$, R$^{4b}$, R$^{5b}$, R$^{7b}$ represents a hydrogen atom, and R$^{1b}$, R$^{3b}$, R$^{6b}$, A$^{1b}$, A$^{3b}$, and n represent a combination of R$^{1x}$, R$^{3x}$, R$^{6x}$, A$^{1x}$, A$^{3x}$, and n, respectively, shown in Tables 38-58 (Compounds ((1B)-1)-((1B)-504)).

A compound of the formula (1C):

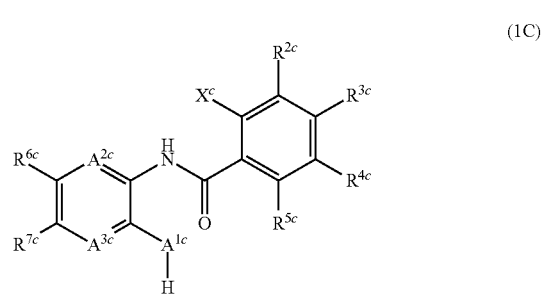

(1C)

wherein, X$^C$ represents a fluorine atom, A$^{2C}$ represents =CH—, R$^{2C}$, R$^{4C}$, R$^{5C}$, R$^{7C}$ represents a hydrogen atom, and $R^{3C}$, $R^{6C}$, $A^{1C}$, and $A^{3C}$ represent a combination of $R^{3x}$, $R^{6x}$, $A^{1x}$, and $A^{3x}$, respectively, shown in Tables 38-52 (Compound (1C)-F1 to Compound (1C)-F9, Compound (1C)-F37 to Compound (1C)-F45, Compound (1C)-F55 to Compound (1C)-F63, Compound (1C)-F73 to Compound (1C)-F81, Compound (1C)-F109 to Compound (1C)-F117, Compound (1C)-F127 to Compound (1C)-F135, Compound (1C)-F145 to Compound (1C)-F153, Compound (1C)-F181 to Compound (1C)-F189, Compound (1C)-F199 to Compound (1C)-F207, Compound (1C)-F217 to Compound (1C)-F225, Compound (1C)-F253 to Compound (1C)-F261, Compound (1C)-F271 to Compound (1C)-F279, Compound (1C)-F289 to Compound (1C)-F297, Compound (1C)-F325 to Compound (1C)-F333, and Compound (1C)-F343 to Compound (1C)-F351).

A compound of the formula (1C) wherein $X^C$ is a chlorine atom, $A^{2C}$ is =CH—, $R^{2C}$, $R^{4C}$, $R^{5C}$, $R^{7C}$ is a hydrogen atom, $R^{3C}$, $R^{6C}$, $A^{1C}$ and $A^{3C}$, represent a combination of $R^{3x}$, $R^{6x}$, $A^{1x}$ and $A^{3x}$, respectively, shown in Tables 38-52 (Compound (1C)-C1 to Compound (1C)-C9, Compound (1C)-C37 to Compound (1C)-C45, Compound (1C)-C55 to Compound (1C)-C63, Compound (1C)-C73 to Compound (1C)-C81, Compound (1C)-C109 to Compound (1C)-C117, Compound (1C)-C127 to Compound (1C)-C135, Compound (1C)-C145 to Compound (1C)-C153, Compound (1C)-C181 to Compound (1C)-C189, Compound (1C)-C199 to Compound (1C)-C207, Compound (1C)-C217 to Compound (1C)-C225, Compound (1C)-C253 to Compound (1C)-C261, Compound (1C)-C271 to Compound (1C)-C279, Compound (1C)-C289 to Compound (1C)-C297, Compound (1C)-C325 to Compound (1C)-C333, and Compound (1C)-C343 to Compound (1C)-C351).

A compound of the formula (1D):

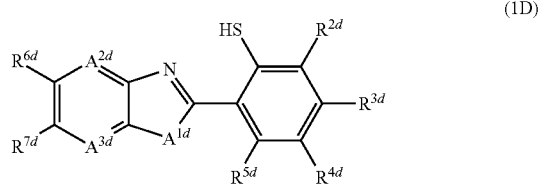

(1D)

wherein, $A^{2d}$ represents =CH—, $R^{2d}$, $R^{4d}$, $R^{5d}$, $R^{7d}$ represents a hydrogen atom, and $R^{3d}$, $R^{6d}$, $A^{1d}$ and $A^{3d}$, represent a combination of $R^{3x}$, $R^{6x}$, $A^{1x}$ and $A^{3x}$, respectively, shown in Tables 38-58 (Compound (1D)-1 to Compound (1D)-9, Compound (1D)-37 to Compound (1D)-45, Compound (1D)-55 to Compound (1D)-63, Compound (1D)-73 to Compound (1D)-81, Compound (1D)-109 to Compound (1D)-117, Compound (1D)-127 to Compound (1D)-135, Compound (1D)-145 to Compound (1D)-153, Compound (1D)-181 to Compound (1D)-189, Compound (1D)-199 to Compound (1D)-207, Compound (1D)-217 to Compound (1D)-225, Compound (1D)-253 to Compound (1D)-261, Compound (1D)-271 to Compound (1D)-279, Compound (1D)-289 to Compound (1D)-297, Compound (1D)-325 to Compound (1D)-333, Compound (1D)-343 to Compound (1D)-351, Compound (1D)-361 to Compound (1D)-369, Compound (1D)-397 to Compound (1D)-405, Compound (1D)-415 to Compound (1D)-423, Compound (1D)-433 to Compound (1D)-441, Compound (1D)-469 to Compound (1D)-477, and Compound (1D)-487 to Compound (1D)-495).

A compound of the formula (1E):

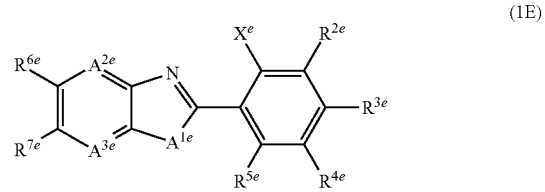

(1E)

wherein, $X^e$ represents a fluorine atom, $A^{2e}$ represents =CH—, $R^{2e}$, $R^{4e}$, $R^{5e}$, $R^{7e}$ represents a hydrogen atom, $R^{3e}$, $R^{6e}$, $A^{1e}$, and $A^{3e}$ represent a combination of $R^{3x}$, $R^{6x}$, and $A^{3x}$, respectively, shown in Tables 38-52 (Compound (1E)-F1 to Compound (1E)-F9, Compound (1E)-F37 to Compound (1E)-F45, Compound (1E)-F55 to Compound (1E)-F63, Compound (1E)-F73 to Compound (1E)-F81, Compound (1E)-F109 to Compound (1E)-F117, Compound (1E)-F127 to Compound (1E)-F135, Compound (1E)-F145 to Compound (1E)-F153, Compound (1E)-F181 to Compound (1E)-F189, Compound (1E)-F199 to Compound (1E)-F207, Compound (1E)-F217 to Compound (1E)-F225, Compound (1E)-F253 to Compound (1E)-F261, Compound (1E)-F271 to Compound (1E)-F279, Compound (1E)-F289 to Compound (1E)-F297, Compound (1E)-F325 to Compound (1E)-F333, and Compound (1E)-F343 to Compound (1E)-F351).

A compound of the formula (1E) wherein, $X^e$ represents a chlorine atom, $A^{2e}$ represents =CH—, $R^{2e}$, $R^{4e}$, $R^{5e}$, $R^{7e}$ represents a hydrogen atom, $R^{3e}$, $R^{6e}$, $A^{1e}$, and $A^{3e}$ represent a combination of $R^{3x}$, $R^{6x}$, $A^{1x}$, and $A^{3x}$, respectively, shown in Tables 38-52 (Compound (1E)-C1 to Compound (1E)-C9, Compound (1E)-C37 to Compound (1E)-C45, Compound (1E)-C55 to Compound (1E)-C63, Compound (1E)-C73 to Compound (1E)-C81, Compound (1E)-C109 to Compound (1E)-C117, Compound (1E)-C127 to Compound (1E)-C135, Compound (1E)-C145 to Compound (1E)-C153, Compound (1E)-C181 to Compound (1E)-C189, Compound (1E)-C199 to Compound (1E)-C207, Compound (1E)-C217 to Compound (1E)-C225, Compound (1E)-C253 to Compound (1E)-C261, Compound (1E)-C271 to Compound (1E)-C279, Compound (1E)-C289 to Compound (1E)-C297, Compound (1E)-C325 to Compound (1E)-C333, and Compound (1E)-C343 to Compound (1E)-C351).

TABLE 38

| Intermediate | $R^{1x}$ | $R^{3x}$ | $R^{6x}$ | $A^{1x}$ | $A^{3x}$ | n |
|---|---|---|---|---|---|---|
| 1 | Me | H | $CF_3$ | NMe | N | 0 |
| 2 | Me | F | $CF_3$ | NMe | N | 0 |
| 3 | Me | Cl | $CF_3$ | NMe | N | 0 |
| 4 | Me | Br | $CF_3$ | NMe | N | 0 |
| 5 | Me | Me | $CF_3$ | NMe | N | 0 |
| 6 | Me | $CF_3$ | $CF_3$ | NMe | N | 0 |
| 7 | Me | $OCF_3$ | $CF_3$ | NMe | N | 0 |
| 8 | Me | $C_2F_5$ | $CF_3$ | NMe | N | 0 |
| 9 | Me | $SF_5$ | $CF_3$ | NMe | N | 0 |
| 10 | Me | H | $CF_3$ | NMe | N | 2 |
| 11 | Me | F | $CF_3$ | NMe | N | 2 |
| 12 | Me | Cl | $CF_3$ | NMe | N | 2 |
| 13 | Me | Br | $CF_3$ | NMe | N | 2 |
| 14 | Me | Me | $CF_3$ | NMe | N | 2 |
| 15 | Me | $CF_3$ | $CF_3$ | NMe | N | 2 |
| 16 | Me | $OCF_3$ | $CF_3$ | NMe | N | 2 |
| 17 | Me | $C_2F_5$ | $CF_3$ | NMe | N | 2 |
| 18 | Me | $SF_5$ | $CF_3$ | NMe | N | 2 |
| 19 | Et | H | $CF_3$ | NMe | N | 0 |
| 20 | Et | F | $CF_3$ | NMe | N | 0 |
| 21 | Et | Cl | $CF_3$ | NMe | N | 0 |

TABLE 38-continued

| Intermediate | $R^{1x}$ | $R^{3x}$ | $R^{6x}$ | $A^{1x}$ | $A^{3x}$ | n |
|---|---|---|---|---|---|---|
| 22 | Et | Br | $CF_3$ | NMe | N | 0 |
| 23 | Et | Me | $CF_3$ | NMe | N | 0 |
| 24 | Et | $CF_3$ | $CF_3$ | NMe | N | 0 |
| 25 | Et | $OCF_3$ | $CF_3$ | NMe | N | 0 |

TABLE 39

| Intermediate | $R^{1x}$ | $R^{3x}$ | $R^{6x}$ | $A^{1x}$ | $A^{3x}$ | n |
|---|---|---|---|---|---|---|
| 26 | Et | $C_2F_5$ | $CF_3$ | NMe | N | 0 |
| 27 | Et | $SF_5$ | $CF_3$ | NMe | N | 0 |
| 28 | Et | H | $CF_3$ | NMe | N | 2 |
| 29 | Et | F | $CF_3$ | NMe | N | 2 |
| 30 | Et | Cl | $CF_3$ | NMe | N | 2 |
| 31 | Et | Br | $CF_3$ | NMe | N | 2 |
| 32 | Et | Me | $CF_3$ | NMe | N | 2 |
| 33 | Et | $CF_3$ | $CF_3$ | NMe | N | 2 |
| 34 | Et | $OCF_3$ | $CF_3$ | NMe | N | 2 |
| 35 | Et | $C_2F_5$ | $CF_3$ | NMe | N | 2 |
| 36 | Et | $SF_5$ | $CF_3$ | NMe | N | 2 |
| 37 | Et | H | $CF_3$ | NMe | CH | 0 |
| 38 | Et | F | $CF_3$ | NMe | CH | 0 |
| 39 | Et | Cl | $CF_3$ | NMe | CH | 0 |
| 40 | Et | Br | $CF_3$ | NMe | CH | 0 |
| 41 | Et | Me | $CF_3$ | NMe | CH | 0 |
| 42 | Et | $CF_3$ | $CF_3$ | NMe | CH | 0 |
| 43 | Et | $OCF_3$ | $CF_3$ | NMe | CH | 0 |
| 44 | Et | $C_2F_5$ | $CF_3$ | NMe | CH | 0 |
| 45 | Et | $SF_5$ | $CF_3$ | NMe | CH | 0 |
| 46 | Et | H | $CF_3$ | NMe | CH | 2 |
| 47 | Et | F | $CF_3$ | NMe | CH | 2 |
| 48 | Et | Cl | $CF_3$ | NMe | CH | 2 |
| 49 | Et | Br | $CF_3$ | NMe | CH | 2 |
| 50 | Et | Me | $CF_3$ | NMe | CH | 2 |

TABLE 40

| Intermediate | $R^{1x}$ | $R^{3x}$ | $R^{6x}$ | $A^{1x}$ | $A^{3x}$ | n |
|---|---|---|---|---|---|---|
| 51 | Et | $CF_3$ | $CF_3$ | NMe | CH | 2 |
| 52 | Et | $OCF_3$ | $CF_3$ | NMe | CH | 2 |
| 53 | Et | $C_2F_5$ | $CF_3$ | NMe | CH | 2 |
| 54 | Et | $SF_5$ | $CF_3$ | NMe | CH | 2 |
| 55 | Et | H | $CF_3$ | S | N | 0 |
| 56 | Et | F | $CF_3$ | S | N | 0 |
| 57 | Et | Cl | $CF_3$ | S | N | 0 |
| 58 | Et | Br | $CF_3$ | S | N | 0 |
| 59 | Et | Me | $CF_3$ | S | N | 0 |
| 60 | Et | $CF_3$ | $CF_3$ | S | N | 0 |
| 61 | Et | $OCF_3$ | $CF_3$ | S | N | 0 |
| 62 | Et | $C_2F_5$ | $CF_3$ | S | N | 0 |
| 63 | Et | $SF_5$ | $CF_3$ | S | N | 0 |
| 64 | Et | H | $CF_3$ | S | N | 2 |
| 65 | Et | F | $CF_3$ | S | N | 2 |
| 66 | Et | Cl | $CF_3$ | S | N | 2 |
| 67 | Et | Br | $CF_3$ | S | N | 2 |
| 68 | Et | Me | $CF_3$ | S | N | 2 |
| 69 | Et | $CF_3$ | $CF_3$ | S | N | 2 |
| 70 | Et | $OCF_3$ | $CF_3$ | S | N | 2 |
| 71 | Et | $C_2F_5$ | $CF_3$ | S | N | 2 |
| 72 | Et | $SF_5$ | $CF_3$ | S | N | 2 |
| 73 | Me | H | $CF_2CF_3$ | NMe | N | 0 |
| 74 | Me | F | $CF_2CF_3$ | NMe | N | 0 |
| 75 | Me | Cl | $CF_2CF_3$ | NMe | N | 0 |

TABLE 41

| Intermediate | $R^{1x}$ | $R^{3x}$ | $R^{6x}$ | $A^{1x}$ | $A^{3x}$ | n |
|---|---|---|---|---|---|---|
| 76 | Me | Br | $CF_2CF_3$ | NMe | N | 0 |
| 77 | Me | Me | $CF_2CF_3$ | NMe | N | 0 |

TABLE 41-continued

| Intermediate | $R^{1x}$ | $R^{3x}$ | $R^{6x}$ | $A^{1x}$ | $A^{3x}$ | n |
|---|---|---|---|---|---|---|
| 78 | Me | $CF_3$ | $CF_2CF_3$ | NMe | N | 0 |
| 79 | Me | $OCF_3$ | $CF_2CF_3$ | NMe | N | 0 |
| 80 | Me | $C_2F_5$ | $CF_2CF_3$ | NMe | N | 0 |
| 81 | Me | $SF_5$ | $CF_2CF_3$ | NMe | N | 0 |
| 82 | Me | H | $CF_2CF_3$ | NMe | N | 2 |
| 83 | Me | F | $CF_2CF_3$ | NMe | N | 2 |
| 84 | Me | Cl | $CF_2CF_3$ | NMe | N | 2 |
| 85 | Me | Br | $CF_2CF_3$ | NMe | N | 2 |
| 86 | Me | Me | $CF_2CF_3$ | NMe | N | 2 |
| 87 | Me | $CF_3$ | $CF_2CF_3$ | NMe | N | 2 |
| 88 | Me | $OCF_3$ | $CF_2CF_3$ | NMe | N | 2 |
| 89 | Me | $C_2F_5$ | $CF_2CF_3$ | NMe | N | 2 |
| 90 | Me | $SF_5$ | $CF_2CF_3$ | NMe | N | 2 |
| 91 | Et | H | $CF_2CF_3$ | NMe | N | 0 |
| 92 | Et | F | $CF_2CF_3$ | NMe | N | 0 |
| 93 | Et | Cl | $CF_2CF_3$ | NMe | N | 0 |
| 94 | Et | Br | $CF_2CF_3$ | NMe | N | 0 |
| 95 | Et | Me | $CF_2CF_3$ | NMe | N | 0 |
| 96 | Et | $CF_3$ | $CF_2CF_3$ | NMe | N | 0 |
| 97 | Et | $OCF_3$ | $CF_2CF_3$ | NMe | N | 0 |
| 98 | Et | $C_2F_5$ | $CF_2CF_3$ | NMe | N | 0 |
| 99 | Et | $SF_5$ | $CF_2CF_3$ | NMe | N | 0 |
| 100 | Et | H | $CF_2CF_3$ | NMe | N | 2 |

TABLE 42

| Intermediate | $R^{1x}$ | $R^{3x}$ | $R^{6x}$ | $A^{1x}$ | $A^{3x}$ | n |
|---|---|---|---|---|---|---|
| 101 | Et | F | $CF_2CF_3$ | NMe | N | 2 |
| 102 | Et | Cl | $CF_2CF_3$ | NMe | N | 2 |
| 103 | Et | Br | $CF_2CF_3$ | NMe | N | 2 |
| 104 | Et | Me | $CF_2CF_3$ | NMe | N | 2 |
| 105 | Et | $CF_3$ | $CF_2CF_3$ | NMe | N | 2 |
| 106 | Et | $OCF_3$ | $CF_2CF_3$ | NMe | N | 2 |
| 107 | Et | $C_2F_5$ | $CF_2CF_3$ | NMe | N | 2 |
| 108 | Et | $SF_5$ | $CF_2CF_3$ | NMe | N | 2 |
| 109 | Et | H | $CF_2CF_3$ | NMe | CH | 0 |
| 110 | Et | F | $CF_2CF_3$ | NMe | CH | 0 |
| 111 | Et | Cl | $CF_2CF_3$ | NMe | CH | 0 |
| 112 | Et | Br | $CF_2CF_3$ | NMe | CH | 0 |
| 113 | Et | Me | $CF_2CF_3$ | NMe | CH | 0 |
| 114 | Et | $CF_3$ | $CF_2CF_3$ | NMe | CH | 0 |
| 115 | Et | $OCF_3$ | $CF_2CF_3$ | NMe | CH | 0 |
| 116 | Et | $C_2F_5$ | $CF_2CF_3$ | NMe | CH | 0 |
| 117 | Et | $SF_5$ | $CF_2CF_3$ | NMe | CH | 0 |
| 118 | Et | H | $CF_2CF_3$ | NMe | CH | 2 |
| 119 | Et | F | $CF_2CF_3$ | NMe | CH | 2 |
| 120 | Et | Cl | $CF_2CF_3$ | NMe | CH | 2 |
| 121 | Et | Br | $CF_2CF_3$ | NMe | CH | 2 |
| 122 | Et | Me | $CF_2CF_3$ | NMe | CH | 2 |
| 123 | Et | $CF_3$ | $CF_2CF_3$ | NMe | CH | 2 |
| 124 | Et | $OCF_3$ | $CF_2CF_3$ | NMe | CH | 2 |
| 125 | Et | $C_2F_5$ | $CF_2CF_3$ | NMe | CH | 2 |

TABLE 43

| Intermediate | $R^{1x}$ | $R^{3x}$ | $R^{6x}$ | $A^{1x}$ | $A^{3x}$ | n |
|---|---|---|---|---|---|---|
| 126 | Et | $SF_5$ | $CF_2CF_3$ | NMe | CH | 2 |
| 127 | Et | H | $CF_2CF_3$ | S | N | 0 |
| 128 | Et | F | $CF_2CF_3$ | S | N | 0 |
| 129 | Et | Cl | $CF_2CF_3$ | S | N | 0 |
| 130 | Et | Br | $CF_2CF_3$ | S | N | 0 |
| 131 | Et | Me | $CF_2CF_3$ | S | N | 0 |
| 132 | Et | $CF_3$ | $CF_2CF_3$ | S | N | 0 |
| 133 | Et | $OCF_3$ | $CF_2CF_3$ | S | N | 0 |
| 134 | Et | $C_2F_5$ | $CF_2CF_3$ | S | N | 0 |
| 135 | Et | $SF_5$ | $CF_2CF_3$ | S | N | 0 |
| 136 | Et | H | $CF_2CF_3$ | S | N | 2 |
| 137 | Et | F | $CF_2CF_3$ | S | N | 2 |
| 138 | Et | Cl | $CF_2CF_3$ | S | N | 2 |
| 139 | Et | Br | $CF_2CF_3$ | S | N | 2 |
| 140 | Et | Me | $CF_2CF_3$ | S | N | 2 |

TABLE 43-continued

| Intermediate | $R^{1x}$ | $R^{3x}$ | $R^{6x}$ | $A^{1x}$ | $A^{3x}$ | n |
|---|---|---|---|---|---|---|
| 141 | Et | $CF_3$ | $CF_2CF_3$ | S | N | 2 |
| 142 | Et | $OCF_3$ | $CF_2CF_3$ | S | N | 2 |
| 143 | Et | $C_2F_5$ | $CF_2CF_3$ | S | N | 2 |
| 144 | Et | $SF_5$ | $CF_2CF_3$ | S | N | 2 |
| 145 | Me | H | $SCF_3$ | NMe | N | 0 |
| 146 | Me | F | $SCF_3$ | NMe | N | 0 |
| 147 | Me | Cl | $SCF_3$ | NMe | N | 0 |
| 148 | Me | Br | $SCF_3$ | NMe | N | 0 |
| 149 | Me | Me | $SCF_3$ | NMe | N | 0 |
| 150 | Me | $CF_3$ | $SCF_3$ | NMe | N | 0 |

TABLE 44

| Intermediate | $R^{1x}$ | $R^{3x}$ | $R^{6x}$ | $A^{1x}$ | $A^{3x}$ | n |
|---|---|---|---|---|---|---|
| 151 | Me | $OCF_3$ | $SCF_3$ | NMe | N | 0 |
| 152 | Me | $C_2F_5$ | $SCF_3$ | NMe | N | 0 |
| 153 | Me | $SF_5$ | $SCF_3$ | NMe | N | 0 |
| 154 | Me | H | $SCF_3$ | NMe | N | 2 |
| 155 | Me | F | $SCF_3$ | NMe | N | 2 |
| 156 | Me | Cl | $SCF_3$ | NMe | N | 2 |
| 157 | Me | Br | $SCF_3$ | NMe | N | 2 |
| 158 | Me | Me | $SCF_3$ | NMe | N | 2 |
| 159 | Me | $CF_3$ | $SCF_3$ | NMe | N | 2 |
| 160 | Me | $OCF_3$ | $SCF_3$ | NMe | N | 2 |
| 161 | Me | $C_2F_5$ | $SCF_3$ | NMe | N | 2 |
| 162 | Me | $SF_5$ | $SCF_3$ | NMe | N | 2 |
| 163 | Et | H | $SCF_3$ | NMe | N | 0 |
| 164 | Et | F | $SCF_3$ | NMe | N | 0 |
| 165 | Et | Cl | $SCF_3$ | NMe | N | 0 |
| 166 | Et | Br | $SCF_3$ | NMe | N | 0 |
| 167 | Et | Me | $SCF_3$ | NMe | N | 0 |
| 168 | Et | $CF_3$ | $SCF_3$ | NMe | N | 0 |
| 169 | Et | $OCF_3$ | $SCF_3$ | NMe | N | 0 |
| 170 | Et | $C_2F_5$ | $SCF_3$ | NMe | N | 0 |
| 171 | Et | $SF_5$ | $SCF_3$ | NMe | N | 0 |
| 172 | Et | H | $SCF_3$ | NMe | N | 2 |
| 173 | Et | F | $SCF_3$ | NMe | N | 2 |
| 174 | Et | Cl | $SCF_3$ | NMe | N | 2 |
| 175 | Et | Br | $SCF_3$ | NMe | N | 2 |

TABLE 45

| Intermediate | $R^{1x}$ | $R^{3x}$ | $R^{6x}$ | $A^{1x}$ | $A^{3x}$ | n |
|---|---|---|---|---|---|---|
| 176 | Et | Me | $SCF_3$ | NMe | N | 2 |
| 177 | Et | $CF_3$ | $SCF_3$ | NMe | N | 2 |
| 178 | Et | $OCF_3$ | $SCF_3$ | NMe | N | 2 |
| 179 | Et | $C_2F_5$ | $SCF_3$ | NMe | N | 2 |
| 180 | Et | $SF_5$ | $SCF_3$ | NMe | N | 2 |
| 181 | Et | H | $SCF_3$ | NMe | CH | 0 |
| 182 | Et | F | $SCF_3$ | NMe | CH | 0 |
| 183 | Et | Cl | $SCF_3$ | NMe | CH | 0 |
| 184 | Et | Br | $SCF_3$ | NMe | CH | 0 |
| 185 | Et | Me | $SCF_3$ | NMe | CH | 0 |
| 186 | Et | $CF_3$ | $SCF_3$ | NMe | CH | 0 |
| 187 | Et | $OCF_3$ | $SCF_3$ | NMe | CH | 0 |
| 188 | Et | $C_2F_5$ | $SCF_3$ | NMe | CH | 0 |
| 189 | Et | $SF_5$ | $SCF_3$ | NMe | CH | 0 |
| 190 | Et | H | $SCF_3$ | NMe | CH | 2 |
| 191 | Et | F | $SCF_3$ | NMe | CH | 2 |
| 192 | Et | Cl | $SCF_3$ | NMe | CH | 2 |
| 193 | Et | Br | $SCF_3$ | NMe | CH | 2 |
| 194 | Et | Me | $SCF_3$ | NMe | CH | 2 |
| 195 | Et | $CF_3$ | $SCF_3$ | NMe | CH | 2 |
| 196 | Et | $OCF_3$ | $SCF_3$ | NMe | CH | 2 |
| 197 | Et | $C_2F_5$ | $SCF_3$ | NMe | CH | 2 |
| 198 | Et | $SF_5$ | $SCF_3$ | NMe | CH | 2 |
| 199 | Et | H | $SCF_3$ | S | N | 0 |
| 200 | Et | F | $SCF_3$ | S | N | 0 |

TABLE 46

| Intermediate | $R^{1x}$ | $R^{3x}$ | $R^{6x}$ | $A^{1x}$ | $A^{3x}$ | n |
|---|---|---|---|---|---|---|
| 201 | Et | Cl | $SCF_3$ | S | N | 0 |
| 202 | Et | Br | $SCF_3$ | S | N | 0 |
| 203 | Et | Me | $SCF_3$ | S | N | 0 |
| 204 | Et | $CF_3$ | $SCF_3$ | S | N | 0 |
| 205 | Et | $OCF_3$ | $SCF_3$ | S | N | 0 |
| 206 | Et | $C_2F_5$ | $SCF_3$ | S | N | 0 |
| 207 | Et | $SF_5$ | $SCF_3$ | S | N | 0 |
| 208 | Et | H | $SCF_3$ | S | N | 2 |
| 209 | Et | F | $SCF_3$ | S | N | 2 |
| 210 | Et | Cl | $SCF_3$ | S | N | 2 |
| 211 | Et | Br | $SCF_3$ | S | N | 2 |
| 212 | Et | Me | $SCF_3$ | S | N | 2 |
| 213 | Et | $CF_3$ | $SCF_3$ | S | N | 2 |
| 214 | Et | $OCF_3$ | $SCF_3$ | S | N | 2 |
| 215 | Et | $C_2F_5$ | $SCF_3$ | S | N | 2 |
| 216 | Et | $SF_5$ | $SCF_3$ | S | N | 2 |
| 217 | Me | H | $SOCF_3$ | NMe | N | 0 |
| 218 | Me | F | $SOCF_3$ | NMe | N | 0 |
| 219 | Me | Cl | $SOCF_3$ | NMe | N | 0 |
| 220 | Me | Br | $SOCF_3$ | NMe | N | 0 |
| 221 | Me | Me | $SOCF_3$ | NMe | N | 0 |
| 222 | Me | $CF_3$ | $SOCF_3$ | NMe | N | 0 |
| 223 | Me | $OCF_3$ | $SOCF_3$ | NMe | N | 0 |
| 224 | Me | $C_2F_5$ | $SOCF_3$ | NMe | N | 0 |
| 225 | Me | $SF_5$ | $SOCF_3$ | NMe | N | 0 |

TABLE 47

| Intermediate | $R^{1x}$ | $R^{3x}$ | $R^{6x}$ | $A^{1x}$ | $A^{3x}$ | n |
|---|---|---|---|---|---|---|
| 226 | Me | H | $SOCF_3$ | NMe | N | 2 |
| 227 | Me | F | $SOCF_3$ | NMe | N | 2 |
| 228 | Me | Cl | $SOCF_3$ | NMe | N | 2 |
| 229 | Me | Br | $SOCF_3$ | NMe | N | 2 |
| 230 | Me | Me | $SOCF_3$ | NMe | N | 2 |
| 231 | Me | $CF_3$ | $SOCF_3$ | NMe | N | 2 |
| 232 | Me | $OCF_3$ | $SOCF_3$ | NMe | N | 2 |
| 233 | Me | $C_2F_5$ | $SOCF_3$ | NMe | N | 2 |
| 234 | Me | $SF_5$ | $SOCF_3$ | NMe | N | 2 |
| 235 | Et | H | $SOCF_3$ | NMe | N | 0 |
| 236 | Et | F | $SOCF_3$ | NMe | N | 0 |
| 237 | Et | Cl | $SOCF_3$ | NMe | N | 0 |
| 238 | Et | Br | $SOCF_3$ | NMe | N | 0 |
| 239 | Et | Me | $SOCF_3$ | NMe | N | 0 |
| 240 | Et | $CF_3$ | $SOCF_3$ | NMe | N | 0 |
| 241 | Et | $OCF_3$ | $SOCF_3$ | NMe | N | 0 |
| 242 | Et | $C_2F_5$ | $SOCF_3$ | NMe | N | 0 |
| 243 | Et | $SF_5$ | $SOCF_3$ | NMe | N | 0 |
| 244 | Et | H | $SOCF_3$ | NMe | N | 2 |
| 245 | Et | F | $SOCF_3$ | NMe | N | 2 |
| 246 | Et | Cl | $SOCF_3$ | NMe | N | 2 |
| 247 | Et | Br | $SOCF_3$ | NMe | N | 2 |
| 248 | Et | Me | $SOCF_3$ | NMe | N | 2 |
| 249 | Et | $CF_3$ | $SOCF_3$ | NMe | N | 2 |
| 250 | Et | $OCF_3$ | $SOCF_3$ | NMe | N | 2 |

TABLE 48

| Intermediate | $R^{1x}$ | $R^{3x}$ | $R^{6x}$ | $A^{1x}$ | $A^{3x}$ | n |
|---|---|---|---|---|---|---|
| 251 | Et | $C_2F_5$ | $SOCF_3$ | NMe | N | 2 |
| 252 | Et | $SF_5$ | $SOCF_3$ | NMe | N | 2 |
| 253 | Et | H | $SOCF_3$ | NMe | CH | 0 |
| 254 | Et | F | $SOCF_3$ | NMe | CH | 0 |
| 255 | Et | Cl | $SOCF_3$ | NMe | CH | 0 |
| 256 | Et | Br | $SOCF_3$ | NMe | CH | 0 |
| 257 | Et | Me | $SOCF_3$ | NMe | CH | 0 |
| 258 | Et | $CF_3$ | $SOCF_3$ | NMe | CH | 0 |
| 259 | Et | $OCF_3$ | $SOCF_3$ | NMe | CH | 0 |
| 260 | Et | $C_2F_5$ | $SOCF_3$ | NMe | CH | 0 |
| 261 | Et | $SF_5$ | $SOCF_3$ | NMe | CH | 0 |
| 262 | Et | H | $SOCF_3$ | NMe | CH | 2 |
| 263 | Et | F | $SOCF_3$ | NMe | CH | 2 |

TABLE 48-continued

| Intermediate | $R^{1x}$ | $R^{3x}$ | $R^{6x}$ | $A^{1x}$ | $A^{3x}$ | n |
|---|---|---|---|---|---|---|
| 264 | Et | Cl | SOCF$_3$ | NMe | CH | 2 |
| 265 | Et | Br | SOCF$_3$ | NMe | CH | 2 |
| 266 | Et | Me | SOCF$_3$ | NMe | CH | 2 |
| 267 | Et | CF$_3$ | SOCF$_3$ | NMe | CH | 2 |
| 268 | Et | OCF$_3$ | SOCF$_3$ | NMe | CH | 2 |
| 269 | Et | C$_2$F$_5$ | SOCF$_3$ | NMe | CH | 2 |
| 270 | Et | SF$_5$ | SOCF$_3$ | NMe | CH | 2 |
| 271 | Et | H | SOCF$_3$ | S | N | 0 |
| 272 | Et | F | SOCF$_3$ | S | N | 0 |
| 273 | Et | Cl | SOCF$_3$ | S | N | 0 |
| 274 | Et | Br | SOCF$_3$ | S | N | 0 |
| 275 | Et | Me | SOCF$_3$ | S | N | 0 |

TABLE 49

| Intermediate | $R^{1x}$ | $R^{3x}$ | $R^{6x}$ | $A^{1x}$ | $A^{3x}$ | n |
|---|---|---|---|---|---|---|
| 276 | Et | CF$_3$ | SOCF$_3$ | S | N | 0 |
| 277 | Et | OCF$_3$ | SOCF$_3$ | S | N | 0 |
| 278 | Et | C$_2$F$_5$ | SOCF$_3$ | S | N | 0 |
| 279 | Et | SF$_5$ | SOCF$_3$ | S | N | 0 |
| 280 | Et | H | SOCF$_3$ | S | N | 2 |
| 281 | Et | F | SOCF$_3$ | S | N | 2 |
| 282 | Et | Cl | SOCF$_3$ | S | N | 2 |
| 283 | Et | Br | SOCF$_3$ | S | N | 2 |
| 284 | Et | Me | SOCF$_3$ | S | N | 2 |
| 285 | Et | CF$_3$ | SOCF$_3$ | S | N | 2 |
| 286 | Et | OCF$_3$ | SOCF$_3$ | S | N | 2 |
| 287 | Et | C$_2$F$_5$ | SOCF$_3$ | S | N | 2 |
| 288 | Et | SF$_5$ | SOCF$_3$ | S | N | 2 |
| 289 | Me | H | SO$_2$CF$_3$ | NMe | N | 0 |
| 290 | Me | F | SO$_2$CF$_3$ | NMe | N | 0 |
| 291 | Me | Cl | SO$_2$CF$_3$ | NMe | N | 0 |
| 292 | Me | Br | SO$_2$CF$_3$ | NMe | N | 0 |
| 293 | Me | Me | SO$_2$CF$_3$ | NMe | N | 0 |
| 294 | Me | CF$_3$ | SO$_2$CF$_3$ | NMe | N | 0 |
| 295 | Me | OCF$_3$ | SO$_2$CF$_3$ | NMe | N | 0 |
| 296 | Me | C$_2$F$_5$ | SO$_2$CF$_3$ | NMe | N | 0 |
| 297 | Me | SF$_5$ | SO$_2$CF$_3$ | NMe | N | 0 |
| 298 | Me | H | SO$_2$CF$_3$ | NMe | N | 2 |
| 299 | Me | F | SO$_2$CF$_3$ | NMe | N | 2 |
| 300 | Me | Cl | SO$_2$CF$_3$ | NMe | N | 2 |

TABLE 50

| Intermediate | $R^{1x}$ | $R^{3x}$ | $R^{6x}$ | $A^{1x}$ | $A^{3x}$ | n |
|---|---|---|---|---|---|---|
| 301 | Me | Br | SO$_2$CF$_3$ | NMe | N | 2 |
| 302 | Me | Me | SO$_2$CF$_3$ | NMe | N | 2 |
| 303 | Me | CF$_3$ | SO$_2$CF$_3$ | NMe | N | 2 |
| 304 | Me | OCF$_3$ | SO$_2$CF$_3$ | NMe | N | 2 |
| 305 | Me | C$_2$F$_5$ | SO$_2$CF$_3$ | NMe | N | 2 |
| 306 | Me | SF$_5$ | SO$_2$CF$_3$ | NMe | N | 2 |
| 307 | Et | H | SO$_2$CF$_3$ | NMe | N | 0 |
| 308 | Et | F | SO$_2$CF$_3$ | NMe | N | 0 |
| 309 | Et | Cl | SO$_2$CF$_3$ | NMe | N | 0 |
| 310 | Et | Br | SO$_2$CF$_3$ | NMe | N | 0 |
| 311 | Et | Me | SO$_2$CF$_3$ | NMe | N | 0 |
| 312 | Et | CF$_3$ | SO$_2$CF$_3$ | NMe | N | 0 |
| 313 | Et | OCF$_3$ | SO$_2$CF$_3$ | NMe | N | 0 |
| 314 | Et | C$_2$F$_5$ | SO$_2$CF$_3$ | NMe | N | 0 |
| 315 | Et | SF$_5$ | SO$_2$CF$_3$ | NMe | N | 0 |
| 316 | Et | H | SO$_2$CF$_3$ | NMe | N | 2 |
| 317 | Et | F | SO$_2$CF$_3$ | NMe | N | 2 |
| 318 | Et | Cl | SO$_2$CF$_3$ | NMe | N | 2 |
| 319 | Et | Br | SO$_2$CF$_3$ | NMe | N | 2 |
| 320 | Et | Me | SO$_2$CF$_3$ | NMe | N | 2 |
| 321 | Et | CF$_3$ | SO$_2$CF$_3$ | NMe | N | 2 |
| 322 | Et | OCF$_3$ | SO$_2$CF$_3$ | NMe | N | 2 |
| 323 | Et | C$_2$F$_5$ | SO$_2$CF$_3$ | NMe | N | 2 |
| 324 | Et | SF$_5$ | SO$_2$CF$_3$ | NMe | N | 2 |
| 325 | Et | H | SO$_2$CF$_3$ | NMe | CH | 0 |

TABLE 51

| Intermediate | $R^{1x}$ | $R^{3x}$ | $R^{6x}$ | $A^{1x}$ | $A^{3x}$ | n |
|---|---|---|---|---|---|---|
| 326 | Et | F | SO$_2$CF$_3$ | NMe | CH | 0 |
| 327 | Et | Cl | SO$_2$CF$_3$ | NMe | CH | 0 |
| 328 | Et | Br | SO$_2$CF$_3$ | NMe | CH | 0 |
| 329 | Et | Me | SO$_2$CF$_3$ | NMe | CH | 0 |
| 330 | Et | CF$_3$ | SO$_2$CF$_3$ | NMe | CH | 0 |
| 331 | Et | OCF$_3$ | SO$_2$CF$_3$ | NMe | CH | 0 |
| 332 | Et | C$_2$F$_5$ | SO$_2$CF$_3$ | NMe | CH | 0 |
| 333 | Et | SF$_5$ | SO$_2$CF$_3$ | NMe | CH | 0 |
| 334 | Et | H | SO$_2$CF$_3$ | NMe | CH | 2 |
| 335 | Et | F | SO$_2$CF$_3$ | NMe | CH | 2 |
| 336 | Et | Cl | SO$_2$CF$_3$ | NMe | CH | 2 |
| 337 | Et | Br | SO$_2$CF$_3$ | NMe | CH | 2 |
| 338 | Et | Me | SO$_2$CF$_3$ | NMe | CH | 2 |
| 339 | Et | CF$_3$ | SO$_2$CF$_3$ | NMe | CH | 2 |
| 340 | Et | OCF$_3$ | SO$_2$CF$_3$ | NMe | CH | 2 |
| 341 | Et | C$_2$F$_5$ | SO$_2$CF$_3$ | NMe | CH | 2 |
| 342 | Et | SF$_5$ | SO$_2$CF$_3$ | NMe | CH | 2 |
| 343 | Et | H | SO$_2$CF$_3$ | S | N | 0 |
| 344 | Et | F | SO$_2$CF$_3$ | S | N | 0 |
| 345 | Et | Cl | SO$_2$CF$_3$ | S | N | 0 |
| 346 | Et | Br | SO$_2$CF$_3$ | S | N | 0 |
| 347 | Et | Me | SO$_2$CF$_3$ | S | N | 0 |
| 348 | Et | CF$_3$ | SO$_2$CF$_3$ | S | N | 0 |
| 349 | Et | OCF$_3$ | SO$_2$CF$_3$ | S | N | 0 |
| 350 | Et | C$_2$F$_5$ | SO$_2$CF$_3$ | S | N | 0 |

TABLE 52

| Intermediate | $R^{1x}$ | $R^{3x}$ | $R^{6x}$ | $A^{1x}$ | $A^{3x}$ | n |
|---|---|---|---|---|---|---|
| 351 | Et | SF$_5$ | SO$_2$CF$_3$ | S | N | 0 |
| 352 | Et | H | SO$_2$CF$_3$ | S | N | 2 |
| 353 | Et | F | SO$_2$CF$_3$ | S | N | 2 |
| 354 | Et | Cl | SO$_2$CF$_3$ | S | N | 2 |
| 355 | Et | Br | SO$_2$CF$_3$ | S | N | 2 |
| 356 | Et | Me | SO$_2$CF$_3$ | S | N | 2 |
| 357 | Et | CF$_3$ | SO$_2$CF$_3$ | S | N | 2 |
| 358 | Et | OCF$_3$ | SO$_2$CF$_3$ | S | N | 2 |
| 359 | Et | C$_2$F$_5$ | SO$_2$CF$_3$ | S | N | 2 |
| 360 | Et | SF$_5$ | SO$_2$CF$_3$ | S | N | 2 |

TABLE 53

| Intermediate | $R^{1x}$ | $R^{3x}$ | $R^{6x}$ | $A^{1x}$ | $A^{3x}$ | n |
|---|---|---|---|---|---|---|
| 361 | Me | H | Br | NMe | N | 0 |
| 362 | Me | F | Br | NMe | N | 0 |
| 363 | Me | Cl | Br | NMe | N | 0 |
| 364 | Me | Br | Br | NMe | N | 0 |
| 365 | Me | Me | Br | NMe | N | 0 |
| 366 | Me | CF$_3$ | Br | NMe | N | 0 |
| 367 | Me | OCF$_3$ | Br | NMe | N | 0 |
| 368 | Me | C$_2$F$_5$ | Br | NMe | N | 0 |
| 369 | Me | SF$_5$ | Br | NMe | N | 0 |
| 370 | Me | H | Br | NMe | N | 2 |
| 371 | Me | F | Br | NMe | N | 2 |
| 372 | Me | Cl | Br | NMe | N | 2 |
| 373 | Me | Br | Br | NMe | N | 2 |
| 374 | Me | Me | Br | NMe | N | 2 |
| 375 | Me | CF$_3$ | Br | NMe | N | 2 |
| 376 | Me | OCF$_3$ | Br | NMe | N | 2 |
| 377 | Me | C$_2$F$_5$ | Br | NMe | N | 2 |
| 378 | Me | SF$_5$ | Br | NMe | N | 2 |
| 379 | Et | H | Br | NMe | N | 0 |
| 380 | Et | F | Br | NMe | N | 0 |
| 381 | Et | Cl | Br | NMe | N | 0 |
| 382 | Et | Br | Br | NMe | N | 0 |
| 383 | Et | Me | Br | NMe | N | 0 |
| 384 | Et | CF$_3$ | Br | NMe | N | 0 |
| 385 | Et | OCF$_3$ | Br | NMe | N | 0 |

TABLE 54

| Intermediate | $R^{1x}$ | $R^{3x}$ | $R^{6x}$ | $A^{1x}$ | $A^{3x}$ | n |
|---|---|---|---|---|---|---|
| 386 | Et | $C_2F_5$ | Br | NMe | N | 0 |
| 387 | Et | $SF_5$ | Br | NMe | N | 0 |
| 388 | Et | H | Br | NMe | N | 2 |
| 389 | Et | F | Br | NMe | N | 2 |
| 390 | Et | Cl | Br | NMe | N | 2 |
| 391 | Et | Br | Br | NMe | N | 2 |
| 392 | Et | Me | Br | NMe | N | 2 |
| 393 | Et | $CF_3$ | Br | NMe | N | 2 |
| 394 | Et | $OCF_3$ | Br | NMe | N | 2 |
| 395 | Et | $C_2F_5$ | Br | NMe | N | 2 |
| 396 | Et | $SF_5$ | Br | NMe | N | 2 |
| 397 | Et | H | Br | NMe | CH | 0 |
| 398 | Et | F | Br | NMe | CH | 0 |
| 399 | Et | Cl | Br | NMe | CH | 0 |
| 400 | Et | Br | Br | NMe | CH | 0 |
| 401 | Et | Me | Br | NMe | CH | 0 |
| 402 | Et | $CF_3$ | Br | NMe | CH | 0 |
| 403 | Et | $OCF_3$ | Br | NMe | CH | 0 |
| 404 | Et | $C_2F_5$ | Br | NMe | CH | 0 |
| 405 | Et | $SF_5$ | Br | NMe | CH | 0 |
| 406 | Et | H | Br | NMe | CH | 2 |
| 407 | Et | F | Br | NMe | CH | 2 |
| 408 | Et | Cl | Br | NMe | CH | 2 |
| 409 | Et | Br | Br | NMe | CH | 2 |
| 410 | Et | Me | Br | NMe | CH | 2 |

TABLE 55

| Intermediate | $R^{1x}$ | $R^{3x}$ | $R^{6x}$ | $A^{1x}$ | $A^{3x}$ | n |
|---|---|---|---|---|---|---|
| 411 | Et | $CF_3$ | Br | NMe | CH | 2 |
| 412 | Et | $OCF_3$ | Br | NMe | CH | 2 |
| 413 | Et | $C_2F_5$ | Br | NMe | CH | 2 |
| 414 | Et | $SF_5$ | Br | NMe | CH | 2 |
| 415 | Et | H | Br | S | N | 0 |
| 416 | Et | F | Br | S | N | 0 |
| 417 | Et | Cl | Br | S | N | 0 |
| 418 | Et | Br | Br | S | N | 0 |
| 419 | Et | Me | Br | S | N | 0 |
| 420 | Et | $CF_3$ | Br | S | N | 0 |
| 421 | Et | $OCF_3$ | Br | S | N | 0 |
| 422 | Et | $C_2F_5$ | Br | S | N | 0 |
| 423 | Et | $SF_5$ | Br | S | N | 0 |
| 424 | Et | H | Br | S | N | 2 |
| 425 | Et | F | Br | S | N | 2 |
| 426 | Et | Cl | Br | S | N | 2 |
| 427 | Et | Br | Br | S | N | 2 |
| 428 | Et | Me | Br | S | N | 2 |
| 429 | Et | $CF_3$ | Br | S | N | 2 |
| 430 | Et | $OCF_3$ | Br | S | N | 2 |
| 431 | Et | $C_2F_5$ | Br | S | N | 2 |
| 432 | Et | $SF_5$ | Br | S | N | 2 |
| 433 | Me | H | I | NMe | N | 0 |
| 434 | Me | F | I | NMe | N | 0 |
| 435 | Me | Cl | I | NMe | N | 0 |

TABLE 56

| Intermediate | $R^{1x}$ | $R^{3x}$ | $R^{6x}$ | $A^{1x}$ | $A^{3x}$ | n |
|---|---|---|---|---|---|---|
| 436 | Me | Br | I | NMe | N | 0 |
| 437 | Me | Me | I | NMe | N | 0 |
| 438 | Me | $CF_3$ | I | NMe | N | 0 |
| 439 | Me | $OCF_3$ | I | NMe | N | 0 |
| 440 | Me | $C_2F_5$ | I | NMe | N | 0 |
| 441 | Me | $SF_5$ | I | NMe | N | 0 |
| 442 | Me | H | I | NMe | N | 2 |
| 443 | Me | F | I | NMe | N | 2 |
| 444 | Me | Cl | I | NMe | N | 2 |
| 445 | Me | Br | I | NMe | N | 2 |
| 446 | Me | Me | I | NMe | N | 2 |
| 447 | Me | $CF_3$ | I | NMe | N | 2 |
| 448 | Me | $OCF_3$ | I | NMe | N | 2 |

TABLE 56-continued

| Intermediate | $R^{1x}$ | $R^{3x}$ | $R^{6x}$ | $A^{1x}$ | $A^{3x}$ | n |
|---|---|---|---|---|---|---|
| 449 | Me | $C_2F_5$ | I | NMe | N | 2 |
| 450 | Me | $SF_5$ | I | NMe | N | 2 |
| 451 | Et | H | I | NMe | N | 0 |
| 452 | Et | F | I | NMe | N | 0 |
| 453 | Et | Cl | I | NMe | N | 0 |
| 454 | Et | Br | I | NMe | N | 0 |
| 455 | Et | Me | I | NMe | N | 0 |
| 456 | Et | $CF_3$ | I | NMe | N | 0 |
| 457 | Et | $OCF_3$ | I | NMe | N | 0 |
| 458 | Et | $C_2F_5$ | I | NMe | N | 0 |
| 459 | Et | $SF_5$ | I | NMe | N | 0 |
| 460 | Et | H | I | NMe | N | 2 |

TABLE 57

| Intermediate | $R^{1x}$ | $R^{3x}$ | $R^{6x}$ | $A^{1x}$ | $A^{3x}$ | n |
|---|---|---|---|---|---|---|
| 461 | Et | F | I | NMe | N | 2 |
| 462 | Et | Cl | I | NMe | N | 2 |
| 463 | Et | Br | I | NMe | N | 2 |
| 464 | Et | Me | I | NMe | N | 2 |
| 465 | Et | $CF_3$ | I | NMe | N | 2 |
| 466 | Et | $OCF_3$ | I | NMe | N | 2 |
| 467 | Et | $C_2F_5$ | I | NMe | N | 2 |
| 468 | Et | $SF_5$ | I | NMe | N | 2 |
| 469 | Et | H | I | NMe | CH | 0 |
| 470 | Et | F | I | NMe | CH | 0 |
| 471 | Et | Cl | I | NMe | CH | 0 |
| 472 | Et | Br | I | NMe | CH | 0 |
| 473 | Et | Me | I | NMe | CH | 0 |
| 474 | Et | $CF_3$ | I | NMe | CH | 0 |
| 475 | Et | $OCF_3$ | I | NMe | CH | 0 |
| 476 | Et | $C_2F_5$ | I | NMe | CH | 0 |
| 477 | Et | $SF_5$ | I | NMe | CH | 0 |
| 478 | Et | H | I | NMe | CH | 2 |
| 479 | Et | F | I | NMe | CH | 2 |
| 480 | Et | Cl | I | NMe | CH | 2 |
| 481 | Et | Br | I | NMe | CH | 2 |
| 482 | Et | Me | I | NMe | CH | 2 |
| 483 | Et | $CF_3$ | I | NMe | CH | 2 |
| 484 | Et | $OCF_3$ | I | NMe | CH | 2 |
| 485 | Et | $C_2F_5$ | I | NMe | CH | 2 |

TABLE 58

| Intermediate | $R^{1x}$ | $R^{3x}$ | $R^{6x}$ | $A^{1x}$ | $A^{3x}$ | n |
|---|---|---|---|---|---|---|
| 486 | Et | $SF_5$ | I | NMe | CH | 2 |
| 487 | Et | H | I | S | N | 0 |
| 488 | Et | F | I | S | N | 0 |
| 489 | Et | Cl | I | S | N | 0 |
| 490 | Et | Br | I | S | N | 0 |
| 491 | Et | Me | I | S | N | 0 |
| 492 | Et | $CF_3$ | I | S | N | 0 |
| 493 | Et | $OCF_3$ | I | S | N | 0 |
| 494 | Et | $C_2F_5$ | I | S | N | 0 |
| 495 | Et | $SF_5$ | I | S | N | 0 |
| 496 | Et | H | I | S | N | 2 |
| 497 | Et | F | I | S | N | 2 |
| 498 | Et | Cl | I | S | N | 2 |
| 499 | Et | Br | I | S | N | 2 |
| 500 | Et | Me | I | S | N | 2 |
| 501 | Et | $CF_3$ | I | S | N | 2 |
| 502 | Et | $OCF_3$ | I | S | N | 2 |
| 503 | Et | $C_2F_5$ | I | S | N | 2 |
| 504 | Et | $SF_5$ | I | S | N | 2 |

In the above Tables 38-58, Me represents a methyl group, and Et represents an ethyl group.

The $^1$H-NMR data of Compound (1B) are shown below.
Compound (1B)-505

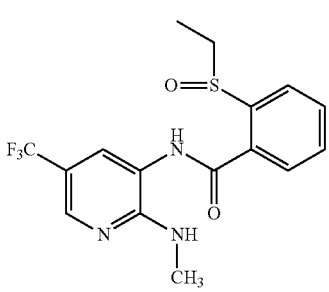 [SMILES: CCS(=O)c1ccccc1C(=O)Nc1cc(C(F)(F)F)cnc1NC]

¹H-NMR (CDCl₃) δ: 8.76 (1H, S), 8.33 (1H, s), 8.04 (1H, S), 7.88-7.76 (2H, m), 7.78-7.60 (2H, m), 6.30 (1H, brs), 3.30-3.20 (1H, m), 3.10 (3H, d), 3.10-2.98 (1H, m), 1.26 (3H, t).

Compound (1B)-28

¹H-NMR (CDCl₃) δ: 8.39 (1H, S), 8.08 (1H, d), 7.85-7.55 (4H, m), 7.26-7.20 (1H, m), 6.29 (1H, brs), 3.51 (2H, q), 3.05 (3H, d), 1.33 (3H, t).

Compound (1B)-379

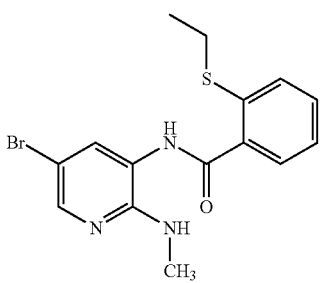 [SMILES: CCSc1ccccc1C(=O)Nc1cc(Br)cnc1NC]

¹H-NMR (CDCl₃) δ: 8.28 (1H, brs), 8.14 (1H, d), 7.90-7.75 (2H, m), 7.58-7.35 (3H, m), 5.06 (1H, brs), 3.20-2.96 (5H, m), 1.32 (3H, q).

Compound (1B)-507

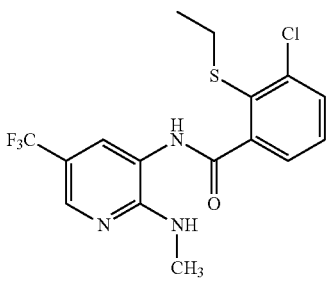 [SMILES: CCSc1c(Cl)cccc1C(=O)Nc1cc(C(F)(F)F)cnc1NC]

¹H-NMR (CDCl₃) δ: 8.39-8.38 (1H, m), 7.80 (1H, brs), 7.70-7.68 (1H, m), 7.67-7.61 (2H, m), 7.44-7.39 (1H, m), 5.80 (1H, brs), 3.10-3.07 (3H, m), 3.00 (2H, q), 1.26 (3H, t).

Compound (1B)-508

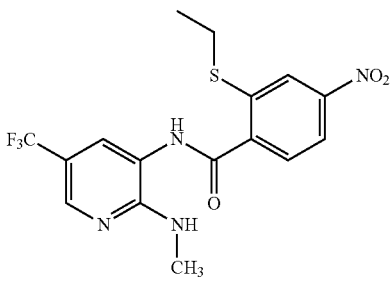 [SMILES: CCSc1cc([N+](=O)[O-])ccc1C(=O)Nc1cc(C(F)(F)F)cnc1NC]

¹H-NMR (CDCl₃) δ: 8.41-8.38 (1H, m), 8.29-8.26 (1H, m), 8.16-8.12 (1H, m), 7.93-7.89 (1H, m), 7.86 (1H, brs), 7.76-7.73 (1H, m), 5.39-5.33 (1H, brm), 3.14 (2H, q), 3.08 (3H, d), 1.42 (3H, t).

Compound (1B)-24

¹H-NMR (CDCl₃) δ: 8.39 (1H, brs), 7.96 (1H, brs), 7.92 (1H, d), 7.77-7.71 (2H, m), 7.62 (1H, d), 5.42 (1H, brs), 3.12-3.03 (5H, m), 1.37 (3H, t).

Compound (1B)-509

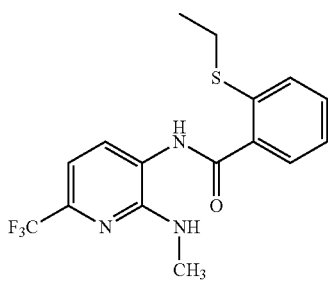 [SMILES: CCSc1ccccc1C(=O)Nc1ccc(C(F)(F)F)nc1NC]

¹H-NMR (CDCl₃) δ: 8.38 (1H, brs), 7.89 (1H, d), 7.80 (1H, d), 7.57-7.51 (1H, m), 7.50-7.44 (1H, m), 7.43-7.36 (1H, m), 7.05-6.99 (1H, m), 5.22 (1H, brs), 3.06 (3H, s), 3.00 (2H, q), 1.32 (3H, t).

Compound (1B)-451

¹H-NMR (CDCl₃) δ: 8.26 (1H, brs), 7.87 (1H, s), 7.84 (1H, d), 7.52 (1H, d), 7.49-7.42 (1H, m), 7.41-7.35 (1H, m), 7.20-7.15 (1H, m), 5.12 (1H, brs), 3.02-2.97 (5H, m), 1.32 (3H, t).

Compound (1B)-511

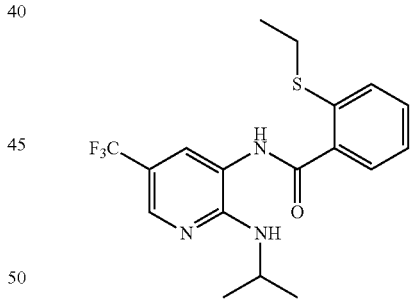

¹H-NMR (CDCl₃) δ: 8.30 (1H, s), 8.10 (1H, brs), 7.76-7.76 (2H, m), 7.50 (1H, d), 7.45 (1H, t), 7.36 (1H, t), 5.41 (1H, d), 4.37-4.27 (1H, m), 2.99 (2H, q), 1.30-1.28 (9H, m).

Compound (1B)-37

¹H-NMR (CDCl₃) δ: 8.18 (1H, brs), 7.84 (1H, d), 7.60-7.30 (5H, m), 6.77 (1H, d), 4.85 (1H, brs), 3.01 (2H, q), 2.93 (3H, d), 1.32 (3H, t).

Compound (1B)-33

¹H-NMR (Acetone-d₆) δ: 9.56 (1H, brs), 8.36-8.35 (1H, m), 8.30-8.23 (3H, m), 7.87-7.85 (1H, m), 6.44 (1H, brs), 3.65 (2H, q), 3.03 (3H, d), 1.31 (3H, t).

Compound (1B)-516

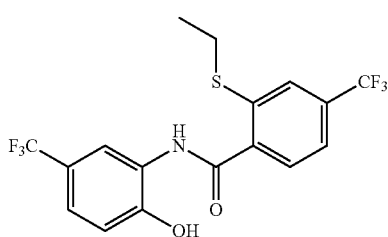 [SMILES: CCSc1cc(C(F)(F)F)ccc1C(=O)Nc1cc(C(F)(F)F)ccc1O]

¹H-NMR (CDCl₃) δ: 9.35 (1H, s), 8.92 (1H, s), 8.03 (1H, d), 7.74 (1H, s), 7.62 (1H, d), 7.57 (1H, s), 7.44 (1H, d), 7.14 (1H, d), 3.05 (2H, q), 1.36 (3H, t).

The ¹H-NMR data of Compound (1C) are shown below.

Compound (1C)-F505

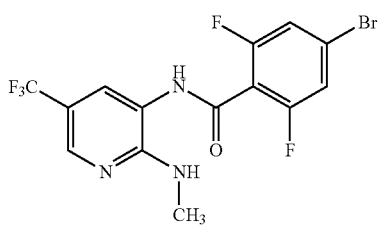 [SMILES: CNc1ncc(C(F)(F)F)cc1NC(=O)c1c(F)cc(Br)cc1F]

¹H-NMR (CDCl₃) δ: 8.40 (1H, s), 7.73-7.71 (1H, m), 7.29-7.24 (3H, m), 4.99 (1H, brs), 3.08 (3H, d).

Compound (1C)-F3

¹H-NMR (CDCl₃) δ: 8.40 (1H, s), 8.14 (1H, dd), 7.93 (1H, d), 7.72 (1H, s), 7.36 (1H, d), 7.32-7.27 (1H, m), 4.99 (1H, brs), 3.08 (3H, d).

Compound (1C)-F4

¹H-NMR (CDCl₃) δ: 8.39 (1H, s), 8.06 (1H, dd), 7.93 (1H, d), 7.72 (1H, s), 7.51 (1H, d), 7.44 (1H, d), 4.99 (1H, brs), 3.07 (3H, d).

Compound (1C)-F5

¹H-NMR (CDCl₃) δ: 8.38 (1H, s), 8.15-7.94 (2H, m), 7.73 (1H, s), 7.15 (1H, d), 7.03 (1H, d), 5.06 (1H, brs), 3.07 (3H, d), 2.45 (3H, s).

Compound (1C)-F6

¹H-NMR (CDCl₃) δ: 8.41 (1H, brs), 8.33 (1H, t), 7.99 (1H, d), 7.75 (1H, d), 7.64 (1H, d), 7.53 (1H, d), 4.97 (1H, brs), 3.08 (3H, d).

Compound (1C)-F37

¹H-NMR (CDCl₃) δ: 8.25-8.06 (2H, m), 7.64-7.53 (2H, m), 7.47 (1H, d), 7.34 (1H, t), 7.24-7.15 (1H, m), 6.80 (1H, d), 4.38 (1H, brs), 2.93 (3H, d).

Compound (1C)-C37

¹H-NMR (CDCl₃) δ: 7.85 (1H, d), 7.64 (1H, brs), 7.56 (1H, s), 7.52-7.38 (4H, m), 6.80 (1H, d), 4.49 (1H, brs), 2.93 (3H, s).

Compound (1C)-F42

¹H-NMR (CDCl₃) δ: 8.33 (1H, t), 8.10 (1H, d), 7.66-7.57 (2H, m), 7.55-7.45 (2H, m), 6.82 (1H, d), 4.29 (1H, brs), 2.93 (3H, d).

Compound (1C)-F145

¹H-NMR (CDCl₃) δ: 8.35 (1H, s), 8.19 (1H, t), 8.02 (1H, d), 7.76 (1H, s), 7.64-7.54 (1H, m), 7.36 (1H, t), 7.25-7.20 (1H, m), 5.06 (1H, brs), 3.07 (3H, d).

Compound (1C)-C145

¹H-NMR (CDCl₃) δ: 8.35 (1H, brs), 7.86 (1H, d), 7.77-7.71 (1H, m), 7.63-7.39 (4H, m), 5.19 (1H, brs), 3.08 (3H, d).

Compound (1C)-F150

¹H-NMR (CDCl₃) δ: 8.40-8.28 (2H, m), 7.98 (1H, d), 7.77 (1H, s), 7.64 (1H, d), 7.53 (1H, d), 4.98 (1H, brs), 3.08 (3H, d).

Compound (1C)-F73

¹H-NMR (CDCl₃) δ: 8.34 (1H, brs), 8.24-8.15 (1H, m), 8.05 (1H, d), 7.68 (1H, s), 7.65-7.54 (1H, m), 7.40-7.32 (1H, m), 7.25-7.18 (1H, m), 5.09 (1H, brs), 3.09 (3H, d).

Compound (1C)-C73

¹H-NMR (CDCl₃) δ: 8.35 (1H, s), 7.87 (1H, d), 7.65 (1H, s), 7.62 (1H, brs), 7.54-7.40 (3H, m), 5.21 (1H, brs), 3.09 (3H, d).

Compound (1C)-F78

¹H-NMR (CDCl₃) δ: 8.40-8.29 (2H, m), 8.01 (1H, d), 7.69 (1H, s), 7.64 (1H, d), 7.53 (1H, d), 5.00 (1H, brs), 3.09 (3H, d).

Compound (1C)-F1

¹H-NMR (CDCl₃) δ: 8.39 (1H, s), 8.19 (1H, t), 8.03 (1H, d), 7.74 (1H, s), 7.66-7.55 (1H, m), 7.36 (1H, t), 7.25-7.19 (1H, m), 5.05 (1H, brs), 3.08 (3H, d).

Compound (1C)-C1

¹H-NMR (CDCl₃) δ: 8.40 (1H, s), 7.86 (1H, d), 7.72 (1H, s), 7.59 (1H, brs), 7.54-7.40 (3H, m), 5.15 (1H, brs), 3.08 (3H, d).

Compound (1C)-F506

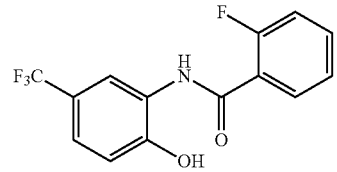 [SMILES: O=C(Nc1cc(C(F)(F)F)ccc1O)c1ccccc1F]

¹H-NMR (DMSO-D₆) δ: 9.59 (1H, d), 8.50 (1H, s), 7.91 (1H, t), 7.70-7.60 (1H, m), 7.45-7.33 (4H, m), 7.07 (1H, d).

The ¹H-NMR data of Compound (1D) are shown below.

Compound (1D)-1

¹H-NMR (CDCl₃) δ: 8.75-8.72 (1H, m), 8.35-8.33 (1H, m), 7.55-7.51 (1H, m), 7.47-7.41 (2H, m), 7.37-7.32 (1H, m), 4.12 (1H, brs), 3.84 (3H, s).

The ¹H-NMR data of Compound (1E) are shown below.

Compound (1E)-F505

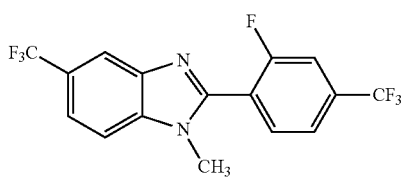 [SMILES: Cn1c(-c2ccc(C(F)(F)F)cc2F)nc2cc(C(F)(F)F)ccc21]

¹H-NMR (CDCl₃) δ: 8.29 (1H, d), 7.90 (1H, t), 7.81 (1H, dd), 7.66 (1H, d), 7.57 (1H, d), 7.48 (1H, d), 3.82 (3H, d).

Compound (1E)-F9

¹H-NMR (CDCl₃) δ: 8.77-8.75 (1H, m), 8.37-8.35 (1H, m), 7.93-7.87 (1H, m), 7.80 (1H, dd), 7.74 (1H, dd), 3.92 (3H, d).

Compound (1E)-F7

¹H-NMR (CDCl₃) δ: 8.75-8.73 (1H, m), 8.34-8.32 (1H, m), 7.81 (1H, t), 7.29-7.25 (1H, m), 7.22-7.18 (1H, m), 3.91 (3H, d).

Compound (1E)-F42

¹H-NMR (CDCl₃) δ: 8.13 (1H, s), 7.91 (1H, t), 7.67-7.61 (2H, m), 7.58-7.51 (2H, m), 3.82 (3H, d).

Compound (1E)-C1

¹H-NMR (CDCl₃) δ: 8.73 (1H, dd), 8.33 (1H, dd), 7.61-7.51 (3H, m), 7.51-7.45 (1H, m), 3.81 (3H, s)

Compound (1E)-F1

¹H-NMR (CDCl₃) δ: 8.72 (1H, d), 8.32 (1H, d), 7.79-7.65 (1H, m), 7.63-7.58 (1H, m), 7.42-7.36 (1H, m), 7.33-7.25 (1H, m), 3.89 (3H, d)

Compound (1E)-F506

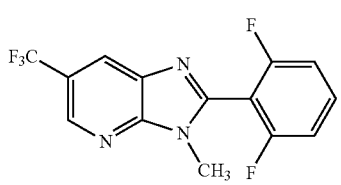

¹H-NMR (CDCl₃) δ: 8.76-8.74 (1H, m), 8.37-8.35 (1H, m), 7.63-7.55 (1H, m), 7.15 (2H, t), 3.86 (3H, s).

Compound (1E)-F507

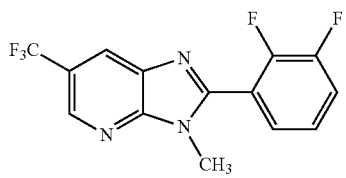 [SMILES: Cn1c(-c2cccc(F)c2F)nc2cc(C(F)(F)F)cnc21]

¹H-NMR (CDCl₃) δ: 8.76-8.73 (1H, m), 8.35-8.33 (1H, m), 7.53-7.40 (2H, m), 7.37-7.30 (1H, m), 3.92 (3H, d).

Compound (1E)-F508

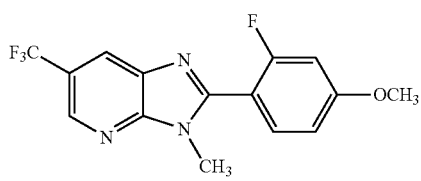 [SMILES: COc1ccc(-c2nc3cc(C(F)(F)F)cnc3n2C)c(F)c1]

¹H-NMR (CDCl₃) δ: 8.73-8.71 (1H, m), 8.33-8.31 (1H, m), 7.33-7.18 (3H, m), 3.99 (3H, s), 3.89 (3H, d).

Compound (1E)-F509

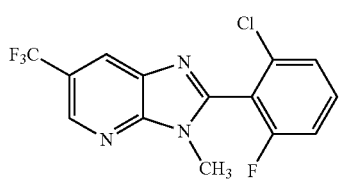 [SMILES: Cn1c(-c2c(F)cccc2Cl)nc2cc(C(F)(F)F)cnc21]

¹H-NMR (CDCl₃) δ: 8.70-8.69 (1H, m), 8.30-8.28 (1H, m), 7.66 (1H, t), 6.91 (1H, dd), 6.81 (1H, dd), 3.91 (3H, s), 3.88 (3H, d).

Compound (1E)-F3

¹H-NMR (CDCl₃) δ: 8.74-8.72 (1H, m), 8.33-8.31 (1H, m), 7.70 (1H, t), 7.39 (1H, dd), 7.34 (1H, dd), 3.89 (3H, d).

Compound (1E)-C505

¹H-NMR (CDCl₃) δ: 8.76-8.74 (1H, m), 8.38-8.36 (1H, m), 7.58-7.51 (1H, m), 7.43 (1H, d), 7.23 (1H, t), 3.80 (3H, s).

Compound (1E)-F510

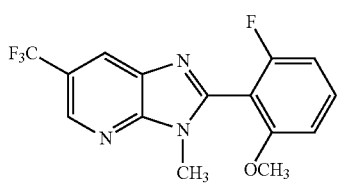 [SMILES: COc1cccc(F)c1-c1nc2cc(C(F)(F)F)cnc2n1C]

¹H-NMR (CDCl₃) δ: 8.72-8.70 (1H, m), 8.33-8.31 (1H, m), 7.56-7.49 (1H, m), 6.93-6.86 (2H, m), 3.84 (3H, s), 3.77 (3H, s).

Compound (1E)-F511

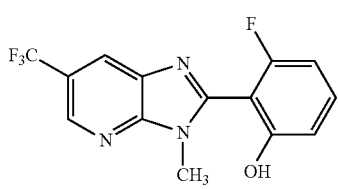

¹H-NMR (CDCl₃) δ: 10.78 (1H, brs), 8.76-8.74 (1H, m), 8.33-8.31 (1H, m), 7.46-7.39 (1H, m), 6.98 (1H, d), 6.84-6.78 (1H, m), 3.96 (3H, d).

Compound (1E)-C506

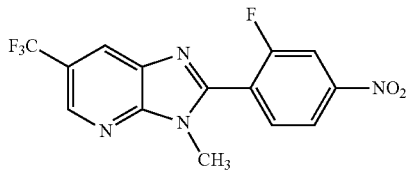 [SMILES: Cn1c(-c2ccc([N+](=O)[O-])cc2F)nc2cc(C(F)(F)F)cnc21]

¹H-NMR (CDCl₃) δ: 8.79-8.77 (1H, m), 8.48 (1H, d), 8.38-8.36 (1H, m), 8.34 (1H, dd), 7.82 (1H, d), 3.84 (3H, s).

Compound (1E)-C507

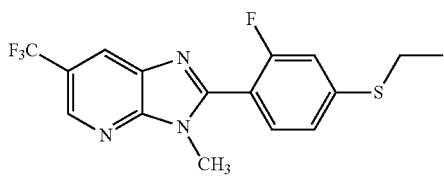 [SMILES: CCSc1ccc(-c2nc3cc(C(F)(F)F)cnc3n2C)c(F)c1]

¹H-NMR (CDCl₃) δ: 8.73-8.71 (1H, m), 8.33-8.31 (1H, m), 7.48-7.43 (2H, m), 7.32 (1H, dd), 3.81 (3H, s), 3.06 (2H, q), 1.41 (3H, t).

Compound (1E)-F512

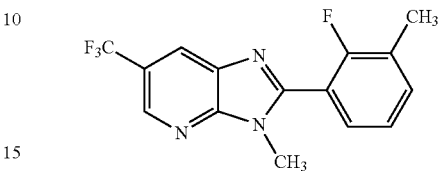

¹H-NMR (CDCl₃) δ: 8.73-8.70 (1H, m), 8.32-8.30 (1H, m), 7.55-7.49 (1H, m), 7.47-7.41 (1H, m), 7.31-7.22 (1H, m), 3.88 (3H, d), 2.40 (3H, d).

Compound (1E)-F5

¹H-NMR (CDCl₃) δ: 8.71-8.69 (1H, m), 8.31-8.30 (1H, m), 7.61 (1H, t), 7.18 (1H, d), 7.10 (1H, d), 3.88 (3H, d), 2.48 (3H, s).

Compound (1E)-F4

¹H-NMR (CDCl₃) δ: 8.74-8.72 (1H, m), 8.33-8.32 (1H, m), 7.63 (1H, t), 7.56-7.48 (2H, m), 3.88 (3H, d).

Compound (1E)-F513

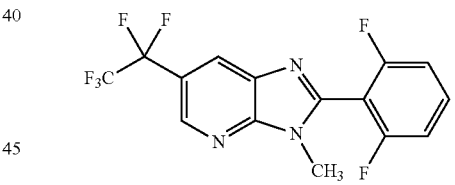

¹H-NMR (CDCl₃) δ: 8.70-8.68 (1H, m), 8.35-8.33 (1H, m), 7.64-7.55 (1H, m), 7.18-7.12 (2H, m), 3.86 (3H, s).

Compound (1E)-F514

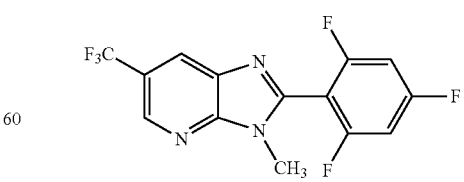

¹H-NMR (CDCl₃) δ: 8.77-8.75 (1H, m), 8.40-8.38 (1H, m), 6.96-6.90 (2H, m), 6.75 (1H, t), 3.86-3.85 (3H, m).

Compound (1E)-F515

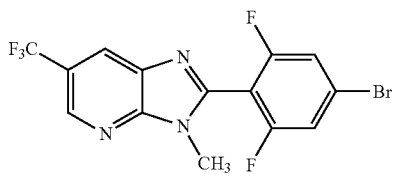 [SMILES: Cn1c(-c2c(F)cc(Br)cc2F)nc2cc(C(F)(F)F)cnc21]

¹H-NMR (CDCl₃) δ: 8.76-8.74 (1H, m), 8.37-8.35 (1H, m), 7.38-7.33 (2H, m), 3.85 (3H, s).

Compound (1E)-F516

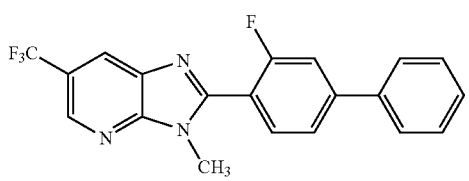

¹H-NMR (CDCl₃) δ: 8.74-8.73 (1H, m), 8.35-8.33 (1H, m), 7.81 (1H, t), 7.69-7.65 (2H, m), 7.63-7.60 (1H, m), 7.55-7.49 (3H, m), 7.48-7.43 (1H, m), 3.94 (3H, d).

Compound (1E)-F517

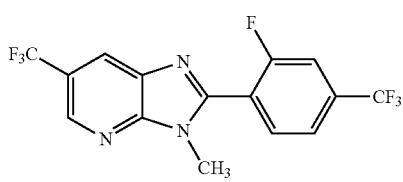 [SMILES: Cn1c(-c2ccc(C(F)(F)F)cc2F)nc2cc(C(F)(F)F)cnc21]

¹H-NMR (CDCl₃) δ: 8.79-8.77 (1H, m), 8.40-8.38 (1H, m), 7.47-7.42 (2H, m), 3.87 (3H, s).

Compound (1E)-F518

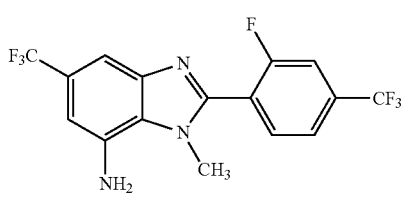 [SMILES: Cn1c(-c2ccc(C(F)(F)F)cc2F)nc2cc(C(F)(F)F)cc(N)c21]

¹H-NMR (CDCl₃) δ: 7.90 (1H, t), 7.63 (1H, dd), 7.59 (1H, d), 7.54 (1H, d), 6.84 (1H, d), 4.05 (3H, d), 4.02 (2H, brs).

Compound (1E)-C508

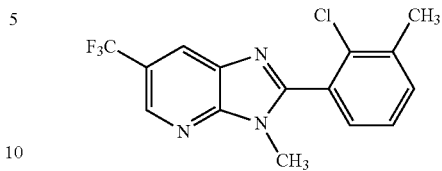

¹H-NMR (CDCl₃) δ: 8.74-8.72 (1H, m), 8.35-8.33 (1H, m), 7.50-7.47 (1H, m), 7.41-7.34 (2H, m), 3.79 (3H, s), 2.50 (3H, s).

Compound (1E)-F519

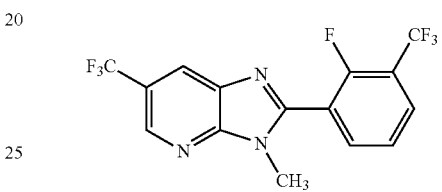

¹H-NMR (CDCl₃) δ: 8.76-8.75 (1H, m), 8.36-8.34 (1H, m), 7.99-7.94 (1H, m), 7.91-7.86 (1H, m), 7.54-7.49 (1H, m), 3.92 (3H, d).

Compound (1E)-F78

¹H-NMR (CDCl₃) δ: 8.71-8.69 (1H, m), 8.34-8.33 (1H, m), 7.93-7.88 (1H, m), 7.69-7.66 (1H, m), 7.61-7.57 (1H, m), 3.92 (3H, d).

Compound (1E)-F77

¹H-NMR (CDCl₃) δ: 8.65 (1H, s), 8.29 (1H, s), 7.64-7.58 (1H, m), 7.20-7.17 (1H, m), 7.13-7.08 (1H, m), 3.90-3.87 (3H, m), 2.49 (3H, s).

Compound (1E)-F149

¹H-NMR (CDCl₃) δ: 8.66-8.64 (1H, m), 8.39-8.37 (1H, m), 7.60 (1H, t), 7.20-7.16 (1H, m), 7.12-7.08 (1H, m), 3.86 (3H, d), 2.48 (3H, s).

Compound (1E)-F73

¹H-NMR (CDCl₃) δ: 8.67 (1H, d), 8.30 (1H, d), 7.74 (1H, td), 7.66-7.57 (1H, m), 7.39 (1H, td), 7.34-7.27 (1H, m), 3.90 (3H, d).

Compound (1E)-C73

¹H-NMR (CDCl₃) δ: 8.68 (1H, d), 8.31 (1H, d), 7.62-7.53 (3H, m), 7.48 (1H, td), 3.81 (3H, s).

Compound (1E)-F79

¹H-NMR (CDCl₃) δ: 8.70-8.68 (1H, m), 8.33-8.30 (1H, m), 7.81 (1H, t), 7.30-7.25 (1H, m), 7.22-7.18 (1H, m), 3.91 (3H, d).

The above intermediate, Compounds (1F)-(1G) are shown in the following tables.

A compound of the formula (1F):

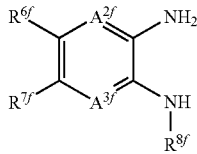

wherein $A^{2f}$ represents =CH—, $R^{7f}$ represents a hydrogen atom, and $R^{6f}$, $R^{8f}$, and $A^{3f}$ represent a combination of $R^{6x}$, $R^{8x}$, and $A^{3x}$, respectively, shown in Tables 59-61 (Compounds ((1F)-1)-((1F)-56)).

A compound of the formula (1G):

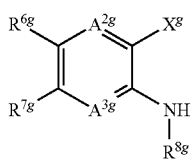

wherein $X^g$ represents a chlorine atom, $A^{2g}$ represents =CH—, $R^{7g}$ represents a hydrogen atom, and $R^{6g}$, $R^{8g}$, and $A^{3g}$ represent a combination of $R^{6x}$, $R^{8x}$, and $A^{3x}$, respectively, shown in Tables 59-61 (Compounds ((1G)-C1)-((1G)-C56)).

A compound of the formula (1G) wherein $X^g$ represents a bromine atom, $A^{2g}$ represents =CH—, $R^{7g}$ represents a hydrogen atom, and $R^{6g}$, $R^{8g}$, and $A^{3g}$ represent a combination of $R^{6x}$, $R^{8x}$, and $A^{3x}$, respectively, shown in Tables 59-61 (Compounds ((1G)-B1)-((1G)-B56)).

TABLE 59

| Intermediate | $R^{6x}$ | $R^{8x}$ | $A^{3x}$ |
|---|---|---|---|
| 1 | $CF_3$ | $CH_3$ | N |
| 2 | $CF_2CF_3$ | $CH_3$ | N |
| 3 | $SCF_3$ | $CH_3$ | N |
| 4 | $SOCF_3$ | $CH_3$ | N |
| 5 | $SO_2CF_3$ | $CH_3$ | N |
| 6 | I | $CH_3$ | N |
| 7 | $SF_5$ | $CH_3$ | N |
| 8 | $CF_3$ | $CH_2CH_3$ | N |
| 9 | $CF_2CF_3$ | $CH_2CH_3$ | N |
| 10 | $SCF_3$ | $CH_2CH_3$ | N |
| 11 | $SOCF_3$ | $CH_2CH_3$ | N |
| 12 | $SO_2CF_3$ | $CH_2CH_3$ | N |
| 13 | I | $CH_2CH_3$ | N |
| 14 | $SF_5$ | $CH_2CH_3$ | N |
| 15 | $CF_3$ | $CH(CH_3)_2$ | N |
| 16 | $CF_2CF_3$ | $CH(CH_3)_2$ | N |
| 17 | $SCF_3$ | $CH(CH_3)_2$ | N |
| 18 | $SOCF_3$ | $CH(CH_3)_2$ | N |
| 19 | $SO_2CF_3$ | $CH(CH_3)_2$ | N |
| 20 | I | $CH(CH_3)_2$ | N |
| 21 | $SF_5$ | $CH(CH_3)_2$ | N |
| 22 | $CF_3$ | H | N |
| 23 | $CF_2CF_3$ | H | N |
| 24 | $SCF_3$ | H | N |
| 25 | $SOCF_3$ | H | N |

TABLE 60

| Intermediate | $R^{6x}$ | $R^{8x}$ | $A^{3x}$ |
|---|---|---|---|
| 26 | $SO_2CF_3$ | H | N |
| 27 | I | H | N |
| 28 | $SF_5$ | H | N |
| 29 | $CF_3$ | $CH_3$ | CH |
| 30 | $CF_2CF_3$ | $CH_3$ | CH |
| 31 | $SCF_3$ | $CH_3$ | CH |
| 32 | $SOCF_3$ | $CH_3$ | CH |
| 33 | $SO_2CF_3$ | $CH_3$ | CH |
| 34 | I | $CH_3$ | CH |
| 35 | $SF_5$ | $CH_3$ | CH |
| 36 | $CF_3$ | $CH_2CH_3$ | CH |
| 37 | $CF_2CF_3$ | $CH_2CH_3$ | CH |
| 38 | $SCF_3$ | $CH_2CH_3$ | CH |
| 39 | $SOCF_3$ | $CH_2CH_3$ | CH |
| 40 | $SO_2CF_3$ | $CH_2CH_3$ | CH |
| 41 | I | $CH_2CH_3$ | CH |
| 42 | $SF_5$ | $CH_2CH_3$ | CH |
| 43 | $CF_3$ | $CH(CH_3)_2$ | CH |
| 44 | $CF_2CF_3$ | $CH(CH_3)_2$ | CH |
| 45 | $SCF_3$ | $CH(CH_3)_2$ | CH |
| 46 | $SOCF_3$ | $CH(CH_3)_2$ | CH |
| 47 | $SO_2CF_3$ | $CH(CH_3)_2$ | CH |
| 48 | I | $CH(CH_3)_2$ | CH |
| 49 | $SF_5$ | $CH(CH_3)_2$ | CH |
| 50 | $CF_3$ | H | CH |

TABLE 61

| Intermediate | $R^{6x}$ | $R^{8x}$ | $A^{3x}$ |
|---|---|---|---|
| 51 | $CF_2CF_3$ | H | CH |
| 52 | $SCF_3$ | H | CH |
| 53 | $SOCF_3$ | H | CH |
| 54 | $SO_2CF_3$ | H | CH |
| 55 | I | H | CH |
| 56 | $SF_5$ | H | CH |

The above intermediate, Compounds (1H)-(1I) are shown in the following tables.

A compound of the formula (1H):

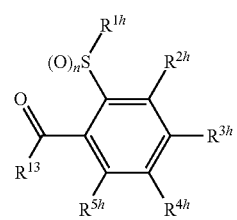

wherein, $R^{1h}$, $R^{2h}$, $R^{3h}$, $R^{4h}$, $R^{5h}$, $R^{13h}$, and n represent a combination of $R^{1x}$, $R^{2x}$, $R^{3x}$, $R^{4x}$, $R^{5x}$, $R^{13x}$, and n, respectively, shown in Tables 62-75 (Compounds ((1H)-1)-((1H)-288)).

A compound of the formula (1I):

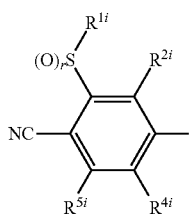

wherein, $R^{1i}$, $R^{2i}$, $R^{3i}$, $R^{4i}$, $R^{5i}$, and r represent a combination of $R^{1x}$, $R^{2x}$, $R^{3x}$, $R^{4x}$, $R^{5x}$, and n, respectively, shown in Tables 63, 64, 66, and 67 (Compounds ((1I)-17)-((1I)-48) and Compounds ((1I)-65)-((1I)-96).

TABLE 62

| Intermediate | $R^{1x}$ | $R^{2x}$ | $R^{3x}$ | $R^{4x}$ | $R^{5x}$ | $R^{13x}$ | n |
|---|---|---|---|---|---|---|---|
| 1 | Me | H | H | H | H | H | 0 |
| 2 | Me | H | F | H | H | H | 0 |
| 3 | Me | H | Cl | H | H | H | 0 |
| 4 | Me | H | Br | H | H | H | 0 |
| 5 | Me | H | Me | H | H | H | 0 |
| 6 | Me | H | Et | H | H | H | 0 |
| 7 | Me | H | Pr | H | H | H | 0 |
| 8 | Me | H | $CF_3$ | H | H | H | 0 |
| 9 | Me | H | $C_2F_5$ | H | H | H | 0 |
| 10 | Me | H | $SF_5$ | H | H | H | 0 |
| 11 | Me | H | $OCH_3$ | H | H | H | 0 |
| 12 | Me | H | $OC_2H_5$ | H | H | H | 0 |
| 13 | Me | H | $OCF_3$ | H | H | H | 0 |
| 14 | Me | H | $SCF_3$ | H | H | H | 0 |
| 15 | Me | H | $SOCF_3$ | H | H | H | 0 |
| 16 | Me | H | $SO_2CF_3$ | H | H | H | 0 |

TABLE 63

| Intermediate | $R^{1x}$ | $R^{2x}$ | $R^{3x}$ | $R^{4x}$ | $R^{5x}$ | $R^{13x}$ | n |
|---|---|---|---|---|---|---|---|
| 17 | Me | H | H | H | H | H | 1 |
| 18 | Me | H | F | H | H | H | 1 |
| 19 | Me | H | Cl | H | H | H | 1 |
| 20 | Me | H | Br | H | H | H | 1 |
| 21 | Me | H | Me | H | H | H | 1 |
| 22 | Me | H | Et | H | H | H | 1 |
| 23 | Me | H | Pr | H | H | H | 1 |
| 24 | Me | H | $CF_3$ | H | H | H | 1 |
| 25 | Me | H | $C_2F_5$ | H | H | H | 1 |

TABLE 64

| Intermediate | $R^{1x}$ | $R^{2x}$ | $R^{3x}$ | $R^{4x}$ | $R^{5x}$ | $R^{13x}$ | n |
|---|---|---|---|---|---|---|---|
| 26 | Me | H | $SF_5$ | H | H | H | 1 |
| 27 | Me | H | $OCH_3$ | H | H | H | 1 |
| 28 | Me | H | $OC_2H_5$ | H | H | H | 1 |
| 29 | Me | H | $OCF_3$ | H | H | H | 1 |
| 30 | Me | H | $SCF_3$ | H | H | H | 1 |
| 31 | Me | H | $SOCF_3$ | H | H | H | 1 |
| 32 | Me | H | $SO_2CF_3$ | H | H | H | 1 |
| 33 | Me | H | H | H | H | H | 2 |
| 34 | Me | H | F | H | H | H | 2 |
| 35 | Me | H | Cl | H | H | H | 2 |
| 36 | Me | H | Br | H | H | H | 2 |
| 37 | Me | H | Me | H | H | H | 2 |
| 38 | Me | H | Et | H | H | H | 2 |
| 39 | Me | H | Pr | H | H | H | 2 |
| 40 | Me | H | $CF_3$ | H | H | H | 2 |
| 41 | Me | H | $C_2F_5$ | H | H | H | 2 |

TABLE 64-continued

| Intermediate | $R^{1x}$ | $R^{2x}$ | $R^{3x}$ | $R^{4x}$ | $R^{5x}$ | $R^{13x}$ | n |
|---|---|---|---|---|---|---|---|
| 42 | Me | H | $SF_5$ | H | H | H | 2 |
| 43 | Me | H | $OCH_3$ | H | H | H | 2 |
| 44 | Me | H | $OC_2H_5$ | H | H | H | 2 |
| 45 | Me | H | $OCF_3$ | H | H | H | 2 |
| 46 | Me | H | $SCF_3$ | H | H | H | 2 |
| 47 | Me | H | $SOCF_3$ | H | H | H | 2 |
| 48 | Me | H | $SO_2CF_3$ | H | H | H | 2 |

TABLE 65

| Intermediate | $R^{1x}$ | $R^{2x}$ | $R^{3x}$ | $R^{4x}$ | $R^{5x}$ | $R^{13x}$ | n |
|---|---|---|---|---|---|---|---|
| 49 | Et | H | H | H | H | H | 0 |
| 50 | Et | H | F | H | H | H | 0 |
| 51 | Et | H | Cl | H | H | H | 0 |
| 52 | Et | H | Br | H | H | H | 0 |
| 53 | Et | H | Me | H | H | H | 0 |
| 54 | Et | H | Et | H | H | H | 0 |
| 55 | Et | H | Pr | H | H | H | 0 |
| 56 | Et | H | $CF_3$ | H | H | H | 0 |
| 57 | Et | H | $C_2F_5$ | H | H | H | 0 |
| 58 | Et | H | $SF_5$ | H | H | H | 0 |
| 59 | Et | H | $OCH_3$ | H | H | H | 0 |
| 60 | Et | H | $OC_2H_5$ | H | H | H | 0 |
| 61 | Et | H | $OCF_3$ | H | H | H | 0 |
| 62 | Et | H | $SCF_3$ | H | H | H | 0 |
| 63 | Et | H | $SOCF_3$ | H | H | H | 0 |
| 64 | Et | H | $SO_2CF_3$ | H | H | H | 0 |

TABLE 66

| Intermediate | $R^{1x}$ | $R^{2x}$ | $R^{3x}$ | $R^{4x}$ | $R^{5x}$ | $R^{13x}$ | n |
|---|---|---|---|---|---|---|---|
| 65 | Et | H | H | H | H | H | 1 |
| 66 | Et | H | F | H | H | H | 1 |
| 67 | Et | H | Cl | H | H | H | 1 |
| 68 | Et | H | Br | H | H | H | 1 |
| 69 | Et | H | Me | H | H | H | 1 |
| 70 | Et | H | Et | H | H | H | 1 |
| 71 | Et | H | Pr | H | H | H | 1 |
| 72 | Et | H | $CF_3$ | H | H | H | 1 |
| 73 | Et | H | $C_2F_5$ | H | H | H | 1 |
| 74 | Et | H | $SF_5$ | H | H | H | 1 |
| 75 | Et | H | $OCH_3$ | H | H | H | 1 |
| 76 | Et | H | $OC_2H_5$ | H | H | H | 1 |
| 77 | Et | H | $OCF_3$ | H | H | H | 1 |
| 78 | Et | H | $SCF_3$ | H | H | H | 1 |
| 79 | Et | H | $SOCF_3$ | H | H | H | 1 |
| 80 | Et | H | $SO_2CF_3$ | H | H | H | 1 |
| 81 | Et | H | H | H | H | H | 2 |
| 82 | Et | H | F | H | H | H | 2 |
| 83 | Et | H | Cl | H | H | H | 2 |
| 84 | Et | H | Br | H | H | H | 2 |
| 85 | Et | H | Me | H | H | H | 2 |
| 86 | Et | H | Et | H | H | H | 2 |
| 87 | Et | H | Pr | H | H | H | 2 |
| 88 | Et | H | $CF_3$ | H | H | H | 2 |
| 89 | Et | H | $C_2F_5$ | H | H | H | 2 |

TABLE 67

| Intermediate | $R^{1x}$ | $R^{2x}$ | $R^{3x}$ | $R^{4x}$ | $R^{5x}$ | $R^{13x}$ | n |
|---|---|---|---|---|---|---|---|
| 90 | Et | H | $SF_5$ | H | H | H | 2 |
| 91 | Et | H | $OCH_3$ | H | H | H | 2 |
| 92 | Et | H | $OC_2H_5$ | H | H | H | 2 |
| 93 | Et | H | $OCF_3$ | H | H | H | 2 |
| 94 | Et | H | $SCF_3$ | H | H | H | 2 |
| 95 | Et | H | $SOCF_3$ | H | H | H | 2 |
| 96 | Et | H | $SO_2CF_3$ | H | H | H | 2 |

TABLE 68

| Intermediate | $R^{1x}$ | $R^{2x}$ | $R^{3x}$ | $R^{4x}$ | $R^{5x}$ | $R^{13x}$ | n |
|---|---|---|---|---|---|---|---|
| 97 | Me | H | H | H | H | OH | 0 |
| 98 | Me | H | F | H | H | OH | 0 |
| 99 | Me | H | Cl | H | H | OH | 0 |
| 100 | Me | H | Br | H | H | OH | 0 |
| 101 | Me | H | Me | H | H | OH | 0 |
| 102 | Me | H | Et | H | H | OH | 0 |
| 103 | Me | H | Pr | H | H | OH | 0 |
| 104 | Me | H | $CF_3$ | H | H | OH | 0 |
| 105 | Me | H | $C_2F_5$ | H | H | OH | 0 |
| 106 | Me | H | $SF_5$ | H | H | OH | 0 |
| 107 | Me | H | $OCH_3$ | H | H | OH | 0 |
| 108 | Me | H | $OC_2H_5$ | H | H | OH | 0 |
| 109 | Me | H | $OCF_3$ | H | H | OH | 0 |
| 110 | Me | H | $SCF_3$ | H | H | OH | 0 |
| 111 | Me | H | $SOCF_3$ | H | H | OH | 0 |
| 112 | Me | H | $SO_2CF_3$ | H | H | OH | 0 |
| 113 | Me | H | H | H | H | OH | 1 |
| 114 | Me | H | F | H | H | OH | 1 |
| 115 | Me | H | Cl | H | H | OH | 1 |
| 116 | Me | H | Br | H | H | OH | 1 |
| 117 | Me | H | Me | H | H | OH | 1 |
| 118 | Me | H | Et | H | H | OH | 1 |
| 119 | Me | H | Pr | H | H | OH | 1 |
| 120 | Me | H | $CF_3$ | H | H | OH | 1 |

TABLE 69

| Intermediate | $R^{1x}$ | $R^{2x}$ | $R^{3x}$ | $R^{4x}$ | $R^{5x}$ | $R^{13x}$ | n |
|---|---|---|---|---|---|---|---|
| 121 | Me | H | $C_2F_5$ | H | H | OH | 1 |
| 122 | Me | H | $SF_5$ | H | H | OH | 1 |
| 123 | Me | H | $OCH_3$ | H | H | OH | 1 |
| 124 | Me | H | $OC_2H_5$ | H | H | OH | 1 |
| 125 | Me | H | $OCF_3$ | H | H | OH | 1 |
| 126 | Me | H | $SCF_3$ | H | H | OH | 1 |
| 127 | Me | H | $SOCF_3$ | H | H | OH | 1 |
| 128 | Me | H | $SO_2CF_3$ | H | H | OH | 1 |
| 129 | Me | H | H | H | H | OH | 2 |
| 130 | Me | H | F | H | H | OH | 2 |
| 131 | Me | H | Cl | H | H | OH | 2 |
| 132 | Me | H | Br | H | H | OH | 2 |
| 133 | Me | H | Me | H | H | OH | 2 |
| 134 | Me | H | Et | H | H | OH | 2 |
| 135 | Me | H | Pr | H | H | OH | 2 |
| 136 | Me | H | $CF_3$ | H | H | OH | 2 |
| 137 | Me | H | $C_2F_5$ | H | H | OH | 2 |
| 138 | Me | H | $SF_5$ | H | H | OH | 2 |
| 139 | Me | H | $OCH_3$ | H | H | OH | 2 |
| 140 | Me | H | $OC_2H_5$ | H | H | OH | 2 |
| 141 | Me | H | $OCF_3$ | H | H | OH | 2 |
| 142 | Me | H | $SCF_3$ | H | H | OH | 2 |
| 143 | Me | H | $SOCF_3$ | H | H | OH | 2 |
| 144 | Me | H | $SO_2CF_3$ | H | H | OH | 2 |
| 145 | Et | H | H | H | H | OH | 0 |

TABLE 70

| Intermediate | $R^{1x}$ | $R^{2x}$ | $R^{3x}$ | $R^{4x}$ | $R^{5x}$ | $R^{13x}$ | n |
|---|---|---|---|---|---|---|---|
| 146 | Et | H | F | H | H | OH | 0 |
| 147 | Et | H | Cl | H | H | OH | 0 |
| 148 | Et | H | Br | H | H | OH | 0 |
| 149 | Et | H | Me | H | H | OH | 0 |
| 150 | Et | H | Et | H | H | OH | 0 |
| 151 | Et | H | Pr | H | H | OH | 0 |
| 152 | Et | H | $CF_3$ | H | H | OH | 0 |
| 153 | Et | H | $C_2F_5$ | H | H | OH | 0 |
| 154 | Et | H | $SF_5$ | H | H | OH | 0 |
| 155 | Et | H | $OCH_3$ | H | H | OH | 0 |
| 156 | Et | H | $OC_2H_5$ | H | H | OH | 0 |
| 157 | Et | H | $OCF_3$ | H | H | OH | 0 |
| 158 | Et | H | $SCF_3$ | H | H | OH | 0 |
| 159 | Et | H | $SOCF_3$ | H | H | OH | 0 |
| 160 | Et | H | $SO_2CF_3$ | H | H | OH | 0 |
| 161 | Et | H | H | H | H | OH | 1 |
| 162 | Et | H | F | H | H | OH | 1 |
| 163 | Et | H | Cl | H | H | OH | 1 |
| 164 | Et | H | Br | H | H | OH | 1 |
| 165 | Et | H | Me | H | H | OH | 1 |
| 166 | Et | H | Et | H | H | OH | 1 |
| 167 | Et | H | Pr | H | H | OH | 1 |
| 168 | Et | H | $CF_3$ | H | H | OH | 1 |
| 169 | Et | H | $C_2F_5$ | H | H | OH | 1 |
| 170 | Et | H | $SF_5$ | H | H | OH | 1 |

TABLE 71

| Intermediate | $R^{1x}$ | $R^{2x}$ | $R^{3x}$ | $R^{4x}$ | $R^{5x}$ | $R^{13x}$ | n |
|---|---|---|---|---|---|---|---|
| 171 | Et | H | $OCH_3$ | H | H | OH | 1 |
| 172 | Et | H | $OC_2H_5$ | H | H | OH | 1 |
| 173 | Et | H | $OCF_3$ | H | H | OH | 1 |
| 174 | Et | H | $SCF_3$ | H | H | OH | 1 |
| 175 | Et | H | $SOCF_3$ | H | H | OH | 1 |
| 176 | Et | H | $SO_2CF_3$ | H | H | OH | 1 |
| 177 | Et | H | H | H | H | OH | 2 |
| 178 | Et | H | F | H | H | OH | 2 |
| 179 | Et | H | Cl | H | H | OH | 2 |
| 180 | Et | H | Br | H | H | OH | 2 |
| 181 | Et | H | Me | H | H | OH | 2 |
| 182 | Et | H | Et | H | H | OH | 2 |
| 183 | Et | H | Pr | H | H | OH | 2 |
| 184 | Et | H | $CF_3$ | H | H | OH | 2 |
| 185 | Et | H | $C_2F_5$ | H | H | OH | 2 |
| 186 | Et | H | $SF_5$ | H | H | OH | 2 |
| 187 | Et | H | $OCH_3$ | H | H | OH | 2 |
| 188 | Et | H | $OC_2H_5$ | H | H | OH | 2 |
| 189 | Et | H | $OCF_3$ | H | H | OH | 2 |
| 190 | Et | H | $SCF_3$ | H | H | OH | 2 |
| 191 | Et | H | $SOCF_3$ | H | H | OH | 2 |
| 192 | Et | H | $SO_2CF_3$ | H | H | OH | 2 |
| 193 | Me | H | H | H | H | Cl | 0 |
| 194 | Me | H | F | H | H | Cl | 0 |
| 195 | Me | H | Cl | H | H | Cl | 0 |

TABLE 72

| Intermediate | $R^{1x}$ | $R^{2x}$ | $R^{3x}$ | $R^{4x}$ | $R^{5x}$ | $R^{13x}$ | n |
|---|---|---|---|---|---|---|---|
| 196 | Me | H | Br | H | H | Cl | 0 |
| 197 | Me | H | Me | H | H | Cl | 0 |
| 198 | Me | H | Et | H | H | Cl | 0 |
| 199 | Me | H | Pr | H | H | Cl | 0 |
| 200 | Me | H | $CF_3$ | H | H | Cl | 0 |
| 201 | Me | H | $C_2F_5$ | H | H | Cl | 0 |
| 202 | Me | H | $SF_5$ | H | H | Cl | 0 |
| 203 | Me | H | $OCH_3$ | H | H | Cl | 0 |
| 204 | Me | H | $OC_2H_5$ | H | H | Cl | 0 |
| 205 | Me | H | $OCF_3$ | H | H | Cl | 0 |
| 206 | Me | H | $SCF_3$ | H | H | Cl | 0 |
| 207 | Me | H | $SOCF_3$ | H | H | Cl | 0 |
| 208 | Me | H | $SO_2CF_3$ | H | H | Cl | 0 |
| 209 | Me | H | H | H | H | Cl | 1 |
| 210 | Me | H | F | H | H | Cl | 1 |
| 211 | Me | H | Cl | H | H | Cl | 1 |
| 212 | Me | H | Br | H | H | Cl | 1 |
| 213 | Me | H | Me | H | H | Cl | 1 |
| 214 | Me | H | Et | H | H | Cl | 1 |
| 215 | Me | H | Pr | H | H | Cl | 1 |
| 216 | Me | H | $CF_3$ | H | H | Cl | 1 |
| 217 | Me | H | $C_2F_5$ | H | H | Cl | 1 |
| 218 | Me | H | $SF_5$ | H | H | Cl | 1 |
| 219 | Me | H | $OCH_3$ | H | H | Cl | 1 |
| 220 | Me | H | $OC_2H_5$ | H | H | Cl | 1 |

TABLE 73

| Intermediate | $R^{1x}$ | $R^{2x}$ | $R^{3x}$ | $R^{4x}$ | $R^{5x}$ | $R^{13x}$ | n |
|---|---|---|---|---|---|---|---|
| 221 | Me | H | $OCF_3$ | H | H | Cl | 1 |
| 222 | Me | H | $SCF_3$ | H | H | Cl | 1 |
| 223 | Me | H | $SOCF_3$ | H | H | Cl | 1 |
| 224 | Me | H | $SO_2CF_3$ | H | H | Cl | 1 |
| 225 | Me | H | H | H | H | Cl | 2 |
| 226 | Me | H | F | H | H | Cl | 2 |
| 227 | Me | H | Cl | H | H | Cl | 2 |
| 228 | Me | H | Br | H | H | Cl | 2 |
| 229 | Me | H | Me | H | H | Cl | 2 |
| 230 | Me | H | Et | H | H | Cl | 2 |
| 231 | Me | H | Pr | H | H | Cl | 2 |
| 232 | Me | H | $CF_3$ | H | H | Cl | 2 |
| 233 | Me | H | $C_2F_5$ | H | H | Cl | 2 |
| 234 | Me | H | $SF_5$ | H | H | Cl | 2 |
| 235 | Me | H | $OCH_3$ | H | H | Cl | 2 |
| 236 | Me | H | $OC_2H_5$ | H | H | Cl | 2 |
| 237 | Me | H | $OCF_3$ | H | H | Cl | 2 |
| 238 | Me | H | $SCF_3$ | H | H | Cl | 2 |
| 239 | Me | H | $SOCF_3$ | H | H | Cl | 2 |
| 240 | Me | H | $SO_2CF_3$ | H | H | Cl | 2 |
| 241 | Et | H | H | H | H | Cl | 0 |
| 242 | Et | H | F | H | H | Cl | 0 |
| 243 | Et | H | Cl | H | H | Cl | 0 |
| 244 | Et | H | Br | H | H | Cl | 0 |
| 245 | Et | H | Me | H | H | Cl | 0 |

TABLE 74

| Intermediate | $R^{1x}$ | $R^{2x}$ | $R^{3x}$ | $R^{4x}$ | $R^{5x}$ | $R^{13x}$ | n |
|---|---|---|---|---|---|---|---|
| 246 | Et | H | Et | H | H | Cl | 0 |
| 247 | Et | H | Pr | H | H | Cl | 0 |
| 248 | Et | H | $CF_3$ | H | H | Cl | 0 |
| 249 | Et | H | $C_2F_5$ | H | H | Cl | 0 |
| 250 | Et | H | $SF_5$ | H | H | Cl | 0 |
| 251 | Et | H | $OCH_3$ | H | H | Cl | 0 |
| 252 | Et | H | $OC_2H_5$ | H | H | Cl | 0 |
| 253 | Et | H | $OCF_3$ | H | H | Cl | 0 |
| 254 | Et | H | $SCF_3$ | H | H | Cl | 0 |
| 255 | Et | H | $SOCF_3$ | H | H | Cl | 0 |
| 256 | Et | H | $SO_2CF_3$ | H | H | Cl | 0 |
| 257 | Et | H | H | H | H | Cl | 1 |
| 258 | Et | H | F | H | H | Cl | 1 |
| 259 | Et | H | Cl | H | H | Cl | 1 |
| 260 | Et | H | Br | H | H | Cl | 1 |
| 261 | Et | H | Me | H | H | Cl | 1 |
| 262 | Et | H | Et | H | H | Cl | 1 |
| 263 | Et | H | Pr | H | H | Cl | 1 |
| 264 | Et | H | $CF_3$ | H | H | Cl | 1 |
| 265 | Et | H | $C_2F_5$ | H | H | Cl | 1 |
| 266 | Et | H | $SF_5$ | H | H | Cl | 1 |
| 267 | Et | H | $OCH_3$ | H | H | Cl | 1 |
| 268 | Et | H | $OC_2H_5$ | H | H | Cl | 1 |
| 269 | Et | H | $OCF_3$ | H | H | Cl | 1 |
| 270 | Et | H | $SCF_3$ | H | H | Cl | 1 |

TABLE 75

| Intermediate | $R^{1x}$ | $R^{2x}$ | $R^{3x}$ | $R^{4x}$ | $R^{5x}$ | $R^{13x}$ | n |
|---|---|---|---|---|---|---|---|
| 271 | Et | H | $SOCF_3$ | H | H | Cl | 1 |
| 272 | Et | H | $SO_2CF_3$ | H | H | Cl | 1 |
| 273 | Et | H | H | H | H | Cl | 2 |
| 274 | Et | H | F | H | H | Cl | 2 |
| 275 | Et | H | Cl | H | H | Cl | 2 |
| 276 | Et | H | Br | H | H | Cl | 2 |
| 277 | Et | H | Me | H | H | Cl | 2 |
| 278 | Et | H | Et | H | H | Cl | 2 |
| 279 | Et | H | Pr | H | H | Cl | 2 |
| 280 | Et | H | $CF_3$ | H | H | Cl | 2 |
| 281 | Et | H | $C_2F_5$ | H | H | Cl | 2 |
| 282 | Et | H | $SF_5$ | H | H | Cl | 2 |
| 283 | Et | H | $OCH_3$ | H | H | Cl | 2 |
| 284 | Et | H | $OC_2H_5$ | H | H | Cl | 2 |
| 285 | Et | H | $OCF_3$ | H | H | Cl | 2 |
| 286 | Et | H | $SCF_3$ | H | H | Cl | 2 |
| 287 | Et | H | $SOCF_3$ | H | H | Cl | 2 |
| 288 | Et | H | $SO_2CF_3$ | H | H | Cl | 2 |

In the above Tables 62-75, Me represents a methyl group, and Et represents an ethyl group.

The $^1$H-NMR data of Compound (1H) are shown below.

Compound (1H)-184

$^1$H-NMR (CDCl$_3$) δ: 9.23 (1H, brs), 8.37 (1H, brs), 8.03-7.98 (2H, m), 3.63 (2H, q), 1.39 (3H, t)

Compound (1H)-280

$^1$H-NMR (CDCl$_3$) δ: 8.33 (1H, brs), 8.09-7.98 (2H, m), 3.43 (2H, q), 1.38 (3H, t)

Compound (1H)-177

$^1$H-NMR (CDCl$_3$) δ: 8.12 (1H, dd), 7.87 (1H, dd), 7.77-7.68 (2H, m), 3.59 (2H, q), 1.35 (3H, t).

Compound (1H)-248

$^1$H-NMR (CDCl$_3$) δ: 8.22 (1H, d), 7.55 (1H, s), 7.43 (1H, d), 3.02 (2H, q), 1.43 (3H, t).

The $^1$H-NMR data of Compound (1I) are shown below.

Compound (1I)-88

$^1$H-NMR (CDCl$_3$) δ: 8.43-8.42 (1H, m), 8.10-8.03 (2H, m), 3.45 (2H, q), 1.38 (3H, t)

Formulation Example 1

Any one of Present Compounds 1-427 (10 parts) is dissolved in a mixture of xylene (35 parts) and N,N-dimethylformamide (35 parts), and to the mixture is added polyoxyethylene styryl phenyl ether (14 parts) and calcium dodecylbenzenesulfonate (6 parts), and stirred to give emulsions of each compound.

Formulation Example 2

Sodium lauryl sulfate (4 parts), calcium lignin sulfonate (2 parts), synthetic hydrated silicone oxide powder (20 parts) and diatomite (54 parts) are mixed, then to the mixture is added any one of Present Compounds 1-427 (20 parts), and mixed to give wettable powders of each compound.

Formulation Example 3

To any one of Present Compounds 1-427 (2 parts) is added synthetic hydrated silicone oxide powder (1 part), calcium lignin sulfonate (2 parts), bentonite (30 parts), and kaolin clay (65 parts), and mixed. Then, to the mixture is added an appropriate amount of water, further stirred, granulated with a granulator, and draft-dried to give granules of each compound.

Formulation Example 4

Any one of Present Compounds 1-427 (1 part) is dissolved in an appropriate amount of acetone. To the mixture is added synthetic hydrated silicone oxide powder (5 parts), PAP (0.3 parts), and Fubasami clay (93.7 parts), and well stirred. Then, acetone is removed by evaporation to give powders of each compound.

Formulation Example 5

A mixture (ratio by weight=1:1) of polyoxyethylene alkyl ether sulfate ammonium salt and white carbon (35 parts), any one of Present Compounds 1-427 (10 parts), and water (55 parts) are mixed, pulverized by a wet grinding method to give formulations of each compounds.

Formulation Example 6

Any one of Present Compounds 1-427 (0.1 parts) is dissolved in xylene (5 parts) and trichloroethane (5 parts), and mixed with deodorized kerosine (89.9 parts) to give oil solutions of each compounds.

Formulation Example 7

Any one of Present Compounds 1-427 (10 mg) is dissolved in acetone (0.5 ml). The mixture is added to animal powdered solid feed (powdered solid feed for breeding, CE-2, from CLEA Japan, Inc.), (5 g) and mixed uniformly. Then, acetone is removed by evaporation to give poison baits of each compound.

Formulation Example 8

Any one of Present Compounds 1-427 (0.1 parts) and Neothiosol (Chuo Kasei Co. Ltd.) (49.9 parts) are charged into an aerosol container. After an aerosol valve is attached to the container, dimethyl ether (25 parts) and LPG (25 parts) are charged into the container. The container is vibrated, and attaching an actuator to give oily aerosols of each compound.

Formulation Example 9

Any one of Present Compounds 1-427 (0.6 parts), BHT (2,6-di-tert-butyl-4-methylphenol) (0.01 parts), xylene (5 parts), deodorized kerosine (3.39 parts), and an emulsifier (Atmos 300 (a registered trade name for Atmos Chemical Ltd.)) (1 part) are mixed and dissolved. The mixture and distilled water (50 parts) are charged into an aerosol container, and attaching a valve. Then, propellant (LPG) (40 parts) is pressure-charged into the container through the valve to give aqueous aerosols of each compound.

The effects of the present compounds to control pests are shown in Test Examples.

Test Example 1

The test spray solutions were prepared by diluting the formulations of each of Present Compounds 1-7, 10-14, 18-23, 33-38, 46, 53, 55, 66, 68-70, 72, 75, 81-83, 88-90, 98-99, 102-104, 112-113, 115-118, 121-123, 126-142, 144, 151, 156-159, 161, 167-171, 174-176, 183, 185-186, 188, 192-194, 209-210, 214-215, 235, 238-243, 246-256, 259, 262, 264, 270-273, 279-280, 285, 291-292, 294, 297-299, 301-302, 306-313, 316-319, 324-325, 327, 330-331, 333, 343, 345, 353, 357-361, 371 and 374-379 obtained in Formulation Example 5 with water so as to give 500 ppm of an active ingredient concentration.

On the other hand, on a cucumber seedling (the first true leaf stage) planted in a plastic cup was inoculated with about 30 *Aphis gossypii*, and leaving it for a day. Twenty ml of each of the above test spray solutions was sprayed on this seedling.

Six days after spraying, the number of the surviving *Aphis gossypii* parasitized on the leaves of the cucumber was examined, and a control value was calculated according to the following equation:

Control value (%)={1−($Cb \times Tai$)/($Cai \times Tb$)}×100 wherein symbols represent as follows:
Cb: the number of insects in a non-treated section before treatment,
Cai: the number of insects in a non-treated section in observation,
Tb: the number of insects in a treated-section before treatment,
Tai: the number of insects in a treated-section in observation;
wherein the non-treated section represents a section where the test spray solution prepared by diluting the formulation without the present compound in Formulation Example 5 with the same amount of water as in the treated-section was sprayed.

As a result, in the treated-section of the test spray solution of each of Present Compounds 1-7, 10-14, 18-23, 33-38, 46, 53, 55, 66, 68-70, 72, 75, 81-83, 88-90, 98-99, 102-104, 112-113, 115-118, 121-123, 126-142, 144, 151, 156-159, 161, 167-171, 174-176, 183, 185-186, 188, 192-194, 209-210, 214-215, 235, 238-243, 246-256, 259, 262, 264, 270-273, 279-280, 285, 291-292, 294, 297-299, 301-302, 306-313, 316-319, 324-325, 327, 330-331, 333, 343, 345, 353, 357-361, 371 and 374-379, the control value of 90% or more was shown.

Test Example 2

The test diluted solutions were prepared by diluting the formulations of each of Present Compounds 1-6, 13, 14, 16, 21-23, 33, 34, 36, 43, 46, 48-50, 53, 55, 66, 69, 70, 82, 83, 88, 89, 98-100, 116-118, 122-123, 133-135, 137, 139-140, 142-143, 156-159, 167, 169, 171, 175-176, 192-194, 224, 237-239, 241-243, 247, 254, 256, 280, 299, 306, 317-319, 330-331, 333, 353, 376 and 379 obtained in Formulation Example 5 with water so as to give 500 ppm of an active ingredient concentration.

A root part of a cucumber seedling (the first true leaf stage) from which soil had been washed off was immersed in 5 ml of each of the diluted solutions, and one day after treatment, on the cucumber leaf surface was inoculated with 30 *Aphis gossypii* (whole stage). After further seven days, the number of insect of living *Aphis gossypii* parasitized on the leaves of the cucumber was examined, and a control value was calculated according to the following equation:

Control value (%)={1−($Cb \times Tai$)/($Cai \times Tb$)}×100 wherein symbols represent as follows:
Cb: the number of insects in a non-treated section before treatment,
Cai: the number of insects in a non-treated section in observation,
Tb: the number of insects in a treated-section before treatment,
Tai: the number of insects in a treated-section in observation;
wherein the non-treated section represents a section where the test diluted solution prepared by diluting the formulation without the present compound in Formulation Example 5 with the same amount of water as in the treated-section was used.

As a result, in the treated-section of the test diluted solution of each of Present Compounds 1-6, 13, 14, 16, 21-23, 33, 34, 36, 43, 46, 48-50, 53, 55, 66, 69, 70, 82, 83, 88, 89, 98-100, 116-118, 122-123, 133-135, 137, 139-140, 142-143, 156-159, 167, 169, 171, 175-176, 192-194, 224, 237-239, 241-243, 247, 247, 254, 256, 280, 299, 306, 317-319, 330-331, 333, 353, 376 and 379, the control value of 90% or more was shown.

Test Example 3

The test diluted solutions were prepared by diluting the formulations of each of Present Compounds 2-6, 35-38, 50, 55, 89, 90, 112-113, 116-118, 123, 130, 132, 134-135, 157-158, 169-171, 175-176, 194, 209-210, 214-215, 239-240, 242-243, 248, 254, 270-273, 280, 299, 302, 306, 309, 318-319, 330-331, 333, 345, 359, 361 and 375-376 obtained in Formulation Example 5 with water so as to give 500 ppm of an active ingredient concentration.

On the other hand, a cucumber seedling (the second true leaf stage) planted in a plastic cup was drenched at its foot with 5 ml of each of the diluted solutions, and kept in a greenhouse of 25° C. for 7 days. On the cucumber leaf surface was inoculated with 30 *Aphis gossypii* (whole stage), and further kept in the greenhouse for 6 days, then the number of insect of living *Aphis gossypii* parasitized on the leaves of this cucumber was examined, and a control value was calculated according to the following equation:

$$\text{Control value (\%)} = \{1-(Cb \times Tai)/(Cai \times Tb)\} \times 100$$

wherein symbols represent as follows:
Cb: the number of insects in a non-treated section before treatment,
Cai: the number of insects in a non-treated section in observation,
Tb: the number of insects in a treated-section before treatment,
Tai: the number of insects in a treated-section in observation;
wherein the non-treated section represents a section where the test diluted solution prepared by diluting the formulation without the present compound in Formulation Example 5 with the same amount of water as in the treated-section was used.

As a result, in the treated-section of the test diluted solution of each of Present Compounds 2-6, 35-38, 50, 55, 89, 90, 112-113, 116-118, 123, 130, 132, 134-135, 157-158, 169-171, 175-176, 194, 209-210, 214-215, 239-240, 242-243, 248, 254, 270-273, 280, 299, 302, 306, 309, 318-319, 330-331, 333, 345, 359, 361 and 375-376, the control value of 90% or more was shown.

Test Example 4

The test spray solutions were prepared by diluting the formulations of each of Present Compounds 1, 3-7, 12, 14, 21, 33-38, 46, 55, 68, 69, 83, 84, 88-90, 102, 112-113, 116-118, 128, 130-133, 136-139, 142-143, 152, 156-158, 161, 169-171, 174-176, 183-186, 188, 201, 209-210, 214-215, 238, 246, 248, 251, 262, 292, 298-299, 301-302, 306, 308-309, 314, 324-325, 327, 343, 353, 360, 374 and 376 obtained in Formulation Example 5 with water so as to give 500 ppm of an active ingredient concentration.

On the other hand, a rice seedling (the second leaf stage) planted in a polyethylene cup was sprayed with 10 ml of each of the above test spray solutions. After air-drying, third-fourth instar larvae of *Nilaparvata lugens* were released, and kept in the greenhouse of 25° C. After 6 days, the number of insect of living *Nilaparvata lugens* parasitized on the rice was examined, and a control value was calculated according to the following equation:

$$\text{Control value (\%)} = \{1-(Cb \times Tai)/(Cai \times Tb)\} \times 100$$

wherein symbols represent as follows:
Cb: the number of insects in a non-treated section before treatment,
Cai: the number of insects in a non-treated section in observation,
Tb: the number of insects in a treated-section before treatment,
Tai: the number of insects in a treated-section in observation;
wherein the non-treated section represents a section where the test spray solution prepared by diluting the formulation without the present compound in Formulation Example 5 with the same amount of water as in the treated-section was sprayed.

As a result, in the treated-section of the test spray solution of each of Present Compounds 1, 3-7, 12, 14, 21, 33-38, 46, 55, 68, 69, 83, 84, 88-90, 102, 112-113, 116-118, 128, 130-133, 136-139, 142-143, 152, 156-158, 161, 169-171, 174-176, 183-186, 188, 201, 209-210, 214-215, 238, 246, 248, 251, 262, 292, 298-299, 301-302, 306, 308-309, 314, 324-325, 327, 343, 353, 360, 374 and 376, the control value of 90% or more was shown.

Test Example 5

The test diluted solutions were prepared by diluting the formulations of each of Present Compounds 4-6, 33-36, 38, 55, 89, 90, 112-113, 117-118, 123, 130, 132, 137-138, 143, 156-158, 169-171, 174-176, 185, 214, 248, 251, 272, 292, 294, 297-299, 301-302, 306, 324, 327, 343, 345, 353, 357, 359-361 and 374-376 obtained in Formulation Example 5 with water so as to give 500 ppm of an active ingredient concentration.

On the other hand, a rice seedling (2 weeks after sowing, the second leaf stage) planted in a plastic cup was drenched at its foot with 5 ml of each of the diluted solutions, and kept in a greenhouse of 25° C. for 7 days. Twenty third-fourth instar larvae of *Nilaparvata lugens* were released, and further kept in the greenhouse for 6 days, then the number of insect of living *Nilaparvata lugens* parasitized on the rice was examined, and a control value was calculated according to the following equation:

$$\text{Control value (\%)} = \{1-(Cb \times Tai)/(Cai \times Tb)\} \times 100$$

wherein symbols represent as follows:
Cb: the number of insects in a non-treated section before treatment,
Cai: the number of insects in a non-treated section in observation,
Tb: the number of insects in a treated-section before treatment,
Tai: the number of insects in a treated-section in observation;
wherein the non-treated section represents a section where the test diluted solution prepared by diluting the formulation without the present compound in Formulation Example 5 with the same amount of water as in the treated-section was used.

As a result, in the treated-section of the test diluted solution of each of Present Compounds 4-6, 33-36, 38, 55, 89, 90, 112-113, 117-118, 123, 130, 132, 137-138, 143, 156-158, 169-171, 174-176, 185, 214, 248, 251, 272, 292, 294, 297-299, 301-302, 306, 324, 327, 343, 345, 353, 357, 359-361 and 374-376, the control value of 90% or more was shown.

Test Example 6

The test spray solutions were prepared by diluting the formulations of each of Present Compounds 4-6, 21, 22, 49, 50, 55, 75, 88, 112-113, 116-118, 128-132, 161, 169-171, 174-176, 188, 209-210, 214-215, 238-240, 247-248, 255, 259, 262, 270-273, 280, 291-292, 296-299, 301-302, 306-311, 317, 319, 331, 333, 343, 345, 357, 360, 374 and 376 obtained in Formulation Example 5 with water so as to give 500 ppm of an active ingredient concentration.

On the other hand, *Bemisia tabaci* adult was released on a tomato seedling (the third true leaf stage) planted in a polyethylene cup, and made to lay eggs for about 72 hours. The tomato seedling was kept in a greenhouse for 8 days. When instar larvae hatched from the eggs, the above test spray solution was sprayed in the amount of 20 ml/cup. The cup was kept in a greenhouse at 25° C. After the keeping for 7 days, the number of surviving instar larvae on the tomato leaves was examined, and a control value was calculated according to the following equation:

Control value (%)={1−($Cb \times Tai$)/($Cai \times Tb$)}×100 wherein symbols represent as follows:

Cb: the number of insects in a non-treated section before treatment,

Cai: the number of insects in a non-treated section in observation,

Tb: the number of insects in a treated-section before treatment,

Tai: the number of insects in a treated-section in observation;

wherein the non-treated section represents a section where the test spray solution prepared by diluting the formulation without the present compound in Formulation Example 5 with the same amount of water as in the treated-section was sprayed.

As a result, in the treated-section of the test spray solution of each of Present Compounds 4-6, 21, 22, 49, 50, 55, 75, 88, 112-113, 116-118, 128-132, 161, 169-171, 174-176, 188, 209-210, 214-215, 238-240, 247-248, 255, 259, 262, 270-273, 280, 291-292, 296-299, 301-302, 306-311, 317, 319, 331, 333, 343, 345, 357, 360, 374 and 376, the control value of 90% or more was shown.

Test Example 7

The test spray solutions were prepared by diluting the formulations of each of Present Compounds 1-14, 16-23, 25, 28-36, 42-47, 49, 50, 53-55, 59, 64, 66, 68-76, 80, 81-83, 85-90, 97-98, 100, 116-118, 123, 133-142, 144, 151-154, 156-160, 169-171, 174-176, 181, 183-188, 190-191, 193-194, 197-198, 201-203, 209-210, 214-215, 230, 238-243, 246-248, 262-264, 278-281, 285-287, 292, 294, 299-303, 306-307, 311, 313-316, 318-319, 327, 330-333, 335, 341-343, 345, 348-349, 353, 358, 360, 365, 369-371 and 374-378 obtained in Formulation Example 5 with water so as to give 500 ppm of an active ingredient concentration.

On the other hand, Cabbage (the third leaf stage) planted in a polyethylene cup was sprayed with 20 mL/cup of each of the test spray solution. After the test solution was dried, the aerial part was cut off, and then placed in a 50 mL volume cup. Five second instar larvae of *Plutella xylostella* were released into the cup, and the cup was sealed with a lid. After the cup was kept at 25° C. for 5 days, the number of living insects was counted. A death rate was calculated according to the following equation:

Death rate (%)=(Number of dead insects/Number of tested insects)×100

As a result, in the treated-section of the test spray solution of each of Present Compounds 1-14, 16-23, 25, 28-36, 42-47, 49, 50, 53-55, 59, 64, 66, 68-76, 80-83, 85-90, 97-98, 100, 116-118, 123, 133-142, 144, 151-154, 156-160, 169-171, 174-176, 181, 183-188, 190-191, 193-194, 197-198, 201-203, 209-210, 214-215, 230, 238-243, 246-248, 262-264, 278-281, 285-287, 292, 294, 299-303, 306-307, 311, 313-316, 318-319, 327, 330-333, 335, 341-343, 345, 348-349, 353, 358, 360, 365, 369-371 and 374-378, the death rate of 80% or more was shown.

Test Example 8

The test spray solutions were prepared by diluting the formulations of each of Present Compounds 2-9, 11, 13, 14, 17-20, 22, 23, 28, 29, 31, 35-37, 43-47, 54-55, 68-83, 86-90, 106, 112-113, 117-118, 128-129, 131-138, 140-142, 157-158, 161, 164, 169-171, 174-176, 183-185, 187-188, 191, 194, 201-203, 209-210, 214-215, 230, 238-240, 242-243, 246-248, 251, 262-263, 270-275, 278-281, 285-287, 290, 292, 294, 296-302, 305-316, 318-319, 324-325, 327, 329-333, 335, 341-343, 345, 349, 355-357, 360, 369-371 and 374-378 obtained in Formulation Example 5 with water so as to give 500 ppm of an active ingredient concentration.

On the other hand, an apple tree was planted in a plastic cup, and grown until the seventh-eighth leaf was spread. The apple tree was sprayed with 20 mL/cup of each of the test spray solution. After the test solution was dried, 60 first-instar *Adoxophyes orana* fasciata were released, and the cup was covered with a plastic cup upside-down which the bottom was cut off and a filter paper was put thereon. After 7 days, the number of living insects was counted, and a death rate was calculated according to the following equation:

Death rate (%)=(Number of dead insects/Number of tested insects)×100

As a result, in the treated-section of the test spray solution of each of Present Compounds 2-9, 11, 13, 14, 17-20, 22, 23, 28, 29, 31, 35-37, 43-47, 54-55, 68-83, 86-90, 106, 112-113, 117-118, 128-129, 131-138, 140-142, 157-158, 161, 164, 169-171, 174-176, 183-185, 187-188, 191, 194, 201-203, 209-210, 214-215, 230, 238-240, 242-243, 246-248, 251, 262-263, 270-275, 278-281, 285-287, 290, 292, 294, 296-302, 305-316, 318-319, 324-325, 327, 329-333, 335, 341-343, 345, 349, 355-357, 360, 369-371 and 374-378, the death rate of 90% or more was shown.

INDUSTRIAL APPLICABILITY

The present compound has an activity of controlling pests and is useful as an active ingredient of a pest controlling agent.

The invention claimed is:

1. A fused heterocyclic compound of the formula (I):

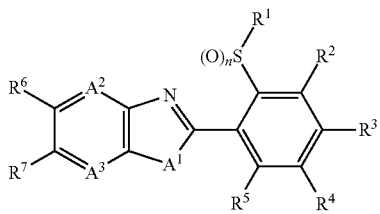

wherein:
- $A^1$ represents —$NR^8$—, an oxygen atom, or a sulfur atom;
- $A^2$ represents =$CR^9$—;
- $A^3$ represents a nitrogen atom;
- $R^1$ represents a C1-C6 chain hydrocarbon group optionally having one or more atoms or groups selected from Group X, or a C3-C6 alicyclic hydrocarbon group optionally having one or more atoms or groups selected from Group Y;
- $R^2$, $R^3$, $R^4$, and $R^5$ are same or different and independently represent a C1-C6 chain hydrocarbon group optionally having one or more halogen atoms, a phenyl group optionally having one or more atoms or groups selected from Group Z, a 5-membered heterocyclic group optionally having one or more atoms or groups selected from Group Z, a 6-membered heterocyclic group optionally having one or more atoms or groups selected from Group Z, —$OR^{11}$, —$S(O)_mR^{11}$, —$NR^{11}R^{12}$, —$CO_2R^{11}$, —$C(O)R^{11}$, a cyano group, a nitro group, a halogen atom, —$SF_5$, or a hydrogen atom, provided that at least two of $R^2$, $R^3$, $R^4$, and $R^5$ represent a hydrogen atom;
- $R^6$ and $R^7$ are same or different and independently represent a C1-C6 chain hydrocarbon group optionally having one or more atoms or groups selected from Group X, a phenyl group optionally having one or more atoms or groups selected from Group Z, a 5-membered heterocyclic group optionally having one or more atoms or groups selected from Group Z, a 6-membered heterocyclic group optionally having one or more atoms or groups selected from Group Z, —$OR^{11}$, —$S(O)_mR^{11}$, —$S(O)_2NR^{11}R^{12}$, —$NR^{11}R^{12}$, —$NR^{11}$—$CO_2R^{12}$, —$NR^{11}C(O)R^{12}$, —$CO_2R^{11}$, —$C(O)R^{11}$, a cyano group, a nitro group, a halogen atom, —$SF_5$, or a hydrogen atom;
- $R^8$ represents a C1-C6 chain hydrocarbon group optionally having one or more atoms or groups selected from Group W, —$CO_2R^{11}$, —$C(O)R^{11}$, or a C3-C6 alicyclic hydrocarbon group optionally having one or more atoms or groups selected from Group Y;
- $R^9$ represents a C1-C6 chain hydrocarbon group optionally having one or more halogen atoms, —$OR^{11}$, —$S(O)_mR^{11}$, —$NR^{11}R^{12}$, —$CO_2R^{11}$, —$C(O)R^{11}$, a cyano group, a nitro group, a halogen atom, or a hydrogen atom;
- $R^{11}$ and $R^{12}$ are same or different and independently represent a C1-C6 chain hydrocarbon group optionally having one or more halogen atoms, or a hydrogen atom; and
- m represents 0, 1, or 2; and n represents 0, 1, or 2;
- (except in cases as follows: both $R^6$ and $R^7$ are a hydrogen atom; and in —$S(O)_mR^{11}$, when m is 1 or 2, $R^{11}$ is a hydrogen atom)
- the Group X consists of a C1-C6 alkoxy group optionally having one or more halogen atoms, a C2-C6 alkenyloxy group optionally having one or more halogen atoms, a C2-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C2-C6 alkylcarbonyl group optionally having one or more halogen atoms, a C2-C6 alkoxycarbonyl group optionally having one or more halogen atoms, a C3-C6 cycloalkyl group optionally having one or more halogen atoms, a cyano group, a hydroxy group, and a halogen atom;
- the Group Y consists of a C1-C6 chain hydrocarbon group optionally having one or more halogen atoms, a C1-C6 alkoxy group optionally having one or more halogen atoms, a C2-C6 alkenyloxy group optionally having one or more halogen atoms, a C2-C6 alkynyloxy group optionally having one or more halogen atoms, a hydroxy group, and a halogen atom;
- the Group Z consists of a C1-C6 chain hydrocarbon group optionally having one or more halogen atoms, a C1-C6 alkoxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C2-C6 alkylcarbonyl group optionally having one or more halogen atoms, a C2-C6 alkoxycarbonyl group optionally having one or more halogen atoms, a C1-C6 alkylamino group optionally having one or more halogen atoms, a C2-C8 dialkylamino group optionally having one or more halogen atoms, a halogen atom, a cyano group, and a nitro group; and
- the Group W consists of a C1-C6 alkoxy group optionally having one or more halogen atoms, a C2-C6 alkenyloxy group optionally having one or more halogen atoms, a C2-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C2-C6 alkylcarbonyl group, a C2-C6 alkoxycarbonyl group, a C3-C6 cycloalkyl group, a halogen atom, a cyano group, and a hydroxy group.

2. The fused heterocyclic compound according to claim 1, wherein $R^6$ and $R^7$ are same or different and are independently a C1-C6 chain hydrocarbon group optionally having one or more halogen atoms, —$OR^{11}$, —$S(O)_mR^{11}$, —$NR^{11}R^{12}$, a cyano group, a nitro group, a halogen atom, or a hydrogen atom.

3. The fused heterocyclic compound according to claim 1, wherein $R^6$ and $R^7$ are same or different and are independently a C1-C6 chain hydrocarbon group optionally having one or more halogen atoms, —$OR^{11}$, —$S(O)_mR^{11}$, a halogen atom, or a hydrogen atom.

4. The fused heterocyclic compound according to claim 1, wherein $A^2$ is =CH—.

5. The fused heterocyclic compound according to claim 1, wherein $R^2$, $R^4$, and $R^5$ are same or different and are independently a hydrogen atom or a halogen atom, and $R^3$ is a C1-C6 chain hydrocarbon group optionally having one or more halogen atoms, —$OR^{11}$, a halogen atom, or a hydrogen atom.

6. The fused heterocyclic compound according to claim 1, wherein $A^1$ is —$NR^8$—, and $R^8$ is a C1-C6 chain hydrocarbon group having one C1-C6 alkoxy group optionally having one or more halogen atoms, a C1-C6 chain hydrocarbon group optionally having one or more halogen atoms, or a cyclopropyl group.

7. The fused heterocyclic compound according to claim 1, wherein $A^1$ is —$NR^8$—, and $R^8$ is a methyl group, an ethyl group, a methoxymethyl group, or an ethoxymethyl group.

8. The fused heterocyclic compound according to claim 1, wherein $A^1$ is an oxygen atom.

9. The fused heterocyclic compound according to claim 1, wherein $A^1$ is a sulfur atom.

10. The fused heterocyclic compound according to claim 1 which is represented by the formula (1-1):

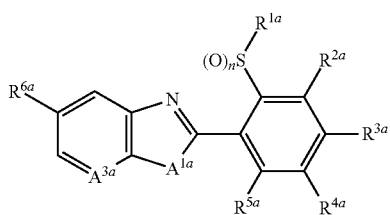

(1-1)

wherein:

$A^{1a}$ represents —$NR^{8a}$— or a sulfur atom;

$A^{3a}$ represents a nitrogen atom;

$R^{1a}$ represents a C1-C6 chain hydrocarbon group optionally having one or more halogen atoms;

$R^{2a}$, $R^{4a}$, and $R^{5a}$ are same or different and independently represent a C1-C6 chain hydrocarbon group optionally having one or more halogen atoms, a halogen atom, or a hydrogen atom;

$R^{3a}$ represents a C1-C6 chain hydrocarbon group optionally having one or more halogen atoms, —$OR^{11a}$, a halogen atom, or a hydrogen atom;

$R^{6a}$ represents a C1-C6 chain hydrocarbon group optionally having one or more halogen atoms, —$OR^{11a}$, —$S(O)_m R^{11a}$, a bromine atom, or an iodine atom;

$R^{8a}$ represents a C1-C6 chain hydrocarbon group optionally having one or more halogen atoms;

$R^{11a}$ represents a C1-C6 chain hydrocarbon group optionally having one or more halogen atoms; and m represents 0, 1, or 2, and n represents 0, 1, or 2;

provided that in —$S(O)_m R^{11}$, when m is 1 or 2, $R^{11}$ is not a hydrogen atom.

11. The fused heterocyclic compound according to claim 10, wherein $A^{1a}$ is —$NR^{8a}$— or a sulfur atom, $R^{8a}$ is a methyl group, $A^{3a}$ is a nitrogen atom, $R^{1a}$ is an ethyl group, $R^{2a}$, $R^{4a}$, and $R^{5a}$ are same or different and are independently a halogen atom or a hydrogen atom, $R^{3a}$ is a trifluoromethyl group, a halogen atom, or a hydrogen atom, and $R^{6a}$ is a C1-C3 alkyl group having one or more fluorine atoms, a C1-C3 alkoxy group having one or more fluorine atoms, a C1-C3 alkylsulfanyl group having one or more fluorine atoms, a C1-C3 alkylsulfinyl group having one or more fluorine atoms, or a C1-C3 alkylsulfonyl group having one or more fluorine atoms.

12. A pest controlling composition which comprises the fused heterocyclic compound according to claim 1 and an inert carrier.

13. A method of controlling pests which comprises applying an effective amount of the fused heterocyclic compound according to claim 1 to pests or habitats of pests.

* * * * *